(12) United States Patent
Jakobovits et al.

(10) Patent No.: US 7,226,594 B2
(45) Date of Patent: *Jun. 5, 2007

(54) NUCLEIC ACID AND CORRESPONDING PROTEIN ENTITLED 161P2F10B USEFUL IN TREATMENT AND DETECTION OF CANCER

(75) Inventors: Aya Jakobovits, Beverly Hills, CA (US); Arthur B. Raitano, Los Angeles, CA (US); Mary Faris, Los Angeles, CA (US); Rene S. Hubert, Los Angeles, CA (US); Wangmao Ge, Culver City, CA (US); Karen Jane Meyrick Morrison, Santa Monica, CA (US); Robert Kendall Morrison, Santa Monica, CA (US); Pia M. Challita-Eid, Encino, CA (US)

(73) Assignee: Agensys, Inc., Santa Monica, CA (US)

( * ) Notice: Subject to any disclaimer, the term of this patent is extended or adjusted under 35 U.S.C. 154(b) by 582 days.

This patent is subject to a terminal disclaimer.

(21) Appl. No.: 10/291,241

(22) Filed: Nov. 7, 2002

(65) Prior Publication Data

US 2003/0206905 A1 Nov. 6, 2003

(51) Int. Cl.
*A61K 39/395* (2006.01)
(52) U.S. Cl. .................. 424/145.1; 514/2; 530/350; 530/387.1
(58) Field of Classification Search .............. 514/2; 424/145.1

See application file for complete search history.

(56) References Cited

U.S. PATENT DOCUMENTS

| | | | | |
|---|---|---|---|---|
| 5,001,225 A | * | 3/1991 | Taylor ................ | 530/388.6 |
| 6,323,321 B1 | | 11/2001 | Bühring .............. | 530/387.2 |
| 6,342,219 B1 | | 1/2002 | Thorpe et al. ........ | 424/145.1 |
| 2003/0165505 A1 | * | 9/2003 | Challita-Eid et al. .... | 424/146.1 |
| 2005/0265921 A1 | * | 12/2005 | Challita-Eid et al. .... | 424/1.11 |
| 2005/0265924 A1 | * | 12/2005 | Challita-Eid et al. .... | 424/1.49 |

FOREIGN PATENT DOCUMENTS

| WO | WO9960164 | 11/1999 |
|---|---|---|
| WO | WO200021990 A1 | 4/2000 |
| WO | WO200157272 A2 | 8/2001 |
| WO | WO200157273 | 8/2001 |
| WO | WO200157274 A2 | 8/2001 |
| WO | WO200157275 A2 | 8/2001 |
| WO | WO200157276 A2 | 8/2001 |
| WO | WO200157277 A2 | 8/2001 |
| WO | WO200157278 A2 | 8/2001 |
| WO | WO200160860 | 8/2001 |
| WO | WO200175067 A2 | 10/2001 |
| WO | WO200186003 A2 | 11/2001 |
| WO | WO200279411 | 10/2002 |
| WO | WO2003004514 | 1/2003 |
| WO | WO2003016475 | 2/2003 |
| WO | WO2003040340 | 5/2003 |

OTHER PUBLICATIONS

Colbern et al (J Inorg Biocehm, 1999, 77:117-120).*
Houghton and Scheinberg (Seminars in Oncology, 1986, 13:165-179).*
Bühring et al., Blood 94(7):2343-2356 (1999).
Bühring et al., Blood 97(10):3303-3305 (2001).
Burgess et al., Journal of Cell Biology 111:2129-2138 (1990).
Coleman, Research in Immunology 145:33-36 (1994).
Jin-Hua et al., Genomics 45(2):412-415 (1997).
Lazar et al., Molecular and Cellular Biology 8(3):1247-1252 (1988).
Lederman et al., Molecular Immunology 28:1171-1181 (1991).
Li et al., Proc Natl Acad Sci USA 77:3211-3214 (1980).
Paul (Ed.), Fundamental Immunology, 3rd ed., p. 242, 1993.
Reiger et al., Glossary of Genetics and Cytogenetics, Classical and Molecular, 4th Ed., Springer-Verlag, Berlin (1976).
Schwartz et al., Proc Natl Acad Sci USA 84:6408-6411 (1987).
Deissler et al., Journal of Biological Chemistry (1995) 270(17):9849-9855.
International Search Report for PCT/US02/36002, mailed on Jan. 5, 2005, 5 pages.

* cited by examiner

*Primary Examiner*—Jeffrey Siew
*Assistant Examiner*—Laura B Goddard
(74) *Attorney, Agent, or Firm*—Morrison & Foerster LLP

(57) ABSTRACT

A novel gene 0161P2F10B (also designated 161P2F10B) and its encoded protein, and variants thereof, are described wherein 161P2F10B exhibits tissue specific expression in normal adult tissue, and is aberranty expressed in the cancers listed in Table I. Consequently, 161P2F10B provides a diagnostic, prognostic, prophylactic and/or therapeutic target for cancer. The 161P2F10B gene or fragment thereof, or its encoded protein, or variants thereof, or a fragment thereof, can be used to elicit a humoral or cellular immune response; antibodies or T cells reactive with 161P2F10B can be used in active or passive immunization.

13 Claims, 70 Drawing Sheets

Figure 1: 161P2F10B SSH sequence of 182 nucleotides (SEQ ID NO: 1)

```
  1 GATCACACAT TAGGTTATNG ACTTCAATAT TTTCAAATGG TTCAACTTCA GTCTTCTCTT
 61 TAAAACTGGG TCCATGTGCC AAGAAAGATA GCCTCCATGC TCCTAAACTC ATTGTTATAA
121 CCATGGTTGC CTCCTCCACA ATTTGTATTT GATTTACTCC TAACAGCCAG CCACTGTTGA
181 TC
```

Figure 2:

Figure 2A-1. The cDNA (SEQ ID NO : 2) and amino acid sequence (SEQ ID NO : 3) of 161P2F10B variant 1. The 3858 nucleotide sequence of 161P2F10B variant 1 is shown. The open reading frame extends from nucleic acid 44-2671 including the stop codon.

```
                                              M   E   S   T   L   T
  1 ctactttattctgataaaacaggtctatgcagctaccaggacaATGGAATCTACGTTGAC
  7   L   A   T   E   Q   P   V   K   K   N   T   L   K   K   Y   K   I   A   C   I
 61 TTTAGCAACGGAACAACCTGTTAAGAAGAACACTCTTAAGAAATATAAAATAGCTTGCAT
 27   V   L   L   A   L   L   V   I   M   S   L   G   L   G   L   G   L   R
121 TGTTCTTCTTGCTTTGCTGGTGATCATGTCACTTGGATTAGGCCTGGGGCTTGGACTCAG
 47   K   L   E   K   Q   G   S   C   R   K   K   C   F   D   A   S   F   R   G   L
181 GAAACTGGAAAAGCAAGGCAGCTGCAGGAAGAAGTGCTTTGATGCATCATTTAGAGGACT
 67   E   N   C   R   C   D   V   A   C   K   D   R   G   D   C   C   W   D   F   E
241 GGAGAACTGCCGGTGTGATGTGGCATGTAAAGACCGAGGTGATTGCTGCTGGGATTTTGA
 87   D   T   C   V   E   S   T   R   I   W   M   C   N   K   F   R   C   G   E   T
301 AGACACCTGTGTGGAATCAACTCGAATATGGATGTGCAATAAATTTCGTTGTGGAGAGAC
107   R   L   E   A   S   L   C   S   C   S   D   D   C   L   Q   K   K   D   C   C
361 CAGATTAGAGGCCAGCCTTTGCTCTTGTTCAGATGACTGTTTGCAGAAGAAAGATTGCTG
127   A   D   Y   K   S   V   C   Q   G   E   T   S   W   L   E   E   N   C   D   T
421 TGCTGACTATAAGAGTGTTTGCCAAGGAGAAACCTCATGGCTGGAAGAAAACTGTGACAC
147   A   Q   Q   S   Q   C   P   E   G   F   D   L   P   P   V   I   L   F   S   M
481 AGCCCAGCAGTCTCAGTGCCCAGAAGGGTTTGACCTGCCACCAGTTATCTTGTTTTCTAT
167   D   G   F   R   A   E   Y   L   Y   T   W   D   T   L   M   P   N   I   N   K
541 GGATGGATTTAGAGCTGAATATTTATACACATGGGATACTTTAATGCCAAATATCAATAA
187   L   K   T   C   G   I   H   S   K   Y   M   R   A   M   Y   P   T   K   T   F
601 ACTGAAAACATGTGGAATTCATTCAAAATACATGAGAGCTATGTATCCTACCAAAACCTT
207   P   N   H   Y   T   I   V   T   G   L   Y   P   E   S   H   G   I   I   D   N
661 CCCAAATCATTACACCATTGTCACGGGCTTGTATCCAGAGTCACATGGCATCATTGACAA
227   N   M   Y   D   V   N   L   N   K   N   F   S   L   S   S   K   E   Q   N   N
721 TAATATGTATGATGTAAATCTCAACAAGAATTTTTCACTTTCTTCAAAGGAACAAAATAA
247   P   A   W   W   H   G   Q   P   M   W   L   T   A   M   Y   Q   G   L   K   A
781 TCCAGCCTGGTGGCATGGGCAACCAATGTGGCTGACAGCAATGTATCAAGGTTTAAAAGC
267   A   T   Y   F   W   P   G   S   E   V   A   I   N   G   S   F   P   S   I   Y
841 CGCTACCTACTTTTGGCCCGGATCAGAAGTGGCTATAAATGGCTCCTTTCCTTCCATATA
287   M   P   Y   N   G   S   V   P   F   E   E   R   I   S   T   L   L   K   W   L
901 CATGCCTTACAACGGAAGTGTCCCATTTGAAGAGAGGATTTCTACACTGTTAAAATGGCT
307   D   L   P   K   A   E   R   P   R   F   Y   T   M   Y   F   E   E   P   D   S
961 GGACCTGCCCAAAGCTGAAAGACCCAGGTTTTATACCATGTATTTTGAAGAACCTGATTC
```

Figure 2A-2

```
 327  S   G   H   A   G   G   P   V   S   A   R   V   I   K   A   L   Q   V   V   D
1021  CTCTGGACATGCAGGTGGACCAGTCAGTGCCAGAGTAATTAAAGCCTTACAGGTAGTAGA
 347  H   A   F   G   M   L   M   E   G   L   K   Q   R   N   L   H   N   C   V   N
1081  TCATGCTTTTGGGATGTTGATGGAAGGCCTGAAGCAGCGGAATTTGCACAACTGTGTCAA
 367  I   I   L   L   A   D   H   G   M   D   Q   T   Y   C   N   K   M   E   Y   M
1141  TATCATCCTTCTGGCTGACCATGGAATGGACCAGACTTATTGTAACAAGATGGAATACAT
 387  T   D   Y   F   P   R   I   N   F   F   Y   M   Y   E   G   P   A   P   R   I
1201  GACTGATTATTTTCCCAGAATAAACTTCTTCTACATGTACGAAGGGCCTGCCCCCCGCAT
 407  R   A   H   N   I   P   H   D   F   F   S   F   N   S   E   E   I   V   R   N
1261  CCGAGCTCATAATATACCTCATGACTTTTTTAGTTTTAATTCTGAGGAAATTGTTAGAAA
 427  L   S   C   R   K   P   D   Q   H   F   K   P   Y   L   T   P   D   L   P   K
1321  CCTCAGTTGCCGAAAACCTGATCAGCATTTCAAGCCCTATTTGACTCCTGATTTGCCAAA
 447  R   L   H   Y   A   K   N   V   R   I   D   K   V   H   L   F   V   D   Q   Q
1381  GCGACTGCACTATGCCAAGAACGTCAGAATCGACAAAGTTCATCTCTTTGTGGATCAACA
 467  W   L   A   V   R   S   K   S   N   T   C   G   G   G   N   H   G   Y   N
1441  GTGGCTGGCTGTTAGGAGTAAATCAAATACAAATTGTGGAGGAGGCAACCATGGTTATAA
 487  N   E   F   R   S   M   E   A   I   F   L   A   H   G   P   S   F   K   E   K
1501  CAATGAGTTTAGGAGCATGGAGGCTATCTTTCTGGCACATGGACCCAGTTTTAAAGAGAA
 507  T   E   V   E   P   F   E   N   I   E   V   Y   N   L   M   C   D   L   L   R
1561  GACTGAAGTTGAACCATTTGAAAATATTGAAGTCTATAACCTAATGTGTGATCTTCTACG
 527  I   Q   P   A   P   N   N   G   T   H   G   S   L   N   H   L   L   K   V   P
1621  CATTCAACCAGCACCAAACAATGGAACCCATGGTAGTTTAAACCATCTTCTGAAGGTGCC
 547  F   Y   E   P   S   H   A   E   E   V   S   K   F   S   V   C   G   F   A   N
1681  TTTTTATGAGCCATCCCATGCAGAGGAGGTGTCAAAGTTTTCTGTTTGTGGCTTTGCTAA
 567  P   L   P   T   E   S   L   D   C   F   C   P   H   L   Q   N   S   T   Q   L
1741  TCCATTGCCCACAGAGTCTCTTGACTGTTTCTGCCCTCACCTACAAAATAGTACTCAGCT
 587  E   Q   V   N   Q   M   L   N   L   T   Q   E   E   I   T   A   T   V   K   V
1801  GGAACAAGTGAATCAGATGCTAAATCTCACCCAAGAAGAAATAACAGCAACAGTGAAAGT
 607  N   L   P   F   G   R   P   R   V   L   Q   K   N   V   D   H   C   L   L   Y
1861  AAATTTGCCATTTGGGAGGCCTAGGGTACTGCAGAAGAACGTGGACCACTGTCTCCTTTA
 627  H   R   E   Y   V   S   G   F   G   K   A   M   R   M   P   M   W   S   S   Y
1921  CCACAGGGAATATGTCAGTGGATTTGGAAAAGCTATGAGGATGCCCATGTGGAGTTCATA
 647  T   V   P   Q   L   G   D   T   S   P   L   P   P   T   V   P   D   C   L   R
1981  CACAGTCCCCCAGTTGGGAGACACATCGCCTCTGCCTCCCACTGTCCCAGACTGTCTGCG
 667  A   D   V   R   V   P   P   S   E   S   Q   K   C   S   F   Y   L   A   D   K
2041  GGCTGATGTCAGGGTTCCTCCTTCTGAGAGCCAAAAATGTTCCTTCTATTTAGCAGACAA
 687  N   I   T   H   G   F   L   Y   P   P   A   S   N   R   T   S   D   S   Q   Y
2101  GAATATCACCCACGGCTTCCTCTATCCTCCTGCCAGCAATAGAACATCAGATAGCCAATA
 707  D   A   L   I   T   S   N   L   V   P   M   Y   E   E   F   R   K   M   W   D
```

Figure 2A-3

```
2161 TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341 CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
 827  W  V  E  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
 867  Y  L  P  T  F  E  T  T  I  *
2641 ATATTTACCAACATTTGAAACCACTATTTAActtaataatgtctacttaatatataattt
2701 actgtataaagtaattttggcaaaatataagtgatttttctggagaattgtaaaataaa
2761 gttttctattttccttaaaaaaaaaccggaattccgggcttgggaggctgaggcagga
2821 gactcgcttgaacccgggaggcagaggttgcagtgagccaagattgcgccattgcactcc
2881 agcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgacccccgagtggttctccaggctccctgccccac
3841 ccattcaggccggaattc
```

Figure 2B-1: The cDNA (SEQ ID NO: 4) and amino acid sequence (SEQ ID NO: 5) of 161P2F10B variant 2. The 3858 nucleotide sequence of 161P2F10B variant 2 is shown. The open reading frame extends from nucleic acid 44-2671 including the stop codon.

```
      1                                        M   E   S   T   L   T
      1 ctactttattctgataaaacaggtctatgcagctaccaggacaATGGAATCTACGTTGAC
      7 L   A   T   E   Q   P   V   K   K   N   T   L   K   K   Y   K   I   A   C   I
     61 TTTAGCAACGGAACAACCTGTTAAGAAGAACACTCTTAAGAAATATAAAATAGCTTGCAT
     27 V   L   L   A   L   L   V   I   M   S   L   G   L   G   L   G   L   G   L   R
    121 TGTTCTTCTTGCTTTGCTGGTGATCATGTCACTTGGATTAGGCCTGGGGCTTGGACTCAG
     47 K   L   E   K   Q   G   S   C   R   K   K   C   F   D   A   S   F   R   G   L
    181 GAAACTGGAAAAGCAAGGCAGCTGCAGGAAGAAGTGCTTTGATGCATCATTTAGAGGACT
     67 E   N   C   R   C   D   V   A   C   K   D   R   G   D   C   C   W   D   F   E
    241 GGAGAACTGCCGGTGTGATGTGGCATGTAAAGACCGAGGTGATTGCTGCTGGGATTTTGA
     87 D   T   C   V   E   S   T   R   I   W   M   C   N   K   F   R   C   G   E   T
    301 AGACACCTGTGTGGAATCAACTCGAATATGGATGTGCAATAAATTTCGTTGTGGAGAGAC
    107 R   L   E   A   S   L   C   S   C   S   D   D   C   L   Q   R   K   D   C   C
    361 .CAGATTAGAGGCCAGCCTTTGCTCTTGTTCAGATGACTGTTTGCAGAGGAAAGATTGCTG
    127 A   D   Y   K   S   V   C   Q   G   E   T   S   W   L   E   E   N   C   D   T
    421 TGCTGACTATAAGAGTGTTTGCCAAGGAGAAACCTCATGGCTGGAAGAAAACTGTGACAC
    147 A   Q   Q   S   Q   C   P   E   G   F   D   L   P   P   V   I   L   F   S   M
    481 AGCCCAGCAGTCTCAGTGCCCAGAAGGGTTTGACCTGCCACCAGTTATCTTGTTTTCTAT
    167 D   G   F   R   A   E   Y   L   Y   T   W   D   T   L   M   P   N   I   N   K
    541 GGATGGATTTAGAGCTGAATATTTATACACATGGGATACTTTAATGCCAAATATCAATAA
    187 L   K   T   C   G   I   H   S   K   Y   M   R   A   M   Y   P   T   K   T   F
    601 ACTGAAAACATGTGGAATTCATTCAAAATACATGAGAGCTATGTATCCTACCAAAACCTT
    207 P   N   H   Y   T   I   V   T   G   L   Y   P   E   S   H   G   I   I   D   N
    661 CCCAAATCATTACACCATTGTCACGGGCTTGTATCCAGAGTCACATGGCATCATTGACAA
    227 N   M   Y   D   V   N   L   N   K   N   F   S   L   S   S   K   E   Q   N   N
    721 TAATATGTATGATGTAAATCTCAACAAGAATTTTTCACTTTCTTCAAAGGAACAAAATAA
    247 P   A   W   W   H   G   Q   P   M   W   L   T   A   M   Y   Q   G   L   K   A
    781 TCCAGCCTGGTGGCATGGGCAACCAATGTGGCTGACAGCAATGTATCAAGGTTTAAAAGC
    267 A   T   Y   F   W   P   G   S   E   V   A   I   N   G   S   F   P   S   I   Y
    841 CGCTACCTACTTTTGGCCCGGATCAGAAGTGGCTATAAATGGCTCCTTTCCTTCCATATA
    287 M   P   Y   N   G   S   V   P   F   E   E   R   I   S   T   L   L   K   W   L
    901 CATGCCTTACAACGGAAGTGTCCCATTTGAAGAGAGGATTTCTACACTGTTAAAATGGCT
    307 D   L   P   K   A   E   R   P   R   F   Y   T   M   Y   F   E   E   P   D   S
    961 GGACCTGCCCAAAGCTGAAAGACCCAGGTTTTATACCATGTATTTTGAAGAACCTGATTC
    327 S   G   H   A   G   G   P   V   S   A   R   V   I   K   A   L   Q   V   V   D
   1021 CTCTGGACATGCAGGTGGACCAGTCAGTGCCAGAGTAATTAAAGCCTTACAGGTAGTAGA
    347 H   A   F   G   M   L   M   E   G   L   K   Q   R   N   L   H   N   C   V   N
   1081 TCATGCTTTTGGGATGTTGATGGAAGGCCTGAAGCAGCGGAATTTGCACAACTGTGTCAA
    367 I   I   L   L   A   D   H   G   M   D   Q   T   Y   C   N   K   M   E   Y   M
   1141 TATCATCCTTCTGGCTGACCATGGAATGGACCAGACTTATTGTAACAAGATGGAATACAT
```

Figure 2B-2

```
 387  T  D  Y  F  P  R  I  N  F  F  Y  M  Y  E  G  P  A  P  R  I
1201  GACTGATTATTTTCCCAGAATAAACTTCTTCTACATGTACGAAGGGCCTGCCCCCCGCAT
 407  R  A  H  N  I  P  H  D  F  F  S  F  N  S  E  E  I  V  R  N
1261  CCGAGCTCATAATATACCTCATGACTTTTTTAGTTTTAATTCTGAGGAAATTGTTAGAAA
 427  L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447  R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467  W  L  A  V  R  S  K  S  N  T  N  C  G  G  G  N  H  G  Y  N
1441  GTGGCTGGCTGTTAGGAGTAAATCAAATACAAATTGTGGAGGAGGCAACCATGGTTATAA
 487  N  E  F  R  S  M  E  A  I  F  L  A  H  G  P  S  F  K  E  K
1501  CAATGAGTTTAGGAGCATGGAGGCTATCTTTCTGGCACATGGACCCAGTTTTAAAGAGAA
 507  T  E  V  E  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527  I  Q  P  A  P  N  N  G  T  H  G  S  L  N  H  L  L  K  V  P
1621  CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567  P  L  P  T  E  S  L  D  C  F  C  P  H  L  Q  N  S  T  Q  L
1741  TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861  AAATTTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647  T  V  P  Q  L  G  D  T  S  P  L  P  P  T  V  P  D  C  L  R
1981  CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041  GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101  GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161  TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221  CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281  TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341  CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401  TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
```

Figure 2B-3

```
2461 TATCATCCCTCACCGACCTACCAACGTGGAGAGCTGTCCTGAAGGTAAACCAGAAGCTCT
 827  W   V   E   E   R   F   T   A   H   I   A   R   V   R   D   V   E   L   L   T
2521 TTGGGTTGAAGAAAGATTTACAGCTCACATTGCCCGGGTCCGTGATGTAGAACTTCTCAC
 847  G   L   D   F   Y   Q   D   K   V   Q   P   V   S   E   I   L   Q   L   K   T
2581 TGGGCTTGACTTCTATCAGGATAAAGTGCAGCCTGTCTCTGAAATTTTGCAACTAAAGAC
 867  Y   L   P   T   F   E   T   T   I   *
2641 ATATTTACCAACATTTGAAACCACTATTTAActtaataatgtctacttaatatataattt
2701 actgtataaagtaattttggcaaaatataagtgattttttctggagaattgtaaaataaa
2761 gttttctattttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagaccctgataccatctgccagtccccgacagc
3781 ttaggcactccttgccatcaacctgaccccccgagtggttctccaggctccctgccccac
3841 ccattcaggccggaattc
```

Figure 2C-1: The cDNA (SEQ ID NO: 6) and amino acid sequence (SEQ ID NO: 7) of 161P2F10B variant 3. The 3858 nucleotide sequence of 161P2F10B variant 3 is shown. The open reading frame extends from nucleic acid 44-2671 including the stop codon.

```
   1                                                    M   E   S   T   L   T
   1 ctactttattctgataaaacaggtctatgcagctaccaggacaATGGAATCTACGTTGAC
   7   L   A   T   E   Q   P   V   K   K   N   T   L   K   K   Y   K   I   A   C   I
  61 TTTAGCAACGGAACAACCTGTTAAGAAGAACACTCTTAAGAAATATAAAATAGCTTGCAT
  27   V   L   L   A   L   L   V   I   M   S   L   G   L   G   L   G   L   R
 121 TGTTCTTCTTGCTTTGCTGGTGATCATGTCACTTGGATTAGGCCTGGGGCTTGGACTCAG
  47   K   L   E   K   Q   G   S   C   R   K   K   C   F   D   A   S   F   R   G   L
 181 GAAACTGGAAAAGCAAGGCAGCTGCAGGAAGAAGTGCTTTGATGCATCATTTAGAGGACT
  67   E   N   C   R   C   D   V   A   C   K   D   R   G   D   C   C   W   D   F   E
 241 GGAGAACTGCCGGTGTGATGTGGCATGTAAAGACCGAGGTGATTGCTGCTGGGATTTTGA
  87   D   T   C   V   E   S   T   R   I   W   M   C   N   K   F   R   C   G   E   T
 301 AGACACCTGTGTGGAATCAACTCGAATATGGATGTGCAATAAATTTCGTTGTGGAGAGAC
 107   R   L   E   A   S   L   C   S   C   S   D   D   C   L   Q   K   K   D   C   C
 361 CAGATTAGAGGCCAGCCTTTGCTCTTGTTCAGATGACTGTTTGCAGAAGAAAGATTGCTG
 127   A   D   Y   K   S   V   C   Q   G   E   T   S   W   L   E   E   N   C   D   T
 421 TGCTGACTATAAGAGTGTTTGCCAAGGAGAAACCTCATGGCTGGAAGAAAACTGTGACAC
 147   A   Q   Q   S   Q   C   P   E   G   F   D   L   P   P   V   I   L   F   S   M
 481 AGCCCAGCAGTCTCAGTGCCCAGAAGGGTTTGACCTGCCACCAGTTATCTTGTTTTCTAT
 167   D   G   F   R   A   E   Y   L   Y   T   W   D   T   L   M   P   N   I   N   K
 541 GGATGGATTTAGAGCTGAATATTTATACACATGGGATACTTTAATGCCAAATATCAATAA
 187   L   K   T   C   G   I   H   S   K   Y   M   R   A   M   Y   P   T   K   T   F
 601 ACTGAAAACATGTGGAATTCATTCAAAATACATGAGAGCTATGTATCCTACCAAAACCTT
 207   P   N   H   Y   T   I   V   T   G   L   Y   P   E   S   H   G   I   I   D   N
 661 CCCAAATCATTACACCATTGTCACGGGCTTGTATCCAGAGTCACATGGCATCATTGACAA
 227   N   M   Y   D   V   N   L   K   N   F   S   L   S   S   K   E   Q   N   N
 721 TAATATGTATGATGTAAATCTCAACAAGAATTTTTCACTTTCTTCAAAGGAACAAAATAA
 247   P   A   W   W   H   G   Q   P   M   W   L   T   A   M   Y   Q   G   L   K   A
 781 TCCAGCCTGGTGGCATGGGCAACCAATGTGGCTGACAGCAATGTATCAAGGTTTAAAAGC
 267   A   T   Y   F   W   P   G   S   E   V   A   I   N   G   S   F   P   S   I   Y
 841 CGCTACCTACTTTTGGCCCGGATCAGAAGTGGCTATAAATGGCTCCTTTCCTTCCATATA
 287   M   P   Y   N   G   S   V   P   F   E   E   R   I   S   T   L   L   K   W   L
 901 CATGCCTTACAACGGAAGTGTCCCATTTGAAGAGAGGATTTCTACACTGTTAAAATGGCT
 307   D   L   P   K   A   E   R   P   R   F   Y   T   M   Y   F   E   E   P   D   S
 961 GGACCTGCCCAAAGCTGAAAGACCCAGGTTTTATACCATGTATTTTGAAGAACCTGATTC
 327   S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
 347   H   A   F   G   M   L   E   G   L   K   Q   R   N   L   H   N   C   V   N
1081 TCATGCTTTTGGGATGTTGATGGAAGGCCTGAAGCAGCGGAATTTGCACAACTGTGTCAA
 367   I   I   L   L   A   D   H   G   M   D   Q   T   Y   C   N   K   M   E   Y   M
1141 TATCATCCTTCTGGCTGACCATGGAATGGACCAGACTTATTGTAACAAGATGGAATACAT
 387   T   D   Y   F   P   R   I   N   F   F   Y   M   Y   E   G   P   A   P   R   I
1201 GACTGATTATTTTCCCAGAATAAACTTCTTCTACATGTACGAAGGGCCTGCCCCCCGCAT
 407   R   A   H   N   I   P   H   D   F   F   S   F   N   S   E   E   I   V   R   N
1261 CCGAGCTCATAATATACCTCATGACTTTTTTAGTTTTAATTCTGAGGAAATTGTTAGAAA
 427   L   S   C   R   K   P   D   Q   H   F   K   P   Y   L   T   P   D   L   P   K
1321 CCTCAGTTGCCGAAAACCTGATCAGCATTTCAAGCCCTATTTGACTCCTGATTTGCCAAA
 447   R   L   H   Y   A   K   N   V   R   I   D   K   V   H   L   F   V   D   Q   Q
1381 GCGACTGCACTATGCCAAGAACGTCAGAATCGACAAAGTTCATCTCTTTGTGGATCAACA
 467   W   L   A   V   R   S   K   S   N   T   N   C   G   G   G   N   H   G   Y   N
1441 GTGGCTGGCTGTTAGGAGTAAATCAAATACAAATTGTGGAGGAGGCAACCATGGTTATAA
 487   N   E   F   R   S   M   E   A   I   F   L   A   H   G   P   S   F   K   E   K
1501 CAATGAGTTTAGGAGCATGGAGGCTATCTTTCTGGCACATGGACCCAGTTTTAAAGAGAA
 507   T   E   V   E   P   F   E   N   I   E   V   Y   N   L   M   C   D   L   L   R
```

Figure 2C-2

```
1561 GACTGAAGTTGAACCATTTGAAAATATTGAAGTCTATAACCTAATGTGTGATCTTCTACG
 527  I  Q  P  A  P  N  N  G  T  H  G  S  L  N  H  L  L  K  V  P
1621 CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681 TTTTTATGAGCCATCCCATGCAGAGGAGGTGTCAAAGTTTTCTGTTTGTGGCTTTGCTAA
 567  P  L  P  T  E  S  L  D  C  F  C  P  H  L  Q  N  S  T  Q  L
1741 TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801 GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861 AAATTTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921 CCACAGGGAATATGTCAGTGGATTTGGAAAAGCTATGAGGATGCCCATGTGGAGTTCATA
 647  T  V  P  Q  L  G  D  T  S  P  L  P  P  T  V  P  D  C  L  R
1981 CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041 GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101 GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161 TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341 CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
 807  I  I  P  H  R  P  T  N  V  E  S  C  P  G  G  K  P  E  A  L
2461 TATCATCCCTCACCGACCTACCAACGTGGAGAGCTGTCCTGGAGGTAAACCAGAAGCTCT
 827  W  V  E  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
 867  Y  L  P  T  F  E  T  T  I  *
2641 ATATTTACCAACATTTGAAACCACTATTTAActtaataatgtctacttaatatataattt
2701 actgtataaagtaattttggcaaaatataagtgatttttctggagaattgtaaaataaa
2761 gttttctattttccttaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagaccccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaggagagttttagaaccagcaca
3661 tccactggagatgctgggccaccagacccctcccagtcaataaagtctggtgcctcattt
3721 gatctcagcctcatcatgaccctggagagacccctgataccatctgccagtccccgacagc
3781 ttaggcactccttgccatcaacctgaccccccgagtggttctccaggctccctgccccac
3841 ccattcaggccggaattc
```

Figure 2D-1: The cDNA (SEQ ID NO: 8) and amino acid sequence (SEQ ID NO: 9) of 161P2F10B variant 4. The 3858 nucleotide sequence of 161P2F10B variant 4 is shown. The open reading frame extends from nucleic acid 44-2671 including the stop codon.

```
                                                   M   E   S   T   L   T
   1 ctactttattctgataaaacaggtctatgcagctaccaggacaATGGAATCTACGTTGAC
   7 L   A   T   E   Q   P   V   K   K   N   T   L   K   K   Y   I   A   C   I
  61 TTTAGCAACGGAACAACCTGTTAAGAAGAACACTCTTAAGAAATATAAAATAGCTTGCAT
  27 V   L   L   A   L   L   V   I   M   S   L   G   L   G   L   G   L   R
 121 TGTTCTTCTTGCTTTGCTGGTGATCATGTCACTTGGATTAGGCCTGGGGCTTGGACTCAG
  47 K   L   E   K   Q   G   S   C   R   K   K   C   F   D   A   S   F   R   G   L
 181 GAAACTGGAAAAGCAAGGCAGCTGCAGGAAGAAGTGCTTTGATGCATCATTTAGAGGACT
  67 E   N   C   R   C   D   V   A   C   K   D   R   G   D   C   C   W   D   F   E
 241 GGAGAACTGCCGGTGTGATGTGGCATGTAAAGACCGAGGTGATTGCTGCTGGGATTTTGA
  87 D   T   C   V   E   S   T   R   I   W   M   C   N   K   F   R   C   G   E   T
 301 AGACACCTGTGTGGAATCAACTCGAATATGGATGTGCAATAAATTTCGTTGTGGAGAGAC
 107 R   L   E   A   S   L   C   S   C   S   D   D   C   L   Q   K   K   D   C   C
 361 CAGATTAGAGGCCAGCCTTTGCTCTTGTTCAGATGACTGTTTGCAGAAGAAAGATTGCTG
 127 A   D   Y   K   S   V   C   Q   G   E   T   S   W   L   E   E   N   C   D   T
 421 TGCTGACTATAAGAGTGTTTGCCAAGGAGAAACCTCATGGCTGGAAGAAAACTGTGACAC
 147 A   Q   Q   S   Q   C   P   E   G   F   D   L   P   P   V   I   L   F   S   M
 481 AGCCCAGCAGTCTCAGTGCCCAGAAGGGTTTGACCTGCCACCAGTTATCTTGTTTTCTAT
 167 D   G   F   R   A   E   Y   L   Y   T   W   D   T   L   M   P   N   I   N   K
 541 GGATGGATTTAGAGCTGAATATTTATACACATGGGATACTTTAATGCCAAATATCAATAA
 187 L   K   T   C   G   I   H   S   K   Y   M   R   A   M   Y   P   T   K   T   F
 601 ACTGAAAACATGTGGAATTCATTCAAAATACATGAGAGCTATGTATCCTACCAAAACCTT
 207 P   N   H   Y   T   I   V   T   G   L   Y   P   E   S   H   G   I   I   D   N
 661 CCCAAATCATTACACCATTGTCACGGGCTTGTATCCAGAGTCACATGGCATCATTGACAA
 227 N   M   Y   D   V   N   L   N   K   N   F   S   L   S   S   K   E   Q   N   N
 721 TAATATGTATGATGTAAATCTCAACAAGAATTTTTCACTTTCTTCAAAGGAACAAAATAA
 247 P   A   W   W   H   G   Q   P   M   W   L   T   A   M   Y   Q   G   L   K   A
 781 TCCAGCCTGGTGGCATGGGCAACCAATGTGGCTGACAGCAATGTATCAAGGTTTAAAAGC
 267 A   T   Y   F   W   P   G   S   E   V   A   I   N   G   S   F   P   S   I   Y
 841 CGCTACCTACTTTTGGCCCGGATCAGAAGTGGCTATAAATGGCTCCTTTCCTTCCATATA
 287 M   P   Y   N   G   S   V   P   F   E   E   R   I   S   T   L   L   K   W   L
 901 CATGCCTTACAACGGAAGTGTCCCATTTGAAGAGAGGATTTCTACACTGTTAAAATGGCT
 307 D   L   P   K   A   E   R   P   R   F   Y   T   M   Y   F   E   E   P   D   S
 961 GGACCTGCCCAAAGCTGAAAGACCCAGGTTTTATACCATGTATTTTGAAGAACCTGATTC
 327 S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
```

Figure 2D-2

```
 347  H  A  F  G  M  L  M  E  G  L  K  Q  R  N  L  H  N  C  V  N
1081  TCATGCTTTTGGGATGTTGATGGAAGGCCTGAAGCAGCGGAATTTGCACAACTGTGTCAA
 367  I  I  L  L  A  D  H  G  M  D  Q  T  Y  C  N  K  M  E  Y  M
1141  TATCATCCTTCTGGCTGACCATGGAATGGACCAGACTTATTGTAACAAGATGGAATACAT
 387  T  D  Y  F  P  R  I  N  F  F  Y  M  Y  E  G  P  A  P  R  I
1201  GACTGATTATTTTCCCAGAATAAACTTCTTCTACATGTACGAAGGGCCTGCCCCCCGCAT
 407  R  A  H  N  I  P  H  D  F  F  S  F  N  S  E  E  I  V  R  N
1261  CCGAGCTCATAATATACCTCATGACTTTTTTAGTTTTAATTCTGAGGAAATTGTTAGAAA
 427  L  S  C  R  K  P  D  Q  H  F  K  P  Y  L  T  P  D  L  P  K
1321  CCTCAGTTGCCGAAAACCTGATCAGCATTTCAAGCCCTATTTGACTCCTGATTTGCCAAA
 447  R  L  H  Y  A  K  N  V  R  I  D  K  V  H  L  F  V  D  Q  Q
1381  GCGACTGCACTATGCCAAGAACGTCAGAATCGACAAAGTTCATCTCTTTGTGGATCAACA
 467  W  L  A  V  R  S  K  S  N  T  N  C  G  G  N  H  G  Y  N
1441  GTGGCTGGCTGTTAGGAGTAAATCAAATACAAATTGTGGAGGAGGCAACCATGGTTATAA
 487  N  E  F  R  S  M  E  A  I  F  L  A  H  G  P  S  F  K  E  K
1501  CAATGAGTTTAGGAGCATGGAGGCTATCTTTCTGGCACATGGACCCAGTTTTAAAGAGAA
 507  T  E  V  E  P  F  E  N  I  E  V  Y  N  L  M  C  D  L  L  R
1561  GACTGAAGTTGAACCATTTGAAAATATTGAAGTCTATAACCTAATGTGTGATCTTCTACG
 527  I  Q  P  A  P  N  N  G  T  H  G  S  L  N  H  L  L  K  V  P
1621  CATTCAACCAGCACCAAACAATGGAACCCATGGTAGTTTAAACCATCTTCTGAAGGTGCC
 547  F  Y  E  P  S  H  A  E  E  V  S  K  F  S  V  C  G  F  A  N
1681  TTTTTATGAGCCATCCCATGCAGAGGAGGTGTCAAAGTTTTCTGTTTGTGGCTTTGCTAA
 567  P  L  P  T  E  S  L  D  C  F  C  P  H  L  Q  N  S  T  Q  L
1741  TCCATTGCCCACAGAGTCTCTTGACTGTTTCTGCCCTCACCTACAAAATAGTACTCAGCT
 587  E  Q  V  N  Q  M  L  N  L  T  Q  E  E  I  T  A  T  V  K  V
1801  GGAACAAGTGAATCAGATGCTAAATCTCACCCAAGAAGAAATAACAGCAACAGTGAAAGT
 607  N  L  P  F  G  R  P  R  V  L  Q  K  N  V  D  H  C  L  L  Y
1861  AAATTTGCCATTTGGGAGGCCTAGGGTACTGCAGAAGAACGTGGACCACTGTCTCCTTTA
 627  H  R  E  Y  V  S  G  F  G  K  A  M  R  M  P  M  W  S  S  Y
1921  CCACAGGGAATATGTCAGTGGATTTGGAAAAGCTATGAGGATGCCCATGTGGAGTTCATA
 647  T  V  P  Q  L  G  D  T  S  P  L  P  P  T  V  P  D  C  L  R
1981  CACAGTCCCCCAGTTGGGAGACACATCGCCTCTGCCTCCCACTGTCCCAGACTGTCTGCG
 667  A  D  V  R  V  P  P  S  E  S  Q  K  C  S  F  Y  L  A  D  K
2041  GGCTGATGTCAGGGTTCCTCCTTCTGAGAGCCAAAAATGTTCCTTCTATTTAGCAGACAA
 687  N  I  T  H  G  F  L  Y  P  P  A  S  N  R  T  S  D  S  Q  Y
2101  GAATATCACCCACGGCTTCCTCTATCCTCCTGCCAGCAATAGAACATCAGATAGCCAATA
 707  D  A  L  I  T  S  N  L  V  P  M  Y  E  E  F  R  K  M  W  D
2161  TGATGCTTTAATTACTAGCAATTTGGTACCTATGTATGAAGAATTCAGAAAAATGTGGGA
 727  Y  F  H  S  V  L  L  I  K  H  A  T  E  R  N  G  V  N  V  V
```

Figure 2D-3

```
2221 CTACTTCCACAGTGTTCTTCTTATAAAACATGCCACAGAAAGAAATGGAGTAAATGTGGT
 747  S  G  P  I  F  D  Y  N  Y  D  G  H  F  D  A  P  D  E  I  T
2281 TAGTGGACCAATATTTGATTATAATTATGATGGCCATTTTGATGCTCCAGATGAAATTAC
 767  K  H  L  A  N  T  D  V  P  I  P  T  H  Y  F  V  V  L  T  S
2341 CAAACATTTAGCCAACACTGATGTTCCCATCCCAACACACTACTTTGTGGTGCTGACCAG
 787  C  K  N  K  S  H  T  P  E  N  C  P  G  W  L  D  V  L  P  F
2401 TTGTAAAAACAAGAGCCACACACCGGAAAACTGCCCTGGGTGGCTGGATGTCCTACCCTT
 807  I  I  P  H  R  P  T  N  V  E  S  C  P  E  G  K  P  E  A  L
2461 TATCATCCCTCACCGACCTACCAACGTGGAGAGCTGTCCTGAAGGTAAACCAGAAGCTCT
 827  W  V  E  E  R  F  T  A  H  I  A  R  V  R  D  V  E  L  L  T
2521 TTGGGTTGAAGAAAGATTTACAGCTCACATTGCCCGGGTCCGTGATGTAGAACTTCTCAC
 847  G  L  D  F  Y  Q  D  K  V  Q  P  V  S  E  I  L  Q  L  K  T
2581 TGGGCTTGACTTCTATCAGGATAAAGTGCAGCCTGTCTCTGAAATTTTGCAACTAAAGAC
 867  Y  L  P  T  F  E  T  P  I  *
2641 ATATTTACCAACATTTGAAACCCCTATTTAActtaataatgtctacttaatatataattt
2701 actgtataaagtaattttggcaaaatataagtgattttttctggagaattgtaaaataaa
2761 gttttctattttttccttaaaaaaaaaaccggaattccgggcttgggaggctgaggcagga
2821 gactcgcttgaacccgggaggcagaggttgcagtgagccaagattgcgccattgcactcc
2881 agagcctgggtgacagagcaagactacatctcaaaaataaataaataaaataaaagtaa
2941 caataaaaataaaaagaacagcagagagaatgagcaaggagaaatgtcacaaactattgc
3001 aaaatactgttacactgggttggctctccaagaagatactggaatctcttcagccatttg
3061 cttttcagaagtagaaaccagcaaaccacctctaagcggagaacatacgattctttatta
3121 agtagctctggggaaggaaagaataaaagttgatagctccctgattgggaaaaaatgcac
3181 aattaataaagaatgaagatgaaagaaagcatgcttatgttgtaacacaaaaaaaattca
3241 caaacgttggtggaaggaaaacagtatagaaaacattactttaactaaaagctggaaaaa
3301 ttttcagttgggatgcgactgacaaaaagaacgggatttccaggcataaagttggcgtga
3361 gctacagagggcaccatgtggctcagtggaagacccttcaagattcaaagttccatttga
3421 cagagcaaaggcacttcgcaaggagaagggtttaaattatgggtccaaaagccaagtggt
3481 aaagcgagcaatttgcagcataactgcttctcctagacagggctgagtgggcaaaatacg
3541 acagtacacacagtgactattagccactgccagaaacaggctgaacagccctgggagaca
3601 agggaaggcaggtggtgggagttgttcatggagagaaaggagagttttagaaccagcaca
3661 tccactggagatgctgggccaccagacccctcccagtcaataaagtctggtgcctcattt
3721 gatctcagcctcatcatgaccctggagagacctgataccatctgccagtccccgacagc
3781 ttaggcactccttgccatcaacctgaccccccgagtggttctccaggctccctgccccac
3841 ccattcaggccggaattc
```

Figure 2E-1: The cDNA (SEQ ID NO: 10) and amino acid sequence (SEQ ID NO: 11) of 161P2F10B variant 5. The 3858 nucleotide sequence of 161P2F10B variant 5 is shown. The open reading frame extends from nucleic acid 44-2671 including the stop codon.

```
1                                          M   E   S   T   L   T
1    ctactttattctgataaaacaggtctatgcagctaccaggacaATGGAATCTACGTTGAC
7    L   A   T   E   Q   P   V   K   K   N   T   L   K   K   Y   I   A   C   I
61   TTTAGCAACGGAACAACCTGTTAAGAAGAACACTCTTAAGAAATATAAAATAGCTTGCAT
27   V   L   L   A   L   L   V   I   M   S   L   G   L   G   L   G   L   R
121  TGTTCTTCTTGCTTTGCTGGTGATCATGTCACTTGGATTAGGCCTGGGGCTTGGACTCAG
47   K   L   E   K   Q   G   S   C   R   K   K   C   F   D   A   S   F   R   G   L
181  GAAACTGGAAAAGCAAGGCAGCTGCAGGAAGAAGTGCTTTGATGCATCATTTAGAGGACT
67   E   N   C   R   C   D   V   A   C   K   D   R   G   D   C   C   W   D   F   E
241  GGAGAACTGCCGGTGTGATGTGGCATGTAAAGACCGAGGTGATTGCTGCTGGGATTTTGA
87   D   T   C   V   E   S   T   R   I   W   M   C   N   K   F   R   C   G   E   T
301  AGACACCTGTGTGGAATCAACTCGAATATGGATGTGCAATAAATTTCGTTGTGGAGAGAC
107  R   L   E   A   S   L   C   S   C   S   D   D   C   L   Q   K   K   D   C   C
361  CAGATTAGAGGCCAGCCTTTGCTCTTGTTCAGATGACTGTTTGCAGAAGAAAGATTGCTG
127  A   D   Y   K   S   V   C   Q   G   E   T   S   W   L   E   E   N   C   D   T
421  TGCTGACTATAAGAGTGTTTGCCAAGGAGAAACCTCATGGCTGGAAGAAAACTGTGACAC
147  A   Q   Q   S   Q   C   P   E   G   F   D   L   P   P   V   I   L   F   S   M
481  AGCCCAGCAGTCTCAGTGCCCAGAAGGGTTTGACCTGCCACCAGTTATCTTGTTTTCTAT
167  D   G   F   R   A   E   Y   L   Y   T   W   D   T   L   M   P   N   I   N   K
541  GGATGGATTTAGAGCTGAATATTTATACACATGGGATACTTTAATGCCAAATATCAATAA
187  L   K   T   C   G   I   H   S   K   Y   M   R   A   M   Y   P   T   K   T   F
601  ACTGAAAACATGTGGAATTCATTCAAAATACATGAGAGCTATGTATCCTACCAAAACCTT
207  P   N   H   Y   T   I   V   T   G   L   Y   P   E   S   H   G   I   I   D   N
661  CCCAAATCATTACACCATTGTCACGGGCTTGTATCCAGAGTCACATGGCATCATTGACAA
227  N   M   Y   D   V   N   L   N   K   N   F   S   L   S   S   K   E   Q   N   N
721  TAATATGTATGATGTAAATCTCAACAAGAATTTTTCACTTTCTTCAAAGGAACAAAATAA
247  P   A   W   W   H   G   Q   P   M   W   L   T   A   M   Y   Q   G   L   K   A
781  TCCAGCCTGGTGGCATGGGCAACCAATGTGGCTGACAGCAATGTATCAAGGTTTAAAAGC
267  A   T   Y   F   W   P   G   S   E   V   A   I   N   G   S   F   P   S   I   Y
841  CGCTACCTACTTTTGGCCCGGATCAGAAGTGGCTATAAATGGCTCCTTTCCTTCCATATA
287  M   P   Y   N   G   S   V   P   F   E   E   R   I   S   T   L   L   K   W   L
901  CATGCCTTACAACGGAAGTGTCCCATTTGAAGAGAGGATTTCTACACTGTTAAAATGGCT
307  D   L   P   K   A   E   R   P   R   F   Y   T   M   Y   F   E   E   P   D   S
961  GGACCTGCCCAAAGCTGAAAGACCCAGGTTTTATACCATGTATTTTGAAGAACCTGATTC
327  S   G   H   A   G   G   P   V   S   A   R   V   I   K   A   L   Q   V   V   D
1021 CTCTGGACATGCAGGTGGACCAGTCAGTGCCAGAGTAATTAAAGCCTTACAGGTAGTAGA
347  H   A   F   G   M   L   M   E   G   L   K   Q   R   N   L   H   N   C   V   N
```

Figure 2E-2

```
1081 TCATGCTTTTGGGATGTTGATGGAAGGCCTGAAGCAGCGGAATTTGCACAACTGTGTCAA
 367   I  I  L  L  A  D  H  G  M  D  Q  T  Y  C  N  K  M  E  Y  M
1141 TATCATCCTTCTGGCTGACCATGGAATGGACCAGACTTATTGTAACAAGATGGAATACAT
 387   T  D  Y  F  P  R  I  N  F  F  Y  M  Y  E  G  P  A  P  R  I
1201 GACTGATTATTTTCCAGAATAAACTTCTTCTACATGTACGAAGGGCCTGCCCCCCGCAT
 407   R  A  H  N  I  P  H  D  F  F  S  F  N  S  E  E  I  V  R  N
1261 CCGAGCTCATAATATACCTCATGACTTTTTTAGTTTTAATTCTGAGGAAATTGTTAGAAA
 427   L  S  C  R  K  P  D  Q  H  F  K  P  Y  L  T  P  D  L  P  K
1321 CCTCAGTTGCCGAAAACCTGATCAGCATTTCAAGCCCTATTTGACTCCTGATTTGCCAAA
 447   R  L  H  Y  A  K  N  V  R  I  D  K  V  H  L  F  V  D  Q  Q
1381 GCGACTGCACTATGCCAAGAACGTCAGAATCGACAAAGTTCATCTCTTTGTGGATCAACA
 467   W  L  A  V  R  S  K  S  N  T  N  C  G  G  G  N  H  G  Y  N
1441 GTGGCTGGCTGTTAGGAGTAAATCAAATACAAATTGTGGAGGAGGCAACCATGGTTATAA
 487   N  E  F  R  S  M  E  A  I  F  L  A  H  G  P  S  F  K  E  K
1501 CAATGAGTTTAGGAGCATGGAGGCTATCTTTCTGGCACATGGACCCAGTTTTAAAGAGAA
 507   T  E  V  E  P  F  E  N  I  E  V  Y  N  L  M  C  D  L  L  R
1561 GACTGAAGTTGAACCATTTGAAAATATTGAAGTCTATAACCTAATGTGTGATCTTCTACG
 527   I  Q  P  A  P  N  N  G  T  H  G  S  L  N  H  L  L  K  V  P
1621 CATTCAACCAGCACCAAACAATGGAACCCATGGTAGTTTAAACCATCTTCTGAAGGTGCC
 547   F  Y  E  P  S  H  A  E  E  V  S  K  F  S  V  C  G  F  A  N
1681 TTTTTATGAGCCATCCCATGCAGAGGAGGTGTCAAAGTTTTCTGTTTGTGGCTTTGCTAA
 567   P  L  P  T  E  S  L  D  C  F  C  P  H  L  Q  N  S  T  Q  L
1741 TCCATTGCCCACAGAGTCTCTTGACTGTTTCTGCCCTCACCTACAAAATAGTACTCAGCT
 587   E  Q  V  N  Q  M  L  N  L  T  Q  E  E  I  T  A  T  V  K  V
1801 GGAACAAGTGAATCAGATGCTAAATCTCACCCAAGAAGAAATAACAGCAACAGTGAAAGT
 607   N  L  P  F  G  R  P  R  V  L  Q  K  N  V  D  H  C  L  L  Y
1861 AAATTTGCCATTTGGGAGGCCTAGGGTACTGCAGAAGAACGTGGACCACTGTCTCCTTTA
 627   H  R  E  Y  V  S  G  F  G  K  A  M  R  M  P  M  W  S  S  Y
1921 CCACAGGGAATATGTCAGTGGATTTGGAAAAGCTATGAGGATGCCCATGTGGAGTTCATA
 647   T  V  P  Q  L  G  D  T  S  P  L  P  P  T  V  P  D  C  L  R
1981 CACAGTCCCCCAGTTGGGAGACACATCGCCTCTGCCTCCCACTGTCCCAGACTGTCTGCG
 667   A  D  V  R  V  P  P  S  E  S  Q  K  C  S  F  Y  L  A  D  K
2041 GGCTGATGTCAGGGTTCCTCCTTCTGAGAGCCAAAAATGTTCCTTCTATTTAGCAGACAA
 687   N  I  T  H  G  F  L  Y  P  P  A  S  N  R  T  S  D  S  Q  Y
2101 GAATATCACCCACGGCTTCCTCTATCCTCCTGCCAGCAATAGAACATCAGATAGCCAATA
 707   D  A  L  I  T  S  N  L  V  P  M  Y  E  E  F  R  K  M  W  D
2161 TGATGCTTTAATTACTAGCAATTTGGTACCTATGTATGAAGAATTCAGAAAAATGTGGGA
 727   Y  F  H  S  V  L  L  I  K  H  A  T  E  R  N  G  V  N  V  V
2221 CTACTTCCACAGTGTTCTTCTTATAAAACATGCCACAGAAAGAAATGGAGTAAATGTGGT
```

Figure 2E-3

```
 747   S   G   P   I   F   D   Y   N   Y   D   G   H   F   D   A   P   D   E   I   T
2281  TAGTGGACCAATATTTGATTATAATTATGATGGCCATTTTGATGCTCCAGATGAAATTAC
 767   K   H   L   A   N   T   D   V   P   I   P   T   H   Y   F   V   V   L   T   S
2341  CAAACATTTAGCCAACACTGATGTTCCCATCCCAACACACTACTTTGTGGTGCTGACCAG
 787   C   N   K   S   H   T   P   E   N   C   P   G   W   L   D   V   L   P   F
2401  TTGTAAAAACAAGAGCCACACACCGGAAAACTGCCCTGGGTGGCTGGATGTCCTACCCTT
 807   I   I   P   H   R   P   T   N   V   E   S   C   P   E   G   K   P   E   A   L
2461  TATCATCCCTCACCGACCTACCAACGTGGAGAGCTGTCCTGAAGGTAAACCAGAAGCTCT
 827   W   V   E   E   R   F   T   A   H   I   A   R   V   R   D   V   E   L   L   T
2521  TTGGGTTGAAGAAAGATTTACAGCTCACATTGCCCGGGTCCGTGATGTAGAACTTCTCAC
 847   G   L   D   F   Y   Q   D   K   V   Q   P   V   S   E   I   L   Q   L   K   T
2581  TGGGCTTGACTTCTATCAGGATAAAGTGCAGCCTGTCTCTGAAATTTTGCAACTAAAGAC
 867   Y   L   P   T   F   E   T   T   I   *
2641  ATATTTACCAACATTTGAAACCACTATTTAActtaataatgtctacttaatatataattt
2701  actgtataaagtaattttggcaaaatataagtgatttttctggagaattgtaaaataaa
2761  gttttctattttccttaaaaaaaaaccggaattccgggcttgggaggctgaggcagga
2821  gactcgcttgaacccggaggcagaggttgcagtgagccaagattgcgccattgcactcc
2881  agagcctgggtgacagagcaagactacatctcaaaaataaataaataaaataaaagtaa
2941  caataaaaataaaagaacagcagagagaatgagcaaggagaaatgtcacaaactattgc
3001  aaaatactgttacactgggttggctctccaagaagatactggaatctcttcagccatttg
3061  cttttcagaagtagaaaccagcaaaccacctctaagcggagaacatacgattctttatta
3121  agtagctctggggaaggaaagaataaaagttgatagctccctgattgggaaaaaatgcac
3181  aattaataaagaatgaagatgaaagaaagcatgcttatgttgtaacacaaaacaaattca
3241  caaacgttggtggaaggaaaacagtatagaaacattactttaactaaaagctggaaaaa
3301  ttttcagttgggatgcgactgacaaaaagaacgggatttccaggcataaagttggcgtga
3361  gctacagagggcaccatgtggctcagtggaagacccttcaagattcaaagttccatttga
3421  cagagcaaaggcacttcgcaaggagaagggtttaaattatgggtccaaaagccaagtggt
3481  aaagcgagcaatttgcagcataactgcttctcctagacagggctgagtgggcaaaatacg
3541  acagtacacacagtgactattagccactgccagaaacaggctgaacagccctgggagaca
3601  agggaaggcaggtggtgggagttgttcatggagagaaaggagagttttagaaccagcaca
3661  tccactggagatgctggccaccagacccctcccagtcaataaagtctggtgcctcattt
3721  gatctcagcctcatcatgaccctggagagaccctgataccatctgccagtccccgacagc
3781  ttaggcactccttgccatcaacctgaccccccgagtggttctccaggctccctgccccac
3841  ccattcaggccggaattc
```

Figure 2F-1: The cDNA (SEQ ID NO: 12) and amino acid sequence (SEQ ID NO: 13) of 161P2F10B variant 6. The 3165 nucleotide sequence of 161P2F10B variant 6 is shown. The open reading frame extends from nucleic acid 84-2711 including the stop codon.

```
   1 atacagtttctctttgccagactagactaaagaaggagcactactttattctgataaaac
   1                         M   E   S   T   L   T   A   T   E   Q   P   V
  61 aggtctatgcagctaccaggacaATGGAATCTACGTTGACTTTAGCAACGGAACAACCTG
  14     K   K   N   T   L   K   K   Y   K   I   A   C   I   V   L   L   A   L   L   V
 121 TTAAGAAGAACACTCTTAAGAAATATAAAATAGCTTGCATTGTTCTTCTTGCTTTGCTGG
  34     I   M   S   L   G   L   G   L   G   L   R   K   L   E   K   Q   G   S
 181 TGATCATGTCACTTGGATTAGGCCTGGGGCTTGGACTCAGGAAACTGGAAAAGCAAGGCA
  54     C   R   K   K   C   F   D   A   S   F   R   G   L   E   N   C   R   C   D   V
 241 GCTGCAGGAAGAAGTGCTTTGATGCATCATTTAGAGGACTGGAGAACTGCCGGTGTGATG
  74     A   C   K   D   R   G   D   C   C   W   D   F   E   D   T   C   V   E   S   T
 301 TGGCATGTAAAGACCGAGGTGATTGCTGCTGGGATTTTGAAGACACCTGTGTGGAATCAA
  94     R   I   W   M   C   N   K   F   R   C   G   E   T   R   L   E   A   S   L   C
 361 CTCGAATATGGATGTGCAATAAATTTCGTTGTGGAGAGACCAGATTAGAGGCCAGCCTTT
 114     S   C   S   D   D   C   L   Q   R   K   D   C   C   A   D   Y   K   S   V   C
 421 GCTCTTGTTCAGATGACTGTTTGCAGAGGAAAGATTGCTGTGCTGACTATAAGAGTGTTT
 134     Q   G   E   T   S   W   L   E   E   N   C   D   T   A   Q   Q   S   Q   C   P
 481 GCCAAGGAGAAACCTCATGGCTGGAAGAAAACTGTGACACAGCCCAGCAGTCTCAGTGCC
 154     E   G   F   D   L   P   P   V   I   L   F   S   M   D   G   F   R   A   E   Y
 541 CAGAAGGGTTTGACCTGCCACCAGTTATCTTGTTTTCTATGGATGGATTTAGAGCTGAAT
 174     L   Y   T   W   D   T   L   M   P   N   I   N   K   L   K   T   C   G   I   H
 601 ATTTATACACATGGGATACTTTAATGCCAAATATCAATAAACTGAAAACATGTGGAATTC
 194     S   K   Y   M   R   A   M   Y   P   T   K   T   F   P   N   H   Y   T   I   V
 661 ATTCAAAATACATGAGAGCTATGTATCCTACCAAAACCTTCCCAAATCATTACACCATTG
 214     T   G   L   Y   P   E   S   H   G   I   I   D   N   N   M   Y   D   V   N   L
 721 TCACGGGCTTGTATCCGGAGTCACATGGCATCATTGACAATAATATGTATGATGTAAATC
 234     N   K   N   F   S   L   S   S   K   E   Q   N   N   P   A   W   W   H   G   Q
 781 TCAACAAGAATTTTTCACTTTCTTCAAAGGAACAAAATAATCCAGCCTGGTGGCATGGGC
 254     P   M   W   L   T   A   M   Y   Q   G   L   K   A   A   T   Y   F   W   P   G
 841 AACCAATGTGGCTGACAGCAATGTATCAAGGTTTAAAAGCCGCTACCTACTTTTGGCCCG
 274     S   E   V   A   I   N   G   S   F   P   S   I   Y   M   P   Y   N   G   S   V
 901 GATCAGAAGTGGCTATAAATGGCTCCTTTCCTTCCATATACATGCCTTACAACGGAAGTG
 294     P   F   E   E   R   I   S   T   L   L   K   W   L   D   L   P   K   A   E   R
 961 TCCCATTTGAAGAGAGGATTTCTACACTGTTAAAATGGCTGGACCTGCCCAAAGCTGAGA
 314     P   R   F   Y   T   M   F   F   E   E   P   D   S   S   G   H   A   G   G   P
1021 GACCCAGGTTTTATACCATGTTTTTTGAAGAACCTGATTCCTCTGGACATGCAGGTGGAC
 334     V   S   A   R   V   I   K   A   L   Q   V   V   D   H   A   F   G   M   L   M
1081 CAGTCAGTGCCAGAGTAATTAAAGCCTTACAGGTAGTAGATCATGCTTTTGGGATGTTGA
```

Figure 2F-2

```
354    E   G   L   K   Q   R   N   L   H   N   C   V   N   I   I   L   L   A   D   H
1141   TGGAAGGCCTGAAGCAGCGGAATTTGCACAACTGTGTCAATATCATCCTTCTGGCTGACC
374    G   M   D   Q   T   Y   C   N   K   M   E   Y   M   T   D   Y   F   P   R   I
1201   ATGGAATGGACCAGACTTATTGTAACAAGATGGAATACATGACTGATTATTTTCCCAGAA
394    N   F   F   Y   M   Y   E   G   P   A   P   R   V   A   H   N   I   P   H
1261   TAAACTTCTTCTACATGTACGAAGGGCCTGCCCCCCGCGTCCGAGCTCATAATATACCTC
414    D   F   F   S   F   N   S   E   E   I   V   R   N   L   S   C   R   K   P   D
1321   ATGACTTTTTTAGTTTTAATTCTGAGGAAATTGTTAGAAACCTCAGTTGCCGAAAACCTG
434    Q   H   F   K   P   Y   L   T   P   D   L   P   K   R   L   H   Y   A   K   N
1381   ATCAGCATTTCAAGCCCTATTTGACTCCTGATTTGCCAAAGCGACTGCACTATGCCAAGA
454    V   R   I   D   K   V   H   L   F   V   D   Q   Q   W   L   A   V   R   S   K
1441   ACGTCAGAATCGACAAAGTTCATCTCTTTGTGGATCAACAGTGGCTGGCTGTTAGGAGTA
474    S   N   T   N   C   G   G   G   N   H   G   Y   N   N   E   F   R   S   M   E
1501   AATCAAATACAAATTGTGGAGGAGGCAACCATGGTTATAACAATGAGTTTAGGAGCATGG
494    A   I   F   L   A   H   G   P   S   F   K   E   K   T   E   V   E   P   F   E
1561   AGGCTATCTTTCTGGCACATGGACCCAGTTTTAAAGAGAAGACTGAAGTTGAACCATTTG
514    N   I   E   V   Y   N   L   M   C   D   L   L   R   I   Q   P   A   P   N   N
1621   AAAATATTGAAGTCTATAACCTAATGTGTGATCTTCTACGCATTCAACCAGCACCAAACA
534    G   T   H   G   S   L   N   H   L   L   K   V   P   F   Y   E   P   S   H   A
1681   ATGGAACCCATGGTAGTTTAAACCATCTTCTGAAGGTGCCTTTTTATGAGCCATCCCATG
554    E   E   V   S   K   F   S   V   C   G   F   A   N   P   L   P   T   E   S   L
1741   CAGAGGAGGTGTCAAAGTTTTCTGTTTGTGGCTTTGCTAATCCATTGCCCACAGAGTCTC
574    D   C   F   C   P   H   L   Q   N   S   T   Q   L   E   Q   V   N   Q   M   L
1801   TTGACTGTTTCTGCCCTCACCTACAAAATAGTACTCAGCTGGAACAAGTGAATCAGATGC
594    N   L   T   Q   E   E   I   T   A   T   V   K   V   N   L   P   F   G   R   P
1861   TAAATCTCACCCAAGAAGAAATAACAGCAACAGTGAAAGTAAATTTGCCATTTGGGAGGC
614    R   V   L   Q   K   N   V   D   H   C   L   L   Y   H   R   E   Y   V   S   G
1921   CTAGGGTACTGCAGAAGAACGTGGACCACTGTCTCCTTTACCACAGGGAATATGTCAGTG
634    F   G   K   A   M   R   M   P   M   W   S   S   Y   T   V   P   Q   L   G   D
1981   GATTTGGAAAAGCTATGAGGATGCCCATGTGGAGTTCATACACAGTCCCCCAGTTGGGAG
654    T   S   P   L   P   P   T   V   P   D   C   L   R   A   D   V   R   V   P   P
2041   ACACATCGCCTCTGCCTCCCACTGTCCCAGACTGTCTGCGGGCTGATGTCAGGGTTCCTC
674    S   E   S   Q   K   C   S   F   Y   L   A   D   K   N   I   T   H   G   F   L
2101   CTTCTGAGAGCCAAAAATGTTCCTTCTATTTAGCAGACAAGAATATCACCCACGGCTTCC
694    Y   P   P   A   S   N   R   T   S   D   S   Q   Y   D   A   L   I   T   S   N
2161   TCTATCCTCCTGCCAGCAATAGAACATCAGATAGCCAATATGATGCTTTAATTACTAGCA
714    L   V   P   M   Y   E   E   F   R   K   M   W   D   Y   F   H   S   V   L   L
2221   ATTTGGTACCTATGTATGAAGAATTCAGAAAAATGTGGGACTACTTCCACAGTGTTCTTC
734    I   K   H   A   T   E   R   N   G   V   N   V   V   S   G   P   I   F   D   Y
```

Figure 2F-3

```
2281 TTATAAAACATGCCACAGAAAGAAATGGAGTAAATGTGGTTAGTGGACCAATATTTGATT
 754    N  Y  D  G  H  F  D  A  P  D  E  I  T  K  H  L  A  N  T  D
2341 ATAATTATGATGGCCATTTTGATGCTCCAGATGAAATTACCAAACATTTAGCCAACACTG
 774    V  P  I  P  T  H  Y  F  V  V  L  T  S  C  K  N  K  S  H  T
2401 ATGTTCCCATCCCAACACACTACTTTGTGGTGCTGACCAGTTGTAAAAACAAGAGCCACA
 794    P  E  N  C  P  G  W  L  D  V  L  P  F  I  I  P  H  R  P  T
2461 CACCGGAAAACTGCCCTGGGTGGCTGGATGTCCTACCCTTTATCATCCCTCACCGACCTA
 814    N  V  E  S  C  P  E  G  K  P  E  A  L  W  V  E  R  F  T
2521 CCAACGTGGAGAGCTGTCCTGAAGGTAAACCAGAAGCTCTTTGGGTTGAAGAAAGATTTA
 834    A  H  I  A  R  V  R  D  V  E  L  L  T  G  L  D  F  Y  Q  D
2581 CAGCTCACATTGCCCGGGTCCGTGATGTAGAACTTCTCACTGGGCTTGACTTCTATCAGG
 854    K  V  Q  P  V  S  E  I  L  Q  L  K  T  Y  L  P  T  F  E  T
2641 ATAAAGTGCAGCCTGTCTCTGAAATTTTGCAACTAAAGACATATTTACCAACATTTGAAA
 874    T  I  *
2701 CCACTATTTAActtaataatgtctacttaatatataatttactgtataaagtaattttgg
2761 caaaatataagtgatttttttctggagaattgtaaaataaagttttctattttttccttaa
2821 gtcccctaaaagccataatttttattattccttttctctttttcaattctatgaatat
2881 gtattattttaaagttatattttttcacacagagatgatgctatattacaccttcccttt
2941 ttgttggtttcttaaactctaatctcatgacagattataccttccttattacttgtttta
3001 tcttactcagaatctttgaatatattttctgcccagaattatctaaacaaaagggagaa
3061 caaagaagtatgtctcacttgggaactgaatcaactctaaatcagttttgtcacaaaac
3121 ttttttgtatttgactggcaatgctgattaaaattaaaaatgcaca
```

Figure 2G-1: The cDNA (SEQ ID NO: 14) and amino acid sequence (SEQ ID NO: 15) of 161P2F10B variant 7. The 3988 nucleotide sequence of 161P2F10B variant 7 is shown. The open reading frame extends from nucleic acid 276-2801 including the stop codon.

```
    1 ctactttattctgataaaacaggtctatgcagctaccaggacaatggaatctacgttgac
   61 tttagcaacggaacaacctgttaagaagaacactcttaagaaatataaaatagcttgcat
  121 tacagggtctctctccttttgggatctcacctcaccacaacctctgtttcccaggctcaag
  181 tgatcctcctgcctcagcctcctgagtagcttggaccacaggcacatgccacaaggctca
    1                                            M  S  L  G  L  G  L
  241 gctaagttttgttcttcttgctttgctggtgatcATGTCACTTGGATTAGGCCTGGGGC
   10  G  L  R  K  L  E  K  Q  G  S  C  R  K  K  C  F  D  A  S  F
  301 TTGGACTCAGGAAACTGGAAAAGCAAGGCAGCTGCAGGAAGAAGTGCTTTGATGCATCAT
   30  R  G  L  E  N  C  R  C  D  V  A  C  K  D  R  G  D  C  C  W
  361 TTAGAGGACTGGAGAACTGCCGGTGTGATGTGGCATGTAAAGACCGAGGTGATTGCTGCT
   50  D  F  E  D  T  C  V  E  S  T  R  I  W  M  C  N  K  F  R  C
  421 GGGATTTTGAAGACACCTGTGTGGAATCAACTCGAATATGGATGTGCAATAAATTTCGTT
   70  G  E  T  R  L  E  A  S  L  C  S  C  D  D  C  L  Q  K  K
  481 GTGGAGAGACCAGATTAGAGGCCAGCCTTTGCTCTTGTTCAGATGACTGTTTGCAGAAGA
   90  D  C  C  A  D  Y  K  S  V  C  Q  G  E  T  S  W  L  E  E  N
  541 AAGATTGCTGTGCTGACTATAAGAGTGTTTGCCAAGGAGAAACCTCATGGCTGGAAGAAA
  110  C  D  T  A  Q  Q  S  Q  C  P  E  G  F  D  L  P  P  V  I  L
  601 ACTGTGACACAGCCCAGCAGTCTCAGTGCCCAGAAGGGTTTGACCTGCCACCAGTTATCT
  130  F  S  M  D  G  F  R  A  E  Y  L  Y  T  W  D  T  L  M  P  N
  661 TGTTTTCTATGGATGGATTTAGAGCTGAATATTTATACACATGGGATACTTTAATGCCAA
  150  I  N  K  L  K  T  C  G  I  H  S  K  Y  M  R  A  M  Y  P  T
  721 ATATCAATAAACTGAAAACATGTGGAATTCATTCAAAATACATGAGAGCTATGTATCCTA
  170  K  T  F  P  N  H  Y  T  I  V  T  G  L  Y  P  E  S  H  G  I
  781 CCAAAACCTTCCCAAATCATTACACCATTGTCACGGGCTTGTATCCAGAGTCACATGGCA
  190  I  D  N  N  M  Y  D  V  N  L  N  K  N  F  S  L  S  S  K  E
  841 TCATTGACAATAATATGTATGATGTAAATCTCAACAAGAATTTTTCACTTTCTTCAAAGG
  210  Q  N  N  P  A  W  W  H  G  Q  P  M  W  L  T  A  M  Y  Q  G
  901 AACAAAATAATCCAGCCTGGTGGCATGGGCAACCAATGTGGCTGACAGCAATGTATCAAG
  230  L  K  A  A  T  Y  F  W  P  G  S  E  V  A  I  N  G  S  F  P
  961 GTTTAAAAGCCGCTACCTACTTTTGGCCCGGATCAGAAGTGGCTATAAATGGCTCCTTTC
  250  S  I  Y  M  P  Y  N  G  S  V  P  F  E  E  R  I  S  T  L  L
 1021 CTTCCATATACATGCCTTACAACGGAAGTGTCCCATTTGAAGAGAGGGATTTCTACACTGT
  270  K  W  L  D  L  P  K  A  E  R  P  R  F  Y  T  M  Y  F  E  E
 1081 TAAAATGGCTGGACCTGCCCAAAGCTGAAAGACCCAGGTTTTATACCATGTATTTTGAAG
  290  P  D  S  S  G  H  A  G  G  P  V  S  A  R  V  I  K  A  L  Q
 1141 AACCTGATTCCTCTGGACATGCAGGTGGACCAGTCAGTGCCAGAGTAATTAAAGCCTTAC
  310  V  V  D  H  A  F  G  M  L  M  E  G  L  K  Q  R  N  L  H  N
 1201 AGGTAGTAGATCATGCTTTTGGGATGTTGATGGAAGGCCTGAAGCAGCGGAATTTGCACA
  330  C  V  N  I  I  L  L  A  D  H  G  M  D  Q  T  Y  C  N  K  M
 1261 ACTGTGTCAATATCATCCTTCTGGCTGACCATGGAATGGACCAGACTTATTGTAACAAGA
  350  E  Y  M  T  D  Y  F  P  R  I  N  F  F  Y  M  Y  E  G  P  A
 1321 TGGAATACATGACTGATTATTTTCCCAGAATAAACTTCTTCTACATGTACGAAGGGCCTG
  370  P  R  I  R  A  H  N  I  P  H  D  F  F  S  F  N  S  E  E  I
 1381 CCCCCCGCATCCGAGCTCATAATATACCTCATGACTTTTTTAGTTTTAATTCTGAGGAAA
  390  V  R  N  L  S  C  R  K  P  D  Q  H  F  K  P  Y  L  T  P  D
 1441 TTGTTAGAAACCTCAGTTGCCGAAAACCTGATCAGCATTTCAAGCCCTATTTGACTCCTG
  410  L  P  K  R  L  H  Y  A  K  N  V  R  I  D  K  V  H  L  F  V
 1501 ATTTGCCAAAGCGACTGCACTATGCCAAGAACGTCAGAATCGACAAAGTTCATCTCTTTG
  430  D  Q  Q  W  L  A  V  R  S  K  S  N  T  N  C  G  G  G  N  H
 1561 TGGATCAACAGTGGCTGGCTGTTAGGAGTAAATCAAATACAAATTGTGGAGGAGGCAACC
  450  G  Y  N  N  E  F  R  S  M  E  A  I  F  L  A  H  G  P  S  F
 1621 ATGGTTATAACAATGAGTTTAGGAGCATGGAGGCTATCTTTCTGGCACATGGACCCAGTT
  470  K  E  K  T  E  V  E  P  F  E  N  I  E  V  Y  N  L  M  C  D
 1681 TTAAAGAGAAGACTGAAGTTGAACCATTTGAAAATATTGAAGTCTATAACCTAATGTGTG
  490  L  L  R  I  Q  P  A  P  N  N  G  T  H  G  S  L  N  H  L  L
```

Figure 2G-2

```
1741 ATCTTCTACGCATTCAACCAGCACCAAACAATGGAACCCATGGTAGTTTAAACCATCTTC
 510   K  V  P  F  Y  E  P  S  H  A  E  E  V  S  K  F  S  V  C  G
1801 TGAAGGTGCCTTTTTATGAGCCATCCCATGCAGAGGAGGTGTCAAAGTTTTCTGTTTGTG
 530   F  A  N  P  L  P  T  E  S  L  D  C  F  C  P  H  L  Q  N  S
1861 GCTTTGCTAATCCATTGCCCACAGAGTCTCTTGACTGTTTCTGCCCTCACCTACAAAATA
 550   T  Q  L  E  Q  V  N  Q  M  L  N  L  T  Q  E  E  I  T  A  T
1921 GTACTCAGCTGGAACAAGTGAATCAGATGCTAAATCTCACCCAAGAAGAAATAACAGCAA
 570   V  K  V  N  L  P  F  G  R  P  R  V  L  Q  K  N  V  D  H  C
1981 CAGTGAAAGTAAATTTGCCATTTGGGAGGCCTAGGGTACTGCAGAAGAACGTGGACCACT
 590   L  L  Y  H  R  E  Y  V  S  G  F  G  K  A  M  R  M  P  M  W
2041 GTCTCCTTTACCACAGGGAATATGTCAGTGGATTTGGAAAAGCTATGAGGATGCCCATGT
 610   S  S  Y  T  V  P  Q  L  G  D  T  S  P  L  P  P  T  V  P  D
2101 GGAGTTCATACACAGTCCCCCAGTTGGGAGACACATCGCCTCTGCCTCCCACTGTCCCAG
 630   C  L  R  A  D  V  R  V  P  P  S  E  S  Q  K  C  S  F  Y  L
2161 ACTGTCTGCGGGCTGATGTCAGGGTTCCTCCTTCTGAGAGCCAAAAATGTTCCTTCTATT
 650   A  D  K  N  I  T  H  G  F  L  Y  P  P  A  S  N  R  T  S  D
2221 TAGCAGACAAGAATATCACCCACGGCTTCCTCTATCCTCCTGCCAGCAATAGAACATCAG
 670   S  Q  Y  D  A  L  I  T  S  N  L  V  P  M  Y  E  E  F  R  K
2281 ATAGCCAATATGATGCTTTAATTACTAGCAATTTGGTACCTATGTATGAAGAATTCAGAA
 690   M  W  D  Y  F  H  S  V  L  L  I  K  H  A  T  E  R  N  G  V
2341 AAATGTGGGACTACTTCCACAGTGTTCTTCTTATAAAACATGCCACAGAAAGAAATGGAG
 710   N  V  V  S  G  P  I  F  D  Y  N  Y  D  G  H  F  D  A  P  D
2401 TAAATGTGGTTAGTGGACCAATATTTGATTATAATTATGATGGCCATTTTGATGCTCCAG
 730   E  I  T  K  H  L  A  N  T  D  V  P  I  P  T  H  Y  F  V  V
2461 ATGAAATTACCAAACATTTAGCCAACACTGATGTTCCCATCCCAACACACTACTTTGTGG
 750   L  T  S  C  K  N  K  S  H  T  P  E  N  C  P  G  W  L  D  V
2521 TGCTGACCAGTTGTAAAAACAAGAGCCACACACCGGAAAACTGCCCTGGGTGGCTGGATG
 770   L  P  F  I  I  P  H  R  P  T  N  V  E  S  C  P  E  G  K  P
2581 TCCTACCCTTTATCATCCCTCACCGACCTACCAACGTGGAGAGCTGTCCTGAAGGTAAAC
 790   E  A  L  W  V  E  E  R  F  T  A  H  I  A  R  V  R  D  V  E
2641 CAGAAGCTCTTTGGGTTGAAGAAAGATTTACAGCTCACATTGCCCGGGTCCGTGATGTAG
 810   L  L  T  G  L  D  F  Y  Q  D  K  V  Q  P  V  S  E  I  L  Q
2701 AACTTCTCACTGGGCTTGACTTCTATCAGGATAAAGTGCAGCCTGTCTCTGAAATTTTGC
 830   L  K  T  Y  L  P  T  F  E  T  T  I  *
2761 AACTAAAGACATATTTACCAACATTTGAAACCACTATTTAActtaataatgtctacttaa
2821 tatataatttactgtataaagtaattttggcaaaatataagtgattttttctggagaatt
2881 gtaaaataaagttttctattttttccttaaaaaaaaaaccggaattccgggcttgggaggc
2941 tgaggcaggagactcgcttgaacccgggaggcagaggttgcagtgagccaagattgcgcc
```

Figure 2G-3

```
3001 attgcactccagagcctgggtgacagagcaagactacatctcaaaaaataaataaataaa
3061 ataaaagtaacaataaaaataaaaagaacagcagagagaatgagcaaggagaaatgtcac
3121 aaactattgcaaaatactgttacactgggttggctctccaagaagatactggaatctctt
3181 cagccatttgcttttcagaagtagaaaccagcaaaccacctctaagcggagaacatacga
3241 ttctttattaagtagctctggggaaggaaagaataaaagttgatagctccctgattggga
3301 aaaaatgcacaattaataaagaatgaagatgaaagaaagcatgcttatgttgtaacacaa
3361 aaaaaattcacaaacgttggtggaaggaaaacagtatagaaaacattactttaactaaaa
3421 gctggaaaaattttcagttgggatgcgactgacaaaaagaacgggatttccaggcataaa
3481 gttggcgtgagctacagagggcaccatgtggctcagtggaagacccttcaagattcaaag
3541 ttccatttgacagagcaaaggcacttcgcaaggagaagggtttaaattatgggtccaaaa
3601 gccaagtggtaaagcgagcaatttgcagcataactgcttctcctagacagggctgagtgg
3661 gcaaaatacgacagtacacacagtgactattagccactgccagaaacaggctgaacagcc
3721 ctgggagacaagggaaggcaggtggtgggagttgttcatggagagaaaggagagttttag
3781 aaccagcacatccactggagatgctgggccaccagacccctcccagtcaataaagtctgg
3841 tgcctcatttgatctcagcctcatcatgaccctggagagaccctgataccatctgccagt
3901 ccccgacagcttaggcactccttgccatcaacctgaccccccgagtggttctccaggctc
3961 cctgccccacccattcaggccggaattc
```

Figure 3A. Amino acid sequence of 161P2F10B variant 1 (SEQ ID NO: 16). The 161P2F10B variants 1 protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QKKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETTI
```

Figure 3B. Amino acid sequence of 161P2F10B variant 2 (SEQ ID NO: 17). The 161P2F10B variant 2 protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QRKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETTI
```

Figure 3C. Amino acid sequence of 161P2F10B variant 3 (SEQ ID NO: 18). The 161P2F10B variant 3 protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QKKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPG GKPEALWVEE RFTAHIARVR
841 DVELLTGLDF YQDKVQPVSE ILQLKTYLPT FETTI
```

Figure 3D. Amino acid sequence of 161P2F10B variant 4 (SEQ ID NO: 19). The 161P2F10B variant 4 protein has 875 amino acids.

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QKKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
781 FVVLTSCKNK SHTPENCPGW LDVLPFIIPH RPTNVESCPE GKPEALWVEE RFTAHIARVR
841 DVELLTGLDF YQDKVQPVSE ILQLKTYLPT FETPI
```

Figure 3E. Amino acid sequence of 161P2F10B variant 7 (SEQ ID NO: 20). The 161P2F10B variant 7 protein has 841 amino acids.

```
  1 MSLGLGLGLG LRKLEKQGSC RKKCFDASFR GLENCRCDVA CKDRGDCCWD FEDTCVESTR
 61 IWMCNKFRCG ETRLEASLCS CSDDCLQRKD CCADYKSVCQ GETSWLEENC DTAQQSQCPE
121 GFDLPPVILF SMDGFRAEYL YTWDTLMPNI NKLKTCGIHS KYMRAMYPTK TFPNHYTIVT
181 GLYPESHGII DNNMYDVNLN KNFSLSSKEQ NNPAWWHGQP MWLTAMYQGL KAATYFWPGS
241 EVAINGSFPS IYMPYNGSVP FEERISTLLK WLDLPKAERP RFYTMFFEEP DSSGHAGGPV
301 SARVIKALQV VDHAFGMLME GLKQRNLHNC VNIILLADHG MDQTYCNKME YMTDYFPRIN
361 FFYMYEGPAP RVRAHNIPHD FFSFNSEEIV RNLSCRKPDQ HFKPYLTPDL PKRLHYAKNV
421 RIDKVHLFVD QQWLAVRSKS NTNCGGGNHG YNNEFRSMEA IFLAHGPSFK EKTEVEPFEN
481 IEVYNLMCDL LRIQPAPNNG THGSLNHLLK VPFYEPSHAE EVSKFSVCGF ANPLPTESLD
541 CFCPHLQNST QLEQVNQMLN LTQEEITATV KVNLPFGRPR VLQKNVDHCL LYHREYVSGF
601 GKAMRMPMWS SYTVPQLGDT SPLPPTVPDC LRADVRVPPS ESQKCSFYLA DKNITHGFLY
661 PPASNRTSDS QYDALITSNL VPMYEEFRKM WDYFHSVLLI KHATERNGVN VVSGPIFDYN
721 YDGHFDAPDE ITKHLANTDV PIPTHYFVVL TSCKNKSHTP ENCPGWLDVL PFIIPHRPTN
781 VESCPEGKPE ALWVEERFTA HIARVRDVEL LTGLDFYQDK VQPVSEILQL KTYLPTFETT
841 I
```

Figure 4: Comparison of 161P2F10B with known genes: identification of 2 variants for 161P2F10B.

Figure 4A: Alignment of 161P2F10 (SEQ ID NO: 21) with variant 1 (SEQ ID NO: 22) carrying a K to R mutation.

```
161P2: 1    MESTLTLATEQPVKKNTLKKYKIACIVLLALLVIMSLGLGLGLGLRKLEKQGSCRKKCFD 60
            MESTLTLATEQPVKKNTLKKYKIACIVLLALLVIMSLGLGLGLGLRKLEKQGSCRKKCFD
Sbjct: 1    MESTLTLATEQPVKKNTLKKYKIACIVLLALLVIMSLGLGLGLGLRKLEKQGSCRKKCFD 60

Query: 61   ASFRGLENCRCDVACKDRGDCCWDFEDTCVESTRIWMCNKFRCGETRLEASLCSCSDDCL 120
            ASFRGLENCRCDVACKDRGDCCWDFEDTCVESTRIWMCNKFRCGETRLEASLCSCSDDCL
Sbjct: 61   ASFRGLENCRCDVACKDRGDCCWDFEDTCVESTRIWMCNKFRCGETRLEASLCSCSDDCL 120

Query: 121  QKKDCCADYKSVCQGETSWLEENCDTAQQSQCPEGFDLPPVILFSMDGFRAEYLYTWDTL 180
            Q+KDCCADYKSVCQGETSWLEENCDTAQQSQCPEGFDLPPVILFSMDGFRAEYLYTWDTL
Sbjct: 121  QRKDCCADYKSVCQGETSWLEENCDTAQQSQCPEGFDLPPVILFSMDGFRAEYLYTWDTL 180

Query: 181  MPNINKLKTCGIHSKYMRAMYPTKTFPNHYTIVTGLYPESHGIIDNNMYDVNLNKNFSLS 240
            MPNINKLKTCGIHSKYMRAMYPTKTFPNHYTIVTGLYPESHGIIDNNMYDVNLNKNFSLS
Sbjct: 181  MPNINKLKTCGIHSKYMRAMYPTKTFPNHYTIVTGLYPESHGIIDNNMYDVNLNKNFSLS 240

Query: 241  SKEQNNPAWWHGQPMWLTAMYQGLKAATYFWPGSEVAINGSFPSIYMPYNGSVPFEERIS 300
            SKEQNNPAWWHGQPMWLTAMYQGLKAATYFWPGSEVAINGSFPSIYMPYNGSVPFEERIS
Sbjct: 241  SKEQNNPAWWHGQPMWLTAMYQGLKAATYFWPGSEVAINGSFPSIYMPYNGSVPFEERIS 300

Query: 301  TLLKWLDLPKAERPRFYTMYFEEPDSSGHAGGPVSARVIKALQVVDHAFGMLMEGLKQRN 360
            TLLKWLDLPKAERPRFYTMYFEEPDSSGHAGGPVSARVIKALQVVDHAFGMLMEGLKQRN
Sbjct: 301  TLLKWLDLPKAERPRFYTMYFEEPDSSGHAGGPVSARVIKALQVVDHAFGMLMEGLKQRN 360

Query: 361  LHNCVNIILLADHGMDQTYCNKMEYMTDYFPRINFFYMYEGPAPRIRAHNIPHDFFSFNS 420
            LHNCVNIILLADHGMDQTYCNKMEYMTDYFPRINFFYMYEGPAPRIRAHNIPHDFFSFNS
Sbjct: 361  LHNCVNIILLADHGMDQTYCNKMEYMTDYFPRINFFYMYEGPAPRIRAHNIPHDFFSFNS 420

Query: 421  EEIVRNLSCRKPDQHFKPYLTPDLPKRLHYAKNVRIDKVHLFVDQQWLAVRSKSNTNCGG 480
            EEIVRNLSCRKPDQHFKPYLTPDLPKRLHYAKNVRIDKVHLFVDQQWLAVRSKSNTNCGG
Sbjct: 421  EEIVRNLSCRKPDQHFKPYLTPDLPKRLHYAKNVRIDKVHLFVDQQWLAVRSKSNTNCGG 480

Query: 481  GNHGYNNEFRSMEAIFLAHGPSFKEKTEVEPFENIEVYNLMCDLLRIQPAPNNGTHGSLN 540
            GNHGYNNEFRSMEAIFLAHGPSFKEKTEVEPFENIEVYNLMCDLLRIQPAPNNGTHGSLN
Sbjct: 481  GNHGYNNEFRSMEAIFLAHGPSFKEKTEVEPFENIEVYNLMCDLLRIQPAPNNGTHGSLN 540

Query: 541  HLLKVPFYEPSHAEEVSKFSVCGFANPLPTESLDCFCPHLQNSTQLEQVNQMLNLTQEEI 600
            HLLKVPFYEPSHAEEVSKFSVCGFANPLPTESLDCFCPHLQNSTQLEQVNQMLNLTQEEI
Sbjct: 541  HLLKVPFYEPSHAEEVSKFSVCGFANPLPTESLDCFCPHLQNSTQLEQVNQMLNLTQEEI 600

Query: 601  TATVKVNLPFGRPRVLQKNVDHCLLYHREYVSGFGKAMRMPMWSSYTVPQLGDTSPLPPT 660
            TATVKVNLPFGRPRVLQKNVDHCLLYHREYVSGFGKAMRMPMWSSYTVPQLGDTSPLPPT
Sbjct: 601  TATVKVNLPFGRPRVLQKNVDHCLLYHREYVSGFGKAMRMPMWSSYTVPQLGDTSPLPPT 660

Query: 661  VPDCLRADVRVPPSESQKCSFYLADKNITHGFLYPPASNRTSDSQYDALITSNLVPMYEE 720
            VPDCLRADVRVPPSESQKCSFYLADKNITHGFLYPPASNRTSDSQYDALITSNLVPMYEE
Sbjct: 661  VPDCLRADVRVPPSESQKCSFYLADKNITHGFLYPPASNRTSDSQYDALITSNLVPMYEE 720

Query: 721  FRKMWDYFHSVLLIKHATERNGVNVVSGPIFDYNYDGHFDAPDEITKHLANTDVPIPTHY 780
            FRKMWDYFHSVLLIKHATERNGVNVVSGPIFDYNYDGHFDAPDEITKHLANTDVPIPTHY
Sbjct: 721  FRKMWDYFHSVLLIKHATERNGVNVVSGPIFDYNYDGHFDAPDEITKHLANTDVPIPTHY 780

Query: 781  FVVLTSCKNKSHTPENCPGWLDVLPFIIPHRPTNVESCPEGKPEALWVEERFTAHIARVR 840
            FVVLTSCKNKSHTPENCPGWLDVLPFIIPHRPTNVESCPEGKPEALWVEERFTAHIARVR
Sbjct: 781  FVVLTSCKNKSHTPENCPGWLDVLPFIIPHRPTNVESCPEGKPEALWVEERFTAHIARVR 840

Query: 841  DVELLTGLDFYQDKVQPVSEILQLKTYLPTFETTI 875
            DVELLTGLDFYQDKVQPVSEILQLKTYLPTFETTI
Sbjct: 841  DVELLTGLDFYQDKVQPVSEILQLKTYLPTFETTI 875
```

Figure 4B: Alignment of 161P2F10B (SEQ ID NO: 23) and SNP variant (SEQ ID NO: 24) carrying a T to P mutation.

```
161P2: 492  MEAIFLAHGPSFKEKTEVEPFENIEVYNLMCDLLRIQPAPNNGTHGSLNHLLKVPFYEPS 551
            MEAIFLAHGPSFKEKTEVEPFENIEVYNLMCDLLRIQPAPNNGTHGSLNHLLKVPFYEPS
Sbjct: 1    MEAIFLAHGPSFKEKTEVEPFENIEVYNLMCDLLRIQPAPNNGTHGSLNHLLKVPFYEPS 60

Query: 552  HAEEVSKFSVCGFANPLPTESLDCFCPHLQNSTQLEQVNQMLNLTQEEITATVKVNLPFG 611
            HAEEVSKFSVCGFANPLPTESLDCFCPHLQNSTQLEQVNQMLNLTQEEITATVKVNLPFG
Sbjct: 61   HAEEVSKFSVCGFANPLPTESLDCFCPHLQNSTQLEQVNQMLNLTQEEITATVKVNLPFG 120

Query: 612  RPRVLQKNVDHCLLYHREYVSGFGKAMRMPMWSSYTVPQLGDTSPLPPTVPDCLRADVRV 671
            RPRVLQKNVDHCLLYHREYVSGFGKAMRMPMWSSYTVPQLGDTSPLPPTVPDCLRADVRV
Sbjct: 121  RPRVLQKNVDHCLLYHREYVSGFGKAMRMPMWSSYTVPQLGDTSPLPPTVPDCLRADVRV 180

Query: 672  PPSESQKCSFYLADKNITHGFLYPPASNRTSDSQYDALITSNLVPMYEEFRKMWDYFHSV 731
            PPSESQKCSFYLADKNITHGFLYPPASNRTSDSQYDALITSNLVPMYEEFRKMWDYFHSV
Sbjct: 181  PPSESQKCSFYLADKNITHGFLYPPASNRTSDSQYDALITSNLVPMYEEFRKMWDYFHSV 240

Query: 732  LLIKHATERNGVNVVSGPIFDYNYDGHFDAPDEITKHLANTDVPIPTHYFVVLTSCKNKS 791
            LLIKHATERNGVNVVSGPIFDYNYDGHFDAPDEITKHLANTDVPIPTHYFVVLTSCKNKS
Sbjct: 241  LLIKHATERNGVNVVSGPIFDYNYDGHFDAPDEITKHLANTDVPIPTHYFVVLTSCKNKS 300

Query: 792  HTPENCPGWLDVLPFIIPHRPTNVESCPEGKPEALWVEERFTAHIARVRDVELLTGLDFY 851
            HTPENCPGWLDVLPFIIPHRPTNVESCPEGKPEALWVEERFTAHIARVRDVELLTGLDFY
Sbjct: 301  HTPENCPGWLDVLPFIIPHRPTNVESCPEGKPEALWVEERFTAHIARVRDVELLTGLDFY 360

Query: 852  QDKVQPVSEILQLKTYLPTFETTI 875
            QDKVQPVSEILQLKTYLPTFET I
Sbjct: 361  QDKVQPVSEILQLKTYLPTFETPI 384
```

Figure 5: 161P2F10B Hydrophilicity profile
(Hopp T.P., Woods K.R., 1981.
Proc. Natl. Acad. Sci. U.S.A. 78:3824-3828)
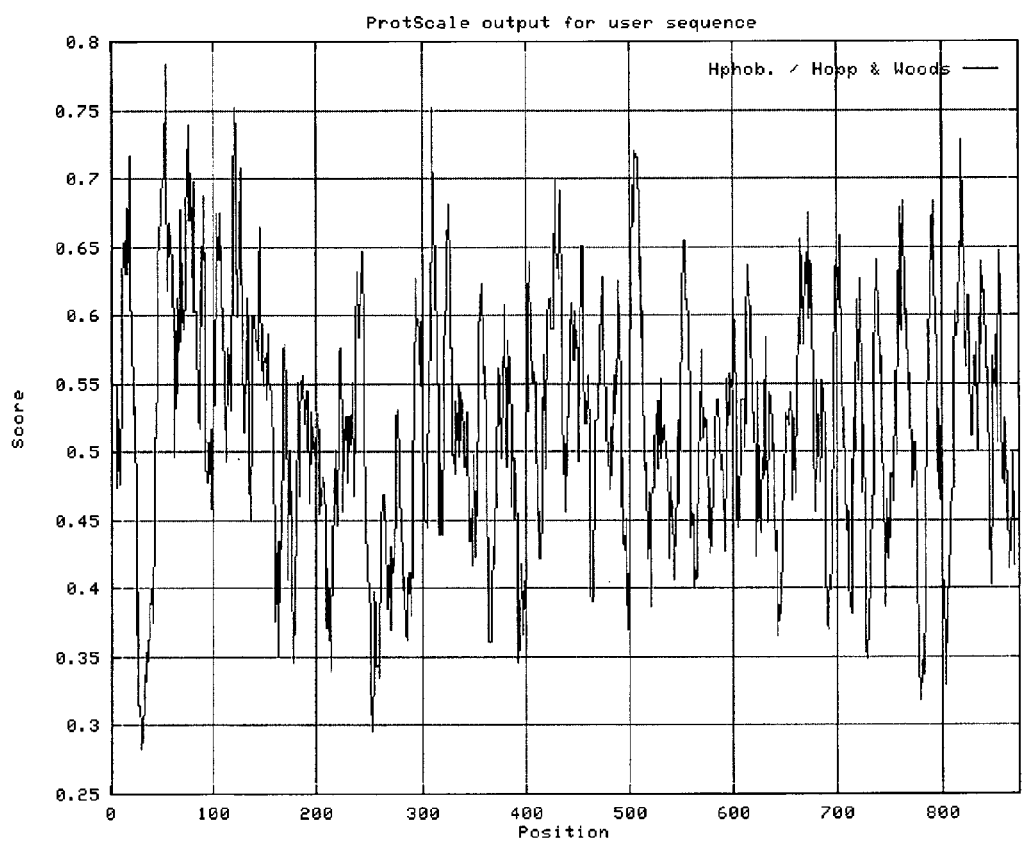

Figure 6: 161P2F10B Hydropathicity Profile
(Kyte J., Doolittle R.F., 1982. J. Mol. Biol. 157:105-132)
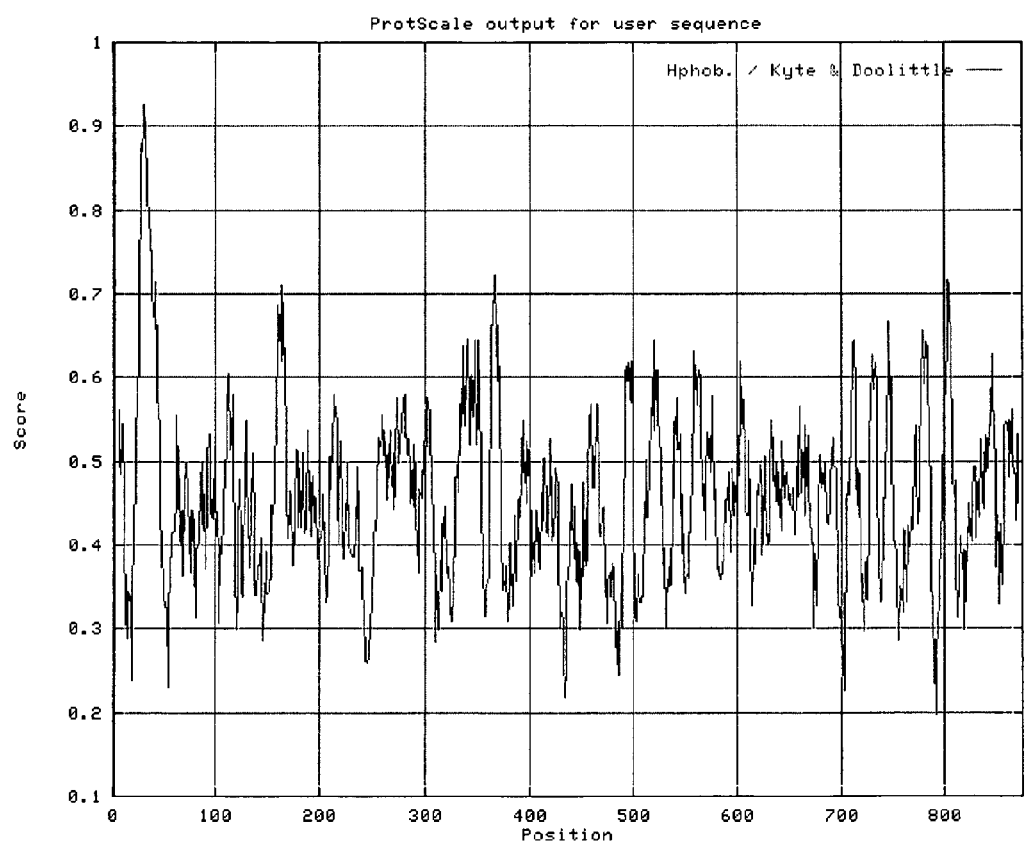

Figure 7: 161P2F10B % Accessible Residues Profile
(Janin J., 1979. Nature 277:491-492)
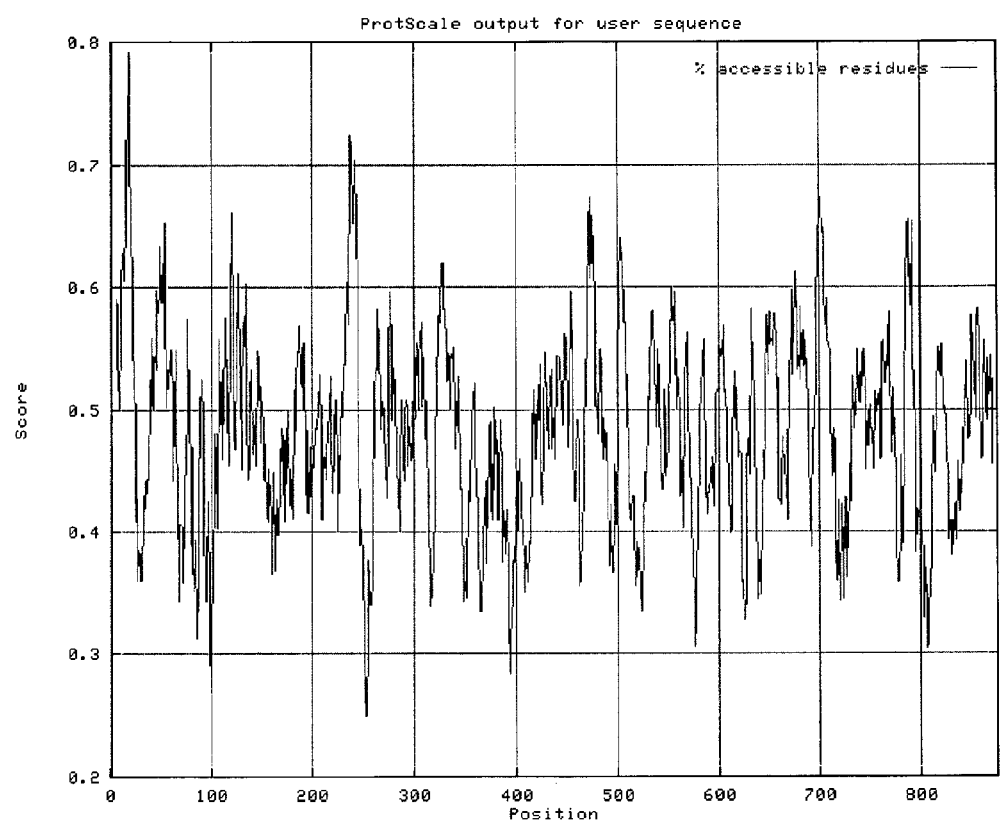

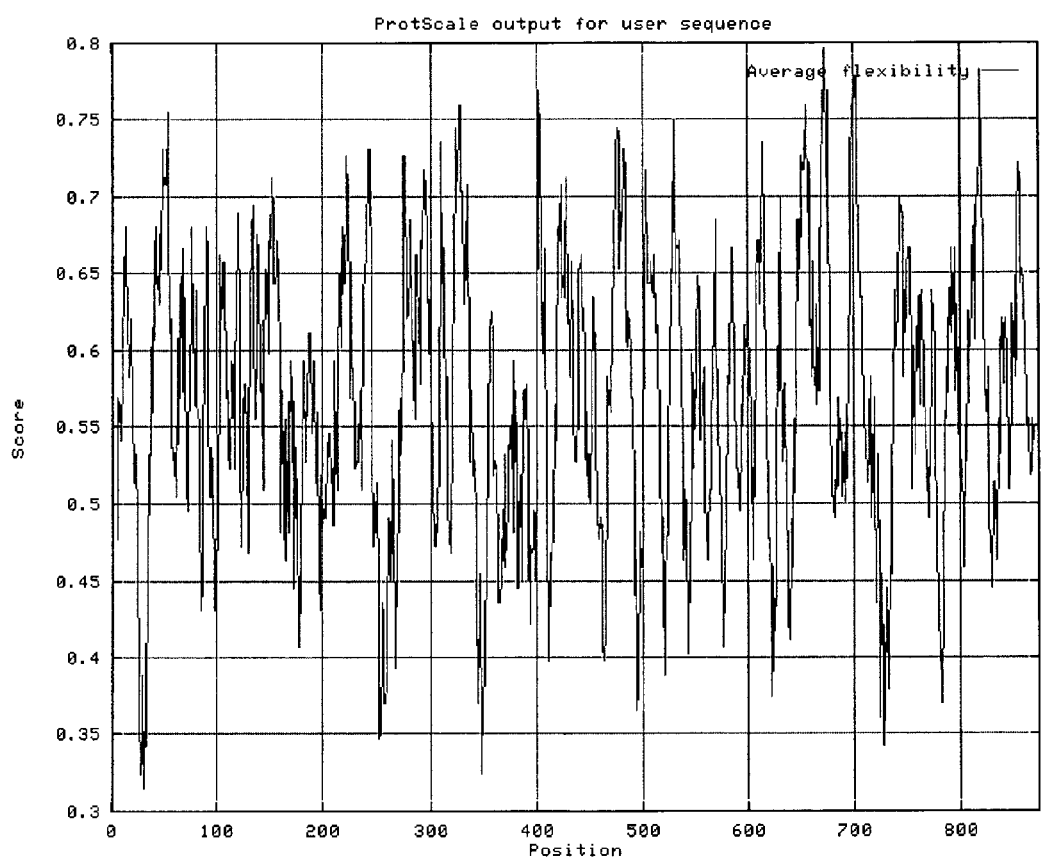
Figure 8: 161P2F10B Average Flexibility Profile
(Bhaskaran R., Ponnuswamy P.K., 1988.
Int. J. Pept. Protein Res. 32:242-255)

Figure 9: 161P2F10B Beta-turn Profile
(Deleage, G., Roux B. 1987. Protein Engineering 1:289-294)
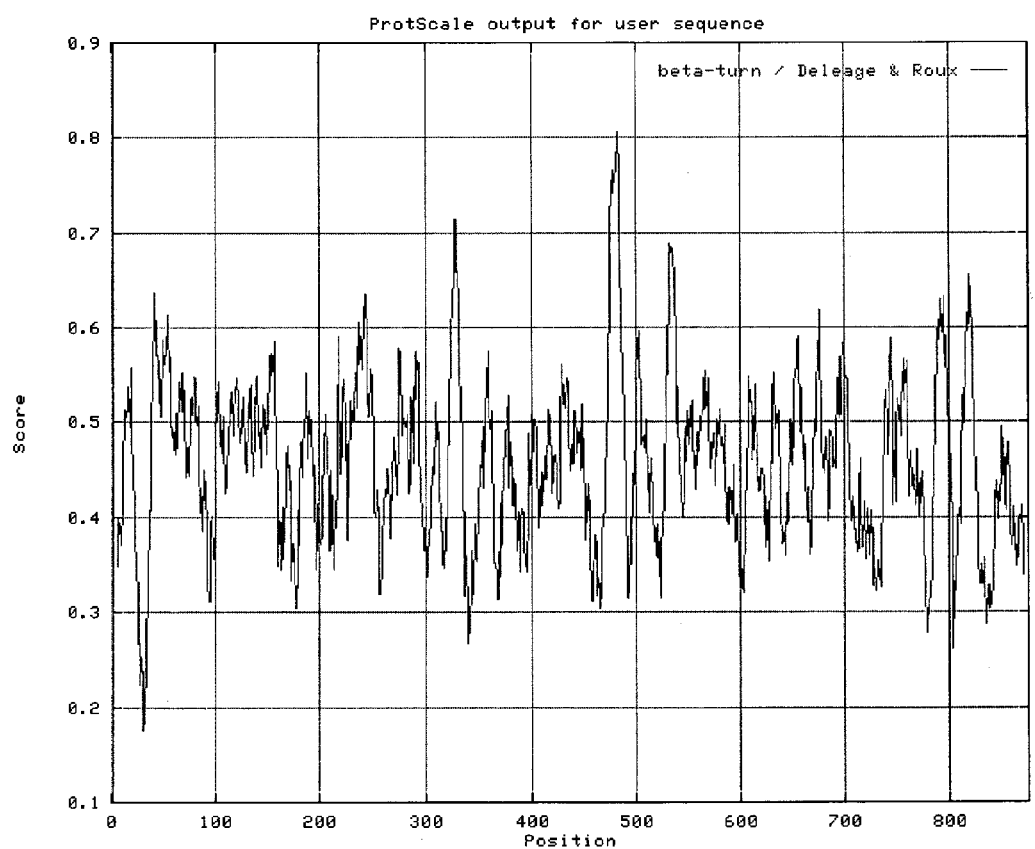

Figure 13A

```
          10        20        30        40        50        60        70
          |         |         |         |         |         |         |
MESTLTLATEQPVKKNTLKKYKIACIVLLALLVIMSLGLGLGLGLRKLEKQGSCRKKCFDASFRGLENCR
cccceeeeecccccccchhhhhhhhhhhhhhhhhhhhhchhhhhhhhhhhccccccccccccccchhcccc
CDVACKDRGDCCWDFEDTCVESTRIWMCNKFRCGETRLEASLCSCSDDCLQKKDCCADYKSVCQGETSWL
ccccccccccccccccchhhhhehhhhhccccccceeechccccccccccccccccccccccccccch
EENCDTAQQSQCPEGFDLPPVILFSMDGFRAEYLYTWDTLMPNINKLKTCGIHSKYMRAMYPTKTFPNHY
cccccccccccccccccceeeeecccchhhhhhhhhhhchhhhccccchhhhheeccccccccccce
TIVTGLYPESHGIIDNNMYDVNLNKNFSLSSKEQNNPAWWHGQPMWLTAMYQGLKAATYFWPGSEVAING
eeeeecccccchhccccccccccceeecccccccccccchhhhhhhhccccceeeecccceeeecc
SFPSIYMPYNGSVPFEERISTLLKWLDLPKAERPRFYTMYFEEPDSSGHAGGPVSARVIKALQVVDHAFG
cccceeecccccchhhhhhhhhhhccccccccceeeeeecccccccccchhhhhhhhhhhhhhhh
MLMEGLKQRNLHNCVNIILLADHGMDQTYCNKMEYMTDYFPRINFFYMYEGPAPRIRAHNIPHDFFSFNS
hhhhhhhhhcccceeeeeecccccccccccchhhhhhccceeeeecccccccccccccccchhhcch
EEIVRNLSCRKPDQHFKPYLTPDLPKRLHYAKNVRIDKVHLFVDQQWLAVRSKSNTNCGGGNHGYNNEFR
hhhhhhhccccccccccccccchhhhhcccccchhhhhhhhhheeecccccccccccccchhhh
SMEAIFLAHGPSFKEKTEVEPFENIEVYNLMCDLLRIQPAPNNGTHGSLNHLLKVPFYEPSHAEEVSKFS
hhhhhhhhccccccccccccchhhhhhhhhhhhccccccccccccchheecccccccccccchccee
VCGFANPLPTESLDCFCPHLQNSTQLEQVNQMLNLTQEEITATVKVNLPFGRPRVLQKNVDHCLLYHREY
eeccccccccchhccccccccchhhhhhhhhhchhhhheeeecccccccehccccccceeeehhhh
VSGFGKAMRMPMWSSYTVPQLGDTSPLPPTVPDCLRADVRVPPSESQKCSFYLADKNITHGFLYPPASNR
hhccccceeecccccccccccccccccccccccccccccceeeeccccccccccccccccccc
TSDSQYDALITSNLVPMYEEFRKMWDYFHSVLLIKHATERNGVNVVSGPIFDYNYDGHFDAPDEITKHLA
ccchhhhhhhhhcccchhhhhhhhhhhhhhhhhhhehhccccccceeccccccccccccchhhhhhhcc
NTDVPIPTHYFVVLTSCKNKSHTPENCPGWLDVLPFIIPHRPTNVESCPEGKPEALWVEERFTAHIARVR
cccccccceeeeeeecccccccccccccccccceeeeccccccccccccccchhhhhhhhhhhhhh
DVELLTGLDFYQDKVQPVSEILQLKTYLPTFETTI
hheehcccccchcchhchhhhehhhhccccccc
``` c: random coil (31.31%)
e: extended strand (11.31%)
h: alpha helix (57.37%)

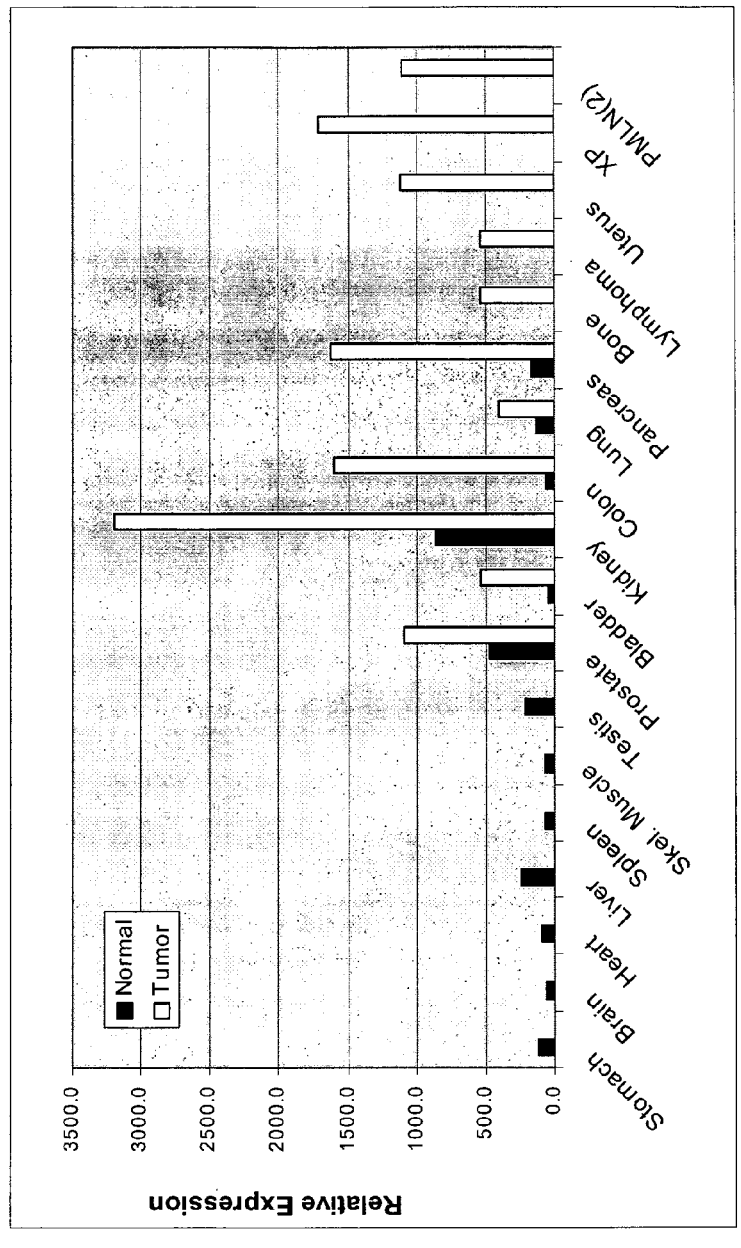
Figure 14  161P2F10B Expression in Normal and Patient Cancer Tissues
XP = Prostate xenograft pool
PMLN(2) = Pool of 2 prostate metastasis to lymph node

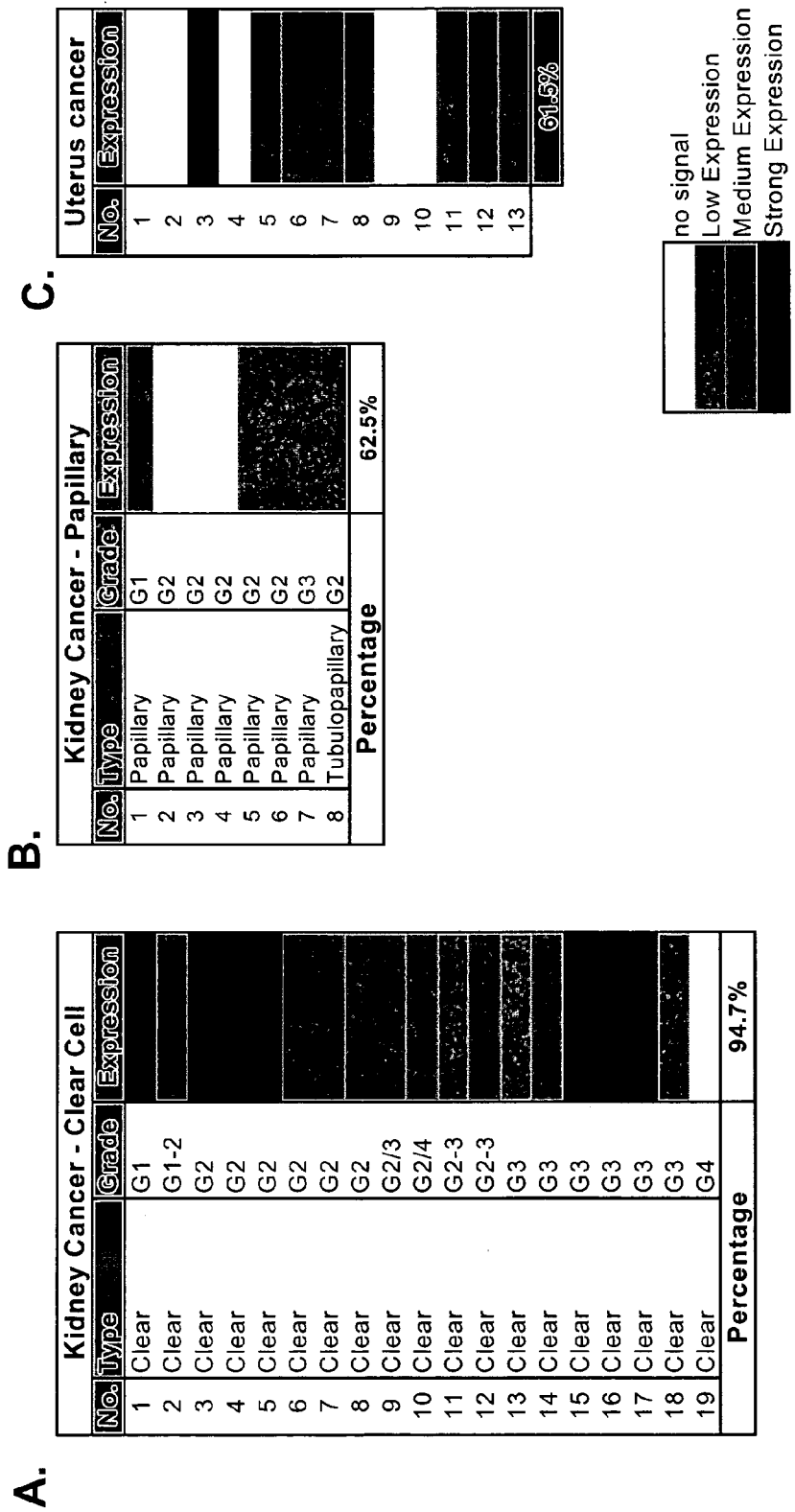
Figure 15  161P2F10B Expression in Kidney and Uterus Patient Cancer Specimens

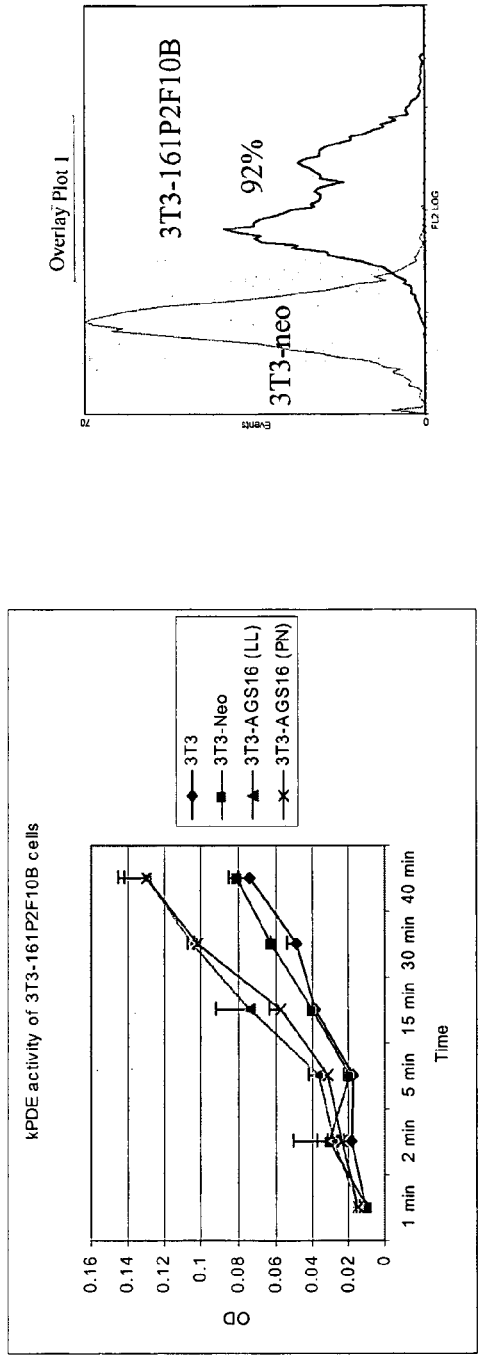
Figure 16: Phosphodiesterase Activity of 3T3-AGS16 Stable Cells
Cell surface phosphodiesterase activity is assayed on 3T3 and 3T3-161P2F10B using the substrate p-nitrophenyl thymidine -5'-L-monophosphate.

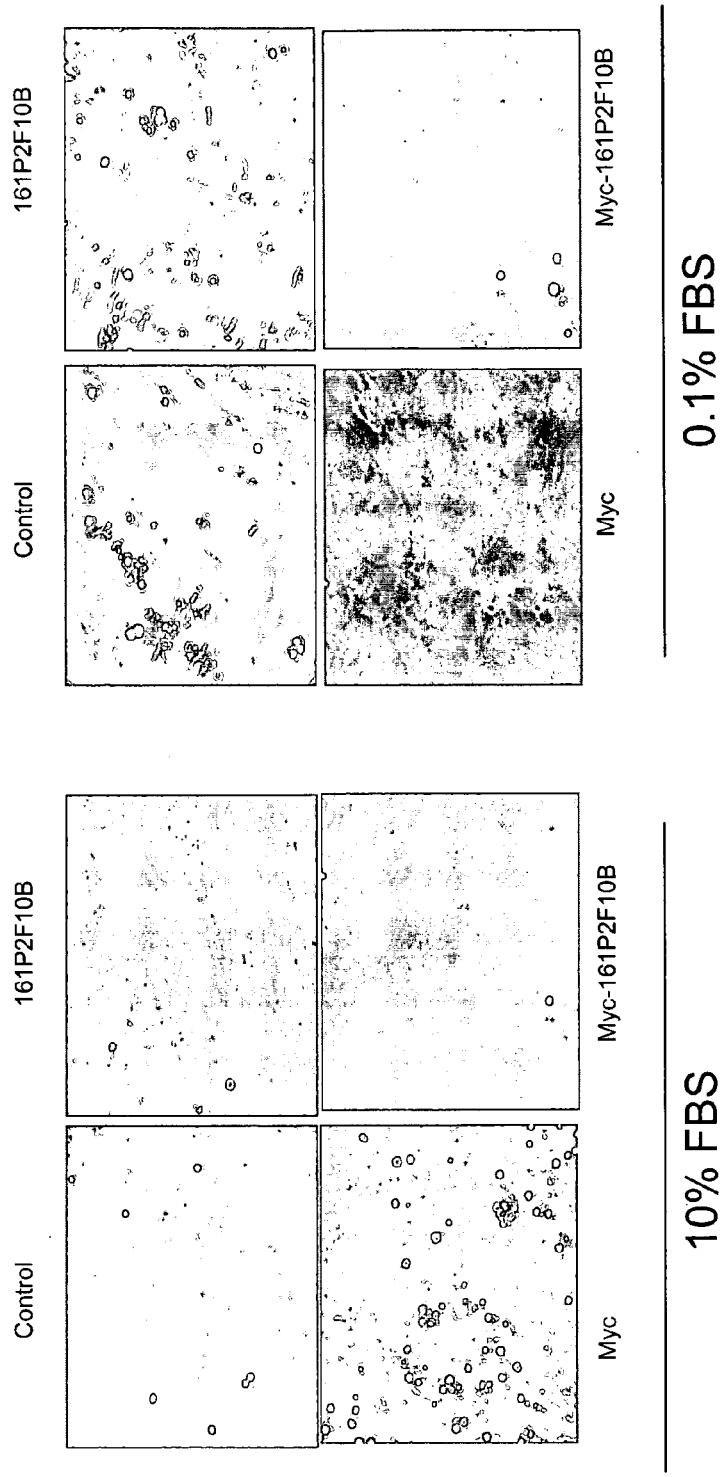
Figure 17: Protection from Apoptosis by 161P2F10B

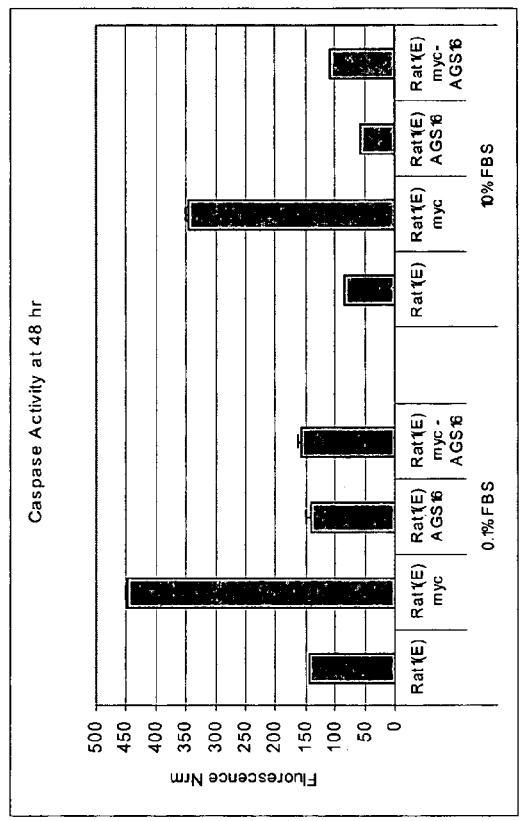
Figure 18: 161P2F10B Protects from Apoptotic Signals
• Rat1(E) cells were analyzed using Apo1 caspase assay

Figure 19: 161P2F10B Protects from Staurosporine and UV-Induced Apoptosis
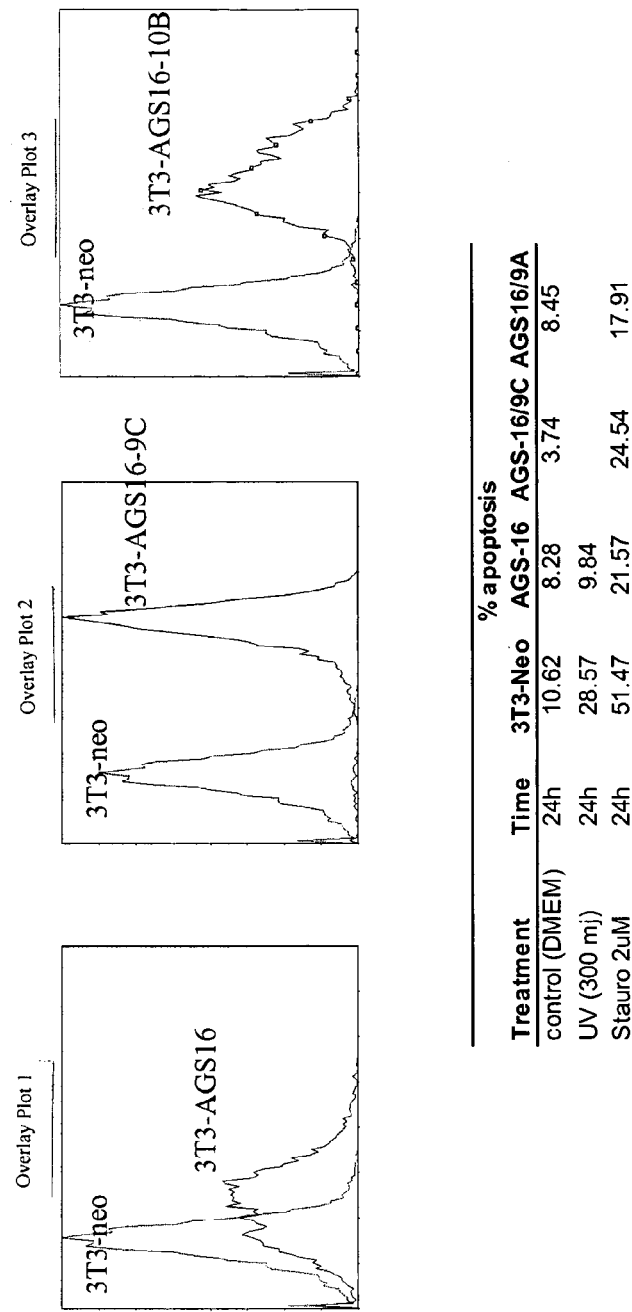

Figure 20: 161P2F10B Expression Protects Cells from Drug and UV-Induced Apoptosis

| Cell Line | Treatment | Time | % Apoptosis |
|---|---|---|---|
| 3T3 neo | control | 24h | 3.62 |
| | Staurosporine, 2.14 uM | 24h | 64.93 |
| | UV (300 mjoules/cm$^2$) | 24h | 62.92 |
| 3T3-AGS16 | control | 24h | 1.72 |
| | Staurosporine, 2.14 uM | 24h | 14.76 |
| | UV (300 mjoules/cm$^2$) | 24h | 30.8 |

NIH 3T3 cells were treated with the staurosporine or UV, stained with Annexin V-FITC and propidium iodide, and analyzed by FACS.

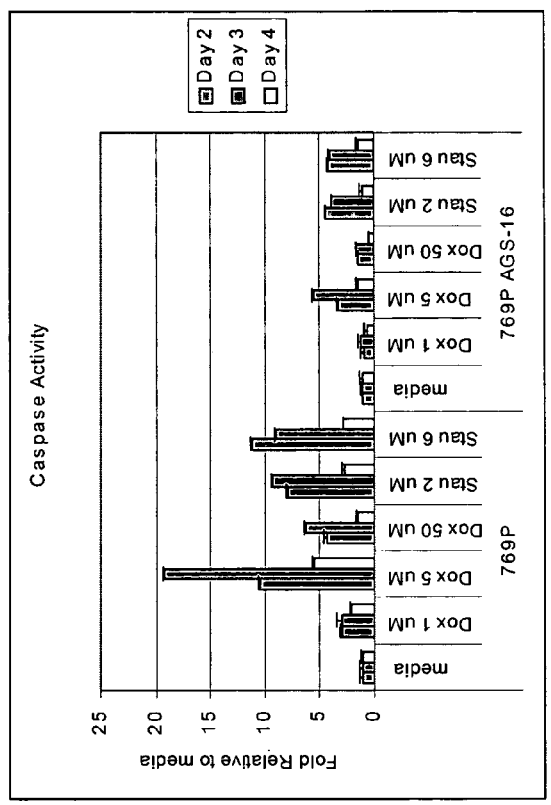
Figure 21: 161P2F10B Protects from Apoptosis By Chemotherapeutic Agents Figure 22: Effect of 161P2F10B on *In Vitro* Invasion
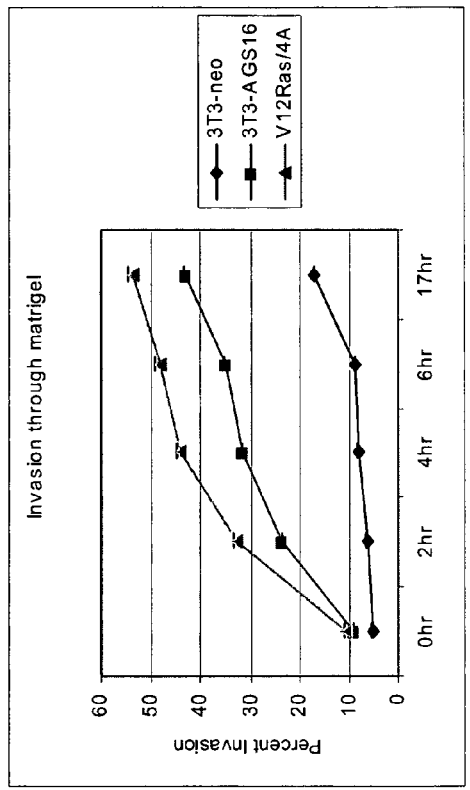
- 3T3 cells stably expressing 161P2F10B were assayed using a Transwell Insert System.
- Invasion was determined by measuring the fluorescence of cells in the lower chamber relative to the fluorescence of the entire cell population.
- The assay was performed in triplicate.

Figure 23: 161P2F10B MAb Attenuates the Growth of Human Kidney Cancer Xenograft in SCID Mice
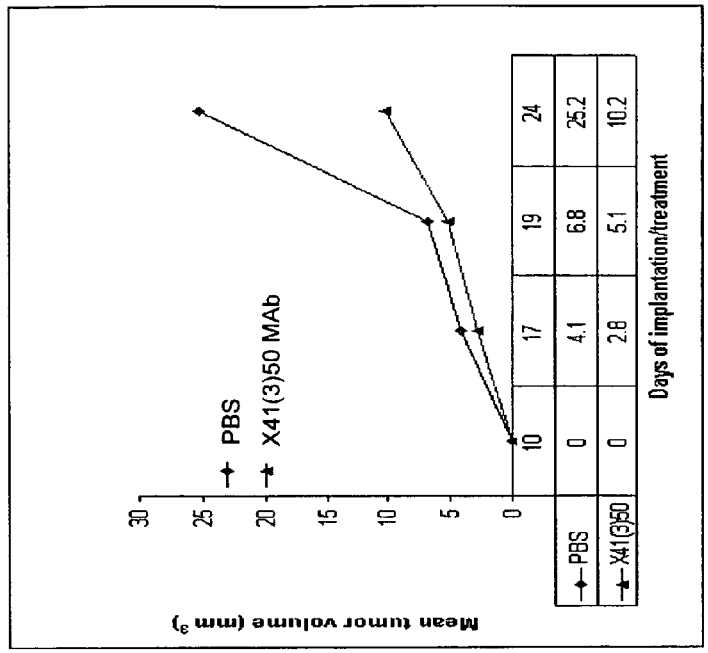
| Group | Mouse # | Tumor volume (mm³) | | | |
|---|---|---|---|---|---|
| | | 10/28/02 | 10/30/02 | 11/4/02 | |
| PBS control | 6738 | 0.00 | 0.00 | 40.00 | |
| | 6739 | 20.25 | 20.25 | 31.50 | |
| | 6740 | 0.00 | 13.50 | 50.63 | |
| | 6741 | 0.00 | 0.00 | 4.00 | |
| | 6742 | 0.00 | 0.00 | 0.00 | |
| | Mean | 4.05 | 6.75 | 25.23 | |
| | SD | 9.1 | 9.5 | 22.3 | |
| X41(3)50 MAb | 6733 | 0.00 | 4.00 | 4.00 | |
| | 6734 | 0.00 | 0.00 | 0.00 | |
| | 6735 | 4.00 | 4.00 | 40.00 | |
| | 6736 | 6.00 | 13.50 | 6.00 | |
| | 6737 | 4.00 | 4.00 | 1.00 | |
| | Mean | 2.80 | 5.10 | 10.20 | |
| | SD | 2.7 | 5.0 | 16.8 | |
- Tumor injection/first MAb injection – 10/11/02
- 2.5 x 10⁶ UG-K3 tumor cells were injected s.c. into the mouse flank; MAbs (500 µg) injected i.p. twice weekly.

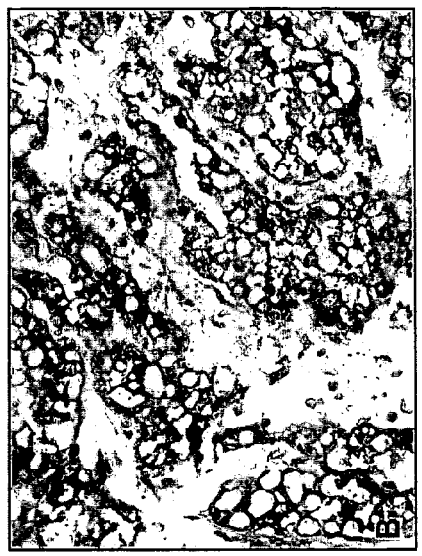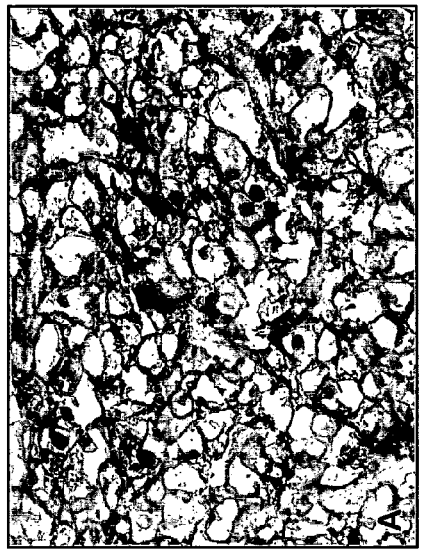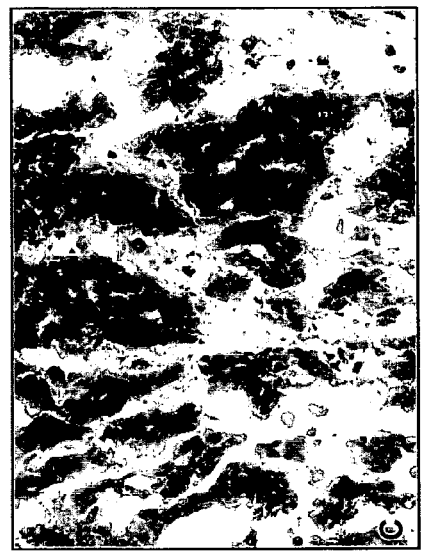
Figure 24: 161P2F10B protein expression in kidney cancer specimens

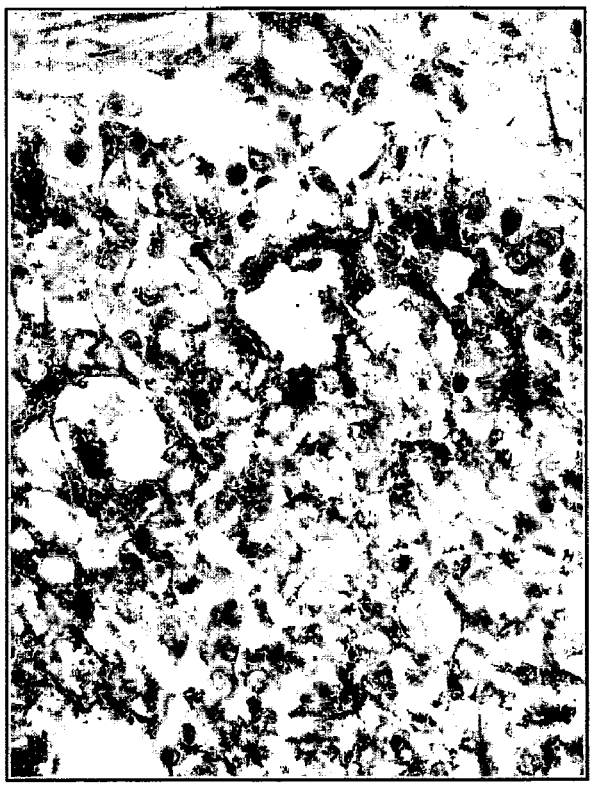
Figure 25: 161P2F10B protein expression in prostate cancer specimen

Figure 26: 161P2F10B protein expression in colon cancer specimen

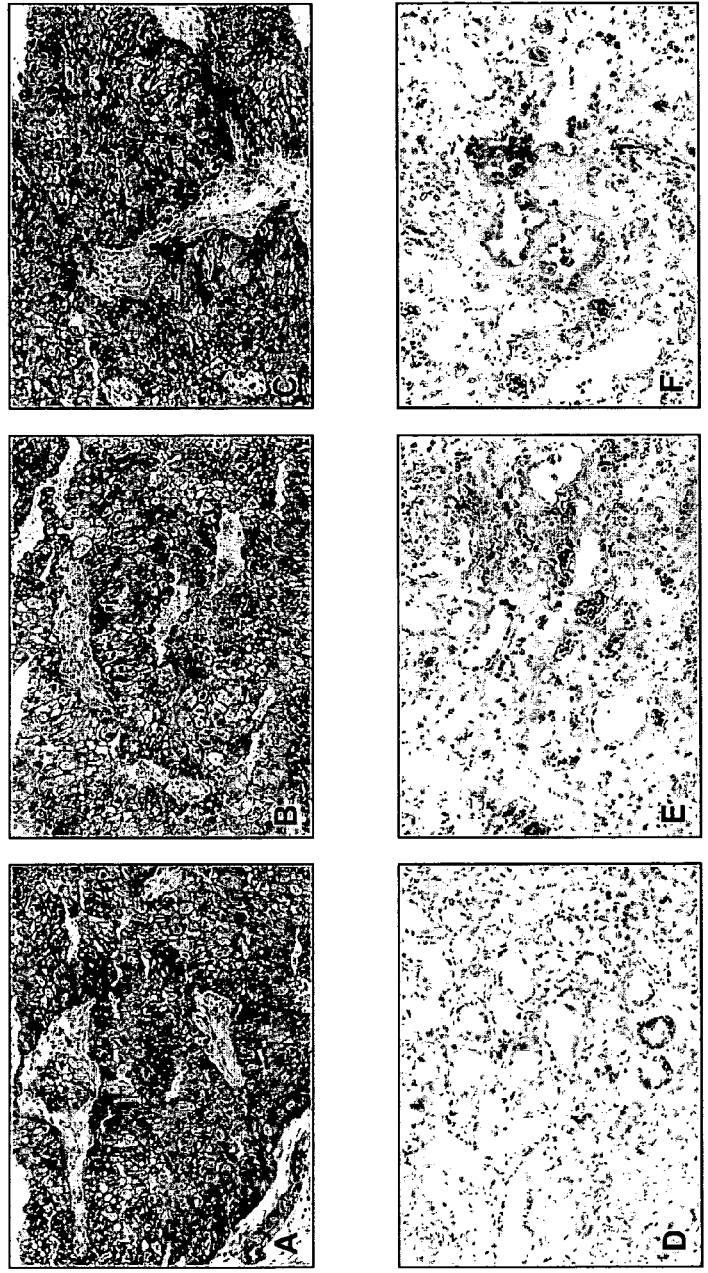
Figure 27: Immunohistochemistry showing expression of 161P2F10B protein to kidney clear cell cancer patient specimens by specific binding of mouse monoclonal antibodies

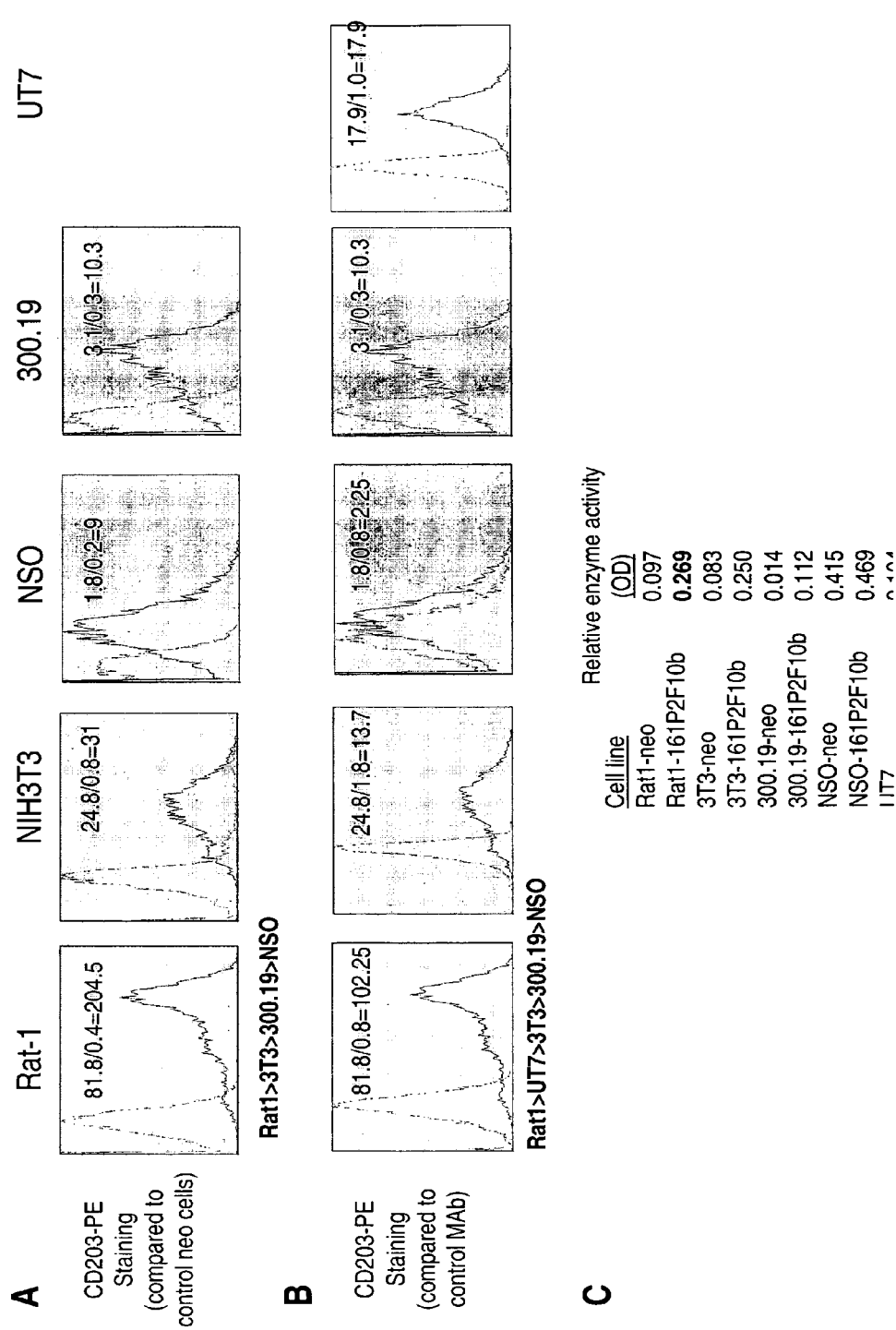
Figure 28: Expression of 161P2F10b in recombinant cell lines

Figure 29: Surface expression and phosphodiesterase activity of 161P2F10b

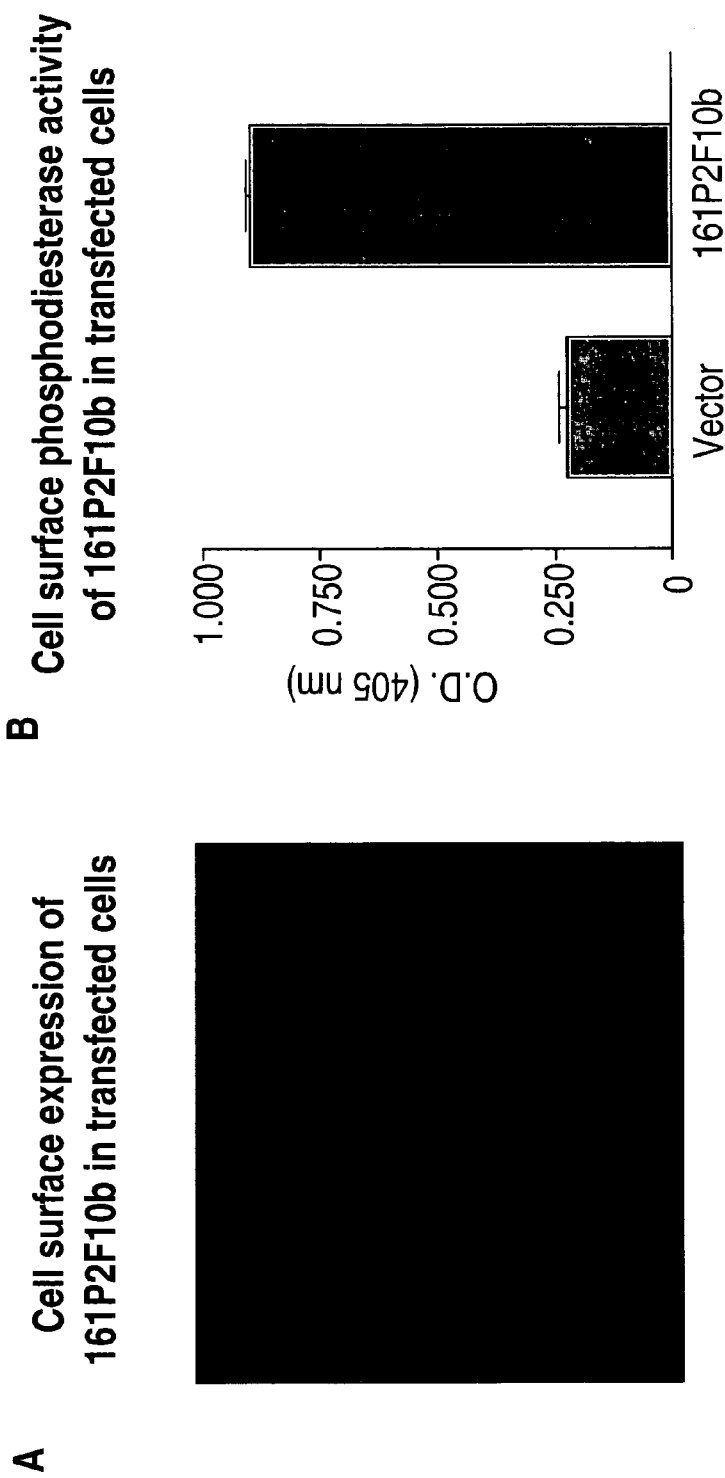

A  Cell surface expression of 161P2F10b in transfected cells

161P2F10b transfected 293T cells were stained with PE-conjugated anti-CD-203c MAb and examined by fluorescent microscopy.

B  Cell surface phosphodiesterase activity of 161P2F10b in transfected cells

161P2F10b and vector transfected 293T cells were incubated in assay buffer containing the phosphodiesterase-1 colorimetric substrate p-nitrophenyl thymidine-5'-L-monophosphate and optical densities (O.D.) were obtained at 405nm.

Figure 30: Relative expression and enzymatic activity of 161P2F10b mutants in recombinant Caki kidney cancer cells
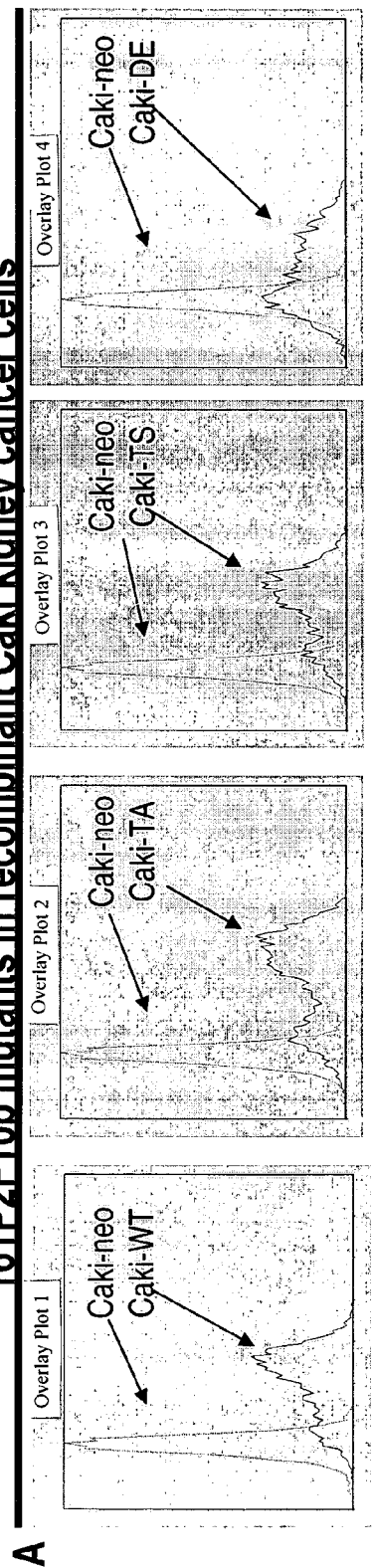
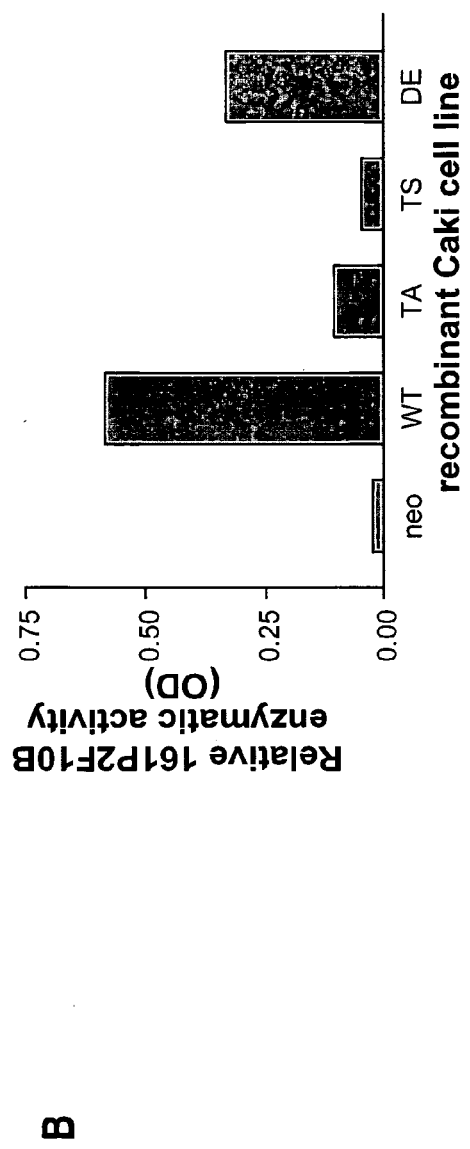

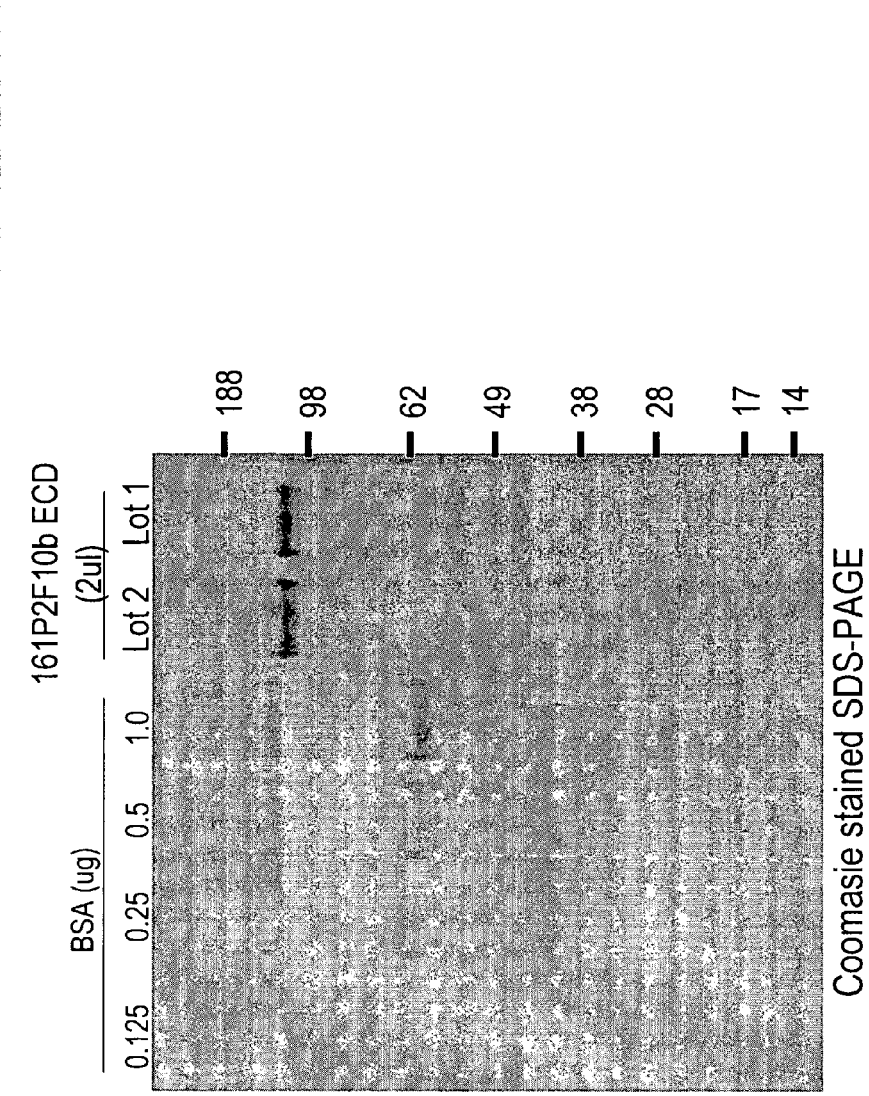
Figure 31: Purification of the recombinant extracellular domain (ECD) of 61P2F10b

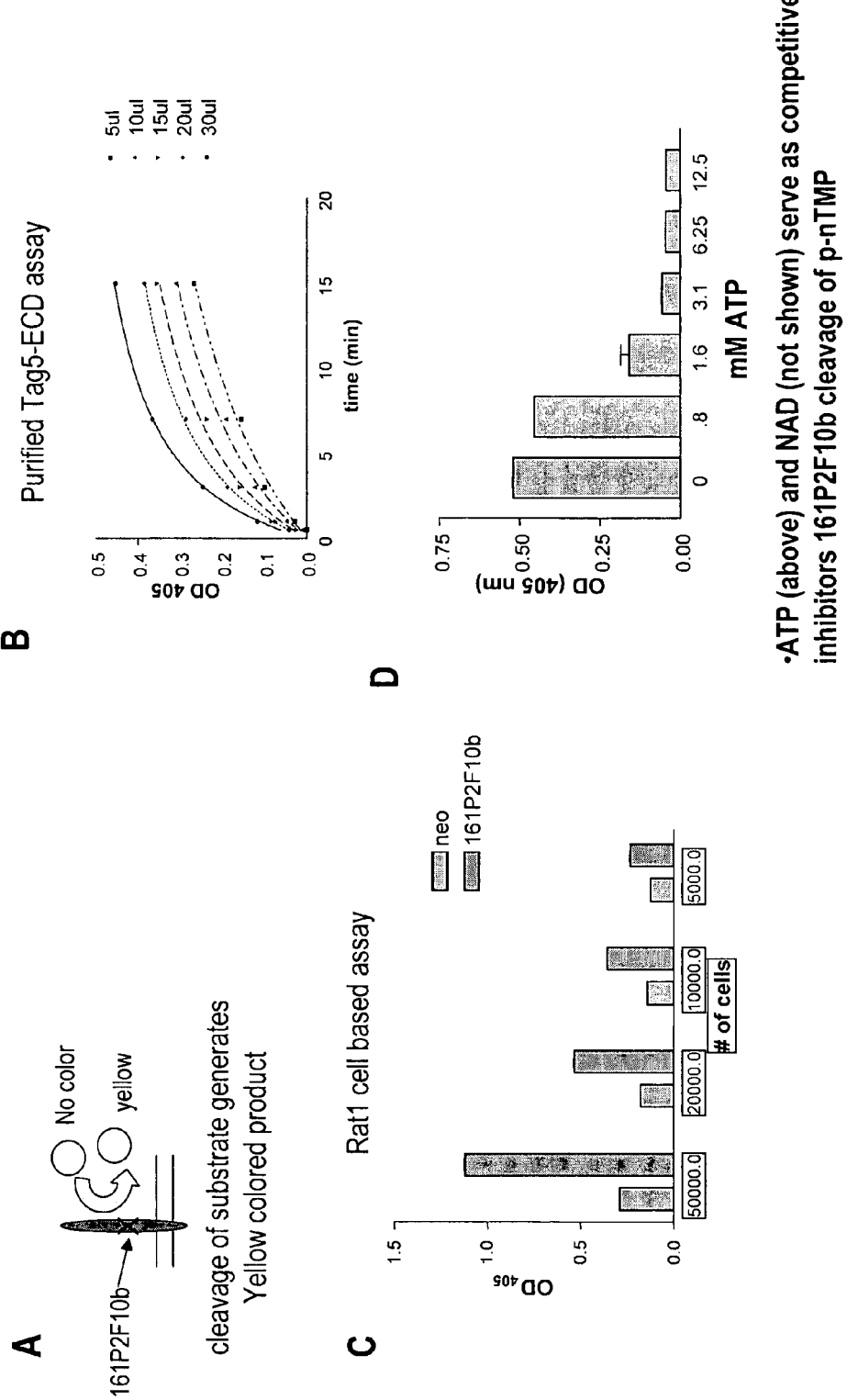
Figure 32: 161P2F10b enzymatic assays utilizing P-nitrophenyl-thymidine monophosphate (p-nTMP)

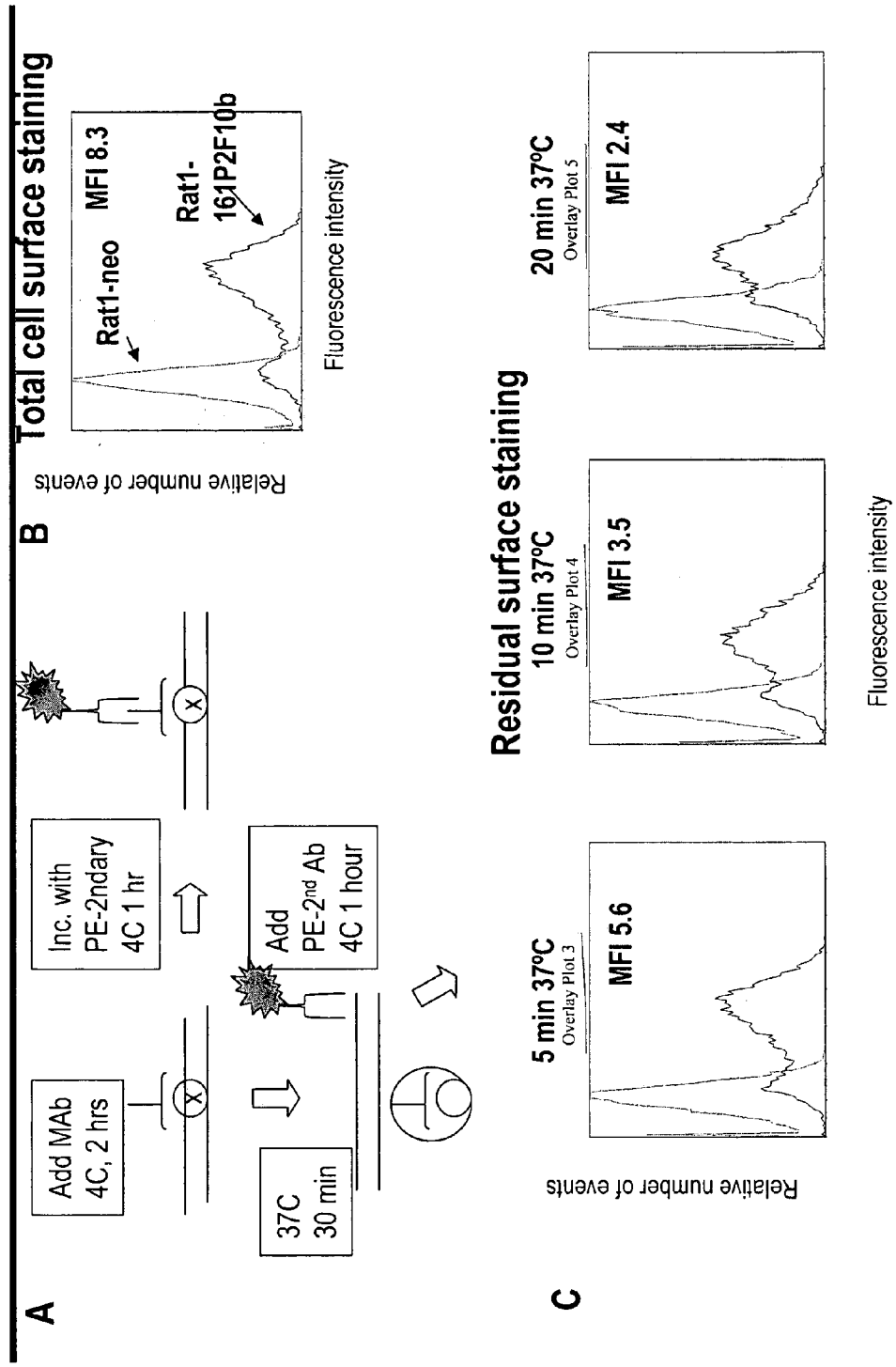
Figure 33: Analysis of the internalization of anti-161P2F10b MAb

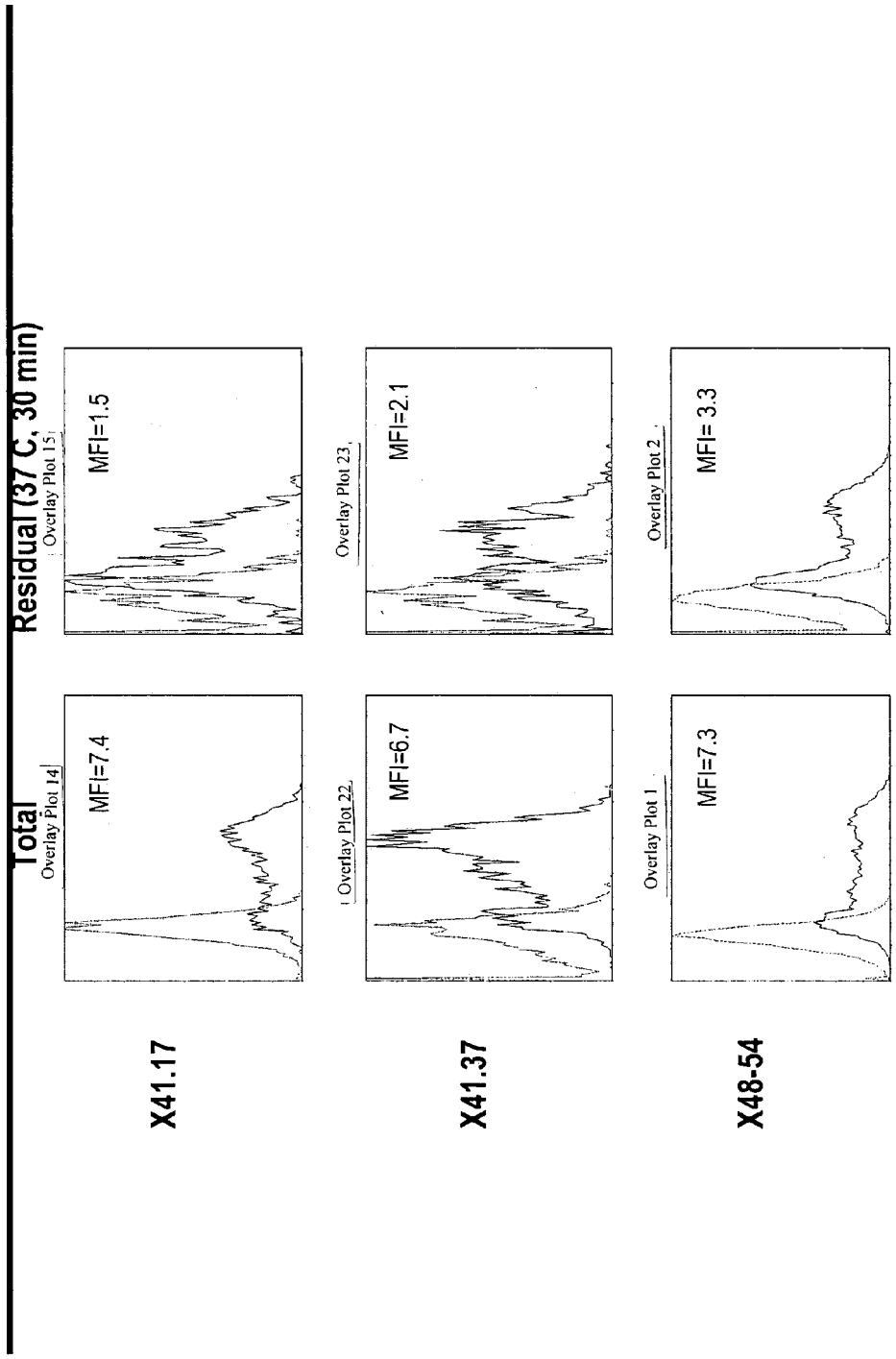
Figure 34: Internalization of selected anti-161P2F10b murine MAbs

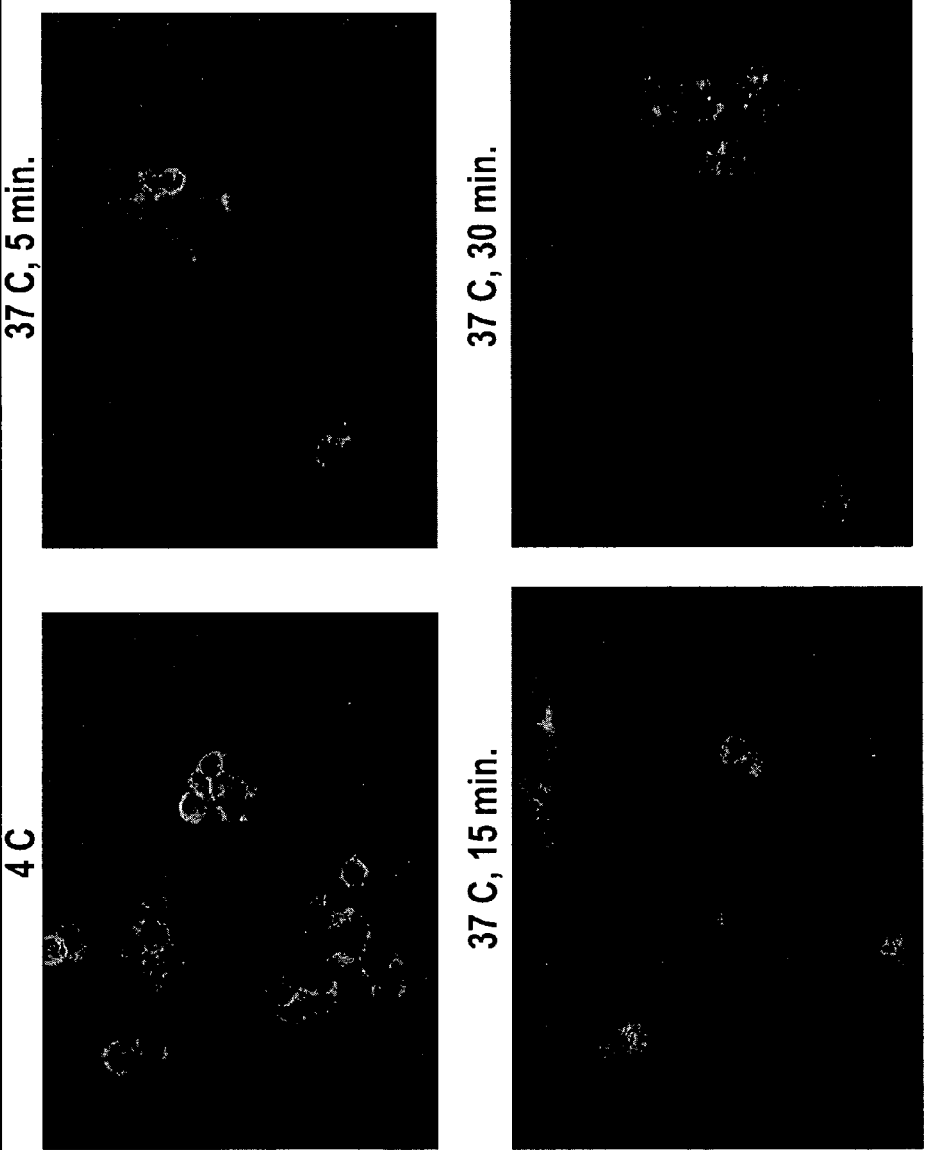
Figure 35: Antibody engagement of 161P2F10b results in its internalization

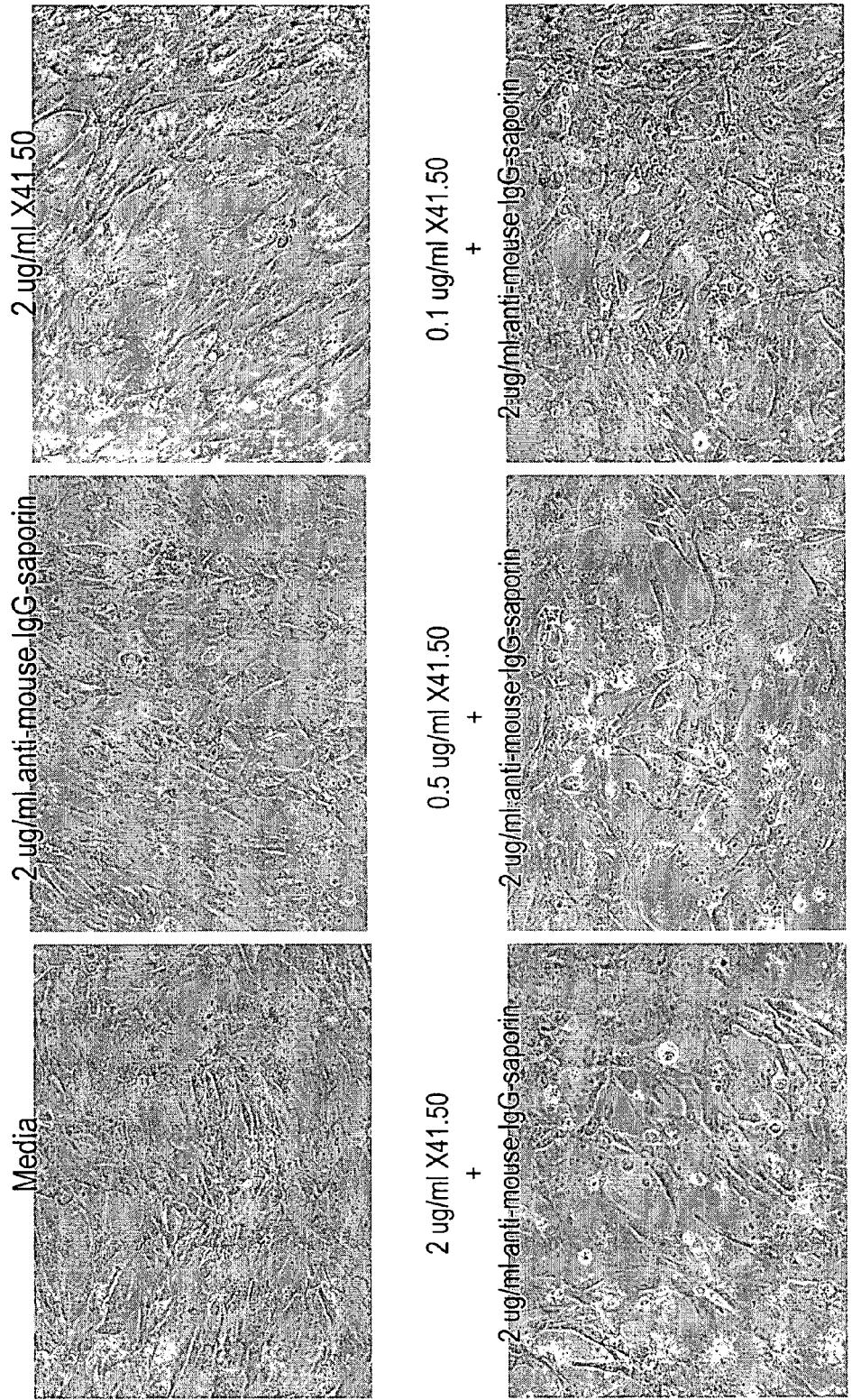
Figure 36: Effects of X41.50 MAb-saporin toxin conjugate on Caki-161P2F10b cells

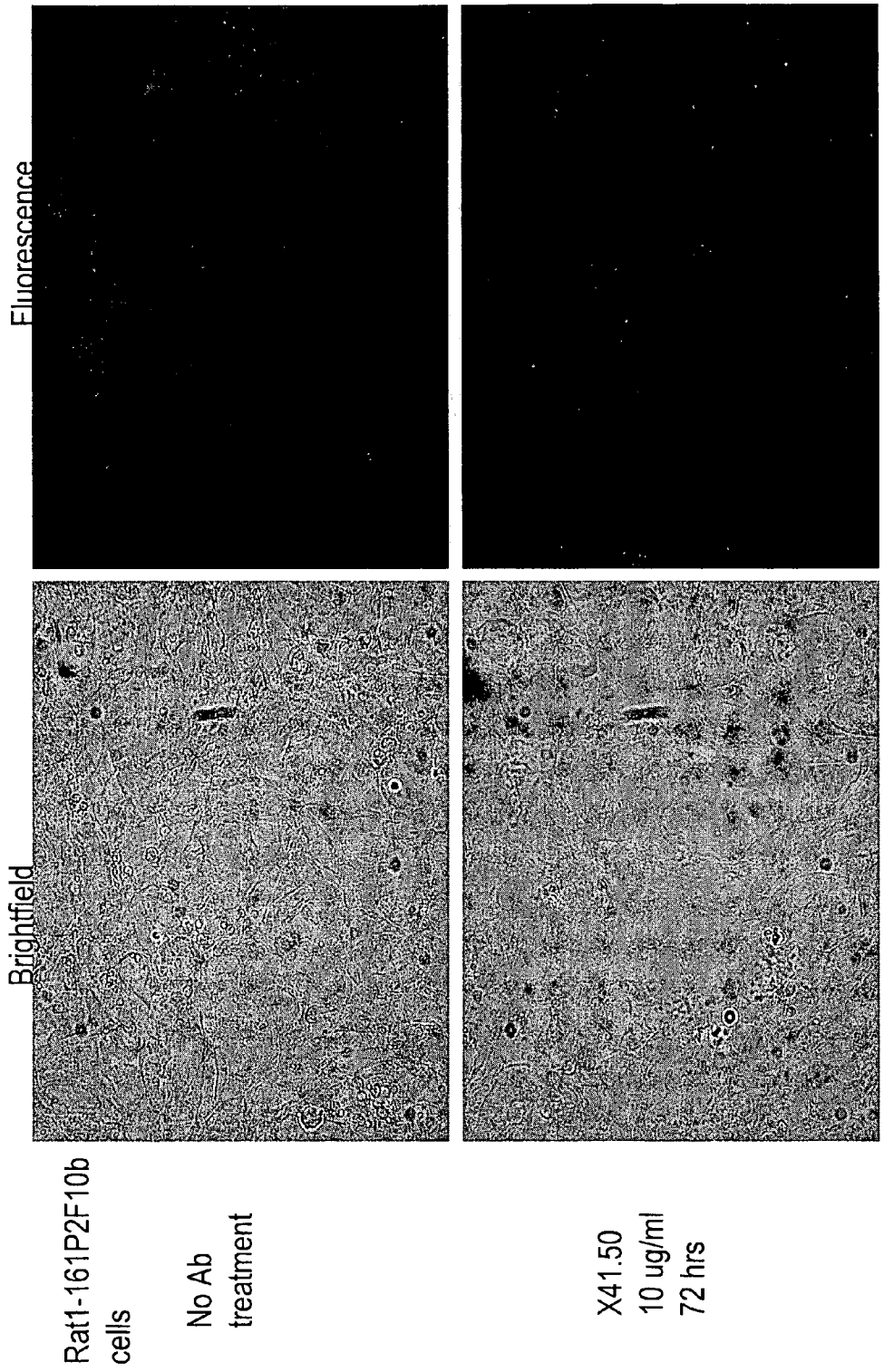
Figure 37: Internalization mediated downregulation of 161P2E10 protein by MAb X41.50

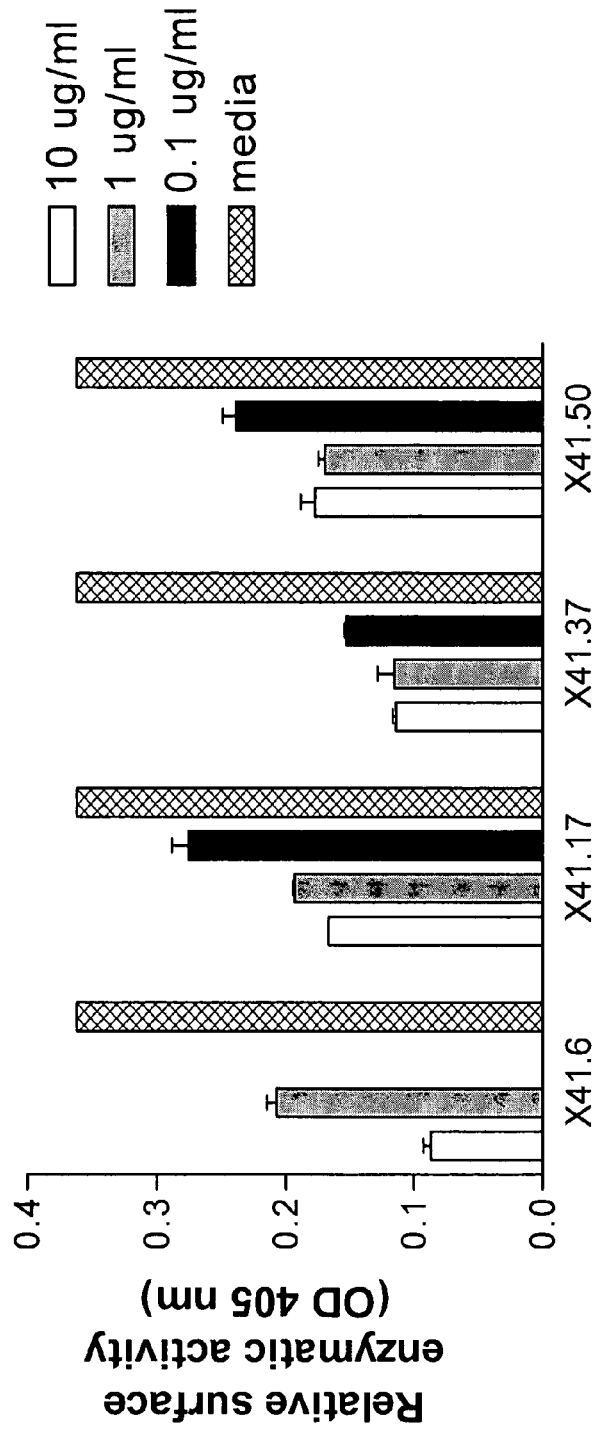
Figure 38: Anti-161P2F10b MAbs downregulate surface 161P2F10b enzymatic activity
Rat1-161P2F10b cells were treated with and without various concentrations of the indicated MAbs for 48 hours and then assayed for surface enzymatic activity.

Figure 39: Characteristics of mouse 161P2F10b MAbs

| MAb Clone | Isotype | Relative Affinity (nM) | Surface Staining | Internalization (FACS) | Downregulation of enzyme activity | Specific IHC staining | Epitope family |
|---|---|---|---|---|---|---|---|
| X41(4)6 | IgG1 | 0.09 | s | ++ | m | s | 1 |
| X41(3)15 | IgG2b | 0.23 | m | + | - | s | 1 |
| X41(3)17 | IgG1 | 0.12 | s | +++ | s | m | 2 |
| X41(3)29 | IgG2a | 169.9 | w | + | - | s | ND |
| X41(3)37 | IgG1 | 0.24 | m | +++ | s | s | 2 |
| X41(3)50 | IgG1 | 0.09 | s | +++ | s | s | 2 |
| 97A6(CD203c) | IgG1 | 0.28 | s | +++ | ND | s | 2 | s = strong = +++
m = moderate = ++
w = weak = +
Negative = -
ND = not determined

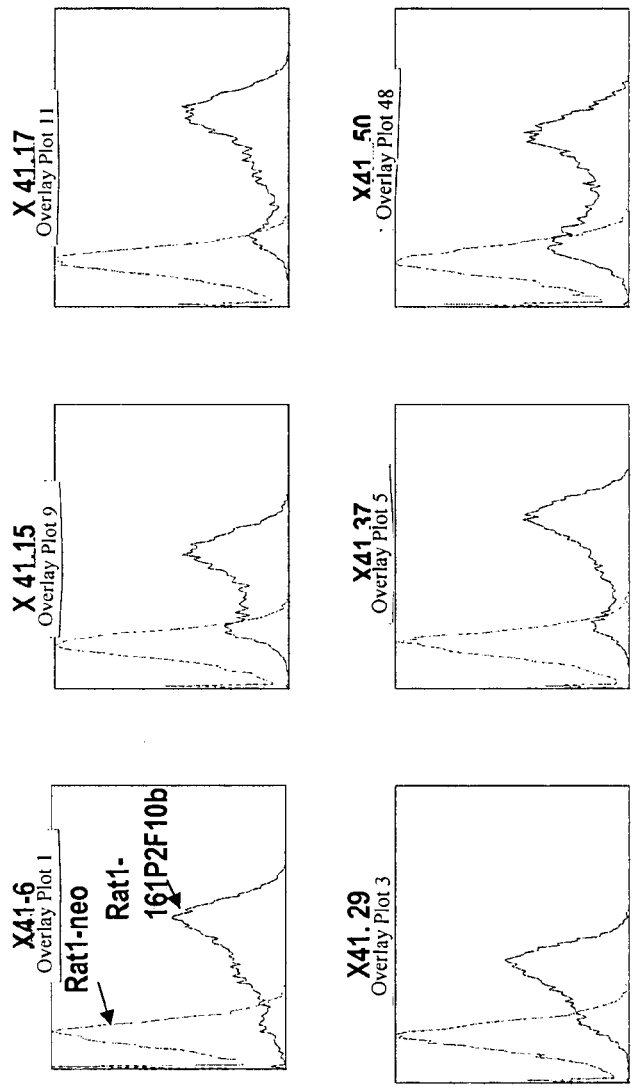
Figure 40: Surface staining of selected anti-161P2F10b MAbs

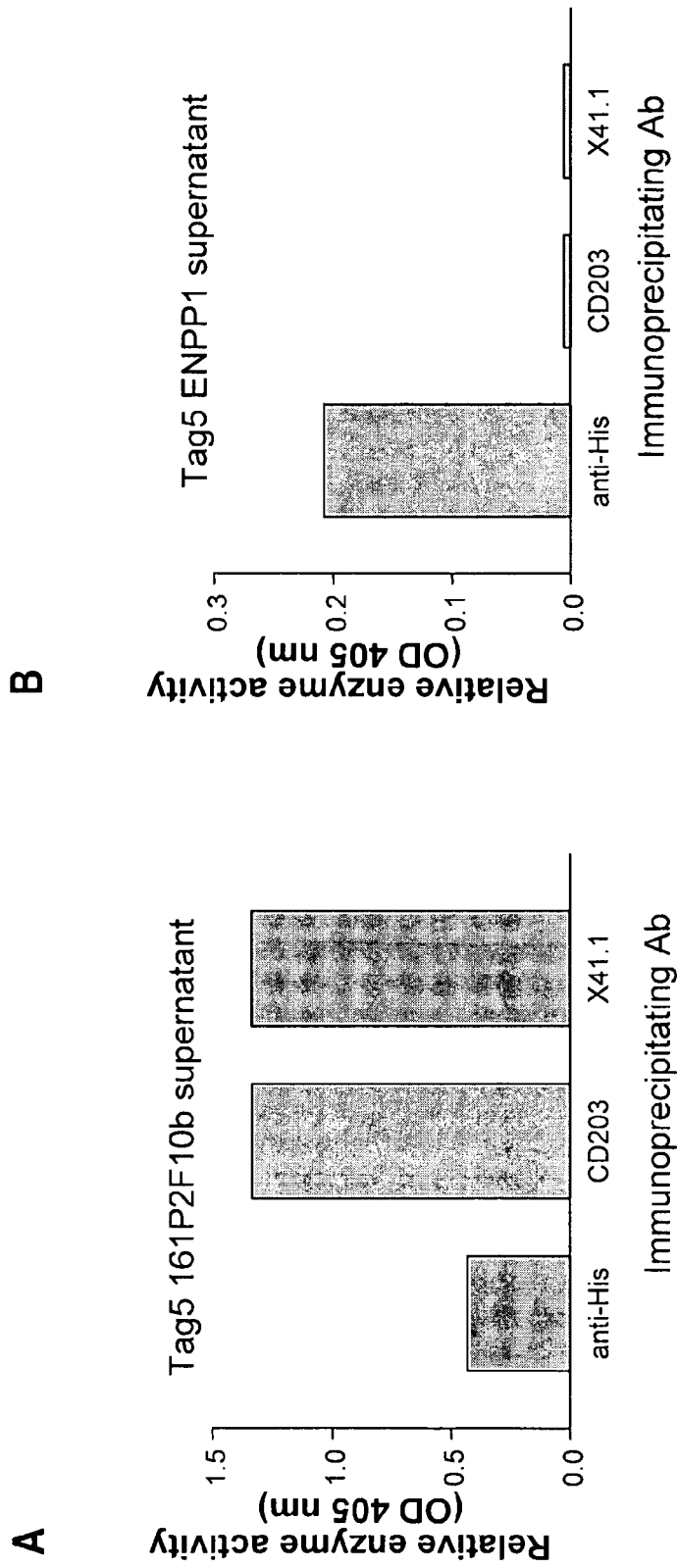
Figure 41: Anti-161P2F10b MAbs X41.6 does not cross-react with ENPP1

Figure 42: Detection of 161P2F10b in the conditioned media of 161P2F10b-expressing cells
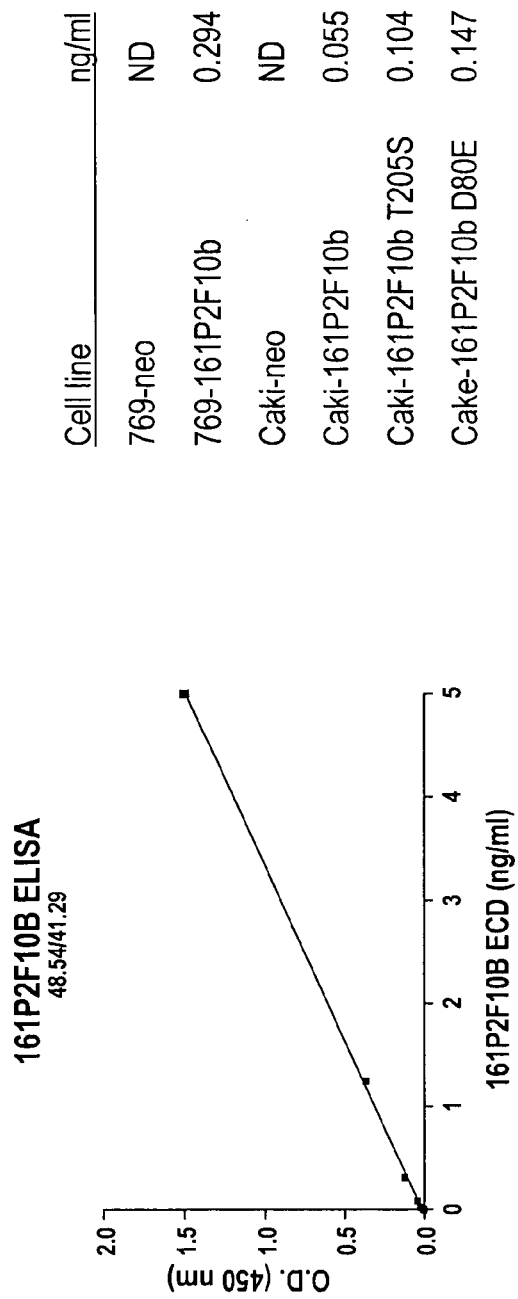

Figure 43: Detection of secreted 161P2F10b in the serum of mice bearing UGK3 human kidney cancer xenografts
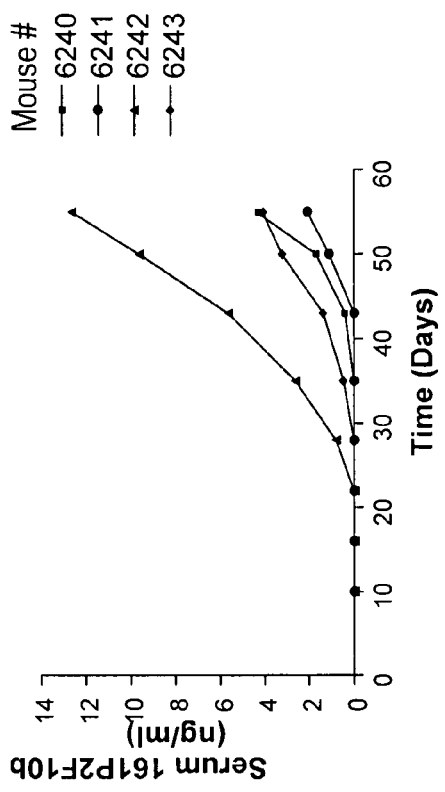
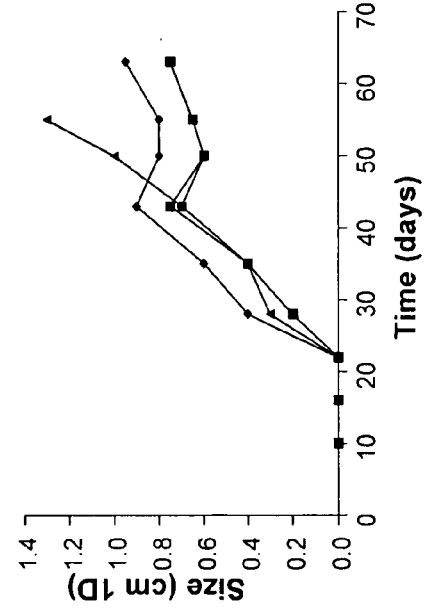
Mice were implanted with UGK3 xenograft cells and monitored for tumor size at the indicated times and bled to measure 161P2F10b expression in the serum by an 161P2F10b capture ELISA.

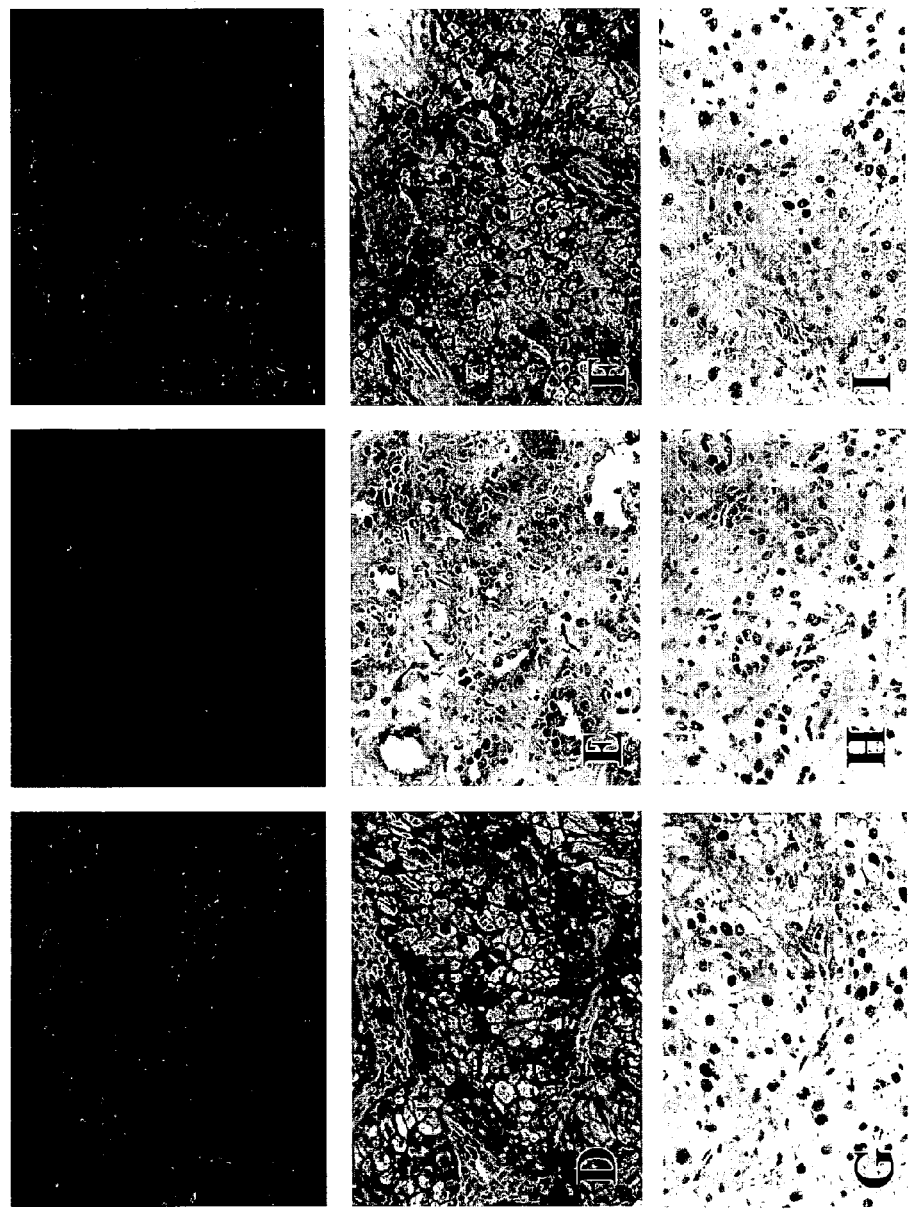
Figure 44: Expression of 161P2F10B Protein by Immunohistochemistry in Kidney Cancer Patient Specimens

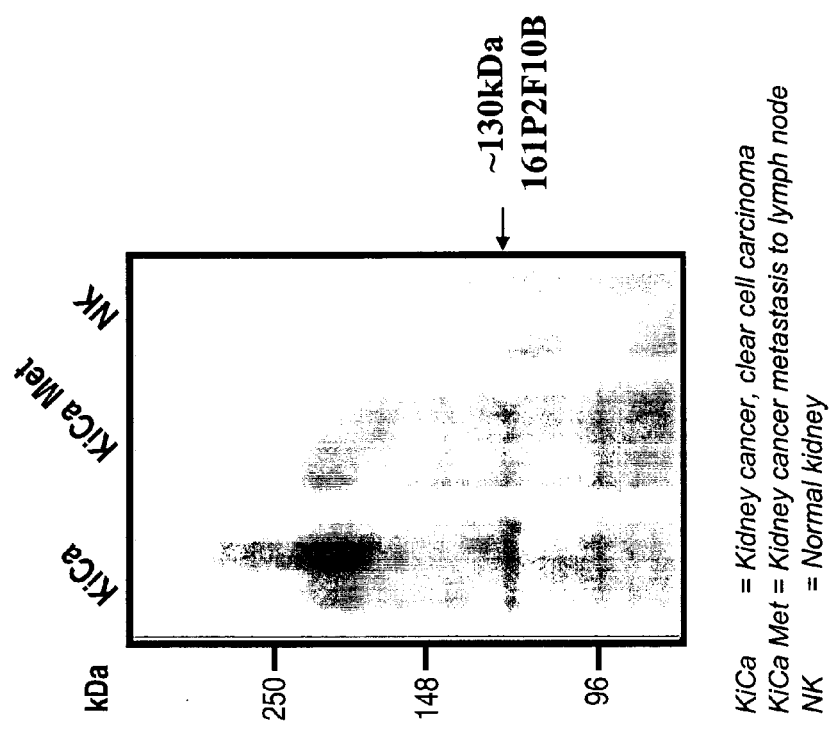
Figure 45 Expression of 161P2F10B in Human Patient Cancers by Western Blot
KiCa = Kidney cancer, clear cell carcinoma
KiCa Met = Kidney cancer metastasis to lymph node
NK = Normal kidney

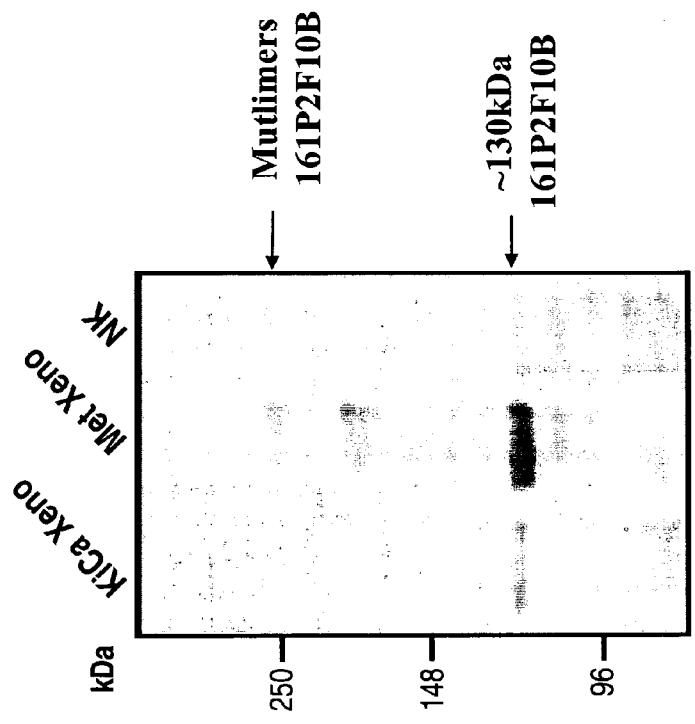
Figure 46 Expression of 161P2F10B in Human Xenograft Tissues by Western Blot
KiCa Xeno = Xenograft of kidney cancer, clear cell carcinoma
Met Xeno = Xenograft from Kidney cancer metastasis to lymph node
NK = Normal kidney

NUCLEIC ACID AND CORRESPONDING PROTEIN ENTITLED 161P2F10B USEFUL IN TREATMENT AND DETECTION OF CANCER

CROSS-REFERENCE TO RELATED APPLICATIONS

This application claims priority from U.S. patent application Ser. No. 10/005,480, filed Nov. 7, 2001 (now abandoned); and U.S. patent application Ser. No. 10/062,109, filed Jan. 31, 2002. The contents of each application listed in this paragraph are fully incorporated by reference herein for all purposes.

STATEMENT OF RIGHTS TO INVENTIONS MADE UNDER FEDERALLY SPONSORED RESEARCH

Not applicable.

FIELD OF THE INVENTION

The invention described herein relates to a gene and its encoded protein, termed 161P2F10B, expressed in certain cancers, and to diagnostic and therapeutic methods and compositions useful in the management of cancers that express 161P2F10B.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 30,000 men die annually of this disease—second only to lung cancer. Despite the magnitude of these figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res 1996 Sep 2 (9): 1445–51), STEAP (Hubert, et al., Proc Natl Acad Sci USA. Dec. 7, 1999; 96(25): 14523–8) and prostate stem cell antigen (PSCA) (Reiter et a., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

Renal cell carcinoma (RCC) accounts for approximately 3 percent of adult malignancies. Once adenomas reach a diameter of 2 to 3 cm, malignant potential exists. In the adult, the two principal malignant renal tumors are renal cell adenocarcinoma and transitional cell carcinoma of the renal pelvis or ureter. The incidence of renal cell adenocarcinoma is estimated at more than 29,000 cases in the United States, and more than 11,600 patients died of this disease in 1998. Transitional cell carcinoma is less frequent, with an incidence of approximately 500 cases per year in the United States.

Surgery has been the primary therapy for renal cell adenocarcinoma for many decades. Until recently, metastatic disease has been refractory to any systemic therapy. With recent developments in systemic therapies, particularly, immunotherapies, metastatic renal cell carcinoma may be approached aggressively in appropriate patients with a possibility of durable responses. Nevertheless, there is a remaining need for effective therapies for these patients.

Of all new cases of cancer in the United States, bladder cancer represents approximately 5 percent in men (fifth most common neoplasm) and 3 percent in women (eighth most common neoplasm). The incidence is increasing slowly, concurrent with an increasing older population. In 1998, there was an estimated 54,500 cases, including 39,500 in men and 15,000 in women. The age-adjusted incidence in the United States is 32 per 100,000 for men and eight per 100,000 in women. The historic male/female ratio of 3:1 may be decreasing related to smoking patterns in women. There were an estimated 11,000 deaths from bladder cancer in 1998 (7,800 in men and 3,900 in women). Bladder cancer incidence and mortality strongly increase with age and will be an increasing problem as the population becomes more elderly.

Most bladder cancers recur in the bladder. Bladder cancer is managed with a combination of transurethral resection of the bladder (TUR) and intravesical chemotherapy or immunotherapy. The multifocal and recurrent nature of bladder cancer points out the limitations of TUR. Most muscle-invasive cancers are not cured by TUR alone. Radical cystectomy and urinary diversion is the most effective means to eliminate the cancer but carry an undeniable impact on urinary and sexual function. There continues to be a significant need for treatment modalities that are beneficial for bladder cancer patients.

An estimated 130,200 cases of colorectal cancer occurred in 2000 in the United States, including 93,800 cases of colon cancer and 36,400 of rectal cancer. Colorectal cancers are the third most common cancers in men and women. Incidence rates declined significantly during 1992–1996 (−2.1% per year). Research suggests that these declines have been due to increased screening and polyp removal, preventing progression of polyps to invasive cancers. There were an estimated 56,300 deaths (47,700 from colon cancer, 8,600 from rectal cancer) in 2000, accounting for about 11% of all U.S. cancer deaths.

At present, surgery is the most common form of therapy for colorectal cancer, and for cancers that have not spread, it is frequently curative. Chemotherapy, or chemotherapy plus radiation, is given before or after surgery to most patients whose cancer has deeply perforated the bowel wall or has spread to the lymph nodes. A permanent colostomy (creation of an abdominal opening for elimination of body wastes) is occasionally needed for colon cancer and is infrequently required for rectal cancer. There continues to be a need for effective diagnostic and treatment modalities for colorectal cancer.

There were an estimated 164,100 new cases of lung and bronchial cancer in 2000, accounting for 14% of all U.S. cancer diagnoses. The incidence rate of lung and bronchial cancer is declining significantly in men, from a high of 86.5 per 100,000 in 1984 to 70.0 in 1996 In the 1990s, the rate of increase among women began to slow. In 1996, the incidence rate in women was 42.3 per 100,000.

Lung and bronchial cancer caused an estimated 156,900 deaths in 2000, accounting for 28% of all cancer deaths. During 1992–1996, mortality from lung cancer declined significantly among men (−1.7% per year) while rates for women were still significantly increasing (0.9% per year). Since 1987, more women have died each year of lung cancer than breast cancer, which, for over 40 years, was the major cause of cancer death in women. Decreasing lung cancer incidence and mortality rates most likely resulted from decreased smoking rates over the previous 30 years; however, decreasing smoking patterns among women lag behind those of men. Of concern, although the declines in adult tobacco use have slowed, tobacco use in youth is increasing again.

Treatment options for lung and bronchial cancer are determined by the type and stage of the cancer and include surgery, radiation therapy, and chemotherapy. For many localized cancers, surgery is usually the treatment of choice. Because the disease has usually spread by the time it is discovered, radiation therapy and chemotherapy are often needed in combination with surgery. Chemotherapy alone or combined with radiation is the treatment of choice for small cell lung cancer; on this regimen, a large percentage of patients experience remission, which in some cases is long lasting. There is however, an ongoing need for effective treatment and diagnostic approaches for lung and bronchial cancers.

An estimated 182,800 new invasive cases of breast cancer were expected to occur among women in the United States during 2000. Additionally, about 1,400 new cases of breast cancer were expected to be diagnosed in men in 2000. After increasing about 4% per year in the 1980s, breast cancer incidence rates in women have leveled off in the 1990s to about 110.6 cases per 100,000.

In the U.S. alone, there were an estimated 41,200 deaths (40,800 women, 400 men) in 2000 due to breast cancer. Breast cancer ranks second among cancer deaths in women. According to the most recent data, mortality rates declined significantly during 1992–1996 with the largest decreases in younger women, both white and black. These decreases were probably the result of earlier detection and improved treatment.

Taking into account the medical circumstances and the patient's preferences, treatment of breast cancer may involve lumpectomy (local removal of the tumor) and removal of the lymph nodes under the arm; mastectomy (surgical removal of the breast) and removal of the lymph nodes under the arm; radiation therapy; chemotherapy; or hormone therapy. Often, two or more methods are used in combination. Numerous studies have shown that, for early stage disease, long-term survival rates after lumpectomy plus radiotherapy are similar to survival rates after modified radical mastectomy. Significant advances in reconstruction techniques provide several options for breast reconstruction after mastectomy. Recently, such reconstruction has been done at the same time as the mastectomy.

Local excision of ductal carcinoma in situ (DCIS) with adequate amounts of surrounding normal breast tissue may prevent the local recurrence of the DCIS. Radiation to the breast and/or tamoxifen may reduce the chance of DCIS occurring in the remaining breast tissue. This is important because DCIS, if left untreated, may develop into invasive breast cancer. Nevertheless, there are serious side effects or sequelae to these treatments. There is, therefore, a need for efficacious breast cancer treatments.

There were an estimated 23,100 new cases of ovarian cancer in the United States in 2000. It accounts for 4% of all cancers among women and ranks second among gynecologic cancers. During 1992–1996, ovarian cancer incidence rates were significantly declining. Consequent to ovarian cancer, there were an estimated 14,000 deaths in 2000. Ovarian cancer causes more deaths than any other cancer of the female reproductive system.

Surgery, radiation therapy, and chemotherapy are treatment options for ovarian cancer. Surgery usually includes the removal of one or both ovaries, the fallopian tubes (salpingo-oophorectomy), and the uterus (hysterectomy). In some very early tumors, only the involved ovary will be removed, especially in young women who wish to have children. In advanced disease, an attempt is made to remove all intra-abdominal disease to enhance the effect of chemotherapy. There continues to be an important need for effective treatment options for ovarian cancer.

There were an estimated 28,300 new cases of pancreatic cancer in the United States in 2000. Over the past 20 years, rates of pancreatic cancer have declined in men. Rates among women have remained approximately constant but may be beginning to decline. Pancreatic cancer caused an estimated 28,200 deaths in 2000 in the United States. Over the past 20 years, there has been a slight but significant decrease in mortality rates among men (about −0.9% per year) while rates have increased slightly among women.

Surgery, radiation therapy, and chemotherapy are treatment options for pancreatic cancer. These treatment options can extend survival and/or relieve symptoms in many patients but are not likely to produce a cure for most. There is a significant need for additional therapeutic and diagnostic options for pancreatic cancer.

SUMMARY OF THE INVENTION

The present invention relates to a gene, designated 161P2F10B, that has now been found to be over-expressed in the cancer(s) listed in Table I. Northern blot expression analysis of 161P2F10B gene expression in normal tissues shows a restricted expression pattern in adult tissues. The nucleotide (FIG. 2) and amino acid (FIG. 2, and FIG. 3) sequences of 161P2F10B are provided. The tissue-related profile of 161P2F10B in normal adult tissues, combined with the over-expression observed in the tissues listed in Table I, shows that 161P2F10B is aberrantly over-expressed in at least some cancers, and thus serves as a useful diagnostic, prophylactic, prognostic, and/or therapeutic target for cancers of the tissue(s) such as those listed in Table I.

The invention provides polynucleotides corresponding or complementary to all or part of the 161P2F10B genes, mRNAs, and/or coding sequences, preferably in isolated form, including polynucleotides encoding 161P2F10B-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 161P2F10B-related protein, as well as the peptides/proteins themselves; DNA, RNA, DNA/RNA hybrids, and related molecules, polynucleotides or oligonucleotides complementary or having at least a 90% homology to the 161P2F10B genes or mRNA sequences or parts thereof, and polynucleotides or oligonucleotides that hybridize to the 161P2F10B genes, mRNAs, or to 161P2F10B-encoding polynucleotides. Also provided are means for isolating cDNAs and the genes encoding 161P2F10B. Recombinant DNA molecules containing 161P2F10B polynucleotides, cells transformed or transduced with such molecules, and host-vector systems for the expression of 161P2F10B gene products are also provided. The invention further provides antibodies that bind to 161P2F10B proteins and polypeptide fragments thereof, including polyclonal and monoclonal antibodies, murine and other mammalian antibodies, chimeric antibodies, humanized and fully human antibodies, and antibodies labeled with a detectable marker or therapeutic agent. In certain embodiments, there is a proviso that the entire nucleic acid sequence of FIG. 2 is not encoded and/or the entire amino acid sequence of FIG. 2 is not prepared. In certain embodiments, the entire nucleic acid sequence of FIG. 2 is encoded and/or the entire amino acid sequence of FIG. 2 is prepared, either of which are in respective human unit dose forms.

The invention further provides methods for detecting the presence and status of 161P2F10B polynucleotides and proteins in various biological samples, as well as methods for identifying cells that express 161P2F10B. A typical embodiment of this invention provides methods for monitoring 161P2F10B gene products in a tissue or hematology sample having or suspected of having some form of growth dysregulation such as cancer.

The invention further provides various immunogenic or therapeutic compositions and strategies for treating cancers that express 161P2F10B such as cancers of tissues listed in Table I, including therapies aimed at inhibiting the transcription, translation, processing or function of 161P2F10B as well as cancer vaccines. In one aspect, the invention provides compositions, and methods comprising them, for treating a cancer that expresses 161P2F10B in a human subject wherein the composition comprises a carrier suitable for human use and a human unit dose of one or more than one agent that inhibits the production or function of 161P2F10B. Preferably, the carrier is a uniquely human carrier. In another aspect of the invention, the agent is a moiety that is immunoreactive with 161P2F10B protein. Non-limiting examples of such moieties include, but are not limited to, antibodies (such as single chain, monoclonal, polyclonal, humanized, chimeric, or human antibodies), functional equivalents thereof (whether naturally occurring or synthetic), and combinations thereof. The antibodies can be conjugated to a diagnostic or therapeutic moiety. In another aspect, the agent is a small molecule as defined herein.

In another aspect, the agent comprises one or more than one peptide which comprises a cytotoxic T lymphocyte (CTL) epitope that binds an HLA class I molecule in a human to elicit a CTL response to 161P2F10B and/or one or more than one peptide which comprises a helper T lymphocyte (HTL) epitope which binds an HLA class II molecule in a human to elicit an HTL response. The peptides of the invention may be on the same or on one or more separate polypeptide molecules. In a further aspect of the invention, the agent comprises one or more than one nucleic acid molecule that expresses one or more than one of the CTL or HTL response stimulating peptides as described above. In yet another aspect of the invention, the one or more than one nucleic acid molecule may express a moiety that is immunologically reactive with 161P2F10B as described above. The one or more than one nucleic acid molecule may also be, or encodes, a molecule that inhibits production of 161P2F10B. Non-limiting examples of such molecules include, but are not limited to, those complementary to a nucleotide sequence essential for production of 161P2F10B (e.g. antisense sequences or molecules that form a triple helix with a nucleotide double helix essential for 161P2F10B production) or a ribozyme effective to lyse 161P2F10B mRNA.

Note that to determine the starting position of any peptide set forth in Tables VIII–XXI and XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides in Table VII. Generally, a unique Search Peptide is used to obtain HLA peptides of a particular for a particular variant. The position of each Search Peptide relative to its respective parent molecule is listed in Table VII. Accordingly, if a Search Peptide begins at position "X", one must add the value "X−1" to each position in Tables VIII–XXI and XXII to XLIX to obtain the actual position of the HLA peptides in their parental molecule. For example, if a particular Search Peptide begins at position 150 of its parental molecule, one must add 150-1, i.e., 149 to each HLA peptide amino acid position to calculate the position of that amino acid in the parent molecule.

One embodiment of the invention comprises an HLA peptide, that occurs at least twice in Tables VIII–XXI and XXII to XLIX collectively, or an oligonucleotide that encodes the HLA peptide. Another embodiment of the invention comprises an HLA peptide that occurs at least once in Tables VIII-XXI and at least once in tables XXII to XLIX, or an oligonucleotide that encodes the HLA peptide.

Another embodiment of the invention is antibody epitopes, which comprise a peptide regions, or an oligonucleotide encoding the peptide region, that has one two, three, four, or five of the following characteristics:

i) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a peptide region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or v) a peptide region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-turn profile of FIG. 9.

BRIEF DESCRIPTION OF THE FIGURES

FIG. 1. The 161P2F10B SSH sequence of 182 nucleotides.

FIG. 2. A) The cDNA and amino acid sequence of 161P2F10B variant 1 (also called "161P2F10B v 1" or "161P2F10B variant 1") is shown in FIG. 2A. The start methionine is underlined. The open reading frame extends from nucleic acid 44-2671 including the stop codon.

Figure 10:
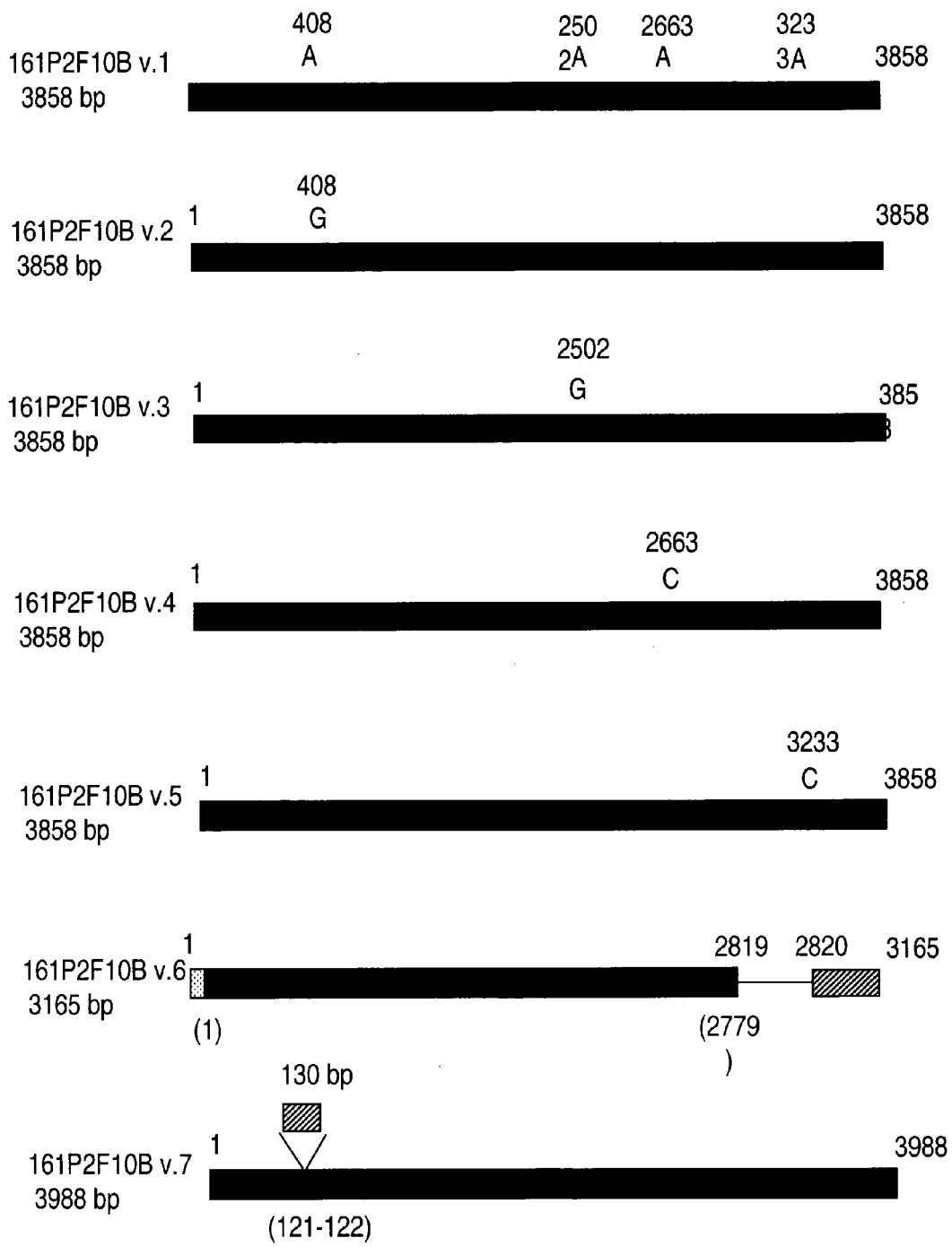

B) The cDNA and amino acid sequence of 161P2F10B variant 2 (also called "161P2F10B v.2") is shown in FIG. 2B. The codon for the start methionine is underlined. The open reading frame extends from nucleic acid 44-2671 including the stop codon.

C) The cDNA and amino acid sequence of 161P2F10B variant 3 (also called "161P2F10B v.3") is shown in FIG. 2C. The codon for the start methionine is underlined. The open reading frame extends from nucleic acid 44-2671 including the stop codon. The cDNA and amino acid sequence of 161P2F10B variant4 (also called "161P2F10B v.4") is shown in D) FIG. 2D. The codon for the start methionine is underlined. The open reading frame extends from nucleic acid 44-2671 including the stop codon.

E) The cDNA and amino acid sequence of 161P2F10B variant 5 (also called "161P2F10B v.5") is shown in FIG. 2E. The codon for the start methionine is underlined. The open reading frame extends from nucleic acid 44-2671 including the stop codon.

F) The cDNA and amino acid sequence of 161P2F10B variant 6 (also called "161P2F10B v.6") is shown in FIG. 2F. The codon for the start methionine is underlined. The open reading frame extends from nucleic acid 84–2711 including the stop codon.

G) The cDNA and amino acid sequence of 161P2F10B variant 7 (also called "161P2F10B v.7") is shown in FIG. 2G. The codon for the start methionine is underlined. The open reading frame extends from nucleic acid 276-2801 including the stop codon.

FIG. 3.

A) Amino acid sequence of 161P2F10B v.1 is shown in FIG. 3A; it has 875 amino acids.

B) The amino acid sequence of 161P2F10B v.2 is shown in FIG. 3B; it has 875 amino acids.

C) The amino acid sequence of 161P2F10B v.3 is shown in FIG. 3C; it has 875 amino acids.

D) The amino acid sequence of 161P2F10B v.4 is shown in FIG. 3D; it has 875 amino acids.

E) The amino acid sequence of 161P2F10B v.7 is shown in FIG. 3E; it has 841 amino acids. As used herein, a reference to 161P2F-10B includes all variants thereof, including those shown in FIGS. 2, 3, 10, and 11, unless the context clearly indicates otherwise.

FIG. 4. FIG. 4A: Alignment of 161P2F10 with variant 1 carrying a K to R mutation. FIG. 4B: Alignment of 161P2F10B and SNP variant carrying a T to P mutation.

FIG. 5. Hydrophilicity amino acid profile of 161P2F10B determined by computer algorithm sequence analysis using the method of Hopp and Woods (Hopp T. P., Woods K. R., 1981. Proc. Natl. Acad. Sci. U.S.A. 78:3824–3828) accessed on the Protscale website located on the World Wide Web through the ExPasy molecular biology server.

FIG. 6. Hydropathicity amino acid profile of 161P2F10B determined by computer algorithm sequence analysis using the method of Kyte and Doolittle (Kyte J., Doolittle R. F., 1982. J. Mol. Biol. 157:105–132) accessed on the ProtScale website located on the World Wide Web through the ExPasy molecular biology server.

FIG. 7. Percent accessible residues amino acid profile of 161P2F10B determined by computer algorithm sequence analysis using the method of Janin (Janin J., 1979 Nature 277:49 1–492) accessed on the ProtScale website located on the World Wide Web through the ExPasy molecular biology server.

FIG. 8. Average flexibility amino acid profile of 161P2F10B determined by computer algorithm sequence analysis using the method of Bhaskaran and Ponnuswamy (Bhaskaran R., and Ponnuswamy P. K., 1988. Int. J. Pept. Protein Res. 32:242–255) accessed on the ProtScale website located on the World Wide Web through the ExPasy molecular biology server.

FIG. 9. Beta-turn amino acid profile of 161P2F10B determined by computer algorithm sequence analysis using the method of Deleage and Roux (Deleage, G., Roux B. 1987 Protein Engineering 1:289–294) accessed on the ProtScale website located on the World Wide Web through the ExPasy molecular biology server.

FIG. 10. Variants 161P2F10B v.2 through v.5 are variants with single nucleotide differences. Though these SNP variants are shown separately, they could also occur in any combinations and in any transcript variants that contains the base pairs. Variants 161P2F10B v.6 and v.7 are transcript variants. Variant 161P2F10B v.6 has extra 40 bases at the 5' end and a different 3' end portion, while variant 161P2F10B v.7 has an insertion of 130 bases in between positions 121 and 122 of 161P2F10B v.1. Numbers in "( )" correspond to those of 161P2F10B v.1. Black box shows the same sequence as 161P2F10B v.1. SNPs are indicated above the box.

Figure 11:
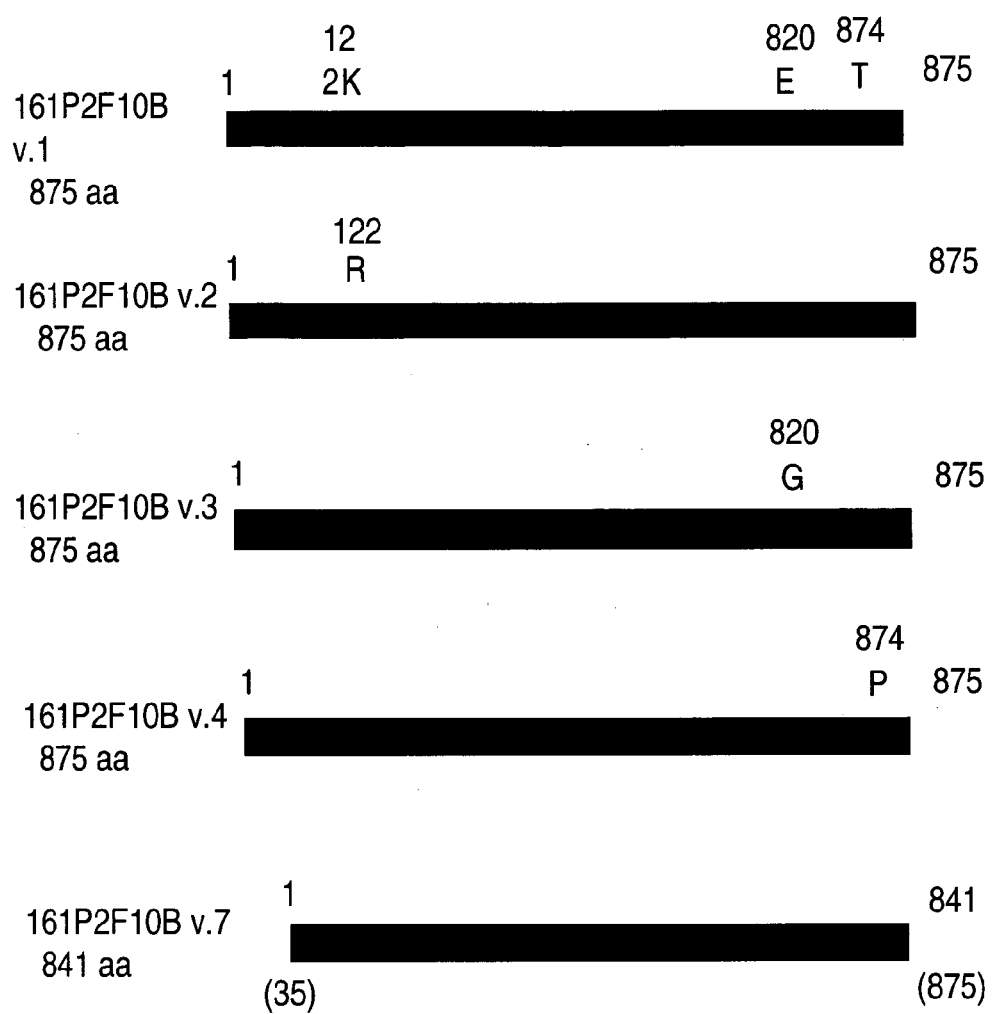

FIG. 11. Protein variants correspond to nucleotide variants. Nucleotide variants 161P2F10B v.5 and v.6 in FIG. 10 code for the same protein as 161P2F10B v.1. Nucleotide variants 161P2F10B v.6 and v.7 are splice variants of v.1, as shown in FIG. 12. Single amino acid differences were indicated above the boxes. Black boxes represent the same sequence as 161 P2F10B v.1. Numbers underneath the box correspond to 161 P2F10B v.1.

FIG. 12. Intentionally Omitted

Figure 13B:
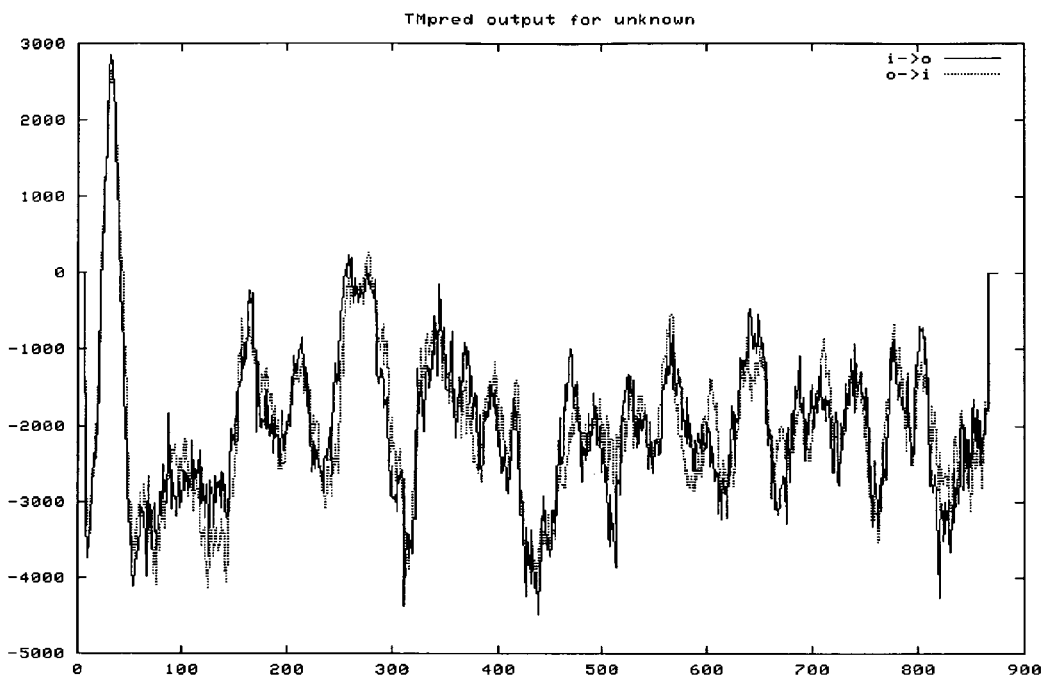
Figure 13C:
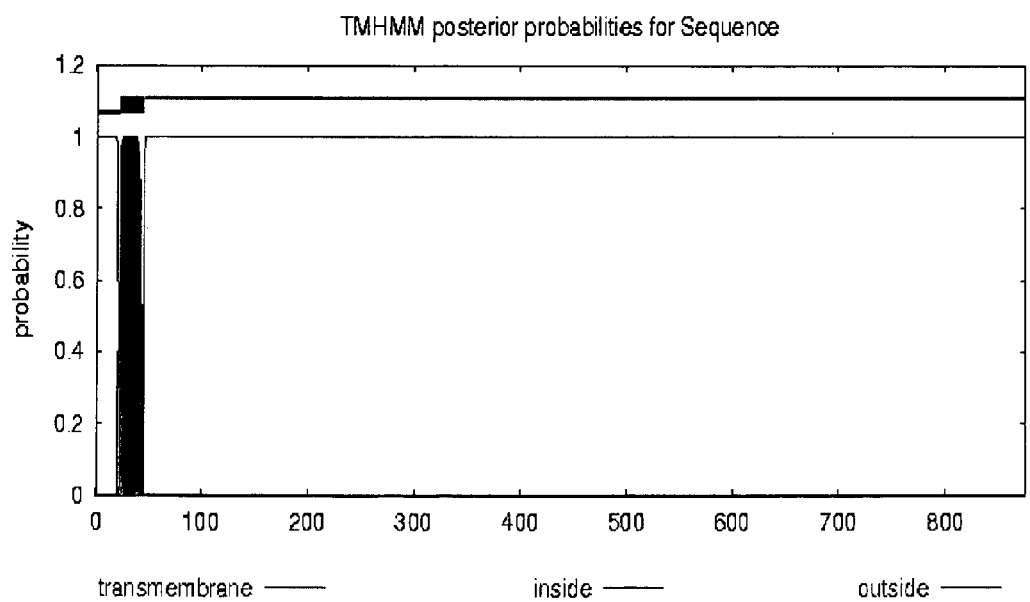

FIG. 13. The secondary structure of 161P2F10B (SEQ ID NO: 103), namely the predicted presence and location of alpha helices, extended strands, and random coils, is predicted from the primary amino acid sequence using the HNN—Hierarchical Neural Network method, accessed from the ExPasy molecular biology server. The analysis indicates that 161P2F10B is composed 31.31% alpha helix, 11.31% extended strand, and 57.37% random coil (FIG. 13A). Shown graphically in FIG. 13 panels B and C are the results of analysis using the TMpred (FIG. 13B) and TMHMM (FIG. 13C) prediction programs depicting the location of the transmembrane domain.

FIG. 14. First strand cDNA was generated from normal stomach, normal brain, normal heart, normal liver, normal skeletal muscle, normal testis, normal prostate, normal bladder, normal kidney, normal colon, normal lung, normal pancreas, and a pool of cancer specimens from prostate cancer patients, bladder cancer patients, kidney cancer patients, colon cancer patients, lung cancer patients, pancreas cancer patients, a pool of prostate cancer xenografts (LAPC-4AD, LAPC-4AI, LAPC-9AD and LAPC-9AI), and a pool of 2 patient prostate metastasis to lymph node. Normalization was performed by PCR using primers to actin. Semi-quantitative PCR, using primers to 161P2F10B, was performed at 26 and 30 cycles of amplification. Samples were run on an agarose gel, and PCR products were quantitated using the AlphaImager software. Results show strong expression in prostate cancer, bladder cancer, kidney cancer, colon cancer, lung cancer, pancreas cancer, bone cancer, lymphoma cancer, uterus cancer, compared to all normal tissues tested. Strong expression was also detected in the xenograft pool as well as the prostate cancer metastasis to lymph node specimens.

FIG. 15. First strand cDNA was prepared from a panel of kidney cancer clear cell carcinoma (A), kidney cancer papillary carcinoma (B), and in uterus patient cancer specimens (C). Normalization was performed by PCR using primers to actin. Semi-quantitative PCR, using primers to 161P2F10B, was performed at 26 and 30 cycles of amplification. Samples were run on an agarose gel, and PCR products were quantitated using the AlphaImager software. Expression was recorded as absent, low, medium or strong. Results show expression of 161P2F10B in 94.7% of clear cell renal carcinoma, 62.5% of papillary renal cell carcinoma, and in 61.5% of uterus cancer.

FIG. 16. Shows Phosphodiesterase Activity of 3T3-161P2F10B Stable Cells. Cell surface phosphodiesterase activity is assayed on 3T3 and 3T3-161P2F10B using the substrate p-nitrophenyl thymidine-5'-L-monophosphate.

FIG. 17. Shows Protection from Apoptosis by 161P2F10B.

FIG. 18. Shows that 161P2F10B Protects from Apoptotic Signals.

FIG. 19. Shows that 161P2F10B Protects from Staurosporine and UV-Induced Apoptosis.

FIG. 20. Shows that 161P2F10B Expression Protects Cells from Drug and UV-Induced Apoptosis. NIH 3T3 cells were treated with the staurosporine or UV, stained with Annexin V-FITC and propidium iodide, and analyzed by FACS.

FIG. 21. Shows that 161P2F10B Protects from Apoptosis by Chemotherapeutic Agents.

FIG. 22 Shows the effect of 161P2F10B on In Vitro Invasion. Invasion was determined by measuring the fluorescence of cells in the lower chamber relative to the fluorescence of the entire cell population.

FIG. 23. Shows that 161P2F10B MAb Attenuates the Growth of Human Kidney Cancer Xenograft in SCID Mice.

FIG. 24. Detection of 161P2F10B protein by immunohistochemistry in kidney cancer patient specimens. Two renal clear cell carcinoma tissue specimens and one renal papillary cell carcinoma were obtained from three different kidney cancer patients. Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed strong expression of 161P2F10B in all three renal carcinoma patient tissues (FIG. 24 panels A–C). The expression was detected mostly around the cell membrane in the renal clear cell carcinoma specimens, indicating that 161P2F10B is membrane associated in this kidney cancer, and throughout the cells in the papillary cell carcinoma with an apparent predisposition towards the cell periphery.

FIG. 25. Detection of 161P2F10B protein by immunohistochemistry in a prostate cancer patient specimen. Tissue specimens of prostate adenocarcinoma were obtained from eight different prostate cancer patients. Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed expression of 161P2F10B in six of the eight prostate cancer patient tissues, one of which is illustrated in this FIG. 25. 161P2F10B was expressed on the tumor cells with an apparent proclivity towards the luminal cell surface.

FIG. 26. Detection of 161P2F10B protein by immunohistochemistry in a colon cancer patient specimen. Tissue specimens of colon adenocarcinoma were obtained from nine different colon cancer patients Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed strong expression of 161P2F10B in two of the nine colon cancer patient tissues, one of which is illustrated in this FIG. 26. 161P2F10B was most strongly expressed on the tumor cells with a luminal cell surface but was also expressed throughout all the tumor tissue.

FIG. 27. Detection by immunohistochemistry of 161P2F10B protein expression in kidney clear cell cancer patient specimens by specific binding of mouse monoclonal antibodies. Renal clear cell carcinoma tissue and its matched normal adjacent were obtained from a kidney cancer patient. Frozen tissues were cut into 4 micron sections and fixed in acetone for 10 minutes. The sections were then incubated either mouse monoclonal anti-ENPP3 antibody (Coulter-Immunotech, Marseilles, France) for 3 hours (FIG. 27 panels A, D), or mouse monoclonal antibody X41(3)50 (FIG. 27 panels B, E), or mouse monoclonal antibody X41 (3)37 (FIG. 27 panels C, F). The slides were washed three times in buffer and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy (FIG. 27 panels A–F). The results showed strong expression of 161P2F10B in the renal clear cell carcinoma patient tissue (FIG. 27 panels A–C), but weakly in normal kidney (FIG. 27 panels D–F). The expression was predominantly around the cell periphery indicating that 161P2F10B is membrane associated in kidney cancer tissues. The weak expression detected in normal kidney was localized to the kidney proximal tubules.

FIG. 28. Expression of 161P2F10b in recombinant cell lines.

A.) Rat1, NIH3T3, NSO, and 300.19 cells stably expressing either 16P2F10b or a control vector (neo) were stained with PE-conjugated anti-CD203c MAb and examined by flow cytometry. (Light dotted line: control neo cells. Dark line: 161P2F10 cells)

B.) Rat1, NIH3T3, NSO, 300.19, and UT7 cells were stained with either PE-conjugated anti-CD203c MAb or control IgG1-PE Ab and examined by flow cytometry. (Light dotted line: control MAb. Dark line: 97A6 (CD203c) MAb.) Shown is the mean fluorescence of the staining of the control and 161P2F10b cells and the ratio of the values. This was used to rank the cells for relative expression levels of 161P2F10b.

C.) The relative cell surface phosphodiesterase enzymatic activity of the recombinant cells was measured by the addition of p-nitrophenyl thymidine-5'-L-monophosphate (p-nTMP) phosphodiesterase substrate. There is a correlation between expression levels determined by flow cytometry and surface enzyme activity.

FIG. 29. Surface expression and phosphodiesterase activity of 161P2F10b.

A. 161P2F10b transfected 293T cells were stained with the commercially available (Coulter Immunotech) PE-conjugated anti-CD-203c MAb, a commercially available anti-ENPP3 (161P2F10b) MAb and examined by fluorescent microscopy.

B. 161P2F10b and vector transfected 293T cells were incubated in assay buffer containing the phosphodiesterase-1 colorimetic substrate p-nitrophenyl thymidine-5'-L-monophosphate (p-nTMP) and optical densities (O.D.) were obtained at 405 nm.

FIG. 30. Relative expression and enzymatic activity of 161P2F10b mutants in recombinant Caki kidney cancer cells. Caki kidney cancer cells were infected with retrovirus containing either wildtype 161P2F120b cDNA, or point mutant cDNAs encoding either a threonine to serine mutation (T/S) at amino acid 205, a threonine to alanine mutation (T/A) at amino acid 205, or a aspartic acid to glutamic acid mutation (DIE) at amino acid 80. Stably expressing cell lines were analyzed for 161P2F10b expression by flow cytometry with 97A6 (CD203c) MAb (A) and for enzymatic activity with p-nTMP substrate (B). Mutation of threonine 205 to aspartic acid or alanine abolishes the ability to cleave the substrate, demonstrating that threonine 205 is critical to the enzymatic activity of 161P2F10b.

FIG. 31. Purification of a recombinant protein encoding the extracellular domain (ECD) of 161P2F10b. 293T cells were transfected with a Tag5 secretion expression vector encoding the ECD of 161P2F10b (amino acids 46–875). The recombinant protein was purified from the conditioned media using either metal chelate affinity chromatography (not shown) or with an immunoaffinity column comprised of anti-161P2F10b MAb X41.6 (shown). 2 ul of 2 separate purified lots were analyzed by SDS-PAGE and Coomasie staining. BSA protein was also analyzed as a quantitative standard.

FIG. 32. 161P2F10b enzymatic assays utilizing P-nitrophenyl-thymidine monophosphate (p-nTMP).

A. Schematic of the colorimetric enzyme assay showing enzymatic cleavage of the p-nTMP substrate generating a soluble yellow product.

B. Kinetics and dose response of the enzymatic action of purified Tag5-ECD 161P2F10b protein on p-nTMP (2.5 mM). Optical densities (OD) of reactions were determined at 405 nm.

C. Cell surface enzymatic assay of 161P2F10b-expressing Rat1 cells. The indicated number of Rat1-161P2F10b cells were incubated with p-nTMP substrate and the OD's of the wells were determined.

D. ATP and NAD (not shown) serve as competitive inhibitors 161P2F10b cleavage of p-nTMP. Purified Tag5-ECD protein (20 ng) was incubated with p-nTMP substrate in the absence or presence of the indicated amounts of ATP. The OD's of reactions were obtained at 405 nm.

FIG. 33. Analysis of the internalization of anti-161P2F10b MAb X41.6.

Panel A. Schematic of the protocol. Rat1-161P2F10b cells are incubated with anti-161P2F10b MAb at 4C, washed, and then either kept at 4C and stained with anti-mouse IgG secondary-PE conjugated Ab at 4C (B, total surface staining) or moved to 37C for various times and then stained with secondary Ab at 4C (C, residual surface staining). Panels B and C demonstrate that MAb X41.6 engagement of surface 161P2F10b causes internalization at 37C of the complex indicated by the progressive decrease in mean fluorescence intensity (MFI).

FIG. 34. Internalization of selected anti-161P2F10b murine MAbs. Internalization of selected anti-161P2F10b MAbs are by flow cytometry are shown. Internalization is indicated by a decrease in the mean fluorescence intensity (MFI) of cells moved to 37C versus cells stained at 4C.

FIG. 35. Antibody engagement of 161P2F10b results in its internalization. Internalization of the commercially available MAb 97A6, anti-CD203c, is shown by fluorescence microscopy following staining of Rat1-161P2F10b cells. The cells were incubated with CD203c-PE conjugated MAb at 4C, washed, and then moved to 37C for the indicated times and then examined by fluorescence microscopy. At 4C, the staining of the cells is cell surface (bright halo of fluorescence around individual cells). Upon moving to 37C, there is a gradual loss of the surface fluorescence, concomitant with capping of the MAb to punctate regions on the surface, followed by the appearance of punctate and diffuse intracellular fluorescence and a total loss of surface fluorescence.

FIG. 36. Effects of X41.50 MAb-saporin toxin conjugate on Caki-161P2F10b cells. Shown is the morphology of Caki-161P2F10b cells that were treated with and without the indicated concentrations of the internalizing anti-161P2F10b MAb and an anti-mouse IgG-saporin toxin secondary Ab (2 ug/ml). Saporin is unable to enter cells efficiently on its own and must be internalized for its toxic mechanism (protein synthesis inhibition) to work. Cells were first incubated at 4C with X41.50 MAb to allow surface binding, than either media or the saporin-conjugated secondary Ab was added and the cells were incubated for 72 hours at 37C. Cells incubated with either media alone, X41.50 alone, or the secondary-saponn Ab alone had no effect on Caki-161P2F10b growth and morphology, exemplified by a viable confluent monolayer. However, cells incubated with X41.50 MAb (2 and 0.5 ug/ml) and the secondary saporin-conjugate exhibited signs of growth inhibition (did not reach confluency) and apoptosis (small round floating apoptotic cells above the attached cell layer). This demonstrates the utility of anti-161P2F10b MAbs drug/toxin conjugates as a therapeutic approach for 161P2F10b-expressing cancers and diseased tissues.

FIG. 37. Internalization-mediated downregulation of 161P2F10 protein by MAb X41.50. Rat1-161P2F10b cells were incubated with and without 10 ug/ml of MAb X41.50 for 72 hours. Cells were washed, fixed, permeabilized, and stained with PE-conjugated CD203c MAb to monitor total 161P2F10b protein expression. The data shows a marked decrease in staining following treatment of the cells with X41.50, demonstrating downregulation of 161P2F10b protein.

FIG. 38. Anti-161P2F10b MAbs downregulate surface 161P2F10b enzymatic activity. Rat1-161P2F10b cells were treated with and without various concentrations of the indicated MAbs for 48 hours and then assayed for surface enzymatic activity using p-n-TMB substrate. The data demonstrates that engagement and internalization of surface 161P2F10b by MAbs results in the concamitant loss of surface 161P2F10b enzymatic activity.

FIG. 39. Characteristics of mouse 161P2F10b MAbs. Shown is a summary of various characteristics of MAbs that recognize 161P2F10b.

The relative affinity of the MAbs was determined by saturation binding ELISA using the recombinant Tag5-ECD protein. The Kd of the binding reaction was determined using a one-site binding non-linear regression analysis of the data using GraphPad Prism software version 3.02 (Graphpad Software, San Diego, Calif.).

Relative surface staining was determined using 10 ug/ml of each MAb on RAT1-161P2F10b cells.

Relative ability to internalize was also carried out on Rat1-161P2F10b cells comparing staining with 10 ug/ml of MAb at 4C versus residual staining following incubation at 37C for 30 minutes.

The ability of the MAbs to downregulate surface enzyme activity was determined by incubation of Rat1-161P2F10b cells with 10 ug/ml of each MAb for 72 hours then assaying surface enzyme activity with p-nTMP substrate.

Relative specific immunohistochemical staining (1HC) was determined using 10 ug/ml of each MAb on 161P2F10b-expressing frozen section kidney clear cell carcinoma samples.

The epitope family was determined by competition binding ELISA using the Tag5-ECD protein as target. Tag5-ECD ELISA coated wells were first incubated with or without 10 ug/ml of competitor MAb, washed, and then incubated with 1 ug/ml of HRP-labeled test MAb. MAb that compete for binding (reduction of the signal of the test MAb with prior incubation with competitor) must share the same or an overlapping epitope and are thus assigned to an epitope family. Of the MAbs listed, at least 2 epitope families are defined.

FIG. 40. Surface staining of selected anti-161P2F10b MAbs. Specific binding of cell surface 161P2F10b was determined by incubation of Rat1-161P2F10 (dark line) and Rat1-neo control cells (light dotted line) with 10 ug/ml of each MAb for 1.5 hours at $4C_1$-Cells-were washed, incubated with goat-anti-mouse-PE conjugated secondary Ab, washed again, and analyzed by flow cytometry. Shown are examples of MAb derived from DNA-based immunization of mice with an FC-fusion of the ECD (X41.6, X41.15, X41.17, X41.29, X41.37, X41.50), also DNA-based immunization with Tag5-ECD, and with Rat1-161P2F10b cells (the last data was generated using the respective hybridoma supernatant at a 1:50 dilution) was performed.

FIG. 41. Anti-161P2F10b MAbs X41.6 and 97A6 (CD203c) do not cross-react with ENPP1. Conditioned media from 293T cells transfected with either Tag5–161P2F10b or ENPP1 His-tagged vectors was subjected to immunoprecipitation analysis using 5 ug of MAb X41.6, MAb 97A6 (CD203c), or anti-His pAb. Following washing of the immune complexes, phosphodiesterase activity was determined by the addition of p-nTMP substrate. Enzymatic activity is seen in anti-His immune complexes from both Tag5 161P2F10b and Tag5 ENPP1 media due to the presence of the His epitope in both proteins. However, enzymatic activity is seen only in the immune complexes of X41.6 and 97A6 from Tag5 161P2F10 conditioned media and not with Tag5 ENPP1 media. These data demonstrate that MAbs X41.6 and 97A6 (CD203c) do not crossreact with the homologous ectonucleotide pyrophosphatase/phosphodiesterase family member ENPP1.

FIG. 42. Detection of 161P2F10b in the conditioned media of 161P2F10b-expressing cells. Supernatants of the indicated 161P2F20b-expressing and non-expressing cell lines were analyzed for for shedding/secretion of 161P2F10b protein by a capture ELISA. The capture ELISA was made using a 161P2F10b-specific MAb as the bottom capture MAb (1 ug/well), and X41.29 as the top detection MAb (2 ug/ml), and an anti-mouse IgG2a-HRP secondary and tetramethylbenzamidine as substrate for development. Recombinant 161P2F10b Tag5 ECD protein was used as a standard. 161P2F10b protein was detected in the media from 769 and Caki kidney cancer cells engineered to express 161P2F10b but not in the parental lines, indicating that 161P2F10b protein is shed or secreted. Shed/secreted 161P2F10b may exert its activity on cells in an autocrine/paracrine manner. In addition, shed/secreted 161P2F10b is useful as a diagnostic marker for 161P2F10b-expressing cancer and/or other 161P2F10b-expressing diseased tissues.

FIG. 43. Detection of secreted 161P2F10B in the serum of mice bearing UGK3 human kidney cancer xenografts. SCID mice inoculated subcutaneously with UGK3 kidney cancer cells were monitored for tumor growth (1 dimensional tumor measurements) and 161P2F10b serum levels (by capture ELISA) over the indicated times. The data demonstrates that 161P2F10b serum levels increase as the tumor size increases. This demonstrates that 161P2F10b is shed/secreted from 161P2F10b-expressing tissues in vivo and further demonstrates the utility of an ELISA to monitor 161P2F10b as a diagnostic marker.

FIG. 44: Detection of 161P2F10B protein by immunohistochemistry in kidney cancer patient specimens. Renal clear cell carcinoma tissue and its matched normal adjacent tissue as well as its metastatic cancer to lymph node were obtained from a kidney cancer patient. Frozen tissues were cut into 4 micron sections and fixed in acetone for 10 minutes. The sections were then incubated with PE-labeled mouse monoclonal anti-ENPP3 antibody (Coulter-Immunotech, Marseilles, France) for 3 hours (FIG. 44 panels A–F), or isotype control antibody (FIG. 44 panels G-1). The slides were washed three times in buffer, and either analyzed by fluorescence microscopy (FIG. 44 panels A, B and C), or further incubated with DAKO EnVision+™ peroxidase-conjugated goat anti-mouse secondary antibody (DAKO Corporation, Carpenteria, Calif.) for 1 hour (FIG. 44 panels D, E, and F). The sections were then washed in buffer, developed using the DAB kit (SIGMA Chemicals), counterstained using hematoxylin, and analyzed by bright field microscopy (FIG. 44 panels D, E and F). The results showed strong expression of 161P2F10B in the renal carcinoma patient tissue (FIG. 44 panels A and D) and the kidney cancer metastasis to lymph node tissue (FIG. 44 panels C and F), but weakly in normal kidney (FIG. 44B and E). The expression was detected mostly around the cell membrane indicating that 161P2F10B is membrane associated in kidney cancer tissues. The weak expression detected in normal kidney was localized to the kidney tubules. The sections stained with the isotype control antibody were negative showing the specificity of the anti-ENPP3 antibody (FIG. 44 panels G-1).

FIG. 45: Expression of 161P2F10B in Human Patient Cancers by Western Blot. Cell lysates from kidney cancer tissues (KiCa), kidney cancer metastasis to lymph node (KiCa Met), as well as normal kidney (NK) were subjected to Western analysis using an anti-161P2F10B mouse monoclonal antibody. Briefly, tissues (~25 µg total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa. These results demonstrate that 161P2F10B is useful as a diagnostic and therapeutic target for kidney cancers, metastatic cancers and other such as tose aas listed in Table I and other human cancers that express 161P2F10B.

FIG. 46: Expression of 161P2F10B in Human Xenograft Tissues by Western Blot. Cell lysates from kidney cancer xenograft (KiCa Xeno), kidney cancer metastasis to lymph node xenograft (Met Xeno), as well as normal kidney (NK) were subjected to Western analysis using an anti-161P2F10B mouse monoclonal antibody. Briefly, tissues (~25 µg total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa, and a multimer of approximately 260 kDa. These results demonstrate that the human cancer xenograft mouse models can be used to study the diagnostic and therapeutic effects of 161P2F10B.

DETAILED DESCRIPTION OF THE INVENTION

Outline of Sections
  I.) Definitions
  II.) 161P2F10B Polynucleotides
    II.A.) Uses of 161P2F10B Polynucleotides
    II.A.1.) Monitoring of Genetic Abnormalities
    II.A.2.) Antisense Embodiments
    II.A.3.) Primers and Primer Pairs
    II.A.4.) Isolation of 161P2F10B-Encoding Nucleic Acid Molecules
    II.A.5.) Recombinant Nucleic Acid Molecules and Host-Vector Systems
  III.) 161P2F10B-related Proteins
    III.A.) Motif-bearing Protein Embodiments
    III.B.) Expression of 161P2F10B-related Proteins
    III.C.) Modifications of 161P2F10B-related Proteins
    III.D.) Uses of 161P2F10B-related Proteins
  IV.) 161P2F10B Antibodies
  V.) 161P2F10B Cellular Immune Responses
  VI.) 161P2F10B Transgenic Animals
  VII.) Methods for the Detection of 161P2F10B
  VIII.) Methods for Monitoring the Status of 161P2F10B-related Genes and Their Products
  IX.) Identification of Molecules That Interact With 161P2F10B
  X.) Therapeutic Methods and Compositions
    X.A.) Anti-Cancer Vaccines
    X.B.) 161P2F10B as a Target for Antibody-Based Therapy
    X.C.) 161P2F10B as a Target for Cellular Immune Responses
    X.C.1. Minigene Vaccines
    X.C.2. Combinations of CTL Peptides with Helper Peptides
    X.C.3. Combinations of CTL Peptides with T Cell Priming Agents
    X.C.4. Vaccine Compositions Comprising DC Pulsed with CTL and/or HTL Peptides
    X.D.) Adoptive Immunotherapy
    X.E.) Administration of Vaccines for Therapeutic or Prophylactic Purposes
  XI.) Diagnostic and Prognostic Embodiments of 161P2F10B.
  XII.) Inhibition of 161P2F10B Protein Function
    XII.A.) Inhibition of 161P2F10B With Intracellular Antibodies
    XII.B.) Inhibition of 161P2F10B with Recombinant Proteins
    XII.C.) Inhibition of 161P2F10B Transcription or Translation
    XII.D.) General Considerations for Therapeutic Strategies
  XIII.) Identification, Characterization and Use of Modulators of 161P2F10b
  XIV.) KITS/Articles of Manufacture I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

The terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1–C2 disease under the Whitmore-Jewelt system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 161P2F10B (either by removing the underlying glycosylation site or by deleting the glycosylation by chemical and/or enzymatic means), and/or adding one or more glycosylation sites that are not present in the native sequence 161P2F10B. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (eg. a 161P2F10B-related protein). For example, an analog of a 161P2F10B protein can be specifically bound by an antibody or T cell that specifically binds to 161P2F10B.

The term "antibody" is used in the broadest sense. Therefore, an "antibody" can be naturally occurring or man-made such as monoclonal antibodies produced by conventional hybridoma technology. Anti-1611P2F10B antibodies comprise monoclonal and polyclonal antibodies as well as fragments containing the antigen-binding domain and/or one or more complementarity determining regions of these antibodies.

An "antibody fragment" is defined as at least a portion of the variable region of the immunoglobulin molecule that binds to its target, i.e., the antigen-binding region. In one embodiment it specifically covers single anti-161P2F10B antibodies and clones thereof (including agonist, antagonist and neutralizing antibodies) and anti-161 P2F10B antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exonaintron splicing signals, elimination of transposon-like repeats and/or optimization of GC content in addition to codon optimization are referred to herein as an "expression enhanced sequences."

A "combinatorial library" is a collection of diverse chemical compounds generated by either chemical synthesis or biological synthesis by combining a number of chemical "building blocks" such as reagents. For example, a linear combinatorial chemical library, such as a polypeptide (e.g., mutein) library, is formed by combining a set of chemical building blocks called amino acids in every possible way for a given compound length (i.e., the number of amino acids in a polypeptide compound). Numerous chemical compounds are synthesized through such combinatorial mixing of chemical building blocks (Gallop et al., J. Med. Chem. 37(9): 1233–1251 (1994)).

Preparation and screening of combinatorial libraries is well known to those of skill in the art. Such combinatorial chemical libraries include, but are not limited to, peptide libraries (see, e.g., U.S. Pat. No. 5,010,175, Furka, Pept. Prot. Res. 37:487–493 (1991), Houghton et al., Nature, 354:84–88 (1991)), peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with a Beta-D-Glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho, et al., Science 261:1303 (1993)), and/or peptidyl phosphonates (Campbell et al., J. Org. Chem. 59:658 (1994)). See, generally, Gordon et al., J. Med. Chem. 37:1385 (1994), nucleic acid libraries (see, e.g., Stratagene, Corp.), peptide nucleic acid libraries (see, e.g., U.S. Pat. No. 5,539,083), antibody libraries (see, e.g., Vaughn et al., Nature Biotechnology 14(3): 309–314 (1996), and PCT/US96/10287), carbohydrate libraries (see, e.g., Liang et al., Science 274:1520–1522 (1996), and U.S. Pat. No. 5,593,853), and small organic molecule libraries (see, e.g., benzodiazepines, Baum, C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514; and the like).

Devices for the preparation of combinatorial libraries are commercially available (see, e.g., 357 NIPS, 390 NIPS, Advanced Chem Tech, Louisville Ky.; Symphony, Rainin, Woburn, Mass.; 433A, Applied Biosystems, Foster City, Calif.; 9050, Plus, Millipore, Bedford, Mass.). A number of well-known robotic systems have also been developed for solution phase chemistries. These systems include automated workstations such as the automated synthesis apparatus developed by Takeda Chemical Industries, LTD. (Osaka, Japan) and many robotic systems utilizing robotic arms (Zymate H, Zymark Corporation, Hopkinton, Mass.; Orca, Hewlett-Packard, Palo Alto, Calif.), which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J.; Asinex, Moscow, RU; Tnpos, Inc., St. Louis, Mo.; ChemStar, Ltd, Moscow, RU; 3D Pharmaceuticals, Exton, Pa.; Martek Biosciences, Columbia, Md.; etc.).

The term "cytotoxic agent" refers to a substance that inhibits or prevents the expression activity of cells, function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to auristatins, auromycins, maytansinoids, yttrium, bismuth, ricin, ricin A-chain, combrestatin, duocarmycins, dolostatins, doxorubicin, daunorubicin, taxol, cisplatin, cc1065, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alphasarcin, gelonin, mitogellin, retstrictocin, phenomycin, enomycin, curicin, crotin, calicheamicin, Sapaonaria officinalis inhibitor, and glucocorticoid and other chemotherapeutic agents, as well as radioisotopes such as $At^{211}$, $I^{131}$, $I^{125}$, $Y^{90}$, $Re^{186}$, $Re^{188}$, $Sm^{153}$, $Bi^{212\ or\ 213}$, $P^{32}$ and radioactive isotopes of Lu including $Lu^{177}$. Antibodies may also be conjugated to an anti-cancer pro-drug activating enzyme capable of converting the pro-drug to its active form.

The "gene product" is sometimes referred to herein as a protein or mRNA. For example, a "gene product of the invention" is sometimes referred to herein as a "cancer amino acid sequence", "cancer protein", "protein of a cancer listed in Table I", a "cancer mRNA", "mRNA of a cancer listed in Table I", etc. In one embodiment, the cancer protein is encoded by a nucleic acid of FIG. 2. The cancer protein can be a fragment, or alternatively, be the full-length protein to the fragment encoded by the nucleic acids of FIG. 2. In one embodiment, a cancer amino acid sequence is used to determine sequence identity or similarity. In another embodiment, the sequences are naturally occurring allelic variants of a protein encoded by a nucleic acid of FIG. 2. In another embodiment, the sequences are sequence variants as further described herein.

"High throughput screening" assays for the presence, absence, quantification, or other properties of particular nucleic acids or protein products are well known to those of skill in the art. Similarly, binding assays and reporter gene assays are similarly well known. Thus, e.g., U.S. Pat. No. 5,559,410 discloses high throughput screening methods for proteins; U.S. Pat. No. 5,585,639 discloses high throughput screening methods for nucleic acid binding (i.e., in arrays); while U.S. Pat. Nos. 5,576,220 and 5,541,061 disclose high throughput methods of screening for ligand/antibody binding.

In addition, high throughput screening systems are commercially available (see, e.g., Amersham Biosciences, Piscataway, N.J.; Zymark Corp., Hopkinton, Mass.; Air Technical Industries, Mentor, Ohio; Beckman Instruments, Inc. Fullerton, Calif.; Precision Systems, Inc., Natick, Mass.; etc.). These systems typically automate entire procedures, including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, e.g., Zymark Corp. provides technical bulletins describing screening systems for detecting the modulation of gene transcription, ligand binding, and the like.

The term "homolog" refers to a molecule which exhibits homology to another molecule, by for example, having sequences of chemical residues that are the same or similar at corresponding positions.

"Human Leukocyte Antigen" or "HLA" is a human class I or class II Major Histocompatibility Complex (MHC) protein (see, e.g., Stites, et al., IMMUNOLOGY, 8TH ED., Lange Publishing, Los Altos, Calif. (1994).

The terms "hybridize", "hybridizing", "hybridizes" and the like, used in the context of polynucleotides, are meant to refer to conventional hybridization conditions, preferably such as hybridization in 50% formamide/6×SSC/0.1% SDS/ 100 μg/ml ssDNA, in which temperatures for hybridization are above 37 degrees C. and temperatures for washing in 0.1×SSC/0.1% SDS are above 55 degrees C.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment. For example, a polynucleotide is said to be "isolated" when it is substantially separated from contaminant polynucleotides that correspond or are complementary to genes other than the 161P2F10B genes or that encode polypeptides other than 161P2F10B gene product or fragments thereof. A skilled artisan can readily employ nucleic acid isolation procedures to obtain an isolated 161P2F10B polynucleotide. A protein is said to be "isolated," for example, when physical, mechanical or chemical methods are employed to remove the 161P2F10B proteins from cellular constituents that are normally associated with the protein. A skilled artisan can readily employ standard purification methods to obtain an isolated 161P2F10B protein. Alternatively, an isolated protein can be prepared by chemical means.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "modulator" or "test compound" or "drug candidate" or grammatical equivalents as used herein describe any molecule, e.g., protein, oligopeptide, small organic molecule, polysaccharide, polynucleotide, etc., to be tested for the capacity to directly or indirectly alter the cancer phenotype or the expression of a cancer sequence, e.g., a nucleic acid or protein sequences, or effects of cancer sequences (e.g., signaling, gene expression, protein interaction, etc.) In one aspect, a modulator will neutralize the effect of a cancer protein of the invention. By "neutralize" is meant that an activity of a protein is inhibited or blocked, along with the consequent effect on the cell. In another aspect, a modulator will neutralize the effect of a gene, and its corresponding protein, of the invention by normalizing levels of said protein. In preferred embodiments, modulators alter expression profiles, or expression profile nucleic acids or proteins provided herein, or downstream effector pathways. In one embodiment, the modulator suppresses a cancer phenotype, e.g. to a normal issue fingerprint. In another embodiment, a modulator induced a cancer phenotype. Generally, a plurality of assay mixtures is run in parallel with different agent concentrations to obtain a differential response to the various concentrations. Typically, one of these concentrations serves as a negative control, i.e., at zero concentration or below the level of detection.

Modulators, drug candidates or test compounds encompass numerous chemical classes, though typically they are organic molecules, preferably small organic compounds having a molecular weight of more than 100 and less than about 2,500 Daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Modulators also comprise biomolecules such as peptides, saccharides, fatty acids, steroids, purines, pyrimidines, derivatives, structural analogs or combinations thereof. Particularly preferred are peptides. One class of modulators are peptides, for example of from about five to about 35 amino acids, with from about five to about 20 amino acids being preferred, and from about 7 to about 15 being particularly preferred. Preferably, the cancer modulatory protein is soluble, includes a non-transmembrane region, and/or, has an N-terminal Cys to aid in solubility. In one embodiment, the C-terminus of the fragment is kept as a free acid and the N-terminus is a free amine to aid in coupling, i.e., to cysteine. In one embodiment, a cancer protein of the invention is conjugated to an immunogenic agent as discussed herein. In one embodiment, the cancer protein is conjugated to BSA. The peptides of the invention, e.g., of preferred lengths, can be linked to each other or to other amino acids to create a longer peptide/protein. The modulatory peptides can be digests of naturally occurring proteins as is outlined above, random peptides, or "biased" random peptides. In a preferred embodiment, peptide/protein-based modulators are antibodies, and fragments thereof, as defined herein.

Modulators of cancer can also be nucleic acids. Nucleic acid modulating agents can be naturally occurring nucleic acids, random nucleic acids, or "biased" random nucleic acids. For example, digests of prokaryotic or eukaryotic genomes can be used in an approach analogous to that outlined above for proteins.

The term "monoclonal antibody" refers to an antibody obtained from a population of substantially homogeneous antibodies, i.e., the antibodies comprising the population are identical except for possible naturally occurring mutations that are present in minor amounts.

A "motif", as in biological motif of a 161P2F10B-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property. In the context of HLA motifs, "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs for HLA binding are typically different for each protein encoded by each human HLA allele and differ in the pattern of the primary and secondary anchor residues.

A "pharmaceutical excipient" comprises a material such as an adjuvant, a carrier, pH-adjusting and buffering agents, tonicity adjusting agents, wetting agents, preservative, and the like.

"Pharmaceutically acceptable" refers to a non-toxic, inert, and/or composition that is physiologically compatible with humans or other mammals.

The term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T), as shown for example in FIG. 2, can also be uracil (U); this definition pertains to the differences between the chemical structures of DNA and RNA, in particular the observation that one of the four major bases in RNA is uracil (U) instead of thymidine (T).

The term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

An HLA "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding groove of an HLA molecule, with their side chains buried in specific pockets of the binding groove. In one embodiment, for example, the primary anchor residues for an HLA class I molecule are located at position 2 (from the amino terminal position) and at the carboxyl terminal position of a 8, 9, 10, 11, or 12 residue peptide epitope in accordance with the invention. Alternatively, in another embodiment, the primary anchor residues of a peptide binds an HLA class II molecule are spaced relative to each other, rather than to the termini of a peptide, where the peptide is generally of at least 9 amino acids in length. The primary anchor positions for each motif and supermotif are set forth in Table IV. For example, analog peptides can be created by altering the presence or absence of particular residues in the primary and/or secondary anchor positions shown in Table IV. Such analogs are used to modulate the binding affinity and/or population coverage of a peptide comprising a particular HLA motif or supermotif.

"Radioisotopes" include, but are not limited to the following (non-limiting exemplary uses are also set forth):
Examples of Medical Isotopes:
Isotope
Description of use
Actinium-225
(AC-225)
See Thorium-229 (Th-229)
Actinium-227
(AC-227)
Parent of Radium-223 (Ra-223) which is an alpha emitter used to treat metastases in the skeleton resulting from cancer (i.e., breast and prostate cancers), and cancer radioimmunotherapy
Bismuth-212
(Bi-212)
See Thorium-228 (Th-228)
Bismuth-213
(Bi-213)
See Thorium-229 (Th-229)
Cadmium-109
(Cd-109)
Cancer detection
Cobalt-60
(Co-60)
Radiation source for radiotherapy of cancer, for food irradiators, and for sterilization of medical supplies
Copper-64
(Cu-64)
A positron emitter used for cancer therapy and SPECT imaging
Copper-67
(Cu-67)
Beta/gamma emitter used in cancer radioimmunotherapy and diagnostic studies (i.e., breast and colon cancers, and lymphoma)
Dysprosium-166
(Dy-166)
Cancer radioimmunotherapy
Erbium-169
(Er-169)
Rheumatoid arthritis treatment, particularly for the small joints associated with fingers and toes
Europium-152
(Eu-152)
Radiation source for food irradiation and for sterilization of medical supplies
Europium-154
(Eu-154)
Radiation source for food irradiation and for sterilization of medical supplies
Gadolinium-153
(Gd-153)
Osteoporosis detection and nuclear medical quality assurance devices
Gold-198
(Au-198)
Implant and intracavity therapy of ovarian, prostate, and brain cancers
Holmium-166
(Ho-166)
Multiple myeloma treatment in targeted skeletal therapy, cancer radioimmunotherapy, bone marrow ablation, and rheumatoid arthritis treatment
Iodine-125
(I-125)
Osteoporosis detection, diagnostic imaging, tracer drugs, brain cancer treatment, radiolabeling, tumor imaging, mapping of receptors in the brain, interstitial radiation therapy, brachytherapy for treatment of prostate cancer, determination of glomerular filtration rate (GFR), determination of plasma volume, detection of deep vein thrombosis of the legs
Iodine-131
(I-131)
Thyroid function evaluation, thyroid disease detection, treatment of thyroid cancer as well as other non-malignant thyroid diseases (i.e., Graves disease, goiters, and hyperthyroidism), treatment of leukemia, lymphoma, and other forms of cancer (e.g., breast cancer) using radioimmunotherapy
Iridium-192
(Ir-192)
Brachytherapy, brain and spinal cord tumor treatment, treatment of blocked arteries (i.e., arteriosclerosis and restenosis), and implants for breast and prostate tumors
Lutetium-177
(Lu-177)
Cancer radioimmunotherapy and treatment of blocked arteries (i.e., arteriosclerosis and restenosis)
Molybdenum-99
(Mo-99)
Parent of Technetium-99m (Tc-99m) which is used for imaging the brain, liver, lungs, heart, and other organs. Currently, Tc-99m is the most widely used radioisotope used for diagnostic imaging of various cancers and diseases involving the brain, heart, liver, lungs; also used in detection of deep vein thrombosis of the legs
Osmium-194
(Os-194)
Cancer radioimmunotherapy
Palladium-103
(Pd-103)
Prostate cancer treatment
Platinum-195m
(Pt-195m)
Studies on biodistribution and metabolism of cisplatin, a chemotherapeutic drug
Phosphorus-32
(P-32)
Polycythemia rubra vera (blood cell disease) and leukemia treatment, bone cancer diagnosis/treatment; colon, pancreatic, and liver cancer treatment; radiolabeling nucleic acids for in vitro research, diagnosis of superficial tumors, treatment of blocked arteries (i.e., arteriosclerosis and restenosis), and intracavity therapy Phosphorus-33
(P-33)
Leukemia treatment, bone disease diagnosis/treatment, radiolabeling, and treatment of blocked arteries (i.e., arteriosclerosis and restenosis)
Radium-223
(Ra-223)
See Actinium-227 (Ac-227)
Rhenium-186
(Re-186)
Bone cancer pain relief, rheumatoid arthritis treatment, and diagnosis and treatment of lymphoma and bone, breast, colon, and liver cancers using radioimmunotherapy
Rhenium-188
(Re-188)
Cancer diagnosis and treatment using radioimmunotherapy, bone cancer pain relief, treatment of rheumatoid arthritis, and treatment of prostate cancer
Rhodium-105
(Rh-105)
Cancer radioimmunotherapy
Samarium-145
(Sm-145)
Ocular cancer treatment
Samarium-153
(Sm-153)
Cancer radioimmunotherapy and bone cancer pain relief
Scandium-47
(Sc-47)
Cancer radioimmunotherapy and bone cancer pain relief
Selenium-75
(Se-75)
Radiotracer used in brain studies, imaging of adrenal cortex by gamma-scintigraphy, lateral locations of steroid secreting tumors, pancreatic scanning, detection of hyperactive parathyroid glands, measure rate of bile acid loss from the endogenous pool
Strontium-85
(Sr-85)
Bone cancer detection and brain scans
Strontium-89
(Sr-89)
Bone cancer pain relief, multiple myeloma treatment, and osteoblastic therapy
Technetium-99m
(Tc-99m)
See Molybdenum-99 (Mo-99)
Thorium-228
(Th-228)
Parent of Bismuth-212 (Bi-212) which is an alpha emitter used in cancer radioimmunotherapy
Thorium-229
(Th-229)
Parent of Actinium-225 (Ac-225) and grandparent of Bismuth-213 (Bi-213) which are alpha emitters used in cancer radioimmunotherapy
Thulium-170
(Tm-170)
Gamma source for blood irradiators, energy source for implanted medical devices
Tin-117m
(Sn-117m)
Cancer immunotherapy and bone cancer pain relief
Tungsten-188
(W-188)
Parent for Rhenium-188 (Re-188) which is used for cancer diagnostics/treatment, bone cancer pain relief, rheumatoid arthritis treatment, and treatment of blocked arteries (i.e., arteriosclerosis and restenosis)
Xenon-127
(Xe-127)
Neuroimaging of brain disorders, high resolution SPECT studies, pulmonary function tests, and cerebral blood flow studies
Ytterbium-175
(Yb-175)
Cancer radioimmunotherapy
Yttrium-90
(Y-90)
Microseeds obtained from irradiating Yttrium-89 (Y-89) for liver cancer treatment
Yttrium-91
(Y-91)
A gamma-emitting label for Yttrium-90 (Y-90) which is used for cancer radioimmunotherapy (i.e., lymphoma, breast, colon, kidney, lung, ovarian, prostate, pancreatic, and inoperable liver cancers)

By "randomized" or grammatical equivalents as herein applied to nucleic acids and proteins is meant that each nucleic acid and peptide consists of essentially random nucleotides and amino acids, respectively. These random peptides (or nucleic acids, discussed herein) can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, a library is "fully randomized," with no sequence preferences or constants at any position. In another embodiment, the library is a "biased random" library. That is, some positions within the sequence either are held constant, or are selected from a limited number of possibilities. For example, the nucleotides or amino acid residues are randomized within a defined class, e.g., of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

A "recombinant DNA or RNA molecule is a DNA or RNA molecule that has been subjected to molecular manipulation in vitro.

Non-limiting examples of small molecules include compounds that bind or interact with 161P2F10B, ligands including hormones, neuropeptides, chemokines, odorants, phospholipids, and functional equivalents thereof that bind and preferably inhibit 161P2F10B protein function. Such non-limiting small molecules preferably have a molecular weight of less than about 10 kDa, more preferably below about 9, about 8, about 7, about 6, about 5 or about 4 kDa. In certain embodiments, small molecules physically associate with, or bind, 161P2F10B protein; are not found in naturally occurring metabolic pathways; and/or are more soluble in aqueous than non-aqueous solutions "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 420C in 0.2×SSC (sodium chloride/sodium. citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

An HLA "supermotif" is a peptide binding specificity shared by HLA molecules encoded by two or more HLA alleles. Overall phenotypic frequencies of HLA-supertypes in different ethnic populations are set forth in Table IV (F). The non-limiting constituents of various supetypes are as follows:

A2: A*0201, A*0202, A*0203, A*0204, A* 0205, A*0206, A*6802, A*6901, A*0207

A3: A3, A11, A31,A*3301,A*6801, A*0301,A*1101, A*3101

B7: B7, B*3501–03, B*51, B*5301, B*5401, B*5501, B*5502, B*5601, B*6701, B*7801, B*0702, B*5101, B*5602

B44: B*3701, B*4402, B*4403, B*60 (B*4001), B61 (B*4006)

A1: A*0102, A*2604, A*3601, A*4301, A*8001

A24: A*24, A*30, A*2403, A*2404, A*3002, A*3003

B27: B*1401–02, B*1503, B*1509, B*1510, B*1518, B*3801–02, B*3901, B*3902, B*3903–04, B*4801–02, B*7301, B*2701–08

B58: B*1516, B*1517, B*5701, B*5702, B58

B62: B*4601, B52, B*1501 (B62), B*1502 (B75), B*1513 (B77)

Calculated population coverage afforded by different HLA-supertype combinations are set forth in Table IV (G).

As used herein "to treat" or "therapeutic" and grammatically related terms, refer to any improvement of any consequence of disease, such as prolonged survival, less morbidity, and/or a lessening of side effects which are the byproducts of an alternative therapeutic modality; full eradication of disease is not required.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

As used herein, an HLA or cellular immune response "vaccine" is a composition that contains or encodes one or more peptides of the invention. There are numerous embodiments of such vaccines, such as a cocktail of one or more individual peptides; one or more peptides of the invention comprised by a polyepitopic peptide; or nucleic acids that encode such individual peptides or polypeptides, e.g., a minigene that encodes a polyepitopic peptide. The "one or more peptides" can include any whole unit integer from 1–150 or more, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I peptides of the invention can be admixed with, or linked to, HLA class II peptides, to facilitate activation of both cytotoxic T lymphocytes and helper T lymphocytes. HLA vaccines can also comprise peptide-pulsed antigen presenting cells, e.g., dendritic cells.

The term "variant" refers to a molecule that exhibits a variation from a described type or norm, such as a protein that has one or more different amino acid residues in the corresponding position(s) of a specifically described protein (e.g. the 161P2F10B protein shown in FIG. 2 or FIG. 3. An analog is an example of a variant protein. Splice isoforms and single nucleotides polymorphisms (SNPs) are further examples of variants.

The "161P2F10B-related proteins" of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 161P2F10B proteins or fragments thereof, as well as fusion proteins of a 161P2F10B protein and a heterologous polypeptide are also included. Such 161P2F10B proteins are collectively referred to as the 161P2F10B-related proteins, the proteins of the invention, or 161P2F10B. The term "161P2F10B-related protein" refers to a polypeptide fragment or a 161P2F10B protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, or 664 or more amino acids.

II.) 161P2F10B Polynucleotides

One aspect of the invention provides polynucleotides corresponding or complementary to all or part of a 161P2F10B gene, mRNA, and/or coding sequence, preferably in isolated form, including polynucleotides encoding a 161P2F10B-related protein and fragments thereof, DNA, RNA, DNA/RNA hybrid, and related molecules, polynucleotides or oligonucleotides complementary to a 161P2F10B gene or mRNA sequence or a part thereof, and polynucleotides or oligonucleotides that hybridize to a 161P2F10B gene, mRNA, or to a 161P2F10B encoding polynucleotide (collectively, "161P2F10B polynucleotides"). In all instances when referred to in this section, T can also be U in FIG. 2.

Embodiments of a 161P2F10B polynucleotide include: a 161P2F10B polynucleotide having the sequence shown in FIG. 2, the nucleotide sequence of 161P2F10B as shown in FIG. 2 wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. For example, embodiments of 161P2F10B nucleotides comprise, without limitation:

(I) a polynucleotide comprising, consisting essentially of, or consisting of a sequence as shown in FIG. 2, wherein T can also be U;

(II) a polynucleotide comprising, consisting essentially of, or consisting of the sequence as shown in FIG. 2A, from nucleotide residue number 44 through nucleotide residue number 2671, including the stop codon, wherein T can also be U;

(III) a polynucleotide comprising, consisting essentially of, or consisting of the sequence as shown in FIG. 2B, from nucleotide residue number 44 through nucleotide residue number 2671, including the stop codon, wherein T can also be U;

(IV) a polynucleotide comprising, consisting essentially of, or consisting of the sequence as shown in FIG. 2C, from nucleotide residue number 44 through nucleotide residue number 2671, including the a stop codon, wherein T can also be U;

(V) a polynucleotide comprising, consisting essentially of, or consisting of the sequence as shown in FIG. 2D, from nucleotide residue number 44 through nucleotide residue number 2671, including the stop codon, wherein T can also be U;

(VI) a polynucleotide comprising, consisting essentially of, or consisting of the sequence as shown in FIG. 2E, from nucleotide residue number 44 through nucleotide residue number 2671, including the stop codon, wherein T can also be U;

(VII) a polynucleotide comprising, consisting essentially of, or consisting of the sequence as shown in FIG. 2F, from nucleotide residue number 84 through nucleotide residue number 2711, including the stop codon, wherein T can also be U;

(VIII) a polynucleotide comprising, consisting essentially of, or consisting of the sequence as shown in FIG. 2G, from nucleotide residue number 276 through nucleotide residue number 2801, including the stop codon, wherein T can also be U;

(IX) a polynucleotide that encodes a 161P2F10B-related protein that is at least 90, 91, 92, 93, 94, 95, 96, 97, 98, 99 or 100% homologous to an entire amino acid sequence shown in FIGS. 2A–G;

(X) a polynucleotide that encodes a 161P2F10B-related protein that is at least 90, 91, 92, 93, 94, 95, 96, 97, 98, 99 or 100% identical to an entire amino acid sequence shown in FIGS. 2A–G;

(XI) a polynucleotide that encodes at least one peptide set forth in Tables VIII–XXI and XXII–XLIX;

(XII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A–D in any whole number increment up to 875 that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A–D in any whole number increment up to 875 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XIV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A–D in any whole number increment up to 875 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XV) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3A–DF in any whole number increment up to 875 that includes 1, 2, 3,4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XVI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIGS. 3A–D in any whole number increment up to 875 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XVII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 841 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(XVIII) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 841 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XIX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 841 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Percent Accessible Residues profile of FIG. 7;

(XX) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 841 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XXI) a polynucleotide that encodes a peptide region of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a peptide of FIG. 3E in any whole number increment up to 841 that includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9

(XXII) a polynucleotide that encodes monocloncal antibody or binding region thereof secreted by a hybridoma entitled X41(3)15 deposited with the American Type Culture Collection (ATCC; 10801 University Blvd., Manassas, Va. 20110-2209 USA) on Nov. 7, 2002 and assigned as Patent Deposit Designation No. PTA-4791;

(XXIII) a polynucleotide that encodes monocloncal antibody or binding region thereof secreted by a hybridoma entitled X41(3)29 deposited with the American Type Culture Collection (ATCC; 10801 University Blvd., Manassas, Va. 20110-2209 USA) on Nov. 7, 2002 and assigned as Patent Deposit Designation No. PTA-4791;

(XXIV) a polynucleotide that encodes monocloncal antibody or binding region thereof secreted by a hybridoma entitled X41(3)37 deposited with the American Type Culture Collection (ATCC; 10801 University Blvd., Manassas, Va. 20110-2209 USA) on Nov. 7, 2002 and assigned as Patent Deposit Designation No. PTA-4791;

(XXV) a polynucleotide that encodes monocloncal antibody or binding region thereof secreted by a hybridoma entitled X41(4)6 deposited with the American Type Culture Collection (ATCC; 10801 University Blvd., Manassas, Va. 20110-2209 USA) on Nov. 7, 2002 and assigned as Patent Deposit Desianation No. PTA-4794;

(XXVI) a polynucleotide that encodes monocloncal antibody or binding region thereof secreted by a hybridoma entitled X41(3)17 deposited with the American Type Culture Collection (ATCC; 10801 University Blvd., Manassas, Va. 20110-2209 USA) on Nov. 7, 2002 and assigned as Patent Deposit Designation No. PTA-4792;

(XXVII) a polynucleotide that encodes monocloncal antibody or binding region thereof secreted by a hybridoma entitled X41(3)50 deposited with the American Type Culture Collection (ATCC; 10801 University Blvd., Manassas, Va. 20110-2209 USA) on Nov. 7, 2002 and assigned as Patent Deposit Designation No. PTA-4793;

(XXVIII) a polynucleotide that is fully complementary to a polynucleotide of any one of (I)–(XXVII).

(XXIX) a peptide that is encoded by any of (I) to (XXVII); and (XXX) a composition comprising a polynucleotide of any of (I)–(XXVII) or peptide of (XXIX) together with a pharmaceutical excipient and/or in a human unit dose form.

(XXXI) a method of using a polynucleotide of any (I)–(XXVII) or peptide of (XXIX) or a composition of (XXX) in a method to modulate a cell expressing 161P2F10b, (XXXII) a method of using a polynucleotide of any (I)–(XXVII) or peptide of (XXIX) or a composition of (XXX) in a method to diagnose, prophylax, prognose, or treat an individual who bears a cell expressing 161P2F10b (XXXIII) a method of using a polynucleotide of any (I)–(XXVII) or peptide of (XXIX) or a composition of (XXX) in a method to diagnose, prophylax, prognose, or treat an individual who bears a cell expressing 161P2F10b, said cell from a cancer of a tissue listed in Table I;

(XXXIV) a method of using a polynucleotide of any (I)–(XLII) or peptide of (XXIX) or a composition of (XXX) in a method to diagnose, prophylax, prognose, or treat a a cancer;

(XXXV) a method of using a polynucleotide of any (I)–(XLII) or peptide of (XXIX) or a composition of (XXX) in a method to diagnose, prophylax, prognose, or treat a a cancer of a tissue listed in Table l; and, (XXXVI) a method of using a polynucleotide of any (I)–(XLII) or peptide of (XXIX) or a composition of (XXX) in a method to identify or characterize a modulator of a cell expressing 161P2F10b.

As used herein, a range is understood to disclose specifically all whole unit positions thereof.

Typical embodiments of the invention disclosed herein include 161P2F10B polynucleotides that encode specific portions of 161P2F10B mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 860, 870, 875 or more contiguous amino acids of 161P2F10B variant 1; the maximal lengths relevant for other variants are: variant 2, 875 amino acids; variant 3, 875 amino acids, variant 4, 875 amino acids, and variant 7, 841 amino acids.

For example, representative embodiments of the invention disclosed herein include: polynucleotides and their encoded peptides themselves encoding about amino acid 1 to about amino acid 10 of the 161P2F10B protein shown in FIG. 2 or FIG. 3, polynucleotides encoding about amino acid 10 to about amino acid 20 of the 161P2F10B protein shown in FIG. 2 or FIG. 3, polynucleotides encoding about amino acid 20 to about amino acid 30 of the 161P2F10B protein shown in FIG. 2 or FIG. 3, polynucleotides encoding about amino acid 30 to about amino acid 40 of the 161P2F10B protein shown in FIG. 2 or FIG. 3, polynucleotides encoding about amino acid 40 to about amino acid 50 of the 161P2F10B protein shown in FIG. 2 or FIG. 3, polynucleotides encoding about amino acid 50 to about amino acid 60 of the 161P2F10B protein shown in FIG. 2 or FIG. 3, polynucleotides encoding about amino acid 60 to about amino acid 70 of the 161P2F10B protein shown in FIG. 2 or FIG. 3, polynucleotides encoding about amino acid 70 to about amino acid 80 of the 161P2F10B protein shown in FIG. 2 or FIG. 3, polynucleotides encoding about amino acid 80 to about amino acid 90 of the 161P2F10B protein shown in FIG. 2 or FIG. 3, polynucleotides encoding about amino acid 90 to about amino acid 100 of the 161P2F10B protein shown in FIG. 2 or FIG. 3, in increments of about 10 amino acids, ending at the carboxyl terminal amino acid set forth in FIG. 2 or FIG. 3. Accordingly, polynucleotides encoding portions of the amino acid sequence (of about 10 amino acids), of amino acids, 100 through the carboxyl terminal amino acid of the 161P2F10B protein are embodiments of the invention. Wherein it is understood that each particular amino acid position discloses that position plus or minus five amino acid residues.

Polynucleotides encoding relatively long portions of a 161P2F10B protein are also within the scope of the invention. For example, polynucleotides encoding from about amino acid 1 (or 20 or 30 or 40 etc.) to about amino acid 20, (or 30, or 40 or 50 etc.) of the 161P2F10B protein "or variant" shown in FIG. 2 or FIG. 3 can be generated by a variety of techniques well known in the art. These polynucleotide fragments can include any portion of the 161P2F10B sequence as shown in FIG. 2.

Additional illustrative embodiments of the invention disclosed herein include 161P2F10B polynucleotide fragments encoding one or more of the biological motifs contained within a 161P2F10B protein "or variant sequence", including one or more of the motif-bearing subsequences of a 161P2F10B protein or variant set forth in Tables VIII–XXI and XXII–XLIX. In another embodiment, typical polynucleotide fragments of the invention encode one or more of the regions of 161P2F10B protein or variant that exhibit homology to a known molecule. In another embodiment of the invention, typical polynucleotide fragments can encode one or more of the 161P2F10B protein or variant N-glycosylation sites, cAMP and cGMP-dependent protein kinase phosphorylation sites, casein kinase II phosphorylation sites or N-myristoylaton site and amidation sites.

Note that to determine the starting position of any peptide set forth in Tables VIII–XXI and Tables XXII to XLIX (collectively HLA Peptide Tables) respective to its parental protein, e.g., variant 1, variant 2, etc., reference is made to three factors: the particular variant, the length of the peptide in an HLA Peptide Table, and the Search Peptides listed in Table LVII. Generally, a unique Search Peptide is used to obtain HLA peptides for a particular variant. The position of each Search Peptide relative to its respective parent molecule is listed in Table VII. Accordingly, if a Search Peptide begins at position "X", one must add the value "X minus 1" to each position in Tables VIII–XXI and Tables XXII–IL to obtain the actual position of the HLA peptides in their parental molecule. For example 1f a particular Search Peptide begins at position 150 of its parental molecule, one must add 150–1, i.e., 149 to each HLA peptide amino acid position to calculate the position of that amino acid in the parent molecule.

II.A.) Uses of 161P2F10B Polynucleotides

II.A.1.) Monitoring of Genetic Abnormalities

The polynucleotides of the preceding paragraphs have a number of different specific uses. The human 161P2F10B gene maps to the chromosomal location set forth in the Example entitled "Chromosomal Mapping of 161P2F10B." For example, because the 161P2F10B gene maps to this chromosome, polynucleotides that encode different regions of the 161P2F10B proteins are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e g. Krajinovic et al, Mutat. Res. 382(3–4): 81–83 (1998); Johansson et al., Blood 86(10): 3905–3914 (1995) and Finger et al., P.N.A.S. 85(23): 9158–9162 (1988)). Thus, polynucleotides encoding specific regions of the 161P2F10B proteins provide new tools that can be used to delineate, with greater precision than previously possible, cytogenetic abnormalities in the chromosomal region that encodes 161P2F10B that may contribute to the malignant phenotype. In this context, these polynucleotides satisfy a need in the art for expanding the sensitivity of chromosomal screening in order to identify more subtle and less common chromosomal abnormalities (see e.g. Evans et a., Am. J. Obstet. Gynecol 171(4): 1055–1057 (1994)).

Furthermore, as 161P2F10B was shown to be highly expressed in bladder and other cancers, 161P2F10B polynucleotides are used in methods assessing the status of 161P2F10B gene products in normal versus cancerous tissues. Typically, polynucleotides that encode specific regions of the 161P2F10B proteins are used to assess the presence of perturbations (such as deletions, insertions, point mutations, or alterations resulting in a loss of an antigen etc.) in specific regions of the 161P2F10B gene, such as regions containing one or more motifs. Exemplary assays include both RT-PCR assays as well as single-strand conformation polymorphism (SSCP) analysis (see, e.g., Marrogi et al, J. Cutan. Pathol. 26(8): 369–378 (1999), both of which utilize polynucleotides encoding specific regions of a protein to examine these regions within the protein.

II.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 161P2F10B. For example, antisense molecules can be RNAs or other molecules, including peptide nucleic acids (PNAs) or non-nucleic acid molecules such as phosphorothioate derivatives that specifically bind DNA or RNA in a base pair-dependent manner. A skilled artisan can readily obtain these classes of nucleic acid molecules using the 161P2F10B polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 161P2F10B. See for example, Jack Cohen, Oligodeoxynucleotides, Antisense Inhibitors of Gene Expression, CRC Press, 1989; and Synthesis 1:1–5 (1988). The 161P2F10B antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See, e.g., Iyer, R. P. et al., J. Org. Chem. 55:4693–4698 (1990); and Iyer, R. P. et al., J. Am. Chem. Soc. 112:1253–1254(1990). Additional 161P2F10B antisense oligonucleotides of the present invention include morpholino antisense oligonucleotides known in the art (see, e.g., Partridge et al., 1996, Antisense & Nucleic Acid Drug Development 6: 169–175).

The 161P2F10B antisense oligonucleotides of the present invention typically can be RNA or DNA that is complementary to and stably hybridizes with the first 100 5' codons or last 100 3' codons of a 161P2F10B genomic sequence or the corresponding mRNA. Absolute complementarity is not required, although high degrees of complementarity are preferred. Use of an oligonucleotide complementary to this region allows for the selective hybridization to 161P2F10B mRNA and not to mRNA specifying other regulatory subunits of protein kinase. In one embodiment, 161P2F10B antisense oligonucleotides of the present invention are 15 to 30-mer fragments of the antisense DNA molecule that have a sequence that hybridizes to 161P2F10B mRNA. Optionally, 161P2F10B antisense oligonucleotide is a 30-mer oligonucleotide that is complementary to a region in the first 10 5' codons or last 10 3' codons of 161P2F10B. Alternatively, the antisense molecules are modified to employ ribozymes in the inhibition of 161P2F10B expression, see, e.g., L. A. Couture & D. T. Stinchcomb; Trends Genet 12: 510–515 (1996).

II.A.3.) Primers and Primer Pairs

Further specific embodiments of these nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 161P2F10B polynucleotide in a sample and as a means for detecting a cell expressing a 161P2F10B protein.

Examples of such probes include polypeptides comprising all or part of the human 161P2F10B cDNA sequence shown in FIG. 2. Examples of primer pairs capable of specifically amplifying 161P2F10B mRNAs are also described in the Examples. As will be understood by the skilled artisan, a great many different primers and probes can be prepared based on the sequences provided herein and used effectively to amplify and/or detect a 161P2F10B mRNA.

The 161P2F10B polynucleotides of the invention are useful for a variety of purposes, including but not limited to their use as probes and primers for the amplification and/or detection of the 161P2F10B gene(s), mRNA(s), or fragments thereof; as reagents for the diagnosis and/or prognosis of prostate cancer and other cancers; as coding sequences capable of directing the expression of 161P2F10B polypeptides; as tools for modulating or inhibiting the expression of the 161P2F10B gene(s) and/or translation of the 161P2F10B transcript(s); and as therapeutic agents.

The present invention includes the use of any probe as described herein to identify and isolate a 161P2F10B or 161P2F10B related nucleic acid sequence from a naturally occurring source, such as humans or other mammals, as well as the isolated nucleic acid sequence per se, which would comprise all or most of the sequences found in the probe used.

II.A.4.) Isolation of 161P2F10B-Encoding Nucleic Acid Molecules

The 161P2F10B cDNA sequences described herein enable the isolation of other polynucleotides encoding 161P2F10B gene product(s), as well as the isolation of polynucleotides encoding 161P2F10B gene product homologs, alternatively spliced isoforms, allelic variants, and mutant forms of a 161P2F10B gene product as well as polynucleotides that encode analogs of 161P2F10B-related proteins. Various molecular cloning methods that can be employed to isolate full length cDNAs encoding a 161P2F10B gene are well known (see, for example, Sambrook, J. et al, Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 161P2F10B gene cDNAs can be identified by probing with a labeled 161P2F10B cDNA or a fragment thereof. For example, in one embodiment, a 161P2F10B cDNA (e.g., FIG. 2) or a portion thereof can be synthesized and used as a probe to retrieve overlapping and full-length cDNAs corresponding to a 161P2F10B gene. A 161P2F10B gene itself can be isolated by screening genomic DNA libraries, bacterial artificial chromosome libraries (BACs), yeast artificial chromosome libraries (YACs), and the like, with 161P2F10B DNA probes or primers.

II.A.5.) Recombinant Nucleic Acid Molecules and Host-Vector Systems

The invention also provides recombinant DNA or RNA molecules containing a 161P2F10B polynucleotide, a fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al., 1989, supra).

The invention further provides a host-vector system comprising a recombinant DNA molecule containing a 161P2F10B polynucleotide, fragment, analog or homologue thereof within a suitable prokaryotic or eukaryotichost cell. Examples of suitable eukaryotic host cells include a yeast cell, a plant cell, or an animal cell, such as a mammalian cell or an insect cell (e.g, a baculovirus-infectible cell such as an Sf9 or HighFive cell). Examples of suitable mammalian cells include various prostate cancer cell lines such as DU145 and TsuPrl, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 161P2F10B or a fragment, analog or homolog thereof can be used to generate 161P2F10B proteins or fragments thereof using any number of host-vector systems routinely used and widely known in the art.

A wide range of host-vector systems suitable for the expression of 161P2F10B proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, 161P2F10B can be expressed in several prostate cancer and non-prostate cell lines, including for example 293, 293T, rat-1, NIH 3T3 and TsuPr1. The host-vector systems of the invention are useful for the production of a 161P2F10B protein or fragment thereof. Such host-vector systems can be employed to study the functional properties of 161P2F10B and 161P2F108 mutations or analogs.

Recombinant human 161P2F10B protein or an analog or homolog or fragment thereof can be produced by mammalian cells transfected with a construct encoding a 161P2F10B-related nucleotide. For example, 293T cells can be transfected with an expression plasmid encoding 161P2F10B or fragment, analog or homolog thereof, a 161P2F10B-related protein is expressed in the 293T cells, and the recombinant 161P2F10B protein is isolated using standard purification methods (e.g., affinity purification using anti-161P2F10B antibodies). In another embodiment, a 161P2F10B coding sequence is subcloned into the retroviral vector pSRaMSVtkneo and used to infect various mammalian cell lines, such as NIH 3T3, TsuPr1, 293 and rat-1 in order to establish 161P2F10B expressing cell lines. Various other expression systems well known in the art can also be employed. Expression constructs encoding a leader peptide joined in frame to a 161P2F10B coding sequence can be used for the generation of a secreted form of recombinant 161P2F10B protein.

As discussed herein, redundancy in the genetic code permits variation in 161P2F10B gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as at URL dna.affrc.go.jp/-nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.,* 9:5073–5080 (1989). Skilled artisans understand that the general rule that eukaryotic ribosomes initiate translation exclusively at the 5' proximal AUG codon is abrogated only under rare conditions (see, e 9. , Kozak PNAS 92(7): 2662–2666, (1995) and Kozak NAR 15(20): 8125–8148 (1987)).

III.) 161P2F10B-Related Proteins

Another aspect of the present invention provides 161P2F10B-related proteins. Specific embodiments of 161P2F10B proteins comprise a polypeptide having all or part of the amino acid sequence of human 161P2F10B as shown in FIG. 2 or FIG. 3. Alternatively, embodiments of 161P2F10B proteins comprise variant, homolog or analog polypeptides that have alterations in the amino acid sequence of 161P2F10B shown in FIG. 2 or FIG. 3.

Embodiments of a 161P2F10B polypeptide include: a 161P2F10B polypeptide having a sequence shown in FIG. 2, a peptide sequence of a 161P2F10B as shown in FIG. 2 wherein T is U; at least 10 contiguous nucleotides of a polypeptide having the sequence as shown in FIG. 2; or, at least 10 contiguous peptides of a polypeptide having the sequence as shown in FIG. 2 where T is U. For example, embodiments of 161P2F10B peptides comprise, without limitation:

(I) a protein comprising, consisting essentially of, or consisting of an amino acid sequence as shown in FIGS. 2A–G or FIGS. 3A–E;

(II) a 161P2F10B-related protein that is at least 90, 91, 92, 93, 94, 95, 96, 97, 98, 99 or 100% homologous to an entire amino acid sequence shown in FIGS. 2A–G;

(III) a 161P2F10B-related protein that is at least 90, 91, 92, 93, 94, 95, 96, 97, 98, 99 or 100% identical to an entire amino acid sequence shown in FIGS. 2A–G or 3A–E;

(IV) a protein that comprises at least one peptide set forth in Tables VII to XLIX, optionally with a proviso that it is not an entire protein of FIG. 2;

(V) a protein that comprises at least one peptide set forth in Tables VIII–XXI, collectively, which peptide is also set forth in Tables XXII to XLIX, collectively, optionally with a proviso that it is not an entire protein of FIG. 2;

(VI) a protein that comprises at least two peptides selected from the peptides set forth in Tables VIII–XLIX, optionally with a proviso that it is not an entire protein of FIG. 2;

(VII) a protein that comprises at least two peptides selected from the peptides set forth in Tables VII to XLIX collectively, with a proviso that the protein is not a contiguous sequence from an amino acid sequence of FIG. 2;

(VIII) a protein that comprises at least one peptide selected from the peptides set forth in Tables VIII–XXI; and at least one peptide selected from the peptides set forth in Tables XXII to XLIX, with a proviso that the protein is not a contiguous sequence from an amino acid sequence of FIG. 2;

(IX) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, or 3E in any whole number increment up to 875, 875, 875, 875, or 841 respectively that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Hydrophilicity profile of FIG. 5;

(X) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, or 3E in any whole number increment up to 875, 875, 875, 875, or 841 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value less than 0.5 in the Hydropathicity profile of FIG. 6;

(XI) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, or 3E in any whole number increment up to 875, 875, 875, 875, or 841 respectively, that includes at least 1, 2, 3, 4, 5, 6, 7, 8, 9, 10, 11, 12, 13, 14, 15, 16, 17, 18, 19, 20,21, 22, 23, 24, 25, 26, 27, 28, 29, 30, 31, 32, 33, 34, 35 amino acid position(s) having a value greater than 0.5 in the Percent Accessible Residues profile of FIG. 7;

(XII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, or 3E in any whole number increment up to 875, 875, 875, 875, or 841 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Average Flexibility profile of FIG. 8;

(XIII) a polypeptide comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acids of a protein of FIG. 3A, 3B, 3C, 3D, or 3E in any whole number increment up to 875, 875, 875, 875, or 841 respectively, that includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 amino acid position(s) having a value greater than 0.5 in the Beta-turn profile of FIG. 9;

(XIV) a peptide that occurs at least twice in Tables VIII–XXI and XXII to XLIX, collectively;

(XV) a peptide that occurs at least three times in Tables VIII–XXI and XXII to XLIX, collectively;

(XVI) a peptide that occurs at least four times in Tables VIII–XXI and XXII to XLIX, collectively;

(XVII) a peptide that occurs at least five times in Tables VIII–XXI and XXII to XLIX, collectively;

(XVIII) a peptide that occurs at least once in Tables VIII–XXI, and at least once in tables XXII to XLIX;

(XIX) a peptide that occurs at least once in Tables VIII–XXI, and at least twice in tables XXII to XLIX;

(XX) a peptide that occurs at least twice in Tables VIII–XXI, and at least once in tables XXII to XLIX;

(XXI) a peptide that occurs at least twice in Tables VIII–XXI, and at least twice in tables XXII to XLIX;

(XXII) a peptide which comprises one two, three, four, or five of the following characteristics, or an oligonucleotide encoding such peptide:

i) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Hydrophilicity profile of FIG. 5;

ii) a region of at least 5 amino acids of a particular peptide of FIG. 3, in any whole number increment up to the full length of that protein in FIG. 3, that includes an amino acid position having a value equal to or less than 0.5, 0.4, 0.3, 0.2, 0.1, or having a value equal to 0.0, in the Hydropathicity profile of FIG. 6;

iii) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Percent Accessible Residues profile of FIG. 7;

iv) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Average Flexibility profile of FIG. 8; or, v) a region of at least 5 amino acids of a particular peptide of FIG. 3, in any whole number increment up to the full length of that protein in FIG. 3, that includes an amino acid position having a value equal to or greater than 0.5, 0.6, 0.7, 0.8, 0.9, or having a value equal to 1.0, in the Beta-tum profile of FIG. 9;

(XXIII) a monocloncal antibody or binding region thereof secreted by a hybridoma entitled X41(3)15 deposited with the American Type Culture Collection (ATCC; 10801 University Blvd., Manassas, Va. 20110-2209 USA) on Nov. 7, 2002 and assigned as Patent Deposit Designation No. PTA-4791;

(XXIV) a monocloncal antibody or binding region thereof secreted by a hybridoma entitled X41(3)29 deposited with the American Type Culture Collection (ATCC; 10801 University Blvd., Manassas, Va. 20110-2209 USA) on Nov. 7, 2002 and assigned as Patent Deposit Designation No. PTA-4791;

(XXV) a monocloncal antibody or binding region thereof secreted by a hybridoma entitled X41(3)37 deposited with the American Type Culture Collection (ATCC; 10801 University Blvd., Manassas, Va. 20110-2209 USA) on Nov. 7, 2002 and assigned as Patent Deposit Designation No. PTA-4791;

(XXVI) a meneleneal monocloncal antibody or binding region thereof secreted by a hybridoma entitled X41(4)6 deposited with the American Type Culture Collection (ATCC; 10801 University Blvd., Manassas, Va. 20110-2209 USA) on Nov. 7, 2002 and assigned as Patent Deposit Designation No. PTA-4794;

(XXVII) a monocloncal antibody or binding region thereof secreted by a hybridoma entitled X41(3)17 deposited with the American Type Culture Collection (ATCC; 10801 University Blvd., Manassas, Va. 20110-2209 USA) on Nov. 7, 2002 and assigned as Patent Deposit Designation No. PTA-4792;

(XXVIII) a monocloncal antibody or binding region thereof secreted by a hybridoma entitled X41(3)50 deposited with the American Type Culture Collection (ATCC; 10801 University Blvd., Manassas, Va. 20110-2209 USA) on Nov. 7, 2002 and assigned as Patent Deposit Designation No. PTA-4793;

(XXIX) a composition comprising a peptide of (I)–(XXII) or an antibody or binding region thereof of (XXIII to XXVIII) together with a pharmaceutical excipient and/or in a human unit dose form;

(XXX) a method of using a peptide of (I)–(XXII), or an antibody or binding region thereof of (XXIII to XXVIII) or a composition of (XXIX) in a method to modulate a cell expressing 161P2F10b, (XXXI) a method of using a peptide of (I)–(XXII) or an antibody or binding region thereof of (XXIII to XXVIII)or a composition of (XXIX) in a method to diagnose, prophylax, prognose, or treat an individual who bears a cell expressing 161P2F10b (XXXII) a method of using a peptide of (I)–(XXII) or an antibody or binding region thereof of (XXIII to XXVIII) or a composition (XXIX) in a method to diagnose, prophylax, prognose, or treat an individual who bears a cell expressing 161P2F10b, said cell from a cancer of a tissue listed in Table I;

(XXXIII) a method of using a peptide of (I)–(XXII) or an antibody or binding region thereof of (XXIII to XXVIII) or a composition of (XXIX) in a method to diagnose, prophylax, prognose, or treat a a cancer;

(XXXIV) a method of using a peptide of (I)–(XXII) or an antibody or binding region thereof of (XXIII to XXVIII) or a composition of (XXIX) in a method to diagnose, prophylax, prognose, or treat a a cancer of a tissue listed in Table I; and, (XXXV) a method of using a a peptide of (I)–(XXII) or an antibody or binding region thereof of (XXIII to XXVIII) or a composition (XXIX) in a method to identify or characterize a modulator of a cell expressing 161P2F10b.

As used herein, a range is understood to specifically disclose all whole unit positions thereof.

Typical embodiments of the invention disclosed herein include 161P2F10B polynucleotides that encode specific portions of 161P2F10B mRNA sequences (and those which are complementary to such sequences) such as those that encode the proteins and/or fragments thereof, for example:

(a) 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500, 525, 550, 575, 600, 625, 650, 675, 700, 725, 750, 775, 800, 825, 850, 860, 870, 875 or more contiguous amino acids of 161P2F10B variant 1; the maximal lengths relevant for other variants are: variant 2, 875 amino acids; variant 3, 875 amino acids, variant 4, 875, and variant 7, 841 amino acids.

In general, naturally occurring allelic variants of human 161P2F10B share a high degree of structural identity and homology (e.g., 90% or more homology). Typically, alleic variants of a 161P2F10B protein contain conservative amino acid substitutions within the 161P2F10B sequences described herein or contain a substitution of an amino acid from a corresponding position in a homologue of 161P2F10B. One class of 161P2F10B allelic variants are proteins that share a high degree of homology with at least a small region of a particular 161P2F10B amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (O) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13–15 Biochemistry" 2nd ED. Lubert Stryer ed (Stanford University); Henikoff et al., PNAS 1992 Vol 89 10915–10919; Lei et al., J Biol Chem 1995 May 19; 270(20):11882–6).

Embodiments of the invention disclosed herein include a wide variety of art-accepted variants or analogs of 161P2F10B proteins such as polypeptides having amino acid insertions, deletions and substitutions. 161P2F10B variants can be made using methods known in the art such as site-directed mutagenesis, alanine scanning, and PCR mutagenesis. Site-directed mutagenesis (Carter et al, *Nucl. Acids Res.,* 13:4331 (1986); Zoller et al, *Nucl. Acids Res.,* 10:6487 (1987)), cassette mutagenesis (Wells et al., Gene, 34:315 (1985)), restriction selection mutagenesis (Wells et al., *Philos. Trans. R. Soc. London SerA,* 317:415 (1986)) or other known techniques can be performed on the cloned DNA to produce the 161P2F10B variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 161P2F10B variants, analogs or homologs, have the distinguishing allribute of having at least one epitope that is "cross reactive" with a 161P2F10B protein having an amino acid sequence of FIG. 3. As used in this sentence, "cross reactive" means that an antibody or T cell that specifically binds to a 161P2F10B variant also specifically binds to a 161P2F10B protein having an amino acid sequence set forth in FIG. 3. A polypeptide ceases to be a variant of a protein shown in FIG. 3, when it no longer contains any epitope capable of being recognized by an antibody or T cell that specifically binds to the starting 161P2F10B protein. Those skilled in the art understand that antbodies that recognize proteins bind to epitopes of varying size, and a grouping of the order of about four or five amino acids, contiguous or not, is regarded as a typical number of amino acids in a minimal epitope. See, e.g., Nair et a., J. Immunol 2000 165(12): 6949–6955; Hebbes et al., Mol Immunol (1989) 26(9):865–73; Schwartz eta!., J Immunol (1985) 135(4):2598–608.

Other classes of 161P2F10B-related protein variants share 70%, 75%, 80%, 85% or 90% or more similarity with an amino acid sequence of FIG. 3, or a fragment thereof. Another specific class of 161P2F10B protein variants or analogs comprises one or more of the 161P2F10B biological motifs described herein or presently known in the art. Thus, encompassed by the present invention are analogs of 161P2F10B fragments (nucleic or amino acid) that have altered functional (e.g. immunogenic) properties relative to the starting fragment. It is to be appreciated that motifs now or which become part of the art are to be applied to the nucleic or amino acid sequences of FIG. 2 or FIG. 3.

As discussed herein, embodiments of the claimed invention include polypeptides containing less than the full amino acid sequence of a 161P2F10B protein shown in FIG. 2 or FIG. 3. For example, representative embodiments of the invention comprise peptides/proteins having any 4, 5, 6, 7, 8, 9, 10, 11, 12, 13, 14, 15 or more contiguous amino acids of a 161P2F10B protein shown in FIG. 2 or FIG. 3.

Moreover, representative embodiments of the invention disclosed herein include polypeptides consisting of about amino acid 1 to about amino acid 10 of a 161P2F10B protein shown in FIG. 2 or FIG. 3, polypeptides consisting of about amino acid 10 to about amino acid 20 of a 161P2F10B protein shown in FIG. 2 or FIG. 3, polypeptides consisting of about amino acid 20 to about amino acid 30 of a 161P2F10B protein shown in FIG. 2 or FIG. 3, polypeptides consisting of about amino acid 30 to about amino acid 40 of a 161P2F10B protein shown in FIG. 2 or FIG. 3, polypeptides consisting of about amino acid 40 to about amino acid 50 of a 161P2F10B protein shown in FIG. 2 or FIG. 3, polypeptides consisting of about amino acid 50 to about amino acid 60 of a 161P2F10B protein shown in FIG. 2 or FIG. 3, polypeptides consisting of about amino acid 60 to about amino acid 70 of a 161P2F10B protein shown in FIG. 2 or FIG. 3, polypeptides consisting of about amino acid 70 to about amino acid 80 of a 161P2F10B protein shown in FIG. 2 or FIG. 3, polypeptides consisting of about amino acid 80 to about amino acid 90 of a 161P2F10B protein shown in FIG. 2 or FIG. 3, polypeptides consisting of about amino acid 90 to about amino acid 100 of a 161P2F10B protein shown in FIG. 2 or FIG. 3, etc. throughout the entirety of a 161P2F10B amino acid sequence. Moreover, polypeptides consisting of about amino acid 1 (or 20 or 30 or 40 etc.) to about amino acid 20, (or 130, or 140 or 150 etc.) of a 161P2F10B protein shown in FIG. 2 or FIG. 3 are embodiments of the invention. It is to be appreciated that the starting and stopping positions in this paragraph refer to the specified position as well as that position plus or minus 5 residues.

161P2F10B-related proteins are generated using standard peptide synthesis technology or using chemical cleavage methods well known in the art. Alternatively, recombinant methods can be used to generate nucleic acid molecules that encode a 161P2F10B-related protein. In one embodiment, nucleic acid molecules provide a means to generate defined fragments of a 161P2F10B protein (or variants, homologs or analogs thereof).

III.A.) Motif-Bearing Protein Embodiments

Additional illustrative embodiments of the invention disclosed herein include 161P2F10B polypeptides comprising the amino acid residues of one or more of the biological motifs contained within a 161P2F10B polypeptide sequence set forth in FIG. 2 or FIG. 3. Various motifs are known in the art, and a protein can be evaluated for the presence of such motifs by a number of publicly available Internet sites (see, e.g., Epimatrix™ and Epimer™, Brown University, and BIMAS.).

Motif bearing subsequences of all 161P2F10B variant proteins are set forth and identified in Tables VIII–XXI and XXII–XLIX.

Table V sets forth several frequently occurring motifs based on pfam searches (see URL address pfam.wustl.eduI). The columns of Table V list (1) motif name abbreviation, (2) percent identity found amongst the different member of the motif family, (3) motif name or description and (4) most common function; location information is included if the motif is relevant for location.

Polypeptides comprising one or more of the 161P2F10B motifs discussed above are useful in elucidating the specific characteristics of a malignant phenotype in view of the observation that the 161P2F10B motifs discussed above are associated with growth dysregulation and because 161P2F10B is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165–174 (1998); Gaiddon et al., Endocrinology 136 (10): 4331–4338 (1995); Hall et al., Nucleic Acids Research 24(6):1119–1126 (1996); Peterziel et al., Oncogene 18(46): 6322–6329 (1999) and O'Brian, Oncol. Rep. 5(2): 305–309 (1998)). Moreover, both glycosylation and myristoylation are protein modifications also associated with cancer and cancer progression (see e.g. Dennis et al., Biochem. Biophys. Acta 1473(1):21–34 (1999); Raju et al., Exp. Cell Res. 235(1): 145–154 (1997)). Amidation is another protein modification also associated with cancer and cancer progression (see e.g. Treston et al., J. Natl. Cancer Inst. Monogr. (13): 169–175 (1992)).

In another embodiment, proteins of the invention comprise one or more of the immunoreactive epitopes identified in accordance with art-accepted methods, such as the peptides set forth in Tables VIII–XXI and XXII–XLIX. CTL epitopes can be determined using specific algorithms to identify peptides within a 161P2F10B protein that are capable of optimally binding to specified HLA alleles (e.g., Table IV; Epimatrix™ and Epimer™, Brown University, and BLMAS). Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I and HLA Class II motifs/supermotifs of Table IV). The epitope is analoged by substituting out an amino acid at one of the specified positions, and replacing it with another amino acid specified for that position. For example, on the basis of residues defined in Table IV, one can substitute out a deleterious residue in favor of any other residue, such as a preferred residue; substitute a less-preferred residue with a preferred residue; or substitute an originally-occurring preferred residue with another preferred residue. Substitutions can occur at primary anchor positions or at other positions in a peptide; see, e.g., Table IV.

A variety of references reflect the art regarding the identification and generation of epitopes in a protein of interest as well as analogs thereof. See, for example, WO 97/33602 to Chesnut et al.; Sette, Immunogenetics 1999 50(3–4): 201–212; Sette et al., J. Immunol. 2001 166(2): 1389–1397; Sidney et al., Hum. Immunol. 1997 58(1): 12–20; Kondo et al., Immunogenetics 1997 45(4): 249–258; Sidney et al., J. Immunol. 1996 157(8): 3480–90; and Falk et al., Nature 351: 290–6 (1991); Hunt et al., Science 255:1261–3(1992); Parker et al., J. Immunol. 149:3580–7 (1992); Parker et al., J. Immunol. 152:163–75 (1994)); Kast et al., 1994 152(8): 3904–12; Borras-Cuesta et al., Hum. Immunol. 2000 61(3): 266–278; Alexander et al., J. Immunol. 2000 164(3); 164(3): 1625–1633; Alexander et al., PMID: 7895164, UI: 95202582; O'Sullivan et al., J. Immunol. 1991 147(8): 2663–2669; Alexander et al., Immunity 1994 1(9): 751–761 and Alexander et al., Immunol. Res. 1998 18(2): 79–92.

Related embodiments of the invention include polypeptides comprising combinations of the different motifs set forth in Table VI, and/or, one or more of the predicted CTL epitopes of Tables VIII–XXI and XXII–XLIX, and/or, one or more of the predicted HTL epitopes of Tables XLVI–XLIX, and/or, one or more of the T cell binding motifs known in the art. Preferred embodiments contain no insertions, deletions or substitutions either within the motifs or within the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically, the number of N-terminal and/or C-terminal amino acid residues on either side of a motif is between about 1 to about 100 amino acid residues, preferably 5 to about 50 amino acid residues.

161P2F10B-related proteins are embodied in many forms, preferably in isolated form. A purified 161P2F10B protein molecule will be substantially free of other proteins or molecules that impair the binding of 161P2F10B to antibody, T cell or other ligand. The nature and degree of isolation and purification will depend on the intended use. Embodiments of a 161P2F10B-related proteins include purified 161P2F10B-related proteins and functional, soluble 161P2F10B-related proteins. In one embodiment, a functional, soluble 161P2F10B protein or fragment thereof retains the ability to be bound by antibody, T cell or other ligand.

The invention also provides 161P2F10B proteins comprising biologically active fragments of a 161P2F10B amino acid sequence shown in FIG. 2 or FIG. 3. Such proteins exhibit properties of the starting 161P2F10B protein, such as the ability to elicit the generation of antibodies that specifically bind an epitope associated with the starting 161P2F10B protein; to be bound by such antibodies; to elicit the activation of HTL or CTL; and/or, to be recognized by HTL or CTL that also specifically bind to the starting protein.

161P2F10B-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or based on immunogenicity. Fragments that contain such structures are particularly useful in generating subunit-specific anti-161P2F10B antibodies or T cells or in identifying cellular factors that bind to 161P2F10B. For example, hydrophilicity profiles can be generated, and immunogenic peptide fragments identified, using the method of Hopp, T. P. and Woods, K. R., 1981, Proc. Natl. Acad. Sci. U.S.A. 78:3824–3828. Hydropathicity profiles can be generated, and immunogenic peptide fragments identified, using the method of Kyte, J. and Doolittle, R. F., 1982, J. Mol. Biol. 157:105–132. Percent (%) Accessible Residues profiles can be generated, and immunogenic peptide fragments identified, using the method of Janin J., 1979, Nature 277:491–492. Average Flexibility profiles can be generated, and immunogenic peptide fragments identified, using the method of Bhaskaran R., Ponnuswamy P. K., 1988, Int. J. Pept. Protein Res. 32:242–255. Beta-turn profiles can be generated, and immunogenic peptide fragments identified, using the method of Deleage, G., Roux B., 1987, Protein Engineering 1:289–294.

CTL epitopes can be determined using specific algorithms to identify peptides within a 161P2F10B protein that are capable of optimally binding to specified HLA alleles (e.g., by using the SYFPEITHI site; the listings in Table IV(A)–(E); Epimatrix™ and Epimer™, Brown University; and BIMAS). Illustrating this, peptide epitopes from 161P2F10B that are presented in the context of human MHC Class I molecules, e.g., HLA-A1, A2, A3, A11, A24, B7 and B35 were predicted (see, e.g., Tables VIII–XXI, XXII–XLIX). Specifically, the complete amino acid sequence of the 161P2F10B protein and relevant portions of other variants, i.e., for HLA Class I predictions 9 flanking residues on either side of a point mutation or exonjunction, and for HLA Class II predictions 14 flanking residues on either side of a point mutation or exon junction corresponding to that variant, were entered into the HLA Peptide Motif Search algorithm found in the Bioinformatics and Molecular Analysis Section (BIMAS) web site listed above; in addition to the site SYFPEITHI.

The HLA peptide motif search algorithm was developed by Dr. Ken Parker based on binding of specific peptide sequences in the groove of HLA Class I molecules, in particular HLA-A2 (see, e.g., Falk et al., Nature 351: 290–6 (1991); Hunt et al., Science 255:1261–3 (1992); Parker et al., J. Immunol. 149:3580–7 (1992); Parker et al., J. Immunol. 152:163–75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for Class I HLA-A2, the epitopes preferably contain a leucine (L) or methionine (M) at position 2 and a valine (V) or leucine (L) at the C-terminus (see, e.g., Parker et al., J. Immunol. 149:3580–7 (1992)). Selected results of 161P2F10B predicted binding peptides are shown in Tables VIII–XXI and XXII–XLIX herein. In Tables VIII–XXI and XXII–XLVII, selected candidates, 9-mers and 10-mers, for each family member are shown along with their location, the amino acid sequence of each specific peptide, and an estimated binding score. In Tables XLVI-XLIX, selected candidates, 15-mers, for each family member are shown along with their location, the amino acid sequence of each specific peptide, and an estimated binding score. The binding score corresponds to the estimated half time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73–8 (1997) and Peshwa et al., Prostate 36:129–38 (1998)). Immunogenicity of specific peptides can be evaluated in vitro by stimulation of CD8+cytotoxic T lymphocytes (CTL) in the presence of antigen presenting cells such as dendritic cells.

It is to be appreciated that every epitope predicted by the BLIMAS site, Epimer™ and Epimatrix™ sites, or specified by the HLA class I or class II motifs available in the art or which become part of the art such as set forth in Table IV (or determined using the SYFPEITHI site or BIMAS are to be "applied" to a 161P2F10B protein in accordance with the invention. As used in this context "applied" means that a 161P2F10B protein is evaluated, e.g., visually or by computer-based patterns finding methods, as appreciated by those of skill in the relevant art. Every subsequence of a 161P2F10B protein of 8, 9, 10, or 11 amino acid residues that bears an HLA Class I motif, or a subsequence of 9 or more amino acid residues that bear an HLA Class II motif are within the scope of the invention.

III.B.) Expression of 161P2F10B-Related Proteins

In an embodiment described in the examples that follow, 161P2F10B can be conveniently expressed in cells (such as 293T cells) transfected with a commercially available expression vector such as a CMV-driven expression vector, encoding 161P2F10B with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 161P2F10B protein in transfected cells. The secreted HIS-tagged 161P2F10B in the culture media can be purified, e.g., using a nickel column using standard techniques.

III.C.) Modifications of 161P2F10B-Related Proteins

Modifications of 161P2F10B-related proteins such as covalent modifications are included within the scope of this invention. One type of covalent modification includes reacting targeted amino acid residues of a 161P2F10B polypeptide with an organic derivatizing agent that is capable of reacting with selected side chains or the N- or C-terminal residues of a 161P2F10B protein. Another type of covalent modification of a 161P2F10B polypeptide included within the scope of this invention comprises altering the native glycosylation pattern of a protein of the invention. Another type of covalent modification of 161P2F10B comprises linking a 161P2F10B polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 161P2F10B-related proteins of the present invention can also be modified to form a chimeric molecule comprising 161P2F10B fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of a 161P2F10B sequence (amino or nucleic acid) such that a molecule is created that is not, through its length, directly homologous to the amino or nucleic acid sequences shown in FIG. 2 or FIG. 3. Such a chimeric molecule can comprise multiples of the same subsequence of 161P2F10B. A chimeric molecule can comprise a fusion of a 161P2F10B-related protein with a polyhistidine epitope tag, which provides an epitope to which immobilized nickel can selectively bind, with cytokines or with growth factors. The epitope tag is generally placed at the amino- or carboxyl-terminus of a 161P2F10B protein. In an alternative embodiment, the chimeric molecule can comprise a fusion of a 161P2F10B-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 161P2F10B polypeptide in place of at least one variable region within an Ig molecule. In a preferred embodiment, the immunoglobulin fusion includes the hinge, CH2 and CH3, or the hinge, CH1, CH2 and CH3 regions of an IgG1 molecule. For the production of immunoglobulin fusions see, e.g., U.S. Pat. No. 5,428,130 issued Jun. 27, 1995.

III.D.) Uses of 161P2F10B-related Proteins

The proteins of the invention have a number of different specific uses. As 161P2F10B is highly expressed in prostate and other cancers, 161P2F10B-related proteins are used in methods that assess the status of 161P2F10B gene products in normal versus cancerous tissues, thereby elucidating the malignant phenotype. Typically, polypeptides from specific regions of a 161P2F10B protein are used to assess the presence of perturbations (such as deletions, insertions, point mutations etc.) in those regions (such as regions containing one or more motifs). Exemplary assays utilize antibodies or T cells targeting 161P2F10B-related proteins comprising the amino acid residues of one or more of the biological motifs contained within a 161P2F10B polypeptide sequence in order to evaluate the characteristics of this region in normal versus cancerous tissues or to elicit an immune response to the epitope. Alternatively, 161P2F10B-related proteins that contain the amino acid residues of one or more of the biological motifs in a 161P2F10B protein are used to screen for factors that interact with that region of 161P2F10B.

161P2F10B protein fragments/subsequences are particularly useful in generating and characterizing domain-specific antibodies (e.g, antibodies recognizing an extracellular or intracellular epitope of a 161P2F10B protein), for identifying agents or cellular factors that bind to 161P2F10B or a particular structural domain thereof, and in various therapeutic and diagnostic contexts, including but not limited to diagnostic assays, cancer vaccines and methods of preparing such vaccines.

Proteins encoded by the 161P2F10B genes, or by analogs, homologs or fragments thereof, have a variety of uses, including but not limited to generating antibodies and in methods for identifying ligands and other agents and cellular constituents that bind to a 161P2F10B gene product Antibodies raised against a 161P2F10B protein or fragment thereof are useful in diagnostic and prognostic assays, and imaging methodologies in the management of human cancers characterized by expression of 161P2F10B protein, such as those listed in Table I. Such antibodies can be expressed intracellularly and used in methods of treating patients with such cancers. 161P2F10B-related nucleic acids or proteins are also used in generating HTL or CTL responses.

Various immunological assays useful for the detection of 161P2F10B proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 161P2F10B-expressing cells (e.g., in radioscintigraphic imaging methods). 161P2F10B proteins are also particularly useful in generating cancer vaccines, as further described herein.

IV.) 161P2F10B Antibodies

Another aspect of the invention provides antibodies that bind to 161P2F10B-related proteins. Preferred antibodies specifically bind to a 161P2F10B-related protein and do not bind (or bind weakly) to peptides or proteins that are not 161P2F10B-related proteins. For example, antibodies that bind 161P2F10B can bind 161P2F10B-related proteins such as the homologs or analogs thereof.

161P2F10B antibodies of the invention are particularly useful in cancer (see, e.g., Table I) diagnostic and prognostic assays, and imaging methodologies. Similarly, such antibodies are useful in the treatment, diagnosis, and/or prognosis of other cancers, to the extent 161P2F10B is also expressed or overexpressed in these other cancers. Moreover, intracellularly expressed antibodies (e.g., single chain antibodies) are therapeutically useful in treating cancers in which the expression of 161P2F10B is involved, such as advanced or metastatic prostate cancers.

The invention also provides various immunological assays useful for the detection and quantification of 161P2F10B and mutant 161P2F10B-related proteins. Such assays can comprise one or more 161P2F10B antibodies capable of recognizing and binding a 161P2F10B-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompabbility complex (MHC) binding assays.

In addition, immunological imaging methods capable of detecting prostate cancer and other cancers expressing 161P2F10B are also provided by the invention, including but not limited to radioscintgraphic imaging methods using labeled 161P2F10B antibodies. Such assays are clinically useful in the detection, monitoring, and prognosis of 161P2F10B expressing cancers such as prostate cancer.

161P2F10B antibodies are also used in methods for purifying a 161P2F10B-related protein and for isolating 161P2F10B homologues and related molecules. For example, a method of purifying a 161P2F10B-related protein comprises incubating a 161P2F10B antibody, which has been coupled to a solid matrix, with a lysate or other solution containing a 161P2F10B-related protein under conditions that permit the 161P2F10B antibody to bind to the 161P2F10B-related protein; washing the solid matrix to eliminate impurities; and eluting the 161P2F10B-related protein from the coupled antibody. Other uses of 161P2F10B antibodies in accordance with the invention include generating anti-idiotypic antibodies that mimic a 161P2F10B protein.

Various methods for the preparation of antibodies are well known in the art. For example, antibodies can be prepared by immunizing a suitable mammalian host using a 161P2F10B-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 161P2F10B can also be used, such as a 161P2F10B GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 161P2F10B-related protein is synthesized and used as an immunogen.

In addition, naked DNA immunization techniques known in the art are used (with or without purified 161P2F10B-related protein or 161P2F10B expressing cells) to generate an immune response to the encoded immunogen (for review, see Donnelly et al, 1997, Ann. Rev. Immunol. 15: 617–648).

The amino acid sequence of a 161P2F10B protein as shown in FIG. 2 or FIG. 3 can be analyzed to select specific regions of the 161P2F10B protein for generating antibodies. For example, hydrophobicity and hydrophilicity analyses of a 161P2F10B amino acid sequence are used to identify hydrophilic regions in the 161P2F10B structure. Regions of a 161P2F10B protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Hydrophilicity profiles can be generated using the method of Hopp, T. P. and Woods, K. R., 1981, Proc. Natl. Acad. Sci. U.S.A. 78:3824–3828. Hydropathicity profiles can be generated using the method of Kyte, J. and Doolittle, R. F., 1982, J. Mol. Biol. 157:105–132. Percent (%) Accessible Residues profiles can be generated using the method of Janin J., 1979, Nature 277:491–492. Average Flexibility profiles can be generated using the method of Bhaskaran R., Ponnuswamy P. K., 1988, Int. J. Pept. Protein Res. 32:242–255. Beta-turn profiles can be generated using the method of Deleage, G., Roux B., 1987, Protein Engineering 1:289–294. Thus, each region identified by any of these programs or methods is within the scope of the present invention. Methods for the generation of 161P2F10B antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 161P2F10B immunogen is often conducted by injection over a suitable time period and with use of a suitable adjuvant, as is understood in the art. During the immunization schedule, titers of antibodies can be taken to determine adequacy of antibody formation.

161P2F10B monoclonal antibodies can be produced by various means well known in the art For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 161P2F10B-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of a 161P2F10B protein can also be produced in the context of chimeric or complementarity-determining region (CDR) grafted antbodies of multiple species origin. Humanized or human 161P2F10B antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522–525; Riechmann et al., 1988, Nature 332: 323–327; Verhoeyen et al., 1988, Science 239: 15341536). See also, Carter et a!, 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535–539). Fully human 161P2F10B monoclonal antibodies can be generated using cloning technologies employing large human 1 g gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45–64 (1993); Burton and Barbas, Human Antibodies from combinatorial libraries. Id., pp 65–82). Fully human 161P2F10B monoclonal antibodies can also be produced using transgenic mice engineered to contain human immunoglobulin gene loci as described in PCT Patent Application WO98124893, Kucheriapati and Jakobovits et a!, published Dec. 3, 1997 (see also, Jakobovits, 1998, Exp. Opin. Invest. Drugs 7(4): 607–614; U.S. Pat. Nos. 6,162,963 issued 2000 Dec. 19; U.S. Pat. No. 6,150,584 issued 2000 Nov. 12; and, U.S. Pat. No. 6,114598 issued 2000 Sep. 5). This method avoids the in vitro manipulation required with phage display technology and efficiently produces high affinity authentic human antibodies.

Reactivity of 161P2F10B antibodies with a 161P2F10B-related protein can be established by a number of well known means, including Western blot, immunoprecipitation, ELISA, and FACS analyses using, as appropriate, 161P2F10B-related proteins, 161P2F10B-expressing cells or extracts thereof. A 161P2F10B antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 161P2F10B epitopes are generated using methods generally known in the art. Homodimeric antibodies can also be generated by cross-linking techniques known in the art (e.g., Wolff et al., Cancer Res. 53: 2560–2565).

V.) 161P2F10B Cellular Immune Responses

The mechanism by which T cells recognize antigens has been delineated. Efficacious peptide epitope vaccine compositions of the invention induce a therapeutic or prophylactic immune responses in very broad segments of the world-wide population. For an understanding of the value and efficacy of compositions of the invention that induce cellular immune responses, a brief review of immunology-related technology is provided.

A complex of an HLA molecule and a peptidic antigen acts as the ligand recognized by HLA-restricted T cells (Buus, S. et al., Cell 47:1071, 1986; Babbitt, B. P. et al., Nature 317:359,1985; Townsend, A. and Bodmer, H., Annu. Rev. Immunol. 7:601, 1989; Germain, R. N., Annu. Rev. Immunol. 11:403, 1993). Through the study of single amino acid substituted antigen analogs and the sequencing of endogenously bound, naturally processed peptides, critical residues that correspond to motifs required for specific binding to HLA antigen molecules have been identified and are set forth in Table IV (see also, e.g., Southwood, et al., J. Immunol. 160:3363, 1998; Rammensee, et al., Immunogenetics 41:178, 1995; Rammensee et al., SYFPEITHI, access via World Wide Web at URL (134.2.96.221/scripts.hlaserver.dll/home.htm); Selte, A. and Sidney, J. Curr. Opin. Immunol. 10 478, 1998; Engelhard, V. H., Curr. Opin. Immunol. 6:13, 1994; Sette, A. and Grey, H. M., Curr. Opin. Immunol. 4:79, 1992; Sinigaglia, F. and Hammer, J. Curr. Biol. 6:52, 1994; Ruppert et al., Cell 74:929–937, 1993; Kondo et al., J. Immunol 155:4307–4312, 1995; Sidney et al., J. Immunol. 157:3480–3490, 1996; Sidney et al., Human Immunol. 45:79–93, 1996; Selte, A. and Sidney, J. Immunogenetics 1999 November; 50(3–4):201-12, Review).

Furthermore, x-ray crystallographic analyses of HLA-peptide complexes have revealed pockets within the peptide binding cleftugroove of HLA molecules which accommodate, in an allele-specific mode, residues borne by peptide ligands; these residues in turn determine the HLA binding capacity of the peptides in which they are present. (See, e.g., Madden, D. R. Annu. Rev. Immunol. 13:587, 1995; Smith, et al., Immunity 4:203, 1996; Fremont et al., Immunity 8:305, 1998; Stern et al., Structure 2:245, 1994; Jones, E. Y. Curr. Opin. Immunol. 9:75, 1997; Brown, J. H. et al., Nature 364:33, 1993; Guo, H. C. et al., Proc. Natl. Acad. Sci. USA 90:8053, 1993; Guo, H. C. et al., Nature 360:364, 1992; Silver, M. L. et al., Nature 360:367, 1992; Matsumura, M. et al., Science 257:927, 1992; Madden et al., Cell 70:1035, 1992; Fremont, D. H. et al., Science 257:919, 1992; Saper, M. A., Bjorkman, P. J. and Wiley, D. C., J. Mol. Biol. 219:277, 1991.)

Accordingly, the definition of class I and class II allele-specific HLA binding motifs, or class I or class II supermotifs allows identification of regions within a protein that are correlated with binding to particular HLA antigen(s).

Thus, by a process of HLA motif identification, candidates for epitope-based vaccines have been identified; such candidates can be further evaluated by HLA-peptide binding assays to determine binding affinity and/or the time period of association of the epitope and its corresponding HLA molecule. Additional confirmatory work can be performed to select, amongst these vaccine candidates, epitopes with preferred characteristics in terms of population coverage, and/or immunogenicity.

Various strategies can be utilized to evaluate cellular immunogenicity, including:

1) Evaluation of primary T cell cultures from normal individuals (see, e.g., Wentworth, P. A. et al., Mol. Immunol 32:603, 1995; Celis, E. et al., Proc. Natl. Acad. Sci. USA 91:2105, 1994; Tsai, V. et al., J. Immunol. 158:1796, 1997; Kawashima, I. et al., Human Immunol. 59:1, 1998). This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., J. Immunol. 26:97, 1996; Wentworth, P. A. et al., Int. Immunol. 8:651, 1996; Alexander, J. et al., J. Immunol. 159:4753, 1997). For example, in such methods peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have been either effectively vaccinated and/or from chronically ill patients (see, e.g., Rehermann, B. et al., J. Exp. Med. 181:1047, 1995; Doolan, D. L. et al., Immunity 7:97, 1997; Bertoni, R. et al., J. Clin. Invest 100:503, 1997; Threlkeld, S. C. et al., J. Immunol. 159:1648, 1997; Diepolder, H. M. et al., J. Virol. 71:6011, 1997). Accordingly, recall responses are detected by culturing PBL from subjects that have been exposed to the antigen due to disease and thus have generated an immune response "naturally", or from patients who were vaccinated against the antigen. PBL from subjects are cultured in vitro for 1–2 weeks in the presence of test peptide plus antigen presenting cells (APC) to allow activation of "memory" T cells, as compared to "naive" T cells. At the end of the culture period, T cell activity is detected using assays including $^{51}$Cr release involving peptide-sensitized targets, T cell proliferation, or lymphokine release.

VI.) 161P2F10B Transgenic Animals

Nucleic acids that encode a 161P2F10B-related protein can also be used to generate either transgenic animals or "knock out" animals that, in turn, are useful in the development and screening of therapeutically useful reagents. In accordance with established techniques, cDNA encoding 161P2F10B can be used to clone genomic DNA that encodes 161P2F10B. The cloned genomic sequences can then be used to generate transgenic animals containing cells that express DNA that encode 161P2F10B. Methods for generating transgenic animals, particularly animals such as mice or rats, have become conventional in the art and are described, for example, in U.S. Pat. No. 4,736,866 issued 1998 Apr. 12, and U.S. Pat. No. 4,870,009 issued 1989 Sep. 26. Typically, particular cells would be targeted for 161P2F10B transgene incorporation with tissue-specific enhancers.

Transgenic animals that include a copy of a transgene encoding 161P2F10B can be used to examine the effect of increased expression of DNA that encodes 161P2F10B. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 161P2F10B can be used to construct a 161P2F10B "knock out" animal that has a defective or altered gene encoding 161P2F10B as a result of homologous recombination between the endogenous gene encoding 161P2F10B and altered genomic DNA encoding 161P2F10B introduced into an embryonic cell of the animal. For example, cDNA that encodes 161P2F10B can be used to clone genomic DNA encoding 161P2F10B in accordance with established techniques. A portion of the genomic DNA encoding 161P2F10B can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, *Cell*, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113–152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of a 161P2F10B polypeptide.

VII.) Methods for the Detection of 161P2F10B

Another aspect of the present invention relates to methods for detecting 161P2F10B polynucleotides and 161P2F10B-related proteins, as well as methods for identifying a cell that expresses 161P2F10B. The expression profile of 161P2F10B makes it a diagnostic marker for metastasized disease. Accordingly, the status of 161P2F10B gene products provides information useful for predicting a variety of factors including susceptibility to advanced stage disease, rate of progression, and/or tumor aggressiveness. As discussed in detail herein, the status of 161P2F10B gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 161P2F10B polynucleotides in a biological sample, such as serum, bone, prostate, and other tissues, urine, semen, cell preparations, and the like. Detectable 161P2F10B polynucleotides include, for example, a 161P2F10B gene or fragment thereof, 161P2F10B mRNA, alternative splice variant 161P2F10B mRNAs, and recombinant DNA or RNA molecules that contain a 161P2F10B polynucleotide. A number of methods for amplifying and/or detecting the presence of 161P2F10B polynucleotides are well known in the art and can be employed in the practice of this aspect of the invention.

In one embodiment, a method for detecting a 161P2F10B mRNA in a biological sample comprises producing cDNA from the sample by reverse transcription using at least one primer; amplifying the cDNA so produced using a 161P2F10B polynucleotides as sense and antisense primers to amplify 161P2F10B cDNAs therein; and detecting the presence of the amplified 161P2F10B cDNA. Optionally, the sequence of the amplified 161P2F10B cDNA can be determined.

In another embodiment, a method of detecting a 161P2F10B gene in a biological sample comprises first isolating genomic DNA from the sample; amplifying the isolated genomic DNA using 161P2F10B polynucleotides as sense and antisense primers; and detecting the presence of the amplified 161P2F10B gene. Any number of appropriate sense and antisense probe combinations can be designed from a 161P2F10B nucleotide sequence (see, e.g., FIG. 2) and used for this purpose.

The invention also provides assays for detecting the presence of a 161P2F10B protein in a issue or other bioloical sample such as serum, semen, bone, prostate, urine, cell preparations, and the like. Methods for detecting a 161P2F10B-related protein are also well known and include, for example, immunoprecipitation, immunohistochemical analysis, Western blot analysis, molecular binding assays, ELISA, ELIFA and the like. For example, a method of detecting the presence of a 161P2F10B-related protein in a biological sample comprises first contacting the sample with a 161P2F10B antibody, a 161P2F10B-reactive fragment thereof, or a recombinant protein containing an antigen-binding region of a 161P2F10B antibody; and then detecting the binding of 161P2F10B-related protein in the sample.

Methods for identifying a cell that expresses 161P2F10B are also within the scope of the invention. In one embodiment, an assay for identifying a cell that expresses a 161P2F10B gene comprises detecting the presence of 161P2F10B mRNA in the cell. Methods for the detection of particular mRNAs in cells are well known and include, for example, hybridization assays using complementary DNA probes (such as in situ hybridization using labeled 161P2F10B riboprobes, Northern blot and related techniques) and various nucleic acid amplification assays (such as RT-PCR using complementary primers specific for 161P2F10B, and other amplification type detection methods, such as, for example, branched DNA, SISBA, TMA and the like). Alternatively, an assay for identifying a cell that expresses a 161P2F10B gene comprises detecting the presence of 161 F10B-related protein in the cell or secreted by the cell. Various methods for the detection of proteins are well known in the art and are employed for the detection of 161P2F10B-related proteins and cells that express 161P2F10B-related proteins.

161P2F10B expression analysis is also useful as a tool for identifying and evaluating agents that modulate 161P2F10B gene expression. For example, 161P2F10B expression is significantly upregulated in prostate cancer, and is expressed in cancers of the tissues listed in Table I. Identification of a molecule or biological agent that inhibits 161P2F10B expression or over-expression in cancer cells is of therapeutic value. For example, such an agent can be identified by using a screen that quantifies 161P2F10B expression by RT-PCR, nucleic acid hybridization or antibody binding.

VIII.) Methods for Monitoring the Status of 161P2F10B-related Genes and their Products Oncogenesis is known to be a multistep process where cellular growth becomes progressively dysregulated and cells progress from a normal physiological state to precancerous and then cancerous states (see, e.g., Alers et al., Lab Invest. 77(5): 437–438 (1997) and Isaacs et al., Cancer Surv. 23: 19–32 (1995)). In this context, examining a biological sample for evidence of-dysregulated cell growth (such as aberrant 161P2F10B expression in cancers) allows for early detection of such aberrant physiology, before a pathologic state such as cancer has progressed to a stage that therapeutic options are more limited and or the prognosis is worse. In such examinations, the status of 161P2F10B in a biological sample of interest can be compared, for example, to the status of 161P2F10B in a corresponding normal sample (e.g. a sample from that individual or alternatively another individual that is not affected by a pathology). An alteration in the status of 161P2F10B in the biological sample (as compared to the normal sample) provides evidence of dysregulated cellular growth. In addition to using a biological sample that is not affected by a pathology as a normal sample, one can also use a predetermined normative value such as a predetermined normal level of mRNA expression (see, e.g., Grever et al., J. Comp. Neurol. 1996 Dec. 9; 376(2): 306–14 and U.S. Pat. No. 5,837,501) to compare 161P2F10B status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 161P2F10B expressing cells) as well as the level, and biological activity of expressed gene products (such as 161P2F10B mRNA, polynucleotides and polypeptides). Typically, an alteration in the status of 161P2F10B comprises a change in the location of 161P2F10B and/or 161P2F10B expressing cells and/or an increase in 161P2F10B mRNA and/or protein expression.

161P2F10B status in a sample can be analyzed by a number of means well known in the art, including without limitation, immunohistochemical analysis, in sdu hybridization, RT-PCR analysis on laser capture micro-dissected samples, Western blot analysis, and tissue array analysis. Typical protocols for evaluating the status of a 161P2F10B gene and gene products are found, for example in Ausubel et al. eds., 1995, Current Protocols In Molecular Biology, Units 2 (Northern Blotting), 4 (Southern Blotting), 15 (Immunoblotting) and 18 (PCR Analysis). Thus, the status of 161P2F10B in a biological sample is evaluated by various methods utilized by skilled artisans including, but not limited to genomic Southern analysis (to examine, for example perturbations in a 161P2F10B gene), Northern analysis and/or PCR analysis of 161P2F10B mRNA (to examine, for example alterations in the polynucleotide sequences or expression levels of 161P2F10B mRNAs), and, Western and/or immunohistochemical analysis (to examine, for example alterations in polypeptide sequences, alterations in polypeptide localization within a sample, alterations in expression levels of 161P2F10B proteins and/or associations of 161P2F10B proteins with polypeptide binding partners). Detectable 161P2F10B polynucleotides include, for example, a 161P2F10B gene or fragment thereof, 161P2F10B mRNA, alternative splice variants, 161P2F10B mRNAs, and recombinant DNA or RNA molecules containing a 161P2F10B polynucleotide.

The expression profile of 161P2F10B makes it a diagnostic marker for local and/or metastasized disease, and provides information on the growth or oncogenic potential of a biological sample. In particular, the status of 161P2F10B provides information useful for predicting susceptibility to particular disease stages, progression, and/or tumor aggressiveness. The invention provides methods and assays for determining 161P2F10B status and diagnosing cancers that express 161P2F10B, such as cancers of the tissues listed in Table I. For example, because 161P2F10B mRNA is so highly expressed in prostate and other cancers relative to normal prostate tissue, assays that evaluate the levels of 161P2F10B mRNA transcripts or proteins in a biological sample can be used to diagnose a disease associated with 161P2F10B dysregulation, and can provide prognostic information useful in defining appropriate therapeutic options.

The expression status of 161P2F10B provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 161P2F10B in biological samples such as those from individuals suffering from, or suspected of suffering from a pathology characterized by dysregulated cellular growth, such as cancer.

As described above, the status of 161P2F10B in a biological sample can be examined by a number of well-known procedures in the art. For example, the status of 161P2F10B in a biological sample taken from a specific location in the body can be examined by evaluating the sample for the presence or absence of 161P2F10B expressing cells (e.g. those that express 161P2F10B mRNAs or proteins). This examination can provide evidence of dysregulated cellular growth, for example, when 161P2F10B-expressing cells are found in a biological sample that does not normally contain such cells (such as a lymph node), because such alterations in the status of 161P2F10B in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315–317 (2000);Su et al., Semin. Surg. Oncol. 18(1): 17–28 (2000) and Freeman et al., J Urol 1995 August 154(2 Pt 1):474–8).

In one aspect, the invention provides methods for monitoring 161P2F10B gene products by determining the status of 161P2F10B gene products expressed by cells from an individual suspected of having a disease associated with dysregulated cell growth (such as hyperplasia or cancer) and then comparing the status so determined to the status of 161P2F10B gene products in a corresponding normal sample. The presence of aberrant 161P2F10B gene products in the test sample relative to the normal sample provides an indication of the presence of dysregulated cell growth within the cells of the individual.

In another aspect, the invention provides assays useful in determining the presence of cancer in an individual, comprising detecting a significant increase in 161P2F10B mRNA or protein expression in a test cell or tissue sample relative to expression levels in the corresponding normal cell or tissue. The presence of 161P2F10B mRNA can, for example, be evaluated in tissues including but not limited to those listed in Table I. The presence of significant 161P2F10B expression in any of these tissues is useful to indicate the emergence, presence and/or severity of a cancer, since the corresponding normal tissues do not express 161P2F10B mRNA or express it at lower levels.

In a related embodiment, 161P2F10B status is determined at the protein level rather than at the nucleic acid level. For example, such a method comprises determining the level of 161P2F10B protein expressed by cells in a test tissue sample and comparing the level so determined to the level of 161P2F10B expressed in a corresponding normal sample. In one embodiment, the presence of 161P2F108 protein is evaluated, for example, using immunohistochemical methods. 161P2F10B antibodies or binding partners capable of detecting 161P2F10B protein expression are used in a variety of assay formats well known in the art for this purpose.

In a further embodiment, one can evaluate the status of 161P2F10B nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369–378). For example, a mutation in the sequence of 161P2F10B may be indicative of the presence or promotion of a tumor. Such assays therefore have diagnostic and predictive value where a mutation in 161P2F10B indicates a potential loss of function or increase in tumor growth.

A wide variety of assays for observing perturbations in nucleotide and amino acid sequences are well known in the art. For example, the size and structure of nucleic acid or amino acid sequences of 161P2F10B gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 issued 1999 Sep. 7, and U.S. Pat. No. 5,952,170 issued 1995 Jan. 17).

Additionally, one can examine the methylation status of a 161P2F10B gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536). In another example, expression of the LAGE-1 tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., Int. J. Cancer 76(6): 903–908 (1998)). A variety of assays for examining methylabon status of a gene are well known in the art. For example, one can utilize, in Southern hybridization approaches, methylation-sensitive restriction enzymes that cannot cleave sequences that contain methylated CpG sites to assess the methylabon status of CpG islands. In addition, MSP (methylation specific PCR) can rapidly profile the methylabon status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995.

Gene amplification is an additional method for assessing the status of 161P2F10B. Gene amplification is measured in a sample directly, for example, by conventional Southern blotting or Northern blotting to quantitate the transcription of mRNA (Thomas, 1980, Proc. Natl. Acad. Sci. USA, 77:5201–5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound-to the duplex can be detected.

Biopsied tissue or peripheral blood can be conveniently assayed for the presence of cancer cells using for example, Northern, dot blot or RT-PCR analysis to detect 161P2F10B expression. The presence of RT-PCR amplifiable 161P2F10B mRNA provides an indicaton of the presence of cancer. RT-PCR assays are well known in the arL RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373–384; Ghossein et al., 1995, J. Clin. Oncol. 13:1195–2000; Heston et al., 1995, Clin. Chem. 41:1687–1688).

A further aspect of the invention is an assessment of the susceptibility that an individual has for developing cancer. In one embodiment, a method for predicting susceptibility to cancer comprises detecting 161P2F10B mRNA or 161P2F10B protein in a tissue sample, its presence indicating susceptibility to cancer, wherein the degree of 161P2F10B mRNA expression correlates to the degree of susceptibility. In a specific embodiment, the presence of 161P2F10B in prostate or other bssue is examined, with the presence of 161P2F10B in the sample providing an indication of prostate cancer susceptibility (or the emergence or existence of a prostate tumor). Similarly, one can evaluate the integrity 161P2F10B nucleotide and amino acid sequences in a biological sample, in order to identify perturbations in the structure of these molecules such as insertions, deletions, substitutions and the like. The presence of one or more perturbations in 161P2F10B gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 161P2F10B mRNA or 161P2F10B protein expressed by tumor cells, comparing the level so determined to the level of 161P2F10B mRNA or 161P2F10B protein expressed in a corresponding normal tissue taken from the same individual or a normal tissue reference sample, wherein the degree of 161P2F10B mRNA or 161P2F10B protein expression in the tumor sample relative to the normal sample indicates the degree of aggressiveness. In a specific embodiment, aggressiveness of a tumor is evaluated by determining the extent to which 161P2F10B is expressed in the tumor cells, with higher expression levels indicating more aggressive tumors. Another embodiment is the evaluation of the integrity of 161P2F10B nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 161P2F10B mRNA or 161P2F10B protein expressed by cells in a sample of the tumor, comparing the level so determined to the level of 161P2F10B mRNA or 161P2F10B protein expressed in an equivalent issue sample taken from the same individual at a different time, wherein the degree of 161P2F10B mRNA or 161P2F10B protein expression in the tumor sample over time provides information on the progression of the cancer. In a specific embodiment, the progression of a cancer is evaluated by determining 161P2F10B expression in the tumor cells over time, where increased expression over time indicates a progression of the cancer. Also, one can evaluate the integrity 161P2F10B nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 161P2F10B gene and 161P2F10B gene products (or perturbations in 161P2F10B gene and 161P2F10B gene products) and a factor that is associated with malignancy, as a means for diagnosing and prognosticating the status of a issue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74–88; Epstein, 1995, Hum. Pathol. 26(2):223–9; Thorson et al., 1998, Mod. Pathol. 11 (6):543–51; Baisden et al., 1999, Am. J. Surg. Pathol. 23(8):918–24). Methods for observing a coincidence between the expression of 161P2F10B gene and 161P2F10B gene products (or perturbations in 161P2F10B gene and 161P2F10B gene products) and another factor that is associated with malignancy are useful, for example, because the presence of a set of specific factors that coincide with disease provides information crucial for diagnosing and prognosticating the status of a issue sample.

In one embodiment, methods for observing a coincidence between the expression of 161P2F10B gene and 161P2F10B gene products (or perturbations in 161P2F10B gene and 161P2F10B gene products) and another factor associated with malignancy entails detecting the overexpression of 161P2F10B mRNA or protein in a tissue sample, detecting the overexpression of PSA mRNA or protein in a issue sample (or PSCA or PSM expression), and observing a coincidence of 161P2F10B mRNA or protein and PSA mRNA or protein overexpression (or PSCA or PSM expression). In a specific embodiment, the expression of 161P2F10B and PSA mRNA in prostate bssue is examined, where the coincidence of 161P2F10B and PSA mRNA overexpression in the sample indicates the existence of prostate cancer, prostate cancer susceptibility or the emergence or status of a prostate tumor.

Methods for detecting and quantifying the expression of 161P2F10B mRNA or protein are described herein, and standard nucleic acid and protein detection and quantification technologies are well known in the art. Standard methods for the detection and quantification of 161P2F10B mRNA include in sdu hybridization using labeled 161P2F10B riboprobes, Northern blot and related techniques using 161P2F10B polynucleotide probes, RT-PCR analysis using primers specific for 161P2F10B, and other amplification type detection methods, such as, for example, branched DNA, SISBA, TMA and the like. In a specific embodiment, semi-quantitative RT-PCR is used to detect and quantify 161P2F10B mRNA expression. Any number of primers capable of amplifying 161P2F10B can be used for this purpose, including but not limited to the various primer sets specifically described herein. In a specific embodiment, polyclonal or monoclonal antibodies specifically reactive with the wild-type 161P2F10B protein can be used in an immunohistochemical assay of biopsied tissue.

IX.) Identification of Molecules that Interact with 161P2F10B

The 161P2F10B protein and nucleic acid sequences disclosed herein allow a skilled artisan to identify proteins, small molecules and other agents that interact with 161P2F10B, as well as pathways activated by 161P2F10B via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, where-upon the expression of the reporter gene is assayed. Other systems identify protein-protein interactions in vivo through reconstitution of a eukaryotic transcriptional activator, see, e.g., U.S. Pat. No. 5,955,280 issued 1999 Sep. 21, U.S. Pat. No. 5,925,523 issued 1999 Jul. 20, U.S. Pat. No. 5,846,722 issued 1998 Dec. 8 and U.S. Pat. No. 6,004,746 issued 1999 Dec. 21. Algorithms are also available in the art for genome-based predictions of protein function (see, e.g., Marcole, et al., Nature 402: Nov. 4, 1999, 83–86).

Alternatively one can screen peptide libraries to identify molecules that interact with 161P2F10B protein sequences. In such methods, peptides that bind to 161P2F10B are identified by screening libraries that encode a random or controlled collection of amino acids. Peptides encoded by the libraries are expressed as fusion proteins of bacteriophage coat proteins, the bacteriophage particles are then screened against the 161P2F10B protein(s).

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 161P2F10B protein sequences are disclosed for example in U.S. Pat. No. 5,723,286 issued 1998 Mar. 3 and U.S. Pat. No. 5,733,731 issued 1998 Mar. 31.

Alternatively, cell lines that express 161P2F10B are used to identify protein-protein interactions mediated by 161P2F10B. Such interactions can be examined using immunoprecipitation techniques (see, e.g., Hamilton B. J., et al. Biochem. Biophys. Res. Commun. 1999, 261:646–51). 161P2F10B protein can be immunoprecipitated from 161P2F10B-expressing cell lines using anti-161P2F10B antibodies. Alternatively, antibodies against His-tag can be used in a cell line engineered to express fusions of 161P2F10B and a His-tag (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 161P2F10B can be identified through related embodiments of such screening assays. For example, small molecules can be identified that interfere with protein function, including molecules that interfere with 161P2F10B's ability to mediate phosphorylation and de-phosphorylation, interaction with DNA or RNA molecules as an indication of regulation of cell cycles, second messenger signaling or tumorigenesis. Similarly, small molecules that modulate 161P2F10B-related ion channel, protein pump, or cell communication functions are identified and used to treat patients that have a cancer that expresses 161P2F10B (see, e.g., Hille, B., Ionic Channels of Excitable Membranes $2^{nd}$ Ed., Sinauer Assoc., Sunderland, Mass., 1992). Moreover, ligands that regulate 161P2F10B function can be identified based on their ability to bind 161P2F10B and activate a reporter construct. Typical methods are discussed for example in U.S. Pat. No. 5,928,868 issued 1999 Jul. 27, and include methods for forming hybrid ligands in which at least one ligand is a small molecule. In an illustrative embodiment, cells engineered to express a fusion protein of 161P2F10B and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit 161P2F10B.

An embodiment of this invention comprises a method of screening for a molecule that interacts with a 161P2F10B amino acid sequence shown in FIG. 2 or FIG. 3, comprising the steps of contacting a population of molecules with a 161P2F10B amino acid sequence, allowing the population of molecules and the 161P2F10B amino acid sequence to interact under conditions that facilitate an interaction, determining the presence of a molecule that interacts with the 161P2F10B amino acid sequence, and then separating molecules that do not interact with the 161P2F10B amino acid sequence from molecules that do. In a specific embodiment, the method further comprises purifying, characterizing and identifying a molecule that interacts with the 161P2F10B amino acid sequence. The identified molecule can be used to modulate a function performed by 161P2F10B. In a preferred embodiment, the 161P2F10B amino acid sequence is contacted with a library of peptides.

X.) Therapeutic Methods and Compositions

The identification of 161P2F10B as a protein that is normally expressed in a restricted set of tissues, but which is also expressed in prostate and other cancers, opens a number of therapeutic approaches to the treatment of such cancers. As contemplated herein, 161P2F10B functions as a transcription factor involved in activating tumor-promoting genes or repressing genes that block tumorigenesis.

Accordingly, therapeutic approaches that inhibit the activity of a 161P2F10B protein are useful for patients suffering from a cancer that expresses 161P2F10B. These therapeutic approaches generally fall into two classes. One class comprises various methods for inhibiting the binding or association of a 161P2F10B protein with its binding partner or with other proteins. Another class comprises a variety of methods for inhibiting the transcription of a 161P2F10B gene or translation of 161P2F10B mRNA.

X.A.) Anti-Cancer Vaccines

The invention provides cancer vaccines comprising a 161P2F10B-related protein or 161P2F10B-related nucleic acid. In view of the expression of 161P2F10B, cancer vaccines prevent and/or treat 161P2F10B-expressing cancers with minimal or no effects on non-target tissues. The use of a tumor antigen in a vaccine that generates humoral and/or cell-mediated immune responses as ant-cancer therapy is well known in the art and has been employed in prostate cancer using human PSMA and rodent PAP immunogens (Hodge et al., 1995, Int J. Cancer 63:231–237; Fong et al., 1997, J. Immunol. 159:3113–3117).

Such methods can be readily practiced by employing a 161P2F10B-related protein, or a 161P2F10B-encoding nucleic acid molecule and recombinant vectors capable of expressing and presenting the 161P2F10B immunogen (which typically comprises a number of antibody or T cell epitopes). Skilled artisans understand that a wide variety of vaccine systems for delivery of immunoreactive epitopes are known in the art (see, e.g., Heryln et al., Ann Med 1999 February 31(1):66–78; Maruyama et al., Cancer Immunol Immunother 2000 June 49(3):123–32) Briefly, such methods of generating an immune response (e.g. humoral and/or cell-mediated) in a mammal, comprise the steps of: exposing the mammal's immune system to an immunoreactive epitope (e.g. an epitope present in a 161P2F10B protein shown in FIG. 3 or analog or homolog thereof) so that the mammal generates an immune response that is specific for that epitope (e.g. generates antibodies that specifically recognize that epitope). In a preferred method, a 161P2F10B immunogen contains a biological motif, see e.g., Tables VIII–XXI and XXII–XLIX, or a peptide of a size range from 161P2F10B indicated in FIG. 5, FIG. 6, FIG. 7, FIG. 8, and FIG. 9.

The entire 161P2F10B protein, immunogenic regions or epitopes thereof can be combined and delivered by various means. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287–294, 1991: Alonso et al., *Vaccine* 12:299–306, 1994; Jones et al., *Vaccine* 13:675–681, 1995), peptide compositions contained in immune stimulating complexes (ISCOMS) (see, e.g., Takahashi et al., *Nature* 344:873–875, 1990; Hu et al., *Clin Exp Immunol.* 113:235–243, 1998), multiple antigen peptide systems (MAPs) (see e.g., Tam, J. P., *Proc. Natl. Acad. Sci. U.S.A.* 85:5409–5413, 1988; Tam, J. P., *J. Immunol Methods* 196:17–32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537,1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25,1996; Eldridge, J. H. et al., *Sem. Hematol.* 30:16, 1993; Falo, L. D., Jr. et al., *Nature Med.* 7:649,1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

In patients with 161P2F10B-associated cancer, the vaccine compositions of the invention can also be used in conjunction with other treatments used for cancer, e.g., surgery, chemotherapy, drug therapies, radiation therapies, etc. including use in combination with immune adjuvants such as IL-2, IL-12, GM-CSF, and the like.

Cellular Vaccines:

CTL epitopes can be determined using specific algorithms to identify peptides within 161P2F10B protein that bind corresponding HLA alleles (see e.g., Table IV; Epimer™ and Epimatrix™, Brown University; and, BIMAS; and SYFPEITHI). In a preferred embodiment, a 161P2F10B immunogen contains one or more amino acid sequences identified using techniques well known in the art, such as the sequences shown in Tables VIII–XXI and XXII–XLIX or a peptide of 8, 9, 10 or 11 amino acids specified by an HLA Class I motif/supermotif (e.g., Table IV (A), Table IV (D), or Table IV (E)) and/or a peptide of at least 9 amino acids that comprises an HLA Class II motifYsupermotif (e.g., Table IV (B) or Table IV (C)). As is appreciated in the art, the HLA Class I binding groove is essentially closed ended so that peptides of only a particular size range can fit into the groove and be bound, generally HLA Class I epitopes are 8, 9, 10, or 11 amino acids long. In contrast, the HLA Class II binding groove is essentially open ended; thereforee a peptide of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

Antibody-Based Vaccines

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. a 161P2F10B protein) so that an immune response is generated. A typical embodiment consists of a method for generating an immune response to 161P2F10B in a host, by contacting the host with a sufficient amount of at least one 161P2F10B B cell orcytotoxic T-cell epitope or analog thereof; and at least one periodic interval thereafter re-contacting the host with the 161P2F10B B cell or cytotoxic T-cell epitope or analog thereof. A specific embodiment consists of a method of generating an immune response against a 161P2F10B-related protein or a man-made multiepitopic peptide comprising: administering 161P2F10B immunogen (e.g. a 161P2F10B protein or a peptide fragment thereof, a 161P2F10B fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625–1633; Alexander et al., Immunity 1994 1(9): 751–761 and Alexander et al., Immunol. Res. 1998 18(2): 79–92). An alternative method comprises generating an immune response in an individual against a 161P2F10B immunogen by: administering in vivo to muscle or skin of the individual's body a DNA molecule that comprises a DNA sequence that encodes a 161P2F10B immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). Optionally a genetic vaccine facilitator such as anionic lipids; saponins; lectins; estrogenic compounds; hydroxylated lower alkyls; dimethyl sulfoxide; and urea is also administered. In addition, an antiidiotypic antibody can be administered that mimics 161P2F10B, in order to generate a response to the target antigen.

Nucleic Acid Vaccines:

Vaccine compositions of the invention include nucleic acid-mediated modalities. DNA or RNA that encode protein(s) of the invention can be administered to a patient. Genetic immunization methods can be employed to generate prophylactic or therapeutic humoral and cellular immune responses directed against cancer cells expressing 161P2F10B. Constructs comprising DNA encoding a 161P2F10B-related protein/immunogen and appropriate regulatory sequences can be injected directly into muscle or skin of an individual, such that the cells of the muscle or skin take-up the construct and express the encoded 161P2F10B protein immunogen. Alternatively, a vaccine comprises a 161P2F10B-related protein. Expression of the 161P2F10B-related protein immunogen results in the generation of prophylactic or therapeutic humoral and cellular immunity against cells that bear a 161P2F10B protein. Various prophylactic and therapeutic genetic immunization techniques known in the art can be used (for review, see information and references published at Internet address genweb.com). Nucleic acid-based delivery is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, proteins of the invention can be expressed via viral or bacterial vectors. Various viral gene delivery systems that can be used in the practice of the invention include, but are not limited to, vaccinia, fowlpox, canarypox, adenovirus, influenza, poliovirus, adeno-associated virus, lentivirus, and sindbis virus (see, e.g., Restifo, 1996, Curr. Opin. Immunol. 8:658–663; Tsang et at *J. Natl. Cancer Inst.* 87:982–990 (1995)). Non-viral delivery systems can also be employed by introducing naked DNA encoding a 161P2F10B-related protein into the patient (e.g., intramuscularly or intradermally) to induce an anti-tumor response.

Vaccinia virus is used, for example, as a vector to express nucleotide sequences that encode the peptides of the invention. Upon introduction into a host, the recombinant vaccinia virus expresses the protein immunogenic peptide, and thereby elicits a host immune response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Thus, gene delivery systems are used to deliver a 161P2F10B-related nucleic acid molecule. In one embodiment, the full-length human 161P2F10B cDNA is employed. In another embodiment, 1611P2F10B nucleic acid molecules encoding specific cytotoxic T lymphocyte (CTL) and/or antibody epitopes are employed.

Ex Vivo Vaccines

Various ex vivo strategies can also be employed to generate an immune response. One approach involves the use of antigen presenting cells (APCs) such as dendritic cells (DC) to present 161P2F10B antigen to a patient's immune system. Dendritc cells express MHC class 1 and 11 molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65–69; Murphy et al., 1996, Prostate 29:371–380). Thus, dendritic cells can be used to present 161P2F10B peptides to T cells in the context of MHC class I or II molecules. In one embodiment, autologous dendritic cells are pulsed with 161P2F10B peptides capable of binding to MHC class I and/or class II molecules. In another embodiment, dendritic cells are pulsed with the complete 161P2F10B protein. Yet another embodiment involves engineering the overexpression of a 161P2F10B gene in dendritic cells using various implementing vectors known in the art, such as adenovirus (Arthur et al., 1997, Cancer Gene Ther. 4:17–25), retrovirus (Henderson et al., 1996, Cancer Res. 56:3763–3770), lentivirus, adeno-associated virus, DNA transfection (Ribas et al., 1997, Cancer Res. 57:2865–2869), or tumor-derived RNA transfection (Ashley et al., 1997, J. Exp. Med. 186: 1177–1182). Cells that express 161P2F10B can also be engineered to express immune modulators, such as GM-CSF, and used as immunizing agents.

X.B.) 161P2F10B as a Target for Antibody-Based Therapy

161P2F10B is an attractive target for antibody-based therapeutic strategies. A number of antibody strategies are known in the art for targeting both extracellular and intracellular molecules (see, e.g., complement and ADCC mediated killing as well as the use of intrabodies). Because 161P2F10B is expressed by cancer cells of various lineages relative to corresponding normal cells, systemic administration of 161P2F10B-immunoreactive compositions are prepared that exhibit excellent sensitivity without toxic, non-specific and/or non-target effects caused by binding of the immunoreactive composition to non-target organs and tissues. Antibodies specifically reactive with domains of 161P2F10B are useful to treat 161P2F10B-expressing cancers systemically, either as conjugates with a toxin or therapeutic agent, or as naked antibodies capable of inhibiting cell proliferation or function.

161P2F10B antibodies can be introduced into a patient such that the antibody binds to 161P2F10B and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 161P2F10B, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of a 161P2F10B sequence shown in FIG. 2 or FIG. 3. In addition, skilled artisans understand that it is routine to conjugate antibodies to cytotoxic agents (see, e.g., Slevers et al. *Blood* 93:11 3678–3684 (Jun. 1, 1999)). When cytotoxic and/or therapeutic agents are delivered directly to cells, such as by conjugating them to antibodies specific for a molecule expressed by that cell (e.g. 161P2F10B), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-161P2F10B antibody) that binds to a marker (e.g. 161P2F10B) expressed, accessible to binding or localized on the cell surfaces. A typical embodiment is a method of delivering a cytotoxic and/or therapeutic agent to a cell expressing 161P2F10B, comprising conjugating the cytotoxic agent to an antibody that immunospecifically binds to a 161P2F10B epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-161P2F10B antibodies can be done in accordance with various approaches that have been successfully employed in the treatment of other types of cancer, including but not limited to colon cancer (Arlen et al., 1998, Crit. Rev. Immunol. 18:133–138), multiple myeloma (Ozaki et al., 1997, Blood 90:3179–3186, Tsunenari et al., 1997, Blood 90:2437–2444), gastric cancer (Kasprzyk et a., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166; Velders et al., 1995, Cancer Res. 55:4398–4403), and breast cancer (Shepard et al., 1991, J. Clin. Immunol. 11:117–127). Some therapeutic approaches involve conjugation of naked antibody to a toxin or radioisotope, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). The antibodies can be conjugated to a therapeutic agent. To treat prostate cancer, for example, 161P2F10B antibodies can be administered in conjunction with radiation, chemotherapy or hormone ablation. Also, antibodies can be conjugated to a toxin such as calicheamicin (e.g., Mylotarg™, Wyeth-Ayerst, Madison, N.J., a recombinant humanized IgG4 kappa antibody conjugated to antitumor antibiotic calicheamicin) or a maytansinoid (e.g., taxane-based Tumor-Activated Prodrug, TAP, platform, ImmunoGen, Cambridge, Mass., also see e.g., U.S. Pat. No. 5,416,064).

Although 161P2F10B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well. Fan et al. (Cancer Res. 53:4637–4642, 1993), Prewett et al. (International J. of Onco. 9:217–224, 1996), and Hancock et al. (Cancer Res. 51:4575–4580, 1991) describe the use of various antibodies together with chemotherapeutic agents.

Although 161P2F10B antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 161P2F10B expression, preferably using immunohistochemical assessments of tumor tissue, quantitative 161P2F10B imaging, or other techniques that reliably indicate the presence and degree of 161P2F10B expression. Immunohistochemical analysis of tumor biopsies or surgical specimens is preferred for this purpose. Methods for immunohistochemical analysis of tumor tissues are well known in the art.

Anti-161P2F10B monoclonal antibodies that treat prostate and other cancers include those that initiate a potent immune response against the tumor or those that are directly cytotoxic. In this regard, anti-161P2F10B monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-161P2F10B mAbs that exert a direct biological effect on tumor growth are useful to treat cancers that express 161P2F10B. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-161P2F10B mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 161P2F10B antigen with high affinity but exhibit low or no antigenicity in the patient.

Therapeutic methods of the invention contemplate the administration of single anti-161P2F10B mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-161P2F10B mAbs can be administered concomitantly with other therapeutic modalities, including but not limited to various chemotherapeutic agents, androgen-blockers, immune modulators (e.g., IL-2, GM-CSF), surgery or radiation. The anti-161P2F10B mAbs are administered in their "naked" or unconjugated form, or can have a therapeutic agent(s) conjugated to them.

Anti-161P2F10B antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-161P2F10B antibody preparation, via an acceptable route of administration such as intravenous injection (IV), typically at a dose in the range of about 0.1, 0.2, 0.3, 0.4, 0.5, 0.6, 0.7, 0.8, 0.9, 1, 2, 3, 4, 5, 6, 7, 8, 9, 10, 15, 20, or 25 mg/kg body weight. In general, doses in the range of 10–1000 mg mAb per week are effective and well tolerated.

Based on clinical experience with the Herceptin™ mAb in the treatment of metastatic breast cancer, an initial loading dose of approximately 4 mg/kg patient body weight IV, followed by weekly doses of about 2 mg/kg IV of the anti-161P2F10B mAb preparation represents an acceptable dosing regimen. Preferably, the initial loading dose is administered as a 90-minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 161P2F10B expression in the patient, the extent of circulating shed 161P2F10B antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 161P2F10B in a given sample (e.g. the levels of circulating 161P2F10B antigen and/or 161P2F10B expressing cells) in order to assist in the determination of the most effective dosing regimen, etc. Such evaluations are also used for monitoring purposes throughout therapy, and are useful to gauge therapeutic success in combination with the evaluation of other parameters (for example, urine cytology and/or ImmunoCyt levels in bladder cancer therapy, or by analogy, serum PSA levels in prostate cancer therapy).

Anti-idiotypic anti-161P2F10B antibodies can also be used in anti-cancer therapy as a vaccine for inducing an immune response to cells expressing a 161P2F10B-related protein. In particular, the generation of anti-idiotypic antibodies is well known in the art; this methodology can readily be adapted to generate anti-idiotypic anti-161P2F10B antibodies that mimic an epitope on a 161P2F10B-related protein (see, for example, Wagner et al., 1997, Hybridoma 16: 33–40; Foon et al., 1995, J. Clin. Invest. 96:334–342; Herlyn et al., 1996, Cancer Immunol. Immunother. 43:65–76). Such an anti-idiotypic antibody can be used in cancer vaccine strategies.

X.C.) 161P2F10B as a Target for Cellular Immune Responses

Vaccines and methods of preparing vaccines that contain an immunogenically effective amount of one or more HLA-binding peptides as described herein are further embodiments of the invention. Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine (P3CSS). Moreover, an adjuvant such as a synthetic cytosine-phosphorothiolated-guanine-containing (CpG) oligonucleotides has been found to increase CTL responses 10- to 100-fold. (see, e.g. Davila and Celis, J. Immunol. 165: 539–547 (2000))

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later development of cells that express or overexpress 161P2F10B antigen, or derives at least some therapeutic benefit when the antigen was tumor-associated.

In some embodiments, it may be desirable to combine the class I peptide components with components that induce or facilitate neutralizing antibody and or helper T cell responses directed to the target antigen. A preferred embodiment of such a composition comprises class I and class II epitopes in accordance with the invention. An alternative embodiment of such a composition comprises a class I and/or class II epitope in accordance with the invention, along with a cross reactive HTL epitope such as PADRE™ (Epimmune, San Diego, Calif.) molecule (described e.g., in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo. Vaccine compositions, either DNA- or peptide-based, can also be administered in vivo in combination with dendritic cell mobilization whereby loading of dendritic cells occurs in vivo.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles be balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with tumor clearance. For HLA Class I this includes 3–4 epitopes that come from at least one tumor associated antigen (TM). For HLA Class II a similar rationale is employed; again 3–4 epitopes are selected from at least one TAA (see, e.g., Rosenberg et al., *Science* 278: 1447–1450). Epitopes from one TAA may be used in combination with epitopes from one or more additional TAAs to produce a vaccine that targets tumors with varying expression patterns of frequently-expressed TAAs.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope.

5.) Of particular relevance are epitopes referred to as "nested epitopes." Nested epitopes occur where at least two epitopes overlap in a given peptide sequence. A nested peptide sequence can comprise B cell, HLA class I and/or HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) Where the sequences of multiple variants of the same target protein are present, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

X.C.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, Ishioka et al., *J. Immunol.* 162:3915–3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived 161P2F10B, the PADRE®D universal helper T cell epitope or multiple HTL epitopes from 161P2F10B (see e.g., Tables VIII-XXI and XXII to XLIX), and an endoplasmic reticulum-translocating signal sequence can be engineered. A vaccine may also comprise epitopes that are derived from other TAAs.

The immunogenicity of a multi-epitopic minigene can be confirmed in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA class I epitopes, HLA class II epitopes, antibody epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene.

The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well-known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is confirmed in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

X.C.2. Combinations of CTL Peptides with Helper Peptides

Vaccine compositions comprising CTL peptides of the invention can be modified, e.g., analoged, to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in a majority of a genetically diverse population. This can be accomplished by selecting peptides that bind to many, most, or all of the HLA class II molecules. Examples of such amino acid bind many HLA Class II molecules include sequences from antigens such as tetanus toxoid at positions 830–843 (QYIKAN-SKFIGITE; SEQ ID NO: 25), Plasmodium falc:parum circumsporozoite (CS) protein at positions 378–398 (DIEK-KIAKMEKASSVFNWNS; SEQ ID NO: 26), and *Streptococcus* 18 kD protein at positions 116–131 (GAVD-SILGGVATYGAA; SEQ ID NO: 27). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed, most preferably, to bind most HLA-DR (human HLA class II) molecules. For instance, a pan-DR-binding epitope peptide having the formula: aKXVAAWTLKAa (SEQ ID NO: 28), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

X.C.3. Combinations of CTL Peptides with T Cell Priming Agents

In some embodiments it may be desirable to include in the pharmaceutical compositions of the invention at least one component which primes B lymphocytes or T lymphocytes. Lipids have been identified as agents capable of priming CTL in vivo. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to prime specifically an immune response to the target antigen. Moreover, because the induction of neutralizing antibodies can also be primed with P3CSS-conjugated epitopes, two such compositions can be combined to more effectively elicit both humoral and cell-mediated responses.

X.C.4. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Pharmacia-Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to 161P2F10B. Optionally, a helper T cell (HTL) peptide, such as a natural or artificial loosely restricted HLA Class II peptide, can be included to facilitate the CTL response. Thus, a vaccine in accordance with the invention is used to treat a cancer which expresses or overexpresses 161P2F10B.

X.D. Adoptive Immunotherapy

Antigenic 161P2F10B-refated peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular antigen are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (e.g., a tumor cell). Transfected dendritic cells may also be used as antigen presenting cells.

X.E. Administration of Vaccines for Therapeutic or Prophylactic Purposes

Pharmaceutical and vaccine compositions of the invention are typically used to treat and/or prevent a cancer that expresses or overexpresses 161P2F10B. In therapeutic applications, peptide and/or nucleic acid compositions are administered to a patient in an amount sufficient to elicit an effective B cell, CTL and/or HTL response to the antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already bearing a tumor that expresses 161P2F10B. The peptides or DNA encoding them can be administered individually or as fusions of one or more peptide sequences. Patients can be treated with the immunogenic peptides separately or in conjunction with other treatments, such as surgery, as appropriate.

For therapeutic use, administration should generally begin at the first diagnosis of 161P2F10B-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses 161P2F10B, a vaccine comprising 161P2F10B-specific CTL may be more efficacious in killing tumor cells in patient with advanced disease than alternative embodiments.

It is generally important to provide an amount of the peptide epitope delivered by a mode of administration sufficient to stimulate effectively a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, nasal, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier.

A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of a composition is typically included in a pharmaceutical composition that comprises a human unit dose of an acceptable carrier, in one embodiment an aqueous carrier, and is administered in a volume/quantity that is known by those of skill in the art to be used for administration of such compositions to humans (see, e.g., Remington's Pharmaceutical Sciences, $17^{th}$ Edition, A. Gennaro, Editor, Mack Publishing Co., Easton, Pa., 1985). For example a peptide dose for initial immunization can be from about 1 to about 50,000 µg, generally 100–5,000 µg, for a 70 kg patient. For example, for nucleic acids an initial immunization may be performed using an expression vector in the form of naked nucleic acid administered IM (or SC or ID) in the amounts of 0.55 mg at multiple sites. The nucleic acid (0.1 to 1000 µg) can also be administered using a gene gun. Following an incubation period of 3–4 weeks, a booster dose is then administered. The booster can be recombinant fowlpox virus administered at a dose of $5–10^7$ to $5\times10^9$ pfu.

For antibodies, a treatment generally involves repeated administration of the anti-161 P2F10B antibody preparation, via an acceptable route of administration such as intravenous injection (IV), typically at a dose in the range of about 0.1 to about 10 mg/kg body weight. In general, doses in the range of 10–500 mg mAb per week are effective and well tolerated. Moreover, an initial loading dose of approximately 4 mg/kg patient body weight IV, followed by weekly doses of about 2 mg/kg IV of the anti-161P2F10B mAb preparation represents an acceptable dosing regimen. As appreciated by those of skill in the art, various factors can influence the ideal dose in a particular case. Such factors include, for example, half life of a composition, the binding affinity of an Ab, the immunogenicity of a substance, the degree of 161P2F10B expression in the patient, the extent of circulating shed 161P2F10B antigen, the desired steady-state concentration level, frequency of treatment, and the influence of chemotherapeutic or other agents used in combination with the treatment method of the invention, as well as the health status of a particular patient. Non-limiting preferred human unit doses are, for example, 500 µg–1 mg, 1 mg–50 mg, 50 mg–100 mg, 100 mg–200 mg, 200 mg–300 mg, 400 mg–500 mg, 500 mg–600 mg, 600 mg–700 mg, 700 mg–800 mg, 800 mg–900 mg, 900 mg–1 g, or 1 mg–700 mg. In certain embodiments, the dose is in a range of 2–5 mg/kg body weight, e.g., with follow on weekly doses of 1–3 mg/kg; 0.5 mg, 1, 2, 3, 4, 5, 6, 7, 8, 9, 10 mg/kg body weight followed, e.g., in two, three or four weeks by weekly doses; 0.5–10 mg/kg body weight, e.g., followed in two, three or four weeks by weekly doses; 225, 250, 275, 300, 325, 350, 375, 400 mg m$^2$ of body area weekly; 1–600 mg m$^2$ of body area weekly; 225–400 mg m$^2$ of body area weekly; these does can be followed by weekly doses for 2, 3, 4, 5, 6, 7, 8, 9, 19, 11, 12 or more weeks.

In one embodiment, human unit dose forms of polynucleotides comprise a suitable dosage range or effective amount that provides any therapeutic effect. As appreciated by one of ordinary skill in the art a therapeutic effect depends on a number of factors, including the sequence of the polynucleotide, molecular weight of the polynucleotide and route of administration. Dosages are generally selected by the physician or other health care professional in accordance with a variety of parameters known in the art, such as severity of symptoms, history of the patient and the like. Generally, for a polynucleotide of about 20 bases, a dosage range may be selected from, for example, an independently selected lower limit such as about 0.1, 0.25, 0.5, 1, 2, 5,10, 20, 30, 40, 50, 60, 70, 80, 90, 100, 200, 300, 400 or 500 mg/kg up to an independently selected upper limit, greater than the lower limit, of about 60, 80, 100, 200, 300, 400, 500, 750, 1000, 1500, 2000, 3000, 4000, 5000, 6000, 7000, 8000, 9000 or 10,000 mg/kg. For example, a dose may be about any of the following: 0.1 to 100 mg/kg, 0.1 to 50 mg/kg, 0.1 to 25 mg/kg, 0.1 to 10 mg/kg, 1 to 500 mg/kg, 100 to 400 mg/kg, 200 to 300 mg/kg, 1 to 100 mg/kg, 100 to 200 mg/kg, 300 to 400 mg/kg, 400 to 500 mg/kg, 500 to 1000 mg/kg, 500 to 5000 mg/kg, or 500 to 10,000 mg/kg. Generally, parenteral routes of administration may require higher doses of polynucleotide compared to more direct application to the nucleotide to diseased tissue, as do polynucleotides of increasing length.

In one embodiment, human unit dose forms of T-cells comprise a suitable dosage range or effective amount that provides any therapeutic effect. As appreciated by one of ordinary skill in the art, a therapeutic effect depends on a number of factors. Dosages are generally selected by the physician or other health care professional in accordance with a variety of parameters known in the art, such as severity of symptoms, history of the patient and the like. A dose may be about $10^4$ cells to about $10^6$ cells, about $10^6$ cells to about $10^8$ cells, about $10^8$ to about $10^{11}$ cells, or about $10^8$ to about $5 \times 10^{10}$ cells. A dose may also about $10^6$ cells/m$^2$ to about $10^{10}$ cells/m$^2$, or about $10^6$ cells/m$^2$ to about $10^8$ cells/m$^2$.

Proteins(s) of the invention, and/or nucleic acids encoding the protein(s), can also be administered via liposomes, which may also serve to: 1) target the proteins(s) to a particular tissue, such as lymphoid tissue; 2) to target selectively to diseases cells; or, 3) to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, immunogenic peptides are preferably supplied in finely divided form along with a surfactant and propellant. Typical percentages of peptides are about 0.01%–20% by weight, preferably about 1%–10%. The surfactant must, of course, be nontoxic, and preferably soluble in the propellant. Representative of such agents are the esters or partial esters of fatty acids containing from about 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute about 0.1%–20% by weight of the composition, preferably about 0.25–5%. The balance of the composition is ordinarily propellant. A carrier can also be included, as desired, as with, e.g., lecithin for intranasal delivery.

XI.) Diagnostic and Prognostic Embodiments of 161P2F10B.

As disclosed herein, 161P2F10B polynucleotides, polypeptides, reactive cytotoxic T cells (CTL), reactive helper T cells (HTL) and anti-polypeptide antibodies are used in well known diagnostic, prognostic and therapeutic assays that examine conditions associated with dysregulated cell growth such as cancer, in particular the cancers listed in Table I (see, e.g., both its specific pattern of tissue expression as well as its overexpression in certain cancers as described for example in the Example entitled "Expression analysis of 161P2F10B in normal tissues, and patient specimens").

161P2F10B can be analogized to a prostate associated antigen PSA, the archetypal marker that has been used by medical practitioners for years to identify and monitor the presence of prostate cancer (see, e.g., Merrill et al., J. Urol. 163(2): 503–5120 (2000); Polascik et al., J. Urol. August; 162(2):293–306 (1999) and Fortier et al., J. Nat. Cancer Inst. 91(19): 1635–1640(1999)). A variety of other diagnostic markers are also used in similar contexts including p53 and K-ras (see, e.g., Tulchinsky et al., Int J Mol Med 1999 Jul 4(1):99–102 and Minimoto et al., Cancer Detect Prev 2000; 24(1):1–12). Therefore, this disclosure of 161P2F10B polynucleotides and polypeptides (as well as 161P2F10B polynucleotide probes and anti-161P2F10B antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 161P2F10B polynucleotides, polypeptides, reactive T cells and antibodies are analogous to those methods from well-established diagnostic assays, which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567–74(1994)) and primers (for example in PCR analysis, see, e.g., Okegawa et al., J. Urol. 163(4): 1189–1190 (2000)) to observe the presence and/or the level of PSA mRNAs in methods of monitoring PSA overexpression or the metastasis of prostate cancers, the 161P2F10B polynucleotides described herein can be utilized in the same way to detect 161P2F10B overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4): 560–3 (2000)) or the metastasis of prostate cells (see, e.g., Alanen et al., Pathol. Res. Pract. 192(3):233–7 (1996)), the 161P2F10B polypeptides described herein can be utilized to generate antibodies for use in detecting 161P2F10B overexpression or the metastasis of prostate cells and cells of other cancers expressing this gene.

Specifically, because metastases involves the movement of cancer cells from an organ of origin (such as the lung or prostate gland etc) to a different area of the body (such as a lymph node), assays which examine a biological sample for the presence of cells expressing 161P2F10B polynucleotides and/or polypeptides can be used to provide evidence of metastasis. For example, when a biological sample from tissue that does not normally contain 161P2F10B-expressing cells (lymph node) is found to contain 161P2F10B-expressing cells such as the 161P2F10B expression seen in LAPC4 and LAPC9, xenografts isolated from lymph node and bone metastasis, respectively, this finding is indicative of metastasis.

Alternatively 161P2F10B polynucleotides and/or polypeptides can be used to provide evidence of cancer, for example, when cells in a biological sample that do not normally express 161P2F10B or express 161P2F10B at a different level are found to express 161P2F10B or have an increased expression of 161P2F10B (see, e.g., the 161P2F10B expression in the cancers listed in Table I and in patient samples etc. shown in the accompanying Figures). In such assays, artisans may further wish to generate supplementary evidence of metastasis by testing the biological sample for the presence of a second tissue restricted marker (in addition to 161P2F10B) such as PSA, PSCA etc. (see, e.g., Alanen et al., Pathol. Res. Pract. 192(3): 233–237 (1996)).

Just as PSA polynucleotide fragments and polynucleotide variants are employed by skilled artisans for use in methods of monitoring PSA, 161P2F10B polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472–476, 478–480 (1998); Robertson et al., Methods Mol. Biol. 98:121–154 (1998)). An additional illustration of the use of such fragments is provided in the Example entitled "Expression analysis of 161P2F10B in normal tissues, and patient specimens," where a 161P2F10B polynucleotide fragment is used as a probe to show the expression of 161P2F10B RNAs in cancer cells. In addition, variant polynucleotide sequences are typically used as primers and probes for the corresponding mRNAs in PCR and Northern analyses (see, e.g., Sawai et al., Fetal Diagn. Ther. 1996 Nov–Dec 11 (6):407–13 and Current Protocols In Molecular Biology, Volume 2, Unit 2, Frederick M. Ausubel et al. eds., 1995)). Polynucleotide fragments and variants are useful in this context where they are capable of binding to a target polynucleotide sequence (e.g., a 161P2F10B polynucleotide shown in FIG. 2 or variant thereof) under conditions of high stringency.

Furthermore, PSA polypeptides which contain an epitope that can be recognized by an antibody or T cell that specifically binds to that epitope are used in methods of monitoring PSA. 161P2F10B polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubel et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 161P2F10B biological motifs discussed herein or a motif-bearing subsequence which is readily identified by one of skill in the art based on motifs available in the art. Polypeptide fragments, variants or analogs are typically useful in this context as long as they comprise an epitope capable of generating an antibody or T cell specific for a target polypeptide sequence (e.g. a 161P2F10B polypeptide shown in FIG. 3).

As shown herein, the 161P2F10B polynucleotides and polypeptides (as well as the 161P2F10B polynucleotide probes and anti-161P2F10B antibodies or T cells used to identify the presence of these molecules) exhibit specific properties that make them useful in diagnosing cancers such as those listed in Table I. Diagnostic assays that measure the presence of 161P2F10B gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233–237

(1996)), and consequently, materials such as 161P2F10B polynucleotides and polypeptides (as well as the 161P2F10B polynucleotide probes and anti-161P2F10B antibodies used to identify the presence of these molecules) need to be employed to confirm a metastases of prostatic origin.

Finally, in addition to their use in diagnostic assays, the 161P2F10B polynucleotides disclosed herein have a number of other utilities such as their use in the identification of oncogenetic associated chromosomal abnormalities in the chromosomal region to which the 161P2F10B gene maps (see the Example entitled "Chromosomal Mapping of 161P2F10B" below). Moreover, in addition to their use in diagnostic assays, the 161P2F10B-related proteins and polynucleotides disclosed herein have other utilities such as their use in the forensic analysis of tissues of unknown origin (see, e.g., Takahama K Forensic Sci Int 1996 Jun. 28;80 (1–2): 63–9).

Additionally, 161P2F10B-related proteins or polynucleotides of the invention can be used to treat a pathologic condition characterized by the over-expression of 161P2F10B. For example, the amino acid or nucleic acid sequence of FIG. 2 or FIG. 3, or fragments of either, can be used to generate an immune response to a 161P2F10B antigen. Antibodies or other molecules that react with 161P2F10B can be used to modulate the function of this molecule, and thereby provide a therapeutic benefit.

XII.) Inhibition of 161P2F10B Protein Function

The invention includes various methods and compositions for inhibiting the binding of 161P2F10B to its binding partner or its association with other protein(s) as well as methods for inhibiting 161P2F10B function.

XII.A.) Inhibition of 161P2F10B with Intracellular Antibodies

In one approach, a recombinant vector that encodes single chain antibodies that specifically bind to 161P2F10B are introduced into 161P2F10B expressing cells via gene transfer technologies. Accordingly, the encoded single chain anti-161P2F10B antibody is expressed intracellularly, binds to 161P2F10B protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of-the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to target precisely the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 161P2F10B in the nucleus, thereby preventing its activity within the nucleus. Nuclear targeting signals are engineered into such 161P2F10B intrabodies in order to achieve the desired targeting. Such 161P2F10B intrabodies are designed to bind specifically to a particular 161P2F10B domain. In another embodiment, cytosolic intrabodies that specifically bind to a 161P2F10B protein are used to prevent 161P2F10B from gaining access to the nucleus, thereby preventing it from exerting any biological activity within the nucleus (e.g., preventing 161P2F10B from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XII.B.) Inhibition of 161P2F10B with Recombinant Proteins

In another approach, recombinant molecules bind to 161P2F10B and thereby inhibit 161P2F10B function. For example, these recombinant molecules prevent or inhibit 161P2F10B from accessing/binding to its binding partner(s) or associating with other protein(s). Such recombinant molecules can, for example, contain the reactive part(s) of a 161P2F10B specific antibody molecule. In a particular embodiment, the 161P2F10B binding domain of a 161P2F10B binding partner is engineered into a dimeric fusion protein, whereby the fusion protein comprises two 161P2F10B ligand binding domains linked to the Fc portion of a human IgG, such as human IgG1. Such IgG portion can contain, for example, the $C_H2$ and $C_H3$ domains and the hinge region, but not the CH1 domain. Such dimeric fusion proteins are administered in soluble form to patients suffering from a cancer associated with the expression of 161P2F10B, whereby the dimeric fusion protein specifically binds to 161P2F10B and blocks 161P2F10B interaction with a binding partner. Such dimeric fusion proteins are further combined into multimeric proteins using known antibody linking technologies.

XII.C.) Inhibition of 161P2F10B Transcription or Translation

The present invention also comprises various methods and compositions for inhibiting the transcription of the 161P2F10B gene. Similarly, the invention also provides methods and compositions for inhibiting the translation of 161P2F10B mRNA into protein.

In one approach, a method of inhibiting the transcription of the 161P2F10B gene comprises contacting the 161P2F10B gene with a 161P2F10B antisense polynucleotide. In another approach, a method of inhibiting 161P2F10B mRNA translation comprises contacting a 161P2F10B mRNA with an antisense polynucleotide. In another approach, a 161P2F10B specific ribozyme is used to cleave a 161P2F10B message, thereby inhibiting translation. Such antisense and ribozyme based methods can also be directed to the regulatory regions of the 161P2F10B gene, such as 161P2F10B promoter and/or enhancer elements. Similarly, proteins capable of inhibiting a 161P2F10B gene transcription factor are used to inhibit 161P2F10B mRNA transcription. The various polynucleotides and compositions useful in the aforementioned methods have been described above. The use of antisense and ribozyme molecules to inhibit transcription and translation is well known in the art.

Other factors that inhibit the transcription of 161P2F10B by interfering with 161P2F10B transcriptional activation are also useful to treat cancers expressing 161P2F10B. Similarly, factors that interfere with 161P2F10B processing are useful to treat cancers that express 161P2F10B. Cancer treatment methods utilizing such factors are also within the scope of the invention.

XII.D.) General Considerations for Therapeutic Strategies

Gene transfer and gene therapy technologies can be used to deliver therapeutic polynucleotide molecules to tumor cells synthesizing 161P2F10B (i.e., antisense, ribozyme, polynucleotides encoding intrabodies and other 161P2F10B inhibitory molecules). A number of gene therapy approaches are known in the art. Recombinant vectors encoding 161P2F10B antisense polynucleotides, ribozymes, factors capable of interfering with 161P2F10B transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 161P2F10B to a binding partner, etc.

In vivo, the effect of a 161P2F10B therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402–408). For example, PCT Patent Application WO98/16628 and U.S. Pat. No. 6,107,540 describe various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XIII.) Identification, Characterization and Use of Modulators of 161P2F10b

Methods to Identify and Use Modulators

In one embodiment, screening is performed to identify modulators that induce or suppress a particular expression profile, suppress or induce specific pathways, preferably generating the associated phenotype thereby. In another embodiment, having identified differentially expressed genes important in a particular state; screens are performed to identify modulators that alter expression of individual genes, either increase or decrease. In another embodiment, screening is performed to identify modulators that alter a biological function of the expression product of a differentially expressed gene. Again, having identified the importance of a gene in a particular state, screens are performed to identify agents that bind and/or modulate the biological activity of the gene product.

In addition, screens are done for genes that are induced in response to a candidate agent. After identifying a modulator (one that suppresses a cancer expression pattern leading to a normal expression palem, or a modulator of a cancer gene that leads to expression of the gene as in normal tissue) a screen is performed to identify genes that are specifically modulated in response to the agent. Comparing expression profiles between normal tissue and agent-treated cancer tissue reveals genes that are not expressed in normal tissue or cancer tissue, but are expressed in agent treated tissue, and vice versa. These agent-specific sequences are identified and used by methods described herein for cancer genes or proteins. In particular these sequences and the proteins they encode are used in marking or identifying agent-treated cells. In addition, antibodies are raised against the agent-induced proteins and used to target novel therapeutics to the treated cancer tissue sample.

Modulator-related Identification and Screening Assays:

Gene Expression-related Assays

Proteins, nucleic acids, and antibodies of the invention are used in screening assays. The cancer-associated proteins, antibodies, nucleic acids, modified proteins and cells containing these sequences are used in screening assays, such as evaluating the effect of drug candidates on a "gene expression profile," expression profile of polypeptides or alteration of biological function. In one embodiment, the expression profiles are used, preferably in conjunction with high throughput screening techniques to allow monitoring for expression profile genes after treatment with a candidate agent (e.g., Davis, G F, et al, J Biol Screen 7:69 (2002); Zlokarnik, et al., Science 279:84–8 (1998); Heid, Genome Res 6:986–94, 1996).

The cancer proteins, antibodies, nucleic acids, modified proteins and cells containing the native or modified cancer proteins or genes are used in screening assays. That is, the present invention comprises methods for screening for compositions which modulate the cancer phenotype or a physiological function of a cancer protein of the invention. This is done on a gene itself or by evaluating the effect of drug candidates on a "gene expression profile" or biological function. In one embodiment, expression profiles are used, preferably in conjunction with high throughput screening techniques to allow monitoring after treatment with a candidate agent, see Zlokamik, supra.

A variety of assays are executed directed to the genes and proteins of the invention. Assays are run on an individual nucleic acid or protein level. That is, having identified a particular gene as up regulated in cancer, test compounds are screened for the ability to modulate gene expression or for binding to the cancer protein of the invention. "Modulation" in this context includes an increase or a decrease in gene expression. The preferred amount of modulation will depend on the original change of the gene expression in normal versus tissue undergoing cancer, with changes of at least 10%, preferably 50%, more preferably 100–300%, and in some embodiments 300–1000% or greater. Thus, if a gene exhibits a 4-fold increase in cancer tissue compared to normal tissue, a decrease of about four-fold is often desired; similarly, a 10-fold decrease in cancer tissue compared to normal tissue a target value of a 10-fold increase in expression by the test compound is often desired. Modulators that exacerbate the type of gene expression seen in cancer are also useful, e.g., as an upregulated target in further analyses.

The amount of gene expression is monitored using nucleic acid probes and the quantification of gene expression levels, or, alternatively, a gene product itself is monitored, e.g., through the use of antibodies to the cancer protein and standard immunoassays. Proteomics and separation techniques also allow for quantification of expression.

Expression Monitoring to Identify Compounds that Modify Gene Expression

In one embodiment, gene expression monitoring, i.e., an expression profile, is monitored simultaneously for a number of entities. Such profiles will typically involve one or more of the genes of FIG. 2. In this embodiment, e.g., cancer nucleic acid probes are attached to biochips to detect and quantify cancer sequences in a particular cell. Alternatively, PCR can be used. Thus, a series, e.g., wells of a microtiter plate, can be used with dispensed primers in desired wells. A PCR reaction can then be performed and analyzed for each well.

Expression monitoring is performed to identify compounds that modify the expression of one or more cancer-associated sequences, e.g., a polynucleotide sequence set out in FIG. 2. Generally, a test modulator is added to the cells prior to analysis. Moreover, screens are also provided to identify agents that modulate cancer, modulate cancer proteins of the invention, bind to a cancer protein of the invention, or interfere with the binding of a cancer protein of the invention and an antibody or other binding partner.

In one embodiment, high throughput screening methods involve providing a library containing a large number of potential therapeutic compounds (candidate compounds). Such "combinatorial chemical libraries" are then screened in one or more assays to identify those library members (particular chemical species or subclasses) that display a desired characteristic activity. The compounds thus identified can serve as conventional "lead compounds," as compounds for screening, or as therapeutics.

In certain embodiments, combinatorial libraries of potential modulators are screened for an ability to bind to a cancer polypeptide or to modulate activity. Conventionally, new chemical entities with useful properties are generated by identifying a chemical compound (called a "lead compound") with some desirable property or activity, e.g., inhibiting activity, creating variants of the lead compound, and evaluating the property and activity of those variant compounds. Often, high throughput screening (HTS) methods are employed for such an analysis.

As noted above, gene expression monitoring is conveniently used to test candidate modulators (e.g., protein, nucleic acid or small molecule). After the candidate agent has been added and the cells allowed to incubate for a period, the sample containing a target sequence to be analyzed is, e.g., added to a biochip.

If required, the target sequence is prepared using known techniques. For example, a sample is treated to lyse the cells, using known lysis buffers, electroporation, etc., with purification and/or amplification such as PCR performed as appropriate. For example, an in vitro transcription with labels covalently attached to the nucleotides is performed. Generally, the nucleic acids are labeled with biotin-FITC or PE, or with cy3 or cy5.

The target sequence can be labeled with, e.g., a fluorescent, a chemiluminescent, a chemical, or a radioactive signal, to provide a means of detecting the target sequence's specific binding to a probe. The label also can be an enzyme, such as alkaline phosphatase or horseradish peroxidase, which when provided with an appropriate substrate produces a product that is detected. Alternatively, the label is a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. Unbound labeled streptavidin is typically removed prior to analysis.

As will be appreciated by those in the art, these assays can be direct hybridization assays or can comprise "sandwich assays", which include the use of multiple probes, as is generally outlined in U.S. Pat. Nos. 5, 681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697. In this embodiment, in general, the target nucleic acid is prepared as outlined above, and then added to the biochip comprising a plurality of nucleic acid probes, under conditions that allow the formation of a hybridization complex.

A variety of hybridization conditions are used in the present invention, including high, moderate and low stringency conditions as outlined above. The assays are generally run under stringency conditions which allow formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus, it can be desirable to perform certain steps at higher stringency conditions to reduce non-specific binding.

The reactions outlined herein can be accomplished in a variety of ways. Components of the reaction can be added simultaneously, or sequentially, in different orders, with preferred embodiments outlined below. In addition, the reaction may include a variety of other reagents. These include salts, buffers, neutral proteins, e.g. albumin, detergents, etc. which can be used to facilitate optimal hybridization and detection, and/or reduce nonspecific or background interactions. Reagents that otherwise improve the efficiency of the assay, such as protease inhibitors, nuclease inhibitors, anti-microbial agents, etc., may also be used as appropriate, depending on the sample preparation methods and purity of the target. The assay data are analyzed to determine the expression levels of individual genes, and changes in expression levels as between states, forming a gene expression profile.

Biological Activity-related Assays

The invention provides methods identify or screen for a compound that modulates the activity of a cancer-related gene or protein of the invention. The methods comprise adding a test compound, as defined above, to a cell comprising a cancer protein of the invention. The cells contain a recombinant nucleic acid that encodes a cancer protein of the invention. In another embodiment, a library of candidate agents is tested on a plurality of cells.

In one aspect, the assays are evaluated in the presence or absence or previous or subsequent exposure of physiological signals, e.g. hormones, antibodies, peptides, antigens, cytokines, growth factors, action potentials, pharmacological agents including chemotherapeutics, radiation, carcinogenics, or other cells (i.e., cell-cell contacts). In another example, the determinations are made at different stages of the cell cycle process. In this way, compounds that modulate genes or proteins of the invention are identified. Compounds with pharmacological activity are able to enhance or interfere with the activity of the cancer protein of the invention. Once identified, similar structures are evaluated to identify critical structural features of the compound.

In one embodiment, a method of modulating (e.g., inhibiting) cancer cell division is provided; the method comprises administration of a cancer modulator. In another embodiment, a method of modulating (e.g., inhibiting) cancer is provided; the method comprises administration of a cancer modulator. In a further embodiment, methods of treating cells or individuals with cancer are provided; the method comprises administration of a cancer modulator.

In one embodiment, a method for modulating the status of a cell that expresses a gene of the invention is provided. As used herein status comprises such art-accepted parameters such as growth, proliferation, survival, function, apoptosis, senescence, location, enzymatic activity, signal transduction, etc. of a cell. In one embodiment, a cancer inhibitor is an antibody as discussed above. In another embodiment, the cancer inhibitor is an antisense molecule. A variety of cell growth, proliferation, and metastasis assays are known to those of skill in the art, as described herein.

High Throughput Screening to Identify Modulators

The assays to identify suitable modulators are amenable to high throughput screening. Preferred assays thus detect enhancement or inhibition of cancer gene transcription, inhibition or enhancement of polypeptide expression, and inhibition or enhancement of polypeptide activity.

In one embodiment, modulators evaluated in high throughput screening methods are proteins, often naturally occurring proteins or fragments of naturally occurring proteins. Thus, e.g., cellular extracts containing proteins, or random or directed digests of proteinaceous cellular extracts, are used. In this way, libraries of proteins are made for screening in the methods of the invention. Particularly preferred in this embodiment are libraries of bacterial, fungal, viral, and mammalian proteins, with the latter being preferred, and human proteins being especially preferred. Particularly useful test compound will be directed to the class of proteins to which the target belongs, e.g., substrates for enzymes, or ligands and receptors.

Use of Soft Agar Growth and Colony Formation to Identify and Characterize Modulators Normal cells require a solid substrate to attach and grow. When cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, can regenerate normal phenotype and once again require a solid substrate to attach to and grow. Soft agar growth or colony formation in assays are used to identify modulators of cancer sequences, which when expressed in host cells, inhibit abnormal cellular proliferation and transformation. A modulator reduces or eliminates the host cells' ability to grow suspended in solid or semisolid media, such as agar.

Techniques for soft agar growth or colony formation in suspension assays are described in Freshney, Culture of Animal Cells a Manual of Basic Technique (3rd ed., 1994). See also, the methods section of Garkavtsev et al. (1996), supra.

Evaluation of Contact Inhibition and Growth Density Limitation to Identify and Characterize Modulators Normal cells typically grow in ma flat and organized pattern in cell culture until they touch other cells. When the cells touch one another, they are contact inhibited and stop growing. Transformed cells, however, are not contact inhibited and continue to grow to high densities in disorganized foci. Thus, transformed cells grow to a higher saturation density than corresponding normal cells. This is detected morphologically by the formation of a disoriented monolayer of cells or cells in foci. Alternatively, labeling index with (3H)-thymidine at saturation density is used to measure density limitation of growth, similarly an MTT or Alamar blue assay will reveal proliferation capacity of cells and the the ability of modulators to affect same. See Freshney (1994), supra. Transformed cells, when transfected with tumor suppressor genes, can regenerate a normal phenotype and become contact inhibited and would grow to a lower density.

In this assay, labeling index with $^3$H)-thymidine at saturation density is a preferred method of measuring density limitation of growth. Transformed host cells are transfected with a cancer-associated sequence and are grown for 24 hours at saturation density in non-limiting medium conditions. The percentage of cells labeling with ($^3$H)-thymidine is determined by incorporated cpm.

Contact independent growth is used to identify modulators of cancer sequences, which had led to abnormal cellular proliferation and transformation. A modulator reduces or eliminates contact independent growth, and returns the cells to a normal phenotype.

Evaluation of Growth Factor or Serum Dependence to Identify and Characterize Modulators Transformed cells have lower serum dependence than their normal counterparts (see, e.g., Temin, J. Natl. Cancer Inst. 37:167–175 (1966); Eagle et al., J. Exp. Med 131: 836–879 (1970)); Freshney, supra. This is in part due to release of various growth factors by the transformed cells. The degree of growth factor or serum dependence of transformed host cells can be compared with that of control. For example, growth factor or serum dependence of a cell is monitored in methods to identify and characterize compounds that modulate cancer-associated sequences of the invention.

Use of Tumor-Specific Marker Levels to Identify and Characterize Modulators

Tumor cells release an increased amount of certain factors (hereinafter "tumor specific markers") than their normal counterparts. For example, plasminogen activator (PA) is released from human glioma at a higher level than from normal brain cells (see, e.g., Gullino, Angiogenesis, Tumor Vascularization, and Potential Interference with Tumor Growth, in Biological Responses in Cancer, pp. 178–184 (Mihich (ed.) 1985)). Similarly, Tumor Angiogenesis Factor (TAF) is released at a higher level in tumor cells than their normal counterparts. See, e.g., Folkman, Angiogenesis and Cancer, Sem Cancer Biol. (1992)), while bFGF is released from endothelial tumors (Ensoli, B et al).

Various techniques which measure the release of these factors are described in Freshney (1994), supra. Also, see, Unkless et al., J. Biol. Chem. 249:4295–4305 (1974); Strickland & Beers, J. Biol. Chem. 251:5694–5702 (1976); Whur et al., Br. J. Cancer 42:305 312 (1980); Gullino, Angiogenesis, Tumor Vascularization, and Potential Interference with Tumor Growth, in Biological Responses in Cancer, pp. 178–184 (Mihich (ed.) 1985); Freshney, Anticancer Res. 5:111–130 (1985). For example, tumor specific marker levels are monitored in methods to identify and characterize compounds that modulate cancer-associated sequences of the invention.

Invasiveness into Matrigel to Identify and Characterize Modulators

The degree of invasiveness into Matrigel or an extracellular matrix constituent can be used as an assay to identify and characterize compounds that modulate cancer associated sequences. Tumor cells exhibit a positive correlation between malignancy and invasiveness of cells into Matrigel or some other extracellular matrix constituent. In this assay, tumorigenic cells are typically used as host cells. Expression of a tumor suppressor gene in these host cells would decrease invasiveness of the host cells. Techniques described in Cancer Res. 1999; 59:6010; Freshney (1994), supra, can be used. Briefly, the level of invasion of host cells is measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Evaluation of Tumor Growth In Vivo to Identify and Characterize Modulators

Effects of cancer-associated sequences on cell growth are tested in transgenic or immune-suppressed organisms. Transgenic organisms are prepared in a variety of art-accepted ways. For example, knock-out transgenic organisms, e.g., mammals such as mice, are made, in which a cancer gene is disrupted or in which a cancer gene is inserted. Knock-out transgenic mice are made by insertion of a marker gene or other heterologous gene into the endogenous cancer gene site in the mouse genome via homologous recombination. Such mice can also be made by substituting the endogenous cancer gene with a mutated version of the cancer gene, or by mutating the endogenous cancer gene, e.g., by exposure to carcinogens.

To prepare transgenic chimeric animals, e.g., mice, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells some of which are derived from the mutant cell line. Therefore, by breeding the chimeric mice it is possible to obtain a new line of mice containing the introduced genetic lesion (see, e.g., Capecchi et al., Science 244:1288 (1989)). Chimeric mice can be derived according to U.S. Pat. No. 6,365,797, issued 2 Apr. 2002; U.S. Pat. No. 6,107,540 issued 22 Aug. 2000; Hogan et al., Manipulating the Mouse Embryo: A laboratory Manual, Cold Spring Harbor Laboratory (1988) and Teratocarcinomas and Embryonic Stem Cells: A Practical Approach, Robertson, ed., IRL Press, Washington, D.C., (1987).

Alternatively, various immune-suppressed or immune-deficient host animals can be used. For example, a genetically athymic "nude" mouse (see, e.g., Giovanella et al., J. Natl. Cancer Inst. 52:921 (1974)), a SCID mouse, a thymectornized mouse, or an irradiated mouse (see, e.g., Bradley et al., Br. J. Cancer 38:263 (1978); Selby et al., Br. J. Cancer 41:52 (1980)) can be used as a host. Transplantable tumor cells (typically about $10^6$ cells) injected into isogenic hosts produce invasive tumors in a high proportion of cases, while normal cells of similar origin will not. In hosts which developed invasive tumors, cells expressing cancer-associated sequences are injected subcutaneously or orthotopically. Mice are then separated into groups, including control groups and treated experimental groups) e.g. treated with a modulator). After a suitable length of time, preferably 4–8 weeks, tumor growth is measured (e.g., by volume or by its two largest dimensions, or weight) and compared to the control. Tumors that have statistically significant reduction (using, e.g., Students T test) are said to have inhibited growth.

In Vitro Assays to Identify and Characterize Modulators

Assays to identify compounds with modulating activity can be performed in vitro. For example, a cancer polypeptide is first contacted with a potential modulator and incubated for a suitable amount of time, e.g., from 0.5 to 48 hours. In one embodiment, the cancer polypeptide levels are determined in vitro by measuring the level of protein or mRNA. The level of protein is measured using immunoassays such as Western blotting, ELISA and the like with an antibody that selectively binds to the cancer polypeptide or a fragment thereof. For measurement of mRNA, amplification, e.g., using PCR, LCR, or hybridization assays, e.g., Northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using a cancer protein promoter operably linked to a reporter gene such as luciferase, green fluorescent protein, CAT, or β-gal. The reporter construct is typically transfected into a cell. After treatment with a potential modulator, the amount of reporter gene transcription, translation, or activity is measured according to standard techniques known to those of skill in the art (Davis GF, supra; Gonzalez, J. & Negulescu, P. Curr. Opin. Biotechnol. 1998: 9:624).

As outlined above, in vitro screens are done on individual genes and gene products. That is, having identified a particular differentially expressed gene as important in a particular state, screening of modulators of the expression of the gene or the gene product itself is performed.

In one embodiment, screening for modulators of expression of specific gene(s) is performed. Typically, the expression of only one or a few genes is evaluated. In another embodiment, screens are designed to first find compounds that bind to differentially expressed proteins. These compounds are then evaluated for the ability to modulate differentially expressed activity. Moreover, once initial candidate compounds are identified, variants can be further screened to better evaluate structure activity relationships.

Binding Assays to Identify and Characterize Modulators

In binding assays in accordance with the invention, a purified or isolated gene product of the invention is generally used. For example, antibodies are generated to a protein of the invention, and immunoassays are run to determine the amount and/or location of protein. Alternatively, cells comprising the cancer proteins are used in the assays.

Thus, the methods comprise combining a cancer protein of the invention and a candidate compound such as a ligand, and determining the binding of the compound to the cancer protein of the invention. Preferred embodiments utilize the human cancer protein; animal models of human disease of can also be developed and used. Also, other analogous mammalian proteins also can be used as appreciated by those of skill in the art. Moreover, in some embodiments variant or derivative cancer proteins are used.

Generally, the cancer protein of the invention, or the ligand, is non-diffusibly bound to an insoluble support. The support can, e.g., be one having isolated sample receiving areas (a microtiter plate, an array, etc.). The insoluble supports can be made of any composition to which the compositions can be bound, is readily separated from soluble material, and is otherwise compatible with the overall method of screening. The surface of such supports can be solid or porous and of any convenient shape.

Examples of suitable insoluble supports include microtiter plates, arrays, membranes and beads. These are typically made of glass, plastic (e.g., polystyrene), polysaccharide, nylon, nitrocellulose, or Teflon M, etc. Microtiter plates and arrays are especially convenient because a large number of assays can be carried out simultaneously, using small amounts of reagents and samples. The particular manner of binding of the composition to the support is not crucial so long as it is compatible with the reagents and overall methods of the invention, maintains the activity of the composition and is nondiffusable. Preferred methods of binding include the use of antibodies which do not sterically block either the ligand binding site or activation sequence when attaching the protein to the support, direct binding to "sticky" or ionic supports, chemical crosslinking, the synthesis of the protein or agent on the surface, etc. Following binding of the protein or ligand/binding agent to the support, excess unbound material is removed by washing. The sample receiving areas may then be blocked through incubation with bovine serum albumin (BSA), casein or other innocuous protein or other moiety.

Once a cancer protein of the invention is bound to the support, and a test compound is added to the assay. Alternatively, the candidate binding agent is bound to the support and the cancer protein of the invention is then added. Binding agents include specific antibodies, non-natural binding agents identified in screens of chemical libraries, peptide analogs, etc.

Of particular interest are assays to identify agents that have a low toxicity for human cells. A wide variety of assays can be used for this purpose, including proliferation assays, cAMP assays, labeled in vitro protein-protein binding assays, electrophoretic mobility shift assays, immunoassays for protein binding, functional assays (phosphorylation assays, etc.) and the like.

A determination of binding of the test compound (ligand, binding agent, modulator, etc.) to a cancer protein of the invention can be done in a number of ways. The test compound can be labeled, and binding determined directly, e.g., by attaching all or a portion of the cancer protein of the invention to a solid support, adding a labeled candidate compound (e.g., a fluorescent label), washing off excess reagent, and determining whether the label is present on the solid support. Various blocking and washing steps can be utilized as appropriate.

In certain embodiments, only one of the components is labeled, e.g., a protein of the invention or ligands labeled. Alternatively, more than one component is labeled with different labels, e.g., $I^{125}$, for the proteins and a fluorophor for the compound. Proximity reagents, e.g., quenching or energy transfer reagents are also useful.

Competitive Binding to Identify and Characterize Modulators

In one embodiment, the binding of the "test compound" is determined by competitive binding assay with a competitor. The competitor is a binding moiety that binds to the target molecule (e.g., a cancer protein of the invention). Competitors include compounds such as antibodies, peptides, binding partners, ligands, etc. Under certain circumstances, the competitive binding between the test compound and the competitor displaces the test compound. In one embodiment, the test compound is labeled. Either the test compound, the competitor, or both, is added to the protein for a time sufficient to allow binding. Incubations are performed at a temperature that facilitates optimal activity, typically between four and 40° C. Incubation periods are typically optimized, e.g., to facilitate rapid high throughput screening; typically between zero and one hour will be sufficient. Excess reagent is generally removed or washed away. The second component is then added, and the presence or absence of the labeled component is followed, to indicate binding.

In one embodiment, the competitor is added first, followed by the test compound. Displacement of the competitor is an indication that the test compound is binding to the cancer protein and thus is capable of binding to, and potentially modulating, the activity of the cancer protein. In this embodiment, either component can be labeled. Thus, e.g., if the competitor is labeled, the presence of label in the post-test compound wash solution indicates displacement by the test compound. Alternatively, if the test compound is labeled, the presence of the label on the support indicates displacement.

In an alternative embodiment, the test compound is added first, with incubation and washing, followed by the competitor. The absence of binding by the competitor indicates that the test compound binds to the cancer protein with higher affinity than the competitor. Thus, if the test compound is labeled, the presence of the label on the support, coupled with a lack of competitor binding, indicates that the test compound binds to and thus potentially modulates the cancer protein of the invention.

Accordingly, the competitive binding methods comprise differential screening to identity agents that are capable of modulating the activity of the cancer proteins of the invention. In this embodiment, the methods comprise combining a cancer protein and a competitor in a first sample. A second sample comprises a test compound, the cancer protein, and a competitor. The binding of the competitor is determined for both samples, and a change, or difference in binding between the two samples indicates the presence of an agent capable of binding to the cancer protein and potentially modulating its activity. That is, if the binding of the competitor is different in the second sample relative to the first sample, the agent is capable of binding to the cancer protein.

Alternatively, differential screening is used to identify drug candidates that bind to the native cancer protein, but cannot bind to modified cancer proteins. For example the structure of the cancer protein is modeled and used in rational drug design to synthesize agents that interact with that site, agents which generally do not bind to site-modified proteins. Moreover, such drug candidates that affect the activity of a native cancer protein are also identified by screening drugs for the ability to either enhance or reduce the activity of such proteins.

Positive controls and negative controls can be used in the assays. Preferably control and test samples are performed in at least triplicate to obtain statistically significant results. Incubation of all samples occurs for a time sufficient to allow for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g. albumin, detergents, etc. which are used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components is added in an order that provides for the requisite binding.

Use of Polynucleotides to Down-regulate or Inhibit a Protein of the Invention.

Polynucleotide modulators of cancer can be introduced into a cell containing the target nucleotide sequence by formation of a conjugate with a ligand-binding molecule, as described in WO 91/04753. Suitable ligand-binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a polynucleotide modulator of cancer can be introduced into a cell containing the target nucleic acid sequence, e.g., by formation of a polynucleotide-lipid complex, as described in WO 90/10448. It is understood that the use of antisense molecules or knock out and knock in models may also be used in screening assays as discussed above, in addition to methods of treatment.

Inhibitory and Antisense Nucleotides

In certain embodiments, the activity of a cancer-associated protein is down-regulated, or entirely inhibited, by the use of antisense polynucleotide or inhibitory small nuclear RNA (snRNA), i.e., a nucleic acid complementary to, and which can preferably hybridize specifically to, a coding mRNA nucleic acid sequence, e.g., a cancer protein of the invention, mRNA, or a subsequence thereof. Binding of the antisense polynucleotide to the mRNA reduces the translation and/or stability of the mRNA.

In the context of this invention, antisense polynucleotides can comprise naturally occurring nucleotides, or synthetic species formed from naturally occurring subunits or their close homologs. Antisense polynucleotides may also have altered sugar moieties or inter-sugar linkages. Exemplary among these are the phosphorothioate and other sulfur containing species which are known for use in the art. Analogs are comprised by this invention so long as they function effectively to hybridize with nucleotides of the invention. See, e.g., Isis Pharmaceuticals, Carlsbad, Calif.; Sequitor, Inc., Natick, Mass.

Such antisense polynucleotides can readily be synthesized using recombinant means, or can be synthesized in vitro. Equipment for such synthesis is sold by several vendors, including Applied Biosystems. The preparation of other oligonucleotides such as phosphorothioates and alkylated derivatives is also well known to those of skill in the art.

Antisense molecules as used herein include antisense or sense oligonucleotides. Sense oligonucleotides can, e.g., be employed to block transcription by binding to the anti-sense strand. The antisense and sense oligonucleotide comprise a single stranded nucleic acid sequence (either RNA or DNA) capable of binding to target mRNA (sense) or DNA (antisense) sequences for cancer molecules. Antisense or sense oligonucleotides, according to the present invention, comprise a fragment generally at least about 12 nucleotides, preferably from about 12 to 30 nucleotides. The ability to derive an antisense or a sense oligonucleotide, based upon a cDNA sequence encoding a given protein is described in, e.g., Stein & Cohen (Cancer Res. 48:2659 (1988 and van der Krol et al. (BioTechniques 6:958 (1988)).

Ribozymes

In addition to antisense polynucleotides, ribozymes can be used to target and inhibit transcription of cancer-associated nucleotide sequences. A ribozyme is an RNA molecule that catalytically cleaves other RNA molecules. Different kinds of ribozymes have been described, including group I ribozymes, hammerhead ribozymes, hairpin ribozymes, RNase P, and axhead ribozymes (see, e.g.; Castanotto et al., Adv. in Pharmacology 25: 289–317 (1994) for a general review of the properties of different ribozymes).

The general features of hairpin ribozymes are described, e.g., in Hampel et al., Nucl. Acids Res. 18:299–304 (1990); European Patent Publication No. 0360257; U.S. Pat. No. 5,254,678. Methods of preparing are well known to those of skill in the art (see, e.g., WO 94/26877; Ojwang et al., Proc. Natl. Acad. Sci. USA 90:6340–6344 (1993); Yamada et al., Human Gene Therapy 1:39–45 (1994); Leavitt et al., Proc. Natl. Acad. Sci. USA 92:699–703 (1995); Leavitt et al., Human Gene Therapy 5: 1151–120 (1994); and Yamada et al., Virology 205: 121–126 (1994)).

Use of Modulators in Phenotypic Screening

In one embodiment, a test compound is administered to a population of cancer cells, which have an associated cancer expression profile. By "administration" or "contacting" herein is meant that the modulator is added to the cells in such a manner as to allow the modulator to act upon the cell, whether by uptake and intracellular action, or by action at the cell surface. In some embodiments, a nucleic acid encoding a proteinaceous agent (i.e., a peptide) is put into a viral construct such as an adenoviral or retroviral construct, and added to the cell, such that expression of the peptide agent is accomplished, e.g., PCT US97/01019. Regulatable gene therapy systems can also be used. Once the modulator has been administered to the cells, the cells are washed if desired and are allowed to incubate under preferably physiological conditions for some period. The cells are then harvested and a new gene expression profile is generated. Thus, e.g., cancer tissue is screened for agents that modulate, e.g., induce or suppress, the cancer phenotype. A change in at least one gene, preferably many, of the expression profile indicates that the agent has an effect on cancer activity. Similarly, altering a biological function or a signaling pathway is indicative of modulator activity. By defining such a signature for the cancer phenotype, screens for new drugs that alter the phenotype are devised. With this approach, the drug target need not be known and need not be represented in the original gene/protein expression screening platform, nor does the level of transcript for the target protein need to change. The modulator inhibiting function will serve as a surrogate marker As outlined above, screens are done to assess genes or gene products. That is, having identified a particular differentially expressed gene as important in a particular state, screening of modulators of either the expression of the gene or the gene product itself is performed.

Use of Modulators to Affect Peptides of the Invention

Measurements of cancer polypeptide activity, or of the cancer phenotype are performed using a variety of assays. For example, the effects of modulators upon the function of a cancer polypeptide(s) are measured by examining parameters described above. A physiological change that affects activity is used to assess the influence of a test compound on the polypeptides of this invention. When the functional outcomes are determined using intact cells or animals, a variety of effects can be assesses such as, in the case of a cancer associated with solid tumors, tumor growth, tumor metastasis, neovascularization, hormone release, transcriptional changes to both known and uncharacterized genetic markers (e.g., by Northern blots), changes in cell metabolism such as cell growth or pH changes, and changes in intracellular second messengers such as cGNIP.

Methods of Identifying Characterizing Cancer-associated Sequences

Expression of various gene sequences is correlated with cancer. Accordingly, disorders based on mutant or variant cancer genes are determined. In one embodiment, the invention provides methods for identifying cells containing variant cancer genes, e.g., determining the presence of, all or part, the sequence of at least one endogenous cancer gene in a cell. This is accomplished using any number of sequencing techniques. The invention comprises methods of identifying the cancer genotype of an individual, e.g., determining all or part of the sequence of at least one gene of the invention in the individual. This is generally done in at least one tissue of the individual, e.g., a tissue set forth in Table I, and may include the evaluation of a number of tissues or different samples of the same tissue. The method may include comparing the sequence of the sequenced gene to a known cancer gene, i.e., a wild-type gene to determine the presence of family members, homologies, mutations or variants. The sequence of all or part of the gene can then be compared to the sequence of a known cancer gene to determine if any differences exist. This is done using any number of known homology programs, such as BLAST, Bestfit, etc. The presence of a difference in the sequence between the cancer gene of the patient and the known cancer gene correlates with a disease state or a propensity for a disease state, as outlined herein.

In a preferred embodiment, the cancer genes are used as probes to determine the number of copies of the cancer gene in the genome. The cancer genes are used as probes to determine the chromosomal localization of the cancer genes. Information such as chromosomal localization finds use in providing a diagnosis or prognosis in particular when chromosomal abnormalities such as translocations, and the like are identified in the cancer gene locus.

XIV.) Kits/Articles of Manufacture

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a FIG. 2-*related* protein or a FIG. 2 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequences in FIG. 2 or FIG. 3 or analogs thereof, or a nucleic acid molecules that encodes such amino acid sequences.

The kit of the invention will typically comprise the container described above and one or more other containers comprising materials desirable from a commercial and user standpoint, including buffers, diluents, filters, needles, syringes; carrier, package, container, vial and/or tube labels listing contents and/or instructions for use, and package inserts with instructions for use.

A label can be present on the container to indicate that the composition is used for a specific therapy or non-therapeutic application, such as a diagnostic or laboratory application, and can also indicate directions for either in vivo or in vitro use, such as those described herein. Directions and or other information can also be included on an insert(s) or label(s) which is included with or on the kit.

The terms "kit" and "article of manufacture" can be used as synonyms.

In another embodiment of the invention, an article(s) of manufacture containing compositions, such as amino acid sequence(s), small molecule(s), nucleic acid sequence(s), and/or antibody(s), e.g., materials useful for the diagnosis, prognosis, prophylaxis and/or treatment of neoplasias of tissues such as those set forth in Table I is provided. The article of manufacture typically comprises at least one container and at least one label. Suitable containers include, for example, bottles, vials, syringes, and test tubes. The containers can be formed from a variety of materials such as glass or plastic. The container can hold amino acid sequence(s), small molecule(s), nucleic acid sequence(s), and/or antibody(s), in one embodiment the container holds a polynucleotide for use in examining the mRNA expression profile of a cell, together with reagents used for this purpose.

The container can alternatively hold a composition which is effective for treating, diagnosis, prognosing or prophylaxing a condition and can have a sterile access port (for example the container can be an intravenous solution bag or a vial having a stopper pierceable by a hypodermic injection needle). The active agents in the composition can be an antibody capable of specifically binding 161P2F10B and modulating the function of 161P2F10B.

The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a neoplasia of a tissue set forth in Table I. The article of manufacture can further comprise a second container comprising a pharmaceutically-acceptable buffer, such as phosphate-buffered saline, Ringers solution and/ordextrose solution. It can further include other materials desirable from a commercial and user standpoint, including other buffers, diluents, filters, stirrers, needles, syringes, and/or package inserts with indications and/or instructions for use

EXAMPLES

Various aspects of the invention are further described and illustrated by way of the several examples that follow, none of which are intended to limit the scope of the invention.

Example 1

SSH-Generated Isolation of cDNA Fragment of the STEAP Gene

To isolate genes that are over-expressed in kidney cancer we used the Suppression Subtractive Hybridization (SSH) procedure using cDNA derived from kidney cancer patient tissues.

The 161P2F10B SSH cDNA sequence was derived from a subtraction consisting of a kidney cancer minus normal kidney and a mixture of 9 normal tissues: stomach, skeletal muscle, lung, brain, liver, kidney, pancreas, small intestine and heart. By RT-PCR, the 161P2F10B cDNA was identified as highly expressed in kidney cancer pool, with lower expression detected in prostate cancer xenograft pool, prostate cancer pool, colon cancer pool, lung cancer pool, ovary cancer pool, breast cancer pool, metastasis cancer pool, pancreas cancer pool, 2 different prostate cancer metastasis to lymph node, VP1 and VP2. (FIG. 14).

The 161P2F10B SSH cDNA sequence of 182 bp matches the cDNA for phosphodiesterase I/nucleotide pyrophosphatase 3 (PDNP3). The full-length 161P2F10B cDNA and ORF are described in FIG. 2 with the protein sequence listed in FIG. 3.

Materials and Methods

RNA Isolation:

Tumor tissues were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:
The following HPLC purified oligonucleotides were used.

DPNCDN (cDNA synthesis primer):
(SEQ ID NO: 29)
5'TTTTGATCAAGCTT$_{30}$3'

Adaptor 1:
(SEQ ID NO: 30)
5'CTAATACGACTCACTATAGGGCTCGAGCGGCCGCCCGGGCAG3'

(SEQ ID NO: 31)
3'GGCCCGTCCTAG5'

Adaptor 2:
(SEQ ID NO: 32)
5'GTAATACGACTCACTATAGGGCAGCGTGGTCGCGGCCGAG3'

(SEQ ID NO: 33)
3'CGGCTCCTAG5'

PCR primer 1:
(SEQ ID NO: 34)
5'CTAATACGACTCACTATAGGGC3'

Nested primer (NP)1:
(SEQ ID NO: 35)
5'TCGAGCGGCCGCCCGGGCAGGA3'

Nested primer (NP)2:
(SEQ ID NO: 36)
5'AGCGTGGTCGCGGCCGAGGA3'

Suppression Subtractive Hybridization:

Suppression Subtractive Hybridization (SSH) was used to identify cDNAs corresponding to genes that may be differentially expressed in prostate cancer. The SSH reaction utilized cDNA from kidney cancer patient specimens. The gene 161P2F10B was derived from kidney cancer patient tissues minus normal kidney and a mixture of 9 normal tissues: stomach, skeletal muscle, lung, brain, liver, kidney, pancreas, small intestine and heart. The SSH DNA sequence (FIG. 1) was identified.

The cDNA derived from kidney cancer patient tissues was used as the source of the "driver" cDNA, while the cDNA from normal tissues was used as the source of the "tester" cDNA. Double stranded cDNAs corresponding to tester and driver cDNAs were synthesized from 2 μg of poly(A)$_+$ RNA isolated from the relevant tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Tester cDNA was generated by diluting 1 μl of Dpn II digested cDNA from the relevant tissue source (see above) (400 ng) in 5 μl of water. The diluted cDNA (2 μl 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 rmM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 μg of mRNA with oligo (dT)12–18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 μl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO: 37) and 5'agccacacg-cagctcattgtagaagg 3' (SEQ ID NO: 38) to amplify β-actin. First strand cDNA (5 μl) were amplified in a total volume of 50 μl containing 0.4 μM primers, 0.2 μM each dNTPs, 1×PCR buffer (Clontech, 10 mM Tris-HCl, 1.5 mM MgCl$_2$, 50 mM KCl, pH8.3) and 1× Klentaq DNA polymerase (Clontech). Five μl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 161P2F10B gene, 5 μl of normalized first strand cDNA were analyzed by PCR using 26, and 30 cycles of amplification. Semi-quantitative expression analysis can be achieved by comparing the PCR products at cycle numbers that give light band intensities.

A typical RT-PCR expression analysis is shown in FIG. 14. RT-PCR expression analysis was performed on first strand cDNAs generated using pools of tissues from multiple samples. The cDNAs were shown to be normalized using beta-actin PCR. Strong expression of 161P2F10B was observed in kidney cancer pool. Expression was also detected in VP1, prostate cancer xenograft pool, prostate cancer pool and colon cancer pool. Low expression was observed in VP2, lung cancer pool, ovary cancer pool, breast cancer pool, metastasis pool, pancreas cancer pool, and in the 2 different prostate cancer metastasis to lymph node.

Example 2

Isolation of Full Length 161P2F10B Encoding cDNA

To isolate genes that are involved in kidney cancer, an experiment was conducted using kidney cancer patient specimens. The gene 161P2F10B was derived from a subtraction consisting of kidney cancer specimens, minus normal kidney mixed with a cocktail of 9 normal tissues: stomach, skeletal muscle, lung, brain, liver, kidney, pancreas, small intestine and heart. The SSH DNA sequence (FIG. 1) was designated 161P2F10B. cDNA clone 161P2F10B was cloned from kidney cancer specimens (FIG. 2 and FIG. 3). 161P2F10B showed homology to the gene ENPP3. The amino acid alignment of 161P2F10B with ENPP3 is shown in FIG. 4 (also, see, e.g., Buhring, et al., Blood 97:3303–3305(2001)).

Example 3

Chromosomal Mapping of 161P2F10B

Chromosomal localization can implicate genes in disease pathogenesis. Several chromosome mapping approaches are available including fluorescent in situ hybridization (FISH), human/hamster radiation hybrid (RH) panels (Walter et al., 1994; Nature Genetics 7:22; Research Genetics, Huntsville Ala.), human-rodent somatic cell hybrid panels such as is available from the Coriell Institute (Camden, N.J.), and genomic viewers utilizing BLAST homologies to sequenced and mapped genomic clones (NCBI, Bethesda, Md.).

161P2F10B maps to chromosome 6q22, using 161P2F10B sequence and the NCBI BLAST tool.

Example 4

Expression Analysis of 161P2F10B

To compare expression of 161P2F10B in normal versus patient cancer tissues, RT-PCR experiment was performed using normal and patient cancer tissues (FIG. 14). First strand cDNA was generated from normal stomach, normal brain, normal heart, normal liver, normal skeletal muscle, normal testis, normal prostate, normal bladder, normal kidney, normal colon, normal lung, normal pancreas, and a pool of cancer specimens from prostate cancer patients, bladder cancer patients, kidney cancer patients, colon cancer patients, lung cancer patients, pancreas cancer patients, a pool of prostate cancer xenografts (LAPC-4AD, LAPC-4AI, LAPC-9AD and LAPC-9AI), and a pool of 2 patient prostate metastasis to lymph node. Normalization was performed by PCR using primers to actin. Semi-quantitative PCR, using primers to 161P2F10B, was performed at 26 and 30 cycles of amplification. Samples were run on an agarose gel, and PCR products were quantitated using the Alphalmager software. Results show strong expression in prostate cancer, bladder cancer, kidney cancer, colon cancer, lung cancer, pancreas cancer, bone cancer, lymphoma cancer, uterus cancer, compared to all normal tissues tested. Strong expression was also detected in the xenograft pool as well as the prostate cancer metastasis to lymph node specimens.

FIG. 15 & Table LIX shows expression of 161P2F10B in a panel of kidney cancer clear cell carcinoma (A), kidney cancer papillary carcinoma (B), and in uterus patient cancer specimens (C). First strand cDNA was prepared from the patient specimens. Normalization was performed by PCR using primers to actin. Semi-quantitative PCR, using primers to 161P2F10B, was performed at 26 and 30 cycles of amplification. Samples were run on an agarose gel, and PCR products were quantitated using the Adphalmager software. Expression was recorded as absent, low, medium or strong. Results show expression of 161P2F10B in 94.7% of clear cell renal carcinoma, 62.5% of papillary renal cell carcinoma, and in 61.5% of uterus cancer.

The restricted expression of 161P2F10B in normal tissues and the upregulation detected in kidney cancer, in kidney cancer metastasis, as well as in prostate, bladder, colon, lung, pancreas, bone, lymphoma, uterus, breast, and ovary cancers, suggest that 161P2F10B is a potential therapeutic target and a diagnostic marker for human cancers.

Example 5

Transcript Variants of 161P2F10B

Transcript variants are variants of mature mRNA from the same gene, which arise by alternative transcription or alternative splicing. Alternative transcripts are transcripts from the same gene but start transcription at different points. Splice variants are mRNA variants spliced differently from the same transcript. In eukaryotes, when a multi-exon gene is transcribed from genomic DNA, the initial RNA is spliced to produce functional mRNA, which has only exons and is used for translation into an amino acid sequence. Accordingly, a given gene can have zero to many alternative transcripts and each transcript can have zero to many splice variants. Each transcript variant has a unique exon makeup, and can have different coding and/or non-coding (5' or 3' end) portions, from the original transcript. Transcript variants can code for similar or different proteins with the same or a similar function or can encode proteins with different functions, and can be expressed in the same tissue at the same time, or in different tissues at the same time, or in the same tissue at different times, or in different tissues at different times. Proteins encoded by transcript variants can have similar or different cellular or extracellular localizations, e.g., secreted versus intracellular.

Transcript variants are identified by a variety of art-accepted methods. For example, alternative transcripts and splice variants are identified by full-length cloning experiment, or by use of full-length transcript and EST sequences. First, all human ESTs were grouped into clusters which show direct or indirect identity with each other. Second, ESTs in the same cluster were further grouped into sub-clusters and assembled into a consensus sequence. The original gene sequence is compared to the consensus sequence(s) or other full-length sequences. Each consensus sequence is a potential splice variant for that gene. Even when a variant is identified that is not a full-length clone, that portion of the variant is very useful for antigen generation and for further cloning of the full-length splice variant, using techniques known in the art.

Moreover, computer programs are available in the art that identify transcript variants based on genomic sequences. Genomic-based transcript variant identification programs include FgenesH (A. Salamov and V. Solovyev, "Ab initio gene finding in *Drosophila* genomic DNA," Genome Research. 2000 April; 10(4):516–22); Grail (URL compbio.ornl.gov/Grail-bin/EmptyGrailForm) and Gen Scan (URL genes.mit.edu/GENSCAN.html). For a general discussion of splice variant identification protocols see., e.g., Southan, C., A genomic perspective on human proteases, FEBS Lett. 2001 Jun. 8; 498(2–3):214–8; de Souza, S. J., et al, Identification of human chromosome 22 transcribed sequences with ORF expressed sequence tags, Proc. Natl. Acad Sci USA. 200 Nov. 7; 97(23):12690–3.

To further confirm the parameters of a transcript variant, a variety of techniques are available in the art, such as full-length cloning, proteomic validation, PCR-based validation, and 5' RACE validation, etc. (see e.g., Proteomic Validation: Brennan, S. O., et a., Albumin banks peninsula: a new termination variant characterized by electrospray mass spectrometry, Biochem Biophys Acta. 1999 Aug. 17; 1433(1–2):321–6; Ferranti P, et a., Differential splicing of pre-messenger RNA produces multiple forms of mature caprine alpha(sl)-casein, Eur J. Biochem. 1997 Oct. 31; 249(1):1–7. For PCR-based Validation: Wellmann S, et a., Specific reverse transcription-PCR quantification of vascular endothelial growth factor (VEGF) splice variants by LightCycler technology, Clin Chem. 2001 April; 47(4): 654–60; Jia, H. P., et al, Discovery of new human beta-defensins using a genomics-based approach, Gene. Jan. 24, 2001; 263(1–2):211–8. For PCR-based and 5' RACE Validation: Brigle, K. E., et al., Organization of the murine reduced folate carrier gene and identification of variant splice forms, Biochem Biophys Acta. Aug. 7, 1997; 1353(2): 191–8).

It is known in the art that genomic regions are modulated in cancers. When the genomic region to which a gene maps is modulated in a particular cancer, the alternative transcripts or splice variants of the gene are modulated as well. Disclosed herein is that 161P2F10B has a particular expression profile related to cancer. Alternative transcripts and splice variants of 161P2F10B may also be involved in cancers in the same or different issues, thus serving as tumor-associated markers/antigens.

Using the full-length gene and EST sequences, two transcript variants were identified, designated as 161P2F10B v.6 and v.7. Compared with 161P2F10B v.1, transcript variant 161P2F10B v.6 has extra 40 bases to the 5' starting site of variant 161P2F10B v.1 transcript and has a different 3' end portion, which is on the same chromosome as other exons in the current version of human genome. Variant 161P2F10B v.7 inserted 130 bases in between positions 121 and 122 of variant 161P2F10B v.1. Theoretically, each different combination of exons in spatial order, e.g. exons 2 and 3, is a potential splice variant. Due to the incorrect assembly of the chromosome region in the current version of human genome, the transcript structure cannot be derived computationally.

Tables LI through LVIII are set forth on a variant by variant bases. Tables LI and LV show the nucleotide sequence of the transcript variant. Tables LII and LVI show the alignment of the transcript variant with nucleic acid sequence of 161P2F10B v.1. Tables LIII and LVII lay out amino acid translation of the transcript variant for the identified reading frame orientation. Tables LIV and LVIII display alignments of the amino acid sequence encoded by the splice variant with that of 161P2F10B v.1.

Example 6

Single Nucleotide Polymorphisms of 161P2F10B

A Single Nucleotide Polymorphism (SNP) is a single base pair variation in a nucleotide sequence at a specific location. At any given point of the genome, there are four possible nucleotide base pairs: A/T, C/G, G/C and T/A. Genotype refers to the specific base pair sequence of one or more locations in the genome of an individual. Haplotype refers to the base pair sequence of more than one location on the same DNA molecule (or the same chromosome in higher organisms), often in the context of one gene or in the context of several tightly linked genes. SNPs that occur on a cDNA are called cSNPs. These cSNPs may change amino acids of the protein encoded by the gene and thus change the functions of the protein. Some SNPs cause inherited diseases; others contribute to quantitative variations in phenotype and reactions to environmental factors including diet and drugs among individuals. Therefore, SNPs and/or combinations of alleles (called haplotypes) have many applications, including diagnosis of inherited diseases, determination of drug reactions and dosage, identification of genes responsible for diseases, and analysis of the genetic relationship between individuals (P. Nowotny, J. M. Kwon and A. M. Goate, a "SNP analysis to dissect human traits," Curr. Opin. Neurobiol. 2001 October; 11(5):637–641; M. Pirmohamed and B. K. Park, "Genetic susceptibility to adverse drug reactions," Trends Pharmacol. Sci. 2001 June; 22(6):298–305; J. H. Riley, C. J. Allan, E. Lai and A. Roses, "The use of single nucleotide polymorphisms in the isolation of common disease genes," Pharmacogenomics. 2000 February; 1(1):39–47; R. Judson, J. C. Stephens and A. Windemuth, "The predictive power of haplotypes in clinical response," Pharmacogenomics. 2000 February; 1(1):15–26).

SNPs are identified by a variety of art-accepted methods (P. Bean, "The promising voyage of SNP target discovery," Am. Clin. Lab. 2001 Oct–Nov; 20(9):18–20; K. M. Weiss, "In search of human variation," Genome Res. 1998 July; 8(7):691–697; M. M. She, "Enabling large-scale pharmacogenetic studies by high-throughput mutation detection and genotyping technologies," Clin. Chem. 2001 February; 47(2):164–172). For example, SNPs are identified by sequencing DNA fragments that show polymorphism by gel-based methods such as restriction fragment length polymorphism (RFLP) and denaturing gradient gel electrophoresis (DGGE). They can also be discovered by direct sequencing of DNA samples pooled from different individuals or by comparing sequences from different DNA samples. With the rapid accumulation of sequence data in public and private databases, one can discover SNPs by comparing sequences using computer programs (Z. Gu, L. Hillier and P. Y. Kwok, "Single nucleotide polymorphism hunting in cyberspace," Hum. Mutat. 1998; 12(4):221–225). SNPs can be verified and genotype or haplotype of an individual can be determined by a variety of methods including direct sequencing and high throughput microarrays (P. Y. Kwok, "Methods for genotyping single nucleotide polymorphisms," Annu. Rev. Genomics Hum. Genet. 2001; 2:235–258; M. Kokoris, K. Dix, K. Moynihan, J. Mathis, B. Erwin, P. Grass, B. Hines and A. Duesterhoeft, "High-throughput SNP genotyping with the Masscode system," Mol. Diagn. 2000 December; 5(4):329–340). Using the methods described above, four SNPs were identified in the original transcript, 161P2F10B v.1, at positions 408 (A/G), 2502 (A/G), 2663 (A/C) and 3233 (A/C). The transcripts or proteins with alternative alleles were designated as variants 161P2F10B v.2, v.3, v.4, and v.5, respectively. FIG. 10 shows the schematic alignment of the SNP variants. FIG. 11 shows the schematic alignment of protein variants, corresponding to nucleotide variants. Nucleotide variants that code for the same amino acid sequence as variant I are not shown in FIG. 11. These alleles of the SNPs, though shown separately here, can occur in different combinations (haplotypes) and in any one of the transcript variants (such as 161P2F10B v.7) that contains the sequence context of the SNPS.

Example 7

Production of Recombinant 161P2F10B in Prokaryotic Systems

To express recombinant 161P2F10B in prokaryotic cells, the full or partial length 161P2F10B cDNA sequences can be cloned into any one of a variety of expression vectors known in the art. One or more of the following regions of 161P2F10B are expressed in these contructs, amino acids 1 to 875; or any 8, 9, 10, 11, 12, 13, 14, 15, 16, 17, 18, 19, 20, 21, 22, 23, 24, 25, 26, 27, 28, 29, 30 or more contiguous amino acids from 161P2F10B, variants, or analogs thereof.

A. In Vitro Transcription and Translation Constructs:

pCRII: To generate 161P2F10B sense and anti-sense RNA probes for RNA in situ investigations, pCRII constructs (Invitrogen, Carlsbad Calif.) are generated encoding either all or fragments of the 161P2F10B cDNA. The pCRII vector has Sp6 and T7 promoters flanking the insert to drive the transcription of 161P2F10B RNA for use as probes in RNA in situ hybridization experiments. These probes are used to analyze the cell and tissue expression of 161P2F10B at the RNA level. Transcribed 161P2F10B RNA representing the cDNA amino acid coding region of the 161P2F10B gene is used in in vitro translation systems such as the TnT™ Coupled Reticulolysate System (Promega, Corp., Madison, Wis.) to synthesize 161P2F10B protein.

B. Bacterial Constructs:

pGEX Constructs: To generate recombinant 161P2F10B proteins in bacteria that are fused to the Glutathione S-transferase (GST) protein, all or parts of the 161P2F10B cDNA protein coding sequence are fused to the GST gene by cloning into pGEX-6P-1 or any other GST-fusion vector of the pGEX family (Amersham Pharmacia Biotech, Piscataway, N.J.). These constructs allow controlled expression of recombinant 161P2F10B protein sequences with GST fused at the amino-terminus and a six histidine epitope (6× His) at the carboxyl-terminus. The GST and 6× His tags permit purification of the recombinant fusion protein from induced bacteria with the appropriate affinity matrix and allow recognition of the fusion protein with anti-GST and anti-His antibodies. The 6× His tag is generated by adding 6 histidine codons to the cloning primer at the 3' end, e.g., of the open reading frame (ORF). A proteolytic cleavage site, such as the PreScission™ recognition site in pGEX-6P-1, may be employed such that it permits cleavage of the GST tag from 161P2F10B-related protein. The ampicillin resistance gene and pBR322 origin permits selection and maintenance of the pGEX plasmids in *E coli*.

pMAL Constructs: To generate, in bacteria, recombinant 161P2F10B proteins that are fused to maltose-binding protein (MBP), all or parts of the 161P2F10B cDNA protein coding sequence are fused to the MBP gene by cloning into the pMAL-c2X and pMAL-p2X vectors (New England Biolabs, Beverly, Mass.). These constructs allow controlled expression of recombinant 161P2F10B protein sequences with MBP fused at the amino-terminus and a 6× His epitope tag at the carboxyl-terminus. The MBP and 6× His tags permit purification of the recombinant protein from induced bacteria with the appropriate affinity matrix and allow recognition of the fusion protein with anti-MBP and anti-His antibodies. The 6× His epitope tag is generated by adding 6 histidine codons to the 3' cloning primer. A Factor Xa recognition site permits cleavage of the pMAL tag from 161P2F10B. The pMAL-c2X and pMAL-p2X vectors are optimized to express the recombinant protein in the cytoplasm or periplasm respectively. Periplasm expression enhances folding of proteins with disulfide bonds.

pET Constructs: To express 161P2F10B in bacterial cells, all or parts of the 161P2F10B cDNA protein coding sequence are cloned into the pET family of vectors (Novagen, Madison, Wis.). These vectors allow tightly controlled expression of recombinant 161P2F10B protein in bacteria with and without fusion to proteins that enhance solubility, such as NusA and thioredoxin (Trx), and epitope tags, such as 6× His and S-Tag™ that aid purification and detection of the recombinant protein. For example, constructs are made utilizing pET NusA fusion system 43.1 such that regions of the 161P2F10B protein are expressed as amino-terminal fusions to NusA.

C. Yeast Constructs:

pESC Constructs: To express 161P2F10B in the yeast species *Saccharomyces cerevisiae* for generation of recombinant protein and functional studies, all or parts of the 161P2F108 cDNA protein coding sequence are cloned into the pESC family of vectors each of which contain 1 of 4 selectable markers, HIS3, TRP1, LEU2, and URA3 (Stratagene, La Jolla, Calif.). These vectors allow controlled expression from the same plasmid of up to 2 different genes or cloned sequences containing either Flag™ or Myc epitope tags in the same yeast cell. This system is useful to confirm protein-protein interactions of 161P2F10B. In addition, expression in yeast yields similar post-translational modifications, such as glycosylations and phosphorylations, that are found when expressed in eukaryotic cells.

pESP Constructs: To express 161P2F10B in the yeast species *Saccharomyces pombe*, all or parts of the 161P2F10B cDNA protein coding sequence are cloned into the pESP family of vectors. These vectors allow controlled high level of expression of a 161P2F10B protein sequence that is fused at either the amino terminus or at the carboxyl terminus to GST which aids purification of the recombinant protein. A Flag™ epitope tag allows detection of the recombinant protein with anti-Flag™ antibody.

Example 8

Production of Recombinant 161P2F10B in Higher Eukaryotic Systems

A. Mammalian Constructs:

To express recombinant 161P2F10B in eukaryotic cells, the full or partial length 161P2F10B cDNA sequences can be cloned into any one of a variety of expression vectors known in the art. One or more of the following regions of 161P2F10B are expressed in these constructs, amino acids 1 to 875; or any 8, 9, 10,11, 12, 13, 14, 15, 16, 17, 18, 19, 20, 21, 22, 23, 24, 25, 26, 27, 28, 29, 30 or more contiguous amino acids from 161P2F10B, variants, or analogs thereof.

The constructs were transfected into any one of a wide variety of mammalian cells such as 293T cells or kidney cancer cell lines. Transfected 293T cell lysates were probed with the anti-161P2F10B polyclonal serum and monoclonal antibodies, described herein.

PcDNA3.11MycHis Constructs: To express 161P2F10B in mammalian cells, the 161P2F10B ORF, or portions thereof, of 161P2F10B with a consensus Kozak translation initiation site were cloned into pcDNA3.1/MycHis Version A (Invitrogen, Carlsbad, Calif.). Protein expression is driven from the cytomegalovirus (CMV) promoter. The recombinant proteins have the myc epitope and 6× His epitope fused to the carboxyl-terminus. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in *E. coli*.

The pcDNA3.1/mycHis encoding 161P2F10B was transfected in 293T cells. Cells were harvested 24 hours later and analyzed showing cell surface expression of 161P2F10B driven from the pcDNA3.1/mycHis vector (FIG. 29).

pTaq5: The 161P2F10B ORF, or portions thereof, of 161P2F10B were cloned into pTag-5. This vector is similar to pAPtag but without the alkaline phosphatase fusion. This construct generates 161P2F10B protein with an amino-terminal IgGK signal sequence and myc and 6× His epitope tags at the carboxyl-terminus that facilitate detection and affinity purification. The resulting recombinant 161P2F10B protein was optimized for secretion into the media of transfected mammalian cells, and was used as immunogen or ligand to identify proteins such as ligands or receptors that interact with the 161P2F10B proteins. Protein expression is driven from the CMV promoter. The Zeocin resistance gene present in the vector allows for selection of mammalian cells expressing the protein, and the ampicillin resistance gene permits selection of the plasmid in *E coli*. FIGS. 31 and 32 show expression and enzymatic activity of the soluble pTag5 expressing various growth factors by the transformed cells. The degree of growth factor or serum dependence of transformed host cells PsecFc: The 161P2F10B ORF, or portions thereof, of 161P2F10B were cloned into psecFc. The psecFc vector was assembled by cloning the human immunoglobulin G1 (IgG) Fc (hinge, CH2, CH3 regions) into pSecTag2 (Invitrogen, California). This construct generates an IgG1 Fc fusion at the amino-terminus of the 161P2F10B proteins. 161P2F10B fusions utilizing the murine IgG1 Fc region was also generated and expressed. The resulting recombinant 161P2F10B proteins are optimized for secretion into the media of transfected mammalian cells, and can be used as immunogens or to identify proteins such as ligands or receptors that interact with the 161P2F10B protein. Protein expression is driven from the CMV promoter. The hygromycin resistance gene present in the vector allows for selection of mammalian cells that express the recombinant protein, and the ampicillin resistance gene permits selection of the plasmid in E coli.

pSRα Constructs: To generate mammalian cell lines that express 161P2F10B constitutively, 1611P2F10B ORF, or portions thereof, of 161P2F10B are cloned into pSRa constructs. Amphotropic and ecotropic retroviruses were generated by transfection of pSRα constructs into the 293T-10A1 packaging line or co-transfection of pSRα and a helper plasmid (containing deleted packaging sequences) into the 293 cells. The retrovirus is used to infect a variety of mammalian cell lines, resulting in the integration of the cloned gene, 161P2F10B, into the host cell-lines. Protein expression is driven from a long terminal repeat (LTR). The Neomycin resistance gene present in the vector allows for selection of mammalian cells that express the protein, and the ampicillin resistance gene and ColE1 origin permit selection and maintenance of the plasmid in *E. coli*. The retroviral vectors were thereafter used for infection and generation of various cell lines using, for example, NIH 3T3, 293 Rat-1 cells or kidney cancer cell lines such as Caki and 769 cells. FIGS. 16 and 30 show cell surface expression of 161P2F10B driven from the pSRa construct in Caki and NIH3T3 cells respectively.

Additional pSRα constructs were generated encoding 3 different mutants of 161P2F10B. The first mutant is D80E, converted the D amino acid residue of the RGD domain at position 80 into E. The other mutants are mutants of the active site of 161P2F10B, converting the T205 amino acid residue at position 205 into either A (T205A), or S (T205S). The 3 mutant pSRa constructs were transfected into a variety of mammalian cell lines such as 293T cells and CaKi kidney cancer cells. Expression was confirmed using anti-161P2F10B monoclonal antibody and phosphodiesterase enzyme activity was tested (FIG. 30).

pcDNA4/HisMax Constructs: To express 161P2F10B in mammalian cells, the 161P2F10B ORF, or portions thereof, of 161P2F10B are cloned into pcDNA4/HisMax Version A (Invitrogen, Carlsbad, Calif.). Protein expression is driven from the cytomegalovirus (CMV) promoter and the SP16 translational enhancer. The recombinant protein has XpressT and six histidine (6× His) epitopes fused to the amino-terminus. The pcDNA4/HisMax vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in *E. coli*.

pcDNA3.1/CTGFβ-TOPO Construct: To express 161P2F10B in mammalian cells and to allow detection of the recombinant proteins using fluorescence, the 161P2F10B ORF, or portions thereof, of 161P2F10B with a consensus Kozak translation initiation site are cloned into pcDNA3.1/CT-GFP-TOPO (Invitrogen, CA). Protein expression is driven from the cytomegalovirus (CMV) promoter. The recombinant proteins have the Green Fluorescent Protein (GFP) fused to the carboxyl-terminus facilitating non-invasive, in vivo detection and cell biology studies. The pcDNA3.1/CT-GFP-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in *E coli*. Additional constructs with an amino-terminal GFP fusion are made in pcDNA3.1/NT-GFP-TOPO spanning the entire length of the 161P2F10B proteins.

PAPtag: The 161P2F10B ORF, or portions thereof, of 161P2F10B are cloned into pAPtag-5 (GenHunter Corp. Nashville, Tenn.). This construct generates an alkaline phosphatase fusion at the carboxyl-terminus of the 161P2F10B proteins while fusing the IgGK signal sequence to the amino-terminus. Constructs are also generated in which alkaline phosphatase with an amino-terminal IgGK signal sequence is fused to the amino-terminus of 161P2F10B proteins. The resulting recombinant 161P2F10B proteins are optimized for secretion into the media of transfected mammalian cells and can be used to identify proteins such as ligands or receptors that interact with the 161P2F10B proteins. Protein expression is driven from the CMV promoter and the recombinant proteins also contain myc and 6× His epitopes fused at the carboxyl-terminus that facilitates detection and purification. The Zeocin resistance gene present in the vector allows for selection of mammalian cells expressing the recombinant protein and the ampicillin resistance gene permits selection of the plasmid in *E. coli*.

Additional Viral Vectors: Additional constructs are made for viral-mediated delivery and expression of 161P2F10B. High virus titer leading to high-level expression of 161P2F10B is achieved in viral delivery systems such as adenoviral vectors and herpes amplicon vectors. The 161P2F10B coding sequences or fragments thereof are amplified by PCR and subcloned into the AdEasy shuttle vector (Stratagene). Recombination and virus packaging are performed according to the manufacturer's instructions to generate adenoviral vectors. Alternatively, 161P2F10B coding sequences or fragments thereof are cloned into the HSV-1 vector (Imgenex) to generate herpes viral vectors. The viral vectors are thereafter used for infection of various cell lines such as PC3, NIH 3T3, 293 or rat-1 cells.

Regulated Expression Systems: To control expression of 161P2F10B in mammalian cells, coding sequences of 161P2F10B, or portions thereof, are cloned into regulated mammalian expression systems such as the T-Rex System (Invitrogen), the GeneSwitch System (Invitrogen) and the tightly-regulated Ecdysone System (Sratagene). These systems allow the study of the temporal and concentration dependent effects of recombinant 161P2F10B. These vectors are thereafter used to control expression of 161P2F10B in various cell lines such as PC3, NIH 3T3, 293 or rat-1 cells.

B. Baculovirus Expression Systems

To generate recombinant 161P2F10B proteins in a Baculovirus expression system, 161P2F10B ORF, or portions thereof, are cloned into the Baculovirus transfer vector pBlueBac 4.5 (Invitrogen), which provides a His-tag at the N-terminus. Specifically, pBlueBac-161P2F10B is co-transfected with helper plasmid pBac-N-Blue (Invitrogen) into SF9 (*Spodoptera frugiperda*) insect cells to generate recombinant Baculovirus (see Invitrogen instruction manual for details). Baculovirus is then collected from cell supernatant and purified by plaque assay.

Recombinant 161P2F10B protein is then generated by infection of HighFive insect cells (Invitrogen) with purified Baculovirus. Recombinant 161P2F10B protein can be detected using anti-161P2F10B or anti-His-tag antibody. 161P2F10B protein can be purified and used in various cell-based assays or as immunogen to generate polyclonal and monoclonal antibodies specific for 161P2F10B.

Example 9

Antigenicity Profiles and Secondary Structure

FIG. 5, FIG. 6, FIG. 7, FIG. 8, and FIG. 9 depict graphically five amino acid profiles of the 161P2F10B amino acid sequence, each assessment available by accessing the ProtScale website on the ExPasy molecular biology server.

These profiles: FIG. 5, Hydrophilicity, (Hopp T. P., Woods K. R., 1981. Proc. Natl. Acad. Sci. U.S.A. 78:3824–3828); FIG. 6, Hydropathicity, (Kyte J., Doolittle R. F., 1982. J. Mol. Biol. 157:105–132); FIG. 7, Percentage Accessible Residues (Janin J., 1979 Nature 277:491–492); FIG. 8, Average Flexibility, (Bhaskaran R., and Ponnuswamy P. K., 1988. Int. J. Pept. Protein Res. 32:242–255); FIG. 9, Beta-turn (Deleage, G., Roux B. 1987 Protein Engineering 1:289–294); and optionally others available in the art, such as on the ProtScale website, were used to identify antigenic regions of the 161P2F10B protein. Each of the above amino acid profiles of 161P2F10B were generated using the following ProtScale parameters for analysis: 1) A window size of 9; 2) 100% weight of the window edges compared to the window center; and, 3) amino acid profile values normalized to lie between 0 and 1.

Hydrophilicity (FIG. 5), Hydropathicity (FIG. 6) and Percentage Accessible Residues (FIG. 7) profiles were used to determine stretches of hydrophilic amino acids (i.e., values greater than 0.5 on the Hydrophilicity and Percentage Accessible Residues profile, and values less than 0.5 on the Hydropathicity profile). Such regions are likely to be exposed to the aqueous environment, be present on the surface of the protein, and thus available for immune recognition, such as by antibodies.

Average Flexibility (FIG. 8) and Beta-turn (FIG. 9) profiles determine stretches of amino acids (i.e., values greater than 0.5 on the Beta-turn profile and the Average Flexibility profile) that are not constrained in secondary structures such as beta sheets and alpha helices. Such regions are also more likely to be exposed on the protein and thus accessible to immune recognition, such as by antibodies.

Antigenic sequences of the 161P2F10B protein indicated, e.g., by the profiles set forth in FIG. 5, FIG. 6, FIG. 7, FIG. 8, and/or FIG. 9 are used to prepare immunogens, either peptides or nucleic acids that encode them, to generate therapeutic and diagnostic anti-161P2F10B antibodies. The immunogen can be any 5, 6, 7, 8, 9, 10, 11, 12, 13, 14, 15, 16, 17, 18, 19, 20, 21, 22, 23, 24, 25, 30, 35, 40, 45, 50 or more than 50 contiguous amino acids, or the corresponding nucleic acids that encode them, from the 161P2F10B protein. In particular, peptide immunogens of the invention can comprise, a peptide region of at least 5 amino acids of FIG. 2 in any whole number increment up to 875 that includes an amino acid position having a value greater than 0.5 in the Hydrophilicity profile of FIG. 5; a peptide region of at least 5 amino acids of FIG. 2 in any whole number increment up to 875 that includes an amino acid position having a value less than 0.5 in the Hydropathicity profile of FIG. 6; a peptide region of at least 5 amino acids of FIG. 2 in any whole number increment up to 875 that includes an amino acid position having a value greater than 0.5 in the Percent Accessible Residues profile of FIG. 7; a peptide region of at least 5 amino acids of FIG. 2 in any whole number increment up to 875 that includes an amino acid position having a value greater than 0.5 in the Average Flexibility profile on FIG. 8; and, a peptide region of at least 5 amino acids of FIG. 2 in any whole number increment up to 875 that includes an amino acid position having a value greater than 0.5 in the Beta-turn profile of FIG. 9. Peptide immunogens of the invention can also comprise nucleic acids that encode any of the forgoing.

All immunogens of the invention, peptide or nucleic acid, can be embodied in human unit dose form, or comprised by a composition that includes a pharmaceutical excipient compatible with human physiology.

The secondary structure of 161P2F10B, namely the predicted presence and location of alpha helices, extended strands, and random coils, is predicted from the primary amino acid sequence using the HNN—Hierarchical Neural Network method, accessed from the ExPasy molecular biology server. The analysis indicates that 161P2F10B is composed 31.31% alpha helix, 11.31% extended strand, and 57.37% random coil (FIG. 19A).

Analysis for the potential presence of transmembrane domains in 161P2F10B was carried out using a variety of transmembrane prediction algorithms accessed from the ExPasy molecular biology server. The programs predict the presence of 1 transmembrane domain in 161P2F10B, consistent with that of a Type II cell surface protein. Shown graphically in FIG. 19 are the results of analysis using the TMpred (FIG. 19B) and TMHMM (FIG. 19C) prediction programs depicting the location of the transmembrane domain.

Example 10

Generation of 161P2F10B Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. In addition to immunizing with the full length 161P2F10B protein, computer algorithms are employed in design of immunogens that, based on amino acid sequence analysis contain characteristics of being antigenic and available for recognition by the immune system of the immunized host (see the Example entitled "Antigenicity Profiles"). Such regions would be predicted to be hydrophilic, flexible, in beta-turn conformations, and be exposed on the surface of the protein (see, e.g., FIG. 5, FIG. 6, FIG. 7, FIG. 8, or FIG. 9 for amino acid profiles that indicate such regions of 161P2F10B).

For example, 161P2F10B recombinant bacterial fusion proteins or peptides containing hydrophilic, flexible, beta-turn regions of the 161P2F10B, in which numerous regions are found in the predicted extracellular domain coded by amino acids 45–870, are used as antigens to generate polyclonal antibodies in New Zealand White rabbits. For example, such regions include, but are not limited to, amino acids 43–93, 100–134, 211–246, 467–492, 500–517, and amino acids 810–870. In addition, recombinant proteins are made that encode the whole extracellular domain, amino acids 45–870, or halves of the domain, such as amino acids 45–450 and amino acids 451–870. Antigens are also created encoding the Somatomedin-B-like domain (amino acids 53–133), the catalytic domain (amino acids 158–538), and the nuclease like domain (amino acids 609–875) of 161P2F10B (Bollen et. al., 2000. Crit. Rev. Biochem. Mol. Biol., 35: 393–432), in order to generate antibodies specific to these regions. Ideally antibodies are raised to non-conserved regions of these domains such that they do not crossreact with other homologous nucleotide pyrophosphatases/phosphodiesterases. It is useful to conjugate the immunizing agent to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. In one embodiment, a peptide encoding amino acids 500–517 of 161P2F10B is conjugated to KLH and used to immunize the rabbit. Alternatively the immunizing agent may include all or portions of the 161P2F10B protein, analogs or fusion proteins thereof. For example, the 161P2F10B amino acid sequence can be fused using recombinant DNA techniques to any one of a variety of fusion protein partners that are well known in the art, such as glutathione-S-transferase (GST) and HIS tagged fusion proteins. Such fusion proteins are purified from induced bacteria using the appropriate affinity matrix.

In one embodiment, a GST-fusion protein encoding amino acids 45–875 is produced and purified and used as immunogen. Other recombinant bacterial fusion proteins that may be employed include maltose binding protein, LacZ, thioredoxin, NusA, or an immunoglobulin constant region (see the section entitled Production of 161P2F10B in Prokaryotic Systems' and Current Protocols In Molecular Biology, Volume 2, Unit 16, Frederick M. Ausubul et al. eds., 1995; Linsley, P.S., Brady, W., Urnes, M., Grosmaire, L., Damle, N., and Ledbetter, L.(1991) J. Exp. Med. 174, 561–566).

In addition to bacterial derived fusion proteins, mammalian expressed protein antigens are also used. These antigens are expressed from mammalian expression vectors such as the Tag5 and Fc-fusion vectors (see the section entitled Production of Recombinant 161P2F10B in "Eukaryotic Systems"), and retain post-translational modifications such as glycosylations found in native protein. In one embodiment, amino acids 45–875 is cloned into the Tag5 mammalian secretion vector. The recombinant protein is purified by metal chelate chromatography from tissue culture supernatants of 293T cells stably expressing the recombinant vector. The purified Tag5 161P2F10B protein is then used as immunogen.

During the immunization protocol, it is useful to mix or emulsify the antigen in adjuvants that enhance the immune response of the host animal. Examples of adjuvants include, but are not limited to, complete Freund's adjuvant (CFA) and MPL-TDM adjuvant (monophosphoryl Lipid A, synthetic trehalose dicorynomycolate).

In a typical protocol, rabbits are initially immunized subcutaneously with up to 200 µg, typically 100–200 µg, of fusion protein or peptide conjugated to KLH mixed in complete Freund's adjuvant (CFA). Rabbits are then injected subcutaneously every two weeks with up to 200 µg, typically 100–200 µg, of the immunogen in incomplete Freund's adjuvant (IFA). Test bleeds are taken approximately 7–10 days following each immunization and used to monitor the titer of the antiserum by ELISA.

To test reactivity and specificity of immune serum, such as the rabbit serum derived from immunization with Tag5 161P2F10B encoding amino acids 58–538, the full-length 161P2F10B cDNA is cloned into pcDNA 3.1 myc-his expression vector (Invitrogen, see the Example entitled Production of Recombinant 161P2F10B in "Eukaryotic Systems"). After transfection of the constructs into 293T cells, cell lysates are probed with the anti-161P2F10B serum and with anti-His antibody (Santa Cruz Biotechnologies, Santa Cruz, Calif.) to determine specific reactivity to denatured 161P2F10B protein using the Western blot technique. Immunoprecipitation and flow cytometric analyses of 293T and other recombinant 161P2F10B-expressing cells determine recognition of native protein by the antiserum. In addition, Western blot, immunoprecipitation, fluorescent microscopy, and flow cytometric techniques using cells that endogenously express 161P2F10B are carried out to test specificity.

The anti-serum from the Tag5 161P2F10B immunized rabbit is affinity purified by passage over a column composed of the Tag5 antigen covalently coupled to Affigel matrix (BioRad, Hercules, Calif.). The serum is then further purified by protein G affinity chromatography to isolate the IgG fraction. Serum from rabbits immunized with fusion proteins, such as GST and MBP fusion proteins, are purified by depletion of antibodies reactive to the fusion partner sequence by passage over an affinity column containing the fusion partner either alone or in the context of an irrelevant fusion protein. Sera from other His-tagged antigens and peptide immunized rabbits as well as fusion partner depleted sera are affinity purified by passage over a column matrix composed of the original protein immunogen or free peptide.

Example 11

Generation of 161P2F10B Monoclonal Antibodies (mAbs)

The use of agents to identify the presence of 161P2F10Bin biopsy specimens or to neutralize the effect of 161P2F10B has a beneficial effect in diagnosis, prognoosis, prophylaxis and/or therapy. One particularly useful class of anti 161P2F10B agents is antibodies, in particular monoclonal antibodies (Mabs) to 161P2F10B. Anti 161P2F10B Abs, such as Mabs, are generated that react with the epitopes of the 161P2F10B protein such that they either indicate it's presence, disrupt or modulate it's biological function (for example those that would disrupt the interaction with ligands or proteins that mediate or are involved in it's biological activity) or are able to carry a toxin to the cell which is expressing 161P2F10B.

The term anti 161P2F10B antibody as used herein is to be understood to cover antibodies to any epitope of the 161P2F10B gene product. Diagnostic Mabs, e.g. those used for imaging or immunocytochemistry, comprise those that specifically bind epitopes of 161P2F10B protein and thus demonstrate its presence. Therapeutic Mabs include those that are useful for diagnosis but also comprise those that specifically bind epitopes of 161P2F10B exposed on the cell surface and thus are useful to modulate growth and survival of cells expressing 161P2F10B by disrupting the function of a cell expressing 161P2F10B and/or disrupting the interaction of cells expressing 161P2F10B and the ligand for 161P2F10B.

Preferred antibodies which form one aspect of the invention include but are not limited to antibodies entitled X41(4)6, X41(3)17, X41(3)50, X41(3)15, X41(3)29 and X41(3)37 secreted by a hybridoma deposited with the American Type Culture Collection (ATCC; 10801 University Blvd., Manassas, Va. 20110-2209 USA) on Nov. 7, 2002 and assigned as Patent Deposit Designation No. PTA-4794, Patent Deposit Designation No. PTA-4792, Patent Deposit Designation No. PTA-4793, Patent Deposit Designation No. PTA-4791, Patent Deposit Designation No. PTA-4791, and Patent Deposit Designation No. PTA-4791 (respectively); and derivatives thereof, the production of which is described herein.

Pathological conditions which are characterized by the presence of 161P2F10B expression include, but are not restricted to, neoplasms of tissues such as those listed in Table I. One aspect of the invention provides a method of detecting the presence of 161P2F10B. A further aspect of the invention provides a method of treatment of conditions characterized by the presence of 161P2F10B, comprising administering an effective amount of an anti 161P2F10B antibody. The administration of anti-161 P2F10B antibody is particularly advantageous in the treatment of conditions characterized by the presence of 161P2F10B.

The antibodies against 161P2F10B for use according to the invention can be from any species, and can belong to any immunoglobulin class. Thus, for example, the anti 161P2F10B antibody for use according to the invention can be an immunoglobulin G (IgG), Immunoglobulin M (IgM), immunoglobulin A (IgA), Immunoglobulin E (IgE) or immunoglobulin D (IgD).

The anti 161P2F10B antibody can be from an animal, for example mammaliam or avian origin, and can be for example of murine, rat or human origin. The antibody can be a whole immunoglobulin, or a fragment thereof, for example a fragment derived by proteolytic cleavage of a whole antibody, such as F(ab')2, Fab' or Fab fragments or fragments obtained by recombinant DNA techniques, for example Fv fragments.

Particularly useful antibodies for use according to the invention include humanized or fully human anti 161P2F10B antibodies and fragments thereof. These antibodies are produced by any suitable procedure including, but not restricted to, mammalian cell and bacterial cell fermentation systems.

The anti 161P2F10B Mabs are prepared by immunological techniques employing 161P2F10B antigens. Thus, for example, any suitable host can be injected (immunized) with a suitable reagent which makes 161P2F10B available as an immunogen. Examples of reagents which make 161P2F10B available as an immunogen are purified protein (e.g. the whole extra-cellular domain (ecd) or fragments there of), peptides designed using the full length protein as a template (e.g peptides encompassing the catalytic domain), DNA vectors encoding all or truncated fragments of the ecd, recombinant cells expressing 161P2F10B (e.g. Rat-1, Mouse 3T3, Mouse 300.19, and mouse NSO), Cell lines with endogenous 161P2F10B expression (e.g. human UT-7) or xenografts (i.e. patient derived clear cell and papillary xenografts).

Immune cells, for example splenocytes or lymphocytes, are recovered from the immunized host and immortalized, using for example the method of Kohler et al, Eur. J. Immunol 6, 511 (1976), or their immunoglobulin genes can be isolated and transferred to an appropriate DNA vector for expression in an appropriate cell type. The resulting cells, generated by either technique, will be selected to obtain a single genetic line producing a single unique type of antibody more commonly known as a monoclonal antibody. Antibody fragments can be produced using techniques such as enzymatic digestion of whole antibodies e.g. with pepsin (Parham, J. Immunol 131:2895 (1983)) or papain (Lamoyi and Nisonoff, J. Immunol Meth. 56:235 (1983)), or by recombinant DNA techniques.

Suitable hosts for the production of Mab's to 161P2F10B include mice, rats, hamsters and rabbits. For example, mice are immunized with a number of different reagents which make 161P2F10B available as a source of antigenic material (immunogen). The route and timing if the immunizations will depend on the source and/or embodiment of the immunogen. Sources of immunogen for 161P2F10B include, but are not restricted to, peptide, protein, fusion protein, DNA, RNA, cells or cell membranes as detailed above. These can be used separately as immunogens or in combination to produce a specific immune reaction to 161P2F10B. The use and application of these various immunogens is described fully in the accompanying examples.

Example 12

HLA Class I and Class II Binding Assays

HLA class I and class II binding assays using purified HLA molecules are performed in accordance with disclosed protocols (e.g., PCT publications WO 94/20127 and WO 94/03205; Sidney et al., Current Protocols in Immunology 18.3.1 (1998); Sidney, et al., J. Immunol. 154:247 (1995); Sette, et al., Mol. Immunol. 31:813 (1994)). Briefly, purified MHC molecules (5 to 500 nM) are incubated with various unlabeled peptide inhibitors and 1–10 nM $^{125}$I-radiolabeled probe peptides as described. Following incubation, MHC-peptide complexes are separated from free peptide by gel filtration and the fraction of peptide bound is determined. Typically, in preliminary experiments, each MHC preparation is titered in the presence of fixed amounts of radiolabeled peptides to determine the concentration of HLA molecules necessary to bind 10–20% of the total radioactivity. All subsequent inhibition and direct binding assays are performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For database purposes, and inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation is accurate and consistent for comparing peptides that have been tested on different days, or with different lots of purified MHC.

Binding assays as outlined above may be used to analyze HLA supermotif and/or HLA motif-bearing peptides (see Table IV).

Example 13

Identification of HLA Supermotif- and Motif-Bearing CTL Candidate Epitopes

HLA vaccine compositions of the invention can include multiple epitopes. The multiple epitopes can comprise multiple HLA supermotifs or motifs to achieve broad population coverage. This example illustrates the identification and confirmation of supermotif- and motif-bearing epitopes for the inclusion in such a vaccine composition. Calculation of population coverage is performed using the strategy described below.

Computer Searches and Algorithms for Identification of Supermotif and/or Motif-Bearing Epitopes The searches performed to identify the motif-bearing peptide sequences in the Example entitled "Antigenicity Profiles" and Tables VIII–XXI and XXII–XLIX employ the protein sequence data from the gene product of 161P2F10B set forth in FIGS. 2 and 3, the specific search peptides used to generate the tables are listed in Table VII.

Computer searches for epitopes bearing HLA Class I or Class II supermotifs or motifs are performed as follows. All translated 161P2F10B protein sequences are analyzed using a text string search software program to identify potential peptide sequences containing appropriate HLA binding motifs; such programs are readily produced in accordance with information in the art in view of known motif/supermotif disclosures. Furthermore, such calculations can be made mentally.

Identified A2-, A3-, and DR-supermotif sequences are scored using polynomial algorithms to predict their capacity to bind to specific HLA-Class I or Class II molecules. These polynomial algorithms account for the impact of different amino acids at different positions, and are essentially based on the premise that the overall affinity (or AG) of peptide-HLA molecule interactions can be approximated as a linear polynomial function of the type:

$$"\Delta G" = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide.

The method of derivation of specific algorithm coefficients has been described in Gulukota et al., *J. Mol. Biol.* 267:1258–126, 1997; (see also Sidney et al., *Human Immunol.* 45:79–93, 1996; and Southwood et al., *J. Immunol.* 160:3363–3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Protein sequences from 161P2F10B are scanned utilizing motif identification software, to identify 8-, 9-10- and 11-mer sequences containing the HLA-A2-supermotif main anchor specificity. Typically, these sequences are then scored using the protocol described above and the peptides corresponding to the positive-scoring sequences are synthesized and tested for their capacity to bind purified HLA-A*0201 molecules in vitro (HLA-A*0201 is considered a prototype A2 supertype molecule).

These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The 161P2F10B protein sequence(s) scanned above is also examined for the presence of peptides with the HLA-A3-supermotif primary anchors. Peptides corresponding to the HLA A3 supermotif-bearing sequences are then synthesized and tested for binding to HLA-A*0301 and HLA-A*1101 molecules, the molecules encoded by the two most prevalent A3-supertype alleles. The peptides that bind at least one of the two alleles with binding affinities of $\leq 500$ nM, often $\leq 200$ nM, are then tested for binding cross-reactvity to the other common A3-supertype alleles (e.g., A*3101, A*3301, and A*6801) to identify those that can bind at least three of the five HLA-A3-supertype molecules tested.

Selection of HLA-B7 Supermotif Bearing Epitopes

The 161P2F10B protein(s) scanned above is also analyzed for the presence of 8-, 9–10-, or 11-mer peptides with the HLA-B7-supermotif. Corresponding peptides are synthesized and tested for binding to HLA-B*0702, the molecule encoded by the most common B7-supertype allele (i.e., the prototype B7 supertype allele). Peptides binding B*0702 with $IC_{50}$ of $\leq 500$ nM are identified using standard methods. These peptides are then tested for binding to other common B7-supertype molecules (e.g., B*3501, B*5101, B*5301, and B*5401). Peptides capable of binding to three or more of the five B7-supertype alleles tested are thereby identified.

Selection of A1 and A24 Motif-Bearing Epitopes

To further increase population coverage, HLA-A1 and -A24 epitopes can also be incorporated into vaccine compositions. An analysis of the 161P2F10B protein can also be performed to identify HLA-A1- and A24-motif-containing sequences.

High affinity and/or cross-reactive binding epitopes that bear other motif and/or supermotifs are identified using analogous methodology.

Example 14

Confirmation of Immunogenicity

Cross-reactive candidate CTL A2-supermotif-bearing peptides that are identified as described herein are selected to confirm in vitro immunogenicity. Confirmation is performed using the following methodology:

Target Cell Lines for Cellular Screening:

The 0.221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to confirm the ability of peptide-specific CTLs to recognize endogenous antigen.

Primary CTL Induction Cultures:

Generation of Dendritic Cells (DC): PBMCs are thawed in RPMI with 30 µg/ml DNAse, washed twice and resuspended in complete medium (RPMI-1640 plus 5% AB human serum, non-essential amino acids, sodium pyruvate, L-glutamine and penicillin/streptomycin). The monocytes are purified by plating $10 \times 10^6$ PBMC/well in a 6-well plate.

After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL-4 are then added to each well. TNFα is added to the DCs on day 6 at 75 ng/ml and the cells are used for CTL induction cultures on day 7.

Induction of CTL with DC and Peptide. CD8+ T-cells are isolated by positive selection with Dynal immunomagnetic beads (Dynabeads® M-450) and the detacha-bead(D reagent. Typically about 200–250×10$^6$ PBMC are processed to obtain 24×10$^6$ CD8, T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of 20×10$^6$cells/ml. The magnetic beads are washed 3 times with PBS/AB serum, added to the cells (140 μl beads/20×10$^6$ cells) and incubated for 1 hour at 4° C. with continuous mixing. The beads and cells are washed 4× with PBS/AB serum to remove the nonadherent cells and resuspended at 100×10$^6$ cells/ml (based on the original cell number) in PBS/AB serum containing 100 μl/ml detacha-bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5–7 minutes, washed once with PBS with 1% BSA, counted and pulsed with 40 μg/ml of peptide at a cell concentration of 1–2×10$^6$/ml in the presence of 3 μg/ml β$_2$-microglobulin for 4 hours at 20° C. The DC are then irradiated (4,200 rads), washed 1 time with medium and counted again.

Setting up induction cultures: 0.25 ml cytokine-generated DC (at 1×10$^5$ cells/ml) are co-cultured with 0.25 ml of CD8+ T-cells (at 2×10$^6$ cell/ml) in each well of a 48-well plate in the presence of 10 ng/ml of IL-7. Recombinant human IL-10 is added the next day at a final concentration of 10 ng/ml and rhuman IL-2 is added 48 hours later at 10 IU/ml.

Restimulation of the induction cultures with peptide-pulsed adherent cells: Seven and fourteen days after the primary induction, the cells are restimulated with peptide-pulsed adherent cells. The PBMCs are thawed and washed twice with RPMI and DNAse. The cells are resuspended at 5×10$^6$ cells/ml and irradiated at ~4200 rads. The PBMCs are plated at 2×10$^6$ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml β$_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later recombinant human IL-10 is added at a final concentration of 10 ng/ml and recombinant human IL2 is added the next day and again 2–3 days later at 50 IU/ml (Tsai et al., *Critical Reviews in Immunology* 18(1–2):65–75, 1998). Seven days later, the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side-by-side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 μg/ml peptide overnight at 37° C.

Adherent target cells are removed from culture flasks with trypsin-EDTA. Target cells are labeled with 200 μCi of $^{51}$Cr sodium chromate (Dupont, Wilmington, Del.) for 1 hour at 37° C. Labeled target cells are resuspended at 10$^6$ per ml and diluted 1:10 with K562 cells at a concentration of 3.3×10$^6$/ml (an NK-sensitive erythroblastoma cell line used to reduce non-specific lysis). Target cells (100 μl) and effectors (100 μl) are plated in 96 well round-bottom plates and incubated for 5 hours at 37° C. At that time, 100 μl of supernatant are collected from each well and percent lysis is determined according to the formula:

[(cpm of the test sample-cpm of the spontaneous $^{51}$Cr release sample)/(cpm of the maximal $^{51}$Cr release sample-cpm of the spontaneous $^{51}$Cr release sample)]×100.

Maximum and spontaneous release are determined by incubating the labeled targets with 1% Triton X-100 and media alone, respectively. A positive culture is defined as one in which the specific lysis (sample-background) is 10% or higher in the case of individual wells and is 15% or more at the two highest E:T ratios when expanded cultures are assayed.

In Situ Measurement of Human IFNγ Production as an Indicator of Peptide-Specific and Endogenous Recognition Immulon 2 plates are coated with mouse anti-human IFNγ monoclonal antibody (4 μg/ml 0.1M NaHCO$_3$, pH8.2) overnight at 4° C. The plates are washed with Ca$^{2+}$, Mg$^{2+}$ free PBS/0.05% Tween 20 and blocked with PBS/10% FCS for two hours, after which the CTLs (100 μl/well) and targets (100 μl/well) are added to each well, leaving empty wells for the standards and blanks (which received media only). The target cells, either peptide-pulsed or endogenous targets, are used at a concentration of 1×10$^6$ cells/ml. The plates are incubated for 48 hours at 37° C. with 5% CO2.

Recombinant human IFN-gamma is added to the standard wells starting at 400 μg or 1200 μg/100 microliter/well and the plate incubated for two hours at 37° C. The plates are washed and 100 μl of biotinylated mouse anti-human IFN-gamma monoclonal antibody (2 microgram/ml in PBS/3% FCS/0.05% Tween 20) are added and incubated for 2 hours at room temperature. After washing again, 100 microliter HRP-streptavidin (1:4000) are added and the plates incubated for one hour at room temperature. The plates are then washed 6× with wash buffer, 100 microliter/well developing solution (TMB 1:1) are added, and the plates allowed to develop for 5–15 minutes. The reaction is stopped with 50 microliter/well 1M H$_3$PO$_4$ and read at OD450. A culture is considered positive if it measured at least 50 pg of IFN-gamma/well above background and is twice the background level of expression.

CTL Expansion.

Those cultures that demonstrate specific lytic activity against peptide-pulsed targets and/or tumor targets are expanded over a two week period with anti-CD3. Briefly, 5×10$^4$ CD8+ cells are added to a T25 flask containing the following: 1×10$^6$ irradiated (4,200 rad) PBMC (autologous or allogeneic) per ml, 2×10$^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 μM 2-mercaptoethanol, L-glutamine and penicillin/streptomycin. Recombinant human IL2 is added 24 hours later at a final concentration of 200 IU/ml and every three days thereafter with fresh media at 50IU/ml. The cells are split if the cell concentration exceeds $1 \times 10^6$/ml and the cultures are assayed between days 13 and 15 at E:T ratios of 30, 10, 3 and 1:1 in the $^{51}$Cr release assay or at $1 \times 10^6$/ml in the in situ IFNγ assay using the same targets as before the expansion.

Cultures are expanded in the absence of anti-CD3$^+$ as follows. Those cultures that demonstrate specific lytic activity against peptide and endogenous targets are selected and $5 \times 10^4$ CD8+ cells are added to a T25 flask containing the following: $1 \times 10^6$ autologous PBMC per ml which have been peptide-pulsed with 10 μg/ml peptide for two hours at 37° C. and irradiated (4,200 rad); $2 \times 10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-Bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least individuals, and preferably, also recognizes the endogenously expressed peptide.

Immunogenicity can also be confirmed using PBMCs isolated from patients bearing a tumor that expresses 161P2F10B. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified as set forth herein are confirmed in a manner analogous to the confirmation of A2- and A3-supermotif-bearing peptides.

Peptides bearing other supermotifs/motifs, e.g., HLA-A1, HLA-A24 etc. are also confirmed using similar methodology Example 15

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is confirmed as binding one or all supertype members and then analoged to modulate binding affinity to any one (or more) of the supertype members to add population coverage.

The selection of analogs for immunogenicity in a cellular screening analysis is typically further restricted by the capacity of the parent wild type (WT) peptide to bind at least weakly, i.e., bind at an $IC_{50}$ of 500 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., J. Immunol. 157:2539, 1996; and Pogue et al., Proc. Natl. Acad. Sci. USA 92:8166, 1995).

In the cellular screening of these peptide analogs, it is important to confirm that analog-specific CTLs are also able to recognize the wild-type peptide and, when possible, target cells that endogenously express the epitope.

Analoging of HLA-A3 and B7-supermotif-bearing peptides Analogs of HLA-A3 supermotif-bearing epitopes are generated using strategies similar to those employed in analoging HLA-A2 supermotif-bearing peptides. For example, peptides binding to ⅗ of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate $\leq$500 nM binding capacity are then confirmed as having A3-supertype cross-reactivity.

Similarly to the A2- and A3-motif bearing peptides, peptides binding 3 or more B7-supertype alleles can be improved, where possible, to achieve increased cross-reactive binding or greater binding affinity or binding half life. B7 supermotif-bearing peptides are, for example, engineered to possess a preferred residue (V, I, L, or F) at the C-terminal primary anchor position, as demonstrated by Sidney et al. (J. Immunol. 157:3480–3490, 1996).

Analoging at primary anchor residues of other motif and/or supermotif-bearing epitopes is performed in a like manner.

The analog peptides are then be confirmed for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at position 1 is analyzed. The peptide is then analoged to, for example, substitute L for F at position 1. The analoged peptide is evaluated for increased binding affinity, binding half life and/or increased cross-reactivity. Such a procedure identifies analoged peptides with enhanced properties.

Engineered analogs with sufficiently improved binding capacity or cross-reactivity can also be tested for immunogenicity in HLA-B7-transgenic mice, following for example, IFA immunization or lipopeptide immunization. Analoged peptides are additionally tested for the ability to stimulate a recall response using PBMC from patients with 161P2F10B-expressing tumors.

Other Analoging Strategies

Another form of peptide analoging, unrelated to anchor positions, involves the substitution of a cysteine with α-amino butyric acid. Due to its chemical nature, cysteine has the propensity to form disulfide bridges and sufficiently alter the peptide structurally so as to reduce binding capacity. Substitution of x-amino butyric acid for cysteine not only alleviates this problem, but has been shown to improve binding and crossbinding capabilities in some instances (see, e.g., the review by Selte et al., In: Persistent Viral Infections, Eds. R. Ahmed and 1. Chen, John Wiley & Sons, England, 1999).

Thus, by the use of single amino acid substitutions, the binding properties and/or cross-reactivity of peptide ligands for HLA supertype molecules can be modulated.

Example 16

Identification and Confirmation of 161P2F10B-Derived Sequences with HLA-DR Binding Motifs Peptide epitopes bearing an HLA class II supermotif or motif are identified and confirmed as outlined below using methodology similar to that described for HLA Class I peptides.

Selection of HLA-DR-Supermotif-Bearing Epitopes.

To identify 161P2F10B-derived, HLA class II HTL epitopes, a 161P2F10B antigen is analyzed for the presence of sequences bearing an HLA-DR-motif or supermotif. Specifically, 15-mer sequences are selected comprising a DR-supermotif, comprising a 9-mer core, and three-residue N- and C-terminal flanking regions (15 amino acids total).

Protocols for predicting peptide binding to DR molecules have been developed (Southwood et al., *J. Immunol.* 160: 3363–3373, 1998). These protocols, specific for individual DR molecules, allow the scoring, and ranking, of 9amer core regions. Each protocol not only scores peptide sequences for the presence of DR-supermotif primary anchors (i.e., at position 1 and position 6) within a 9-mer core, but additionally evaluates sequences for the presence of secondary anchors. Using allele-specific selection tables (see, e.g., Southwood et al., ibid), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The 161P2F10B-derived peptides identified above are tested for their binding capacity for various common HLA-DR molecules. All peptides are initially tested for binding to the DR molecules in the primary panel: DR1, DR4w4, and DR7. Peptides binding at least two of these three DR molecules are then tested for binding to DR2w2 P1, DR2w202, DR6w19, and DR9 molecules in secondary assays. Finally, peptides binding at least two of the four secondary panel DR molecules, and thus cumulatively at least four of seven different DR molecules, are screened for binding to DR4w15, DR5w11, and DR8w2 molecules in tertiary assays. Peptides binding at least seven of the ten DR molecules comprising the primary, secondary, and tertiary screening assays are considered cross-reactive DR binders. 161P2F10B-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is a relevant criterion in the selection of HTL epitopes. Thus, peptides shown to be candidates may also be assayed for their DR3 binding capacity. However, in view of the binding specificity of the DR3 motif, peptides binding only to DR3 can also be considered as candidates for inclusion in a vaccine formulation.

To efficiently identify peptides that bind DR3, target 161P2F10B antigens are analyzed for sequences carrying one of the two DR3-specific binding motifs reported by Geluk et al. (*J. Immunol.* 152:5742–5748, 1994). The corresponding peptides are then synthesized and confirmed as having the ability to bind DR3 with an affinity of 1 μM or better, i.e., less than 1 μM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 17

Immunogenicity of 161P2F10B-Derived HTL Epitopes

This example determines immunogenic DR supermotif- and DR3 motif-bearing epitopes among those identified using the methodology set forth herein.

Immunogenicity of HTL epitopes are confirmed in a manner analogous to the determination of immunogenicity of CTL epitopes, by assessing the ability to stimulate HTL responses and/or by using appropriate transgenic mouse models. Immunogenicity is determined by screening for: 1.) in vitro primary induction using normal PBMC or 2.) recall responses from patients who have 161P2F10B-expressing tumors.

Example 18

Calculation of Phenotypic Frequencies of HLA-supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles are determined. Gene frequencies for each HLA allele are calculated from antigen or allele frequencies utilizing the binomial distribution formulae gf=1-(SQRT(1-af) (see, e.g., Sidney et al., *Human Immunol.* 45:79–93, 1996). To obtain overall phenotypic frequencies, cumulative gene frequencies are calculated, and the cumulative antigen frequencies derived by the use of the inverse formula [af=1-(1-Cgf)2].

Where frequency data is not available at the level of DNA typing, correspondence to the serologically defined antigen frequencies is assumed. To obtain total potential supertype population coverage no linkage disequilibrium is assumed, and only alleles confirmed to belong to each of the supertypes are included (minimal estimates). Estimates of total potential coverage achieved by inter-loci combinations are made by adding to the A coverage the proportion of the non-A covered population that could be expected to be covered by the B alleles considered (e.g., total=A+B*(1-A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501–03, B51, B*5301, B*5401, B*5501–2, B*5601, B*6701, and B*7801 (potentially also B*1401, B*3504–06, B*4201, and B*5602).

Population coverage achieved by combining the A2-, A3- and B7-supertypes is approximately 86% in five major ethnic groups. Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%, see, e.g., Table IV (G). An analogous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 19

CTL Recognition of Endogenously Processed Antigens After Priming

This example confirms that CTL induced by native or analoged peptide epitopes identified and selected as described herein recognize endogenously synthesized, i.e., native antigens.

Effector cells isolated from transgenic mice that are immunized with peptide epitopes, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/$K^b$ target cells in the absence or presence of peptide, and also tested on $^{51}$Cr labeled target cells bearing the endogenously synthesized antigen, i.e. cells that are stably transfected with 161P2F10B expression vectors.

The results demonstrate that CTL lines obtained from animals primed with peptide epitope recognize endogenously synthesized 161P2F10B antigen. The choice of transgenic mouse model to be used for such an analysis depends upon the epitope(s) that are being evaluated. In addition to HLA-A*0201/$K^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 20

Activity of CTL-HTL Conjugated Epitopes in Transgenic Mice

This example illustrates the induction of CTLs and HTLs in transgenic mice, by use of a 161P2F10B-derived CTL and HTL peptide vaccine compositions. The vaccine composition used herein comprise peptides to be administered to a patient with a 161P2F10B-expressing tumor. The peptide composition can comprise multiple CTL and/or HTL epitopes. The epitopes are identified using methodology as described herein. This example also illustrates that enhanced immunogenicity can be achieved by inclusion of one or more HTL epitopes in a CTL vaccine composition; such a peptide composition can comprise an HTL epitope conjugated to a CTL epitope. The CTL epitope can be one that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753–4761, 1997). For example, A2/$K^b$ mice, which are transgenic for the human HLA A2.1 allele and are used to confirm the immunogenicity of HLA-A*0201 motif- or HLA-A2 supermotif-bearing epitopes, and are primed subcutaneously (base of the tail) with a 0.1 ml of peptide in Incomplete Freund's Adjuvant, or if the peptide composition is a lipidated CTL/HTL conjugate, in DMSO/saline, or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/$K^b$ chimeric gene (e.g., Vitiello et al., *J. Exp. Med.* 173:1007, 1991)

In vitro CTL activation: One week after priming, spleen cells ($30\times10^6$ cells/flask) are co-cultured at 37° C. with syngeneic, irradiated (3000 rads), peptide coated lymphoblasts ($10\times10^6$ cells/flask) in 10 ml of culture medium/T25 flask. After six days, effector cells are harvested and assayed for cytotoxic activity.

Assay for cytotoxic activity: Target cells (1.0 to 1.5×10⁶) are incubated at 37° C. in the presence of 200 µl of $^{51}$Cr. After 60 minutes, cells are washed three times and resuspended in R10 medium. Peptide is added where required at a concentration of 1 µg/ml. For the assay, $10^4$ $^{51}$Cr-labeled target cells are added to different concentrations of effector cells (final volume of 200 µl) in U-bottom 96-well plates. After a six hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a six hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the effector (E): target (T) ratio of 50:1 (i.e., 5×$10^5$ effector cells for 10,000 targets) in the absence of peptide and 5:1 (i.e., 5×$10^4$ effector cells for 10,000 targets) in the presence of peptide, the specific lytic units would be: $[(1/50,000)-(1/500,000)] \times 10^6 = 18$ LU.

The results are analyzed to assess the magnitude of the CTL responses of animals injected with the immunogenic CTL/HTL conjugate vaccine preparation and are compared to the magnitude of the CTL response achieved using, for example, CTL epitopes as outlined above in the Example entitled "Confirmation of Immunogenicity." Analyses similar to this may be performed to confirm the immunogenicity of peptide conjugates containing multiple CTL epitopes and/or multiple HTL epitopes. In accordance with these procedures, it is found that a CTL response is induced, and concomitantly that an HTL response is induced upon administration of such compositions.

Example 21

Selection of CTL and HTL Epitopes for Inclusion in a 161P2F10B-Specific Vaccine

This example illustrates a procedure for selecting peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting a plurality of epitopes for inclusion in a vaccine composition. Each of the following principles is balanced in order to make the selection.

Epitopes are selected which, upon administration, mimic immune responses that are correlated with 161P2F10B clearance. The number of epitopes used depends on observations of patients who spontaneously clear 161P2F10B. For example, if it has been observed that patients who spontaneously clear 161P2F10B-expressing cells generate an immune response to at least three (3) epitopes from 161P2F10B antigen, then at least three epitopes should be included for HLA class I. A similar rationale is used to determine HLA class II epitopes.

Epitopes are often selected that have a binding affinity of an $IC_{50}$ of 500 nM or less for an HLA class I molecule, or for class II, an $IC_{50}$ of 1000 nM or less; or HLA Class I peptides with high binding scores from the BIMAS web site.

In order to achieve broad coverage of the vaccine through out a diverse population, sufficient supermotif bearing peptides, or a sufficient array of allele-specific motif bearing peptides, are selected to give broad population coverage. In one embodiment, epitopes are selected to provide at least 80% population coverage. A Monte Carlo analysis, a statistical evaluation known in the art, can be employed to assess breadth, or redundancy, of population coverage.

When creating polyepitopic compositions, or a minigene that encodes same, it is typically desirable to generate the smallest peptide possible that encompasses the epitopes of interest. The principles employed are similar, if not the same, as those employed when selecting a peptide comprising nested epitopes. For example, a protein sequence for the vaccine composition is selected because it has maximal number of epitopes contained within the sequence, i.e., it has a high concentration of epitopes. Epitopes may be nested or overlapping (i.e., frame shifted relative to one another). For example, with overlapping epitopes, two 9-mer epitopes and one 10-mer epitope can be present in a 10 amino acid peptide. Each epitope can be exposed and bound by an HLA molecule upon administration of such a peptide. A multi-epitopic, peptide can be generated synthetically, recombinantly, or via cleavage from the native source. Alternatively, an analog can be made of this native sequence, whereby one or more of the epitopes comprise substitutions that alter the cross-reactivity and/or binding affinity properties of the polyepitopic peptide. Such a vaccine composition is administered for therapeutic or prophylactic purposes. This embodiment provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent the creating of any analogs) directs the immune response to multiple peptide sequences that are actually present in 161P2F10B, thus avoiding the need to evaluate any junctional epitopes. Lastly, the embodiment provides an economy of scale when producing nucleic acid vaccine compositions. Related to this embodiment, computer programs can be derived in accordance with principles in the art, which identify in a target sequence, the greatest number of epitopes per sequence length.

A vaccine composition comprised of selected peptides, when administered, is safe, efficacious, and elicits an immune response similar in magnitude to an immune response that controls or clears cells that bear or overexpress 161P2F10B.

Example 22

Construction of "Minigene" Multi-Epitope DNA Plasmids

This example discusses the construction of a minigene expression plasmid Minigene plasmids may, of course, contain various configurations of B cell, CTL and/or HTL epitopes or epitope analogs as described herein.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived 161P2F10B, are selected such that multiple supermotifs/motifs are represented to ensure broad population coverage. Similarly, HLA class II epitopes are selected from 161P2F10B to provide broad population coverage, i.e. both HLA DR-1–4–7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in the art, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene is prepared as follows. For a first PCR reaction, 5 μg of each of two oligonucleotides are annealed and extended: In an example using eight oligonucleotides, i.e., four pairs of primers, oligonucleotides 1+2, 3+4, 5+6, and 7+8 are combined in 100 μl reactions containing Pfu polymerase buffer (1×=10 mM KCL, 10 mM (NH4)$_2$SO$_4$, 20 mM Tris-chloride, pH 8.75, 2 mM MgSO$_4$, 0.1% Triton X-100, 100 μg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 23

The Plasmid Construct and the Degree to which it Induces Immunogenicity

The degree to which a plasmid construct, for example a plasmid constructed in accordance with the previous Example, is able to induce immunogenicity is confirmed in vitro by determining epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683–692, 1996; Demotz et al., *Nature* 342:682–684, 1989); or the number of peptide-HLA class I complexes can be estimated by measuring the amount of lysis or lymphokine release induced by diseased or transfected target cells, and then determining the concentration of peptide necessary to obtain equivalent levels of lysis or lymphokine release (see, e.g., Kageyama et al., *J. Immunol.* 154:567–576, 1995).

Alternatively, immunogenicity is confirmed through in vivo injections into mice and subsequent in vitro assessment of CTL and HTL activity, which are analyzed using cytotoxicity and proliferation assays, respectively, as detailed e.g., in Alexander et al., *Immunity* 1:751–761, 1994.

For example, to confirm the capacity of a DNA minigene construct containing at least one HLA-A2 supermotif peptide to induce CTLs in vivo, HLA-A2.1I/K$^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine.

It is, therefore, found that the minigene elicits immune responses directed toward the HLA-A2 supermotif peptide epitopes as does the polyepitopic peptide vaccine. A similar analysis is also performed using other HLA-A3 and HLA-B7 transgenic mouse models to assess CTL induction by HLA-A3 and HLA-B7 motif or supermotif epitopes, whereby it is also found that the minigene elicits appropriate immune responses directed toward the provided epitopes.

To confirm the capacity of a class II epitope-encoding minigene to induce HTLs in vivo, DR transgenic mice, or for those epitopes that cross react with the appropriate mouse MHC molecule, I-A$^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. *Immunity* 1:751–761, 1994). The results indicate the magnitude of the HTL response, thus demonstrating the in vivo immunogenicity of the minigene.

DNA minigenes, constructed as described in the previous Example, can also be confirmed as a vaccine in combination with a boosting agent using a prime boost protocol. The boosting agent can consist of recombinant protein (e.g., BarneU et al., *Aids Res. and Human Retroviruses* 14, Supplement 3:S299–S309, 1998) or recombinant vaccinia, for example, expressing a minigene or DNA encoding the complete protein of interest (see, e.g., Hanke et al., *Vaccine* 16:439–445, 1998; Sedegah et al., *Proc. Natl. Acad. Sci USA* 95:7648–53,1998; Hanke and McMichael, *Immunol. Letters* 66:177–181, 1999; and Robinson et al., *Nature Med.* 5:526–34, 1999).

For example, the efficacy of the DNA minigene used in a prime boost protocol is initially evaluated in transgenic mice. In this example, A2.1/$K^b$ transgenic mice are immunized IM with 100 μg of a DNA minigene encoding the immunogenic peptides including at least one HLA-A2 supermotif-bearing peptide. After an incubation period (ranging from 3–9 weeks), the mice are boosted IP with $10^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an alpha, beta and/or gamma IFN ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes. The use of prime boost protocols in humans is described below in the Example entitled "Induction of CTL Responses Using a Prime Boost Protocol."

Example 24

Peptide Compositions for Prophylactic Uses

Vaccine compositions of the present invention can be used to prevent 161P2F10B expression in persons who are at risk for tumors that bear this antigen. For example, a polyepitopic peptide epitope composition (or a nucleic acid comprising the same) containing multiple CTL and HTL epitopes such as those selected in the above Examples, which are also selected to target greater than 80% of the population, is administered to individuals at risk for a 161P2F10B-associated tumor.

For example, a peptide-based composition is provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100–5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against 161P2F10B-associated disease.

Alternatively, a composition typically comprising transfecting agents is used for the administration of a nucleic acid-based vaccine in accordance with methodologies known in the art and disclosed herein.

Example 25

Polyepitopic Vaccine Compositions Derived from Native 161P2F10B Sequences

A native 161P2F10B polyprotein sequence is analyzed, preferably using computer algorithms defined for each class I and/or class II supermotif or motif, to identify "relatively short" regions of the polyprotein that comprise multiple epitopes. The "relatively short" regions are preferably less in length than an entire native antigen. This relatively short sequence that contains multiple distinct or overlapping, "nested" epitopes can be used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (ie., frame shifted relative to one another). For example, with overlapping epitopes, two 9-mer epitopes and one 10-mer epitope can be present in a 10 amino acid peptide. Such a vaccine composition is administered for therapeutic or prophylactic purposes.

The vaccine composition will include, for example, multiple CTL epitopes from 161P2F10B antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally, such an embodiment provides for the possibility of motif-bearing epitopes for an HLA makeup(s) that is presently unknown. Furthermore, this embodiment (excluding an analoged embodiment) directs the immune response to multiple peptide sequences that are actually present in native 161P2F10B, thus avoiding the need to evaluate any junctional epitopes. Lastly, the embodiment provides an economy of scale when producing peptide or nucleic acid vaccine compositions.

Related to this embodiment, computer programs are available in the art which can be used to identify in a target sequence, the greatest number of epitopes per sequence length.

Example 26

Polyepitopic Vaccine Compositions from Multiple Antigens

The 161P2F10B peptide epitopes of the present invention are used in conjunction with epitopes from other target tumor-associated antigens, to create a vaccine composition that is useful for the prevention or treatment of cancer that expresses 161P2F10B and such other antigens. For example, a vaccine composition can be provided as a single polypeptide that incorporates multiple epitopes from 161P2F10B as well as tumor-associated antigens that are often expressed with a target cancer associated with 161P2F10B expression, or can be administered as a composition comprising a cocktail of one or more discrete epitopes. Alternatively, the vaccine can be administered as a minigene construct or as dendritic cells which have been loaded with the peptide epitopes in vitro.

Example 27

Use of Peptides to Evaluate an Immune Response

Peptides of the invention may be used to analyze an immune response for the presence of specific antibodies, CTL or HTL directed to 161P2F10B. Such an analysis can be performed in a manner described by Ogg et al., *Science* 279:2103–2106, 1998. In this Example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, 161P2F10B HLA-A*0201-specific CTL frequencies from HLA A*0201-positive individuals at different stages of disease or following immunization comprising a 161P2F10B peptide containing an A*0201 motif. Tetrameric complexes are synthesized as described (Musey et al., *N. Engl. J. Med.* 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5' triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive non-diseased donors. The percentage of cells stained with the tetramer is then determined by flow cytometry. The results indicate the number of cells in the PBMC sample that contain epitope-restricted CTLs, thereby readily indicating the extent of immune response to the 161P2F10B epitope, and thus the status of exposure to 161P2F10B, or exposure to a vaccine that elicits a protective or therapeutic response.

Example 28

Use of Peptide Epitopes to Evaluate Recall Responses

The peptide epitopes of the invention are used as reagents to evaluate T cell responses, such as acute or recall responses, in patients. Such an analysis may be performed on patients who have recovered from 161P2F10B-associated disease or who have been vaccinated with a 161P2F10B vaccine.

For example, the class I restricted CTL response of persons who have been vaccinated may be analyzed. The vaccine may be any 161P2F10B vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128–140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 µl of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with non-diseased control subjects as previously described (Rehermann, et al., *Nature Med.* 2:1104,1108, 1996; Rehermann et al., *J. Clin. Invest.* 97:1655–1665, 1996; and Rehermann et al. *J. Clin. Invest.* 98:1432–1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670–2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amersham Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20–50:1 on day 14. Percent cytotoxicity is determined from the formula: 100×[(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to 161P2F10B or a 161P2F10B vaccine.

Similarly, Class II restricted HTL responses may also be analyzed. Purified PBMC are cultured in a 96-well flat bottom plate at a density of $1.5 \times 10^5$ cells/well and are stimulated with 10 µg/ml synthetic peptide of the invention, whole 161P2F10B antigen, or PHA. Cells are routinely plated in replicates of 4–6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 29

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 30

Phase II Trials in Patients Expressing 161P2F10B

Phase II trials are performed to study the effect of administering the CTL-HTL peptide compositions to patients having cancer that expresses 161P2F10B. The main objectives of the trial are to determine an effective dose and regimen for inducing CTLs in cancer patients that express 161P2F10B, to establish the safety of inducing a CTL and HTL response in these patients, and to see to what extent activation of CTLs improves the clinical picture of these patients, as manifested, e.g., by the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21–65 and represent diverse ethnic backgrounds. All of them have a tumor that expresses 161P2F10B.

Clinical manifestations or antigen-specific T-cell responses are monitored to assess the effects of administering the peptide compositions. The vaccine composition is found to be both safe and efficacious in the treatment of 161P2F10B-associated disease.

Example 31

Induction of CTL Responses Using a Prime Boost Protocol

A prime boost protocol similar in its underlying principle to that used to confirm the efficacy of a DNA vaccine in transgenic mice, such as described above in the Example entitled "The Plasmid Construct and the Degree to Which It Induces Immunogenicity," can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in the Example entitled "Construction of "Minigene" Multi-Epitope DNA Plasmids" in the form of naked nucleic acid administered IM (or SC or ID) in the amounts of 0.5–5 mg at multiple sites. The nucleic acid (0.1 to 1000 µg) can also be administered using a gene gun. Following an incubation period of 3–4 weeks, a booster dose is then administered. The booster can be recombinant fowlpox virus administered at a dose of $5-10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples are obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve a therapeutic or protective immunity against 161P2F10B is generated.

Example 32

Administration of Vaccine Compositions Using Dendritic Cells (DC)

Vaccines comprising peptide epitopes of the invention can be administered using APCs, or "professional" APCs such as DC. In this example, peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction, respectively, of the target cells that bear the 161P2F10B protein from which the epitopes in the vaccine are derived.

For example, a cocktail of epitope-comprising peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides, and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although 2–50×10$^6$ DC per patient are typically administered, larger number of DC, such as 10$^7$ or 10$^8$ can also be provided. Such cell populations typically contain between 50–90% DC.

In some embodiments, peptide-loaded PBMC are injected into patients without purification of the DC. For example, PBMC generated after treatment with an agent such as Progenipoietin™ are injected into patients without purification of the DC. The total number of PBMC that are administered often ranges from 10$^8$ to 10$^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive 5×10$^6$ DC, then the patient will be injected with a total of 2.5×10$^8$ peptide-loaded PBMC. The percent DC mobilized by an agent such as Progenipoietin™ is typically estimated to be between 2–10%, but can vary as appreciated by one of skill in the art.

Ex Vivo Activation of CTL/HTL Responses

Alternatively, ex vivo CTL or HTL responses to 161P2F10B antigens can be induced by incubating, in tissue culture, the patient's, or genetically compatible, CTL or HTL precursor cells together with a source of APC, such as DC, and immunogenic peptides. After an appropriate incubation time (typically about 7–28 days), in which the precursor cells are activated and expanded into effector cells, the cells are infused into the patient, where they will destroy (CTL) or facilitate destruction (HTL) of their specific target cells, i.e., tumor cells.

Example 33

An Alternative Method of Identifying and Confirming Motif-Bearing Peptides

Another method of identifying and confirming motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be transfected with nucleic acids that express the antigen of interest, e.g. 161P2F10B. Peptides produced by endogenous antigen processing of peptides produced as a result of transfection will then bind to HLA molecules within the cell and be transported and displayed on the cell's surface. Peptides are then eluted from the HLA molecules by exposure to mild acid conditions and their amino acid sequence determined, e.g., by mass spectral analysis (e.g., Kubo et al., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can then be transfected with nucleic acids that encode 161P2F10B to isolate peptides corresponding to 161P2F10B that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than transfection, such as loading with a protein antigen, can be used to provide a source of antigen to the cell.

Example 34

Complementary Polynucleotides

Sequences complementary to the 161P2F10B-encoding sequences, or any parts thereof, are used to detect, decrease, or inhibit expression of naturally occurring 161P2F10B. Although use of oligonucleotides comprising from about 15 to 30 base pairs is described, essentially the same procedure is used with smaller or with larger sequence fragments. Appropriate oligonucleotides are designed using, e.g., OLIGO 4.06 software (National Biosciences) and the coding sequence of 161P2F10B. To inhibit transcription, a complementary oligonucleotide is designed from the most unique 5' sequence and used to prevent promoter binding to the coding sequence. To inhibit translation, a complementary oligonucleotide is designed to prevent ribosomal binding to a 161P2F10B-encoding transcript.

Example 35

Purification of Naturally-occurring or Recombinant 161P2F10B Using 161P2F10B-Specific Antibodies Naturally occurring or recombinant 161P2F10B is substantially purified by immunoaffinity chromatography using antibodies specific for 161P2F10B. An immunoaffinity column is constructed by covalently coupling anti-161P2F10B antibody to an activated chromatographic resin, such as CNBr-activated SEPHAROSE (Amersham Pharmacia Biotech). After the coupling, the resin is blocked and washed according to the manufacturers instructions.

Media containing 161P2F10B are passed over the immunoaffinity column, and the column is washed under conditions that allow the preferential absorbance of 161P2F10B (e.g., high ionic strength buffers in the presence of detergent). The column is eluted under conditions that disrupt antibody/161P2F10B binding (e.g., a buffer of pH 2 to pH 3, or a high concentration of a chaotrope, such as urea or thiocyanate ion), and GCRP is collected.

Example 36

Identification of Molecules which Interact with 161P2F10B

161P2F10B, or biologically active fragments thereof, are labeled with 121 1 Bolton-Hunter reagent. (See, e.g., Bolton et al. (1973) Biochem. J. 133:529.) Candidate molecules previously arrayed in the wells of a multi-well plate are incubated with the labeled 161P2F10B, washed, and any wells with labeled 161P2F10B complex are assayed. Data obtained using different concentrations of 161P2F10B are used to calculate values for the number, affinity, and association of 161P2F10B with the candidate molecules.

Example 37

In Vivo Assay for 161P2F10B Tumor Growth Promotion

The effect of the 161P2F10B protein on tumor cell growth is evaluated in vivo by gene overexpression in tumor-bearing mice. For example, SCID mice are injected subcutaneously on each flank with $1 \times 10^6$ of either PC3, TSUPR1, or DU145cells containing tkNeo empty vector or 161P2F10B. At least two strategies may be used: (1) Constitutive 161P2F10B expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) regulated expression under control of an inducible vector system, such as ecdysone, tet, etc., provided such promoters are compatible with the host cell systems. Tumor volume is then monitored at the appearance of palpable tumors and followed over time and determines that 161P2F10B-expressing cells grow at a faster rate and/or tumors produced by 161P2F10B-expressing cells demonstrate characteristics of altered aggressiveness (e.g. enhanced metastasis, vascularization, reduced responsiveness to chemotherapeutic drugs).

Additionally, mice can be implanted with $1 \times 10^5$ of the same cells orthotopically to determine that 161P2F10B has an effect on local growth in the prostate and/or on the ability of the cells to metastasize, e.g., to lungs, lymph nodes, and bone marrow.

The assay is also useful to determine the 161P2F10B-inhibitory effect of candidate therapeutic compositions, such as for example, small molecule drugs, 161P2F10B intrabodies, 161P2F10B antisense molecules and ribozymes.

Example 38

161P2F10B Monoclonal Antibody-mediated Inhibition of Prostate Tumors In Vivo

The significant expression of 161P2F10B, in cancer tissues, together with its restricted expression in normal tissues along with its cell surface expression makes 161P2F10B an excellent target for antibody therapy. Similarly, 161P2F10B is a target for T cell-based immunotherapy. Thus, the therapeutic efficacy of anti-161P2F10B mAbs is evaluated, e.g., in human prostate cancer xenograft mouse models using androgen-independent LAPC-4 and LAPC-9 xenografts (Craft, N., et al., Cancer Res, 1999. 59(19): p. 5030–6), kidney cancer xenografts (AGS-K3, AGS-K6), kidney cancer metastases to lymph node (AGS-K6 met) xenografts, and kidney cancer cell lines transfected with 161P2F10B, such as 769P-161P2F10B, A498-161P2F10B.

Antibody efficacy on tumor growth and metastasis formation is studied, e.g., in mouse orthotopic prostate cancer xenograft models and mouse kidney xenograft models. The antibodies can be unconjugated, as discussed in this Example, or can be conjugated to a therapeutic modality, as appreciated.in the art. Anti-161P2F10B mAbs inhibit formation of both the androgen-dependent LAPC-9 and androgen-independent PC3-161P2F10B tumor xenografls. Anti-161P2F10B mAbs also retard the growth of established orthotopic tumors and prolonged survival of tumor-bearing mice. These results indicate the utility of anti-161P2F10B mAbs in the treatment of local and advanced stages of prostate cancer. (See, e.g., Saffran, D., et al., PNAS 10:1073–1078. Similarly, anti-161P2F10B mAbs can inhibit formation of AGS-K3 and AGS-K6 tumors in SCID mice, and prevent or retard the growth A498-161P2F10B tumor xenografts. These results indicate the use of anti-161P2F10B mAbs in the treatment of prostate and/or kidney cancer.

Administration of the anti-161P2F10B mAbs leads to retardation of established orthotopic tumor growth and inhibition of metastasis to distant sites, resulting in a significant prolongation in the survival of tumor-bearing mice. These studies indicate that 161P2F10B is an attractive target for immunotherapy and demonstrate the therapeutic use of anti-161P2F10B mAbs for the treatment of local and metastatic prostate cancer. This example demonstrates that unconjugated 161P2F10B monoclonal antibodies are effective to inhibit the growth of human prostate tumor xenografts and human kidney xenografts grown in SCID mice.

Tumor Inhibition Using Multiple Unconjugated 161P2F10B mAbs

Materials and Methods

161P2F10B Monoclonal Antibodies:

Monoclonal antibodies are raised against 161P2F10B as described in the Example entitled "Generation of 161P2F10B Monoclonal Antibodies (mAbs)" or are obtained commercially, e.g., 97A6 (Coulter Immunotech). The antibodies are characterized by ELISA, Western blot, FACS, and immunoprecipitation for their capacity to bind 161P2F10B. Epitope mapping data for the anti-161P2F10B mAbs, as determined by ELISA and Western analysis, recognize epitopes on the 161P2F10B protein. The 97A6 antibody binds to amino acids 393–405 of the 161P2F10B protein shown in FIG. 2. Immunohistochemical analysis of cancer tissues and cells is performed with these antibodies.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Cancer Xenografts and Cell Lines

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). The AGS-K3 and AGS-K6 kidney xenografts are also passaged by subcutaneous implants in 6- to 8-week old SCID mice. Single-cell suspensions of tumor cells are prepared as described in Craft, et al. The prostate carcinoma cell line PC3 (American Type Culture Collection) is maintained in RPMI supplemented with L-glutamine and 10% FBS, and the kidney carcinoma line A498 (American Type Culture Collection) is maintained in DMEM supplemented with L-glutamine and 10% FBS.

PC3-161P2F10B and A498-161P2F10B cell populations are generated by retroviral gene transfer as described in Hubert, R. S., et al., STEAP: A Prostate-specific Cell-surface Antigen Highly Expressed in Human Prostate Tumors, Proc Natl Acad Sci USA, 1999. 96(25): p. 14523–8. Anti-161P2F10B staining is detected by using an FITC-conjugated goatanti-mouse antibody (Southern Biotechnology Associates) followed by analysis on a Coulter Epics-XL f low cytometer.

Xenograft Mouse Models.

Subcutaneous (s.c.) tumors are generated by injection of 1×10$^6$ LAPC-9, AGS-K3, AGS-K6, PC3, PC3-161P2F10B, A498 or A498-161P2F10B cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-161P2F10B mAbs are determined by a capture ELISA kit (Bethyl Laboratories, Montgomery, Tex.). (See, e.g., (Saffran, D., et al., PNAS 10:1073–1078.

Orthotopic prostate injections are performed under anesthesia by using ketamine/xylazine. For prostate orthotopic studies, an incision is made through the abdominal muscles to expose the bladder and seminal vesicles, which then are delivered through the incision to expose the dorsal prostate. LAPC-9 cells (5×10$^5$) mixed with Matrigel are injected into each dorsal lobe in a 10-μl volume. To monitor tumor growth, mice are bled on a weekly basis for determination of PSA levels. For kidney orhopotic models, an incision is made through the abdominal muscles to expose the kidney. AGS-K3 or AGS-K6 cells mixed with Matrigel are injected under the kidney capsule. The mice are segregated into groups for the appropriate treatments, with anti-161P2F10B or control mAbs being injected i.p.

Anti-161P2F10B mAbs Inhibit Growth of 161P2F10B-Expressing Xenograft-Cancer Tumors The effect of anti-161P2F10B mAbs on tumor formation is tested by using LAPC-9 and/or AGS-K3 orthotopic models. As compared with the s.c. tumor model, the orthotopic model, which requires injection of tumor cells directly in the mouse prostate or kidney, respectively, results in a local tumor growth, development of metastasis in distal sites, deterioration of mouse health, and subsequent death (Saffran, D., et al., PNAS supra; Fu, X., et al., Int J Cancer, 1992. 52(6): p. 987–90; Kubota, T., J Cell Biochem, 1994. 56(1): p. 4–8). The features make the orthotopic model more representative of human disease progression and allowed for tracking of the therapeutic effect of mAbs on clinically relevant end points.

Accordingly, tumor cells are injected into the mouse prostate or kidney, and 2 days later, the mice are segregated into two groups and treated with either: a) 200–500 μg, of anti-161P2F10B Ab, or b) PBS three times per week for two to five weeks.

A major advantage of the orthotopic prostate-cancer model is the ability to study the development of metastases. Formation of metastasis in mice bearing established orthotopic tumors is studies by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523–8) or anti-G250 antibody for kidney cancer models.

Mice bearing established orthotopic LAPC-9 tumors are administered 1000 μg injections of either anti-161P2F10B mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate/kidney and lungs are analyzed for the presence of tumor cells by IHC analysis.

These studies demonstrate a broad anti-tumor efficacy of anti-161P2F10B antibodies on initiation and progression of prostate and kidney cancer in xenograft mouse models. Anti-161P2F10B antibodies inhibit tumor formation of both androgen-dependent and androgen-independent prostate tumors as well as retarding the growth of already established tumors and prolong the survival of treated mice. Moreover, anti-161P2F10B mAbs demonstrate a dramatic inhibitory effect on the spread of local prostate tumor to distal sites, even in the presence of a large tumor burden. Similar therapeutic effects are seen in the kidney cancer model. Thus, anti-161P2F10B mAbs are efficacious on major clinically relevant end points (tumor growth), prolongation of survival, and health.

Example 39

Therapeutic and Diagnostic use of Anti-161P2F10B Antibodies in Humans

Anti-161P2F10B monoclonal antibodies are safely and effectively used for diagnostic, prophylactic, prognostic and/or therapeutic purposes in humans. Western blot and immunohistochemical analysis of cancer tissues and cancer xenografts with anti-161P2F10B mAb show strong extensive staining in carcinoma but significantly lower or undetectable levels in normal tissues. Detection of 161P2F10B in carcinoma and in metastatic disease demonstrates the usefulness of the mAb as a diagnostic and/or prognostic indicator. Anti-161P2F10B antibodies are therefore used in diagnostic applications such as immunohistochemistry of kidney biopsy specimens to detect cancer from suspect patients.

As determined by flow cytometry, anti-161P2F10B mAb specifically binds to carcinoma cells. Thus, anti-161P2F10B antibodies are used in diagnostic whole body imaging applications, such as radioimmunoscintigraphy and radioimmunotherapy, (see, e.g., Potamianos S., et. al. Anticancer Res 20(2A):925–948 (2000)) for the detection of localized and metastatic cancers that exhibit expression of 161P2F10B. Shedding or release of an extracellular domain of 161P2F10B into the extracellular milieu, such as that seen for alkaline phosphodiesterase B10 (Meerson, N. R., Hepatology 27:563–568 (1998)), allows diagnostic detection of 161P2F10B by anti-161P2F10B antibodies in serum and/or urine samples from suspect patients.

Anti-161P2F10B antibodies that specifically bind 161P2F10B are used in therapeutic applications for the treatment of cancers that express 161P2F10B. Anti-161P2F10B antibodies are used as an unconjugated modality and as conjugated form in which the antibodies are attached to one of various therapeutic or imaging modalities well known in the art, such as a prodrugs, enzymes or radioisotopes. In preclinical studies, unconjugated and conjugated anti-161P2F10B antibodies are tested for efficacy of tumor prevention and growth inhibition in the SCID mouse cancer xenograft models, e.g., kidney cancer models AGS-K3 and AGS-K6, (see, e.g., the Example entitled "161P2F10B Monoclonal Antibody-mediated Inhibition of Bladder and Lung Tumors In Vivo"). Either conjugated and unconjugated anti-61 P2F10B antibodies are used as a therapeutic modality in human clinical trials either alone or in combination with other treatments as described in following Examples.

Example 40

Human Clinical Trials for the Treatment and Diagnosis of Human Carcinomas through use of Human Anti-161P2F10B Antibodies In Vivo Antibodies are used in accordance with the present invention which recognize an epitope on 161P2F10B, and are used in the treatment of certain tumors such as those listed in Table I. Based upon a number of factors, including 161P2F10B expression levels, tumors such as those listed in Table I are presently preferred indications. In connection with each of these indications, three clinical approaches are successfully pursued.

I.) Adjunctive therapy: In adjunctive therapy, patients are treated with anti-161P2F10B antibodies in combination with a chemotherapeutic or antineoplastic agent and/or radiation therapy. Primary cancer targets, such as those listed in Table I, are treated under standard protocols by the addition anti-161P2F10B antibodies to standard first and second line therapy. Protocol designs address effectiveness as assessed by reduction in tumor mass as well as the ability to reduce usual doses of standard chemotherapy. These dosage reductions allow additional and/or prolonged therapy by reducing dose-related toxicity of the chemotherapeutic agent. Anti-161P2F10B antibodies are utilized in several adjunctive clinical trials in combination with the chemotherapeutic or antineoplastic agents adriamycin (advanced prostrate carcinoma), cisplatin (advanced head and neck and lung carcinomas), taxol (breast cancer), and doxorubicin (preclinical).

II.) Monotherapy: In connection with the use of the anti-161P2F10B antibodies in monotherapy of tumors, the antibodies are administered to patients without a chemotherapeutic or antineoplastic agent. In one embodiment, monotherapy is conducted clinically in end stage cancer patients with extensive metastatic disease. Patients show some disease stabilization. Trials demonstrate an effect in refractory patients with cancerous tumors.

III.) Imaging Agent: Through binding a radionuclide (e.g., iodine or yttrium ($I^{131}$, $Y^{90}$) to anti-161P2F10B antibodies, the radiolabeled antibodies are utilized as a diagnostic and/or imaging agent. In such a role, the labeled antibodies localize to both solid tumors, as well as, metastatic lesions of cells expressing 161P2F10B. In connection with the use of the anti-161P2F10B antibodies as imaging agents, the antibodies are used as an adjunct to surgical treatment of solid tumors, as both a pre-surgical screen as well as a post-operative follow-up to determine what tumor remains and/or returns. In one embodiment, a ($^{111}$In)-161P2F10B antibody is used as an imaging agent in a Phase I human clinical trial in patients having a carcinoma that expresses 161P2F10B (by analogy see, e.g., Divgi et al. *J. Natl. Cancer Inst.* 83:97–104 (1991)). Patients are followed with standard anterior and posterior gamma camera. The results indicate that primary lesions and metastatic lesions are identified.

Dose and Route of Administration

As appreciated by those of ordinary skill in the art, dosing considerations can be determined through comparison with the analogous products that are in the clinic. Thus, anti-161P2F10B antibodies can be administered with doses in the range of 5 to 400 mg/m$^2$, with the lower doses used, e.g., in connection with safety studies. The affinity of anti-161P2F10B antibodies relative to the affinity of a known antibody for its target is one parameter used by those of skill in the art for determining analogous dose regimens. Further, anti-161P2F10B antibodies that are fully human antibodies, as compared to the chimeric antibody, have slower clearance; accordingly, dosing in patients with such fully human anti-161P2F10B antibodies can be lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

Three distinct delivery approaches are useful for delivery of anti-161P2F10B antibodies. Conventional intravenous delivery is one standard delivery technique for many tumors. However, in connection with tumors in the peritoneal cavity, such as tumors of the ovaries, biliary duct, other ducts, and the like, intraperitoneal administration may prove favorable for obtaining high dose of antibody at the tumor and to also minimize antibody clearance. In a similar manner, certain solid tumors possess vasculature that is appropriate for regional perfusion. Regional perfusion allows for a high dose of antibody at the site of a tumor and minimizes short term clearance of the antibody.

Clinical Development Plan (CDP)

Overview: The CDP follows and develops treatments of anti-161P2F10B antibodies in connection with adjunctive therapy, monotherapy, and as an imaging agent. Trials initially demonstrate safety and thereafter confirm efficacy in repeat doses. Trails are open label comparing standard chemotherapy with standard therapy plus anti-161P2F10B antibodies. As will be appreciated, one criteria that can be utilized in connection with enrollment of patients is 161P2F10B expression levels in their tumors as determined by biopsy.

As with any protein or antibody infusion-based therapeutic, safety concerns are related primarily to (i) cytokine release syndrome, i.e., hypotension, fever, shaking, chills; (ii) the development of an immunogenic response to the material (i.e., development of human antibodies by the patient to the antibody therapeutic, or HAHA response); and, (iii) toxicity to normal cells that express 161P2F10B. Standard tests and follow-up are utilized to monitor each of these safety concerns. Anti-161P2F10B antibodies are found to be safe upon human administration.

Example 41

Human Clinical Trial Adjunctive Therapy with Human Anti-161P2F10B Antibody and Chemotherapeutic Agent A phase I human clinical trial is initiated to assess the safety of six intravenous doses of a human anti-161P2F10B antibody in connection with the treatment of a solid tumor, e.g., a cancer of a tissue listed in Table I. In the study, the safety of single doses of anti-161P2F10B antibodies when utilized as an adjunctive therapy to an antineoplastic or chemotherapeutic agent as defined herein, such as, without limitation: cisplatin, topotecan, doxorubicin, adriamycin, taxol, or the like, is assessed. The trial design includes delivery of six single doses of an anti-161P2F10B antibody with dosage of antibody escalating from approximately about 25 mg/M$^2$ to about 275 mg/m$^2$ over the course of the treatment in accordance with the following schedule:

|  | Day 0 | Day 7 | Day 14 | Day 21 | Day 28 | Day 35 |
|---|---|---|---|---|---|---|
| mAb Dose | 25 mg/m$^2$ | 75 mg/m$^2$ | 125 mg/m$^2$ | 175 mg/m$^2$ | 225 mg/m$^2$ | 275 mg/m$^2$ |
| Chemotherapy (standard dose) | + | + | + | + | + | + |

Patients are closely followed for one-week following each administration of antibody and chemotherapy. In particular, patients are assessed for the safety concerns mentioned above: (i) cytokine release syndrome, i.e., hypotension, fever, shaking, chills; (ii) the development of an immunogenic response to the material (i.e., development of human antibodies by the patient to the human antibody therapeutic, or HAHA response); and, (iii) toxicity to normal cells that express 161P2F10B. Standard tests and follow-up are uilized to monitor each of these safety concerns. Patients are also assessed for clinical outcome, and particularly reduction in tumor mass as evidenced by MRI or other imaging.

The anti-161P2F10B antibodies are demonstrated to be safe and efficacious, Phase II trials confirm the efficacy and refine optimum dosing.

Example 42

Human Clinical Trial: Monotherapy with Human Anti-161P2F10B Antibody

Anti-161P2F10B antibodies are safe in connection with the above-discussed adjunctive trial, a Phase II human clinical trial confirms the efficacy and optimum dosing for monotherapy. Such trial is accomplished, and entails the same safety and outcome analyses, to the above-described adjunctive trial with the exception being that patients do not receive chemotherapy concurrently with the receipt of doses of anti-161P2F10B antibodies.

Example 43

Human Clinical Trial: Diagnostic Imaging with Anti-161P2F10B Antibody

Once again, as the adjunctive therapy discussed above is safe within the safety criteria discussed above, a human clinical trial is conducted concerning the use of anti-161P2F10B antibodies as a diagnostic imaging agent. The protocol is designed in a substantially similar manner to those described in the art, such as in Divgi et al. *J. Natl. Cancer Inst.* 83:97–104 (1991). The antibodies are found to be both safe and efficacious when used as a diagnostic modality.

Example 44

Homology Comparison of 161P2F10B to Known Sequences

The 161P2F10B gene is identical to a previously cloned and sequenced gene, namely ectonucleotide pyrophosphatase/phosphodiesterase 3 (gi 4826896) (Jin-Hua P et al, Genomics 1997, 45:412), also known as phosphodiesterase-I beta; gp130RB13-6; E-NPP3 (ENPP3), PDNP3 and CD203c. The 161P2F10B protein shows 100% identity to human ectonucleotide pyrophosphatase/phosphodiesterase 3 (gi 4826896), and 81% homology and 89% identity to rat alkaline phosphodiesterase (gi 1699034). The 161P2F10B protein consists of 875 amino acids, with calculated molecular weight of 100.09 kDa, and pI of 6.12. 161P2F10B is a cell surface protein as shown by immunostaining in basophils (Buhring H J et al, Blood 2001, 97:3303) and in epithelial tumor cells as shown in the example entitled "Expression of 161P2F10B protein in kidney cancer xenograft tissues". Some localization to the golgi-endoplasmic fraction has also been observed (Geoffroy V et al, Arch Biochem Biophys. 2001, 387:154). Two isoforms of phosphodiesterase 3 have been identified, with one protein containing an additional 145 aa at its aminoterminus (Choi Y H et al, Biochem J. 2001, 353:41). In addition, two variants of 161P2F10B have been identified. The first variant contains a point mutation at amino acid 122 of the 161P2F10B protein, changing a lysine to an arginine at that position. The second variant contains a single nucleotide polymorphisms, identified at position 383, resulting in a change in amino acid from threonine to proline at that position (FIG. 4A and 4B). In addition, we have recently identified another variant of 161P2F10B, namely 161P2F10B v.7. This variant differs from v.1 at its N-terminus as it lacks the first 34 aa found in v.1. The loss of the N-terminal 34 aa affects the localization of 161P2F10B v.7. PSort analysis reveled that, while 161P2F10B v.1 is primarily located at the plasma membrane, 161P2F10B v.7 primarily localizes to the cytoplasm (52%) with some localization to the nucleus (17%).

Motif analysis revealed the presence of several known motifs, including 2-3 somatostatin B domains located at the amino terminus of the 161P2F10B protein, a phosphodiesterase domain and an endonuclease domain at the C-terminus. 161P2F10B belongs to a family of closely related phosphodiesterases, consisting of PDNP1, -2, and -3 (Bollen M et al, Crit. Rev. Biochem Mol. Biol. 2000, 35: 393). All three members of this family are type 11 proteins, with a short N-terminus domain located intracellularly. They contain one transmembrane domain, a catalytic phosphodiesterase domain and a C-terminal nuclease domain.

Phosphodiesterase 3 expression has been detected in human neoplastic submandibular cells, glioma cells, and tansformed lymphocytes (Murata T et al, Anticancer Drugs 2001, 12:79; Andoh K et al, Biochim Biophys Acta 1999, 1446:213; Ekholm D et al, Biochem Pharmacol 1999, 58: 935).

Phosphodiesterase 3 plays an important role in several biological processes, including release of nucleotides, cell differentiation, metabolism, cell growth, survival, angiogenesis and cell motility (Bollen M et al, Crit. Rev. Biochem Mol. Biol. 2000, 35: 393; Rawadi G et al, Endocrinol 2001, 142:4673; DeFouw L et al, Microvasc Res 2001, 62:263). In addition, Phosphodiesterase 3 regulates gene expression in epithelial cells, including the expression of key adhesion molecules such as VCAM-1 (Blease K et al, Br J. Pharmacol. 1998, 124:229).

This information indicates that 161P2F10B plays a role in the growth of mammalian cells, supports cell survival and motility, and regulate gene transcription by regulating events in the nucleus. Accordingly, when 161P2F10B functions as a regulator of cell transformation, tumor formation, or as a modulator of transcription involved in activating genes associated with inflammation, tumorigenesis or proliferation, 161P2F10B is used for therapeutic, diagnostic, prognostic and/or preventative purposes. In addition, when a molecule, such as a a variant, polymorphism or SNP of 161P2F10B is expressed in cancerous tissues, such as those listed in Table I, they are used for therapeutic, diagnostic, prognostic and/or preventative purposes.

Example 45

Regulation of Transcription

The cell surface localization of 161P2F10B and ability to regulate VCAM expression indicate that 161P2F10B is effectively used as a modulator of the transcriptional regulation of eukaryotic genes. Regulation of gene expression is confirmed, e.g., by studying gene expression in cells expressing or lacking 161P2F10B. For this purpose, two types of experiments are performed.

In the first set of experiments, RNA from parental and 161P2F10B-expressing cells are extracted and hybridized to commercially available gene arrays (Clontech) (Smid-Koopman E et al. Br J Cancer. 2000. 83:246). Resting cells as well as cells treated with FBS or androgen are compared. Differentially expressed genes are identified in accordance with procedures known in the art. The differentially expressed genes are then mapped to biological pathways (Chen K et al. Thyroid. 2001. 11:41.).

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

Thus, 161P2F10B plays a role in gene regulation, and it is used as a target for diagnostic, prognostic, preventative and/or therapeutic purposes.

Example 46

Identification and Confirmation of Potential Signal Transduction Pathways

Many mammalian proteins have been reported to interact with signaling molecules and to participate in regulating signaling pathways. (J. Neurochem. 2001; 76:217–223). In particular, GPCRs have been reported to activate MAK cascades as well as G proteins, and been associated with the EGFR pathway in epithelial cells (Naor, Z., et al, Trends Endocrinol Metab. 2000,11:91; Vacca F et al, Cancer Res. 2000, 60:5310; Della Rocca G J et al, J. Biol. Chem. 1999, 274:13978). Using immunoprecipitation and Western blotting techniques, proteins are identified that associate with 161P2F10B and mediate signaling events. Several pathways known to play a role in cancer biology can be regulated by 161P2F10B, including phospholipid pathways such as P13K, AKT, etc, adhesion and migration pathways, including FAK, Rho, Rac-1, etc, as well as mitogenic/survival cascades such as ERK, p38, etc (Cell Growth Differ. 2000, 11:279; J. Biol. Chem. 1999, 274:801; Oncogene. 2000, 19:3003, J. Cell Biol. 1997,138:913.).

To confirm that 161P2F10B directly or indirectly activates known signal transduction pathways in cells, luciferase (luc) based transcriptional reporter assays are carried out in cells expressing individual genes. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; 1k-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress Gene-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 161P2F10B are mapped and used for the identification and validation of therapeutic targets. When 161P2F10B is involved in cell signaling, it is used as target for diagnostic, prognostic, preventative and/or therapeutic purposes.

Example 47

Involvement in Tumor Progression

The 161P2F10B gene can contribute to the growth of cancer cells. The role of 161P2F10B in tumor growth is confirmed in a variety of primary and transfected cell lines including prostate, colon, bladder and kidney cell lines, as well as NIH 3T3 cells engineered to stably express 161P2F10B. Parental cells lacking 161P2F10B and cells expressing 161P2F10B are evaluated for cell growth using a well-documented proliferation assay (Fraser S P, Grimes J A, Djamgoz M B. Prostate. 2000;44:61, Johnson D E, Ochieng J, Evans S L. Anticancer Drugs. 1996, 7:288).

To confirm the role of 161P2F10B in the transformation process, its effect in colony forming assays is investigated. Parental NIH-3T3 cells lacking 161P2F10B are compared to N1H-3T3 cells expressing 161P2F10B, using a soft agar assay under stringent and more permissive conditions (Song Z. et al. Cancer Res. 2000;60:6730).

To confirm the role of 161P2F10B in invasion and metastasis of cancer cells, a well-established assay is used, e.g., a Transwell Insert System assay (Becton Dickinson) (Cancer Res. 1999; 59:6010). Control cells, including prostate, colon, bladder and kidney cell lines lacking 161P2F10B are compared to cells expressing 161P2F10B. Cells are loaded with the fluorescent dye, calcein, and plated in the top well of the Transwell insert coated with a basement membrane analog. Invasion is determined by fluorescence of cells in the lower chamber relative to the fluorescence of the entire cell population. Using this approach we have demonstrated that 161P2F10B induces the invasion of 3T3 cells through the basement membrane analog mabrigel (FIG. 22). As shown in FIG. 22, 3T3-neo cells that do not express 161P2F10B exhibit negligible levels of invasion though matdgel. Compared to 3T3-neo cells, 3T3-161P2F10B cells, which express abundant levels of 161P2F10B (FIG. 16), invade through matrigel and migrate to the lower chamber of the transwell system in a manner similar to that observed with cells expressing the strong protooncogene 12V-Ras.

161P2F10B can also play a role in cell cycle and apoptosis. Parental cells and cells expressing 161P2F10B are compared for differences in cell cycle regulation using a well-established BrdU assay (Abdel-Malek ZA. J Cell Physiol. 1988, 136:247). In short, cells are grown under both optimal (full serum) and limiting (low serum) conditions are labeled with BrdU and stained with anti-BrdU Ab and propidium iodide. Cells are analyzed for entry into the G1, S, and G2M phases of the cell cycle.

In contrast to normal cells, cancer cells have been shown to withstand stress, growth factor deprivation and pro-apoptotic signals, thereby providing tumors with a growth and survival advantage. The effect of stress on apoptosis is evaluated in control parental cells and cells expressing 161P2F10B, including normal and tumor prostate, colon and lung cells using standard assays methods including annexin V binding and caspase activation (Moore A, et al, Methods Cell Biol. 1998;57:265; Porter A G, Janicke R U. Cell Death Differ. 1999; 6:99). Engineered and parental cells were treated with various chemotherapeutic agents, such as etoposide, doxorubicin, kinase inhibitors such as staurosporine, DNA damaging agents such as UV, hypoxia and protein synthesis inhibitors, such as cycloheximide. Cells were stained with annexin V-FITC and cell death measured by FACS analysis. FIG. 20 shows that expression of 161P2F10B prevent the apoptosis of 3T3 cells exposed to staurosporine or UV irradiation. While 64% and 62% of 3T3-neo cells underwent apoptosis in response to staurosporine and UV irradiation, respectively, only 14% and 30% of 161P2F10B-expressing 3T3 cells died under the same conditions. Similar results were obtained in another experiment comparing the effect of staurosporine and UV irradiation on 3T3-neo cells and clonal populations of 3T3-161P2F10B cell lines (FIG. 19). As with the population of 3T3-161P2F10B, clones 3T3-161P2F10B-C and 3T3-161P2F10B-10B were resistant to staurosporine-induced cell death. Since caspase activation is a hallmark of apoptosis and serves to distinguish apoptosis from other forms of cell death, we investigated the effect of to chemotherapeutic agent and, staurosporine on the apoptosis of kidney cancer cells using caspase activation as assay read out (FIG. 21). The 769 kidney tumor cells that normally lack 161P2F10B were engineered to express the 161P2F10B protein as describe in example 8, Production of Recombinant 161P2F10B in Higher Eukaryotic Systems, above. The cells were treated with chemotherapeutic agents or staurosporine, lysed and analyzed for caspase activity. FIG. 21 shows that expression of 161P2F10B prevents caspase activation in 161P2F10B-expressing kidney cancer cells treated with doxorubicin or staurosporine. These results show that 161P2F10B imparts resistance to the chemotherapeutic drug doxorubicin and to saurosporine-induced cell death in kidney cancer cells.

A characteristic that distinguishes cancer cells from normal cells is their ability to become serum independent and survive in low serum conditions. The effect of serum deprivation on the survival of 161P2F10B expressing cells was studied using caspase activation as a read out. The fibroblast cell line Rat-1 becomes growth arrested when serum deprived, thereby mimicking normal non-transformed cells (James L, Eisenman R N. Proc Natl Acad Sci USA. 2002, 99:10429). Rat-1 cells expressing c-Myc (Rat-Myc) undergo apoptosis under serum deprivation conditions (James L, Eisenman R N. Proc Natl Acad Sci USA. 2002, 99:10429). Rat-1 and Rat-Myc cells were engineered to stably express 161P2F10B. The cells were grown in 0.1% or 10% FBS and examined for apoptosis by microscopy and caspase activity (FIGS. 17 and 18). When 161P2F10B is stably expressed in Rat-Myc cells, it inhibits Myc-induced apoptosis and reduces caspase activity to background levels. The inhibition of cell death by 161P2F10B plays a critical role in regulating tumor progression and tumor load.

When 161P2F10B plays a role in cell growth, transformation, invasion or apoptosis, it is used as a target for diagnostic, prognostic, preventative and/or therapeutic purposes.

Example 48

Involvement in Angiogenesis

Angiogenesis or new capillary blood vessel formation is necessary for tumor growth (Hanahan D, Folkman J. Cell. 1996, 86:353; Folkman J. Endocrinology. 1998 139:441). Based on the effect of phsophodieseterase inhibitors on endothelial cells, and the homology of 161P2F10B to other ENPP family members, 161P2F10B plays a role in angiogenesis (DeFouw L et al, Microvasc Res 2001, 62:263). Several assays have been developed to measure angiogenesis in vitro and in vivo, such as the tissue culture assays endothelial cell tube formation and endothelial cell proliferation. Using these assays as well as in vitro neo-vascularization, the role of 161P2F10B in angiogenesis, enhancement or inhibition, is confirmed.

For example, endothelial cells engineered to express 161P2F10B are evaluated using tube formation and proliferation assays. The effect of 161P2F10B is also confirmed in animal models in vivo. For example, cells either expressing or lacking 161P2F10B are implanted subcutaneously in immunocompromised mice. Endothelial cell migration and angiogenesis are evaluated 5–15 days later using immunohistochemistry techniques. Similarly, the secreted extracellular portion of 161P2F10B can function as an angiogenic factor and enhance the proliferation and tube formation of endothelial cells. The effect of the extracellular domain of 161P2F10B on angiogenesis is supported by its similarity to other ENPPs, with biologically active secreted extracellular domain. When 161P2F10B affects angiogenesis, and it is used as a target for diagnostic, prognostic, preventative and/or therapeutic purposes.

Example 49

Involvement in Protein-Protein Interactions

Several phsophodiesterases have been shown to interact with other proteins, thereby regulating gene transcription, as well as cell growth (Butt E et al, Mol Pharmacol. 1995, 47:340). Using immunoprecipitation techniques as well as two yeast hybrid systems, proteins are identified that associate with 161P2F10B. Immunoprecipitates from cells expressing 161P2F10B and cells lacking 161P2F10B are compared for specific protein-protein associations.

Studies are performed to confirm the extent of association of 161P2F10B with effector molecules, such as nuclear proteins, transcription factors, kinases, phsophates etc. Studies comparing 161P2F10B positive and 161P2F10B negative cells as well as studies comparing unstimulated/resting cells and cells treated with epithelial cell activators, such as cytokines, growth factors, androgen and anti-integrin Ab reveal unique interactions.

In addition, protein-protein interactions are confirmed using two yeast hybrid methodology (Curr Opin Chem Biol. 1999, 3:64). A vector carrying a library of proteins fused to the activation domain of a transcription factor is introduced into yeast expressing a 161P2F10B-DNA-binding domain fusion protein and a reporter construct. Protein-protein interaction is detected by colorimetric reporter activity. Specific association with effector molecules and transcription factors directs one of skill to the mode of action of 161P2F10B, and thus identifies therapeutic, prognostic, preventative and/or diagnostic targets for cancer. This and similar assays are also used to identify and screen for small molecules that interact with 161P2F10B. Thus it is found that 161P2F10B associates with proteins and small molecules. Accordingly, 161P2F10Band these proteins and small molecules are used for diagnostic, prognostic, preventative and/or therapeutic purposes.

Example 50

Involvement in Cell Adhesion

Cell adhesion plays a critical role in tissue colonization and metastasis. 161P2F10B can participate in cellular organization, and as a consequence cell adhesion and motility. To confirm that 161P2F10B regulates cell adhesion, control cells lacking 161P2F10B are compared to cells expressing 161P2F10B, using techniques previously described (see, e.g., Haieretal,Br. J. Cancer. 1999, 80:1867; LehrandPienta, J. Natl. Cancer Inst. 1998, 90:118). Briefly, in one embodiment, cells labeled with a fluorescent indicator, such as calcein, are incubated on tissue culture wells coated with media alone or with matrix proteins. Adherent cells are detected by fluorimetric analysis and percent adhesion is calculated. In another embodiment, cells lacking or expressing 161P2F10B are analyzed for their ability to mediate cell-cell adhesion using similar experimental techniques as described above. Both of these experimental systems are used to identify proteins, antibodies and/or small molecules that modulate cell adhesion to extracellular matrix and cell-cell interaction. Cell adhesion plays a critical role in tumor growth, progression, and, colonization, and 161P2F10B is involved in these processes. Thus, it serves as a diagnostic, prognostic, preventative and/or therapeutic modality.

Example 51

Phosphodiesterase Activity of 161P2F10B Expressing Recombinant Cell Lines

In order to delineate the function 161P2F10B, several cell lines that lack 161P2F10B were transduced with 161P2F10B-encoding retovirus as described in example 8, Production of Recombinant 161P2F10B in Higher Eukaryotic Systems, above. Cell lines were characterized for 161P2F10B cell surface expression by FACS analysis (FIGS. 28, 29, 30, and 16). cDNA was stably introduced into the fibroblast lines NIH 3T3 and Rat-1, myeloma NSO cells, and kidney cancer CaKi cells. The cells were immunostained with anti-CD203c mAb and analyzed by flow cytometry. FIGS. 28, 29, 30, and 16 show that while parental cells fail to express 161P2F10B, engineered lines demonstrate abundant expression of 161P2F10B on their cell surface. Expression of 161P2F10B in engineered cells was compared to that in UT7, a cell line that expresses 161P2F10B endogenously (FIG. 28). Our results show that engineered Rat-T and 3T3 cells express 161P2F10B at levels comparable to UT7 cells.

Since 161P2F10B is identical to the ecto-enzyme ENPP3 phosphodieterase, and members of the ENPP family possess pyrophosphatase activities, the recombinant cell lines were also characterized for phosphodiesterase activity (FIGS. 28, 29, 30, and 16). Control and 161P2F10B-expressing cells were lysates or intact cells were incubated for at 37 degrees in 20 mM Tris/HCL, pH 9.6 containing 5 mM $MgCl_2$ and 1 mM p-nitrophenyl thymidine-5'-L-monophosphate. The reaction was terminated by the addition of 0.1 N NaOH and the reaction product quantified by reading absorbance at 410 nm. FIGS. 28, 29, 30, and 16 show that 161P2F10B expression parallels phosphodiesterase activity. Using CaKi cells expressing either wild type or mutant 161P2F10B, we show that mutation of T205 inhibits phosphodiesterase activity (FIG. 30). When 161P2F10B shows phosphodiesterase activity, it is used as a target for diagnostic, prognostic, preventative and/or therapeutic purposes.

In addition to phosphodiesterase activity, members of the ENPP family exhibit lysophospholipase D (lysoPLD) activity (Umezu-Goto M et al, J. Cell Biol. 2002, 158: 227). ENPP-2 (aka autotoxin) in particular was found to act on lysophosphatidylcholine (LPC) to generate lysophosphatidic acid (LPA) (Umezu-Goto M et al, J. Cell Biol. 2002, 158: 227; Tokumura A et al, J boil. Chem 2002, 277:39436). LPA is involved in various biological functions associated with tumor development, including cell proliferation and invasion (Gschwind A, Prenzel N, Ullrich A. Cancer Res. 2002, 62:6329). Based on the homology of 161P1F10B to other ENPP family members, 161P2F10B has lysoPLD activity. The lysoPLD activity of 161P2F10B expressing cells is compared to cells lacking 161P2F10B using a standard choline release assay. In short, cell lysates are incubated with LPC for 1 hr at 37° C. Liberated choline is detected by fluoremetry following the addition of choline oxidase. When 161P2F10B shows lysoPLD activity, it is used as a target for diagnostic, prognostic, preventative and/or therapeutic purposes.

Example 52

RNA Interference (RNAi)

Several methods of reducing or abolishing the expression of specific genes have been used for confirming the importance of said genes in tumor growth and progression. These methods include antisense oligonucleotides, morpholino, ribozyme, etc that function in a sequence specific manner to prevent gene transcription or translation. More recently, RNA interference by duplexes of short nucleotide RNAs has been shown to inhibit gene expression in a sequence specific manner in mammalian cells (Elbashir S et al, Nature 2001, 411:494). RNA interference (RNAi) makes use of sequence specific double stranded RNA known as small interfering RNAs (siRNAs) to prevent gene expression. Small interfering RNA (siRNA) are transfected into mammalian cells and thereby mediate sequence specific mRNA degradation. (Elbashir, et al, Nature, 2001; 411: 494). Similarly, siRNA have been used to generate stable vector systems that can be delivered in vitro and in vivo to mammalian cells, thereby providing therapeutic use for siRNAs (Lee N et al, Nature Biotechnol 2002, 19:500). Several siRNAs can be used to modulate the expression of 161P2F10B in mammalian cells, including for example the following siRNA oligonucleotide sequences:

161P2F10B (1) target: GMUCUACGUUGACUUUAG (corresponding to nucleotides 4–23 of 161P2F10B ORF) (SEQ ID NO: 39)

The sense strand of 161P2F10B (1) can labeled at 3' with fluorescein, 6-FAM (ABS 494 nm, EMM 525 nm, green) for easy detection. The siRNA is dissolved in RNA-free sterile buffer (100 mM KOAc, 30 mM HEPES KOH, 2 mM MOAc, at pH 7.4) to make 20 µM stock (200×). The siRNa is transfected into various normal and tumor cells, including UT7, 3T3-161P2F10B, CaKi-161P2F10B and Rat-161P2F10B cells. Control, non-specific oligonucleotide is used as a control to rule out any non-specific effect of 161P2F10B siRNA oligonucleotides.

Protein expression is determined 24–48 hours after transfection by immunostaining followed by flow cytometry. In addition, confirmation of altered gene expression is performed by Western blotting. Cells transfected with control or 161P2F10B-specific siRNAi are compared using functional assays described above, including invasion, proliferation, colony formation and response to apoptotic stimuli. Therefore, the RNA oligonucleotide sequences are used to assess how modulating the expression of a 161P2F10B gene affects function of cancer cells and/or tissues.

Accordingly, the RNA oligonucleotide sequences are used in therapeutic and prophylactic applications.

Example 53

Generation of Antibodies to 161P2F10B Using Peptide Encoding the Caytalytic Domain of 161P2F10B as the Immunogen In one embodiment peptides of 22 amino acids encompassing the 161P2F10B catalytic domain (Threonine (T) at position 205), CGIHSKYMRAMYPTKTFPNHYT (SEQ ID NO: 40) were generated. These were, synthesized and the peptides were coupled to KLH through the N-terminal cysteine residue.

Balb/c mice were immunized intraperitoneally (i.p.) with 10 µg of peptide every 2 weeks over a 4 week period. The initial immunization was given i.p. in Complete Freunds Adjuvant (CFA) and the subsequent two immunizations were given i.p. in Incomplete Freunds Adjuvant (IFA).

To determine the specificity of the response following immunization, mice were bled 10 days after the final immunization. Reactivity was determined by Enzyme Linked Immunosorbent Assay (ELISA) using non-KLH conjugated (free) peptide as a target. Mice with the highest titers were given a final boost of 10 µg peptide in PBS and sacrificed for fusion 3 days later. Spleen cells from the immunized mice were fused with mouse Sp2/0 myeloma cells using PEG 1500 according to standard protocols (Kohler et al, Eur. J. Immunol 6: 511 (1976)). Fused cells were plated in 10 96 well microtiter plates and hybridomas were selected using HAT media supplement. Supernatants from fusion wells were screened 10–17 days later by ELISA against 161P2F10B peptide, and clones were then checked for the ability of the monoclonal antibody to recognize cell membrane 161P2F10B by FACS on 161P2F10B expressing Rat-1 cells.

Example 54

Generation of Antibodies to 161P2F10B Using Protein Encoding the Whole Extra Cellular Domain (aa 1–975) of 161P2F10B as the Immunogen In one embodiment the whole extra cellular domain of 161P2F10B fused at the C' terminal with 6 Histidines (6-His for purification was purified hor use as an immunogen.

Balb/c mice were immunized intraperitoneally (i.p.) with 10 µg of protein every 2 weeks over a 4 week period. The initial immunization was given i.p. in Complete Freunds Adjuvant (CFA) and the subsequent two immunizations were given i.p. in Incomplete Freunds Adjuvant (IFA).

To determine the specificity of the response following immunization, mice were bled 10 days after the final immunization. Reactivity was determined by Enzyme Linked Immunosorbent Assay (ELISA) using purified protein as a screening agent.

Mice with the highest titers were given a final boost of 10 µg protein in PBS and sacrificed for fusion 3 days later. Spleen cells from the immunized mice were fused with mouse Sp2/0 myeloma cells using PEG 1500 according to standard protocols (Kohler et al, Eur. J. Immunol 6: 511 (1976)). Fused cells were plated in 10 96 well microtiter plates and hybridomas were selected using HAT media supplement. Supernatants from fusion wells were screened 10–17 days later by ELISA against 161P2F10B protein, and clones were then checked for the ability of the monoclonal antibody to recognize cell membrane 161P2F10B by FACS on 161P2F10 expressing Rat-1 cells.

Example 55

Generation Mabs to 161P2F10B Using DNA Immunization with a Vector Encoding 161P2F10B Fused at the C' Terminus with Human IgG Fc In another embodiment, a vector was constructed that encodes the 975 amino acids of the 161P2F10 extra cellular domain fused at the C-terminus to the human immunoglobulin G1 (IgG1 Fc (hinge, CH2, CH3 regions). This construct was used in a DNA based immunization strategy.

Balb/c mice were immunized intra-dermally (ID) at the base of their tail. Three immunizations were given to each mouse of 100 μg of DNA in PBS over a two-week period. To increase the immune response, each mouse was given an i.p. boost of 2 μg of 161P2F10B-Fc protein in tissue culture media 10 days after the final DNA immunization. Bleeds were collected 10 days after the final immunization and reactivity in the sera to the middle loop of 161 P2F10B was tested by ELISA using 161P2F10B-Fc fusion protein as a target (test 1). In parallel the sera were also tested on an unrelated human Fc fusion protein (test 2). Specific reactivity to the 161 P2F10B portion of the fusion protein was indicated. All mice were sacrificed and fusions and hybridoma selection was carried out as described in Example 54. Hybridoma supernatants were screened 10–17 days later by ELISA using 161P2F10B-Fc protein as target. 161P2F10B-Fc positives were subsequently cross-screened on irrelevant Fc proteins to identify 161P2F10 specific clones. Monoclonal antibodies were tested for specificity and reactivity to cell surface 161p2F10B using recombinant Rat 1 cells. Several antibodies were identified this way including X41 (4)6, X41(3)15, X41(3)17, X41(3)29, X41(3)37 and X41(3) 50. These antibodies or binding region thereof secreted by a hybridoma entitled X41(3)15/29/37, X41(4)6, X41(3)50 were deposited with the Anerican Type Culture Collection (ATCC; 10801 University Blvd., Manassas, Va. 20110-2209 USA) on Nov. 7, 2002 and assigned as Patent Deposit Designation No. PTA-4791, Patent Deposit Designation No. PTA-4794, Patent Deposit Designation No. PTA-4792. and Patent Deposit Desianation No. PTA-4793 (respectively). FAGS data for these monoclonal antibodies is shown on (FIG. 40).

Example 56

Generation of Mabs to 161P2F10B Using DNA Immunization with a Vector Encoding 161P2F10B fused at the C' Terminus with the myc His Tag In another embodiment, a vector was constructed that encodes the 975 amino acids of the 161P2F10 extra cellular domain fused at the C-terminus to the myc-His tag. This construct was used in a DNA based immunization strategy.

Balb/c mice were immunized intra-dermally (ID) at the base of their tail. Three immunizations were given to each mouse of 100 μg of DNA in PBS over a two-week period. To increase the immune response, each mouse was given an i.p. boost of 2 μg of 161P2F10B-Fcprotein in tissue culture media 10 days after the final DNA immunization. Bleeds were collected 10 days after the final immunization and reactivity in the sera to the middle loop of 161P2F10B was tested by ELISA using 161P2F10B-Fc fusion protein as a target (test 1). In parallel the sera were also tested on an unrelated human Fc fusion protein (test 2). Specific reactivity to the 161P2F10B portion of the fusion protein was indicated.

All mice were sacrificed and fusions and hybridoma selection was carried out as described in Example 11. Hybridoma supernatants were screened 10–17 days later by ELISA using 161P2F10B-Fc protein as target. 161P2F10B-Fc positives were subsequently cross-screened on irrelevant Fc proteins to identify 161P2F10 specific clones. Monoclonal antibodies were tested for specificity and reactivity to cell surface 161p2F10B using recombinant Rat 1 cells.

Example 57

Generation of Monoclonal Antibodies Specific for 161P2F10B using UT7 Cells Endogenously Expressing 161P2F10B It has been reported in the literature that antibodies to 161P2F10B can be made by immunization with the human erythro-megakaryoblastic cell line UT-7 cultured with IL3 (Buhring et. al. Blood 94(7): 2343. 1999). Antibodies described in this publication are available commercially and have been used as controls in the invention described here. In another embodiment, mice were immunized intraperitoneally with UT-7 cells, 106 cells per immunization. A total of 5 immunizations were given approximately 2 weeks apart with the final injection being given three days befor mice were sacrificed for fusions. Mice were bled 10 days after the third injection and the 161P2F10B specific titer of the sera was determined by ELISA using 161P2F10 as a screening agent. Mice with high titers were then used for fusions as described in Example 11. Monoclonal antibodies generated in this way were selected by ELISA and their ability to recognize cells surface 161P2F10B was confirmed by FACS on Rat 1 cells expressing 161P2F10B.

Example 58

Generation of Monoclonal Antibodies Specific for 161P2F10B Using the Recombinant Cell Line 3T3 Expressing 161P2F10B In another embodiment, mice were immunized inteaperitoneally with 3T3 cells expressing 161P2F10B, $10^6$ cells per immunization. A total of 5 immunizations were given approximately 2 weeks apart with the final injection being given three days before mice were sacrificed for fusions. Mice were bled 10 days after the third injection and the 161P2F10B specific titer of the sera was determined by ELISA using 161P2F10 as a screening agent. Mice with high titers were then used for fusions as described in Example 11. Monoclonal antibodies generated in this way were selected by ELISA and their ability to recognize cells surface 161P2F10B was confirmed by FACS on Rat 1 cells expressing 161P2F10B.

Example 59

Generation of Monoclonal Antibodies Specific for 161P2F10B Using the Recombinant Cell Line Rat 1 Expressing 161P2F10B In another embodiment mice were immunized with Rat-i cells expressing 161P2F10B, Mice were then used for fusions as described in Example 11. Monoclonal antibodies generated in this way were selected by ELISA and their ability to recognize cells surface 161P2F10B was confirmed by FACS on Rat 1 cells expressing 161P2F10B.

Example 60

Detection of 161P2F10B Protein in Kidney Cancer Patient Specimens

To confirm the expression of 161P2F10B protein, kidney cancer specimens were obtained from kidney cancer patients, and stained using the commercially available antibody 97A6 specific for ENPP3 protein (also called anti-CD203c) (Immunotech, Marseilles, France). Briefly, frozen tissues were cut into 4 micron sections and fixed in acetone for 10 minutes. The sections were then incubated with PE-labeled mouse monoclonal anti-ENPP3 antibody for 3 hours (FIGS. 24A–C), or isotype control antibody (FIGS. 44G–I). The slides were washed three times in buffer, and either analyzed by fluorescence microscopy (FIGS. 44A, B and C), or further incubated with DAKO EnVision+™ peroxidase-conjugated goat anti-mouse secondary antibody (DAKO Corporation, Carpenteria, Calif.) for 1 hour (FIGS. 44D, E, and F FIGS. 24A–C). The sections were then washed in buffer, developed using the DAB kit (SIGMA Chemicals), counterstained using hematoxylin, and analyzed by bright field microscopy (FIGS. 44D, E and F). The results showed strong expression of 161P2F10B in the renal carcinoma patient tissue (FIGS. 44A and D) and the kidney cancer metastasis to lymph node tissue (FIGS. 44C and F), but weakly in normal kidney (FIGS. 44B and E). The expression was detected mostly around the cell periphery in renal clear cell carcinoma (FIGS. 44A and D, FIGS. 24A and B) and was strongly expressed throughout the cells with an apparent predisposition towards the cell periphery in renal papillary carcinoma (FIG. 24C) indicating that 161P2F10B is membrane associated in kidney cancer tissues. The weak expression detected in normal kidney was localized to the kidney tubules. The sections stained with the isotype control antibody were negative showing the specificity of the anti-ENPP3 antibody (FIGS. 44G–I). Kidney cancer specimens were obtained from patients with different types of renal tumor including renal clear cell carcinoma; papillary cell carcinoma; renal cell carcinoma, chromophobe type; transitional cell carcinoma and oncocytoma and were stained for 161P2F10B using the commercially available antibody 97A6 specific for ENPP3 protein (also called anti-CD203c) (Immunotech, Marseilles, France). All tissue specimens for renal clear cell carcinoma and papillary cell carcinoma were positive for 161P2F10B (Table LIX).

FIG. 45 shows expression of 161P2F10B in human patient cancers by Western blot analysis. Cell lysates from kidney cancer tissues (KiCa), kidney cancer metastasis to lymph node (KiCa Met), as well as normal kidney (NK) were subjected to western analysis using an anti-161P2F10B mouse monoclonal antibody. Briefly, tissues (~25 µg total protein) were solubilized in SDS-PAGE sample buffer and separated on a 10–20% SDS-PAGE gel and transferred to nitrocellulose. Blots were blocked in Tris-buffered saline (TBS)+3% non-fat milk and then probed with purified anti-161P2F10B antibody in TBS+0.15% Tween-20+1% milk. Blots were then washed and incubated with a 1:4,000 dilution of anti-mouse IgG-HRP conjugated secondary antibody. Following washing, anti-161P2F10B immunoreactive bands were developed and visualized by enhanced chemiluminescence and exposure to autoradiographic film. The specific anti-161P2F10B immunoreactive bands represent a monomeric form of the 161P2F10B protein, which runs at approximately 130 kDa. These results demonstrate that 161P2F10B is useful as a diagnostic and therapeutic target for kidney cancers, metastatic cancers and other human cancers that express this protein.

The strong expression of 161P2F10B in kidney cancer tissues and its restricted expression in normal kidney as well as its membrane localization show that 161P2F10B is a target, e.g., for kidney cancer diagnosis and therapy. The expression detected in kidney cancer metastatic tissue indicates that 161P2F10B is also a target for metastatic disease. As disclosed herein, Western blot and immunohistochemical analysis of kidney cancer tissues and kidney cancer xenografts with mAb 97A6 showed strong extensive staining of ENPP3 in clear cell kidney carcinoma but significantly lower or undetectable levels in normal kidney (FIGS. 44, 45, 46, and 24). Detection of 161P2F10B (ENPP3) in high grade clear cell carcinoma and in metastatic disease.

Example 61

Detection of 161P2F10B Protein in Colon Cancer Patient Specimens

Tissue specimens of colon adenocarcinoma were obtained from nine different colon cancer patients. Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed strong expression of 161P2F10B in two of the nine colon cancer patient tissues, one of which is illustrated (FIG. 26). 161P2F10B was most strongly expressed on the tumor cells with a luminal cell surface but was also expressed throughout all the tumor tissue.

Example 62

Detection of 161P2F10B Protein by Immunohistochemistry in a Prostate Cancer Patient Specimens Tissue specimens of prostate adenocarcinoma were obtained from eight different prostate cancer patients. Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed expression of 161P2F10B in six of the eight prostate cancer patient tissues, one of which is illustrated (FIG. 25). 161P2F10B was expressed on the tumor cells with an apparent proclivity towards the luminal cell surface.

Example 63

Detection of 161P2F10B Protein by Immunohistochemistry in Normal Tissue Specimens Normal tissue specimens from a number of organs were obtained either from patients undergoing surgery or from autopsy. Frozen tissues were cut into 4 micron sections and fixed in acetone for 10 minutes. The sections were then incubated with mouse monoclonal anti-ENPP3 antibody (Coulter-Immunotech, Marseilles, France) for 3 hours. The slides were washed three times in buffer, and further incubated with DAKO EnVision+™ peroxidase-conjugated goat anti-mouse secondary antibody (DAKO Corporation, Carpenteria, Calif.) for 1 hour. The sections were then washed in buffer, developed using the DAB kit (SIGMA Chemicals), counterstained using hematoxylin, and analyzed by bright field microscopy. The results showed weak expression of 161P2F10B in some of the tubules in all of the kidney specimens and weak staining of some glandular epithelium in half of the prostate tissues. There was no expression of 161P2F10B in any of the other normal tissues studied except for expression in a very few cells within one lung, one bladder and two colon samples which could be mast cells (TABLE LX). As disclosed herein, Western blot and immunohistochemical analysis of kidney cancer tissues and kidney cancer xenografts with mAb 97A6 showed strong extensive staining of ENPP3 in clear cell kidney carcinoma but significantly lower or undetectable levels in normal kidney (FIGS. 44, 45, 46, and 24). Detection of 161P2F10B (ENPP3) in high grade clear cell carcinoma and in metastatic disease.

Example 64

Detection by Immunohistochemistry of 161P2F10B Protein Expression in Kidney Clear Cell Cancer Patient Specimens by Specific Binding of Mouse Monoclonal Antibodies Renal clear cell carcinoma tissue and its matched normal adjacent were obtained from a kidney cancer patient. Frozen tissues were cut into 4 micron sections and fixed in acetone for 10 minutes. The sections were then incubated either mouse monoclonal anti-ENPP3 antibody (Coulter-Immunotech, Marseilles, France) for 3 hours (FIG. 27 panels A, D), or mouse monoclonal antibody X41(3)50 (FIG. 27 panels B, E), or mouse monoclonal antibody X41(3)37 (FIG. 27 panels C, F). The slides were washed three times in buffer and further incubated with DAKO EnVision+™ peroxidase-conjugated goat anti-mouse secondary antibody (DAKO Corporation, Carpentena, Calif.) for 1 hour. The sections were then washed in buffer, developed using the DAB kit (SIGMA Chemicals), counterstained using hematoxylin, and analyzed by bright field microscopy (FIG. 27 panels A–F). The results showed strong expression of 161P2F10B in the renal clear cell carcinoma patient tissue (FIG. 27 panels A–C), but weakly in normal kidney (FIG. 27 panels D–F). The expression was predominantly around the cell periphery indicating that 161P2F10B is membrane associated in kidney cancer tissues. The weak expression detected in normal kidney was localized to the kidney proximal tubules. As disclosed herein, Western blot and immunohistochemical analysis of kidney cancer tissues and kidney cancer xenografts with mAb 97A6 showed strong extensive staining of ENPP3 in clear cell kidney carcinoma but significantly lower or undetectable levels in normal kidney (FIGS. 44, 45, 46, and 24). Detection of 161P2F10B (ENPP3) in high grade clear cell carcinoma and in metastatic disease.

Example 65

Characteristics and Utility of Anti-161P2F10b MAbs

Using a variety of immunization strategies as described in Example 11, a panel of MAbs that specifically bind 161P2F10b protein was generated. The characteristics of this panel is summarized in FIG. 39 These antibodies specifically bind with high affinity to 161P2F10b on the surface of endogenously-expressing and recombinant cell lines as determined by flow cytometry (FIGS. 28 and 40). Upon engagement of surface 161P2F10b, these MAbs mediate internalization of the MAb-protein complex (FIGS. 33, 34, and 35). These MAbs are thus useful as a specific targeting modality for toxin-conjugates, as exemplified by the growth inhibition and induction of apoptosis of Caki-161P2F10b cells by MAb X41.50 with a saporin toxin-conjugated secondary Ab (FIG. 36). Treatment of 161P2F10-expressing cancerous cells with the naked MAb also has a therapeutic effect in vivo as exemplified by the inhibition of UGK3 tumor formation in SCID mice injected with MAb X41.50 (FIG. 23).

161P2F10b encodes phosphodiesterase enzymatic activity that is easily monitored both in recombinant purified protein (FIG. 31) and on cells (FIG. 32). The relevance of the enzymatic activity to the function of 161P2F10b may be monitored by utilization of mutants that disrupt this activity (FIG. 30). Engagement of 161P2F10b with MAbs may alter, disrupt, block, or downregulate 161P2F10 enzymatic activity, which may serve as a potential therapeutic mechanism for targeting 161P2F10b-expressing cancers and diseased tissues. Engagement of cell surface 161P2F10b cells with a subset of the MAbs listed in FIG. 39 does mediate internalization and marked downregulation of cell surface enzymatic activity (FIGS. 37 and 38) thus demonstrating the utility of the MAbs for disrupting the function of 161P2F10b in cells and tissues.

161P2F10b protein and the MAbs that bind it are useful in the diagnosis of 161P2F10b-expressing cancer and diseased tissues. Immunohistochemical analysis of the panel of MAbs, as summarized in FIG. 39, specifically stain (to varying degrees) a variety of kidney cancer samples with little to no staining of adjacent normal tissues. These MAbs are thus useful as diagnostic reagents for a variety of 161P2F10b-expressing cancers by immunohistochemistry and are potentially useful as imaging reagents in patients. In addition, the MAbs were used (specifically X48.54 and X41.29, but others that do not compete for the same epitope are also used) to demonstrate the shedding and/or secretion of the protein from 161P2F10b-expressing cancer cells and tissues (FIGS. 42 and 43). This supports the utility of 161P2F10b as a serum and/or urine diagnostic marker and the MAbs as reagents to quantitatively measure serum and/or urine concentrations of 161P2F10b protein.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables:

TABLE I

Tissues that Express 161P2F10B:

a. Exemplary Normal Tissues:
  Prostate
  Kidney
b. Malignant Tissues
  Kidney
  Uterus
  Pancreas
  Prostate
  Colon
  Lung
  Bone
  Lymphoma
  Breast
  Ovary

TABLE II

Amino Acid Abbreviations

| SINGLE LETTER | THREE LETTER | FULL NAME |
|---|---|---|
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

Amino Acid Substitution Matrix

Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | . |
|---|---|---|---|---|---|---|---|---|---|---|---|---|---|---|---|---|---|---|---|---|
| 4 | 0 | -2 | -1 | -2 | 0 | -2 | -1 | -1 | -1 | -1 | -2 | -1 | -1 | -1 | 1 | 0 | 0 | -3 | -2 | A |
|   | 9 | -3 | -4 | -2 | -3 | -3 | -1 | -3 | -1 | -1 | -3 | -3 | -3 | -3 | -1 | -1 | -1 | -2 | -2 | C |
|   |   | 6 | 2 | -3 | -1 | -1 | -3 | -1 | -4 | -3 | 1 | -1 | 0 | -2 | 0 | -1 | -3 | -4 | -3 | D |
|   |   |   | 5 | -3 | -2 | 0 | -3 | 1 | -3 | -2 | 0 | -1 | 2 | 0 | 0 | -1 | -2 | -3 | -2 | E |
|   |   |   |   | 6 | -3 | -1 | 0 | -3 | 0 | 0 | -3 | -4 | -3 | -3 | -2 | -2 | -1 | 1 | 3 | F |
|   |   |   |   |   | 6 | -2 | -4 | -2 | -4 | -3 | 0 | -2 | -2 | -2 | 0 | -2 | -3 | -2 | -3 | G |
|   |   |   |   |   |   | 8 | -3 | -1 | -3 | -2 | 1 | -2 | 0 | 0 | -1 | -2 | -3 | -2 | 2 | H |
|   |   |   |   |   |   |   | 4 | -3 | 2 | 1 | -3 | -3 | -3 | -3 | -2 | -1 | 3 | -3 | -1 | I |
|   |   |   |   |   |   |   |   | 5 | -2 | -1 | 0 | -1 | 1 | 2 | 0 | -1 | -2 | -3 | -2 | K |
|   |   |   |   |   |   |   |   |   | 4 | 2 | -3 | -3 | -2 | -2 | -2 | -1 | 1 | -2 | -1 | L |
|   |   |   |   |   |   |   |   |   |   | 5 | -2 | -2 | 0 | -1 | -1 | -1 | 1 | -1 | -1 | M |
|   |   |   |   |   |   |   |   |   |   |   | 6 | -2 | 0 | 0 | 1 | 0 | -3 | -4 | -2 | N |
|   |   |   |   |   |   |   |   |   |   |   |   | 7 | -1 | -2 | -1 | -1 | -2 | -4 | -3 | P |
|   |   |   |   |   |   |   |   |   |   |   |   |   | 5 | 1 | 0 | -1 | -2 | -2 | -1 | Q |
|   |   |   |   |   |   |   |   |   |   |   |   |   |   | 5 | -1 | -1 | -3 | -3 | -2 | R |
|   |   |   |   |   |   |   |   |   |   |   |   |   |   |   | 4 | 1 | -2 | -3 | -2 | S |
|   |   |   |   |   |   |   |   |   |   |   |   |   |   |   |   | 5 | 0 | -2 | -2 | T |
|   |   |   |   |   |   |   |   |   |   |   |   |   |   |   |   |   | 4 | -3 | -1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV

HLA Class I/II Motifs/Supermotifs
TABLE IV (A): HLA Class I Supermotifs/Motifs

| | POSITION 2 (Primary Anchor) | POSITION 3 (Primary Anchor) | POSITION C Terminus (Primary Anchor) |
|---|---|---|---|
| SUPERMOTIF | | | |
| A1 | T*ILVMS* | | FWY |
| A2 | LIVM*ATQ* | | IV*MATL* |
| A3 | VSM*ATLI* | | RK |
| A24 | YF*WIVLMT* | | FI*YWLM* |
| B7 | P | | VILF*MWYA* |
| B27 | RHK | | FYL*WMIVA* |
| B44 | ED | | FWYLIMVA |
| B58 | ATS | | FWY*LIVMA* |
| B62 | QL*IVMP* | | FWY*MIVLA* |
| MOTIFS | | | |
| A1 | TSM | | Y |
| A1 | | DEAS | Y |
| A2.1 | LM*VQIAT* | | V*LIMAT* |
| A3 | LMVISATF*CGD* | | KYR*HFA* |
| A11 | VTMLISAGN*CDF* | | KR*YH* |
| A24 | YFW*M* | | FLIW |
| A*3101 | MVT*ALIS* | | R*K* |
| A*3301 | MVALF*IST* | | R*K* |
| A*6801 | AVT*MSLI* | | R*K* |
| B*0702 | P | | LMF*WYAIV* |
| B*3501 | P | | LMFWY*IVA* |
| B51 | P | | LIVF*WYAM* |
| B*5301 | P | | IMFWY*ALV* |
| B*5401 | P | | ATIV*LMFWY* |

Bolded residues are preferred, italicized residues are less preferred: A peptide is considered motif-bearing if it has primary anchors at each primary anchor position for a motif or supermotif as specified in the above table.

TABLE IV (B)

| HLA Class II Supermotif | | |
|---|---|---|
| 1 | 6 | 9 |
| W, F, Y, V, I, L | A, V, I, L, P, C, S, T | A, V, I, L, C, S, T, M, Y |

TABLE IV (C)

HLA Class II Motifs

| MOTIFS | | 1° anchor 1 | 2 | 3 | 4 | 5 | 1° anchor 6 | 7 | 8 | 9 |
|---|---|---|---|---|---|---|---|---|---|---|
| DR4 | preferred | FMY*LIVW* | M | T | | I | VST*CPALIM* | MH | | MH |
| | deleterious | | | | W | | | R | | WDE |
| DR1 | preferred | MF*LIVWY* | | | PAMQ | | VMAT*SPLIC* | M | | AVM |
| | deleterious | | C | CH | FD | CWD | | GDE | D | |
| DR7 | preferred | MF*LIVWY* | M | W | A | | IVMSA*CTPL* | M | | IV |
| | deleterious | | C | | G | | | GRD | N | G |
| DR3 | MOTIFS | 1° anchor 1 | 2 | 3 | 1° anchor 4 | 5 | 1° anchor 6 | | | |
| Motif a preferred | | LIVMFY | | | D | | | | | |
| Motif b preferred | | LIVMFAY | | | DNQEST | | KRH | | | |
| DR Supermotif | | MF*LIVWY* | | | | | VMSTA*CPLI* | | | |

Italicized residues indicate less preferred or "tolerated" residues

TABLE IV (D)

HLA Class I Supermotifs

| SUPERMOTIFS | POSITION: | 1 | 2 | 3 | 4 | 5 | 6 | 7 | 8 | C-terminus |
|---|---|---|---|---|---|---|---|---|---|---|
| A1 | | | 1° Anchor T*ILVMS* | | | | | | | 1° Anchor FWY |
| A2 | | | 1° Anchor LIVM*ATQ* | | | | | | | 1° Anchor LIVMAT |
| A3 | Preferred | | 1° Anchor VSMA*TLI* | YFW (4/5) | | | YFW (3/5) | YFW (4/5) | P (4/5) | 1° Anchor RK |
| | deleterious | DE (3/5); P (5/5) | | DE (4/5) | | | | | | |
| A24 | | | 1° Anchor YF*WIVLMT* | | | | | | | 1° Anchor FIY*WLM* |
| B7 | Preferred | FWY (5/5) LIVM (3/5) | 1° Anchor P | FWY (4/5) | | | | | FWY (3/5) | 1° Anchor VILF*MWYA* |
| | deleterious | DE (3/5); P (5/5); G (4/5); A (3/5); QN (3/5) | | | | | DE (3/5) | G (4/5) | QN (4/5) | DE (4/5) |

TABLE IV (D)-continued

HLA Class I Supermotifs

| SUPERMOTIFS | POSITION: 1 | 2 | 3 | 4 | 5 | 6 | 7 | 8 | C-terminus |
|---|---|---|---|---|---|---|---|---|---|
| B27 | | 1° Anchor RHK | | | | | | | 1° Anchor FYL*WMIVA* |
| B44 | | 1° Anchor ED | | | | | | | 1° Anchor FWYLIMVA |
| B58 | | 1° Anchor ATS | | | | | | | 1° Anchor FWY*LIVMA* |
| B62 | | 1° Anchor QL*IVMP* | | | | | | | 1° Anchor FWY*MIVLA* |

Italicized residues indicate less preferred or "tolerated" residues

TABLE IV (E)

HLA Class I Motifs

| | POSITION | 1 | 2 | 3 | 4 | 5 | 6 | 7 | 8 | 9 or C-terminus | C-terminus |
|---|---|---|---|---|---|---|---|---|---|---|---|
| A1 9-mer | preferred | GFYW | 1° Anchor STM | DEA | YFW | | P | DEQN | YFW | 1° Anchor Y | |
| | deleterious | DE | | RHKLIVMP | A | G | A | | | | |
| A1 9-mer | preferred | GRHK | ASTCLIVM | 1° Anchor DEAS | GSTC | | ASTC | LIVM | DE | 1° Anchor Y | |
| | deleterious | A | RHKDEPYFW | | DE | PQN | RHK | PG | GP | | |
| A1 10-mer | preferred | YFW | 1° Anchor STM | DEAQN | A | YFWQN | | PASTC | GDE | P | 1° Anchor Y |
| | deleterious | GP | | RHKGLIVM | DE | | RHK | QNA | RHKYFW | RHK | A | |
| A1 10-mer | preferred | YFW | STCLIVM | 1° Anchor DEAS | A | YFW | QNA | PG | G | YFW | 1° Anchor Y |
| | deleterious | RHK | RHKDEPYFW | | | | P | G | | PRHK | QN | |
| A2.1 9-mer | preferred | YFW | 1° Anchor LM*IVQAT* | YFW | STC | YFW | | A | P | 1° Anchor *VLIMAT* | |
| | deleterious | DEP | | DERKH | | | RKH | | DERKH | | |

| | POSITION: | 1 | 2 | 3 | 4 | 5 | 6 | 7 | 8 | 9 | C-Terminus |
|---|---|---|---|---|---|---|---|---|---|---|---|
| A2.1 10-mer | preferred | AYFW | 1° Anchor LM*IVQAT* | LVIM | G | | G | | FYWL VIM | | 1° Anchor *VLIMAT* |
| | deleterious | DEP | | DE | RKHA | P | | RKH | DERKH | RKH | |
| A3 | preferred | RHK | 1° Anchor LMVISATFCGD | YFW | PRHKYFW | A | YFW | | P | 1° Anchor KYR*HFA* | |
| | deleterious | DEP | | DE | | | | | | | |
| A11 | preferred | A | 1° Anchor VTLMISAGN*CDF* | YFW | YFW | A | YFW | YFW | P | 1° Anchor *KRYH* | |
| | deleterious | DEP | | | | | | | A | G | |
| A24 9-mer | preferred | YFWRHK | 1° Anchor YFW*M* | | STC | | | YFW | YFW | 1° Anchor FLIW | |
| | deleterious | DEG | | DE | G | QNP | DERHK | G | AQN | | |
| A24 10-mer | Preferred | | 1° Anchor YFW*M* | | P | YFWP | | P | | | 1° Anchor FLIW |
| | Deleterious | | | GDE | QN | RHK | DE | A | QN | DEA | |
| A3101 | Preferred | RHK | 1° Anchor MVTA*LIS* | YFW | P | | YFW | YFW | AP | 1° Anchor RK | |
| | Deleterious | DEP | | DE | | ADE | DE | DE | DE | | |
| A3301 | Preferred | | 1° Anchor MVALF*IST* | YFW | | | | | AYFW | 1° Anchor RK | |
| | Deleterious | GP | | DE | | | | | | | |
| A6801 | Preferred | YFWSTC | 1° Anchor AVT*MSLI* | | | YFWLIVM | | YFW | P | 1° Anchor RK | |
| | deleterious | GP | | DEG | | RHK | | | A | | |
| B0702 | Preferred | RHKFWY | 1° Anchor P | RHK | | RHK | RHK | RHK | PA | 1° Anchor LMF*WYAIV* | |
| | deleterious | DEQNP | | DEP | DE | DE | GDE | QN | DE | | |

TABLE IV (E)-continued

| POSITION | 1 | 2 | 3 | 4 | 5 | 6 | 7 | 8 | 9 or C-terminus | C-terminus |
|---|---|---|---|---|---|---|---|---|---|---|
| A1 9-mer preferred | GFYW | STM | DEA | YFW | | P | DEQN | YFW | 1° Anchor Y | |
| deleterious | DE | | RHKLIVMP | A | G | A | | | | |
| A1 9-mer preferred | GRHK | ASTCLIVM | 1° Anchor DEAS | GSTC | | | ASTC | LIVM | DE | 1° Anchor Y |
| deleterious | A | RHKDEPYFW | | DE | PQN | RHK | PG | GP | | |
| B3501 Preferred | FWYLIVM | 1° Anchor P | FWY | | | | FWY | | 1° Anchor LMFWY*IV A* | |
| deleterious | AGP | | | | | G | G | | | |
| B51 Preferred | LIVMFWY | 1° Anchor P | FWY | STC | FWY | | G | FWY | 1° Anchor LIVF*WYA M* | |
| deleterious | AGPDERHKSTC | | | | | DE | G | DEQN | GDE | |
| B5301 preferred | LIVMFWY | 1° Anchor P | FWY | STC | FWY | | LIVMFWY | FWY | 1° Anchor IMFWY*AL V* | |
| deleterious | AGPQN | | | | | G | RHKQN | DE | | |
| B5401 preferred | FWY | 1° Anchor P | FWYLIVM | | LIVM | | ALIVM | FWYAP | 1° Anchor ATIV*LMF WY* | |
| deleterious | GPQNDE | | GDESTC | | RHKDE | DE | QNDGE | DE | | |

TABLE IV (F)

Summary of HLA-supertypes
Overall phenotypic frequencies of HLA-supertypes in different ethnic populations

| | Specificity | | Phenotypic frequency | | | | | |
|---|---|---|---|---|---|---|---|---|
| Supertype | Position 2 | C-Terminus | Caucasian | N.A. Black | Japanese | Chinese | Hispanic | Average |
| B7 | P | AILMVFWY | 43.2 | 55.1 | 57.1 | 43.0 | 49.3 | 49.5 |
| A3 | AILMVST | RK | 37.5 | 42.1 | 45.8 | 52.7 | 43.1 | 44.2 |
| A2 | AILMVT | AILMVT | 45.8 | 39.0 | 42.4 | 45.9 | 43.0 | 42.2 |
| A24 | YF (WIVLMT) | FI (YWLM) | 23.9 | 38.9 | 58.6 | 40.1 | 38.3 | 40.0 |
| B44 | E (D) | FWYLIMVA | 43.0 | 21.2 | 42.9 | 39.1 | 39.0 | 37.0 |
| A1 | TI (LVMS) | FWY | 47.1 | 16.1 | 21.8 | 14.7 | 26.3 | 25.2 |
| B27 | RHK | FYL (WMI) | 28.4 | 6.1 | 13.3 | 13.9 | 35.3 | 23.4 |
| B62 | QL (IVMP) | FWY (MIV) | 12.6 | 4.8 | 36.5 | 25.4 | 11.1 | 18.1 |
| B58 | ATS | FWY (LIV) | 10.0 | 25.1 | 1.6 | 9.0 | 5.9 | 10.3 |

TABLE IV (G)

Calculated population coverage afforded by different HLA-supertype combinations

| | Phenotypic frequency | | | | | |
|---|---|---|---|---|---|---|
| HLA-supertypes | Caucasian | N.A Blacks | Japanese | Chinese | Hispanic | Average |
| A2, A3 and B7 | 83.0 | 86.1 | 87.5 | 88.4 | 86.3 | 86.2 |
| A2, A3, B7, A24, B44 and A1 | 99.5 | 98.1 | 100.0 | 99.5 | 99.4 | 99.3 |
| A2, A3, B7, A24, B44, A1, B27, B62, and B 58 | 99.9 | 99.6 | 100.0 | 99.8 | 99.9 | 99.8 |

Motifs indicate the residues defining supertype specificites. The motifs incorporate residues determined on the basis of published data to be recognized by multiple alleles within the supertype. Residues within brackets are additional residues also predicted to be tolerated by multiple alleles within the supertype.

TABLE V

Frequently Occurring Motifs

| Name | avrg. % identity | Description | Potential Function |
| --- | --- | --- | --- |
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| Ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |
| PDZ | 23% | PDZ domain | may function in targeting signaling molecules to sub-membranous sites |
| LRR | 28% | Leucine Rich Repeat | short sequence motifs involved in protein—protein interactions |
| Pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30–40 amino-acid long found in the extracellular domain of membrane-bound proteins or in secreted proteins |
| Rvt | 49% | Reverse transcriptase (RNA-dependent DNA polymerase) | |
| Ank | 25% | Ank repeat | Cytoplasmic protein, associates integral membrane proteins to the cytoskeleton |
| Oxidored_q1 | 32% | NADH-Ubiquinone/plastoquinone (complex I), various chains | membrane associated. Involved in proton translocation across the membrane |
| Efhand | 24% | EF hand | calcium-binding domain, consists of a12 residue loop flanked on both sides by a 12 residue alpha-helical domain |
| Rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| Fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

TABLE VI

Motifs and Post-translational Modifications of 161P2F10B

N-glycosylation site:
Number of matches: 10

| | | | |
| --- | --- | --- | --- |
| 1 | 236–239 | NFSL | (SEQ ID NO: 41) |
| 2 | 279–282 | NGSF | (SEQ ID NO: 42) |
| 3 | 290–293 | NGSV | (SEQ ID NO: 43) |
| 4 | 426–429 | NLSC | (SEQ ID NO: 44) |
| 5 | 533–536 | NGTH | (SEQ ID NO: 45) |
| 6 | 582–585 | NSTQ | (SEQ ID NO: 46) |
| 7 | 594–597 | NLTQ | (SEQ ID NO: 47) |
| 8 | 687–690 | NITH | (SEQ ID NO: 48) |
| 9 | 699–702 | NRTS | (SEQ ID NO: 49) |
| 10 | 789–792 | NKSH | (SEQ ID NO: 50) | cAMP- and cGMP-dependent protein kinase phosphorylation site

| | | | |
| --- | --- | --- | --- |
| | 14–17 | KKNT | (SEQ ID NO: 51) |

TABLE VI-continued

Motifs and Post-translational Modifications of 161P2F10B

Protein kinase C phosphorylation site
Number of matches: 13

| | | |
|---|---|---|
| 1 | 17–19 | TLK |
| 2 | 53–55 | SCR |
| 3 | 428–430 | SCR |
| 4 | 62–64 | SFR |
| 5 | 92–94 | STR |
| 6 | 240–242 | SSK |
| 7 | 335–337 | SAR |
| 8 | 53–55 | SCR |
| 9 | 428–430 | SCR |
| 10 | 502–504 | SFK |
| 11 | 603–605 | TVK |
| 12 | 676–678 | SQK |
| 13 | 698–700 | SNR |

Casein kinase II phosphorylation site
Number of matches: 15

| | | | |
|---|---|---|---|
| 1 | 88–91 | TCVE | (SEQ ID NO: 52) |
| 2 | 106–109 | TRLE | (SEQ ID NO: 53) |
| 3 | 114–117 | SCSD | (SEQ ID NO: 54) |
| 4 | 138–141 | SWLE | (SEQ ID NO: 55) |
| 5 | 240–243 | SSKE | (SEQ ID NO: 56) |
| 6 | 502–505 | SFKE | (SEQ ID NO: 57) |
| 7 | 507–510 | TEVE | (SEQ ID NO: 58) |
| 8 | 551–554 | SHAE | (SEQ ID NO: 59) |
| 9 | 584–587 | TQLE | (SEQ ID NO: 60) |
| 10 | 596–599 | TQEE | (SEQ ID NO: 61) |
| 11 | 660–663 | TVPD | (SEQ ID NO: 62) |
| 12 | 704–707 | SQYD | (SEQ ID NO: 63) |
| 13 | 813–816 | TNVE | (SEQ ID NO: 64) |
| 14 | 817–820 | SCPE | (SEQ ID NO: 65) |
| 15 | 846–849 | TGLD | (SEQ ID NO: 66) |

TABLE VI-continued

Motifs and Post-translational Modifications of 161P2F10B

Tyrosine kinase phosphorylation site

| | | |
|---|---|---|
| 700–706 | RTSDSQY | (SEQ ID NO: 67) |

N-myristoylation site
Number of matches: 11

| | | | |
|---|---|---|---|
| 1 | 38–43 | GLGLGL | (SEQ ID NO: 68) |
| 2 | 40–45 | GLGLGL | (SEQ ID NO: 69) |
| 3 | 38–43 | GLGLGL | (SEQ ID NO: 70) |
| 4 | 40–45 | GLGLGL | (SEQ ID NO: 71) |
| 5 | 65–70 | GLENCR | (SEQ ID NO: 72) |
| 6 | 222–227 | GIIDNN | (SEQ ID NO: 73) |
| 7 | 263–268 | GLKAAT | (SEQ ID NO: 74) |
| 8 | 273–278 | GSEVAI | (SEQ ID NO: 75) |
| 9 | 280–285 | GSFPSI | (SEQ ID NO. 76) |
| 10 | 331–336 | GGPVSA | (SEQ ID NO: 77) |
| 11 | 374–379 | GMDQTY | (SEQ ID NO: 78) |

Cell attachment sequence

| | |
|---|---|
| 78–80 | RGD |

Somatomedin B domain signature
Number of matches: 2

| | | | |
|---|---|---|---|
| 1 | 69–89 | CRCDVACKDRGDCCWDFEDTC | (SEQ ID NO: 79) |
| 2 | 113–133 | CSCSDDCLQKKDCCADYKSVC | (SEQ ID NO: 80) |

TABLE VII

Search Peptides

161P2F10B variant 1 (SEQ ID NO: 81)

```
  1 MESTLTLATE QPVKKNTLKK YKIACIVLLA LLVIMSLGLG LGLGLRKLEK QGSCRKKCFD
 61 ASFRGLENCR CDVACKDRGD CCWDFEDTCV ESTRIWMCNK FRCGETRLEA SLCSCSDDCL
121 QKKDCCADYK SVCQGETSWL EENCDTAQQS QCPEGFDLPP VILFSMDGFR AEYLYTWDTL
181 MPNINKLKTC GIHSKYMRAM YPTKTFPNHY TIVTGLYPES HGIIDNNMYD VNLNKNFSLS
241 SKEQNNPAWW HGQPMWLTAM YQGLKAATYF WPGSEVAING SFPSIYMPYN GSVPFEERIS
301 TLLKWLDLPK AERPRFYTMY FEEPDSSGHA GGPVSARVIK ALQVVDHAFG MLMEGLKQRN
361 LHNCVNIILL ADHGMDQTYC NKMEYMTDYF PRINFFYMYE GPAPRIRAHN IPHDFFSFNS
421 EEIVRNLSCR KPDQHFKPYL TPDLPKRLHY AKNVRIDKVH LFVDQQWLAV RSKSNTNCGG
481 GNHGYNNEFR SMEAIFLAHG PSFKEKTEVE PFENIEVYNL MCDLLRIQPA PNNGTHGSLN
541 HLLKVPFYEP SHAEEVSKFS VCGFANPLPT ESLDCFCPHL QNSTQLEQVN QMLNLTQEEI
601 TATVKVNLPF GRPRVLQKNV DHCLLYHREY VSGFGKAMRM PMWSSYTVPQ LGDTSPLPPT
661 VPDCLRADVR VPPSESQKCS FYLADKNITH GFLYPPASNR TSDSQYDALI TSNLVPMYEE
721 FRKMWDYFHS VLLIKHATER NGVNVVSGPI FDYNYDGHFD APDEITKHLA NTDVPIPTHY
```

TABLE VII-continued

Search Peptides

781 FVVLTSCKNK SHTPENCPGW LDVLPFIIPH RPTNVESCPE GKPEALWVEE RFTAHIARVR

841 DVELLTGLDF YQDKVQPVSE ILQLKTYLPT FETTI

Variant 2

9-mers
SCSDDCLQKKDCCADYK (SEQ ID NO: 82)

10-mers
CSCSDDCLQKKDCCADYKS (SEQ ID NO: 83)

15-mers
LEASLCSCSDDCLQKKDCCADYKSVCQGE (SEQ ID NO: 84)

Variant 3

9-mers
PTNVESCPGGKPEALWV (SEQ ID NO: 85)

10-mers
RPTNVESCPGGKPEALWVE (SEQ ID NO: 86)

15-mers
FIIPHRPTNVESCPGGKPEALWVEERFTA (SEQ ID NO: 87)

Variant 4

9-mers
TYLPTFETPI (SEQ ID NO: 88)

10-mers
KTYLPTFETPI (SEQ ID NO: 89)

15-mers
EILQLKTYLPTFETPI (SEQ ID NO: 90)

TABLE VIII

| Start | Subsequence | Score |
|---|---|---|
| V1-HLA-A1-9mers-161P2F10B | | |
| Each peptide is a portion of SEQ ID NO: 3; each start position is specified, the length of peptide is 9 amino acids, and the end position for each peptide is the start position plus eight. | | |
| 105 | SMDGFRAEY | 25.000 |
| 754 | NVESCPEGK | 18.000 |
| 55 | CSDDCLQKK | 15.000 |
| 446 | KTEVEPFEN | 11.250 |
| 245 | WLDLPKAER | 10.000 |
| 798 | VSEILQLKT | 6.750 |
| 317 | QTYCNKMEY | 6.250 |
| 371 | KPDQHFKPY | 6.250 |
| 10 | RCDVACKDR | 5.000 |
| 314 | GMDQTYCNK | 5.000 |
| 322 | KMEYMTDYF | 4.500 |
| 454 | NIEVYNLMC | 4.500 |
| 29 | CVESTRIWM | 4.500 |
| 650 | ITSNLVPMY | 2.500 |
| 118 | DTLMPNINK | 2.500 |
| 685 | VVSGPIFDY | 2.500 |
| 559 | NVDHCLLYH | 2.500 |
| 711 | NTDVPIPTH | 2.500 |
| 740 | WLDVLPFII | 2.500 |
| 402 | FVDQQWLAV | 2.500 |
| 431 | SMEAIFLAH | 2.250 |
| 610 | RVPPSESQK | 2.000 |
| 379 | YLTPDLPKR | 2.000 |
| 613 | PSESQKCSF | 1.350 |

TABLE VIII-continued

| Start | Subsequence | Score |
|---|---|---|
| 213 | GSEVAINGS | 1.350 |
| 359 | NSEEIVRNL | 1.350 |
| 128 | KTCGIHSKY | 1.250 |
| 326 | MTDYFPRIN | 1.250 |
| 426 | NNEFRSMEA | 1.125 |
| 632 | FLYPPASNR | 1.000 |
| 163 | IIDNNMYDV | 1.000 |
| 512 | SLDCFCPHL | 1.000 |
| 66 | CADYKSVCQ | 1.000 |
| 653 | NLVPMYEEF | 1.000 |
| 606 | RADVRVPPS | 1.000 |
| 426 | NNEFRSMEA | 1.125 |
| 54 | SCSDDCLQK | 1.000 |
| 767 | WVEERFTAH | 0.900 |
| 448 | EVEPFENIE | 0.900 |
| 525 | QLEQVNQML | 0.900 |
| 79 | WLEENCDTA | 0.900 |
| 492 | HAEEVSKFS | 0.900 |
| 537 | QEEITATVK | 0.900 |
| 5 | GLENCRCDV | 0.900 |
| 47 | RLEASLCSC | 0.900 |
| 641 | TSDSQYDAL | 0.750 |
| 626 | KNITHGFLY | 0.625 |
| 558 | KNVDHCLLY | 0.625 |
| 783 | ELLTGLDFY | 0.500 |
| 62 | KKDCCADYK | 0.500 |
| 310 | LADHGMDQT | 0.500 |
| 167 | NMYDVNLNK | 0.500 |
| 562 | HCLLYHREY | 0.500 |
| 197 | LTAMYQGLK | 0.500 |
| 699 | FDAPDEITK | 0.500 |

TABLE VIII-continued

| Start | Subsequence | Score |
|---|---|---|
| 787 | GLDFYQDKV | 0.500 |
| 83 | NCDTAQQSQ | 0.500 |
| 593 | DTSPLPPTV | 0.500 |
| 284 | VVDHAFGML | 0.500 |
| 144 | KTFPNHYTI | 0.500 |
| 417 | NCGGGNHGY | 0.500 |
| 350 | NIPHDFFSF | 0.500 |
| 97 | DLPPVILFS | 0.500 |
| 742 | DVLPFIIPH | 0.500 |
| 250 | KAERPRFYT | 0.450 |
| 292 | LMEGLKQRN | 0.450 |
| 677 | ATERNGVNV | 0.450 |
| 261 | FEEPDSSGH | 0.450 |
| 618 | KCSFYLADK | 0.400 |
| 571 | VSGFGKAMR | 0.300 |
| 536 | TQEEITATV | 0.270 |
| 193 | QPMWLTAMY | 0.250 |
| 687 | SGPIFDYNY | 0.250 |
| 772 | FTAHIARVR | 0.250 |
| 655 | VPMYEEFRK | 0.250 |
| 476 | HGSLNHLLK | 0.250 |
| 712 | TDVPIPTHY | 0.250 |
| 550 | FGRPRVLQK | 0.250 |
| 601 | VPDCLRADV | 0.250 |
| 578 | MRMPMWSSY | 0.250 |
| 546 | VNLPFGRPR | 0.250 |
| 461 | MCDLLRIQP | 0.250 |
| 395 | RIDKVHLFV | 0.250 |
| 586 | YTVPQLGDT | 0.250 |
| 96 | FDLPPVILF | 0.250 |
| 509 | PTESLDCFC | 0.225 |
| 758 | CPEGKPEAL | 0.225 |
| 733 | TPENCPGWL | 0.225 |
| 493 | AEEVSKFSV | 0.225 |
| 43 | CGETRLEAS | 0.225 |
| 722 | VVLTSCKNK | 0.200 |
| 746 | FIIPHRPTN | 0.200 |
| 436 | FLAHGPSFK | 0.200 |
| 743 | VLPFIIPHR | 0.200 |
| 133 | HSKYMRAMY | 0.150 |
| 201 | YQGLKAATY | 0.150 |
| 231 | GSVPFEERI | 0.150 |
| 686 | VSGPIFDYN | 0.150 |
| 382 | PDLPKRLHY | 0.125 |
| 191 | HGQPMWLTA | 0.125 |
| 701 | APDEITKHL | 0.125 |

V2-HLA-A1-9mers-161P2F10B
Each peptide is a portion of SEQ ID NO: 5;
each start position is specified, the length
of peptide is 9 amino acids, and the end position
for each peptide is the start position plus eight.

| Start | Subsequence | Score |
|---|---|---|
| 2 | CSDDCLQRK | 15.000 |
| 9 | RKDGCADYK | 0.500 |
| 1 | SCSDDCLQR | 0.500 |
| 5 | DCLQRKDCC | 0.010 |
| 8 | QRKDCCADY | 0.005 |
| 3 | SDDCLQRKD | 0.003 |
| 6 | CLQRKDCCA | 0.001 |
| 4 | DDCLQRKDC | 0.001 |
| 7 | LQRKDCCAD | 0.000 |

V3-HLA-A1-9mers-161P2F10B
Each peptide is a portion of SEQ ID NO: 7;
each start position is specified, the length
of peptide is 9 amino acids, and the end position
for each peptide is the start position plus eight.

| Start | Subsequence | Score |
|---|---|---|
| 3 | NVESCPGGK | 18 |
| 6 | SCPGGKPEA | 0.02 |
| 5 | ESCPGGKPE | 0.015 |
| 9 | GGKPEALWV | 0.013 |
| 2 | TNVESCPGG | 0.005 |
| 7 | CPGGKPEAL | 0.003 |
| 1 | PTNVESCPG | 0.003 |
| 4 | VESCPGGKP | 0 |
| 8 | PGGKPEALW | 0 |

V4-HLA-A1-9mers-161P2F10B
Each peptide is a portion of SEQ ID NO: 9;
each start position is specified, the length
of peptide is 9 amino acids, and the end position
for each peptide is the start position plus eight.

| Start | Subsequence | Score |
|---|---|---|
| 2 | YLPTFETPI | 0.01 |
| 1 | TYLPTFETP | 0.001 |

TABLE IX

| Start | Subsequence | Score |
|---|---|---|

V1-HLA-A1-10mers-161P2F10B
Each peptide is a portion of SEQ ID NO: 3;
each start position is specified, the length
of peptide is 10 amino acids, and the end position
for each peptide is the start position plus nine.

| Start | Subsequence | Score |
|---|---|---|
| 798 | VSEILQLKTY | 67.500 |
| 711 | NTDVPIPTHY | 62.500 |
| 326 | MTDYFPRINF | 62.500 |
| 781 | DVELLTGLDF | 45.000 |
| 448 | EVEPFENIEV | 45.000 |
| 220 | GSFPSIYMPY | 37.500 |
| 381 | TPDLPKRLHY | 31.250 |
| 310 | LADHGMDQTY | 25.000 |
| 686 | VSGPIFDYNY | 15.000 |
| 213 | GSEVAINGSF | 13.500 |
| 402 | FVDQQWLAVR | 10.000 |
| 559 | NVDHCLLYHR | 10.000 |
| 613 | PSESQKCSFY | 6.750 |
| 525 | QLEQVNQMLN | 4.500 |
| 567 | HREYVSGFGK | 4.500 |
| 492 | HAEEVSKFSV | 4.500 |
| 536 | TQEEITATVK | 2.700 |
| 684 | NVVSGPIFDY | 2.500 |
| 698 | HFDAPDEITK | 2.500 |
| 284 | VVDHAFGMLM | 2.500 |
| 658 | YEEFRKMWDY | 2.250 |
| 446 | KTEVEPFENI | 2.250 |
| 762 | KPEALWVEER | 2.250 |
| 742 | DVLPFIIPHR | 2.000 |
| 119 | TLMPNINKLK | 2.000 |
| 767 | WVEERFTAHI | 1.800 |
| 53 | CSCSDDCLQK | 1.500 |
| 641 | TSDSQYDALI | 1.500 |
| 104 | FSMDGFRAEY | 1.500 |
| 359 | NSEEIVRNLS | 1.350 |
| 349 | HNIPHDFFSF | 1.250 |
| 328 | DYFPRINFFY | 1.250 |
| 601 | VPDCLRADVR | 1.250 |
| 95 | GFDLPPVILF | 1.250 |
| 157 | YPESHGIIDN | 1.125 |
| 654 | LVPMYEEFRK | 1.000 |
| 653 | NLVPMYEEFR | 1.000 |
| 649 | LITSNLVPMY | 1.000 |
| 47 | RLEASLCSCS | 0.900 |
| 29 | CVESTRIWMC | 0.900 |
| 5 | GLENCRCDVA | 0.900 |
| 110 | RAEYLYTWDT | 0.900 |
| 79 | WLEENCDTAQ | 0.900 |
| 431 | SMEAIFLAHG | 0.900 |
| 356 | FSFNSEEIVR | 0.750 |
| 785 | LTGLDFYQDK | 0.500 |
| 623 | LADKNITHGF | 0.500 |
| 83 | NCDTAQQSQC | 0.500 |
| 66 | CADYKSVCQG | 0.500 |
| 541 | TATVKVNLPF | 0.500 |
| 10 | RCDVACKDRG | 0.500 |
| 794 | KVQPVSEILQ | 0.500 |
| 787 | GLDFYQDKVQ | 0.500 |
| 163 | IIDNNMYDVN | 0.500 |
| 512 | SLDCFCPHLQ | 0.500 |

TABLE IX-continued

| Start | Subsequence | Score |
|---|---|---|
| 461 | MCDLLRIQPA | 0.500 |
| 217 | AINGSFPSIY | 0.500 |
| 97 | DLPPVILFSM | 0.500 |
| 292 | LMEGLKQRNL | 0.450 |
| 487 | FYEPSHAEEV | 0.450 |
| 92 | CPEGFDLPPV | 0.450 |
| 43 | CGETRLEASL | 0.450 |
| 235 | FEERISTLLK | 0.450 |
| 454 | NIEVYNLMCD | 0.450 |
| 261 | FEEPDSSGHA | 0.450 |
| 758 | CPEGKPEALW | 0.450 |
| 338 | MYEGPAPRIR | 0.450 |
| 316 | DQTYCNKMEY | 0.375 |
| 756 | ESCPEGKPEA | 0.300 |
| 263 | EPDSSGHAGG | 0.250 |
| 740 | WLDVLPFIIP | 0.250 |
| 586 | YTVPQLGDTS | 0.250 |
| 314 | GMDQTYCNKM | 0.250 |
| 479 | LNHLLKVPFY | 0.250 |
| 139 | AMYPTKTFPN | 0.250 |
| 168 | MYDVNLNKNF | 0.250 |
| 25 | FEDTCVESTR | 0.250 |
| 377 | KPYLTPDLPK | 0.250 |
| 105 | SMDGFRAEYL | 0.250 |
| 591 | LGDTSPLPPT | 0.250 |
| 166 | NNMYDVNLNK | 0.250 |
| 144 | KTFPNHYTIV | 0.250 |
| 371 | KPDQHFKPYL | 0.250 |
| 690 | IFDYNYDGHF | 0.250 |
| 426 | NNEFRSMEAI | 0.225 |
| 74 | QGETSWLEEN | 0.225 |
| 360 | SEEIVRNLSC | 0.225 |
| 677 | ATERNGVNVV | 0.225 |
| 570 | YVSGFGKAMR | 0.200 |
| 129 | TCGIHSKYMR | 0.200 |
| 721 | FVVLTSCKNK | 0.200 |
| 682 | GVNVVSGPIF | 0.200 |
| 196 | WLTAMYQGLK | 0.200 |
| 434 | AIFLAHGPSF | 0.200 |
| 54 | SCSDDCLQKK | 0.200 |
| 478 | SLNHLLKVPF | 0.200 |
| 437 | LAHGPSFKEK | 0.200 |
| 250 | KAERPRFYTM | 0.180 |
| 231 | GSVPFEERIS | 0.150 |
| 192 | GQPMWLTAMY | 0.150 |

V2-HLA-A1-10mers-161P2F10B
Each peptide is a portion of SEQ ID NO: 5;
each start position is specified, the length
of peptide is 10 amino acids, and the end position
for each peptide is the start position plus nine.

| Start | Subsequence | Score |
|---|---|---|
| 1 | CSCSDDCLQR | 0.750 |
| 2 | SCSDDCLQRK | 0.200 |
| 3 | CSDDCLQRKD | 0.075 |
| 10 | RKDCCADYKS | 0.050 |
| 4 | SDDCLQRKDC | 0.025 |
| 6 | DCLQRKDCCA | 0.010 |
| 8 | LQRKDCCADY | 0.002 |
| 9 | QRKDCCADYK | 0.001 |
| 5 | DDCLQRKDCC | 0.001 |
| 7 | CLQRKDCCAD | 0.000 |

V3-HLA-A1-10mers-161P2F10B
Each peptide is a portion of SEQ ID NO: 7;
each start position is specified, the length
of peptide is 10 amino acids, and the end position
for each peptide is the start position plus nine.

| Start | Subsequence | Score |
|---|---|---|
| 6 | ESCPGGKPEA | 0.3 |
| 4 | NVESCPGGKP | 0.09 |
| 3 | TNVESCPGGK | 0.05 |
| 7 | SCPGGKPEAL | 0.01 |
| 2 | PTNVESCPGG | 0.005 |
| 8 | CPGGKPEALW | 0.005 |
| 1 | RPTNVESCPG | 0.003 |
| 10 | GGKPEALWVE | 0 |
| 9 | PGGKPEALWV | 0 |
| 5 | VESCPGGKPE | 0 |

V4-HLA-A1-10mers-161P2F10B
Each peptide is a portion of SEQ ID NO: 9;
each start position is specified, the length
of peptide is 10 amino acids, and the end position
for each peptide is the start position plus nine.

| Start | Subsequence | Score |
|---|---|---|
| 2 | TYLPTFETPI | 0.005 |
| 1 | KTYLPTFETP | 0.003 |

TABLE X

| Start | Subsequence | Score |
|---|---|---|

V1-HLA-A0201-9mers-161P2F10B
Each peptide is a portion of SEQ ID NO: 3;
each start position is specified, the length
of peptide is 9 amino acids, and the end position
for each peptide is the start position plus eight.

| Start | Subsequence | Score |
|---|---|---|
| 663 | KMWDYFHSV | 11367.476 |
| 563 | CLLYHREYV | 693.538 |
| 325 | YMTDYFPRI | 270.002 |
| 807 | YLPTFETTI | 182.365 |
| 119 | TLMPNINKL | 181.794 |
| 196 | WLTAMYQGL | 147.401 |
| 459 | NLMCDLLRI | 88.783 |
| 113 | YLYTWDTLM | 73.129 |
| 547 | NLPFGRPRV | 69.552 |
| 765 | ALWVEERFT | 68.037 |
| 740 | WLDVLPFII | 45.649 |
| 238 | RISTLLKWL | 37.157 |
| 155 | GLYPESHGI | 33.385 |
| 512 | SLDCFCPHL | 32.471 |
| 579 | RMPMWSSYT | 29.601 |
| 199 | AMYQGLKAA | 26.408 |
| 395 | RIDKVHLFV | 21.039 |
| 402 | FVDQQWLAV | 19.036 |
| 524 | TQLEQVNQM | 17.575 |
| 747 | IIPHRPTNV | 16.258 |
| 163 | IIDNNMYDV | 14.957 |
| 400 | HLFVDQQWL | 14.781 |
| 787 | GLDFYQDKV | 13.632 |
| 90 | SQCPEGFDL | 12.562 |
| 693 | YNYDGHFDA | 11.352 |
| 283 | QVVDHAFGM | 10.337 |
| 300 | NLHNCVNII | 9.838 |
| 555 | VLQKNVDHC | 9.518 |
| 532 | MLNLTQEEI | 8.691 |
| 570 | YVSGFGKAM | 7.599 |
| 802 | LQLKTYLPT | 7.129 |
| 500 | SVCGFANPL | 7.103 |
| 805 | KTYLPTFET | 6.723 |
| 430 | RSMEAIFLA | 6.563 |
| 277 | RVIKALQVV | 5.739 |
| 171 | VNLNKNFSL | 5.087 |
| 59 | CLQKKDCCA | 4.968 |
| 534 | NLTQEEITA | 4.968 |
| 383 | DLPKRLHYA | 4.713 |
| 800 | EILQLKTYL | 4.483 |
| 5 | GLENCRCDV | 4.451 |
| 452 | FENIEVYNL | 4.395 |
| 307 | IILLADHGM | 4.297 |
| 714 | VPIPTHYFV | 4.245 |
| 477 | GSLNHLLKV | 3.864 |
| 111 | AEYLYTWDT | 3.478 |
| 488 | YEPSHAEEV | 3.048 |
| 79 | WLEENCDTA | 2.938 |
| 580 | MPMWSSYTV | 2.856 |
| 30 | VESTRIWMC | 2.833 |
| 217 | AINGSFPSI | 2.726 |
| 649 | LITSNLVPM | 2.671 |
| 51 | SLCSCSDDC | 2.434 |
| 670 | SVLLIKHAT | 2.413 |
| 449 | VEPFENIEV | 2.299 |

TABLE X-continued

| Start | Subsequence | Score |
|---|---|---|
| 380 | LTPDLPKRL | 2.068 |
| 21 | CCWDFEDTC | 2.055 |
| 144 | KTFPNHYTI | 1.876 |
| 297 | KQRNLHNCV | 1.876 |
| 240 | STLLKWLDL | 1.866 |
| 536 | TQEEITATV | 1.850 |
| 535 | LTQEEITAT | 1.659 |
| 356 | FSFNSEEIV | 1.552 |
| 528 | QVNQMLNLT | 1.500 |
| 583 | WSSYTVPQL | 1.475 |
| 622 | YLADKNITH | 1.405 |
| 525 | QLEQVNQML | 1.367 |
| 794 | KVQPVSEIL | 1.314 |
| 72 | VCQGETSWL | 1.304 |
| 467 | IQPAPNNGT | 1.284 |
| 233 | VPFEERIST | 1.255 |
| 192 | GQPMWLTAM | 1.159 |
| 456 | EVYNLMCDL | 1.032 |
| 131 | GIHSKYMRA | 1.025 |
| 280 | KALQVVDHA | 1.007 |
| 291 | MLMEGLKQR | 0.884 |
| 427 | NEFRSMEAI | 0.846 |
| 784 | LLTGLDFYQ | 0.808 |
| 447 | TEVEPFENI | 0.774 |
| 715 | PIPTHYFVV | 0.750 |
| 250 | KAERPRFYT | 0.740 |
| 98 | LPPVILFSM | 0.735 |
| 47 | RLEASLCSC | 0.731 |
| 330 | FPRINFFYM | 0.687 |
| 474 | GTHGSLNHL | 0.682 |
| 337 | YMYEGPAPR | 0.650 |
| 274 | VSARVIKAL | 0.545 |
| 521 | QNSTQLEQV | 0.512 |
| 540 | ITATVKVNL | 0.504 |
| 493 | AEEVSKFSV | 0.502 |
| 270 | AGGPVSARV | 0.454 |
| 665 | WDYFHSVLL | 0.437 |
| 790 | FYQDKVQPV | 0.419 |
| 44 | GETRLEASL | 0.415 |
| 190 | WHGQPMWLT | 0.411 |
| 656 | PMYEEFRKM | 0.394 |
| 436 | FLAHGPSFK | 0.377 |
| 527 | EQVNQMLNL | 0.374 |
| 115 | YTWDTLMPN | 0.373 |
| 708 | HLANTDVPI | 0.355 |

V2-A0201-9mers-161P2F10B
Each peptide is a portion of SEQ ID NO: 5;
each start position is specified, the length
of peptide is 9 amino acids, and the end position
for each peptide is the start position plus eight.

| Start | Subsequence | Score |
|---|---|---|
| 6 | CLQRKDCCA | 4.968 |
| 5 | DCLQRKDCC | 0.004 |
| 4 | DDCLQRKDC | 0.001 |
| 1 | SCSDDCLQR | 0.000 |
| 2 | CSDDCLQRK | 0.000 |
| 7 | LQRKDCCAD | 0.000 |
| 9 | RKDCCADYK | 0.000 |
| 3 | SDDCLQRKD | 0.000 |
| 8 | QRKDCCADY | 0.000 |

V3-HLA-A2-9mers-161P2F10B
Each peptide is a portion of SEQ ID NO: 7;
each start position is specified, the length
of peptide is 9 amino acids, and the end position
for each peptide is the start position plus eight.

| Start | Subsequence | Score |
|---|---|---|
| 9 | GGKPEALWV | 0.087 |
| 7 | CPGGKPEAL | 0.068 |
| 6 | SCPGGKPEA | 0.032 |
| 2 | TNVESCPGG | 0.002 |
| 4 | VESCPGGKP | 0 |
| 1 | PTNVESCPG | 0 |
| 3 | NVESCPGGK | 0 |
| 8 | PGGKPEALW | 0 |
| 5 | ESCPGGKPE | 0 |

TABLE X-continued

| Start | Subsequence | Score |
|---|---|---|

V4-HLA-A2-9mers-161P2F10B
Each peptide is a portion of SEQ ID NO: 9;
each start position is specified, the length
of peptide is 9 amino acids, and the end position
for each peptide is the start position plus eight.

| Start | Subsequence | Score |
|---|---|---|
| 2 | YLPTFETPI | 182.365 |
| 1 | TYLPTFETP | 0 |

TABLE XI

| Start | Subsequence | Score |
|---|---|---|

V1-HLA-A0201-10mers-161P2F10B
Each peptide is a portion of SEQ ID NO: 3;
each start position is specified, the length of
peptide is 10 amino acids, and the end position
for each peptide is the start position plus nine.

| Start | Subsequence | Score |
|---|---|---|
| 663 | KMWDYFHSVL | 2862.980 |
| 337 | YMYEGPAPRI | 454.740 |
| 765 | ALWVEERFTA | 239.160 |
| 102 | ILFSMDGFRA | 181.243 |
| 632 | FLYPPASNRT | 109.693 |
| 379 | YLTPDLPKRL | 98.267 |
| 162 | GIIDNNMYDV | 90.183 |
| 309 | LLADHGMDQT | 58.537 |
| 115 | YTWDTLMPNI | 52.169 |
| 579 | RMPMWSSYTV | 50.232 |
| 746 | FIIPHRPTNV | 43.992 |
| 555 | VLQKNVDHCL | 36.316 |
| 407 | WLAVRSKSNT | 34.279 |
| 34 | RIWMCNKFRC | 32.884 |
| 524 | TQLEQVNQML | 32.857 |
| 600 | TVPDCLRADV | 24.952 |
| 801 | ILQLKTYLPT | 19.003 |
| 199 | AMYQGLKAAT | 17.222 |
| 534 | NLTQEEITAT | 17.140 |
| 105 | SMDGFRAEYL | 16.632 |
| 21 | CCWDFEDTCV | 15.450 |
| 531 | QMLNLTQEEI | 13.661 |
| 520 | LQNSTQLEQV | 13.511 |
| 614 | SESQKCSFYL | 13.251 |
| 648 | ALITSNLVPM | 11.426 |
| 51 | SLCSCSDDCL | 10.468 |
| 387 | RLHYAKNVRI | 10.433 |
| 71 | SVCQGETSWL | 10.281 |
| 120 | LMPNINKLKT | 9.149 |
| 300 | NLHNCVNIIL | 8.759 |
| 795 | VQPVSEILQL | 8.469 |
| 233 | VPFEERISTL | 8.271 |
| 144 | KTFPNHYTIV | 7.693 |
| 4 | RGLENCRCDV | 6.887 |
| 535 | LTQEEITATV | 6.733 |
| 97 | DLPPVILFSM | 4.970 |
| 282 | LQVVDHAFGM | 4.966 |
| 400 | HLFVDQQWLA | 4.687 |
| 767 | WVEERFTAHI | 4.187 |
| 371 | KPDQHFKPYL | 4.080 |
| 224 | SIYMPYNGSV | 3.978 |
| 786 | TGLDFYQDKV | 3.375 |
| 622 | YLADKNITHG | 3.233 |
| 207 | ATYFWPGSEV | 3.091 |
| 546 | VNLPFGRPRV | 2.856 |
| 714 | VPIPTHYFVV | 2.753 |
| 458 | YNLMCDLLRI | 2.666 |
| 532 | MLNLTQEEIT | 2.545 |
| 713 | DVPIPTHYFV | 2.510 |
| 499 | FSVCGFANPL | 2.438 |
| 799 | SEILQLKTYL | 2.285 |
| 291 | MLMEGLKQRN | 1.922 |
| 283 | QVVDHAFGML | 1.893 |
| 136 | YMRAMYPTKT | 1.882 |
| 554 | RVLQKNVDHC | 1.813 |

TABLE XI-continued

| Start | Subsequence | Score |
|---|---|---|
| 155 | GLYPESHGII | 1.779 |
| 547 | NLPFGRPRVL | 1.752 |
| 455 | IEVYNLMCDL | 1.624 |
| 526 | LEQVNQMLNL | 1.624 |
| 167 | NMYDVNLNKN | 1.624 |
| 484 | KVPFYEPSHA | 1.521 |
| 314 | GMDQTYCNKM | 1.435 |
| 123 | NINKLKTCGI | 1.435 |
| 317 | QTYCNKMEYM | 1.369 |
| 128 | KTCGIHSKYM | 1.328 |
| 508 | LPTESLDCFC | 1.243 |
| 358 | FNSEEIVRNL | 1.210 |
| 284 | VVDHAFGMLM | 1.123 |
| 111 | AEYLYTWDTL | 1.107 |
| 805 | KTYLPTFETT | 1.079 |
| 466 | RIQPAPNNGT | 1.025 |
| 139 | AMYPTKTFPN | 0.999 |
| 329 | YFPRINFFYM | 0.962 |
| 640 | RTSDSQYDAL | 0.894 |
| 170 | DVNLNKNFSL | 0.813 |
| 89 | QSQCPEGFDL | 0.809 |
| 28 | TCVESTRIWM | 0.731 |
| 716 | IPTHYFVVLT | 0.723 |
| 306 | NIILLADHGM | 0.683 |
| 242 | LLKWLDLPKA | 0.680 |
| 662 | RKMWDYFHSV | 0.679 |
| 504 | FANPLPTESL | 0.669 |
| 452 | FENIEVYNLM | 0.667 |
| 232 | SVPFEERIST | 0.652 |
| 425 | YNNEFRSMEA | 0.612 |
| 564 | LLYHREYVSG | 0.608 |
| 511 | ESLDCFCPHL | 0.603 |
| 198 | TAMYQGLKAA | 0.587 |
| 401 | LFVDQQWLAV | 0.572 |
| 399 | VHLFVDQQWL | 0.513 |
| 63 | KDCCADYKSV | 0.507 |
| 665 | WDYFHSVLLI | 0.491 |
| 392 | KNVRIDKVHL | 0.488 |
| 29 | CVESTRIWMC | 0.480 |
| 216 | VAINGSFPSI | 0.468 |
| 440 | GPSFKEKTEV | 0.454 |
| 773 | TAHIARVRDV | 0.444 |
| 339 | YEGPAPRIRA | 0.444 |
| 646 | YDALITSNLV | 0.444 |
| 610 | RVPPSESQKC | 0.435 |

V2-A0201-10mers-161P2F10B
Each peptide is a portion of SEQ ID NO: 5; each start position is specified, the length of peptide is 10 amino acids, and the end position for each peptide is the start position plus nine.

| Start | Subsequence | Score |
|---|---|---|
| 7 | CLQRKDCCAD | 0.015 |
| 6 | DCLQRKDCCA | 0.009 |
| 4 | SDDCLQRKDC | 0.003 |
| 8 | LQRKDCCADY | 0.001 |
| 2 | SCSDDCLQRK | 0.001 |
| 5 | DDCLQRKDCC | 0.000 |
| 1 | CSCSDDCLQR | 0.000 |
| 10 | RKDCCADYKS | 0.000 |
| 3 | CSDDCLQRKD | 0.000 |
| 9 | QRKDCCADYK | 0.000 |

V3-HLA-A2-10mers-161P2F10B
Each peptide is a portion of SEQ ID NO: 7; each start position is specified, the length of peptide is 10 amino acids, and the end position for each peptide is the start position plus nine.

| Start | Subsequence | Score |
|---|---|---|
| 7 | SCPGGKPEAL | 0.068 |
| 9 | PGGKPEALWV | 0.055 |
| 6 | ESCPGGKPEA | 0.002 |
| 5 | VESCPGGKPE | 0 |
| 8 | CPGGKPEALW | 0 |
| 1 | RPTNVESCPG | 0 |
| 3 | TNVESCPGGK | 0 |
| 10 | GGKPEALWVE | 0 |
| 2 | PTNVESCPGG | 0 |
| 4 | NVESCPGGKP | 0 |

TABLE XI-continued

| Start | Subsequence | Score |
|---|---|---|

V4-HLA-A2-10mers-161P2F10B
Each peptide is a portion of SEQ ID NO: 9; each start position is specified, the length of peptide is 10 amino acids, and the end position for each peptide is the start position plus nine.

| Start | Subsequence | Score |
|---|---|---|
| 2 | TYLPTFETPI | 0.02 |
| 1 | KTYLPTFETP | 0.002 |

TABLE XII

| Start | Subsequence | Score |
|---|---|---|

V1-HLA-A3-9mers-161P2F10B
Each peptide is a portion of SEQ ID NO: 3; each start position is specified, the length of peptide is 9 amino acids, and the end position for each peptide is the start position plus eight.

| Start | Subsequence | Score |
|---|---|---|
| 167 | NMYDVNLNK | 300.000 |
| 314 | GMDQTYCNK | 60.000 |
| 632 | FLYPPASNR | 45.000 |
| 242 | LLKWLDLPK | 40.000 |
| 337 | YMYEGPAPR | 30.000 |
| 663 | KMWDYFHSV | 27.000 |
| 436 | FLAHGPSFK | 20.000 |
| 136 | YMRAMYPTK | 20.000 |
| 105 | SMDGFRAEY | 18.000 |
| 120 | LMPNINKLK | 15.000 |
| 155 | GLYPESHGI | 13.500 |
| 379 | YLTPDLPKR | 9.000 |
| 803 | QLKTYLPTF | 9.000 |
| 743 | VLPFIIPHR | 9.000 |
| 291 | MLMEGLKQR | 6.750 |
| 245 | WLDLPKAER | 6.000 |
| 322 | KMEYMTDYF | 6.000 |
| 102 | ILESMDGER | 6.000 |
| 672 | LLIKHATER | 6.000 |
| 325 | YMTDYFPRI | 5.400 |
| 653 | NLVPMYEEF | 4.500 |
| 32 | STRIWMCNK | 4.500 |
| 685 | VVSGPIFDY | 4.050 |
| 387 | RLHYAKNVR | 4.000 |
| 610 | RVPPSESQK | 3.000 |
| 400 | HLFVDQQWL | 3.000 |
| 281 | ALQVVDHAF | 3.000 |
| 113 | YLYTWDTLM | 3.000 |
| 459 | NLMCDLLRI | 2.700 |
| 618 | KCSFYLADK | 2.700 |
| 783 | ELLTGLDFY | 2.700 |
| 119 | TLMPNINKL | 2.025 |
| 144 | KTFPNHYTI | 2.025 |
| 317 | QTYCNKMEY | 2.000 |
| 754 | NVESCPEGK | 2.000 |
| 363 | IVRNLSCRK | 2.000 |
| 350 | NIPHDFFSF | 1.800 |
| 431 | SMEAIFLAH | 1.800 |
| 203 | GLKAATYFW | 1.800 |
| 512 | SLDCFCPHL | 1.800 |
| 300 | NLHNCVNII | 1.800 |
| 807 | YLPTFETTI | 1.800 |
| 740 | WLDVLPFII | 1.800 |
| 787 | GLDFYQDKV | 1.800 |
| 722 | VVLTSCKNK | 1.500 |
| 128 | KTCGIHSKY | 1.350 |
| 118 | DTLMPNINK | 1.350 |
| 654 | LVPMYEEFR | 1.200 |
| 34 | RIWMCNKFR | 1.000 |
| 272 | GPVSARVIK | 0.900 |
| 655 | VPMYEEFRK | 0.900 |
| 405 | QQWLAVRSK | 0.900 |
| 197 | LTAMYQGLK | 0.900 |
| 568 | REYVSGFGK | 0.900 |
| 525 | QLEQVNQML | 0.900 |

TABLE XII-continued

| Start | Subsequence | Score |
|---|---|---|
| 199 | AMYQGLKAA | 0.750 |
| 797 | PVSEILQLK | 0.675 |
| 532 | MLNLTQEEI | 0.600 |
| 5 | GLENCRCDV | 0.600 |
| 8 | NCRCDVACK | 0.600 |
| 564 | LLYHREYVS | 0.600 |
| 555 | VLQKNVDHC | 0.600 |
| 384 | LPKRLHYAK | 0.600 |
| 708 | HLANTDVPI | 0.600 |
| 650 | ITSNLVPMY | 0.600 |
| 196 | WLTAMYQGL | 0.600 |
| 390 | YAKNVRIDK | 0.600 |
| 542 | ATVKVNLPF | 0.450 |
| 101 | VILFSMDGF | 0.450 |
| 794 | KVQPVSEIL | 0.405 |
| 534 | NLTQEEITA | 0.400 |
| 54 | SCSDDCLQK | 0.400 |
| 622 | YLADKNITH | 0.400 |
| 805 | KTYLPTFET | 0.338 |
| 79 | WLEENCDTA | 0.300 |
| 579 | RMPMWSSYT | 0.300 |
| 47 | RLEASLCSC | 0.300 |
| 563 | CLLYHREYV | 0.300 |
| 577 | AMRMPMWSS | 0.270 |
| 362 | EIVRNLSCR | 0.270 |
| 217 | AINGSFPSI | 0.270 |
| 482 | LLKVPFYEP | 0.270 |
| 500 | SVCGFANPL | 0.270 |
| 269 | HAGGPVSAR | 0.270 |
| 126 | KLKTCGIHS | 0.240 |
| 474 | GTHGSLNHL | 0.203 |
| 51 | SLCSCSDDC | 0.200 |
| 258 | TMYFEEPDS | 0.200 |
| 547 | NLPFGRPRV | 0.200 |
| 59 | CLQKKDCCA | 0.200 |
| 550 | FGRPRVLQK | 0.180 |
| 290 | GMLMEGLKQ | 0.180 |
| 484 | KVPFYEPSH | 0.180 |
| 371 | KPDQHFKPY | 0.180 |
| 55 | CSDDCLQKK | 0.150 |
| 139 | AMYPTKTFP | 0.150 |
| 450 | EPFENIEVY | 0.135 |
| 481 | HLLKVPFYE | 0.135 |
| 241 | TLLKWLDLP | 0.135 |
| 456 | EVYNLMCDL | 0.135 |

V2-HLA-A3-9mers-161P2F10B
Each peptide is a portion of SEQ ID NO: 5;
each start position is specified, the length of
peptide is 9 amino acids, and the end position
for each peptide is the start position plus eight.

| Start | Subsequence | Score |
|---|---|---|
| 6 | CLQRKDCCA | 0.200 |
| 2 | CSDDCLQRK | 0.150 |
| 1 | SCSDDCLQR | 0.080 |
| 9 | RKDCCADYK | 0.020 |
| 8 | QRKDCCADY | 0.004 |
| 5 | DCLQRKDCC | 0.001 |
| 7 | LQRKDCCAD | 0.001 |
| 4 | DDCLQRKDC | 0.000 |
| 3 | SDDCLQRKD | 0.000 |

V3-HLA-A3-9mers-161P2F10B
Each peptide is a portion of SEQ ID NO: 7;
each start position is specified, the length of
peptide is 9 amino acids, and the end position
for each peptide is the start position plus eight.

| Start | Subsequence | Score |
|---|---|---|
| 3 | NVESCPGGK | 0.6 |
| 7 | CPGGKPEAL | 0.009 |
| 6 | SCPGGKPEA | 0.003 |
| 9 | GGKPEALWV | 0.002 |
| 1 | PTNVESCPG | 0 |
| 2 | TNVESCPGG | 0 |
| 8 | PGGKPEALW | 0 |
| 4 | VESCPGGKP | 0 |
| 5 | ESCPGGKPE | 0 |

TABLE XII-continued

V4-HLA-A3-9mers-161P2F10B
Each peptide is a portion of SEQ ID NO: 9;
each start position is specified, the length of
peptide is 9 amino acids, and the end position
for each peptide is the start position plus eight.

| Start | Subsequence | Score |
|---|---|---|
| 2 | YLPTFETPI | 1.8 |
| 1 | TYLPTFETP | 0 |

TABLE XIII

V1-HLA-A3-10mers-161P2F10B
Each peptide is a portion of SEQ ID NO 3; each
start position is specified, the length of peptide
is 10 amino acids, and the end position for each
peptide is the start position plus nine.

| Start | Subsequence | Score |
|---|---|---|
| 126 | KLKTCGIHSK | 90.000 |
| 241 | TLLKWLDLPK | 60.000 |
| 119 | TLMPNINKLK | 33.750 |
| 663 | KMWDYFHSVL | 27.000 |
| 653 | NLVPMYEEFR | 27.000 |
| 383 | DLPKRLHYAK | 18.000 |
| 196 | WLTAMYQGLK | 18.000 |
| 290 | GMLMEGLKQR | 13.500 |
| 377 | KPYLTPDLPK | 9.000 |
| 337 | YMYEGPAPRI | 6.750 |
| 654 | LVPMYEEFRK | 6.000 |
| 671 | VLLIKHATER | 6.000 |
| 155 | GLYPESHGII | 4.050 |
| 684 | NVVSGPIFDY | 4.050 |
| 577 | AMRMPMWSSY | 4.000 |
| 102 | ILFSMDGFRA | 3.000 |
| 785 | LTGLDFYQDK | 3.000 |
| 765 | ALWVEERFTA | 3.000 |
| 400 | HLFVDQQWLA | 3.000 |
| 478 | SLNHLLKVPF | 2.000 |
| 226 | YMPYNGSVPF | 2.000 |
| 559 | NVDHCLLYHR | 1.800 |
| 314 | GMDQTYCNKM | 1.800 |
| 300 | NLHNCVNIIL | 1.800 |
| 402 | FVDQQWLAVR | 1.800 |
| 217 | AINGSFPSIY | 1.800 |
| 721 | FVVLTSCKNK | 1.500 |
| 220 | GSFPSIYMPY | 1.350 |
| 543 | TVKVNLPFGR | 1.200 |
| 649 | LITSNLVPMY | 1.200 |
| 330 | FPRINFFYMY | 1.080 |
| 762 | KPEALWVEER | 1.080 |
| 434 | AIFLAHGPSF | 1.000 |
| 531 | QMLNLTQEEI | 0.900 |
| 105 | SMDGFRAEYL | 0.900 |
| 295 | GLKQRNLHNC | 0.900 |
| 555 | VLQKNVDHCL | 0.900 |
| 362 | EIVRNLSCRK | 0.900 |
| 536 | TQEEITATVK | 0.900 |
| 632 | FLYPPASNRT | 0.750 |
| 796 | QPVSEILQLK | 0.675 |
| 97 | DLPPVILFSM | 0.608 |
| 742 | DVLPFIIPHR | 0.608 |
| 51 | SLCSCSDDCL | 0.600 |
| 682 | GVNVVSGPIF | 0.600 |
| 579 | RMPMWSSYTV | 0.600 |
| 5 | GLENCRCDVA | 0.600 |
| 387 | RLHYAKNVRI | 0.600 |
| 247 | DLPKAERPRF | 0.600 |
| 570 | YVSGFGKAMR | 0.600 |
| 393 | NVRIDKVHLF | 0.600 |
| 199 | AMYQGLKAAT | 0.500 |
| 139 | AMYPTKTFPN | 0.450 |
| 648 | ALITSNLVPM | 0.450 |
| 379 | YLTPDLPKRL | 0.450 |

TABLE XIII-continued

| Start | Subsequence | Score |
|---|---|---|
| 437 | LAHGPSFKEK | 0.450 |
| 802 | LQLKTYLPTF | 0.405 |
| 162 | GIIDNNMYDV | 0.405 |
| 481 | HLLKVPFYEP | 0.405 |
| 446 | KTEVEPFENI | 0.405 |
| 545 | KVNLPFGRPR | 0.360 |
| 192 | GQPMWLTAMY | 0.360 |
| 34 | RIWMCNKFRC | 0.300 |
| 326 | MTDYFPRINF | 0.300 |
| 711 | NTDVPIPTHY | 0.300 |
| 54 | SCSDDCLQKK | 0.300 |
| 507 | PLPTESLDCF | 0.300 |
| 136 | YMRAMYPTKT | 0.300 |
| 242 | LLKWLDLPKA | 0.300 |
| 686 | VSGPIFDYNY | 0.270 |
| 784 | LLTGLDFYQD | 0.270 |
| 767 | WVEERFTAHI | 0.270 |
| 172 | NLNKNFSLSS | 0.240 |
| 656 | PMYEEFRKMW | 0.225 |
| 115 | YTWDTLMPNI | 0.225 |
| 805 | KTYLPTFETT | 0.225 |
| 144 | KTFPNHYTIV | 0.225 |
| 366 | NLSCRKPDQH | 0.200 |
| 801 | ILQLKTYLPT | 0.200 |
| 356 | FSFNSEEIVR | 0.200 |
| 53 | CSCSDDCLQK | 0.200 |
| 120 | LMPNINKLKT | 0.200 |
| 258 | TMYFEEPDSS | 0.200 |
| 368 | SCRKPDQHFK | 0.200 |
| 113 | YLYTWDTLMP | 0.200 |
| 166 | NNMYDVNLNK | 0.180 |
| 495 | EVSKFSVCGF | 0.180 |
| 740 | WLDVLPFIIP | 0.180 |
| 323 | MEYMTDYFPR | 0.180 |
| 563 | CLLYHREYVS | 0.180 |
| 101 | VILFSMDGFR | 0.180 |
| 203 | GLKAATYFWP | 0.180 |
| 322 | KMEYMTDYFP | 0.180 |
| 534 | NLTQEEITAT | 0.150 |
| 167 | NMYDVNLNKN | 0.150 |
| 309 | LLADHGMDQT | 0.150 |
| 596 | PLPPTVPDCL | 0.135 |
| 280 | KALQVVDHAF | 0.135 |
| 31 | ESTRIWMCNK | 0.135 |
| 474 | GTHGSLNHLL | 0.135 |

V2-HLA-A3-10MERS-161P2F10B
Each peptide is a portion of SEQ ID NO: 5; each start position is specified, the length of peptide is 10 amino acids, and the end position for each peptide is the start position plus nine.

| Start | Subsequence | Score |
|---|---|---|
| 2 | SCSDDCLQRK | 0.300 |
| 8 | LQRKDCCADY | 0.120 |
| 1 | CSCSDDCLQR | 0.040 |
| 7 | CLQRKDCCAD | 0.020 |
| 9 | QRKDCCADYK | 0.020 |
| 6 | DCLQRKDCCA | 0.001 |
| 10 | RKDCCADYKS | 0.000 |
| 4 | SDDCLQRKDC | 0.000 |
| 5 | DDCLQRKDCC | 0.000 |
| 3 | CSDDCLQRKD | 0.000 |

V3-HLA-A3-10MERS-161P2F10B
Each peptide is a portion of SEQ ID NO: 7; each start position is specified, the length of peptide is 10 amino acids, and the end position for each peptide is the start position plus nine.

| Start | Subsequence | Score |
|---|---|---|
| 3 | TNVESCPGGK | 0.027 |
| 7 | SCPGGKPEAL | 0.009 |
| 8 | CPGGKPEALW | 0.005 |
| 4 | NVESCPGGKP | 0.001 |
| 6 | ESCPGGKPEA | 0 |
| 10 | GGKPEALWVE | 0 |
| 1 | RPTNVESCPG | 0 |
| 2 | PTNVESCPGG | 0 |
| 9 | PGGKPEALWV | 0 |
| 5 | VESCPGGKPE | 0 |

V4-HLA-A3-10MERS-161P2F10B
Each peptide is a portion of SEQ ID NO: 9; each start position is specified, the length of peptide is 10 amino acids, and the end position for each peptide is the start position plus nine.

| Start | Subsequence | Score |
|---|---|---|
| 1 | KTYLPTFETP | 0.045 |
| 2 | TYLPTFETPI | 0.004 |

TABLE XIV

V1-HLA-A11-9MERS-161P2F10B
Each peptide is a portion of SEQ ID NO: 3; each start position is specified, the length of peptide is 9 amino acids, and the end position for each peptide is the start position plus eight.

| Start | Subsequence | Score |
|---|---|---|
| 610 | RVPPSESQK | 6.000 |
| 363 | IVRNLSCRK | 2.000 |
| 754 | NVESCPEGK | 2.000 |
| 167 | NMYDVNLNK | 1.600 |
| 722 | VVLTSCKNK | 1.500 |
| 314 | GMDQTYCNK | 1.200 |
| 655 | VPMYEEFRK | 1.200 |
| 568 | REYVSGFGK | 1.080 |
| 32 | STRIWMCNK | 1.000 |
| 197 | LTAMYQGLK | 1.000 |
| 272 | GPVSARVIK | 0.900 |
| 118 | DTLMPNINK | 0.900 |
| 242 | LLKWLDLPK | 0.800 |
| 618 | KCSFYLADK | 0.600 |
| 390 | YAKNVRIDK | 0.400 |
| 654 | LVPMYEEFR | 0.400 |
| 136 | YMRAMYPTK | 0.400 |
| 384 | LPKRLHYAK | 0.400 |
| 436 | FLAHGPSFK | 0.400 |
| 54 | SCSDDCLQK | 0.400 |
| 667 | YFHSVLLIK | 0.400 |
| 720 | YFVVLTSCK | 0.300 |
| 387 | RLHYAKNVR | 0.240 |
| 34 | RIWMCNKFR | 0.240 |
| 797 | PVSEILQLK | 0.200 |
| 8 | NCRCDVACK | 0.200 |
| 120 | LMPNINKLK | 0.200 |
| 632 | FLYPPASNR | 0.160 |
| 337 | YMYEGPAPR | 0.160 |
| 102 | ILFSMDGFR | 0.160 |
| 324 | EYMTDYFPR | 0.144 |
| 405 | QQWLAVRSK | 0.120 |
| 378 | PYLTPDLPK | 0.120 |
| 144 | KTFPNHYTI | 0.120 |
| 672 | LLIKHATER | 0.120 |
| 554 | RVLQKNVDH | 0.090 |
| 283 | QVVDHAFGM | 0.090 |
| 277 | RVIKALQVV | 0.090 |
| 743 | VLPFIIPHR | 0.080 |
| 291 | MLMEGLKQR | 0.080 |
| 357 | SFNSEEIVR | 0.080 |
| 379 | YLTPDLPKR | 0.080 |
| 245 | WLDLPKAER | 0.080 |
| 62 | KKDCCADYK | 0.060 |
| 794 | KVQPVSEIL | 0.060 |
| 537 | QEEITATVK | 0.060 |
| 682 | GVNVVSGPI | 0.060 |
| 484 | KVPFYEPSH | 0.060 |
| 10 | RCDVACKDR | 0.060 |
| 685 | VVSGPIFDY | 0.060 |
| 640 | RTSDSQYDA | 0.060 |
| 2 | SFRGLENCR | 0.040 |
| 476 | HGSLNHLLK | 0.040 |
| 289 | FGMLMEGLK | 0.040 |
| 559 | NVDHCLLYH | 0.040 |

TABLE XIV-continued

| Start | Subsequence | Score |
|---|---|---|
| 317 | QTYCNKMEY | 0.040 |
| 699 | FDAPDEITK | 0.040 |
| 29 | CVESTRIWM | 0.040 |
| 550 | FGRPRVLQK | 0.040 |
| 402 | FVDQQWLAV | 0.040 |
| 269 | HAGGPVSAR | 0.040 |
| 236 | EERISTLLK | 0.036 |
| 362 | EIVRNLSCR | 0.036 |
| 786 | TGLDFYQDK | 0.030 |
| 240 | STLLKWLDL | 0.030 |
| 128 | KTCGIHSKY | 0.030 |
| 474 | GTHGSLNHL | 0.030 |
| 542 | ATVKVNLPF | 0.030 |
| 458 | YNLMCDLLR | 0.024 |
| 663 | KMWDYFHSV | 0.024 |
| 131 | GIHSKYMRA | 0.024 |
| 345 | RIRAHNIPH | 0.024 |
| 155 | GLYPESHGI | 0.024 |
| 203 | GLKAATYFW | 0.024 |
| 395 | RIDKVHLFV | 0.024 |
| 393 | NVRIDKVHL | 0.020 |
| 284 | VVDHAFGML | 0.020 |
| 500 | SVCGFANPL | 0.020 |
| 772 | FTAHIARVR | 0.020 |
| 369 | CRKPDQHFK | 0.020 |
| 71 | SVCQGETSW | 0.020 |
| 55 | CSDDCLQKK | 0.020 |
| 127 | LKTCGIHSK | 0.020 |
| 767 | WVEERFTAH | 0.020 |
| 174 | NKNFSLSSK | 0.020 |
| 544 | VKVNLPFGR | 0.018 |
| 742 | DVLPFIIPH | 0.018 |
| 805 | KTYLPTFET | 0.018 |
| 192 | GQPMWLTAM | 0.018 |
| 90 | SQCPEGFDL | 0.018 |
| 297 | KQRNLHNCV | 0.018 |
| 459 | NLMCDLLRI | 0.016 |
| 130 | CGIHSKYMR | 0.012 |
| 5 | GLENCRCDV | 0.012 |
| 42 | RCGETRLEA | 0.012 |
| 253 | RPRFYTMYF | 0.012 |
| 740 | WLDVLPFII | 0.012 |
| 787 | GLDFYQDKV | 0.012 |
| 616 | SQKCSFYLA | 0.012 |
| 350 | NIPHDFFSE | 0.012 |

V2-HLA-A11-9MERS-161P2F10B
Each peptide is a portion of SEQ ID NO: 5; each start position is specified, the length of peptide is 9 amino acids, and the end position for each peptide is the start position plus eight.

| Start | Subsequence | Score |
|---|---|---|
| 1 | SCSDDCLQR | 0.080 |
| 9 | RKDCCADYK | 0.060 |
| 2 | CSDDCLQRK | 0.020 |
| 6 | CLQRKDCCA | 0.004 |
| 7 | LQRKDCCAD | 0.001 |
| 8 | QRKDCCADY | 0.000 |
| 5 | DCLQRKDCC | 0.000 |
| 4 | DDCLQRKDC | 0.000 |
| 3 | SDDCLQRKD | 0.000 |

V3-HLA-A11-9MERS-161P2F10B
Each peptide is a portion of SEQ ID NO: 7; each start position is specified, the length of peptide is 9 amino acids, and the end position for each peptide is the start position plus eight.

| Start | Subsequence | Score |
|---|---|---|
| 3 | NVESCPGGK | 2 |
| 7 | CPGGKPEAL | 0.002 |
| 6 | SCPGGKPEA | 0.002 |
| 9 | GGKPEALWV | 0.001 |
| 1 | PTNVESCPG | 0 |
| 2 | TNVESCPGG | 0 |
| 4 | VESCPGGKP | 0 |
| 8 | PGGKPEALW | 0 |
| 5 | ESCPGGKPE | 0 |

TABLE XIV-continued

V4-HLA-A11-9MERS-161P2F10B
Each peptide is a portion of SEQ ID NO: 9; each start position is specified, the length of peptide is 9 amino acids, and the end position for each peptide is the start position plus eight.

| Start | Subsequence | Score |
|---|---|---|
| 2 | YLPTFETPI | 0.004 |
| 1 | TYLPTFETP | 0.001 |

TABLE XV

V1-HLA-A11-10mers-161P2F10B
Each peptide is a portion of SEQ ID NO: 3; each start position is specified, the length of peptide is 10 amino acids, and the end position for each peptide is the start position plus nine.

| Start | Subsequence | Score |
|---|---|---|
| 654 | LVPMYEEFRK | 6.000 |
| 377 | KPYLTPDLPK | 2.400 |
| 135 | KYMRAMYPTK | 2.400 |
| 721 | FVVLTSCKNK | 1.500 |
| 543 | TVKVNLPFGR | 1.200 |
| 241 | TLLKWLDLPK | 1.200 |
| 126 | KLKTCGIHSK | 1.200 |
| 785 | LTGLDFYQDK | 1.000 |
| 559 | NVDHCLLYHR | 0.800 |
| 719 | HYFVVLTSCK | 0.800 |
| 389 | HYAKNVRIDK | 0.800 |
| 536 | TQEEITATVK | 0.600 |
| 666 | DYFHSVLLIK | 0.480 |
| 196 | WLTAMYQGLK | 0.400 |
| 402 | FVDQQWLAVR | 0.400 |
| 570 | YVSGFGKAMR | 0.400 |
| 119 | TLMPNINKLK | 0.400 |
| 698 | HFDAPDEITK | 0.400 |
| 435 | IFLAHGPSFK | 0.300 |
| 796 | QPVSEILQLK | 0.300 |
| 383 | DLPKRLHYAK | 0.240 |
| 54 | SCSDDCLQKK | 0.200 |
| 288 | AFGMLMEGLK | 0.200 |
| 368 | SCRKPDQHFK | 0.200 |
| 742 | DVLPFIIPHR | 0.180 |
| 631 | GFLYPPASNR | 0.180 |
| 290 | GMLMEGLKQR | 0.180 |
| 362 | EIVRNLSCRK | 0.180 |
| 336 | FYMEGPAPR | 0.160 |
| 457 | VYNLMCDLLR | 0.160 |
| 166 | NNMYDVNLNK | 0.160 |
| 671 | VLLIKHATER | 0.120 |
| 235 | FEERISTLLK | 0.120 |
| 545 | KVNLPFGRPR | 0.120 |
| 762 | KPEALWVEER | 0.120 |
| 653 | NLVPMYEEFR | 0.120 |
| 101 | VILFSMDGFR | 0.120 |
| 437 | LAHGPSFKEK | 0.100 |
| 684 | NVVSGPIFDY | 0.090 |
| 129 | TCGIHSKYMR | 0.080 |
| 323 | MEYMTDYFPR | 0.072 |
| 567 | HREYVSGFGK | 0.060 |
| 753 | TNVESCPEGK | 0.060 |
| 271 | GGPVSARVIK | 0.060 |
| 682 | GVNVVSGPIF | 0.060 |
| 489 | EPSHAEEVSK | 0.060 |
| 484 | KVPFYEPSHA | 0.060 |
| 144 | KTFPNHYTIV | 0.060 |
| 398 | KVHLFVDQQW | 0.060 |
| 475 | THGSLNHLLK | 0.040 |
| 117 | WDTLMPNINK | 0.040 |
| 173 | LNKNFSLSSK | 0.040 |
| 313 | HGMDQTYCNK | 0.040 |
| 597 | LPPTVPDCLR | 0.040 |
| 284 | VVDHAFGMLM | 0.040 |

TABLE XV-continued

| Start | Subsequence | Score |
|---|---|---|
| 53 | CSCSDDCLQK | 0.040 |
| 601 | VPDCLRADVR | 0.040 |
| 549 | PFGRPRVLQK | 0.040 |
| 162 | GIIDNNMYDV | 0.036 |
| 609 | VRVPPSESQK | 0.030 |
| 283 | QVVDHAFGML | 0.030 |
| 640 | RTSDSQYDAL | 0.030 |
| 446 | KTEVEPFENI | 0.030 |
| 474 | GTHGSLNHLL | 0.030 |
| 282 | LQVVDHAFGM | 0.027 |
| 421 | GNHGYNNEFR | 0.024 |
| 663 | KMWDYFHSVL | 0.024 |
| 765 | ALWVEERFTA | 0.024 |
| 579 | RMPMWSSYTV | 0.024 |
| 155 | GLYPESHGII | 0.024 |
| 102 | ILFSMDGFRA | 0.024 |
| 152 | IVTGLYPESH | 0.020 |
| 71 | SVCQGETSWL | 0.020 |
| 304 | CVNIILLADH | 0.020 |
| 207 | ATYFWPGSEV | 0.020 |
| 767 | WVEERFTAHI | 0.020 |
| 197 | LTAMYQGLKA | 0.020 |
| 115 | YTWDTLMPNI | 0.020 |
| 617 | QKCSFYLADK | 0.020 |
| 326 | MTDYFPRINF | 0.020 |
| 317 | QTYCNKMEYM | 0.020 |
| 61 | QKKDCCADYK | 0.020 |
| 393 | NVRIDKVHLF | 0.020 |
| 386 | KRLHYAKNVR | 0.018 |
| 244 | KWLDLPKAER | 0.018 |
| 192 | GQPMWLTAMY | 0.018 |
| 272 | GPVSARVIKA | 0.018 |
| 170 | DVNLNKNFSL | 0.018 |
| 404 | DQQWLAVRSK | 0.018 |
| 400 | HLFVDQQWLA | 0.016 |
| 356 | FSFNSEEIVR | 0.016 |
| 128 | KTCGIHSKYM | 0.015 |
| 378 | PYLTPDLPKR | 0.012 |
| 771 | RFTAHIARVR | 0.012 |
| 268 | GHAGGPVSAR | 0.012 |
| 250 | KAERPRFYTM | 0.012 |
| 108 | GFRAEYLYTW | 0.012 |
| 573 | GFGKAMRMPM | 0.012 |
| 387 | RLHYAKNVRI | 0.012 |

V2-HLA-A-11-10mers-161P2F10B
Each peptide is a portion of SEQ ID NO: 5; each start position is specified, the length of peptide is 10 amino acids, and the end position for each peptide is the start position plus nine.

| Start | Subsequence | Score |
|---|---|---|
| 2 | SCSDDCLQRK | 0.200 |
| 9 | QRKDCCADYK | 0.020 |
| 1 | CSCSDDCLQR | 0.008 |
| 8 | LQRKDCCADY | 0.006 |
| 6 | DCLQRKDCCA | 0.001 |
| 7 | CLQRKDCCAD | 0.000 |
| 10 | RKDCCADYKS | 0.000 |
| 4 | SDDCLQRKDC | 0.000 |
| 5 | DDCLQRKDCC | 0.000 |
| 3 | CSDDCLQRKD | 0.000 |

V3-HLA-A11-10mers-161P2F10B
Each peptide is a portion of SEQ ID NO: 7; each start position is specified, the length of peptide is 10 amino acids, and the end position for each peptide is the start position plus nine.

| Start | Subsequence | Score |
|---|---|---|
| 3 | TNVESCPGGK | 0.06 |
| 8 | CPGGKPEALW | 0.002 |
| 7 | SCPGGKPEAL | 0.002 |
| 4 | NVESCPGGKP | 0.002 |
| 1 | RPTNVESCPG | 0.001 |
| 10 | GGKPEALWVE | 0 |
| 2 | PTNVESCPGG | 0 |
| 6 | ESCPGGKPEA | 0 |
| 9 | PGGKPEALWV | 0 |
| 5 | VESCPGGKPE | 0 |

V4-HLA-A11-10mers-161P2F10B
Each peptide is a portion of SEQ ID NO: 9; each start position is specified, the length of peptide is 10 amino acids, and the end position for each peptide is the start position plus nine.

| Start | Subsequence | Score |
|---|---|---|
| 2 | TYLPTFETPI | 0.006 |
| 1 | KTYLPTFETP | 0.006 |

TABLE XVI

| Start | Subsequence | Score |
|---|---|---|

V1-HLA-A24-9mers-161P2F10B
Each peptide is a portion of SEQ ID NO: 3, each start position is specified, the length of peptide is 9 amino acids, and the end position for each peptide is the start position plus eight.

| Start | Subsequence | Score |
|---|---|---|
| 112 | EYLYTWDTL | 300.000 |
| 457 | VYNLMCDLL | 300.000 |
| 328 | DYFPRINFF | 144.000 |
| 156 | LYPESHGII | 90.000 |
| 338 | MYEGPAPRI | 75.000 |
| 666 | DYFHSVLLI | 50.000 |
| 424 | GYNNEFRSM | 45.000 |
| 40 | KFRCGETRL | 40.000 |
| 318 | TYCNKMEYM | 25.000 |
| 288 | AFGMLMEGL | 24.000 |
| 794 | KVQPVSEIL | 20.160 |
| 95 | GFDLPPVIL | 20.000 |
| 435 | IFLAHOPSF | 15.000 |
| 135 | KYMRAMYPT | 15.000 |
| 633 | LYPPASNRT | 10.800 |
| 790 | FYQDKVQPV | 10.800 |
| 806 | TYLPTFETT | 10.800 |
| 359 | NSEEIVRNL | 10.080 |
| 525 | QLEQVNQML | 10.080 |
| 660 | EFRKMWDYF | 10.000 |
| 428 | EFRSMEAIF | 10.000 |
| 569 | EYVSGFGKA | 9.900 |
| 238 | RISTLLKWL | 9.600 |
| 119 | TLMPNINKL | 9.504 |
| 657 | MYEEFRKMW | 9.000 |
| 621 | FYLADKNIT | 9.000 |
| 225 | IYMPYNGSV | 9.000 |
| 200 | MYQGLKAAT | 9.000 |
| 380 | LTPDLPKRL | 8.640 |
| 597 | LPPTVPDCL | 8.400 |
| 140 | MYPTKTFPN | 7.500 |
| 800 | EILQLKTYL | 7.200 |
| 149 | HYTIVTGLY | 7.000 |
| 719 | HYFVVLTSC | 7.000 |
| 701 | APDEITKHL | 6.720 |
| 168 | MYDVNLNKN | 6.600 |
| 736 | NCPGWLDVL | 6.000 |
| 259 | MYFEEPDSS | 6.000 |
| 138 | RAMYPTKTF | 6.000 |
| 758 | CPEGKPEAL | 6.000 |
| 733 | TPENCPGWL | 6.000 |
| 527 | EQVNQMLNL | 6.000 |
| 240 | STLLKWLDL | 6.000 |
| 615 | ESQKCSFYL | 6.000 |
| 165 | DNNMYDVNL | 6.000 |
| 72 | VCQGETSWL | 6.000 |
| 322 | KMEYMTDYF | 6.000 |
| 645 | QYDALITSN | 6.000 |
| 796 | QPVSEILQL | 6.000 |
| 171 | VNLNKNFSL | 6.000 |
| 505 | ANPLPTESL | 6.000 |
| 556 | LQKNVDHCL | 5.600 |
| 347 | RAHNIPHDF | 5.600 |
| 540 | ITATVKVNL | 5.600 |
| 274 | VSARVIKAL | 5.600 |

TABLE XVI-continued

| Start | Subsequence | Score |
|---|---|---|
| 208 | TYFWPGSEV | 5.500 |
| 355 | FFSFNSEEI | 5.500 |
| 620 | SFYLADKNI | 5.000 |
| 474 | GTHGSLNHL | 4.800 |
| 456 | EVYNLMCDL | 4.800 |
| 716 | IPTHYFVVL | 4.800 |
| 196 | WLTAMYQGL | 4.800 |
| 90 | SQCPEGFDL | 4.800 |
| 500 | SVCGFANPL | 4.800 |
| 400 | HLFVDQQWL | 4.800 |
| 284 | VVDHAFGML | 4.800 |
| 776 | IARVRDVEL | 4.400 |
| 542 | ATVKVNLPF | 4.200 |
| 764 | EALWVEERF | 4.200 |
| 281 | ALQVVDHAF | 4.200 |
| 189 | WWHGQPMWL | 4.000 |
| 512 | SLDCFCPHL | 4.000 |
| 583 | WSSYTVPQL | 4.000 |
| 302 | HNCVNIILL | 4.000 |
| 664 | MWDYFHSVL | 4.000 |
| 548 | LPFGRPRVL | 4.000 |
| 52 | LCSCSDDCL | 4.000 |
| 253 | RPRFYTMYF | 4.000 |
| 641 | TSDSQYDAL | 4.000 |
| 653 | NLVPMYEEF | 3.960 |
| 234 | PFEERISTL | 3.600 |
| 350 | NIPHDFFSF | 3.600 |
| 101 | VILFSMDGF | 3.000 |
| 299 | RNLHNCVNI | 3.000 |
| 713 | DVPIPTHYF | 3.000 |
| 683 | VNVVSGPIF | 3.000 |
| 202 | QGLKAATYF | 3.000 |
| 421 | QGLKAATYF | 2.640 |
| 739 | GWLDVLPFI | 2.520 |
| 144 | KTFPNHYTI | 2.400 |
| 368 | SCRKPDQHF | 2.400 |
| 479 | LNHLLKVPF | 2.400 |
| 508 | LPTESLDCF | 2.400 |
| 682 | GVNVVSGPI | 2.100 |
| 88 | QQSQCPEGF | 2.000 |
| 227 | MPYNGSVPF | 2.000 |
| 496 | VSKFSVCGF | 2.000 |
| 248 | LPKAERPRF | 2.000 |
| 803 | QLKTYLPTF | 2.000 |

V2-HLA-A24-9mers-161P2F10B
Each peptide is a portion of SEQ ID NO: 5; each start position is specified, the length of peptide is 9 amino acids, and the end position for each peptide is the start position plus eight

| Start | Subsequence | Score |
|---|---|---|
| 5 | DCLQRKDCC | 0.150 |
| 6 | CLQRKDCCA | 0.150 |
| 2 | CSDDCLQRK | 0.014 |
| 8 | QRKDCCADY | 0.012 |
| 1 | SCSDDCLQR | 0.012 |
| 4 | DDCLQRKDC | 0.010 |
| 7 | LQRKDCCAD | 0.010 |
| 9 | RKDCCADYK | 0.002 |
| 3 | SDDCLQRKD | 0.001 |

V3-HLA-A24-9mers-161P2F10B
Each peptide is a portion of SEQ ID NO: 7; each start position is specified, the length of peptide is 9 amino acids, and the end position for each peptide is the start position plus eight.

| Start | Subsequence | Score |
|---|---|---|
| 7 | CPGGKPEAL | 4 |
| 6 | SCPGGKPEA | 0.165 |
| 9 | GGKPEALWV | 0.12 |
| 2 | TNVESCPGG | 0.018 |
| 3 | NVESCPGGK | 0.015 |
| 5 | ESCPGGKPE | 0.012 |
| 8 | PGGKPEALW | 0.01 |
| 1 | PTNVESCPG | 0.002 |
| 4 | VESCPGGKP | 0.001 |

TABLE XVI-continued

V4-HLA-A24-9mers-161P2F10B
Each peptide is a portion of SEQ ID NO: 9; each start position is specified, the length of peptide is 9 amino acids, and the end position for each peptide is the start position plus eight.

| Start | Subsequence | Score |
|---|---|---|
| 2 | YLPTFETPI | 1.5 |
| 1 | TYLPTFETP | 1.08 |

TABLE XVII

V1-HLA-A24-10mers-161P2F10B
Each peptide is a portion of SEQ ID NO: 3; each start position is specified, the length of peptide is 10 amino acids, and the end position for each peptide is the start position plus nine.

| Start | Subsequence | Score |
|---|---|---|
| 645 | QYDALITSNL | 280.000 |
| 168 | MYDVNLNKNF | 120.000 |
| 565 | LYHREYVSGF | 100.000 |
| 806 | TYLPTFETTI | 90.000 |
| 324 | EYMTDYFPRI | 90.000 |
| 569 | EYVSGFGKAM | 37.500 |
| 112 | EYLYTWDTLM | 37.500 |
| 375 | HFKPYLTPDL | 28.800 |
| 428 | EFRSMEAIFL | 20.000 |
| 790 | FYQDKVQPVS | 12.600 |
| 524 | TQLEQVNQML | 12.096 |
| 392 | KNVRIDKVHL | 12.000 |
| 700 | DAPDEITKHL | 10.080 |
| 690 | IFDYNYDGHF | 10.000 |
| 95 | GFDLPPVILF | 10.000 |
| 487 | FYEPSHAEEV | 9.900 |
| 663 | KMWDYFHSVL | 9.600 |
| 640 | RTSDSQYDAL | 9.600 |
| 633 | LYPPASNRTS | 9.000 |
| 283 | QVVDHAFGML | 8.640 |
| 328 | DYFPRINFFY | 8.400 |
| 280 | KALQVVDHAF | 8.400 |
| 555 | VLQKNVDHCL | 8.400 |
| 371 | KPDQHFKPYL | 8.000 |
| 118 | DTLMPNINKL | 7.920 |
| 200 | MYQGLKAATY | 7.500 |
| 692 | DYNYDGHFDA | 7.500 |
| 757 | SCPEGKPEAL | 7.200 |
| 504 | FANPLPTESL | 7.200 |
| 511 | ESLDCFCPHL | 7.200 |
| 195 | MWLTAMYQGL | 7.200 |
| 732 | HTPENCPGWL | 7.200 |
| 499 | FSVCGFANPL | 7.200 |
| 43 | CGETRLEASL | 7.200 |
| 358 | FNSEEIVRNL | 6.720 |
| 547 | NLPFGRPRVL | 6.000 |
| 170 | DVNLNKNFSL | 6.000 |
| 795 | VQPVSEILQL | 6.000 |
| 89 | QSQCPEGFDL | 6.000 |
| 470 | APNNGTHGSL | 6.000 |
| 209 | YFWPGSEVAI | 6.000 |
| 588 | VPQLGDTSPL | 6.000 |
| 292 | LMEGLKQRNL | 6.000 |
| 379 | YLTPDLPKRL | 5.760 |
| 300 | NLHNCVNIIL | 5.600 |
| 539 | EITATVKVNL | 5.600 |
| 68 | DYKSVCQGET | 5.500 |
| 354 | DFFSFNSEEI | 5.500 |
| 234 | PFEERISTLL | 5.040 |
| 114 | LYTWDTLMPN | 5.000 |
| 318 | TYCNKMEYMT | 5.000 |
| 208 | TYFWPGSEVA | 5.000 |
| 585 | SYTVPQLGDT | 5.000 |
| 735 | ENCPGWLDVL | 4.800 |
| 287 | HAFGMLMEGL | 4.800 |

TABLE XVII-continued

V1-HLA-A24-10mers-161P2F10B
Each peptide is a portion of SEQ ID NO: 3; each start position is specified, the length of peptide is 10 amino acids, and the end position for each peptide is the start position plus nine.

| Start | Subsequence | Score |
|---|---|---|
| 473 | NGTHGSLNHL | 4.800 |
| 474 | GTHGSLNHLL | 4.800 |
| 233 | VPFEERISTL | 4.800 |
| 94 | EGFDLPPVIL | 4.800 |
| 775 | HIARVRDVEL | 4.400 |
| 349 | HNIPHDFFSF | 4.320 |
| 213 | GSEVAINGSF | 4.200 |
| 51 | SLCSCSDDCL | 4.000 |
| 239 | ISTLLKWLDL | 4.000 |
| 517 | CPHLQNSTQL | 4.000 |
| 582 | MWSSYTVPQL | 4.000 |
| 188 | AWWHGQPMWL | 4.000 |
| 776 | IARVRDVELL | 4.000 |
| 347 | RAHNIPHDFF | 4.000 |
| 105 | SMDGFRAEYL | 4.000 |
| 556 | LQKNVDHCLL | 4.000 |
| 456 | EVYNLMCDLL | 4.000 |
| 664 | MWDYFHSVLL | 4.000 |
| 420 | GGNHGYNNEF | 3.960 |
| 478 | SLNHLLKVPF | 3.600 |
| 299 | RNLHNCVNII | 3.600 |
| 446 | KTEVEPFENI | 3.600 |
| 652 | SNLVPMYEEF | 3.300 |
| 247 | DLPKAERPRF | 3.000 |
| 802 | LQLKTYLPTF | 3.000 |
| 87 | AQQSQCPEGF | 3.000 |
| 226 | YMPYNGSVPF | 3.000 |
| 451 | PFENIEVYNL | 3.000 |
| 682 | GVNVVSGPIF | 3.000 |
| 781 | DVELLTGLDF | 3.000 |
| 623 | LADKNITHGF | 2.800 |
| 541 | TATVKVNLPF | 2.800 |
| 32 | STRIWMCNKF | 2.640 |
| 573 | GFGKAMRMPM | 2.500 |
| 367 | LSCRKPDQHF | 2.400 |
| 739 | GWLDVLPFII | 2.160 |
| 681 | NGVNVVSGPI | 2.100 |
| 434 | AIFLAHGPSF | 2.000 |
| 393 | NVRIDKVHLF | 2.000 |
| 737 | CPGWLDVLPF | 2.000 |
| 495 | EVSKFSVCGF | 2.000 |
| 326 | MTDYFPRINF | 2.000 |
| 201 | YQGLKAATYF | 2.000 |

V2-HLA-A24-10mers-161P2F10B
Each peptide is a portion of SEQ ID NO: 5; each start position is specified, the length of peptide is 10 amino acids, and the end position for each peptide is the start position plus nine.

| Start | Subsequence | Score |
|---|---|---|
| 6 | DCLQRKDCCA | 0.150 |
| 8 | LQRKDCCADY | 0.100 |
| 10 | RKDCCADYKS | 0.022 |
| 3 | CSDDCLQRKD | 0.016 |
| 7 | CLQRKDCCAD | 0.015 |
| 2 | SCSDDCLQRK | 0.014 |
| 4 | SDDCLQRKDC | 0.010 |
| 1 | CSCSDDCLQR | 0.010 |
| 5 | DDCLQRKDCC | 0.010 |
| 9 | QRKDCCADYK | 0.001 |

V3-HLA-A11-10mers-161P2F10B
Each peptide is a portion of SEQ ID NO: 7; each start position is specified, the length of peptide is 10 amino acids, and the end position for each peptide is the start position plus nine.

| Start | Subsequence | Score |
|---|---|---|
| 7 | SCPGGKPEAL | 6 |
| 6 | ESCPGGKPEA | 0.132 |
| 8 | CPGGKPEALW | 0.1 |
| 1 | RPTNVESCPG | 0.002 |
| 3 | TNVESCPGGK | 0.018 |
| 4 | NVESCPGGKP | 0.017 |
| 10 | GGKPEALWVE | 0.012 |
| 9 | PGGKPEALWV | 0.01 |
| 2 | PTNVESCPGG | 0.002 |
| 5 | VESCPGGKPE | 0.001 |

V4-HLA-A11-10mers-161P2F10B
Each peptide is a portion of SEQ ID NO: 9; each start position is specified, the length of peptide is 10 amino acids, and the end position for each peptide is the start position plus nine.

| Start | Subsequence | Score |
|---|---|---|
| 2 | TYLPTFETPI | 90 |
| 1 | KTYLPTFETP | 0.024 |

TABLE XVIII

| Start | Subsequence | Score |
|---|---|---|

V1-HLA-B7-9mers-161P2F10B
Each peptide is a portion of SEQ ID NO:3; each start position is specified, the length of peptide is 9 amino acids, and the end position for each peptide is the start position plus eight.

| Start | Subsequence | Score |
|---|---|---|
| 343 | APRIRAHNI | 240.000 |
| 330 | FPRINFFYM | 200.000 |
| 393 | NVRIDKVHL | 200.000 |
| 776 | IARVRDVEL | 120.000 |
| 548 | LPFGRPRVL | 80.000 |
| 716 | IPTHYFVVL | 80.000 |
| 796 | QPVSEILQL | 80.000 |
| 597 | LPPTVPDCL | 80.000 |
| 701 | APDEITKHL | 72.000 |
| 552 | RPRVLQKNV | 40.000 |
| 758 | CPEGKPEAL | 24.000 |
| 733 | TPENCPGWL | 24.000 |
| 500 | SVCGFANPL | 20.000 |
| 456 | EVYNLMCDL | 20.000 |
| 98 | LPPVILFSM | 20.000 |
| 794 | KVQPVSEIL | 20.000 |
| 505 | ANPLPTESL | 18.000 |
| 580 | MPMWSSYTV | 12.000 |
| 119 | TLMPNINKL | 12.000 |
| 284 | VVDHAFGML | 6.000 |
| 283 | QVVDHAFGM | 5.000 |
| 570 | YVSGFGKAM | 5.000 |
| 778 | RVRDVELLT | 5.000 |
| 274 | VSARVIKAL | 4.000 |
| 240 | STLLKWLDL | 4.000 |
| 736 | NCPGWLDVL | 4.000 |
| 90 | SQCPEGFDL | 4.000 |
| 714 | VPIPTHYFV | 4.000 |
| 800 | EILQLKTYL | 4.000 |
| 196 | WLTAMYQGL | 4.000 |
| 540 | ITATVKVNL | 4.000 |
| 238 | RISTLLKWL | 4.000 |
| 253 | RPRFYTMYF | 4.000 |
| 72 | VCQGETSWL | 4.000 |
| 474 | GTHGSLNHL | 4.000 |
| 40 | KFRCGETRL | 4.000 |
| 400 | HLFVDQQWL | 4.000 |
| 615 | ESQKCSFYL | 4.000 |
| 171 | VNLNKNFSL | 4.000 |
| 527 | EQVNQMLNL | 4.000 |
| 165 | DNNMYDVNL | 4.000 |
| 583 | WSSYTVPQL | 4.000 |
| 380 | LTPDLPKRL | 4.000 |

TABLE XVIII-continued

| Start | Subsequence | Score |
|---|---|---|
| 556 | LQKNVDHCL | 4.000 |
| 52 | LCSCSDDCL | 4.000 |
| 302 | HNCVNIILL | 4.000 |
| 251 | AERPRFYTM | 3.000 |
| 233 | VPFEERIST | 3.000 |
| 409 | AVRSKSNTN | 3.000 |
| 29 | CVESTRIWM | 2.250 |
| 682 | GVNVVSGPI | 2.000 |
| 485 | VPFYEPSHA | 2.000 |
| 611 | VPPSESQKC | 2.000 |
| 297 | KQRNLHNCV | 2.000 |
| 121 | MPNINKLKT | 2.000 |
| 601 | VPDCLRADV | 1.800 |
| 608 | DVRVPPSES | 1.500 |
| 574 | FGKAMRMPM | 1.500 |
| 219 | NGSFPSIYM | 1.500 |
| 288 | AFGMLMEGL | 1.200 |
| 459 | NLMCDLLRI | 1.200 |
| 525 | QLEQVNQML | 1.200 |
| 512 | SLDCFCPHL | 1.200 |
| 193 | QPMWLTAMY | 1.200 |
| 217 | AINGSFPSI | 1.200 |
| 641 | TSDSQYDAL | 1.200 |
| 777 | ARVRDVELL | 1.200 |
| 359 | NSEEIVRNL | 1.200 |
| 470 | APNNGTHGS | 1.200 |
| 453 | ENIEVYNLM | 1.000 |
| 307 | IILLADHGM | 1.000 |
| 113 | YLYTWDTLM | 1.000 |
| 572 | SGFGKAMRM | 1.000 |
| 524 | TQLEQVNQM | 1.000 |
| 129 | TCGIHSKYM | 1.000 |
| 192 | GQPMWLTAM | 1.000 |
| 649 | LITSNLVPM | 1.000 |
| 45 | ETRLEASLC | 1.000 |
| 277 | RVIKALQVV | 1.000 |
| 198 | TAMYQGLKA | 0.900 |
| 577 | AMRMPMWSS | 0.900 |
| 248 | LPKAERPRF | 0.600 |
| 655 | VPMYEEFRK | 0.600 |
| 647 | DALITSNLV | 0.600 |
| 270 | AGGPVSARV | 0.600 |
| 528 | QVNQMLNLT | 0.500 |
| 363 | IVRNLSCRK | 0.500 |
| 670 | SVLLIKHAT | 0.500 |
| 13 | VACKDRGDC | 0.450 |
| 589 | PQLGDTSPL | 0.400 |
| 708 | HLANTDVPI | 0.400 |
| 299 | RNLHNCVNI | 0.400 |
| 807 | YLPTFETTI | 0.400 |
| 475 | THGSLNHLL | 0.400 |
| 452 | FENIEVYNL | 0.400 |
| 94 | EGFDLPPVI | 0.400 |
| 227 | MPYNGSVPF | 0.400 |
| 471 | PNNGTHGSL | 0.400 |
| 211 | WPGSEVAIN | 0.400 |

V2-HLA-B7-9mers-161P2F10B
Each peptide is a portion of SEQ ID NO:5; each start position is specified, the length of peptide is 9 amino acids, and the end position for each peptide is the start position plus eight.

| Start | Subsequence | Score |
|---|---|---|
| 5 | DCLQRKDCC | 0.100 |
| 6 | CLQRKDCCA | 0.100 |
| 7 | LQRKDCCAD | 0.100 |
| 4 | DDCLQRKDC | 0.015 |
| 1 | SCSDDCLQR | 0.010 |
| 2 | CSDDCLQRK | 0.003 |
| 8 | QRKDCCADY | 0.002 |
| 3 | SDDCLQRKD | 0.000 |
| 9 | RKDCCADYK | 0.000 |

TABLE XVIII-continued

V3-HLA-B7-9mers-161P2F10B
Each peptide is a portion of SEQ ID NO:7; each start position is specified, the length of peptide is 9 amino acids, and the end position for each peptide is the start position plus eight

| Start | Subsequence | Score |
|---|---|---|
| 7 | CPGGKPEAL | 80 |
| 9 | GGKPEALWV | 0.2 |
| 6 | SCPGGKPEA | 0.1 |
| 3 | NVESCPGGK | 0.015 |
| 5 | ESCPGGKPE | 0.01 |
| 2 | TNVESCPGG | 0.01 |
| 8 | PGGKPEALW | 0.003 |
| 4 | VESCPGGKP | 0.002 |
| 1 | PTNVESCPG | 0.001 |

V4-HLA-B7-9mers-161P2F10B
Each peptide is a portion of SEQ ID NO:9; each start position is specified, the length of peptide is 9 amino acids, and the end position for each peptide is the start position plus eight

| Start | Subsequence | Score |
|---|---|---|
| 2 | YLPTFETPI | 0.4 |
| 1 | TYLPTFETP | 0.001 |

TABLE XIX

| Start | Subsequence | Score |
|---|---|---|

V1-HLA-B7-10mers-161P2F10B
Each peptide is a portion of SEQ ID NO:3; each start position is specified, the length of peptide is 10 amino acids, and the end position for each peptide is the start position plus nine.

| Start | Subsequence | Score |
|---|---|---|
| 470 | APNNGTHGSL | 240.000 |
| 776 | IARVRDVELL | 120.000 |
| 588 | VPQLGDTSPL | 80.000 |
| 517 | CPHLQNSTQL | 80.000 |
| 233 | VPFEERISTL | 80.000 |
| 655 | VPMYEEFRKM | 60.000 |
| 371 | KPDQHFKPYL | 24.000 |
| 283 | QVVDHAFGML | 20.000 |
| 186 | NPAWWHGQPM | 20.000 |
| 170 | DVNLNKNFSL | 20.000 |
| 456 | EVYNLMCDLL | 20.000 |
| 71 | SVCQGETSWL | 20.000 |
| 504 | FANPLPTESL | 18.000 |
| 409 | AVRSKSNTNC | 15.000 |
| 287 | HAFGMLMEGL | 12.000 |
| 700 | DAPDEITKHL | 12.000 |
| 94 | EGFDLPPVIL | 6.000 |
| 343 | APRIRAHNIP | 6.000 |
| 275 | SARVIKALQV | 6.000 |
| 300 | NLHNCVNIIL | 4.000 |
| 89 | QSQCPEGFDL | 4.000 |
| 775 | HIARVRDVEL | 4.000 |
| 239 | ISTLLKWLDL | 4.000 |
| 392 | KNVRIDKVHL | 4.000 |
| 440 | GPSFKEKTEV | 4.000 |
| 547 | NLPFGRPRVL | 4.000 |
| 795 | VQPVSEILQL | 4.000 |
| 732 | HTPENCPGWL | 4.000 |
| 473 | NGTHGSLNHL | 4.000 |
| 555 | VLQKNVDHCL | 4.000 |
| 511 | ESLDCFCPHL | 4.000 |
| 51 | SLCSCSDDCL | 4.000 |
| 714 | VPIPTHYFVV | 4.000 |
| 757 | SCPEGKPEAL | 4.000 |

TABLE XIX-continued

| Start | Subsequence | Score |
|---|---|---|
| 330 | FPRINFFYMY | 4.000 |
| 663 | KMWDYFHSVL | 4.000 |
| 640 | RTSDSQYDAL | 4.000 |
| 524 | TQLEQVNQML | 4.000 |
| 428 | EFRSMEAIFL | 4.000 |
| 358 | FNSEEIVRNL | 4.000 |
| 735 | ENCPGWLDVL | 4.000 |
| 118 | DTLMPNINKL | 4.000 |
| 539 | EITATVKVNL | 4.000 |
| 556 | LQKNVDHCLL | 4.000 |
| 474 | GTHGSLNHLL | 4.000 |
| 499 | FSVCGFANPL | 4.000 |
| 379 | YLTPDLPKRL | 4.000 |
| 744 | LPFIIPHRPT | 3.000 |
| 648 | ALITSNLVPM | 3.000 |
| 716 | IPTHYFVVLT | 2.000 |
| 552 | RPRVLQKNVD | 2.000 |
| 595 | SPLPPTVPDC | 2.000 |
| 272 | GPVSARVIKA | 2.000 |
| 273 | PVSARVIKAL | 2.000 |
| 508 | LPTESLDCFC | 2.000 |
| 253 | RPRFYTMYFE | 2.000 |
| 121 | MPNINKLKTC | 2.000 |
| 506 | NPLPTESLDC | 2.000 |
| 701 | APDEITKHLA | 1.800 |
| 600 | TVPDCLRADV | 1.500 |
| 218 | INGSFPSIYM | 1.500 |
| 28 | TCVESTRIWM | 1.500 |
| 284 | WDHAFGMLM | 1.500 |
| 43 | CGETRLEASL | 1.200 |
| 270 | AGGPVSARVI | 1.200 |
| 292 | LMEGLKQRNL | 1.200 |
| 105 | SMDGFRAEYL | 1.200 |
| 624 | ADKNITHGFL | 1.200 |
| 188 | AWWHGQPMWL | 1.200 |
| 216 | VAINGSFPSI | 1.200 |
| 92 | CPEGFDLPPV | 1.200 |
| 111 | AEYLYTWDTL | 1.200 |
| 571 | VSGFGKAMRM | 1.000 |
| 423 | HGYNNEFRSM | 1.000 |
| 713 | DVPIPTHYFV | 1.000 |
| 191 | HGQPMWLTAM | 1.000 |
| 393 | NVRIDKVHLF | 1.000 |
| 159 | ESHGIIDNNM | 1.000 |
| 523 | STQLEQVNQM | 1.000 |
| 282 | LQVVDHAFGM | 1.000 |
| 97 | DLPPVILFSM | 1.000 |
| 136 | YMRAMYPTKT | 1.000 |
| 306 | NIILLADHGM | 1.000 |
| 317 | QTYCNKMEYM | 1.000 |
| 131 | GIHSKYMRAM | 1.000 |
| 128 | KTCGIHSKYM | 1.000 |
| 207 | ATYFWPGSEV | 0.900 |
| 198 | TAMYQGLKAA | 0.900 |
| 250 | KAERPRFYTM | 0.900 |
| 12 | DVACKDRGDC | 0.750 |
| 232 | SVPFEERIST | 0.750 |
| 608 | DVRVPPSESQ | 0.750 |
| 337 | YMYEGPAPRI | 0.600 |
| 676 | HATERNGVNV | 0.600 |
| 390 | YAKNVRIDKV | 0.600 |
| 773 | TAHIARVRDV | 0.600 |
| 193 | QPMWLTAMYQ | 0.600 |
| 767 | WVEERFTAHI | 0.600 |
| 580 | MPMWSSYTVP | 0.600 |
| 269 | HAGGPVSARV | 0.600 |

V2-HLA-B7-10mers-161P2F10B
Each peptide is a portion of SEQ ID NO:5;
each start position is
specified, the length of peptide is 10
amino acids, and the end position
for each peptide is the start position
plus nine.

| Start | Subsequence | Score |
|---|---|---|
| 8 | LQRKDCCADY | 0.200 |
| 6 | DCLQRKDCCA | 0.100 |
| 7 | CLQRKDCCAD | 0.010 |

TABLE XIX-continued

| Start | Subsequence | Score |
|---|---|---|
| 1 | CSCSDDCLQR | 0.010 |
| 5 | DDCLQRKDCC | 0.010 |
| 2 | SCSDDCLQRK | 0.010 |
| 4 | SDDCLQRKDC | 0.004 |
| 3 | CSDDCLQRKD | 0.003 |
| 9 | QRKDCCADYK | 0.001 |
| 10 | RKDCCADYKS | 0.001 |

V3-HLA-B7-10mers-161P2F10B
Each peptide is a portion of SEQ ID NO:7;
each start position is
specified, the length of peptide is 10
amino acids, and the end position
for each peptide is the start position
plus nine.

| Start | Subsequence | Score |
|---|---|---|
| 7 | SCPGGKPEAL | 4 |
| 8 | CPGGKPEALW | 0.6 |
| 1 | RPTNVESCPG | 0.2 |
| 6 | ESCPGGKPEA | 0.1 |
| 4 | NVESCPGGKP | 0.023 |
| 9 | PGGKPEALWV | 0.02 |
| 10 | GGKPEALWVE | 0.01 |
| 3 | TNVESCPGGK | 0.01 |
| 2 | PTNVESCPGG | 0.001 |
| 5 | VESCPGGKPE | 0.001 |

V4-HLA-A24-10mers-161P2F10B
Each peptide is a portion of SEQ ID NO:9;
each start position is
specified, the length of peptide is 10
amino acids, and the end position
for each peptide is the start position
plus nine.

| Start | Subsequence | Score |
|---|---|---|
| 2 | TYLPTFETPI | 0.04 |
| 1 | KTYLPTFETP | 0.01 |

TABLE XX

| Start | Subsequence | Score |
|---|---|---|

V1-HLA-B3501-9mers-161P2F10B
Each peptide is a portion of SEQ ID NO:3;
each start position is
specified, the length of peptide is 9
amino acids, and the end position
for each peptide is the start position
plus eight.

| Start | Subsequence | Score |
|---|---|---|
| 253 | RPRFYTMYF | 120.000 |
| 330 | FPRINFFYM | 120.000 |
| 248 | LPKAERPRF | 90.000 |
| 450 | EPFENIEVY | 80.000 |
| 98 | LPPVILFSM | 40.000 |
| 508 | LPTESLDCF | 40.000 |
| 193 | QPMWLTAMY | 40.000 |
| 133 | HSKYMRAMY | 30.000 |
| 796 | QPVSEILQL | 30.000 |
| 552 | RPRVLQKNV | 24.000 |
| 371 | KPDQHFKPY | 24.000 |
| 343 | APRIRAHNI | 24.000 |
| 597 | LPPTVPDCL | 20.000 |
| 548 | LPFGRPRVL | 20.000 |
| 716 | IPTHYFVVL | 20.000 |
| 227 | MPYNGSVPF | 20.000 |
| 496 | VSKFSVCGF | 15.000 |
| 701 | APDEITKHL | 12.000 |
| 776 | IARVRDVEL | 9.000 |
| 558 | KNVDHCLLY | 8.000 |
| 733 | TPENCPGWL | 6.000 |
| 758 | CPEGKPEAL | 6.000 |
| 347 | RAHNIPHDF | 6.000 |
| 138 | RAMYPTKTF | 6.000 |
| 638 | SNRTSDSQY | 6.000 |
| 233 | VPFEERIST | 6.000 |

TABLE XX-continued

| Start | Subsequence | Score |
|---|---|---|
| 574 | FGKAMRMPM | 6.000 |
| 583 | WSSYTVPQL | 5.000 |
| 615 | ESQKCSFYL | 5.000 |
| 274 | VSARVIKAL | 5.000 |
| 393 | NVRIDKVHL | 4.500 |
| 453 | ENIEVYNLM | 4.000 |
| 128 | KTCGIHSKY | 4.000 |
| 580 | MPMWSSYTV | 4.000 |
| 714 | VPIPTHYFV | 4.000 |
| 351 | IPHDFFSFN | 4.000 |
| 626 | KNITHGFLY | 4.000 |
| 283 | QVVDHAFGM | 4.000 |
| 524 | TQLEQVNQM | 4.000 |
| 803 | QLKTYLPTF | 3.000 |
| 611 | VPPSESQKC | 3.000 |
| 368 | SCRKPDQHF | 3.000 |
| 359 | NSEEIVRNL | 3.000 |
| 556 | LQKNVDHCL | 3.000 |
| 764 | EALWVEERF | 3.000 |
| 485 | VPFYEPSHA | 3.000 |
| 161 | HGIIDNNMY | 3.000 |
| 180 | SSKEQNNPA | 3.000 |
| 211 | WPGSEVAIN | 3.000 |
| 238 | RISTLLKWL | 2.000 |
| 222 | FPSIYMPYN | 2.000 |
| 562 | HCLLYHREY | 2.000 |
| 685 | VVSGPIFDY | 2.000 |
| 649 | LITSNLVPM | 2.000 |
| 650 | ITSNLVPMY | 2.000 |
| 146 | FPNHYTIVT | 2.000 |
| 218 | INGSFPSIY | 2.000 |
| 634 | YPPASNRTS | 2.000 |
| 107 | DGFRAEYLY | 2.000 |
| 783 | ELLTGLDFY | 2.000 |
| 570 | YVSGFGKAM | 2.000 |
| 121 | MPNINKLKT | 2.000 |
| 113 | YLYTWDTLM | 2.000 |
| 317 | QTYCNKMEY | 2.000 |
| 231 | GSVPFEERI | 2.000 |
| 417 | NCGGGNHGY | 2.000 |
| 219 | NGSFPSIYM | 2.000 |
| 129 | TCGIHSKYM | 2.000 |
| 201 | YQGLKAATY | 2.000 |
| 307 | IILLADHGM | 2.000 |
| 687 | SGPIFDYNY | 2.000 |
| 192 | GQPMWLTAM | 2.000 |
| 489 | EPSHAEEVS | 2.000 |
| 794 | KVQPVSEIL | 2.000 |
| 470 | APNNGTHGS | 2.000 |
| 572 | SGFGKAMRM | 2.000 |
| 430 | RSMEAIFLA | 2.000 |
| 380 | LTPDLPKRL | 2.000 |
| 641 | TSDSQYDAL | 1.500 |
| 203 | GLKAATYFW | 1.500 |
| 350 | NIPHDFFSF | 1.500 |
| 400 | HLFVDQQWL | 1.500 |
| 90 | SQCPEGEDL | 1.500 |
| 72 | VCQGETSWL | 1.500 |
| 124 | INKLKTCGI | 1.200 |
| 61 | QKKDCCADY | 1.200 |
| 778 | RVRDVELLT | 1.200 |
| 601 | VPDCLRADV | 1.200 |
| 297 | KQRNLHNCV | 1.200 |
| 736 | NCPGWLDVL | 1.000 |
| 732 | HTPENCPGW | 1.000 |
| 196 | WLTAMYQGL | 1.000 |
| 28 | TCVESTRIW | 1.000 |
| 683 | VNVVSGPIF | 1.000 |
| 202 | QGLKAATYF | 1.000 |
| 500 | SVCGFANPL | 1.000 |
| 527 | EQVNQMLNL | 1.000 |
| 88 | QQSQCPEGF | 1.000 |
| 713 | DVPIPTHYF | 1.000 |
| 302 | HNCVNIILL | 1.000 |

TABLE XX-continued

| Start | Subsequence | Score |
|---|---|---|

V2-HLA-B35-9mers-161P2F10B
Each peptide is a portion of SEQ ID NO:5;
each start position is
specified, the length of peptide is 9
amino acids, and the end position
for each peptide is the start position
plus eight.

| 8 | QRKDCCADY | 1.200 |
| 5 | DCLQRKDCC | 0.100 |
| 6 | CLQRKDCCA | 0.100 |
| 7 | LQRKDCCAD | 0.045 |
| 1 | SCSDDCLQR | 0.030 |
| 2 | CSDDCLQRK | 0.030 |
| 4 | DDCLQRKDC | 0.010 |
| 9 | RKDCCADYK | 0.001 |
| 3 | SDDCLQRKD | 0.000 |

V3-HLA-B35-9mers-161P2F10B
Each peptide is a portion of SEQ ID NO:7
each start position is
specified, the length of peptide is 9
amino acids, and the end position
for each peptide is the start position
plus eight.

| 7 | CPGGKPEAL | 20 |
| 9 | GGKPEALWV | 0.9 |
| 6 | SCPGGKPEA | 0.1 |
| 8 | PGGKPEALW | 0.05 |
| 5 | ESCPGGKPE | 0.05 |
| 2 | TNVESCPGG | 0.02 |
| 3 | NVESCPGGK | 0.003 |
| 1 | PTNVESCPG | 0.002 |
| 4 | VESCPGGKP | 0.001 |

V4-HLA-B35-9mers-161P2F10B
Each peptide is a portion of SEQ ID NO:9;
each start position is
specified, the length of peptide is 9
amino acids, and the end position
for each peptide is the start position
plus eight.

| 2 | YLPTFETPI | 0.4 |
| 1 | TYLPTFETP | 0.001 |

TABLE XXI

| Start | Subsequence | Score |
|---|---|---|

V1-HLA-B35-10mers-161P2F10B
Each peptide is a portion of SEQ ID NO:3;
each start position is
specified, the length of peptide is 10
amino acids, and the end position
for each peptide is the start position
plus nine.

| 248 | LPKAERPRFY | 120.000 |
| 330 | FPRINFFYMY | 120.000 |
| 655 | VPMYEEFRKM | 60.000 |
| 233 | VPFEERISTL | 40.000 |
| 141 | YPTKTFPNHY | 40.000 |
| 186 | NPAWWHGQPM | 40.000 |
| 737 | CPGWLDVLPF | 30.000 |
| 588 | VPQLGDTSPL | 30.000 |
| 104 | FSMDGFRAEY | 20.000 |
| 470 | APNNGTHGSL | 20.000 |
| 517 | CPHLQNSTQL | 20.000 |
| 180 | SSKEQNNPAW | 15.000 |
| 776 | IARVRDVELL | 13.500 |
| 371 | KPDQHFKPYL | 12.000 |
| 381 | TPDLPKRLHY | 12.000 |

TABLE XXI-continued

| Start | Subsequence | Score |
|---|---|---|
| 686 | VSGPIFDYNY | 10.000 |
| 220 | GSFPSIYMPY | 10.000 |
| 571 | VSGFGKAMRM | 10.000 |
| 511 | ESLDCFCPHL | 10.000 |
| 159 | ESHGIIDNNM | 10.000 |
| 637 | ASNRTSDSQY | 10.000 |
| 89 | QSQCPEGFDL | 7.500 |
| 280 | KALQVVDHAF | 6.000 |
| 700 | DAPDEITKHL | 6.000 |
| 347 | RAHNIPHDFF | 6.000 |
| 577 | AMRMPMWSSY | 6.000 |
| 320 | CNKMEYMTDY | 6.000 |
| 440 | GPSFKEKTEV | 6.000 |
| 384 | LPKRLHYAKN | 6.000 |
| 60 | LQKKDCCADY | 6.000 |
| 499 | FSVCGFANPL | 5.000 |
| 239 | ISTLLKWLDL | 5.000 |
| 367 | LSCRKPDQHF | 5.000 |
| 70 | KSVCQGETSW | 5.000 |
| 556 | LQKNVDHCLL | 4.500 |
| 612 | PPSESQKCSF | 4.000 |
| 640 | RTSDSQYDAL | 4.000 |
| 351 | IPHDFFSFNS | 4.000 |
| 508 | LPTESLDCFC | 4.000 |
| 663 | KMWDYFHSVL | 4.000 |
| 714 | VPIPTHYFVV | 4.000 |
| 28 | TCVESTRIWM | 4.000 |
| 450 | EPEENIEVYN | 4.000 |
| 128 | KTCGIHSKYM | 4.000 |
| 250 | KAERPRFYTM | 3.600 |
| 287 | HAFGMLMEGL | 3.000 |
| 32 | STRIWMCNKF | 3.000 |
| 393 | NVRIDKVHLF | 3.000 |
| 14 | ACKDRGDCCW | 3.000 |
| 392 | KNVRIDKVHL | 3.000 |
| 758 | CPEGKPEALW | 3.000 |
| 541 | TATVKVNLPF | 3.000 |
| 423 | HGYNNEFRSM | 3.000 |
| 506 | NPLPTESLDC | 3.000 |
| 798 | VSEILQLKTY | 3.000 |
| 504 | FANPLPTESL | 3.000 |
| 97 | DLPPVILFSM | 2.000 |
| 316 | DQTYCNKMEY | 2.000 |
| 595 | SPLPPTVPDC | 2.000 |
| 272 | GPVSARVIKA | 2.000 |
| 648 | ALITSNLVPM | 2.000 |
| 479 | LNHLLKVPFY | 2.000 |
| 283 | QVVDHAFGML | 2.000 |
| 416 | TNCGGGNHGY | 2.000 |
| 131 | GIHSKYMRAM | 2.000 |
| 649 | LITSNLVPMY | 2.000 |
| 684 | NVVSGPIFDY | 2.000 |
| 306 | NIILLADHGM | 2.000 |
| 121 | MPNINKLKTC | 2.000 |
| 358 | FNSEEIVRNL | 2.000 |
| 218 | INGSFPSIYM | 2.000 |
| 192 | GQPMWLTAMY | 2.000 |
| 317 | QTYCNKMEYM | 2.000 |
| 757 | SCPEGKPEAL | 2.000 |
| 611 | VPPSESQKCS | 2.000 |
| 744 | LPFIIPHRPT | 2.000 |
| 217 | AINGSFPSIY | 2.000 |
| 191 | HGQPMWLTAM | 2.000 |
| 341 | GPAPRIRAHN | 2.000 |
| 732 | HTPENCPGWL | 2.000 |
| 282 | LQVVDHAFGM | 2.000 |
| 716 | IPTHYFVVLT | 2.000 |
| 94 | EGFDLPPVIL | 2.000 |
| 523 | STQLEQVNQM | 2.000 |
| 619 | CSFYLADKNI | 2.000 |
| 524 | TQLEQVNQML | 2.000 |
| 748 | IPHRPTNVES | 2.000 |
| 390 | YAKNVRIDKV | 1.800 |
| 310 | LADHGMDQTY | 1.800 |
| 275 | SARVIKALQV | 1.800 |
| 92 | CPEGFDLPPV | 1.800 |
| 71 | SVCQGETSWL | 1.500 |
| 213 | GSEVAINGSF | 1.500 |
| 349 | HNIPHDFFSF | 1.500 |
| 795 | VQPVSEILQL | 1.500 |
| 574 | FGKAMRMPMW | 1.500 |
| 496 | VSKFSVCGFA | 1.500 |
| 247 | DLPKAERPRF | 1.500 |
| 552 | RPRVLQKNVD | 1.200 |
| 676 | HATERNGVNV | 1.200 |

V2-HLA-B35-10mers-161P2F10B
Each peptide is a portion of SEQ ID NO:5;
each start position is
specified, the length of peptide is 10
amino acids, and the end position
for each peptide is the start position
plus nine.

| Start | Subsequence | Score |
|---|---|---|
| 8 | LQRKDCCADY | 6.000 |
| 6 | DCLQRKDCCA | 0.100 |
| 1 | CSCSDDCLQR | 0.075 |
| 3 | CSDDCLQRKD | 0.030 |
| 2 | SCSDDCLQRK | 0.020 |
| 7 | CLQRKDCCAD | 0.015 |
| 5 | DDCLQRKDCC | 0.010 |
| 9 | QRKDCCADYK | 0.006 |
| 10 | RKDCCADYKS | 0.006 |
| 4 | SDDCLQRKDC | 0.003 |

V3-B35-10mers-161P2F10B
Each peptide is a portion of SEQ ID NO:7;
each start position is
specified, the length of peptide is 10
amino acids, and the end position
for each peptide is the start position
plus nine.

| Start | Subsequence | Score |
|---|---|---|
| 8 | CPGGKPEALW | 10 |
| 7 | SCPGGKPEAL | 1 |
| 1 | RPTNVESCPG | 0.6 |
| 6 | ESCPGGKPEA | 0.5 |
| 9 | PGGKPEALWV | 0.03 |
| 10 | GGKPEALWVE | 0.03 |
| 3 | TNVESCPGGK | 0.02 |
| 4 | NVESCPGGKP | 0.003 |
| 2 | PTNVESCPGG | 0.001 |
| 5 | VESCPGGKPE | 0.001 |

V4-HLA-B35-10mers-161P2F10B
Each peptide is a portion of SEQ ID NO:9;
each start position is
specified, the length of peptide is 10
amino acids, and the end position
for each peptide is the start position
plus nine.

| Start | Subsequence | Score |
|---|---|---|
| 2 | TYLPTFETPI | 0.04 |
| 1 | KTYLPTFETP | 0.02 |

TABLE XXII

| Pos | 123456789 | score |
|---|---|---|

V1-HLA-A1-9mers-161P2F10B
Each peptide is a portion of SEQ ID NO: 81; each
start position is specified, the length of the
peptide is 9 amino acids and the end position for
each peptide is the start position plus 8.

| Pos | 123456789 | score |
|---|---|---|
| 165 | SMDGFRAEY | 29 |
| 431 | KPDQHFKPY | 28 |
| 442 | PDLPKRLHY | 26 |
| 188 | KTCGIHSKY | 24 |
| 618 | KNVDHCLLY | 23 |
| 710 | ITSNLVPMY | 23 |

TABLE XXII-continued

| Pos | 123456789 | score |
|---|---|---|
| 858 | VSEILQLKT | 23 |
| 8 | ATEQPVKKN | 21 |
| 193 | HSKYMRAMY | 21 |
| 202 | PTKTFPNHY | 21 |
| 377 | QTYCNKMEY | 21 |
| 491 | SMEAIFLAH | 21 |
| 209 | HYTIVTGLY | 19 |
| 391 | PRINFFYMY | 19 |
| 462 | FVDQQWLAV | 19 |
| 477 | NCGGGNHGY | 19 |
| 514 | NIEVYNLMC | 19 |
| 638 | MRMPMWSSY | 19 |
| 772 | TDVPIPTHY | 19 |
| 859 | SEILQLKTY | 19 |
| 13 | VKKNTLKKY | 18 |
| 389 | YFPRINFFY | 18 |
| 455 | RIDKVHLFV | 18 |
| 686 | KNITHGFLY | 18 |
| 737 | ATERNGVNV | 18 |
| 745 | VVSGPIFDY | 18 |
| 843 | ELLTGLDFY | 18 |
| 152 | CPEGFDLPP | 17 |
| 167 | DGFRAEYLY | 17 |
| 217 | YPESHGIID | 17 |
| 221 | HGIIDNNMY | 17 |
| 261 | YQGLKAATY | 17 |
| 281 | SFPSIYMPY | 17 |
| 371 | ADHGMDQTY | 17 |
| 420 | SEEIVRNLS | 17 |
| 674 | SESQKCSFY | 17 |
| 698 | SNRTSDSQY | 17 |
| 747 | SGPIFDYNY | 17 |
| 771 | NTDVPIPTH | 17 |
| 839 | VRDVELLTG | 17 |
| 115 | CSDDCLQKK | 16 |
| 134 | QGETSWLEE | 16 |
| 253 | QPMWLTAMY | 16 |
| 312 | ERPRFYTMY | 16 |
| 381 | NKMEYMTDY | 16 |
| 386 | MTDYFPRIN | 16 |
| 506 | KTEVEPFEN | 16 |
| 510 | EPFENIEVY | 16 |
| 540 | NHLLKVPFY | 16 |
| 569 | PTESLDCFC | 16 |
| 602 | ATVKVNLPF | 16 |
| 619 | NVDHCLLYH | 16 |
| 622 | HCLLYHREY | 16 |
| 651 | LGDTSPLPP | 16 |
| 659 | PTVPDCLRA | 16 |
| 673 | PSESQKCSF | 16 |
| 701 | TSDSQYDAL | 16 |
| 89 | CVESTRIWM | 15 |
| 121 | QKKDCCADY | 15 |
| 210 | YTIVTGLYP | 15 |
| 278 | INGSFPSIY | 15 |
| 309 | PKAERPRFY | 15 |
| 321 | FEEPDSSGH | 15 |
| 344 | VVDHAFGML | 15 |
| 419 | NSEEIVRNL | 15 |
| 521 | MCDLLRIQP | 15 |
| 547 | FYEPSHAEE | 15 |
| 585 | QLEQVNQML | 15 |
| 719 | EEFRKMWDY | 15 |
| 851 | YQDKVQPVS | 15 |
| 47 | KLEKQGSCR | 14 |
| 116 | SDDCLQKKD | 14 |
| 273 | GSEVAINGS | 14 |
| 300 | STLLKWLDL | 14 |
| 508 | EVEPFENIE | 14 |
| 646 | YTVPQLGDT | 14 |
| 754 | NYDGHFDAP | 14 |
| 847 | GLDFYQDKV | 14 |

TABLE XXII-continued

| Pos | 123456789 | score |
|---|---|---|

V2-HLA-A1-9mers-161P2F10B
Each peptide is a portion of SEQ ID NO: 82; each start position is specified, the length of the peptide is 9 amino acids and the end position for each peptide is the start position plus 8.

| 8 | QRKDCCADY | 15 |
|---|---|---|
| 2 | CSDDCLQRK | 14 |
| 3 | SDDCLQRKD | 14 |
| 9 | RKDCCADYK | 10 |
| 1 | SCSDDCLQR | 8 |

V3-HLA-A1-9mers-161P2F108
Each peptide is a portion of SEQ ID NO: 85; each start position is specified, the length of the peptide is 9 amino acids and the end position for each peptide is the start position plus 8.

| 5 | ESCPGGKPE | 11 |
|---|---|---|
| 3 | NVESCPGGK | 10 |
| 9 | GGKPEALWV | 10 |
| 1 | PTNVESCPG | 6 |
| 4 | VESCPGGKP | 5 |

V4-HLA-A1-9mers-161P2F10B
Each peptide is a portion of SEQ ID NO: 88; each start position is specified, the length of the peptide is 9 amino acids and the end position for each peptide is the start position plus 8.

| 1 | TYLPTFETP | 7 |
|---|---|---|
| 2 | YLPTFETPI | 3 |

TABLE XXIII

| Pos | 123456789 | score |
|---|---|---|

V1-HLA-A0201-9mers-161P2F10B
Each peptide is a portion of SEQ ID NO: 81; each start position is specified, the length of the peptide is 9 amino acids and the end position for each peptide is the start position plus 8.

| 179 | TLMPNINKL | 30 |
|---|---|---|
| 40 | GLGLGLRKL | 29 |
| 723 | KMWDYFHSV | 25 |
| 27 | VLLALLVIM | 24 |
| 29 | LALLVIMSL | 24 |
| 31 | LLVIMSLGL | 24 |
| 215 | GLYPESHGI | 24 |
| 277 | AINGSFPSI | 24 |
| 519 | NLMCDLLRI | 24 |
| 572 | SLDCFCPHL | 24 |
| 33 | VIMSLGLGL | 23 |
| 360 | NLHNCVNII | 23 |
| 847 | GLDFYQDKV | 23 |
| 867 | YLPTFETTI | 23 |
| 23 | IACIVLLAL | 22 |
| 298 | RISTLLKWL | 22 |
| 534 | GTHGSLNHL | 22 |
| 607 | NLPFGRPRV | 22 |
| 768 | HLANTDVPI | 22 |
| 24 | ACIVLLALL | 21 |
| 26 | IVLLALLVI | 21 |
| 223 | IIDNNMYDV | 21 |
| 259 | AMYQGLKAA | 21 |
| 460 | HLFVDQQWL | 21 |
| 592 | MLNLTQEEI | 21 |
| 623 | CLLYHREYV | 21 |
| 21 | YKIACIVLL | 20 |
| 22 | KIACIVLLA | 20 |
| 25 | CIVLLALLV | 20 |
| 65 | GLENCRCDV | 20 |
| 256 | WLTAMYQGL | 20 |
| 300 | STLLKWLDL | 20 |
| 337 | RVIKALQVV | 20 |

TABLE XXIII-continued

| Pos | 123456789 | score |
|---|---|---|
| 385 | YMTDYFPRI | 20 |
| 439 | YLTPDLPKR | 20 |
| 537 | GSLNHLLKV | 20 |
| 560 | SVCGFANPL | 20 |
| 600 | ITATVKVNL | 20 |
| 807 | IIPHRPTNV | 20 |
| 836 | IARVRDVEL | 20 |
| 28 | LLALLVIMS | 19 |
| 37 | LGLGLGLGL | 19 |
| 204 | KTFPNHYTI | 19 |
| 451 | AKNVRIDKV | 19 |
| 455 | RIDKVHLFV | 19 |
| 585 | QLEQVNQML | 19 |
| 653 | DTSPLPPTV | 19 |
| 709 | LITSNLVPM | 19 |
| 800 | WLDVLPFII | 19 |
| 5 | LTLATEQPV | 18 |
| 36 | SLGLGLGLG | 18 |
| 285 | IYMPYNGSV | 18 |
| 351 | MLMEGLKQR | 18 |
| 443 | DLPKRLHYA | 18 |
| 682 | YLADKNITH | 18 |
| 731 | VLLIKHATE | 18 |
| 834 | AHIARVRDV | 18 |
| 840 | RDVELLTGL | 18 |
| 860 | EILQLKTYL | 18 |
| 35 | MSLGLGLGL | 17 |
| 38 | GLGLGLGLR | 17 |
| 139 | WLEENCDTA | 17 |
| 165 | SMDGFRAEY | 17 |
| 173 | YLYTWDTLM | 17 |
| 334 | VSARVIKAL | 17 |
| 397 | YMYEGPAPR | 17 |
| 440 | LTPDLPKRL | 17 |
| 462 | FVDQQWLAV | 17 |
| 512 | FENIEVYNL | 17 |
| 538 | SLNHLLKVP | 17 |
| 565 | ANPLPTESL | 17 |
| 595 | LTQEEITAT | 17 |
| 596 | TQEEITATV | 17 |
| 737 | ATERNGVNV | 17 |
| 738 | TERNGVNVV | 17 |
| 799 | GWLDVLPFI | 17 |
| 825 | ALWVEERFT | 17 |
| 850 | FYQDKVQPV | 17 |
| 854 | KVQPVSEIL | 17 |
| 863 | QLKTYLPTF | 17 |
| 34 | IMSLGLGLG | 16 |
| 157 | DLPPVILFS | 16 |
| 208 | NHYTIVTGL | 16 |
| 231 | VNLNKNFSL | 16 |
| 301 | TLLKWLDLP | 16 |
| 330 | AGGPVSARV | 16 |
| 453 | NVRIDKVHL | 16 |
| 520 | LMCDLLRIQ | 16 |
| 646 | YTVPQLGDT | 16 |
| 706 | YDALITSNL | 16 |
| 707 | DALITSNLV | 16 |
| 732 | LLIKHATER | 16 |
| 774 | VPIPTHYFV | 16 |
| 796 | NCPGWLDVL | 16 |
| 806 | FIIPHRPTN | 16 |
| 837 | ARVRDVELL | 16 |
| 861 | ILQLKTYLP | 16 |
| 18 | LKKYKIACI | 15 |
| 104 | GETRLEASL | 15 |
| 107 | RLEASLCSC | 15 |
| 119 | CLCKKDCCA | 15 |
| 132 | VCQGETSWL | 15 |
| 211 | TIVTGLYPE | 15 |
| 305 | WLDLPKAER | 15 |
| 328 | GHAGGPVSA | 15 |
| 340 | KALQVVDHA | 15 |
| 344 | VVDHAFGML | 15 |
| 369 | LLADHGMDQ | 15 |
| 419 | NSEEIVRNL | 15 |
| 496 | FLAHGPSFK | 15 |
| 542 | LLKVPFYEP | 15 |
| 591 | QMLNLTQEE | 15 |
| 594 | NLTQEEITA | 15 |
| 598 | EEITATVKV | 15 |
| 608 | LPFGRPRVL | 15 |
| 615 | VLQKNVDHC | 15 |
| 692 | FLYPPASNR | 15 |
| 708 | ALITSNLVP | 15 |
| 735 | KHATERNGV | 15 |
| 761 | APDEITKHL | 15 |
| 775 | PIPTHYFVV | 15 |
| 803 | VIPFIIPHR | 15 |
| 831 | RFTAHLARV | 15 |
| 843 | ELLTGLDFY | 15 |
| 856 | QPVSEILQL | 15 |
| 865 | KTYLPTFET | 15 |
| 30 | ALLVIMSLG | 14 |
| 42 | GLGLRKLEK | 14 |
| 150 | SQCPEGFDL | 14 |
| 155 | GFDLPPVIL | 14 |
| 191 | GIHSKYMRA | 14 |
| 268 | TYFWPGSEV | 14 |
| 270 | FWPGSEVAI | 14 |
| 284 | SIYMPYNGS | 14 |
| 294 | PFEERISTL | 14 |
| 303 | LKWLDLPKA | 14 |
| 336 | ARVIKALQV | 14 |
| 341 | ALQVVDHAF | 14 |
| 348 | AFGMLMEGL | 14 |
| 350 | GMLMEGLKQ | 14 |
| 362 | HNCVNIILL | 14 |
| 368 | ILLADHGMD | 14 |
| 436 | FKPYLTPDL | 14 |
| 448 | LHYAKNVRI | 14 |
| 524 | LLRIQPAPN | 14 |
| 548 | YEPSHAEEV | 14 |
| 581 | QNSTQLEQV | 14 |
| 588 | QVNQMLNLT | 14 |
| 624 | LLYHREYVS | 14 |
| 640 | MPMWSSYTV | 14 |
| 643 | WSSYTVPQL | 14 |
| 656 | PLPPTVPDC | 14 |
| 661 | VPDCLRADV | 14 |
| 664 | CLRADVRVP | 14 |
| 688 | ITHGFLYPP | 14 |
| 713 | NLVPMYEEF | 14 |
| 716 | PMYEEFRKM | 14 |
| 730 | SVLLIKHAT | 14 |
| 742 | GVNVVSGPI | 14 |
| 764 | EITKHLANT | 14 |
| 776 | IPTHYFVVL | 14 |
| 844 | LLTGLDFYQ | 14 |
| 853 | DKVQPVSEI | 14 |

V2-HLA-A0201-9mers-161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 6 | CLQRKDCCA | 15 |
| 2 | CSDDCLQRK | 5 |
| 3 | SDDCLQRKD | 5 |

V3-HLA-A0201-9mers-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
| 7 | CPGGKPEAL | 14 |
| 8 | SCPGGKPEA | 13 |
| 9 | GGKPEALWV | 13 |

TABLE XXIII-continued

| Pos | 123456789 | score |
|---|---|---|
| V4-HLA-A0201-9mers-161P2F10B  Each peptide is a portion of SEQ ID NO: 88; each start position is specified, the length of the peptide is 9 amino acids and the end position for each peptide is the start position plus 8. | | |
| 2 | YLPTFETPI | 21 |

TABLE XXIV

| Pos | 123456789 | score |
|---|---|---|
| V1-HLA-A0203-9mers-161P2F10B | | |
| No Results Found. | | |
| V2-HLA-A0203-9mers-161P2F10B | | |
| No Results Found. | | |
| V3-HLA-A0203-9mers-161P2F10B | | |
| No Results Found. | | |
| V4-HLA-A0203-9mers-161P2F10B | | |
| No Results Found. | | |

TABLE XXV

| Pos | 123456789 | score |
|---|---|---|
| V1-HLA-A3-9mers-161P2F10B  Each peptide is a portion of SEQ ID NO: 81; each start position is specified, the length of the peptide is 9 amino acids and the end position for each peptide is the start position plus 8. | | |
| 670 | RVPPSESQK | 33 |
| 496 | FLAHGPSFK | 27 |
| 692 | FLYPPASNR | 27 |
| 42 | GLGLRKLEK | 26 |
| 423 | IVRNLSCRK | 26 |
| 6 | TLATEQPVK | 25 |
| 614 | RVLQKNVDH | 25 |
| 12 | PVKKNTLKK | 24 |
| 302 | LLKWLDLPK | 24 |
| 610 | FGRPRVLQK | 24 |
| 47 | KLEKQGSCR | 23 |
| 708 | ALITSNLVP | 23 |
| 26 | IVLLALLVI | 22 |
| 447 | RLHYAKNVR | 22 |
| 782 | VVLTSCKNK | 22 |
| 838 | RVRDVELLT | 22 |
| 337 | RVIKALQVV | 21 |
| 405 | RIRAHNIPH | 21 |
| 469 | AVRSKSNTN | 21 |
| 597 | QEEITATVK | 21 |
| 628 | REYVSGFGK | 21 |
| 682 | YLADKNITH | 21 |
| 731 | VLLIKHATE | 21 |
| 732 | LLIKHATER | 21 |
| 814 | NVESCPEGK | 21 |
| 857 | PVSEILQLK | 21 |
| 863 | QLKTYLPTF | 21 |
| 39 | LGLGLGLRK | 20 |
| 351 | MLMEGLKQR | 20 |
| 624 | LLYHREYVS | 20 |
| 843 | ELLTGLDFY | 20 |
| 196 | YMRAMYPTK | 19 |
| 227 | NMYDVNLNK | 19 |
| 338 | VIKALQVVD | 19 |
| 341 | ALQVVDHAF | 19 |
| 544 | KVPFYEPSH | 19 |
| 664 | CLRADVRVP | 19 |

TABLE XXV-continued

| Pos | 123456789 | score |
|---|---|---|
| 802 | DVLPFIIPH | 19 |
| 806 | FIIPHRPTN | 19 |
| 827 | WVEERFTAH | 19 |
| 27 | VLLALLVIM | 18 |
| 30 | ALLVIMSLG | 18 |
| 38 | GLGLGLGLR | 18 |
| 107 | RLEASLCSC | 18 |
| 114 | SCSDDCLQK | 18 |
| 261 | YQGLKAATY | 18 |
| 275 | EVAINGSFP | 18 |
| 306 | WLDLPKAER | 18 |
| 368 | ILLADHGMD | 18 |
| 422 | EIVRNLSCR | 18 |
| 453 | NVRIDKVHL | 18 |
| 524 | LLRIQPAPN | 18 |
| 550 | PSHAEEVSK | 18 |
| 745 | VVSGPIFDY | 18 |
| 759 | FDAPDEITK | 18 |
| 835 | HIARVRDVE | 18 |
| 157 | DLPPVILFS | 17 |
| 162 | ILFSMDGFR | 17 |
| 186 | KLKTCGIHS | 17 |
| 215 | GLYPESHGI | 17 |
| 296 | EERISTLLK | 17 |
| 439 | YLTPDLPKR | 17 |
| 458 | KVHLFVDQQ | 17 |
| 619 | NVDHCLLYH | 17 |
| 647 | TVPQLGDTS | 17 |
| 668 | DVRVPPSES | 17 |
| 713 | NLVPMYEEF | 17 |
| 854 | KVQPVSEIL | 17 |
| 7 | LATEQPVKK | 16 |
| 44 | GLRKLEKQG | 16 |
| 68 | NCRCDVACK | 16 |
| 94 | RIWMCNKFR | 16 |
| 122 | KKDCCADYK | 16 |
| 131 | SVCQGETSW | 16 |
| 343 | QVVDHAFGM | 16 |
| 355 | GLKQRNLHN | 16 |
| 369 | LLADHGMDQ | 16 |
| 442 | PDLPKRLHY | 16 |
| 455 | RIDKVHLFV | 16 |
| 498 | AHGPSFKEK | 16 |
| 523 | DLLRIQPAP | 16 |
| 526 | RIQPAPNNG | 16 |
| 560 | SVCGFANPL | 16 |
| 630 | YVSGFGKAM | 16 |
| 678 | KCSFYLADK | 16 |
| 698 | SNRTSDSQY | 16 |
| 768 | HLANTDVPI | 16 |
| V2-HLA-A3-9mers-161P2F10B  Each peptide is a portion of SEQ ID NO: 82; each start position is specified, the length of the peptide is 9 amino acids and the end position for each peptide is the start position plus 8. | | |
| 9 | RKDCCADYK | 17 |
| 6 | CLQRKDCCA | 14 |
| 8 | QRKDCCADY | 13 |
| 1 | SCSDDCLQR | 12 |
| 2 | CSDDCLQRK | 11 |
| V3-HLA-A3-9mers-161P2F10B  Each peptide is a portion of SEQ ID NO: 85; each start position is specified, the length of the peptide is 9 amino acids and the end position for each peptide is the start position plus 8. | | |
| 3 | NVESCPGGK | 22 |
| 9 | GGKPEALWV | 11 |
| V4-HLA-A3-9mers-161P2F10B  Each peptide is a portion of SEQ ID NO: 88; each start position is specified, the length of the peptide is 9 amino acids and the end position for each peptide is the start position plus 8. | | |
| 2 | YLPTFETPI | 11 |

TABLE XXVI

| Pos | 123456789 | score |
|---|---|---|
| | V1-HLA-A26-9mers-161P2F10B | |

Each peptide is a portion of SEQ ID NO: 81; each start position is specified, the length of the peptide is 9 amino acids and the end position for each peptide is the start position plus 8.

| Pos | 123456789 | score |
|---|---|---|
| 510 | EPFENIEVY | 31 |
| 516 | EVYNLMCDL | 29 |
| 773 | DVPIPTHYF | 26 |
| 388 | DYFPRINFF | 25 |
| 719 | EEFRKMWDY | 25 |
| 422 | EIVRNLSCR | 24 |
| 710 | ITSNLVPMY | 24 |
| 745 | VVSGPIFDY | 24 |
| 802 | DVLPFIIPH | 24 |
| 843 | ELLTGLDFY | 24 |
| 275 | EVAINGSFP | 23 |
| 587 | EQVNQMLNL | 23 |
| 860 | EILQLKIYL | 23 |
| 167 | DGFRAEYLY | 22 |
| 188 | KTCGIHSKY | 22 |
| 297 | ERISTLLKW | 21 |
| 312 | ERPRFYTMY | 21 |
| 508 | EVEPFENIE | 21 |
| 602 | ATVKVNLPF | 21 |
| 10 | EQPVKKNTL | 20 |
| 344 | VVDHAFGML | 20 |
| 534 | GTHGSLNHL | 20 |
| 555 | EVSKFSVCG | 20 |
| 841 | DVELLTGLD | 20 |
| 859 | SEILQLKTY | 20 |
| 32 | LVIMSLGLG | 19 |
| 72 | DVACKDRGD | 19 |
| 105 | ETRLEASLC | 19 |
| 136 | ETSWLEENC | 19 |
| 172 | EYLYTWDTL | 19 |
| 230 | DVNLNKNFS | 19 |
| 300 | STLLKWLDL | 19 |
| 377 | QTYCNKMEY | 19 |
| 488 | EFRSMEAIF | 19 |
| 560 | SVCGFANPL | 19 |
| 599 | EITATVKVN | 19 |
| 653 | DTSPLPP1V | 19 |
| 668 | DVRVPPSES | 19 |
| 764 | EITKHLANT | 19 |
| 840 | RDVELLTGL | 19 |
| 854 | KVQPVSEIL | 19 |
| 856 | QPVSEILQL | 19 |
| 202 | PTKTFPNHY | 18 |
| 337 | RVIKALQVV | 18 |
| 364 | CVNIILLAD | 18 |
| 440 | LTPDLPKRL | 18 |
| 453 | NVRIDKVHL | 18 |
| 454 | VRIDKVHLF | 18 |
| 646 | YTVPQLGDT | 18 |
| 675 | ESQKCSFYL | 18 |
| 720 | EFRKMWDYF | 18 |
| 772 | TDVPIPTHY | 18 |
| 824 | EALWVEERF | 18 |
| 857 | PVSEILQLK | 18 |
| 24 | ACIVLLALL | 17 |
| 77 | DRGDCCWDF | 17 |
| 178 | DTLMPNINK | 17 |
| 274 | SEVAINGSF | 17 |
| 298 | RISTLLKWL | 17 |
| 551 | SHAEEVSKF | 17 |
| 554 | EEVSKFSVC | 17 |
| 629 | EYVSGFGKA | 17 |
| 660 | TVPDCLRAD | 17 |
| 685 | DKNITHGFL | 17 |
| 726 | DYFHSVLLI | 17 |
| 853 | DKVQPVSEI | 17 |
| 2 | ESTLTLATE | 16 |
| 21 | YKIACIVLL | 16 |
| 33 | VIMSLGLGL | 16 |
| 87 | DTCVESTRI | 16 |
| 145 | DTAQQSQCP | 16 |

TABLE XXVI-continued

| Pos | 123456789 | score |
|---|---|---|
| 154 | EGFDLPPVI | 16 |
| 179 | TLMPNINKL | 16 |
| 219 | ESHGIIDNN | 16 |
| 225 | DNNMVDVNL | 16 |
| 294 | PFEERISTL | 16 |
| 333 | PVSARVIKA | 16 |
| 419 | NSEEIVRNL | 16 |
| 421 | EEIVRNLSC | 16 |
| 513 | ENIEVYNLM | 16 |
| 600 | ITATVKVNL | 16 |
| 603 | TVKVNLPFG | 16 |
| 618 | KNVDHCLLY | 16 |
| 744 | NVVSGPIFD | 16 |
| 830 | ERFTAHIAR | 16 |
| 837 | ARVRDVELL | 16 |
| 13 | VKKNTLKKY | 15 |
| 26 | IVLLALLVI | 15 |
| 204 | KTFPNHYTI | 15 |
| 221 | HGIIDNNMY | 15 |
| 343 | QVVDHAFGM | 15 |
| 391 | PRINFFYMY | 15 |
| 458 | KVHLFVDQQ | 15 |
| 493 | EAIFLAHGP | 15 |
| 540 | NHLLKVPFY | 15 |
| 568 | LPTESLDCF | 15 |
| 595 | LTQEEITAT | 15 |
| 598 | EEITATVKV | 15 |
| 619 | NVDHCLLYH | 15 |
| 626 | YHREYVSGF | 15 |
| 686 | KNITHGFLY | 15 |
| 763 | DEITKHLAN | 15 |
| 781 | FVVLTSCKN | 15 |

V2-HLA-A26-9mers-161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 8 | QRKDCCADY | 11 |
| 4 | DDCLQRKDC | 8 |
| 5 | DCLQRKDCC | 8 |
| 2 | CSDDCLQRK | 5 |

V3-HLA-A26-9mers-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
| 3 | NVESCPGGK | 12 |
| 5 | ESCPGGKPE | 12 |
| 7 | CPGGKPEAL | 10 |
| 1 | PTNVESCPG | 8 |
| 2 | TNVESCPGG | 7 |

V4-HLA-A26-9mers-161P2F10B
Each peptide is a portion of SEQ ID NO: 88; each start position is specified, the length of the peptide is 9 amino acids and the end position for each peptide is the start position plus 8.

| Pos | 123456789 | score |
|---|---|---|
| 1 | TYLPTFETP | 3 |

TABLE XXVII

| Pos | 123456789 | score |
|---|---|---|
| | V1-HLA-B0702-9mers-161P2F10B | |

Each peptide is a portion of SEQ ID NO: 81; each start position is specified, the length of the peptide is 9 amino acids and the end position for each peptide is the start position plus 8.

| Pos | 123456789 | score |
|---|---|---|
| 776 | IPTHYFVVL | 25 |
| 761 | APDEITKHL | 24 |
| 608 | LPFGRPRVL | 23 |

TABLE XXVII-continued

| Pos | 123456789 | score |
|---|---|---|
| 818 | CPEGKPEAL | 23 |
| 856 | QPVSEILQL | 22 |
| 313 | RPRFYTMYF | 20 |
| 403 | APRIRAHNI | 20 |
| 657 | LPPTVPDCL | 20 |
| 793 | TPENCPGWL | 20 |
| 287 | MPYNGSVPF | 19 |
| 308 | LPKAERPRF | 19 |
| 390 | FPRINFFYM | 19 |
| 612 | RPRVLQKNV | 19 |
| 661 | VPDCLRADV | 19 |
| 181 | MPNINKLKT | 18 |
| 206 | FPNHYTIVT | 18 |
| 655 | SPLPPTVPD | 18 |
| 774 | VPIPTHYFV | 18 |
| 293 | VPFEERIST | 17 |
| 640 | MPMWSSYTV | 17 |
| 155 | GFDLPPVIL | 16 |
| 158 | LPPVILFSM | 16 |
| 545 | VPFYEPSHA | 16 |
| 565 | ANPLPTESL | 16 |
| 568 | LPTESLDCF | 16 |
| 808 | IPHRPTNVE | 16 |
| 35 | MSLGLGLGL | 15 |
| 37 | LGLGLGLGL | 15 |
| 152 | CPEGFDLPP | 15 |
| 836 | IARVRDVEL | 15 |
| 23 | IACIVLLAL | 14 |
| 33 | VIMSLGLGL | 14 |
| 100 | KFRCGETRL | 14 |
| 323 | EPDSSGHAG | 14 |
| 431 | KPDQHFKPY | 14 |
| 441 | TPDLPKRLH | 14 |
| 453 | NVRIDKVHL | 14 |
| 549 | EPSHAEEVS | 14 |
| 600 | ITATVKVNL | 14 |
| 643 | WSSYTVPQL | 14 |
| 649 | PQLGDTSPL | 14 |
| 822 | KPEALWVEE | 14 |
| 21 | YKIACIVLL | 13 |
| 24 | ACIVLLALL | 13 |
| 58 | CFDASFRGL | 13 |
| 132 | VCQGETSWL | 13 |
| 201 | YPTKTFPNH | 13 |
| 253 | QPMWLTAMY | 13 |
| 271 | WPGSEVAIN | 13 |
| 282 | FPSIYMPYN | 13 |
| 298 | RISTLLKWL | 13 |
| 332 | GPVSARVIK | 13 |
| 348 | AFGMLMEGL | 13 |
| 401 | GPAPRIRAH | 13 |
| 411 | IPHDFFSFN | 13 |
| 489 | FRSMEAIFL | 13 |
| 530 | APNNGTHGS | 13 |
| 560 | SVCGFANPL | 13 |
| 587 | EQVNQMLNL | 13 |
| 658 | PPTVPDCLR | 13 |
| 695 | PPASNRTSD | 13 |
| 796 | NCPGWLDVL | 13 |
| 797 | CPGWLDVLP | 13 |
| 837 | ARVRDVELL | 13 |
| 1 | MESTLTLAT | 12 |
| 11 | QPVKKNTLK | 12 |
| 20 | KYKIACIVL | 12 |
| 31 | LLVIMSLGL | 12 |
| 112 | LCSCSDDCL | 12 |
| 150 | SQCPEGFDL | 12 |
| 179 | TLMPNINKL | 12 |
| 198 | RAMYPTKTF | 12 |
| 208 | NHYTIVTGL | 12 |
| 225 | DNNMYDVNL | 12 |
| 249 | WWHGQPMWL | 12 |
| 277 | AINGSFPSI | 12 |
| 300 | STLLKWLDL | 12 |
| 311 | AERPRFYTM | 12 |
| 334 | VSARVIKAL | 12 |
| 344 | VVDHAFGML | 12 |

TABLE XXVII-continued

| Pos | 123456789 | score |
|---|---|---|
| 398 | MYEGPAPRI | 12 |
| 400 | EGPAPRIRA | 12 |
| 408 | AHNIPHDFF | 12 |
| 428 | SCRKPDQHF | 12 |
| 436 | FKPYLTPDL | 12 |
| 455 | RIDKVHLFV | 12 |
| 500 | GPSFKEKTE | 12 |
| 510 | EPFENIEVY | 12 |
| 528 | QPAPNNGTH | 12 |
| 531 | PNNGTHGSL | 12 |
| 534 | GTHGSLNHL | 12 |
| 572 | SLDCFCPHL | 12 |
| 602 | ATVKVNLPF | 12 |
| 630 | YVSGFGKAM | 12 |
| 672 | PPSESQKCS | 12 |
| 675 | ESQKCSFYL | 12 |
| 701 | TSDSQYDAL | 12 |
| 706 | YDALITSNL | 12 |
| 724 | MWDYFHSVL | 12 |
| 725 | WDYFHSVLL | 12 |
| 840 | RDVELLTGL | 12 |
| 854 | KVQPVSEIL | 12 |
| 860 | EILQLKTYL | 12 |

V2-B0702-9mers-161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 6 | CLQRKDCCA | 6 |
| 1 | SCSDDCLQR | 4 |
| 7 | LQRKDCCAD | 4 |
| 9 | RKDCCADYK | 2 |
| 2 | CSDDCLQRK | 1 |
| 3 | SDDCLQRKD | 1 |
| 4 | DDCLQRKDC | 1 |
| 8 | QRKDCCADY | 1 |

V3-HLA-B0702-9mers-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
| 7 | CPGGKPEAL | 24 |

V4-HLA-B0702-9mers-161P2F10B
Each peptide is a portion of SEQ ID NO: 88; each start position is specified, the length of the peptide is 9 amino acids and the end position for each peptide is the start position plus 8.

| Pos | 123456789 | score |
|---|---|---|
| 2 | YLPTFETPI | 8 |

TABLE XXVIII

| Pos | 123456789 | score |
|---|---|---|

V1-HLA-B08-9mers-161P2F10B
Each peptide is a portion of SEQ ID NO: 81; each start position is specified, the length of the peptide is 9 amino acids and the end position for each peptide is the start position plus 8.

| Pos | 123456789 | score |
|---|---|---|
| 836 | IARVRDVEL | 32 |
| 18 | LKKYKIACI | 28 |
| 184 | INKLKTCGI | 28 |
| 818 | CPEGKPEAL | 27 |
| 355 | GLKQRNLHN | 26 |
| 403 | APRIRAHNI | 26 |
| 502 | SFKEKTEVE | 24 |
| 608 | LPFGRPRVL | 24 |
| 10 | EQPVKKNTL | 23 |
| 300 | STLLKWLDL | 23 |
| 231 | VNLKNFSL | 22 |
| 308 | LPKAERPRF | 22 |

TABLE XXVIII-continued

| Pos | 123456789 | score |
|---|---|---|
| 786 | SCKNKSHTP | 22 |
| 863 | QLKTYLPTF | 22 |
| 294 | PFEERISTL | 21 |
| 353 | MEGLKQRNL | 21 |
| 20 | KYKIACIVL | 20 |
| 616 | LQKNVDHCL | 20 |
| 98 | CNKFRCGET | 19 |
| 761 | APDEITKHL | 19 |
| 40 | GLGLGLRKL | 18 |
| 53 | SCRKKCFDA | 18 |
| 74 | ACKDRGDCC | 18 |
| 166 | MDGFRAEYL | 18 |
| 238 | SLSSKEQNN | 18 |
| 313 | RPRFYTMYF | 18 |
| 448 | LHYAKNVRI | 18 |
| 454 | VRIDKVHLF | 18 |
| 460 | HLFVDQQWL | 18 |
| 500 | GPSFKEKTE | 18 |
| 542 | LLKVPFYEP | 18 |
| 556 | VSKFSVCGF | 18 |
| 572 | SLDCFCPHL | 18 |
| 776 | IPTHYYFWL | 18 |
| 861 | ILQLKTYLP | 18 |
| 11 | QPVKKNTLK | 17 |
| 15 | KNTLKKYKI | 17 |
| 17 | TLKKYKIAC | 17 |
| 42 | GLGLRKLEK | 17 |
| 179 | TLMPNINKL | 17 |
| 263 | GLKAATYFW | 17 |
| 401 | GPAPRIRAH | 17 |
| 444 | LPKRLHYAK | 17 |
| 453 | NVRIDKVHL | 17 |
| 504 | KEKTEVEPF | 17 |
| 585 | QLEQVNQML | 17 |
| 682 | YLADKNITH | 17 |
| 731 | VLLIKHATE | 17 |
| 856 | QPVSEILQL | 17 |
| 23 | IACIVLLAL | 16 |
| 29 | LALLVIMSL | 16 |
| 31 | LLVIMSLGL | 16 |
| 55 | RKKCFDASF | 16 |
| 100 | KFRCGETRL | 16 |
| 119 | CLQKKDCCA | 16 |
| 126 | CADYKSVCQ | 16 |
| 186 | KLKFCGIHS | 16 |
| 256 | WLTAMYQGL | 16 |
| 302 | LLKWLDLPK | 16 |
| 338 | VIKALQVVD | 16 |
| 467 | WLAVRSKSN | 16 |
| 469 | AVRSKSNTN | 16 |
| 601 | TATVKVNLP | 16 |
| 610 | FGRPRVLQK | 16 |
| 657 | LPPTVPDCL | 16 |
| 684 | ADKNITHGF | 16 |
| 736 | HATERNGVN | 16 |
| 793 | TPENCPGWL | 16 |
| 860 | EILQLKTYL | 16 |
| 33 | VIMSLGLGL | 15 |
| 51 | QGSCRKKCF | 15 |
| 191 | GIHSKYMRA | 15 |
| 240 | SSKEQNNPA | 15 |
| 298 | RISTLLKWL | 15 |
| 388 | DYFPRINFF | 15 |
| 626 | YHREYVSGF | 15 |

V2-B08-9mers-161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 6 | CLQRKDCCA | 16 |
| 8 | QRKDCCADY | 10 |
| 5 | DCLQRKDCC | 8 |
| 7 | LQRKDCCAD | 7 |

V3-HLA-B08-9mers-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
| 7 | CPGGKPEAL | 27 |

V4-HLA-B08-9mers-161P2F10B
Each peptide is a portion of SEQ ID NO: 88; each start position is specified, the length of the peptide is 9 amino acids and the end position for each peptide is the start position plus 8.

| Pos | 123456789 | score |
|---|---|---|
| 2 | YLPTFETPI | 12 |

TABLE XXIX

| Pos | 123456789 | score |
|---|---|---|

V1-HLA-B1510-9mers-161P2F10B
Each peptide is a portion of SEQ ID NO: 81; each start position is specified, the length of the peptide is 9 amino acids and the end position for each peptide is the start position plus 8.

| Pos | 123456789 | score |
|---|---|---|
| 192 | IHSKYMRAM | 24 |
| 578 | PHLQNSTQL | 22 |
| 208 | NHYTIVTGL | 21 |
| 535 | THGSLNHLL | 21 |
| 361 | LHNCVNIIL | 20 |
| 551 | SHAEEVSKF | 19 |
| 626 | YHREYVSGF | 19 |
| 328 | GHAGGPVSA | 17 |
| 408 | AHNIPHDFF | 17 |
| 220 | SHGIIDNNM | 16 |
| 600 | ITATVKVNL | 16 |
| 608 | LPFGRPRVL | 16 |
| 776 | IPTHYFVVL | 16 |
| 836 | IARVRDVEL | 16 |
| 155 | GFDLPPVIL | 15 |
| 179 | TLMPNINKL | 15 |
| 419 | NSEEIVRNL | 15 |
| 809 | PHRPTNVES | 15 |
| 10 | EQPVKKNTL | 14 |
| 21 | YKIACIVLL | 14 |
| 40 | GLGLGLRKL | 14 |
| 294 | PFEERISTL | 14 |
| 440 | LTPDLPKRL | 14 |
| 448 | LHYAKNVRI | 14 |
| 757 | GHFDAPDEI | 14 |
| 818 | CPEGKPEAL | 14 |
| 23 | IACIVLLAL | 13 |
| 100 | KFRCGETRL | 13 |
| 250 | WHGQPMWLT | 13 |
| 334 | VSARVIKAL | 13 |
| 346 | DHAFGMLME | 13 |
| 362 | HNCVNIILL | 13 |
| 434 | QHFKPYLTP | 13 |
| 453 | NVRIDKVHL | 13 |
| 498 | AHGPSFKEK | 13 |
| 643 | WSSYTVPQL | 13 |
| 767 | KNLANTDVP | 13 |
| 778 | THYFVVLTS | 13 |
| 793 | TPENCPGWL | 13 |
| 796 | NCPGWLDVL | 13 |
| 834 | AHIARVRDV | 13 |
| 860 | EILQLKTYL | 13 |
| 20 | KYKIACIVL | 12 |
| 58 | CFDASFRGL | 12 |
| 150 | SQCPEGFDL | 12 |
| 172 | EYLYFWDTL | 12 |
| 225 | DNNMYDVNL | 12 |
| 249 | WWHGQPMWL | 12 |
| 353 | MEGLKQRNL | 12 |

TABLE XXIX-continued

| Pos | 123456789 | score |
|---|---|---|
| 432 | PDQHFKPYL | 12 |
| 516 | EVYNLMCDL | 12 |
| 534 | GTHGSLNHL | 12 |
| 540 | NHLLKVPFY | 12 |
| 585 | QLEQVNQML | 12 |
| 587 | EQVNQMLNL | 12 |
| 621 | DHCLLYHRE | 12 |
| 675 | ESQKCSFYL | 12 |
| 689 | THGFLYPPA | 12 |
| 701 | TSDSQYDAL | 12 |
| 706 | YDALITSNL | 12 |
| 724 | MWDYFHSVL | 12 |
| 725 | WDYFHSVLL | 12 |
| 728 | FHSVLLIKH | 12 |
| 735 | KHATERNGV | 12 |
| 791 | SHTPENCPG | 12 |
| 854 | KVQPVSEIL | 12 |
| 24 | ACIVILALL | 11 |
| 29 | LALLVIMSL | 11 |
| 35 | MSLGLGLGL | 11 |
| 37 | LGLGLGLGL | 11 |
| 104 | GETRLEASL | 11 |
| 112 | LCSCSDDCL | 11 |
| 132 | VCQGETSWL | 11 |
| 295 | FEERISTLL | 11 |
| 298 | RISTLLKWL | 11 |
| 348 | AFGMLMEGL | 11 |
| 436 | FKPYLTPDL | 11 |
| 460 | HLFVDQQWL | 11 |
| 482 | NHGYNNEFR | 11 |
| 489 | FRSMEAIFL | 11 |
| 512 | FENIEVYNL | 11 |
| 531 | PNNGTHGSL | 11 |
| 560 | SVCGFANPL | 11 |
| 565 | ANPLPTESL | 11 |
| 572 | SLDCFCPHL | 11 |
| 617 | QKNVDHCLL | 11 |
| 649 | PQLGDTSPL | 11 |
| 657 | LPPTVPDCL | 11 |
| 761 | APDEITKHL | 11 |
| 837 | ARVRDVELL | 11 |
| 840 | RDVELLTGL | 11 |
| 856 | QPVSEILQL | 11 |

V2-B1510-9mers: 161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 2 | CSDDCLQRK | 3 |
| 1 | SCSDDCLQR | 2 |
| 3 | SDDCLQRKD | 2 |
| 5 | DCLQRKDCC | 2 |
| 7 | LQRKDCCAD | 2 |
| 4 | DDCLQRKDC | 1 |
| 8 | QRKDCCADY | 1 |

V3-HLA-B1510-9mers-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
| 7 | CPGGKPEAL | 13 |

V4-HLA-B1510-9mers-161P2F10B
Each peptide is a portion of SEQ ID NO: 88; each start position is specified, the length of the peptide is 9 amino acids and the end position for each peptide is the start position plus 8.

| Pos | 123456789 | score |
|---|---|---|
| 1 | TYLPTFETP | 4 |
| 2 | YLPTFETPI | 1 |

TABLE XXX

| Pos | 123456789 | score |
|---|---|---|

V1-HLA-B2705-9mers-161P2F10B
Each peptide is a portion of SEQ ID NO: 81; each start position is specified, the length of the peptide is 9 amino acids and the end position for each peptide is the start position plus 8.

| Pos | 123456789 | score |
|---|---|---|
| 93 | TRIWMCNKF | 25 |
| 454 | VRIDKVHLF | 24 |
| 830 | ERFTAHIAR | 24 |
| 429 | CRKPDQHFK | 23 |
| 489 | FRSMEAIFL | 23 |
| 837 | ARVRDVELL | 23 |
| 77 | DRGDCCWDF | 21 |
| 391 | PRINFFYMY | 21 |
| 638 | MRMPMWSSY | 21 |
| 312 | ERPRFYTMY | 20 |
| 721 | FRKMWDYFH | 20 |
| 840 | RDVELLTGL | 20 |
| 29 | LALLVIMSL | 19 |
| 40 | GLGLGLRKL | 19 |
| 525 | LRIQPAPNN | 19 |
| 614 | RVLQKNVDH | 19 |
| 39 | LGLGLGLRK | 18 |
| 100 | KFRCGETRL | 18 |
| 388 | DYFPRINFF | 18 |
| 470 | VRSKSNTNC | 18 |
| 481 | GNHGYNNEF | 18 |
| 534 | GTHGSLNHL | 18 |
| 578 | PHLQNSTQL | 18 |
| 632 | SGFGKAMRM | 18 |
| 670 | RVPPSESQK | 18 |
| 692 | FLYPPASNR | 18 |
| 732 | LLIKHATER | 18 |
| 860 | EILQLKTYL | 18 |
| 11 | QPVKKNTLK | 17 |
| 38 | GLGLGLGLR | 17 |
| 42 | GLGLRKLEK | 17 |
| 48 | LEKQGSCRK | 17 |
| 55 | RKKCFDASF | 17 |
| 178 | DTLMPNINK | 17 |
| 179 | TLMPNINKL | 17 |
| 227 | NMYDVNLNK | 17 |
| 262 | QGLKAATYF | 17 |
| 374 | GMDQTYCNK | 17 |
| 446 | KRLHYAKNV | 17 |
| 447 | RLHYAKNVR | 17 |
| 602 | ATVKVNLPF | 17 |
| 611 | GRPRVLQKN | 17 |
| 628 | REYVSGFGK | 17 |
| 856 | QPVSEILQL | 17 |
| 21 | YKIACIVLL | 16 |
| 24 | ACIVLLALL | 16 |
| 35 | MSLGLGLGL | 16 |
| 37 | LGLGLGLGL | 16 |
| 104 | GETRLEASL | 16 |
| 155 | GFDLPPVIL | 16 |
| 156 | FDLPPVILF | 16 |
| 187 | LKTCGIHSK | 16 |
| 188 | KTCGIHSKY | 16 |
| 198 | RAMYPTKTF | 16 |
| 208 | NHYTIVTGL | 16 |
| 287 | MPYNGSVPF | 16 |
| 294 | PFEERISTL | 16 |
| 297 | ERISTLLKW | 16 |
| 298 | RISTLLKWL | 16 |
| 336 | ARVIKALQV | 16 |
| 353 | MEGLKQRNL | 16 |
| 387 | TDYFPRINF | 16 |
| 397 | YMYEGPAPR | 16 |
| 510 | EPFENIEVY | 16 |
| 551 | SHAEEVSKF | 16 |
| 600 | ITATVKVNL | 16 |
| 608 | LPFGRPRVL | 16 |
| 739 | ERNGVNVVS | 16 |
| 760 | DAPDEITKH | 16 |
| 6 | TLATEQPVK | 15 |
| 12 | PVKKNTLKK | 15 |

TABLE XXX-continued

| Pos | 123456789 | score |
|---|---|---|
| 47 | KLEKQGSCR | 15 |
| 49 | EKQGSCRKK | 15 |
| 63 | FRGLENCRC | 15 |
| 94 | RIWMCNKFR | 15 |
| 106 | TRLEASLCS | 15 |
| 162 | ILFSMDGFR | 15 |
| 190 | CGIHSKYMR | 15 |
| 229 | YDVNLNKNF | 15 |
| 231 | VNLNKNFSL | 15 |
| 300 | STLLKWLDL | 15 |
| 305 | WLDLPKAER | 15 |
| 313 | RPRFYTMYF | 15 |
| 329 | HAGGPVSAR | 15 |
| 332 | GPVSARVIK | 15 |
| 351 | MLMEGIKQR | 15 |
| 359 | RNLHNCVNI | 15 |
| 401 | GPAPRIRAH | 15 |
| 406 | IRAHNIPHD | 15 |
| 407 | RAHNIPHDF | 15 |
| 419 | NSEEIVRNL | 15 |
| 423 | IVRNLSCRK | 15 |
| 438 | PYLTPDLPK | 15 |
| 439 | YLTPDLPKR | 15 |
| 460 | HLFVDQQWL | 15 |
| 463 | VDQQWLAVR | 15 |
| 495 | IFLAHGPSF | 15 |
| 512 | FENIEVYNL | 15 |
| 613 | PRVLQKNVD | 15 |
| 649 | PQLGDTSPL | 15 |
| 669 | VRVPPSESQ | 15 |
| 706 | YDALITSNL | 15 |
| 782 | VVLTSCKNK | 15 |
| 802 | DVLPFIIPH | 15 |
| 803 | VLPFIIPHR | 15 |
| 824 | EALWVEERF | 15 |
| 854 | KVQPVSEIL | 15 |
| 7 | LATEQPVKK | 14 |
| 10 | EQPVKKNTL | 14 |
| 14 | KKNTLKKYK | 14 |
| 15 | KNTLKKYKI | 14 |
| 20 | KYKIACIVL | 14 |
| 23 | IACIVLLAL | 14 |
| 56 | KKCFDASFR | 14 |
| 62 | SFRGLENCR | 14 |
| 69 | CRCDVACKD | 14 |
| 70 | RCDVACKDR | 14 |
| 99 | NKFRCGETR | 14 |
| 132 | VCQGETSWL | 14 |
| 169 | FRAEYLYTW | 14 |
| 197 | MRAMYPTKT | 14 |
| 204 | KTFPNHYTI | 14 |
| 215 | GLYPESHGI | 14 |
| 225 | DNNMYDVNL | 14 |
| 234 | NKNFSLSSK | 14 |
| 252 | GQPMWLTAM | 14 |
| 274 | SEVAINGSF | 14 |
| 295 | FEERISTLL | 14 |
| 308 | LPKAERPRF | 14 |
| 314 | PRFYTMYPE | 14 |
| 334 | VSARVIKAL | 14 |
| 362 | HNCVNIILL | 14 |
| 405 | RIRAHNIPH | 14 |
| 424 | VRNLSCRKP | 14 |
| 428 | SCRKPDQHF | 14 |
| 452 | KNVRIDKVH | 14 |
| 498 | AHGPSFKEK | 14 |
| 504 | KEKTEVEPF | 14 |
| 518 | YNLMCDLLR | 14 |
| 533 | NGTHGSLNH | 14 |
| 539 | LNHLLKVPF | 14 |
| 540 | NHLLKVPFY | 14 |
| 560 | SVCGFANPL | 14 |
| 565 | ANPLPTESL | 14 |
| 584 | TQLEQVNQM | 14 |
| 585 | QLEQVNQML | 14 |
| 587 | EQVNQMLNL | 14 |
| 597 | QEEITATVK | 14 |
| 610 | FGRPRVLQK | 14 |
| 631 | VSGFGKAMR | 14 |
| 678 | KCSFYLADK | 14 |
| 716 | PMYEEFRKM | 14 |
| 725 | WDYFHSVLL | 14 |
| 745 | VVSGPIFDY | 14 |
| 771 | NTDVPIPTH | 14 |
| 796 | NCPGWLDVL | 14 |
| 799 | GWLDVLPFI | 14 |
| 836 | IARVRDVEL | 14 |
| 839 | VRDVELLTG | 14 |
| 842 | VELLTGLDF | 14 |
| 26 | IVLLALLVI | 13 |
| 27 | VLLALLVIM | 13 |
| 31 | LLVIMSLGL | 13 |
| 45 | LRKLEKQGS | 13 |
| 86 | EDTCVESTR | 13 |
| 101 | FRCGETRLE | 13 |
| 115 | CSDDCLQKK | 13 |
| 122 | KKDCCADYK | 13 |
| 161 | VILFSMDGF | 13 |
| 172 | EYLYTWDTL | 13 |
| 173 | YLYTWDTLM | 13 |
| 201 | YPTKTFPNH | 13 |
| 220 | SHGIIDNNM | 13 |
| 249 | WWHGQPMWL | 13 |
| 261 | YQGLKAATY | 13 |
| 291 | GSVPFEERI | 13 |
| 302 | LLKWLDLPK | 13 |
| 341 | ALQVVDHAF | 13 |
| 354 | EGLKQRNLH | 13 |
| 358 | QRNLHNCVN | 13 |
| 361 | LHNCVNIIL | 13 |
| 365 | VNIILLADH | 13 |
| 367 | IILLADHGM | 13 |
| 371 | ADHGMDQTY | 13 |
| 377 | QTYCNKMEY | 13 |
| 398 | MYEGPAPRI | 13 |
| 404 | PRIRAHNIP | 13 |
| 417 | SFNSEEIVR | 13 |
| 422 | EIVRNLSCR | 13 |
| 440 | LTPDLPKRL | 13 |
| 442 | PDLPKRLHY | 13 |
| 448 | LHYAKNVRI | 13 |
| 465 | QQWLAVRSK | 13 |
| 477 | NCGGGNHGY | 13 |
| 484 | GYNNEFRSM | 13 |
| 496 | FLAHGPSFK | 13 |
| 513 | ENIEVYNLM | 13 |
| 516 | EVYNLMCDL | 13 |
| 531 | PNNGTHGSL | 13 |
| 550 | PSHAEEVSK | 13 |
| 568 | LPTESLDCF | 13 |
| 606 | VNLPFGRPR | 13 |
| 620 | VDHCLLYHR | 13 |
| 626 | YHREYVSGF | 13 |
| 643 | WSSYIVPQL | 13 |
| 662 | PDCLRADVR | 13 |
| 675 | ESQKCSFYL | 13 |
| 713 | NLVPMYEEF | 13 |
| 715 | VPMYEEFRK | 13 |
| 719 | EEFRKMWDY | 13 |
| 727 | YFHSVLLIK | 13 |
| 728 | FHSVLLIKH | 13 |
| 743 | VNVSGPIF | 13 |
| 751 | FDYNYDGHF | 13 |
| 757 | GHFDAPDEI | 13 |
| 759 | FDAPDEITK | 13 |
| 761 | APDEITKHL | 13 |
| 772 | TDVPIPTHY | 13 |
| 776 | IPTHYFVVL | 13 |
| 780 | YFVVLTSCK | 13 |
| 798 | PGWLDVLPF | 13 |
| 818 | CPEGKPEAL | 13 |
| 823 | PEALWVEER | 13 |
| 832 | FTAHIARVR | 13 |
| 843 | ELLTGLDFY | 13 |

TABLE XXX-continued

| Pos | 123456789 | score |
|---|---|---|
| 853 | DKVQPVSEI | 13 |
| 857 | PVSEILQLK | 13 |
| 859 | SEILQLKTY | 13 |
| 863 | QLKTYLPTF | 13 |
| 33 | VIMSLGLGL | 12 |
| 54 | CRKKCFDAS | 12 |
| 68 | NCRCDVACK | 12 |
| 87 | DTCVESTRI | 12 |
| 92 | STRIWMCNK | 12 |
| 112 | LCSCSDDCL | 12 |
| 114 | SCSDDCLQK | 12 |
| 148 | QQSQCPEGF | 12 |
| 150 | SQCPEGFDL | 12 |
| 154 | EGFDLPPVI | 12 |
| 165 | SMDGFRAEY | 12 |
| 167 | DGFRAEYLY | 12 |
| 180 | LMPNINKLK | 12 |
| 185 | NKLKTCGIH | 12 |
| 196 | YMRAMYPTK | 12 |
| 221 | HGIIDNNMY | 12 |
| 257 | LTAMYQGLK | 12 |
| 277 | AINGSFPSI | 12 |
| 280 | GSFPSIYMP | 12 |
| 290 | NGSVPFEER | 12 |
| 296 | EERISTLLK | 12 |
| 307 | DLPKAERPR | 12 |
| 311 | AERPRFYTM | 12 |
| 331 | GGPVSARVI | 12 |
| 339 | IKALQVVDH | 12 |
| 348 | AFGMLMEGL | 12 |
| 382 | KMEYMTDYF | 12 |
| 408 | AHNIPHDFF | 12 |
| 431 | KPDQHFKPY | 12 |
| 432 | PDQHFKPYL | 12 |
| 436 | FKPYLTPDL | 12 |
| 444 | LPKRLHYAK | 12 |
| 450 | YAKNVRIDK | 12 |
| 453 | NVRIDKVHL | 12 |
| 475 | NTNCGGGNH | 12 |
| 535 | THGSLNHLL | 12 |
| 536 | HGSLNHLLK | 12 |
| 544 | KVPFYEPSH | 12 |
| 556 | VSKFSVCGF | 12 |
| 604 | VKVNLPFGR | 12 |
| 616 | LQKNVDHCL | 12 |
| 618 | KNVDHCLLY | 12 |
| 622 | HCLLYHREY | 12 |
| 627 | HREYVSGFG | 12 |
| 658 | PPTVPDCLR | 12 |
| 665 | LRADVRVPP | 12 |
| 673 | PSESQKCSF | 12 |
| 674 | SESQKCSFY | 12 |
| 680 | SFYLADKNI | 12 |
| 682 | YLADKNITH | 12 |
| 684 | ADKNITHGF | 12 |
| 686 | KNITHGFLY | 12 |
| 698 | SNRTSDSQY | 12 |
| 710 | ITSNLVPMY | 12 |
| 720 | EFRKMWDYF | 12 |
| 724 | MWDYFHSVL | 12 |
| 726 | DYFHSVLLI | 12 |
| 747 | SGPIFDYNY | 12 |
| 810 | HRPTNVESC | 12 |
| 846 | TGLDFYQDK | 12 |

V2-HLA-B2705-9mers-161P2F10B
Each peptide is a portion of SEQ ID NO: 82; each start position is specified, the length of the peptide is 9 amino acids and the end position for each peptide is the start position plus 8.

| 8 | QRKDCCADY | 19 |
| 9 | RKDCCADYK | 15 |
| 2 | CSDDCLQRK | 13 |
| 1 | SCSDDCLQR | 12 |

TABLE XXX-continued

| Pos | 123456789 | score |
|---|---|---|

V3-HLA-B2705-9mers-161P2F10B
Each peptide is a portion of SEQ ID NO: 85; each start position is specified, the length of the peptide is 9 amino acids and the end position for each peptide is the start position plus 8.

| 7 | CPGGKPEAL | 13 |
| 3 | NVESCPGGK | 10 |
| 6 | SCPGGKPEA | 7 |

V4-HLA-B2705-9mers-161P2F10B
Each peptide is a portion of SEQ ID NO: 88; each start position is specified, the length of the peptide is 9 amino acids and the end position for each peptide is the start position plus 8.

| 2 | YLPTFETPI | 8 |
| 1 | TYLPTFETP | 4 |

TABLE XXXI

| Pos | 123456789 | score |
|---|---|---|

V1-HLA-B2709-9mers-161P2F10B
Each peptide is a portion of SEQ ID NO: 81; each start position is specified, the length of the peptide is 9 amino acids and the end position for each peptide is the start position plus 8.

| 446 | KRLHYAKNV | 24 |
| 837 | ARVRDVELL | 24 |
| 336 | ARVIKALQV | 23 |
| 489 | FRSMEAIFL | 21 |
| 454 | VRIDKVHLF | 20 |
| 93 | TRIWMCNKF | 19 |
| 77 | DRGDCCWDF | 18 |
| 359 | RNLHNCVNI | 16 |
| 840 | RDVELLTGL | 15 |
| 19 | KKYKIACIV | 14 |
| 104 | GETRLEASL | 14 |
| 155 | GFDLPPVIL | 14 |
| 204 | KTFPNHYTI | 14 |
| 208 | NHYTIVTGL | 14 |
| 215 | GLYPESHGI | 14 |
| 291 | GSVPFEERI | 14 |
| 298 | RISTLLKWL | 14 |
| 525 | LRIQPAPNN | 14 |
| 537 | GSLNHLLKV | 14 |
| 799 | GWLDVLPFI | 14 |
| 831 | RFTAHIARV | 14 |
| 856 | QPVSEILQL | 14 |
| 35 | MSLGLGLGL | 13 |
| 37 | LGLGLGLGL | 13 |
| 40 | GLGLGLRKL | 13 |
| 100 | KFRCGETRL | 13 |
| 106 | TRLEASLCS | 13 |
| 297 | ERISTLLKW | 13 |
| 300 | STLLKWLDL | 13 |
| 314 | PRFYTMYFE | 13 |
| 337 | RVIKALQVV | 13 |
| 407 | RAHNIPHDF | 13 |
| 419 | NSEEIVRNL | 13 |
| 455 | RIDKVHLFV | 13 |
| 460 | HLFVDQQWL | 13 |
| 512 | FENIEVYNL | 13 |
| 534 | GTHGSLNHL | 13 |
| 578 | PHLQNSTQL | 13 |
| 587 | EQVNQMLNL | 13 |
| 600 | ITATVKVNL | 13 |
| 611 | GRPRVLQKN | 13 |
| 612 | RPRVLQKNV | 13 |
| 643 | WSSYTVPQL | 13 |
| 649 | PQLGDTSPL | 13 |
| 699 | NRTSDSQYD | 13 |
| 725 | WDYFHSVLL | 13 |

TABLE XXXI-continued

| Pos | 123456789 | score |
|---|---|---|
| 757 | GHFDAPDEI | 13 |
| 776 | IPTHYFVVL | 13 |
| 854 | KVQPVSEIL | 13 |
| 15 | KNTLKKYKI | 12 |
| 20 | KYKIACIVL | 12 |
| 21 | YKIACIVLL | 12 |
| 23 | IACIVLLAL | 12 |
| 24 | ACIVLLALL | 12 |
| 26 | IVLLALLVI | 12 |
| 29 | LALLVIMSL | 12 |
| 31 | LLVIMSLGL | 12 |
| 33 | VIMSLGLGL | 12 |
| 55 | RKKCFDASF | 12 |
| 156 | FDLPPVILF | 12 |
| 172 | EYLYTWDTL | 12 |
| 198 | RAMYPTKTF | 12 |
| 225 | DNNMYDVNL | 12 |
| 231 | VNLNKNFSL | 12 |
| 313 | RPRFYTMYF | 12 |
| 331 | GGPVSARVI | 12 |
| 391 | PRINFFYMY | 12 |
| 406 | IRAHNIPHD | 12 |
| 429 | CRKPDQHFK | 12 |
| 448 | LHYAKNVRI | 12 |
| 453 | NVRIDKVHL | 12 |
| 495 | IFLAHGPSF | 12 |
| 516 | EVYNLMCDL | 12 |
| 584 | TQLEQVNQM | 12 |
| 608 | LPFGRPRVL | 12 |
| 632 | SGFGKAMRM | 12 |
| 663 | DCLRADVRV | 12 |
| 669 | VRVPPSESQ | 12 |
| 706 | YDALITSNL | 12 |
| 726 | DYFHSVLLI | 12 |
| 761 | APDEITKHL | 12 |
| 830 | ERFTAHIAR | 12 |
| 836 | IARVRDVEL | 12 |
| 860 | EILQLKTYL | 12 |
| 25 | CIVLLALLV | 11 |
| 27 | VLLALLVIM | 11 |
| 63 | FRGLENCRC | 11 |
| 65 | GLENCRCDV | 11 |
| 69 | CRCDVACKD | 11 |
| 150 | SQCPEGFDL | 11 |
| 154 | EGFDLPPVI | 11 |
| 166 | MDGFRAEYL | 11 |
| 169 | FRAEYLYTW | 11 |
| 179 | TLMPNINKL | 11 |
| 252 | GQPMWLTAM | 11 |
| 256 | WLTAMYQGL | 11 |
| 262 | QGLKAATYF | 11 |
| 287 | MPYNGSVPF | 11 |
| 295 | FEERISTLL | 11 |
| 311 | AERPRFYTM | 11 |
| 330 | AGGPVSARV | 11 |
| 348 | AFGMLMEGL | 11 |
| 353 | MEGLKQRNL | 11 |
| 367 | IILLADHGM | 11 |
| 385 | YMTDYFPRI | 11 |
| 387 | TDYFPRINF | 11 |
| 388 | DYFPRINFF | 11 |
| 398 | MYEGPAPRI | 11 |
| 403 | APRIRAHNI | 11 |
| 404 | PRIRAHNIP | 11 |
| 432 | PDQHFKPYL | 11 |
| 436 | FKPYLTPDL | 11 |
| 440 | LTPDLPKRL | 11 |
| 470 | VRSKSNTNC | 11 |
| 481 | GNHGYNNEF | 11 |
| 484 | GYNNEFRSM | 11 |
| 504 | KEKTEVEPF | 11 |
| 519 | NIMCDLLRI | 11 |
| 535 | THGSLNHLL | 11 |
| 560 | SVCGFANPL | 11 |
| 565 | ANPLPTESL | 11 |
| 572 | SLDCFCPHL | 11 |
| 602 | ATVKVNLPF | 11 |
| 613 | PRVLQKNVD | 11 |
| 617 | QKNVDHCLL | 11 |
| 638 | MRMPMWSSY | 11 |
| 665 | LRADVRVPP | 11 |
| 680 | SFYLADKNI | 11 |
| 701 | TSDSQYDAL | 11 |
| 709 | LITSNLVPM | 11 |
| 721 | FRKMWDYFH | 11 |
| 737 | ATERNGVNV | 11 |
| 739 | ERNGVNVVS | 11 |
| 742 | GVNVVSGPI | 11 |
| 774 | VPIPTHYFV | 11 |
| 798 | PGWLDVLPF | 11 |
| 810 | HRPTNVESC | 11 |
| 820 | EGKPEALWV | 11 |
| 824 | EALWVEERF | 11 |
| 834 | AHIARVRDV | 11 |
| 839 | VRDVELLTG | 11 |
| 842 | VELLTGLDF | 11 |
| 847 | GLDFYQDKV | 11 |

V2-HLA-B2709-9mers-161P2F10B

Each peptide is a portion of SEQ ID NO: 82; each start position is specified, the length of the peptide is 9 amino acids and the end position for each peptide is the start position plus 8.

| Pos | 123456789 | score |
|---|---|---|
| 8 | QRKDCCADY | 10 |
| 9 | RKDCCADYK | 5 |

V3-HLA-B2709-9mers-161P2F10B

Each peptide is a portion of SEQ ID NO: 85; each start position is specified, the length of the peptide is 9 amino acids and the end position for each peptide is the start position plus 8.

| Pos | 123456789 | score |
|---|---|---|
| 9 | GGKPEALWV | 14 |
| 7 | CPGGKPEAL | 10 |

V4-HLA-B2709-9mers-161P2F10B

Each peptide is a portion of SEQ ID NO: 88; each start position is specified, the length of the peptide is 9 amino acids and the end position for each peptide is the start position plus 8.

| Pos | 123456789 | score |
|---|---|---|
| 2 | YLPTFETPI | 8 |
| 1 | TYLPTFETP | 3 |

TABLE XXXII

| Pos | 123456789 | score |
|---|---|---|

V1-HLA-B4402-9mers-161P2F10B

Each peptide is a portion of SEQ ID NO: 81; each start position is specified, the length of the peptide is 9 amino acids and the end position for each peptide is the start position plus 8.

| Pos | 123456789 | score |
|---|---|---|
| 859 | SEILQLKTY | 29 |
| 719 | EEFRKMWDY | 25 |
| 242 | KEQNNPAWW | 24 |
| 487 | NEFRSMEAI | 24 |
| 295 | FEERISTLL | 23 |
| 504 | KEKTEVEPF | 23 |
| 842 | VELLTGLDF | 23 |
| 274 | SEVAINGSF | 22 |
| 353 | MEGLKQRNL | 22 |
| 674 | SESQKCSFY | 22 |
| 104 | GETRLEASL | 21 |
| 512 | FENIEVYNL | 21 |
| 819 | PEGKPEALW | 21 |
| 179 | TLMPNINKL | 20 |
| 388 | DYFPRINFF | 20 |
| 828 | VEERFTAHI | 20 |

TABLE XXXII-continued

| Pos | 123456789 | score |
|---|---|---|
| 311 | AERPRFYTM | 19 |
| 507 | TEVEPFENI | 19 |
| 510 | EPFENIEVY | 19 |
| 598 | EEITATVKV | 19 |
| 21 | YKIACIVLL | 18 |
| 24 | ACIVLLALL | 18 |
| 297 | ERISTLLKW | 18 |
| 334 | VSARVIKAL | 18 |
| 761 | APDEITKHL | 18 |
| 156 | FDLPPVILF | 17 |
| 421 | EEIVRNLSC | 17 |
| 454 | VRIDKVHLF | 17 |
| 608 | LPFGRPRVL | 17 |
| 684 | ADKNITHGF | 17 |
| 763 | DEITKHLAN | 17 |
| 1 | MESTLTLAT | 16 |
| 90 | VESTRIWMC | 16 |
| 204 | KTFPNHYTI | 16 |
| 341 | ALQWDIIAF | 16 |
| 362 | HNCVNIILL | 16 |
| 442 | PDLPKRLHY | 16 |
| 565 | ANPLPTESL | 16 |
| 686 | KNITHGFLY | 16 |
| 837 | ARVRDVELL | 16 |
| 9 | TEQPVKKNT | 15 |
| 10 | EQPVKKNTL | 15 |
| 13 | VKKNTLKKY | 15 |
| 29 | LALLVIMSL | 15 |
| 93 | TRIWMCNKF | 15 |
| 154 | EGFDLPPVI | 15 |
| 171 | AEYLYIWDT | 15 |
| 198 | RAMYPTKTF | 15 |
| 218 | PESHGIIDN | 15 |
| 294 | PFEERISTL | 15 |
| 296 | EERISTLLK | 15 |
| 298 | RISTLLKWL | 15 |
| 371 | ADHGMDQTY | 15 |
| 391 | PRINFFYMY | 15 |
| 399 | YEGPAPRIR | 15 |
| 431 | KPDQIFKPY | 15 |
| 440 | LTPDLPKRL | 15 |
| 745 | VVSGPIFDY | 15 |
| 772 | TDVPIPTHY | 15 |
| 796 | NCPGWLDVL | 15 |
| 843 | ELLTGLDFY | 15 |
| 856 | ELLTGLDFY | 15 |
| 23 | IACIVLLAL | 14 |
| 40 | GLGLGLRKL | 14 |
| 51 | QGSCRKKCF | 14 |
| 141 | EENCDTAQQ | 14 |
| 150 | SQCPEGFDL | 14 |
| 155 | GFDLPPVIL | 14 |
| 165 | SMDGFRAEY | 14 |
| 167 | DGFRAEYLY | 14 |
| 172 | EYLYTWDTL | 14 |
| 188 | KTCGIHSKY | 14 |
| 208 | NHYTIVTGL | 14 |
| 221 | HGIIDNNMY | 14 |
| 241 | SKEQNNPAW | 14 |
| 300 | STLLKWLDL | 14 |
| 312 | ERPRFYTMY | 14 |
| 322 | EEPDSSGHA | 14 |
| 403 | APRIRAHNI | 14 |
| 407 | RAHNIPHDF | 14 |
| 419 | NSEEIVRNL | 14 |
| 420 | SEEIVRNLS | 14 |
| 540 | NHLLKVPFY | 14 |
| 554 | EEVSKFSVC | 14 |
| 560 | SVCGFANPL | 14 |
| 587 | EQVNQMLNL | 14 |
| 602 | ATVKVNLPF | 14 |
| 618 | KNVDHCLLY | 14 |
| 638 | MRMPMWSSY | 14 |
| 713 | NLVPMYEEF | 14 |
| 738 | TERNGVNVV | 14 |
| 818 | CPEGKPEAL | 14 |
| 829 | EERFTAHIA | 14 |
| 854 | KVQPVSEIL | 14 |

V2-HLA-B4402-9MERS-161P2F10B
Each peptide is a portion of SEQ ID NO: 82; each start position is specified, the length of the peptide is 9 amino acids and the end position for each peptide is the start position plus 8.

| Pos | 123456789 | score |
|---|---|---|
| 8 | QRKDCCADY | 11 |
| 1 | SCSDDCLQR | 5 |

V3-HLA-B4402-9MERS-161P2F10B
Each peptide is a portion of SEQ ID NO: 85; each start position is specified, the length of the peptide is 9 amino acids and the end position for each peptide is the start position plus 8.

| Pos | 123456789 | score |
|---|---|---|
|  | CPGGKPEAL | 14 |
| 4 | VESCPGGKP | 12 |
| 8 | PGGKPEALW | 11 |
| 5 | ESCPGGKPE | 7 |

V4-HLA-B4402-9MERS-161P2F10B
Each peptide is a portion of SEQ ID NO: 88; each start position is specified, the length of the peptide is 9 amino acids and the end position for each peptide is the start position plus 8.

| Pos | 123456789 | score |
|---|---|---|
| 2 | YLPTFETPI | 10 |
| 1 | TYLPTFETP | 6 |

TABLE XXXIIII

| Pos | 123456789 | score |
|---|---|---|

V1-HLA-B5101-9mers-161P2F10B
Each peptide is a portion of SEQ ID NO: 81; each start position is specified, the length of the peptide is 9 amino acids and the end position for each peptide is the start position plus 8.

| Pos | 123456789 | score |
|---|---|---|
| 707 | DALITSNLV | 26 |
| 608 | LPFGRPRVL | 25 |
| 776 | IPTHYFVVL | 24 |
| 29 | LALLVIMSL | 23 |
| 331 | GGPVSARVI | 23 |
| 657 | LPPTVPDCL | 23 |
| 23 | IACIVLLAL | 22 |
| 154 | EGFDLPPVI | 22 |
| 640 | MPMWSSYTV | 22 |
| 403 | APRIRAHNI | 21 |
| 448 | LHYAKNVRI | 21 |
| 760 | DAPDEITKH | 20 |
| 761 | APDEITKHL | 20 |
| 774 | VPIPTHYFV | 20 |
| 26 | IVLLALLVI | 19 |
| 612 | RPRVLQKNV | 19 |
| 661 | VPDCLRADV | 19 |
| 694 | YPPASNRTS | 19 |
| 726 | DYFHSVLLI | 19 |
| 818 | CPEGKPEAL | 19 |
| 836 | IARVRDVEL | 19 |
| 7 | LATEQPVKK | 18 |
| 37 | LGLGLGLGL | 18 |
| 793 | TPENCPGWL | 18 |
| 856 | QPVSEILQL | 18 |
| 330 | AGGPVSARV | 17 |
| 340 | KALQVVDHA | 17 |
| 510 | EPFENIEVY | 17 |
| 867 | YLPTFETTI | 17 |
| 87 | DTCVESTRI | 16 |
| 206 | FPNHYTIVT | 16 |
| 216 | LYPESHGII | 16 |
| 287 | MPYNGSVPF | 16 |

TABLE XXXIIII-continued

| Pos | 123456789 | score |
|---|---|---|
| 385 | YMTDYFPRI | 16 |
| 437 | KPYLTPDLP | 16 |
| 568 | LPTESLDCF | 16 |
| 663 | DCLRADVRV | 16 |
| 683 | LADKNITHG | 16 |
| 736 | HATERNGVN | 16 |
| 799 | GWLDVLPFI | 16 |
| 808 | IPHRPTNVE | 16 |
| 820 | EGKPEALWV | 16 |
| 853 | DKVQPVSEI | 16 |
| 60 | DASFRGLEN | 15 |
| 201 | YPTKTFPNH | 15 |
| 208 | NHYTIVTGL | 15 |
| 270 | FWPGSEVAI | 15 |
| 293 | VPFEERIST | 15 |
| 450 | YAKNVRIDK | 15 |
| 497 | LAHGPSFKE | 15 |
| 552 | HAEEVSKFS | 15 |
| 601 | TATVKVNLP | 15 |
| 653 | DTSPLPPTV | 15 |
| 680 | SFYLADKNI | 15 |
| 738 | TERNGVNVV | 15 |
| 769 | LANTDVPIP | 15 |
| 804 | LPFIIPHRP | 15 |
| 824 | EALWVEERF | 15 |
| 5 | LTLATEQPV | 14 |
| 11 | QPVKKNTLK | 14 |
| 18 | LKKYKIACI | 14 |
| 19 | KKYKIACIV | 14 |
| 43 | LGLRKLEKQ | 14 |
| 124 | DCCADYKSV | 14 |
| 158 | LPPVILFSM | 14 |
| 181 | MPNINKLKT | 14 |
| 215 | GLYPESHGI | 14 |
| 258 | TAMYQGLKA | 14 |
| 308 | LPKAERPRF | 14 |
| 347 | HAFGMLMEG | 14 |
| 360 | NLHNCVNII | 14 |
| 398 | MYEGPAPRI | 14 |
| 411 | IPHDFFSFN | 14 |
| 500 | GPSFKEKTE | 14 |
| 507 | TEVEPFENI | 14 |
| 519 | NLMCDLLRI | 14 |
| 537 | GSLNHLLKV | 14 |
| 545 | VPFYEPSHA | 14 |
| 566 | NPLPTESLD | 14 |
| 671 | VPPSESQKC | 14 |
| 672 | PPSESQKCS | 14 |
| 15 | KNTLKKYKI | 13 |
| 39 | LGLGLGLRK | 13 |
| 184 | INKLKTCGI | 13 |
| 198 | RAMYPTKTF | 13 |
| 204 | KTFPNHYTI | 13 |
| 217 | YPESHGIID | 13 |
| 265 | KAATYFWPG | 13 |
| 277 | AINGSFPSI | 13 |
| 329 | HAGGPVSAR | 13 |
| 337 | RVIKALQVV | 13 |
| 359 | RNLHNCVNI | 13 |
| 440 | LTPDLPKRL | 13 |
| 446 | KRLHYAKNV | 13 |
| 468 | LAVRSKSNT | 13 |
| 487 | NEFRSMEAI | 13 |
| 528 | QPAPNNGTH | 13 |
| 529 | PAPNNGTHG | 13 |
| 549 | EPSHAEEVS | 13 |
| 564 | FANPLPTES | 13 |
| 577 | CPHLQNSTQ | 13 |
| 596 | TQEEITATV | 13 |
| 655 | SPLPPTVPD | 13 |
| 757 | GHFDAPDEI | 13 |
| 775 | PIPTHYFVV | 13 |
| 796 | NCPGWLDVL | 13 |
| 807 | IIPHRPTNV | 13 |
| 833 | TAHIARVRD | 13 |

TABLE XXXIIII-continued

| Pos | 123456789 | score |
|---|---|---|
| 850 | FYQDKVQPV | 13 |
| 41 | LGLGLRKLE | 12 |
| 73 | VACKDRGDC | 12 |
| 126 | CADYKSVCQ | 12 |
| 146 | TAQQSQCPE | 12 |
| 152 | CPEGFDLPP | 12 |
| 176 | TWDTLMPNI | 12 |
| 225 | DNNMYDVNL | 12 |
| 271 | WPGSEVAIN | 12 |
| 272 | PGSEVAING | 12 |
| 282 | FPSIYMPYN | 12 |
| 285 | IYMPYNGSV | 12 |
| 361 | LHNCVNIIL | 12 |
| 370 | LADHGMDQT | 12 |
| 390 | FPRINFFYM | 12 |
| 401 | GPAPRIRAH | 12 |
| 402 | PAPRIRAHN | 12 |
| 419 | NSEEIVRNL | 12 |
| 431 | KPDQHFKPY | 12 |
| 441 | TPDLPKRLH | 12 |
| 444 | LPKRLHYAK | 12 |
| 455 | RIDKVHLFV | 12 |
| 509 | VEPFENIEV | 12 |
| 548 | YEPSHAEEV | 12 |
| 592 | MLNLTQEEI | 12 |
| 598 | EEITATVKV | 12 |
| 600 | ITATVKVNL | 12 |
| 636 | KAMRMPMWS | 12 |
| 648 | VPQLGDTSP | 12 |
| 651 | LGDTSPLPP | 12 |
| 666 | RADVRVPPS | 12 |
| 715 | VPMYEEFRK | 12 |
| 723 | KMWDYFHSV | 12 |
| 742 | GVNVVSGPI | 12 |
| 768 | HLANTDVPI | 12 |
| 778 | THYFVVLTS | 12 |
| 811 | RPTNVESCP | 12 |
| 822 | KPEALWVEE | 12 |
| 828 | VEERFTAHI | 12 |
| 834 | AHIARVRDV | 12 |

V2-HLA-B5101-9mers-161P2F10B
Each peptide is a portion of SEQ ID NO: 82; each start position is specified, the length of the peptide is 9 amino acids and the end position for each peptide is the start position plus 8.

| | | |
|---|---|---|
| 5 | DCLQRKDCC | 6 |
| 4 | DDCLQRKDC | 5 |
| 2 | CSDDCLQRK | 3 |
| 3 | SDDCLQRKD | 3 |
| 7 | LQRKDCCAD | 3 |
| 1 | SCSDDCLQR | 2 |

V3-HLA-B5101-9mers-161P2F10B
Each peptide is a portion of SEQ ID NO: 85; each start position is specified, the length of the peptide is 9 amino acids and the end position for each peptide is the start position plus 8.

| | | |
|---|---|---|
| 7 | CPGGKPEAL | 19 |
| 9 | GGKPEALWV | 16 |

V4-HLA-B5101-9mers-161P2F10B
Each peptide is a portion of SEQ ID NO: 88; each start position is specified, the length of the peptide is 9 amino acids and the end position for each peptide is the start position plus 8.

| | | |
|---|---|---|
| 2 | YLPTFETPI | 15 |
| 1 | TYLPTFETP | 7 |

TABLE XXXIV

| Pos | 1234567890 | score |
|---|---|---|
| \multicolumn{3}{c}{V1-HLA-A1-10MERS-161P2F10B} | | |

Each peptide is a portion of SEQ ID NO: 81; each start position is specified, the length of the peptide is 10 amino acids and the end position for each peptide is the start position plus 9.

| Pos | 1234567890 | score |
|---|---|---|
| 441 | TPDLPKRLHY | 32 |
| 771 | NTDVPIPTHY | 31 |
| 858 | VSEILQLKTY | 30 |
| 673 | PSESQKCSFY | 29 |
| 718 | YEEFRKMWDY | 27 |
| 370 | LADHGMDQTY | 25 |
| 746 | VSGPIFDYNY | 24 |
| 280 | GSFPSIYMPY | 23 |
| 617 | QKNVDHCLLY | 23 |
| 164 | FSMDGFRAEY | 21 |
| 311 | AERPRFYTMY | 21 |
| 386 | MTDYFPRINF | 21 |
| 388 | DYFPRINFFY | 20 |
| 390 | FPRINFFYMY | 20 |
| 697 | ASNRTSDSQY | 20 |
| 220 | SHGIIDNNMY | 19 |
| 295 | FEERISTLLK | 19 |
| 420 | SEEIVRNLSC | 19 |
| 506 | KTEVEPFENI | 19 |
| 508 | EVEPFENIEV | 19 |
| 737 | ATERNGVNVV | 19 |
| 430 | RKPDQHFKPY | 18 |
| 685 | DKNITHGFLY | 18 |
| 800 | WLDVLPFIIP | 18 |
| 8 | ATEQPVKKNT | 17 |
| 12 | PVKKNTLKKY | 17 |
| 155 | GFDLPPVILF | 17 |
| 166 | MDGFRAEYLY | 17 |
| 187 | LKTCGIHSKY | 17 |
| 192 | IHSKYMRAMY | 17 |
| 201 | YPTKTFPNHY | 17 |
| 208 | NHYTIVTGLY | 17 |
| 277 | AINGSFPSIY | 17 |
| 419 | NSEEIVRNLS | 17 |
| 476 | TNCGGGNHGY | 17 |
| 509 | VEPFENIEVY | 17 |
| 709 | LITSNLVPMY | 17 |
| 841 | DVELLTGLDF | 17 |
| 115 | CSDDCLQKKD | 16 |
| 217 | YPESHGIIDN | 16 |
| 252 | GQPMWLTAMY | 16 |
| 260 | MYQGLKAATY | 16 |
| 539 | LNHLLKVPFY | 16 |
| 569 | PTESLDCFCP | 16 |
| 637 | AMRMPMWSSY | 16 |
| 701 | TSDSQYDALI | 16 |
| 762 | PDEITKHLAN | 16 |
| 842 | VELLTGLDFY | 16 |
| 120 | LQKKDCCADY | 15 |
| 257 | LTAMYQGLKA | 15 |
| 273 | GSEVAINGSF | 15 |
| 308 | LPKAERPRFY | 15 |
| 321 | FEEPDSSGHA | 15 |
| 376 | DQTYCNKMEY | 15 |
| 380 | CNKMEYMTDY | 15 |
| 547 | FYEPSHAEEV | 15 |
| 553 | AEEVSKFSVC | 15 |
| 572 | SLDCFCPHLQ | 15 |
| 621 | DHCLLYHREY | 15 |
| 744 | NVVSGPIFDY | 15 |
| \multicolumn{3}{c}{V2-HLA-A1-10mers-161P2F10B} | | |

Each peptide is a portion of SEQ ID NO: 83; each start position is specified, the length of the peptide is 10 amino acids and the end position for each peptide is the start position plus 9.

| Pos | 1234567890 | score |
|---|---|---|
| 3 | CSDDCLQRKD | 16 |
| 8 | LQRKDCCADY | 15 |
| 4 | SDDCLQRKDC | 13 |
| 10 | RKDCCADYKS | 12 |
| 1 | CSCSDDCLQR | 10 |

V3-HLA-A1-10mers-161P2F10B

Each peptide is a portion of SEQ ID NO: 86; each start position is specified, the length of the peptide is 10 amino acids and the end position for each peptide is the start position plus 9.

| Pos | 1234567890 | score |
|---|---|---|
| 4 | NVESCPGGKP | 13 |
| 6 | ESCPGGKPEA | 8 |
| 2 | PTNVESCPGG | 6 |
| 9 | PGGKPEALWV | 6 |

V4-HLA-A1-10mers-161P2F10B

Each peptide is a portion of SEQ ID NO: 89; each start position is specified, the length of the peptide is 10 amino acids and the end position for each peptide is the start position plus 9.

| Pos | 1234567890 | score |
|---|---|---|
| 1 | KTYLPTFETP | 9 |
| 2 | TYLPTFETPI | 4 |

TABLE XXXV

| Pos | 1234567890 | score |
|---|---|---|
| \multicolumn{3}{c}{V1-HLA-A0201-10mers-161P2F10B} | | |

Each peptide is a portion of SEQ ID NO: 81; each start position is specified, the length of the peptide is 10 amino acids and the end position for each peptide is the start position plus 9.

| Pos | 1234567890 | score |
|---|---|---|
| 28 | LLALLVIMSL | 30 |
| 22 | KIACIVLLAL | 27 |
| 30 | ALLVIMSLGL | 26 |
| 36 | SLGLGLGLGL | 24 |
| 708 | ALITSNLVPM | 24 |
| 835 | HIARVRDVEL | 24 |
| 17 | TLKKYKIACI | 23 |
| 222 | GIIDNNMYDV | 23 |
| 284 | SIYMPYNGSV | 23 |
| 806 | FIIPHRPTNV | 23 |
| 23 | IACIVLLALL | 22 |
| 34 | IMSLGLGLGL | 22 |
| 39 | LGLGLGLRKL | 22 |
| 111 | SLCSCSDDCL | 22 |
| 165 | SMDGFRAEYL | 22 |
| 178 | DTLMPNINKL | 22 |
| 215 | GLYPESHGII | 22 |
| 302 | LLKWLDLPKA | 22 |
| 397 | YMYEGPAPRI | 22 |
| 439 | YLTPDLPKRL | 22 |
| 595 | LTQEEITATV | 22 |
| 615 | VLQKNVDHCL | 22 |
| 25 | CIVLLALLVI | 21 |
| 157 | DLPPVILFSM | 21 |
| 352 | LMEGLKQRNL | 21 |
| 450 | YAKNVRIDKV | 21 |
| 639 | RMPMWSSYTV | 21 |
| 723 | KMWDYFHSVL | 21 |
| 32 | LVIMSLGLGL | 20 |
| 293 | VPFEERISTL | 20 |
| 360 | NLHNCVNIIL | 20 |
| 564 | FANPLPTESL | 20 |
| 591 | QMLNLTQEEI | 20 |
| 737 | ATERNGVNVV | 20 |
| 836 | IARVRDVELL | 20 |
| 4 | TLTLATEQPV | 19 |
| 369 | LLADHGMDQT | 19 |
| 447 | RLHYAKNVRI | 19 |
| 607 | NLPFGRPRVL | 19 |
| 656 | PLPPTVPDCL | 19 |

TABLE XXXV-continued

| Pos | 1234567890 | score |
|---|---|---|
| 682 | YLADKNITHG | 19 |
| 692 | FLYPPASNRT | 19 |
| 825 | ALWVEERFTA | 19 |
| 26 | IVLLALLVIM | 18 |
| 183 | NINKLKTCGI | 18 |
| 204 | KTFPNHYTIV | 18 |
| 259 | AMYQGLKAAT | 18 |
| 267 | ATYFWPGSEV | 18 |
| 276 | VAINGSFPSI | 18 |
| 329 | HAGGPVSARV | 18 |
| 347 | HAFGMLMEGL | 18 |
| 534 | GTHGSLNHLL | 18 |
| 594 | NLTQEEITAT | 18 |
| 833 | TAHIARVRDV | 18 |
| 27 | VLLALLVIMS | 17 |
| 42 | GLGLRKLEKQ | 17 |
| 162 | ILFSMDGFRA | 17 |
| 175 | YTWDTLMPNI | 17 |
| 180 | LMPNINKLKT | 17 |
| 186 | KLKTCGIHSK | 17 |
| 227 | NMYDVNLNKN | 17 |
| 335 | SARVIKALQV | 17 |
| 361 | LHNCVNIILL | 17 |
| 418 | FNSEEIVRNL | 17 |
| 518 | YNLMCDLLRI | 17 |
| 536 | HGSLNHLLKV | 17 |
| 552 | HAEEVSKFSV | 17 |
| 580 | LQNSTQLEQV | 17 |
| 624 | LLYHREYVSG | 17 |
| 660 | TVPDCLRADV | 17 |
| 736 | HATERNGVNV | 17 |
| 768 | HLANTDVPIP | 17 |
| 775 | PIPTHYFVVL | 17 |
| 861 | ILQLKTYLPT | 17 |
| 6 | TLATEQPVKK | 16 |
| 20 | KYKIACIVLL | 16 |
| 31 | LLVIMSLGLG | 16 |
| 131 | SVCQGETSWL | 16 |
| 152 | CPEGFDLPPV | 16 |
| 196 | YMRAMYPTKT | 16 |
| 230 | DVNLNKNFSL | 16 |
| 269 | YFWPGSEVAI | 16 |
| 336 | ARVIKALQVV | 16 |
| 366 | NIILLADHGM | 16 |
| 374 | GMDQTYCNKM | 16 |
| 467 | WLAVRSKSNT | 16 |
| 526 | RIQPAPNNGT | 16 |
| 599 | EITATVKVNL | 16 |
| 606 | VNLPFGRPRV | 16 |
| 700 | RTSDSQYDAL | 16 |
| 792 | HTPENCPGWL | 16 |
| 839 | VRDVELLTGL | 16 |
| 855 | VQPVSEILQL | 16 |
| 9 | TEQPVKKNTL | 15 |
| 24 | ACIVLLALLV | 15 |
| 171 | AEYLYTWDTL | 15 |
| 224 | IDNNMYDVNL | 15 |
| 257 | LTAMYQGLKA | 15 |
| 333 | PVSARVIKAL | 15 |
| 343 | QVVDHAFGML | 15 |
| 355 | GLKQRNLHNC | 15 |
| 359 | RNLHNCVNII | 15 |
| 454 | VRIDKVHLFV | 15 |
| 460 | HLFVDQQWLA | 15 |
| 461 | LFVDQQWLAV | 15 |
| 491 | SMEAIFLAHG | 15 |
| 496 | FLAHGPSFKE | 15 |
| 519 | NLMCDLLRIQ | 15 |
| 530 | APNNGTHGSL | 15 |
| 538 | SLNHLLKVPF | 15 |
| 541 | HLLKVPFYEP | 15 |
| 583 | STQLEQVNQM | 15 |
| 592 | MLNLTQEEIT | 15 |
| 642 | MWSSYTVPQL | 15 |
| 706 | YDALITSNLV | 15 |
| 731 | VLLIKHATER | 15 |
| 765 | ITKHLANTDV | 15 |
| 774 | VPIPTHYFVV | 15 |
| 817 | SCPEGKPEAL | 15 |
| 827 | WVEERFTAHI | 15 |
| 846 | TGLDFYQDKV | 15 |
| 33 | VIMSLGLGLG | 14 |
| 57 | KCFDASFRGL | 14 |
| 64 | RGLENCRCDV | 14 |
| 65 | GLENCRCDVA | 14 |
| 173 | YLYTWDTLMP | 14 |
| 191 | GIHSKYMRAM | 14 |
| 232 | NLNKNFSLSS | 14 |
| 338 | VIKALQVVDH | 14 |
| 341 | ALQVVDHAFG | 14 |
| 350 | GMLMEGLKQR | 14 |
| 368 | ILLADHGMDQ | 14 |
| 494 | AIFLAHGPSF | 14 |
| 508 | EVEPFENIEV | 14 |
| 533 | NGTHGSLNHL | 14 |
| 547 | FYEPSHAEEV | 14 |
| 584 | TQLEQVNQML | 14 |
| 709 | LITSNLVPMY | 14 |
| 722 | RKMWDYFHSV | 14 |
| 732 | LLIKHATERN | 14 |
| 734 | IKHATERNGV | 14 |
| 773 | DVPIPTHYFV | 14 |
| 830 | ERFTAHIARV | 14 |
| 844 | LLTGLDFYQD | 14 |
| 849 | DFYQDKVQPV | 14 |
| 859 | SEILQLKTYL | 14 |
| 866 | TYLPTFETTI | 14 |

V2-HLA-A0201-10mers-161P2F10B
Each peptide is a portion of SEQ ID NO: 83; each start position is specified, the length of the peptide is 10 amino acids and the end position for each peptide is the start position plus 9.

| Pos | 1234567890 | score |
|---|---|---|
| 7 | CLQRKDCCAD | 11 |
| 2 | SCSDDCLQRK | 7 |
| 6 | DCLQRKDCCA | 5 |

V3-HLA-A0201-10mers-161P2F10B
Each peptide is a portion of SEQ ID NO: 86; each start position is specified, the length of the peptide is 10 amino acids and the end position for each peptide is the start position plus 9.

| Pos | 1234567890 | score |
|---|---|---|
| 7 | SCPGGKPEAL | 15 |
| 9 | PGGKPEALWV | 8 |

V4-HLA-A0201-10mers-161P2F10B
Each peptide is a portion of SEQ ID NO: 89; each start position is specified, the length of the peptide is 10 amino acids and the end position for each peptide is the start position plus 9.

| Pos | 1234567890 | score |
|---|---|---|
| 2 | TYLPTFETPI | 12 |
| 1 | KTYLPTFETP | 8 |

TABLE XXXVI

| Pos | 1234567890 | score |
|---|---|---|

V1-HLA-A0203-10mers-161P2F10B
Each peptide is a portion of SEQ ID NO: 81; each start position is specified, the length of the peptide is 10 amino acids and the end position for each peptide is the start position plus 9.

| Pos | 1234567890 | score |
|---|---|---|
| 258 | TAMYQGLKAA | 19 |
| 259 | AMYQGLKAAT | 17 |
| 15 | KNTLKKYKIA | 10 |
| 21 | YKIACIVLLA | 10 |
| 52 | GSCRKKCFDA | 10 |
| 65 | GLENCRCDVA | 10 |
| 101 | FRCGETRLEA | 10 |
| 118 | DCLQKKDCCA | 10 |

TABLE XXXVI-continued

| Pos | 1234567890 | score |
|---|---|---|
| 138 | SWLEENCDTA | 10 |
| 162 | ILFSMDGFRA | 10 |
| 190 | CGIHSKYMRA | 10 |
| 239 | LSSKEQNNPA | 10 |
| 250 | WHGQPMWLTA | 10 |
| 257 | LTAMYQGLKA | 10 |
| 268 | TYFWPGSEVA | 10 |
| 302 | LLKWLDLPKA | 10 |
| 321 | FEEPDSSGHA | 10 |
| 327 | SGHAGGPVSA | 10 |
| 332 | GPVSARVIKA | 10 |
| 339 | IKALQVVDHA | 10 |
| 362 | HNCVNIILLA | 10 |
| 394 | NFFYMYEGPA | 10 |
| 399 | YEGPAPRIRA | 10 |
| 442 | PDLPKRLHYA | 10 |
| 460 | HLFVDQQWLA | 10 |
| 485 | YNNEFRSMEA | 10 |
| 489 | FRSMEAIFLA | 10 |
| 521 | MCDLLRIQPA | 10 |
| 544 | KVPFYEPSHA | 10 |
| 556 | VSKFSVCGFA | 10 |
| 593 | LNLTQEEITA | 10 |
| 628 | REYVSGFGKA | 10 |
| 658 | PPTVPDCLRA | 10 |
| 675 | ESQKCSFYLA | 10 |
| 688 | ITHGFLYPPA | 10 |
| 699 | NRTSDSQYDA | 10 |
| 728 | FHSVLLIKHA | 10 |
| 752 | DYNYDGHFDA | 10 |
| 761 | APDEITKHLA | 10 |
| 816 | ESCPEGKPEA | 10 |
| 825 | ALWVEERFTA | 10 |
| 828 | VEERFTAHIA | 10 |
| 16 | NTLKKYKIAC | 9 |
| 22 | KIACIVLLAL | 9 |
| 53 | SCRKKCFDAS | 9 |
| 66 | LENCRODVAC | 9 |
| 102 | RCGETRLEAS | 9 |
| 119 | CLQKKDCCAD | 9 |
| 139 | WLEENCDTAQ | 9 |
| 163 | LFSMDGFRAE | 9 |
| 191 | GIHSKYMRAM | 9 |
| 240 | SSKEQNNPAW | 9 |
| 251 | HGQPMWLTAM | 9 |
| 269 | YFWPGSEVAI | 9 |
| 303 | LKWLDLPKAE | 9 |
| 322 | EEPDSSGHAG | 9 |
| 328 | GHAGGPVSAR | 9 |
| 333 | PVSARVIKAL | 9 |
| 340 | KALQVVDHAF | 9 |
| 363 | NCVNIILLAD | 9 |
| 395 | FFYMYEGPAP | 9 |
| 400 | EGPAPRIRAH | 9 |
| 443 | DLPKRLHYAK | 9 |
| 461 | LFVDQQWLAV | 9 |
| 486 | NNEFRSMEAI | 9 |
| 490 | RSMEAIFLAH | 9 |
| 522 | CDLLRIQPAP | 9 |
| 545 | VPFYEPSHAE | 9 |
| 557 | SKFSVCGFAN | 9 |
| 594 | NLTQEEITAT | 9 |
| 629 | EYVSGFGKAM | 9 |
| 659 | PTVPOCLRAD | 9 |
| 676 | SQKCSFYLAD | 9 |
| 689 | THGFLYPPAS | 9 |
| 700 | RTSDSQYDAL | 9 |
| 729 | HSVLLIKHAT | 9 |
| 753 | YNYDGHFDAP | 9 |
| 762 | PDEITKHLAN | 9 |
| 817 | SCPEGKPEAL | 9 |
| 826 | LWVEERFTAH | 9 |
| 829 | EERFTAHIAR | 9 |

TABLE XXXVI-continued

| Pos | 1234567890 | score |
|---|---|---|

V2-HLA-A0203-10mers-161P2F10B
Each peptide is a portion of SEQ ID NO: 83; each start position is specified, the length of the peptide is 10 amino acids and the end position for each peptide is the start position plus 9.

| 6 | DCLQRKDCCA | 10 |
| 7 | CLQRKDCCAD | 9 |
| 8 | LQRKDCCADY | 8 |

V3-HLA-A0203-10mers-161P2F10B
Each peptide is a portion of SEQ ID NO: 86; each start position is specified, the length of the peptide is 10 amino acids and the end position for each peptide is the start position plus 9.

| 6 | ESCPGGKPEA | 10 |
| 7 | SCPGGKPEAL | 9 |
| 8 | CPGGKPEALW | 8 |

V2-HLA-A0203-10mers-161P2F10B

No Results Found.

TABLE XXXVII

| Pos | 1234567890 | score |
|---|---|---|

V1-HLA-A3-10mers-161P2F10B
Each peptide is a portion of SEQ ID NO: 81; each start position is specified, the length of the peptide is 10 amino acids and the end position for each peptide is the start position plus 9.

| 38 | GLGLGLGLRK | 27 |
| 6 | TLATEQPVKK | 26 |
| 186 | KLKTCGIHSK | 26 |
| 301 | TLLKWLDLPK | 25 |
| 337 | RVIKALQVVD | 25 |
| 838 | RVRDVELLTG | 25 |
| 47 | KLEKQGSCRK | 23 |
| 179 | TLMPNINKLK | 23 |
| 256 | WLTAMYQGLK | 23 |
| 277 | AINGSFPSIY | 23 |
| 212 | IVTGLYPESH | 21 |
| 422 | EIVRNLSCRK | 21 |
| 437 | KPYLTPDLPK | 21 |
| 443 | DLPKRLHYAK | 21 |
| 462 | FVDQQWLAVR | 21 |
| 494 | AIFLAHGPSF | 21 |
| 605 | KVNLPFGRPR | 21 |
| 730 | SVLLJKHATE | 21 |
| 731 | VLLIKHATER | 21 |
| 781 | FVVLTSCKNK | 21 |
| 841 | DVELLTGLDF | 21 |
| 195 | KYMRAMYPTK | 20 |
| 368 | ILLADHGMDQ | 20 |
| 495 | IFLAHGPSFK | 20 |
| 624 | LLYHREYVSG | 20 |
| 630 | YVSGFGKAMR | 20 |
| 664 | CLRADVRVPP | 20 |
| 708 | ALITSNLVPM | 20 |
| 714 | LVPMYEEFRK | 20 |
| 26 | IVLLALLVIM | 19 |
| 32 | LVIMSLGLGL | 19 |
| 107 | RLEASLCSCS | 19 |
| 338 | VIKALQVVDH | 19 |
| 523 | DLLRIQPAPN | 19 |
| 538 | SLNHLLKVPF | 19 |
| 588 | QVNQMLNLTQ | 19 |
| 596 | TQEEITATVK | 19 |
| 609 | PFGRPRVLQK | 19 |
| 669 | VRVPPSESQK | 19 |
| 802 | DVLPFIIPHR | 19 |
| 5 | LTLATEQPVK | 18 |
| 30 | ALLVIMSLGL | 18 |

TABLE XXXVII-continued

| Pos | 1234567890 | score |
|---|---|---|
| 36 | SLGLGLGLGL | 18 |
| 160 | PVILFSMDGF | 18 |
| 173 | YLYTWDTLMP | 18 |
| 215 | GLYPESHGII | 18 |
| 260 | MYQGLKAATY | 18 |
| 364 | CVNIILLADH | 18 |
| 426 | NLSCRKPDQH | 18 |
| 447 | RLHYAKNVRI | 18 |
| 453 | NVRIDKVHLF | 18 |
| 697 | ASNRTSDSQY | 18 |
| 825 | ALWVEERFTA | 18 |
| 12 | PVKKNTLKKY | 17 |
| 41 | LGLGLRKLEK | 17 |
| 46 | RKLEKQGSCR | 17 |
| 121 | QKKDCCADYK | 17 |
| 233 | LNKNFSLSSK | 17 |
| 311 | AERPRFYTMY | 17 |
| 405 | RIRAHNIPHD | 17 |
| 458 | KVHLFVDQQW | 17 |
| 469 | AVRSKSNTNC | 17 |
| 524 | LLRIQPAPNN | 17 |
| 544 | KVPFYEPSHA | 17 |
| 637 | AMRMPMWSSY | 17 |
| 650 | QLGDTSPLPP | 17 |
| 670 | RVPPSESQKC | 17 |
| 692 | FLYPPASNRT | 17 |
| 713 | NLVPMYEEFR | 17 |
| 742 | GVNVVSGPIF | 17 |
| 831 | RFTAHIARVR | 17 |
| 22 | KIACIVLLAL | 16 |
| 25 | CIVLLALLVI | 16 |
| 67 | ENCRCDVACK | 16 |
| 113 | CSCSDDCLQK | 16 |
| 284 | SIYMPYNGSV | 16 |
| 295 | FEERISTLLK | 16 |
| 341 | ALQVVDHAFG | 16 |
| 423 | IVRNLSCRKP | 16 |
| 455 | RIDKVHLFVD | 16 |
| 549 | EPSHAEEVSK | 16 |
| 603 | TVKVNLPFGR | 16 |
| 614 | RVLQKNVDHC | 16 |
| 623 | CLLYHREYVS | 16 |
| 744 | NVVSGPIFDY | 16 |
| 758 | HFDAPDEITK | 16 |
| 775 | PIPTHYFVVL | 16 |
| 783 | VLTSCKNKSH | 16 |
| 806 | FIIPHRPTNV | 16 |
| 835 | HIARVRDVEL | 16 |
| 854 | KVQPVSEILQ | 16 |
| 861 | ILQKTYLPT | 16 |
| 11 | QPVKKNTLKK | 15 |
| 27 | VLLALLVIMS | 15 |
| 28 | LLALLVIMSL | 15 |
| 55 | RKKCFDASFR | 15 |
| 65 | GLENCRCDVA | 15 |
| 131 | SVCQGETSWL | 15 |
| 157 | DLPPVILFSM | 15 |
| 161 | VILFSMDGFR | 15 |
| 162 | ILFSMDGFRA | 15 |
| 223 | IIDNNMYDVN | 15 |
| 232 | NLNKNFSLSS | 15 |
| 285 | IYMPYNGSVP | 15 |
| 307 | DLPKAERPRF | 15 |
| 331 | GGPVSARVIK | 15 |
| 343 | QVVDHAFGML | 15 |
| 367 | IILLADHGMD | 15 |
| 369 | LLADHGMDQT | 15 |
| 516 | EVYNLMCDLL | 15 |
| 526 | RIQPAPNNGT | 15 |
| 607 | NLPFGRPRVL | 15 |
| 660 | TVPDCLRADV | 15 |
| 668 | DVRVPPSESQ | 15 |
| 677 | QKCSFYLADK | 15 |
| 709 | LITSNLVPMY | 15 |
| 764 | EITKHLANTD | 15 |
| 844 | LLTGLDFYQD | 15 |
| 863 | QLKTYLPTFE | 15 |
| 17 | TLKKYKIACI | 14 |
| 263 | GLKAATYFWP | 14 |
| 292 | SVPFEERIST | 14 |
| 305 | WLDLPKAERP | 14 |
| 344 | VVDHAFGMLM | 14 |
| 348 | AFGMLMEGLK | 14 |
| 428 | SCRKPDQHFK | 14 |
| 439 | YLTPDLPKRL | 14 |
| 467 | WLAVRSKSNT | 14 |
| 555 | EVSKFSVCGF | 14 |
| 567 | PLPTESLDCF | 14 |
| 579 | HLQNSTQLEQ | 14 |
| 599 | EITATVKVNL | 14 |
| 619 | NVDHCLLYHR | 14 |
| 656 | PLPPTVPDCL | 14 |
| 807 | IIPHRPTNVE | 14 |
| 827 | WVEERFTAHI | 14 |
| 847 | GLDFYQDKVQ | 14 |
| 857 | PVSEILQLKT | 14 |
| 44 | GLRKLEKQGS | 13 |
| 72 | DVACKDRGDC | 13 |
| 91 | ESTRIWMCNK | 13 |
| 139 | WLEENCDTAQ | 13 |
| 192 | IHSKYMRAMY | 13 |
| 226 | NNMYDVNLNK | 13 |
| 230 | DVNLNKNFSL | 13 |
| 267 | ATYFWPGSEV | 13 |
| 304 | KWLDLPKAER | 13 |
| 330 | AGGPVSARVI | 13 |
| 333 | PVSARVIKAL | 13 |
| 335 | SARVIKALQV | 13 |
| 446 | KRLHYAKNVR | 13 |
| 490 | RSMEAIFLAH | 13 |
| 508 | EVEPFENIEV | 13 |
| 527 | IQPAPNNGTH | 13 |
| 535 | THGSLNHLLK | 13 |
| 560 | SVCGFANPLP | 13 |
| 585 | QLEQVNQMLN | 13 |
| 627 | HREYVSGFGK | 13 |
| 647 | TVPQLGDTSP | 13 |
| 682 | YLADKNITHG | 13 |
| 726 | DYFHSVLLIK | 13 |
| 732 | LLIKHATERN | 13 |
| 749 | PIFDYNYDGH | 13 |
| 779 | HYFVVLTSCK | 13 |
| 834 | AHIARVRDVE | 13 |

V2-HLA-A3-10mers-161P2F10B
Each peptide is a portion of SEQ ID NO: 83; each start position is specified, the length of the peptide is 10 amino acids and the end position for each peptide is the start position plus 9.

| | | |
|---|---|---|
| 9 | QRKDCCADYK | 17 |
| 7 | CLQRKDCCAD | 14 |
| 2 | SCSDDCLQRK | 12 |
| 8 | LQRKDCCADY | 12 |
| 1 | CSCSDDCLQR | 10 |

V3-HLA-A3-10mers-161P2F10B
Each peptide is a portion of SEQ ID NO: 86; each start position is specified, the length of the peptide is 10 amino acids and the end position for each peptide is the start position plus 9.

| | | |
|---|---|---|
| 4 | NVESCPGGKP | 14 |
| 3 | TNVESCPGGK | 13 |
| 10 | GGKPEALWVE | 8 |
| 9 | PGGKPEALWV | 7 |

V4-HLA-A3-10mers-161P2F10B
Each peptide is a portion of SEQ ID NO: 89; each start position is specified, the length of the peptide is 10 amino acids and the end position for each peptide is the start position plus 9.

| | | |
|---|---|---|
| 1 | KTYLPTFETP | 12 |
| 2 | TYLPTFETPI | 6 |

TABLE XXXVIII

| Pos | 1234567890 | score |
|---|---|---|
| V1-HLA-A26-10mers-161P2F10B Each peptide is a portion of SEQ ID NO: 81; each start position is specified, the length of the peptide is 10 amino acids and the end position for each peptide is the start position plus 9. | | |
| 555 | EVSKFSVCGF | 32 |
| 178 | DTLMPNINKL | 29 |
| 744 | NVVSGPIFDY | 29 |
| 516 | EVYNLMCDLL | 28 |
| 841 | DVELLTGLDF | 28 |
| 230 | DVNLNKNFSL | 27 |
| 297 | ERISTLLKWL | 27 |
| 12 | PVKKNTLKKY | 25 |
| 343 | QVVDHAFGML | 25 |
| 32 | LVIMSLGLGL | 24 |
| 154 | EGFDLPPVIL | 23 |
| 333 | PVSARVIKAL | 23 |
| 388 | DYFPRINFFY | 23 |
| 599 | EITATVKVNL | 23 |
| 795 | ENCPGWLDVL | 23 |
| 802 | DVLPFIIPHR | 23 |
| 160 | PVILFSMDGF | 22 |
| 453 | NVRIDKVHLF | 22 |
| 508 | EVEPFENIEV | 22 |
| 719 | EEFRKMWDYF | 22 |
| 709 | LITSNLVPMY | 21 |
| 131 | SVCQGETSWL | 20 |
| 275 | EVAINGSFPS | 20 |
| 293 | VPFEERISTL | 20 |
| 488 | EFRSMEAIFL | 20 |
| 853 | DKVQPVSEIL | 20 |
| 72 | DVAGKDRGDC | 19 |
| 105 | ETRLEASLCS | 19 |
| 376 | DQTYCNKMEY | 19 |
| 421 | EEIVRNLSCR | 19 |
| 571 | ESLDCFCPHL | 19 |
| 668 | DVRVPPSESQ | 19 |
| 685 | DKNITHGFLY | 19 |
| 742 | GVNVVSGPIF | 19 |
| 792 | HTPENCPGWL | 19 |
| 22 | KIACIVLLAL | 18 |
| 92 | STRIWMCNKF | 18 |
| 136 | ETSWLEENCD | 18 |
| 312 | ERPRFYTMYF | 18 |
| 422 | EIVRNLSCRK | 18 |
| 494 | AIFLAHGPSF | 18 |
| 513 | ENIEVVNLMC | 18 |
| 587 | EQVNQMLNLT | 18 |
| 598 | EEITATVKVN | 18 |
| 621 | DHCLLYHREY | 18 |
| 659 | PTVPDGLRAD | 18 |
| 700 | RISDSQYDAL | 18 |
| 771 | NTDVPIPTHY | 18 |
| 773 | DVPIPTHYFV | 18 |
| 830 | ERFTAHIARV | 18 |
| 386 | MTDYFPRINF | 17 |
| 457 | DKVHLFVDQQ | 17 |
| 629 | EYVSGFGKAM | 17 |
| 653 | DTSPLPPTVP | 17 |
| 726 | DYFHSVLLIK | 17 |
| 760 | DAPDEITKHL | 17 |
| 838 | RVRDVELLTG | 17 |
| 87 | DTCVESTRIW | 16 |
| 89 | CVESTRIWMC | 16 |
| 145 | DTAQQSQGPE | 16 |
| 210 | YTIVTGLYPE | 16 |
| 296 | EERISTLLKW | 16 |
| 307 | DLPKAERPRF | 16 |
| 510 | EPFENIEVYN | 16 |
| 534 | GTHGSLNHLL | 16 |
| 574 | DCFCPHLQNS | 16 |
| 602 | ATVKVNLPFG | 16 |
| 763 | DEITKHLANT | 16 |
| 764 | EITKHLANTD | 16 |
| 277 | AINGSFPSIY | 15 |
| 280 | GSFPSIYMPY | 15 |

TABLE XXXVIII-continued

| Pos | 1234567890 | score |
|---|---|---|
| 400 | EGPAPRIRAH | 15 |
| 493 | EAIFLAHGPS | 15 |
| 554 | EEVSKFSVCG | 15 |
| 646 | YTVPQLGDTS | 15 |
| 739 | ERNGVNVVSG | 15 |
| 820 | EGKPEALWVE | 15 |
| 858 | VSEILQLKTY | 15 |
| V2-HLA-A26-10mers-161P2F10B Each peptide is a portion of SEQ ID NO: 83; each start position is specified, the length of the peptide is 10 amino acids and the end position for each peptide is the start position plus 9. | | |
| 8 | LQRKDCCADY | 10 |
| 5 | DDCLQRKDCC | 8 |
| 6 | DCLQRKDCCA | 8 |
| 2 | SCSDDCLQRK | 6 |
| V3-HLA-A26-10mers-161P2F10B Each peptide is a portion of SEQ ID NO: 86; each start position is specified, the length of the peptide is 10 amino acids and the end position for each peptide is the start position plus 9. | | |
| 4 | NVESCPGGKP | 14 |
| 6 | ESCPGGKPEA | 11 |
| 7 | SCPGGKPEAL | 10 |
| 2 | PINVESCPGG | 8 |
| 3 | TNVESCPGGK | 8 |
| V4-HLA-A26-10mers-161P2F10B Each peptide is a portion of SEQ ID NO: 89; each start position is specified, the length of the peptide is 10 amino acids and the end position for each peptide is the start position plus 9. | | |
| 1 | KTYLPTFETP | 9 |

TABLE XXXIX

| Pos | 1234567890 | score |
|---|---|---|
| V1-HLA-B0702-10mers-161P2F10B Each peptide is a portion of SEQ ID NO: 81; each start position is specified, the length of the peptide is 10 amino acids and the end position for each peptide is the start position plus 9. | | |
| 431 | KPDQHFKPYL | 23 |
| 530 | APNNGTHGSL | 22 |
| 648 | VPQLGDTSPL | 22 |
| 577 | CPHLQNSTQL | 21 |
| 797 | CPGWLDVLPF | 21 |
| 152 | CPEGFDLPPV | 20 |
| 293 | VPFEERISTL | 20 |
| 776 | IPTHYFVVLT | 20 |
| 500 | GPSFKEKTEV | 19 |
| 761 | APDEITKHLA | 19 |
| 246 | NPAWWHGQPM | 18 |
| 658 | PPTVPDCLRA | 18 |
| 672 | PPSESQKCSF | 18 |
| 715 | VPMYEEFRKM | 18 |
| 774 | VPIPTHYFVV | 18 |
| 332 | GPVSARVIKA | 17 |
| 804 | LPFIIPHRPT | 17 |
| 22 | KIACIVLLAL | 15 |
| 34 | IMSLGLGLGL | 15 |
| 549 | EPSHAEEVSK | 15 |
| 608 | LPFGRPRVLQ | 15 |
| 11 | QPVKKNTLKK | 14 |
| 30 | ALLVIMSLGL | 14 |
| 313 | RPRFYTMYFE | 14 |
| 333 | PVSARVIKAL | 14 |
| 401 | GPAPRIRAHN | 14 |
| 403 | APRIRAHNIP | 14 |
| 437 | KPYLTPDLPK | 14 |

TABLE XXXIX-continued

| Pos | 1234567890 | score |
|---|---|---|
| 441 | TPDLPKRLHY | 14 |
| 488 | EFRSMEAIFL | 14 |
| 599 | EITATVKVNL | 14 |
| 612 | RPRVLQKNVD | 14 |
| 642 | MWSSYYTVPQ | 14 |
| 700 | RTSOSQYDAL | 14 |
| 775 | PIPTHYFVVL | 14 |
| 836 | IARVRDVELL | 14 |
| 19 | KKYKIACIVL | 13 |
| 20 | KYKIACIVLL | 13 |
| 36 | SLGLGLGLGL | 13 |
| 154 | EGFDLPPVIL | 13 |
| 165 | SMDGFRAEYL | 13 |
| 224 | IDNNMYDVNL | 13 |
| 287 | MPYNGSVPFE | 13 |
| 299 | ISTLLKWLDL | 13 |
| 323 | EPDSSGHAGG | 13 |
| 390 | EPRINEFYMY | 13 |
| 418 | FNSEEIVRNL | 13 |
| 435 | HFKPYLTPDL | 13 |
| 452 | KNVRIDKVHL | 13 |
| 510 | EPFENIEVYN | 13 |
| 528 | QPAPNNGTHG | 13 |
| 566 | NPLPTESLDC | 13 |
| 640 | MPMWSSYYTVP | 13 |
| 655 | SPLPPTVPDC | 13 |
| 684 | ADKNITHGFL | 13 |
| 694 | YPPASNRTSD | 13 |
| 705 | QYDALITSNL | 13 |
| 724 | MWDYFHSVLL | 13 |
| 795 | ENCPGWLDVL | 13 |
| 808 | IPHRPTNVES | 13 |
| 818 | CPEGKPEALW | 13 |
| 822 | KPEALWVEER | 13 |
| 835 | HIARVRDVEL | 13 |
| 23 | IACIVLLALL | 12 |
| 32 | LVIMSLGLGL | 12 |
| 39 | LGLGLGLRKL | 12 |
| 57 | KCFDASFRGL | 12 |
| 171 | AEYLYTWDTL | 12 |
| 206 | FPNHYTIVTG | 12 |
| 207 | PNHYTIVTGL | 12 |
| 248 | AWWHGQPMWL | 12 |
| 282 | FPSIYMPYNG | 12 |
| 308 | LPKAERPRFY | 12 |
| 347 | HAFGMLMEGL | 12 |
| 352 | LMEGLKQRNL | 12 |
| 534 | GTHGSLNHLL | 12 |
| 564 | FANPLPTESL | 12 |
| 571 | ESLDCFCPHL | 12 |
| 586 | LEQVNQMLNL | 12 |
| 661 | VPDCLRADVR | 12 |
| 674 | SESQKCSFYL | 12 |
| 695 | PPASNRTSDS | 12 |
| 723 | KMWDYFHSVL | 12 |
| 811 | RPTNVESCPE | 12 |
| 839 | VRDVELLTGL | 12 |
| 855 | VQPVSEILQL | 12 |
| 9 | TEQPVKKNTL | 11 |
| 28 | LIALLVIMSL | 11 |
| 76 | KDRGDCCWDF | 11 |
| 99 | NKFRCGETRL | 11 |
| 101 | FRCGETRLEA | 11 |
| 103 | CGETRLEASL | 11 |
| 131 | SVCQGETSWL | 11 |
| 158 | LPPVILFSMD | 11 |
| 201 | YPTKTFPNHY | 11 |
| 253 | QPMWLTAMYQ | 11 |
| 271 | WPGSEVAING | 11 |
| 294 | PFEERISTLL | 11 |
| 297 | ERISTLLKWL | 11 |
| 325 | DSSGHAGGPV | 11 |
| 330 | AGGPVSARVI | 11 |
| 343 | QVVDHAFGML | 11 |
| 411 | IPHDFFSFNS | 11 |

TABLE XXXIX-continued

| Pos | 1234567890 | score |
|---|---|---|
| 439 | YLTPDLPKRL | 11 |
| 444 | LPKRLHYAKN | 11 |
| 511 | PFENIEVYNL | 11 |
| 515 | IEVYNLMCDL | 11 |
| 516 | EVYNLMCDLL | 11 |
| 545 | VPFYEPSHAE | 11 |
| 555 | EVSKFSVCGF | 11 |
| 559 | FSVCGFANPL | 11 |
| 568 | LPTESLDCFC | 11 |
| 607 | NLPFGRPRVL | 11 |
| 615 | VLQKNVDHCL | 11 |
| 656 | PLPPTVPDCL | 11 |
| 688 | ITHGFLYPPA | 11 |
| 708 | ALITSNLVPM | 11 |
| 760 | DAPDEITKHL | 11 |
| 767 | KHLANTDVPI | 11 |
| 817 | SCPEGKPEAL | 11 |
| 859 | SEILQLKTYL | 11 |

V2-HLA-B0702-10mers-161P2F10B
Each peptide is a portion of SEQ ID NO: 83; each start position is specified, the length of the peptide is 10 amino acids and the end position for each peptide is the start position plus 9.

| | | |
|---|---|---|
| 6 | DCLQRKDCCA | 6 |
| 8 | LQRKDCCADY | 4 |
| 1 | CSCSDDCLQR | 2 |
| 2 | SCSDDCLQRK | 2 |
| 4 | SDDCLQRKDC | 2 |
| 10 | RKDCCADYKS | 2 |
| 3 | CSDDCLQRKD | 1 |
| 7 | CLQRKDCCAD | 1 |

V3-HLA-B0702-10mers-161P2F10B
Each peptide is a portion of SEQ ID NO: 86; each start position is specified, the length of the peptide is 10 amino acids and the end position for each peptide is the start position plus 9.

| | | |
|---|---|---|
| 8 | CPGGKPEALW | 14 |
| 7 | SCPGGKPEAL | 13 |
| 1 | RPTNVESCPG | 12 |
| 9 | PGGKPEALWV | 10 |
| 6 | ESCPGGKPEA | 9 |

V4-HLA-B0702-10mers-161P2F10B
Each peptide is a portion of SEQ ID NO: 89; each start position is specified, the length of the peptide is 10 amino acids and the end position for each peptide is the start position plus 9.

| | | |
|---|---|---|
| 2 | TYLPTFETPI | 9 |

TABLE XL

| Pos | 1234567890 | score |
|---|---|---|

V1-HLA-B08-10mers-161P2F10B

No Results Found.
V2-HLA-B08-10mers-161P2F10B

No Results Found.
V3-HLA-B08-10mers-161P2F10B

No Results Found.
V4-HLA-B08-10mers-161P2F10B

No Results Found.

TABLE XLI

| Pos | 1234567890 | score |
|---|---|---|
| | V1-HLA-B1510-10mers-161P2F10B | |
| | No Results Found. | |
| | V2-HLA-B1510-10mers-161P2F10B | |
| | No Results Found. | |
| | V3-HLA-B1510-10mers-161P2F10B | |
| | No Results Found. | |
| | V4-HLA-B1510-10mers-161P2F10B | |
| | No Results Found. | |

TABLE XLII

| Pos | 1234567890 | score |
|---|---|---|
| | V1-HLA-B2705-10mers-161P2F10B | |
| | No Results Found. | |
| | V2-HLA-B2705-10mers-161P2F10B | |
| | No Results Found. | |
| | V3-HLA-B2705-10mers-161P2F10B | |
| | No Results Found. | |
| | V4-HLA-B2705-10mers-161P2F10B | |
| | No Results Found. | |

TABLE XLIII

| Pos | 1234567890 | score |
|---|---|---|
| | V1-HLA-B2709-10mers-161P2F10B | |
| | No Results Found. | |
| | V2-HLA-B2709-10mers-161P2F10B | |
| | No Results Found. | |
| | V3-HLA-B2709-10mers-161P2F10B | |
| | No Results Found. | |
| | V4-HLA-B2709-10mers-161P2F10B | |
| | No Results Found. | |

TABLE XLIV

| Pos | 1234567890 | score |
|---|---|---|
| | V1-HLA-B4402-10mers-161P2F10B | |

Each peptide is a portion of SEQ ID NO: 81; each start position is specified, the length of the peptide is 10 amino acids and the end position for each peptide is the start position plus 9.

| Pos | 1234567890 | score |
|---|---|---|
| 311 | AERPRFYTMY | 26 |
| 9 | TEQPVKKNTL | 25 |
| 171 | AEYLYTWDTL | 25 |
| 296 | EERISTLLKW | 25 |
| 509 | VEPFENIEVY | 25 |
| 719 | EEFRKMWDYF | 25 |
| 859 | SEILQLKTYL | 25 |
| 487 | NEFRSMEAIF | 24 |
| 842 | VELLTGLDFY | 23 |
| 674 | SESQKCSFYL | 22 |
| 586 | LEQVNQMLNL | 21 |
| 823 | PEALWVEERF | 21 |
| 153 | PEGFDLPPVI | 20 |

TABLE XLIV-continued

| Pos | 1234567890 | score |
|---|---|---|
| 515 | IEVYNLMCDL | 20 |
| 598 | EEITATVKVN | 20 |
| 718 | YEEFRKMWDY | 20 |
| 297 | ERISTLLKWL | 18 |
| 333 | PVSARVIKAL | 18 |
| 154 | EGFDLPPVIL | 17 |
| 322 | EEPDSSGHAG | 17 |
| 330 | AGGPVSARVI | 17 |
| 409 | HNIPHDFFSF | 17 |
| 795 | ENCPGWLDVL | 17 |
| 20 | KYKIACIVLL | 16 |
| 57 | KCFDASFRGL | 16 |
| 178 | DTLMPNINKL | 16 |
| 293 | VPFEERISTL | 16 |
| 421 | EEIVRNLSCR | 16 |
| 439 | YLTPDLPKRL | 16 |
| 494 | AIFLAHGPSF | 16 |
| 855 | VQPVSEILQL | 16 |
| 22 | KIACIVLLAL | 15 |
| 30 | ALLVIMSLGL | 15 |
| 39 | LGLGLGLRKL | 15 |
| 155 | GFDLPPVILF | 15 |
| 277 | AINGSFPSIY | 15 |
| 280 | GSFPSIYMPY | 15 |
| 312 | ERPRFYTMYF | 15 |
| 340 | KALQWVVHAF | 15 |
| 361 | LHNCVNIILL | 15 |
| 388 | DYFPRINFFY | 15 |
| 399 | YEGPAPRIRA | 15 |
| 430 | RKPDQHFKPY | 15 |
| 553 | AEEVSKFSVC | 15 |
| 607 | NLPFGRPRVL | 15 |
| 656 | PLPPTVPDCL | 15 |
| 697 | ASNRTSDSQY | 15 |
| 760 | DAPDEITKHL | 15 |
| 763 | DEITKHLANT | 15 |
| 772 | TDVPIPTHYF | 15 |
| 775 | PIPTHYFVVL | 15 |
| 817 | SCPEGKPEAL | 15 |
| 829 | EERFTAHIAR | 15 |
| 1 | MESTLTLATE | 14 |
| 12 | PVKKNTLKKY | 14 |
| 28 | LLALLVIMSL | 14 |
| 32 | LVIMSLGLGL | 14 |
| 74 | ACKDRGDCCW | 14 |
| 99 | NKFRCGETRL | 14 |
| 141 | EENCDTAQQS | 14 |
| 147 | AQQSQCPEGF | 14 |
| 160 | PVILFSMDGF | 14 |
| 165 | SMDGFRAEYL | 14 |
| 197 | MRAMYPTKTF | 14 |
| 208 | NHYTIVTGLY | 14 |
| 218 | PESHGIIDNN | 14 |
| 248 | AWWHGQPMWL | 14 |
| 269 | YFWPGSEVAI | 14 |
| 295 | FEERISTLLK | 14 |
| 353 | MEGLKQRNLH | 14 |
| 387 | TDYFPRINFF | 14 |
| 435 | HFKPYLTPDL | 14 |
| 441 | TPDLPKRLHY | 14 |
| 453 | NVRIDKVHLF | 14 |
| 488 | EFRSMEAIFL | 14 |
| 516 | EVVNLMCDLL | 14 |
| 530 | APNNGTHGSL | 14 |
| 555 | EVSKFSVCGF | 14 |
| 564 | FANPLPTESL | 14 |
| 571 | ESLDCFCPHL | 14 |
| 684 | ADKNITHGFL | 14 |
| 700 | RTSDSQYDAL | 14 |
| 744 | NVVSGPIFDY | 14 |
| 791 | SHTPENCPGW | 14 |
| 858 | VSEILQLKTY | 14 |
| 19 | KKYKIACIVL | 13 |
| 34 | IMSLGLGLGL | 13 |
| 36 | SLGLGLGLGL | 13 |
| 50 | KQGSGRKKCF | 13 |
| 66 | LENCRCDVAC | 13 |

TABLE XLIV-continued

| Pos | 1234567890 | score |
|---|---|---|
| 85 | FEDTCVESTR | 13 |
| 92 | STRIWMCNKF | 13 |
| 104 | GETRLEASLC | 13 |
| 140 | LEENCDTAQQ | 13 |
| 164 | FSMDGFRAEY | 13 |
| 228 | MYDVNLNKNF | 13 |
| 240 | SSKEQNNPAW | 13 |
| 242 | KEQNNPAWWH | 13 |
| 260 | MYQGLKPATY | 13 |
| 276 | VAINGSFPSI | 13 |
| 321 | FEEPDSSGHA | 13 |
| 347 | HAFGMLMEGL | 13 |
| 360 | NLHNCVNIIL | 13 |
| 381 | NKMEYMTDYF | 13 |
| 384 | EYMTDYFPRI | 13 |
| 386 | MTDYFPRINF | 13 |
| 418 | FNSEEIVRNL | 13 |
| 452 | KNVRIDKVHL | 13 |
| 458 | KVHLFVDQQW | 13 |
| 533 | NGTHGSLNHL | 13 |
| 534 | GTHGSLNHLL | 13 |
| 554 | EEVSKFSVCG | 13 |
| 567 | PLPTESLDCF | 13 |
| 570 | TESLDCFCPH | 13 |
| 597 | QEEITATVKV | 13 |
| 599 | EITATVKVNL | 13 |
| 637 | AMRMPMWSSY | 13 |
| 642 | MWSSYTVPQL | 13 |
| 683 | LADKNITHGF | 13 |
| 716 | PMYEEFRKMW | 13 |
| 723 | KMWDYFHSVL | 13 |
| 724 | MWDYFHSVLL | 13 |
| 738 | TERNGVNVVS | 13 |
| 746 | VSGPIFDYNY | 13 |
| 771 | NTDVPIPTHY | 13 |
| 815 | VESCPEGKPE | 13 |
| 828 | VEERETAHIA | 13 |
| 862 | LQLKTYLPTF | 13 |
| 866 | TYLPTFETTI | 13 |
| 23 | IACIVLLALL | 12 |
| 25 | CIVLLALLVI | 12 |
| 48 | LEKQGSCRKK | 12 |
| 76 | KDRGDCCWDF | 12 |
| 87 | DTCVESTRIW | 12 |
| 90 | VESTRIWMCN | 12 |
| 131 | SVCQGETSWL | 12 |
| 168 | GFRAEYLYTW | 12 |
| 192 | IHSKYMRAMY | 12 |
| 201 | YPTKTFPNHY | 12 |
| 220 | SHGIIDNNMY | 12 |
| 224 | IDNNMYOVNL | 12 |
| 241 | SKEQNNPAWW | 12 |
| 252 | GQPMWLTAMY | 12 |
| 255 | MWLTAMYQGL | 12 |
| 261 | YQGLKPATYF | 12 |
| 262 | QGLKAATYFW | 12 |
| 286 | YMPYNGSVPF | 12 |
| 299 | ISTLLKWLDL | 12 |
| 307 | DLPKAERPRF | 12 |
| 308 | LPKAERPRFY | 12 |
| 343 | QVVDHAFGML | 12 |
| 352 | LMEGLKQRNL | 12 |
| 370 | LADHGMDQTY | 12 |
| 402 | PAPRIRAHNI | 12 |
| 406 | IRAHNIPHDF | 12 |
| 420 | SEEIVRNLSC | 12 |
| 431 | KPDQHFKPYL | 12 |
| 476 | TNCGGGNHGY | 12 |
| 492 | MEAIFLAHGP | 12 |
| 504 | KEKTEVEPFE | 12 |
| 511 | PFENIEVYNL | 12 |
| 512 | FENIEVYNLM | 12 |
| 538 | SLNHLLKVPF | 12 |
| 539 | LNHLLKVPFY | 12 |

TABLE XLIV-continued

| Pos | 1234567890 | score |
|---|---|---|
| 548 | YEPSHAEEVS | 12 |
| 550 | PSHAEEVSKF | 12 |
| 559 | FSVCGFANPL | 12 |
| 577 | CPHLQNSTQL | 12 |
| 616 | LQKNVDHCLL | 12 |
| 617 | QKNVDHCLLY | 12 |
| 621 | DHCLLYHREY | 12 |
| 625 | LYHREYVSGF | 12 |
| 628 | REYVSGFGKA | 12 |
| 648 | VPQLGDTSPL | 12 |
| 679 | CSFYLADKNI | 12 |
| 705 | QYDALITSNL | 12 |
| 712 | SNLVPMYEEF | 12 |
| 792 | HTPENCPGWL | 12 |
| 797 | CPGWLDVLPF | 12 |
| 818 | CPEGKPEALW | 12 |
| 819 | PEGKPEALWV | 12 |
| 835 | HIARVRDVEL | 12 |
| 836 | IARVRDVELL | 12 |
| 839 | VRDVELLTGL | 12 |
| 841 | DVELLTGLDF | 12 |

V2-HLA-B4402-10mers-161P2F10B
Each peptide is a portion of SEQ ID NO: 83; each start position is specified, the length of the peptide is 10 amino acids and the end position for each peptide is the start position plus 9.

| 8 | LQRKDCCADY | 10 |
|---|---|---|
| 4 | SDDCLQRKDC | 5 |
| 2 | SCSDDCLQRK | 4 |
| 3 | CSDDCLQRKD | 4 |

V3-HLA-B4402-10mers-161P2F10B
Each peptide is a portion of SEQ ID NO: 86; each start position is specified, the length of the peptide is 10 amino acids and the end position for each peptide is the start position plus 9.

| 7 | SCPGGKPEAL | 16 |
|---|---|---|
| 5 | VESCPGGKPE | 13 |
| 8 | CPGGKPEALW | 12 |

V4-HLA-B4402-10mers-161P2F10B
Each peptide is a portion of SEQ ID NO: 89; each start position is specified, the length of the peptide is 10 amino acids and the end position for each peptide is the start position plus 9.

| 2 | TYLPTFETPI | 12 |
|---|---|---|

TABLE XLV

| Pos | 1234567890 | score |
|---|---|---|

V1-HLA-B5101-10mers-161P2F10B

No Results Found.
V2-HLA-B5101-10mers-161P2F10B

No Results Found.
V3-HLA-B5101-10mers-161P2F10B

No Results Found.
V4-HLA-B5101-10mers-161P2F10B

No Results Found.

TABLE XLVI

V1-DRB1-0101-15mers-161P2F10B
Each peptide is a position of SEQ ID NO: 81; each start position is specified, the length of the peptide is 15 amino acids and the end position for each peptide is the start position plus 14.

| Pos | 123456789012345 | score |
|---|---|---|
| 207 | PNHYTIVTGLYPESH | 36 |
| 181 | MPNINKLKTCGIHSK | 35 |
| 486 | NNEFRSMEAIFLAHG | 35 |
| 839 | VRDVELLTGLDFYQD | 33 |
| 703 | DSQYDALITSNLVPM | 32 |
| 42 | GLGLRKLEKQGSCRK | 31 |
| 740 | RNGVNVVSGPIFDYN | 31 |
| 28 | LLALLVIMSLGLGLG | 30 |
| 160 | PVILFSMDGFRAEYL | 30 |
| 797 | CPGWLDVLPFIIPHR | 30 |
| 858 | VSEILQLKVYLPTFE | 30 |
| 801 | LDVLPFIIPHRPTNV | 29 |
| 393 | INFFYMYEGPAPRIR | 28 |
| 421 | EEIVRNLSCRKPDQH | 28 |
| 627 | HREYVSGFGKAMRMP | 28 |
| 30 | ALLVIMSLGLGLGLG | 27 |
| 32 | LVIMSLGLGLGLGLR | 27 |
| 34 | IMSLGLGLGLGLRKL | 27 |
| 364 | CVNIILLADHGMDQT | 27 |
| 522 | CDLLRIQPAPNNGTH | 27 |
| 23 | IACIVLLALLVIMSL | 26 |
| 258 | TAMYQGLKAATYFWP | 26 |
| 273 | GSEVAINGSFPSIYM | 26 |
| 283 | PSIYMPYNGSVPFEE | 26 |
| 300 | STLLKWLDLPKAERP | 26 |
| 545 | VPFYEPSHAEEVSKF | 26 |
| 645 | SYTVPQLGDTSPLPP | 26 |
| 778 | THYFVVLTSCKNKSH | 26 |
| 26 | IVLLALLVIMSLGLG | 25 |
| 230 | DVNLNKNFSLSSKEQ | 25 |
| 266 | AATYFWPGSEVAING | 25 |
| 292 | SVPFEERISTLLKWL | 25 |
| 303 | LKWLDLPKAERPRFY | 25 |
| 350 | GMLMEGLKQRNLHNC | 25 |
| 433 | DQHFKPYLTPDLPKR | 25 |
| 459 | VHLFVDQQWLAVRSK | 25 |
| 492 | MEAIFLAHGPSFKEK | 25 |
| 509 | VEPFENIEVYNLMCD | 25 |
| 536 | HGSLNHLLKVPFYEP | 25 |
| 561 | VCGFANPLPTESLDC | 25 |
| 22 | KIACIVLLALLVIMS | 24 |
| 25 | CIVLLALLVIMSLGL | 24 |
| 163 | LFSMDGFRAEYLYTW | 24 |
| 174 | LYTWDTLMPNINKLK | 24 |
| 194 | SKYMRAMYPTKTFPN | 24 |
| 246 | NPAWWHGQPMWLTAM | 24 |
| 313 | RPRFYTMYFEEPDSS | 24 |
| 316 | FYTMYFEEPDSSGHA | 24 |
| 333 | PVSARVIKALQVVDH | 24 |
| 342 | LQVVDHAFGMLMEGL | 24 |
| 387 | TDYFPRINFFYMYEG | 24 |
| 392 | RINFFYMYEGPAPRI | 24 |
| 395 | FFYMYEGPAPRIRAH | 24 |
| 412 | PHDFFSFNSEEIVRN | 24 |
| 437 | KPYLTPDLPKRLHYA | 24 |
| 514 | NIEVYNLMCDLLRIQ | 24 |
| 518 | YNLMCDLLRIQPAPN | 24 |
| 539 | LNHLLKVPFYEPSHA | 24 |
| 542 | LLKVPFYEPSHAEEV | 24 |
| 589 | VNQMLNLTQEEITAT | 24 |
| 605 | KVNLPFGRPRVLQKN | 24 |
| 722 | RKMWDYFHSVLLIKH | 24 |
| 798 | PGWLDVLPFIIPHRP | 24 |
| 45 | LRKLEKQGSCRKKCF | 23 |
| 84 | DFEDTCVESTRIWMC | 23 |
| 129 | YKSVCQGETSWLEEN | 23 |
| 191 | GIHSKYMRAMYPTKT | 23 |
| 210 | YTIVTGLYPESHGII | 23 |
| 272 | PGSEVAINGSFPSIY | 23 |
| 284 | SIYMPYNGSVPFEER | 23 |
| 328 | GHAGGPVSARVIKAL | 23 |
| 464 | DQQWLAVRSKSNTNC | 23 |
| 562 | CGFANPLPTESLDCF | 23 |
| 637 | AMRMPMWSSYTVPQL | 23 |
| 644 | SSYTVPQLGDTSPLP | 23 |
| 651 | LGDTSPLPPTVPDCL | 23 |
| 687 | NITHGFLYPPASNRT | 23 |
| 804 | LPFIIPHRPTNVESC | 23 |
| 1 | MESTLTLATEQPVKK | 22 |
| 18 | LKKYKIACIVLLALL | 22 |
| 20 | KYKIACIVLLALLVI | 22 |
| 145 | DTAQQSQCPEGFDLP | 22 |
| 152 | CPEGFDLPPVILFSM | 22 |
| 155 | GFDLPPVILFSMDGF | 22 |
| 171 | AEYLYTWDTLMPNIN | 22 |
| 380 | CNKMEYMTDYFPRIN | 22 |
| 400 | EGPAPRIRAHNIPHD | 22 |
| 434 | QHFKPYLTPDLPKRL | 22 |
| 575 | CFCPHLQNSTQLEQV | 22 |
| 648 | VPQLGDTSPLPPTVP | 22 |
| 654 | TSPLPPTVPDCLRAD | 22 |
| 777 | PTHYFVVLTSCKNKS | 22 |
| 825 | ALWVEERFTAHIARV | 22 |
| 833 | TAHIARVRDVELLTG | 22 |
| 60 | DASFRGLENCRCDVA | 21 |
| 142 | ENCDTAQQSQCPEGF | 21 |
| 186 | KLKTCGIHSKYMRAM | 21 |
| 451 | AKNVRIDKVHLFVDQ | 21 |
| 490 | RSMEAIFLAHGPSFK | 21 |
| 665 | LRADVRPPSESQKC | 21 |
| 704 | SQYDALITSNLVPMY | 21 |
| 739 | ERNGVNVVSGPIFDY | 21 |
| 770 | ANTDVPIPTHYFVVL | 21 |
| 98 | CNKFRCGETRLEASL | 20 |
| 253 | QPMWLTAMYQGLKAA | 20 |
| 443 | DLPKRLHYAKNVRID | 20 |
| 521 | MCDLLRIQPAPNNGT | 20 |
| 553 | AEEVSKFSVCGFANP | 20 |
| 623 | CLLYHREYVSGFGKA | 20 |
| 631 | VSGFGKAMRMPMWSS | 20 |
| 718 | YEEFRKMWDYFHSVL | 20 |
| 729 | HSVLLIKHATERNGV | 20 |
| 750 | IFDYNYDGHFDAPDE | 20 |
| 829 | EERFTAHIARVRDVE | 20 |
| 15 | KNTLKKYKIACIVLL | 19 |
| 37 | LGLGLGLGLRKLEKQ | 19 |
| 153 | PEGFDLPPVILFSMD | 19 |
| 158 | LPPVILFSMDGFRAE | 19 |
| 170 | RAEYLYTWDTLMPNI | 19 |
| 226 | NNMYDVNLNKNFSLS | 19 |
| 305 | WLDLPKAERPRFYTM | 19 |
| 340 | KALQVVDHAFGMLME | 19 |
| 346 | DHAFGMLMEGLKQRN | 19 |
| 363 | NCVNIILLADHGMDQ | 19 |
| 413 | HDFFSFNSEEIVRNL | 19 |
| 500 | GPSFKEKTEVEPFEN | 19 |
| 556 | VSKFSVCGFANPLPT | 19 |
| 603 | TVKVNLPFGRPRVLQ | 19 |
| 691 | GFLYPPASNRTSDSQ | 19 |
| 762 | PDEITKHLANTDVPI | 19 |
| 771 | NTDVPIPTHYFVVLT | 19 |
| 817 | SCPEGKPEALWVEER | 19 |
| 2 | ESTLTLATEQPVKKN | 18 |
| 12 | PVKKNTLKKYKIACI | 18 |
| 29 | LALLVIMSLGLGLGL | 18 |
| 102 | RCGETRLEASLCSCS | 18 |
| 136 | ETSWLEENCDTAQQS | 18 |
| 157 | DLPPVILFSMDGFRA | 18 |
| 183 | NINKLKTCGIHSKYM | 18 |
| 214 | TGLYPESHGIIDNNM | 18 |
| 228 | MYDVNLNKNFSLSSK | 18 |
| 255 | MWLTAMYQGLKAATY | 18 |
| 259 | AMYQGLKAATYFWPG | 18 |
| 267 | ATYFWPGSEVAINGS | 18 |
| 297 | ERISTLLKWLDLPKA | 18 |
| 302 | LLKWLDLPKAERPRF | 18 |
| 318 | TMYFEEPDSSGHAGG | 18 |
| 322 | EEPDSSGHAGGPVSA | 18 |

TABLE XLVI-continued

| Pos | 123456789012345 | score |
|---|---|---|
| 362 | HNCVNIILLADHGMD | 18 |
| 382 | KMEYMTDYFPRINFF | 18 |
| 515 | IEVYNLMCDLLRIQP | 18 |
| 595 | LTQEEITATVKVNLP | 18 |
| 613 | PRVLQKNVDHCLLYH | 18 |
| 640 | MPMWSSYTVPQLGDT | 18 |
| 662 | PDCLRADVRVPPSES | 18 |
| 681 | FYLADKNITHGFLYP | 18 |
| 689 | THGFLYPPASNRTSD | 18 |
| 748 | GPIFDYNYDGHFDAP | 18 |
| 847 | GLDFYQDKVQPVSEI | 18 |
| 848 | LDFYQDKVQPVSEIL | 18 |
| 16 | NTLKKYKIACIVLLA | 17 |
| 21 | YKIACIVLLALLVIM | 17 |
| 24 | ACIVLLALLVIMSLG | 17 |
| 31 | LLVIMSLGLGLGLGL | 17 |
| 36 | SLGLGLGLGLRKLEK | 17 |
| 80 | DCCWDFEDTCVESTR | 17 |
| 103 | CGETRLEASLCSCSD | 17 |
| 126 | CADYKSVCQGETSWL | 17 |
| 139 | WLEENCDTAQQSQCP | 17 |
| 147 | AQQSQCPEGFDLPPV | 17 |
| 189 | TCGIHSKYMRAMYPT | 17 |
| 209 | HYTIVTGLYPESHGI | 17 |
| 212 | IVTGLYPESHGIIDN | 17 |
| 227 | NMYDVNLNKNFSLSS | 17 |
| 236 | NFSLSSKEQNNPAWW | 17 |
| 261 | YQGLKAATYFWPGSE | 17 |
| 265 | KAATYFWPGSEVAIN | 17 |
| 282 | FPSIYMPYNGSVPFE | 17 |
| 286 | YMPYNGSVPFEERIS | 17 |
| 324 | PDSSGHAGGPVSARV | 17 |
| 331 | GGPVSARVIKALQVV | 17 |
| 336 | ARVIKALQVVDHAFG | 17 |
| 341 | ALQVVDHAFGMLMEG | 17 |
| 347 | HAFGMLMEGLKQRNL | 17 |
| 372 | DHGMDQTYCNKMEYM | 17 |
| 394 | NFFYMYEGPAPRIRA | 17 |
| 396 | FYMYEGPAPRIRAHN | 17 |
| 491 | SMEAIFLAHGPSFKE | 17 |
| 493 | EAIFLAHGPSFKEKT | 17 |
| 506 | KTEVEPFENIEVYNL | 17 |
| 519 | NLMCDLLRIQPAPNN | 17 |
| 527 | IQPAPNNGTHGSLNH | 17 |
| 540 | NHLLKVPFYEPSHAE | 17 |
| 557 | SKFSVCGFANPLPTE | 17 |
| 597 | QEEITATVKVNLPFG | 17 |
| 601 | TATVKVNLPFGRPRV | 17 |
| 602 | ATVKVNLPFGRPRVL | 17 |
| 629 | EYVSGFGKAMRMPMW | 17 |
| 677 | QKCSFYLADKNITHG | 17 |
| 685 | DKNITHGFLYPPASN | 17 |
| 725 | WDYFHSVLLIKHATE | 17 |
| 726 | DYFHSVLLIKHATER | 17 |
| 734 | IKHATERNGVNVVSG | 17 |
| 780 | YFVVLTSCKNKSHTP | 17 |
| 812 | PTNVESCPEGKPEAL | 17 |
| 823 | PEALWVEERFTAHIA | 17 |
| 836 | IARVRDVELLTGLDF | 17 |
| 842 | VELLTGLDFYQDKVQ | 17 |

V2-DRB1-0101-15mers-161P2F10B
Each peptide is a position of SEQ ID NO: 84; each start position is specified, the length of the peptide is 15 amino acids and the end position for each peptide is the start position plus 14.

| Pos | 123456789012345 | score |
|---|---|---|
| 2 | EASLCSCSDDCLQRK | 16 |
| 7 | SCSDDCLQRKDCCAD | 9 |
| 12 | CLQRKDCCADYKSVC | 9 |
| 13 | LQRKDCCADYKSVCQ | 9 |
| 14 | QRKDCCADYKSVCQG | 9 |
| 9 | SDDCLQRKDCCADYK | 8 |
| 10 | DDCLQRKDCCADYKS | 8 |
| 8 | CSDDCLQRKDCCADY | 7 |

V3-HLA-DRB1-0101-15mers-161P2F10B
Each peptide is a position of SEQ ID NO: 87; each start position is specified, the length of the peptide is 15 amino acids and the end position for each peptide is the start position plus 14.

| Pos | 123456789012345 | score |
|---|---|---|
| 7 | PTNVESCPGGKPEAL | 25 |
| 12 | SCPGGKPEALWVEER | 19 |
| 4 | PHRPTNVESCPGGKP | 14 |
| 10 | VESCPGGKPEALWVE | 14 |

V4-HLA-DRB1-0101-15mers-161P2F10B
Each peptide is a position of SEQ ID NO: 90; each start position is specified, the length of the peptide is 15 amino acids and the end position for each peptide is the start position plus 14.

| Pos | 123456789012345 | score |
|---|---|---|
| 2 | ILQLKTYLPTFETPI | 16 |
| 1 | EILQLKTYLPTFETP | 10 |

TABLE XLVII

V1-HLA-DRB1-0301-15mers-161P2F10B
Each peptide is a position of SEQ ID NO: 81; each start position is specified, the length of the peptide is 15 amino acids and the end position for each peptide is the start position plus 14.

| Pos | 123456789012345 | score |
|---|---|---|
| 437 | KPYLTPDLPKRLHYA | 31 |
| 451 | AKNVRIDKVHLFVDQ | 31 |
| 662 | PDCLRADVRVPPSES | 28 |
| 458 | KVHLFVDQQWLAVRS | 27 |
| 597 | QEEITATVKVNLPFG | 27 |
| 228 | MYDVNLNKNFSLSSK | 26 |
| 350 | GMLMEGLKQRNLHNC | 26 |
| 536 | HGSLNHLLKVPFYEP | 26 |
| 305 | WLDLPKAERPRFYTM | 25 |
| 358 | QRNLHNCVNIILLAD | 24 |
| 30 | ALLVIMSLGLGLGLG | 22 |
| 366 | NIILLADHGMDQTYD | 22 |
| 28 | LLALLVIMSLGLGLG | 21 |
| 32 | LVIMSLGLGLGLGLR | 21 |
| 34 | IMSLGLGLGLGLRKL | 21 |
| 158 | LPPVILFSMDGFRAE | 21 |
| 161 | VILFSMDGFRAEYLY | 21 |
| 517 | VYNLMCDLLRIQPAP | 21 |
| 707 | DALITSNLVPMYEEF | 21 |
| 742 | GVNVVSGPIFDYNYD | 21 |
| 10 | EQPVKKNTLKKYKIA | 20 |
| 20 | KYKIACIVLLALLVI | 20 |
| 109 | EASLCSCSDDCLQKK | 20 |
| 118 | DCLQKKDCCADYKSV | 20 |
| 236 | NFSLSSKEQNNPAWW | 20 |
| 284 | SIYMPYNGSVPFEER | 20 |
| 408 | AHNIPHDFFSFNSEE | 20 |
| 467 | WLAVRSKSNTNCGGG | 20 |
| 615 | VLQKNVDHCLLYHRE | 20 |
| 635 | GKAMRMPMWSSYTVP | 20 |
| 780 | YFVVLTSCKNKSHTP | 20 |
| 839 | VRDVELLTGLDFYQD | 20 |
| 847 | GLDFYQDKVQPVSEI | 20 |
| 855 | VQPVSEILQLKTYLP | 20 |
| 2 | ESTLTLATEQPVKKN | 19 |
| 26 | IVLLALLVIMSLGLG | 19 |
| 38 | GLGLGLGLRKLEKQG | 19 |
| 42 | GLGLRKLEKQGSCRK | 19 |
| 74 | ACKDRGCCWDFEDT | 19 |
| 129 | YKSVCQGETSWLEEN | 19 |
| 153 | PEGFDLPPVILFSMD | 19 |
| 257 | LTAMYQGLKAATYFW | 19 |
| 331 | GGPVSARVIKALQVV | 19 |
| 335 | SARVIKALQVVDHAF | 19 |
| 341 | ALQVVDHAFGMLMEG | 19 |

TABLE XLVII-continued

| Pos | 123456789012345 | score |
|---|---|---|
| 349 | FGMLMEGLKQRNLHN | 19 |
| 433 | DQHFKPYLTPDLPKR | 19 |
| 486 | NNEFRSMEAIFLAHG | 19 |
| 492 | MEAIFIAHGPSFKEK | 19 |
| 514 | NIEVYNLMCDLLRIQ | 19 |
| 524 | LLRIQPAPNNGTHGS | 19 |
| 553 | AEEVSKFSVCGFANP | 19 |
| 565 | ANPLPTESLDCFCPH | 19 |
| 654 | TSPLPPTVPDCLRAD | 19 |
| 679 | CSFYLADKNITHGFL | 19 |
| 697 | ASNRTSDSQYDALIT | 19 |
| 740 | RNGVNVVSGPIFDYN | 19 |
| 773 | DVPIPTHYFVVLTSC | 19 |
| 781 | FVVLTSCKNKSHTPE | 19 |
| 812 | PTNVFSCPEGKPEAL | 19 |
| 833 | TAHIARVRDVELLTG | 19 |
| 835 | HIARVRDVELLTGLD | 19 |
| 852 | QDKVQPVSEILQLKT | 19 |
| 163 | LFSMDGFRAEYLYTW | 18 |
| 177 | WDTLMPNINKLKTCG | 18 |
| 178 | DTLMPNINKLKTCGI | 18 |
| 224 | IDNNMYDVNLNKNFS | 18 |
| 254 | PMWLTAMYQGLKAAT | 18 |
| 267 | ATYFWPGSEVAINGS | 18 |
| 275 | EVAINGSFPSIYMPY | 18 |
| 292 | SVPFEERISTLLKWL | 18 |
| 296 | EERISTLLKWLDLPK | 18 |
| 445 | PKRLHYAKNVRIDKV | 18 |
| 465 | QQWLAVRSKSNTNCG | 18 |
| 506 | KTEVEPFENIEVYNL | 18 |
| 509 | VEPFENIEVYNLMCD | 18 |
| 582 | NSTQLEQVNQMLNLT | 18 |
| 586 | LEQVNQMLNLTQEEI | 18 |
| 589 | VNQMLNLTQEEITAT | 18 |
| 605 | KVNLPFGRPRVLQKN | 18 |
| 613 | PRVLQKNVDHCLLYH | 18 |
| 621 | DHCLLYHREYVSGFG | 18 |
| 628 | REYVSGFGKAMRMPM | 18 |
| 658 | PPTVPDCLRADVRVP | 18 |
| 711 | TSNLVPMYEEFRKMW | 18 |
| 712 | SNLVPMYEEFRKMWD | 18 |
| 721 | FRKMWDYFHSVLLIK | 18 |
| 731 | VLLIKHATERNGVNV | 18 |
| 7 | LATEQPVKKNTLKKY | 17 |
| 92 | STRIWMCNKFRCGET | 17 |
| 219 | ESHGIIDNNMYDVNL | 17 |
| 282 | FPSIYMPYNGSVPFE | 17 |
| 290 | NGSVPFEERISTLLK | 17 |
| 439 | YLTPDLPKRLHYAKN | 17 |
| 457 | DKVHLFVDQQWLAVR | 17 |
| 500 | GPSFKEKTEVEPFEN | 17 |
| 518 | YNLMCDLLRIQPAPN | 17 |
| 558 | KFSVCGFANPLPTES | 17 |
| 573 | LDCFCPHLQNSTQLE | 17 |
| 577 | CPHLQNSTQLEQVNQ | 17 |
| 583 | STQLEQVNQMLNLTQ | 17 |
| 590 | NQMLNLTQEEITATV | 17 |
| 714 | LVPMYEEFRKMWDYF | 17 |
| 746 | VSGPIFDYNYDGHFD | 17 |
| 823 | PEALWVEERFTAHIA | 17 |
| 857 | PVSEILQLKTYLPTF | 17 |
| 60 | DASFRGLENCRCDVA | 16 |
| 70 | RCDVACKDRGDCCWD | 16 |
| 78 | RGDCCWDFEDTCVES | 16 |
| 94 | RIWMCNKFRCGETRL | 16 |
| 101 | FRCGETRLEASLCSC | 16 |
| 122 | KKDCCADYKSVCQGE | 16 |
| 226 | NNMYDVNLNKNFSLS | 16 |
| 234 | NKNFSLSSKEQNNPA | 16 |
| 346 | DHAFGMLMEGLKQRN | 16 |
| 384 | EYMTDYFPRINFFYM | 16 |
| 450 | YAKNVRIDKVHLFVD | 16 |
| 532 | NNGTHGSLNHLLKVP | 16 |
| 599 | EITATVKVNLPFGRP | 16 |
| 678 | KCSFYLADKNITHGF | 16 |
| 748 | GPIFDYNYDGHFDAP | 16 |
| 24 | ACIVLLALLVIMSLG | 15 |

TABLE XLVII-continued

| Pos | 123456789012345 | score |
|---|---|---|
| 48 | LEKQGSCRKKCFDAS | 15 |
| 56 | KKCFDASFRGLENCR | 15 |
| 97 | MCNKFRCGETRLEAS | 15 |
| 162 | ILFSMDGFRAEYLYT | 15 |
| 164 | FSMDGFRAEYLYTWD | 15 |
| 190 | CGIHSKYMRAMYPTK | 15 |
| 218 | PESHGIIDNNMYDVN | 15 |
| 374 | GMDQTYCNKMEYMTD | 15 |
| 386 | MTDYFPRINFFYMYE | 15 |
| 413 | HDFFSFNSEEIVRNL | 15 |
| 474 | SNTNCGGGNHGYNNE | 15 |
| 478 | CGGGNHGYNNEFRSM | 15 |
| 485 | YNNEFRSMEAIFLAH | 15 |
| 670 | RVPPSESQKCSFYLA | 15 |
| 728 | FHSVLLIKHATERNG | 15 |
| 803 | VLPFIIPHRPTNVES | 15 |
| 821 | GKPEALWVEERFTAH | 15 |

V2-DRB1-0301-15mers-161P2F10B
Each peptide is a position of SEQ ID NO: 84; each start position is specified, the length of the peptide is 15 amino acids and the end position for each peptide is the start position plus 14.

| Pos | 123456789012345 | score |
|---|---|---|
| 2 | EASLCSCSDDCLQRK | 20 |
| 11 | DCLQRKDCCADYKSV | 20 |
| 15 | RKDCCADYKSVCQGE | 16 |
| 4 | SLCSCSDDCLQRKDC | 12 |
| 5 | LCSCSDDCLQRKDCC | 11 |
| 10 | DDCLQRKDCCADYKS | 11 |

V3-HLA-DRB1-0301-15mers-161P2F10B
Each peptide is a position of SEQ ID NO: 87; each start position is specified, the length of the peptide is 15 amino acids and the end position for each peptide is the start position plus 14.

| Pos | 123456789012345 | score |
|---|---|---|
| 7 | PTNVESCPGGKPEAL | 13 |
| 10 | VESCPGGKPEALWVE | 10 |
| 11 | ESCPGGKPEALWVEE | 9 |
| 9 | NVESCPGGKPEALWV | 8 |
| 1 | FIIPHRPTNVESCPG | 7 |
| 3 | IPHRPTNVESCPGGK | 6 |

V4-HLA-DRB1-0301-15mers-161P2F10B
Each peptide is a position of SEQ ID NO: 90; each start position is specified, the length of the peptide is 15 amino acids and the end position for each peptide is the start position plus 14.

| Pos | 123456789012345 | score |
|---|---|---|
| 2 | ILQLKTYLPTFETPIJ | 12 |
| 1 | EILQLKTYLPTFETPJ | 10 |

TABLE XLVIII

| Pos | 123456789012345 | score |
|---|---|---|

V1-HLA-DRB1-0401-15mers-161P2F10B
Each peptide is a position of SEQ ID NO: 81; each start position is specified, the length of the peptide is 15 amino acids and the end position for each peptide is the start position plus 14.

| Pos | 123456789012345 | score |
|---|---|---|
| 126 | CADYKSVCQGETSWL | 28 |
| 412 | PHDFFSFNSEEIVRN | 28 |
| 464 | DQQWLAVRSKSNTNC | 28 |
| 631 | VSGFGKAMRMPMWSS | 28 |
| 691 | GFLYPPASNRTSDSQ | 28 |
| 703 | DSQYDALITSNLVPM | 28 |
| 722 | RKMWDYFHSVLLIKH | 28 |
| 750 | IFDYNYDGHFDAPDE | 28 |
| 777 | PTHYFVVLTSCKNKS | 28 |
| 778 | THYFVVLTSCKNKSH | 28 |
| 28 | LLALLVIMSLGLGLG | 26 |
| 181 | MPNINKLKVCGIHSK | 26 |
| 213 | VTGLYPESHGIIDNN | 26 |
| 290 | NGSVPFEERISTLLK | 26 |

TABLE XLVIII-continued

| Pos | 123456789012345 | score |
|---|---|---|
| 350 | GMLMEGLKQRNLHNC | 26 |
| 445 | PKRLHYAKNVRIDKV | 26 |
| 458 | KVHLFVDQQWLAVRS | 26 |
| 506 | KTEVEPFENIEVYNL | 26 |
| 524 | LLRIQPAPNNGTHGS | 26 |
| 583 | STQLEQVNQMLNLTQ | 26 |
| 589 | VNQMLNLTQEEITAT | 26 |
| 823 | PEALWVEERFTAHIA | 26 |
| 855 | VQPVSEILQLKYLP | 26 |
| 18 | LKKYKIACIVLLALL | 22 |
| 60 | DASFRGLENCRCDVA | 22 |
| 80 | DCCWDFEDTCVESTR | 22 |
| 136 | ETSWLEENCDTAQQS | 22 |
| 172 | EYLYTWDTLMPNINK | 22 |
| 174 | LYTWDTLMPNINKLK | 22 |
| 193 | HSKYMRAMYPTKTFP | 22 |
| 203 | TKVFPNHYTIVTGLY | 22 |
| 253 | QPMWLTAMYQGLKAA | 22 |
| 266 | AATYFWPGSEVAING | 22 |
| 279 | NGSFPSIYMPYNGSV | 22 |
| 346 | DHAFGMLMEGLKQRN | 22 |
| 382 | KMEYMTDYFPRINFF | 22 |
| 387 | TDYFPRINFFYMEG | 22 |
| 415 | FFSFNSEEIVRNLSC | 22 |
| 433 | DQHFKPYLTPDLPKR | 22 |
| 447 | RLHYAKNVRIDKVHL | 22 |
| 482 | NHGYNNEFRSMEAIF | 22 |
| 509 | VEPFENIEVYNLMCD | 22 |
| 573 | LDCFCPHLQNSTQLE | 22 |
| 678 | KCSFYLADKNITHGF | 22 |
| 679 | CSFYLADKNITHGFL | 22 |
| 797 | CPGWLDVLPFIIPHR | 22 |
| 803 | VLPFIIPHRPTNVES | 22 |
| 847 | GLDFYQDKVQPVSEI | 22 |
| 2 | ESTLTLATEQPVKKN | 20 |
| 4 | TLTLATEQPVKKNTL | 20 |
| 20 | KYKIACIVLLALLVI | 20 |
| 23 | IACIVLLALLVIMSL | 20 |
| 24 | ACIVLLALLVIMSLG | 20 |
| 25 | CIVLLALLVIMSLGL | 20 |
| 26 | IVLLALLVIMSLGLG | 20 |
| 42 | GLGLRKLEKQGSCRK | 20 |
| 45 | LRKLEKQGSCRKKCF | 20 |
| 129 | YKSVCQGETSWLEEN | 20 |
| 155 | GFDLPPVILFSMDGF | 20 |
| 163 | LFSMDGFRAEYLYTW | 20 |
| 177 | WDTLMPNINKLKTCG | 20 |
| 178 | DTLMPNINKLKTCGI | 20 |
| 197 | MRAMYPTKTFPNHYT | 20 |
| 225 | DNNMYDVNLNKNFSL | 20 |
| 228 | MYDVNLNKNFSLSSK | 20 |
| 230 | DVNLNKNFSLSSKEQ | 20 |
| 254 | PMWLTAMYQGLKAAT | 20 |
| 273 | GSEVAINGSFPSIYM | 20 |
| 282 | FPSIYMPYNGSVPFE | 20 |
| 300 | STLLKWLDLPKAERP | 20 |
| 305 | WLDLPKAERPRFYTM | 20 |
| 316 | FYTMYFEEPDSSGHA | 20 |
| 335 | SARVIKALQWDHAF | 20 |
| 339 | IKALQVVDHAFGMLM | 20 |
| 342 | LQVVDHAFGMLMEGL | 20 |
| 358 | QRNLHNCVNIILLAD | 20 |
| 364 | CVNIILLADHGMDQT | 20 |
| 365 | VNIILLADHGMDQTY | 20 |
| 366 | NIILLADHGMDQTYC | 20 |
| 408 | AHNIPHDFFSFNSEE | 20 |
| 420 | SEEIVRNLSCRKPDQ | 20 |
| 437 | KPYLTPDLPKRLHYA | 20 |
| 514 | NIEVYNLMCDLLRIQ | 20 |
| 517 | VYNLMCDLLRIQPAP | 20 |
| 518 | YNLMCDLLRQPAPN | 20 |
| 521 | MCDLLRIQPAPNNGT | 20 |
| 558 | KFSVCGFANPLPTES | 20 |
| 570 | TESLDGFCPHLQNST | 20 |
| 577 | CPHLQNSTQLEQVNQ | 20 |
| 586 | LEQVNQMLNLTQEEI | 20 |
| 592 | MLNLTQEEITATVKV | 20 |

TABLE XLVIII-continued

| Pos | 123456789012345 | score |
|---|---|---|
| 637 | AMRMPMWSSYTVPQL | 20 |
| 639 | RMPMWSSYTVPQLGD | 20 |
| 658 | PPTVPDCLRADVRVP | 20 |
| 662 | PDCLRADVRVPPSES | 20 |
| 666 | RADVRVPPSESQKCS | 20 |
| 690 | HGFLYPPASNRTSDS | 20 |
| 714 | LVPMYEEFRKMWDYF | 20 |
| 721 | FRKMWDYFHSVLLIK | 20 |
| 728 | FHSVLLIKHATERNG | 20 |
| 730 | SVLLIKHATERNGVN | 20 |
| 771 | NTDVPIPTHYFWLT | 20 |
| 833 | TAHIARVRDVELLTG | 20 |
| 852 | QDKVQPVSEILQLKT | 20 |
| 858 | VSEILQLKTYLPTFE | 20 |
| 84 | DFEDTCVESTRIWMC | 18 |
| 99 | NKFRCGETRLEASLC | 18 |
| 103 | CGETRLEASLCSCSD | 18 |
| 135 | GETSWLEENCDTAQQ | 18 |
| 168 | GFRAEYLYTWDTLMP | 18 |
| 186 | KLKTCGIHSKYMRAM | 18 |
| 200 | MYPTKTFPNHYTIVT | 18 |
| 224 | IDNNMYDVNLNKNFS | 18 |
| 233 | LNKNFSLSSKEQNNP | 18 |
| 237 | FSLSSKEQNNPAWWH | 18 |
| 276 | VAINGSFPSIYMPYN | 18 |
| 293 | VPFEERISTLLKWLD | 18 |
| 319 | MYFEEPDSSGHAGGP | 18 |
| 355 | GLKQRNLHNCVNIIL | 18 |
| 370 | LADHGMDQTYCNKME | 18 |
| 397 | YMYEGPAPRIRAHNI | 18 |
| 409 | HNIPHDFFSFNSEEI | 18 |
| 417 | SFNSEEIVRNLSCRK | 18 |
| 457 | DKVHLFVDQQWLAVR | 18 |
| 463 | VDQQWLAVRSKSNTN | 18 |
| 483 | HGYNNEFRSMEAIFL | 18 |
| 491 | SMEAIFLAHGPSFKE | 18 |
| 533 | NGTHGSLNHLLKVPF | 18 |
| 549 | EPSHAEEVSKFSVCG | 18 |
| 562 | CGFANPLPTESLDCF | 18 |
| 547 | DCFCPHLQNSTQLEQ | 18 |
| 580 | LQNSTQLEQVNQMLN | 18 |
| 593 | LNLTQEEITATVKVN | 18 |
| 604 | VKVNLPFGRPRVLQK | 18 |
| 609 | PFGRPRVLQKNVDHC | 18 |
| 614 | RVLQKNVDHCLLYHR | 18 |
| 669 | VRVPPSESQKCSFYL | 18 |
| 682 | YLADKNITHGFLYPP | 18 |
| 697 | ASNRTSDSQYDALIT | 18 |
| 704 | SQYDALITSNLVPMY | 18 |
| 733 | LIKHATERNGVNVVS | 18 |
| 739 | ERNGVNVVSGPIFDY | 18 |
| 758 | HFDAPDEITKHLANT | 18 |
| 763 | DEITKHLANTDVPIP | 18 |
| 802 | DVLPFIIPHRPTNVE | 18 |
| 844 | LLTGLDFYQDKVQPV | 18 |
| 848 | LDFYQDKVQPVSEIL | 17 |
| 292 | SVPFEERISTLLKWL | 17 |
| 56 | KKCFDASFRGLENCR | 16 |
| 82 | CWDFEDTCVESTRIW | 16 |
| 98 | CNKFRCGETRLEASL | 16 |
| 161 | VILFSMDGFRAEYLY | 16 |
| 166 | MDGFRAEYLYTWDTL | 16 |
| 170 | RAEYLYTWDTLMPNI | 16 |
| 207 | PNHYTIVTGLYPESH | 16 |
| 226 | NNMYDVNLNKNFSLS | 16 |
| 234 | NKNFSLSSKEQNNPA | 16 |
| 246 | NPAWWHGQPMQLTAM | 16 |
| 247 | PAWWHGQPMQLTAMY | 16 |
| 258 | TAMYQGLKAATYFWP | 16 |
| 267 | ATYFWPGSEVAINGS | 16 |
| 268 | TYFWPGSEVAINGSF | 16 |
| 302 | LLKWLDLPKAERPRF | 16 |
| 317 | YTMYFEEPDSSGHAG | 16 |
| 318 | TMYFEEPDSSGHAGG | 16 |
| 392 | RINFFYMEGPAPRI | 16 |
| 394 | NFFYMEGPAPRIRA | 16 |
| 413 | HDFFSFNSEEIVRNL | 16 |

TABLE XLVIII-continued

| Pos | 123456789012345 | score |
|---|---|---|
| 459 | VHLFVDQQWLAVRSK | 16 |
| 486 | NNEFRSMEAIFLAHG | 16 |
| 493 | EAIFLAHGPSFKEKT | 16 |
| 544 | KVPFYEPSHAEEVSK | 16 |
| 545 | VPFYEPSHAEEVSKF | 16 |
| 561 | VCGFANPLPTESLDC | 16 |
| 607 | NLPFGRPRVLQKNVD | 16 |
| 623 | CLLYHREYVSGFGKA | 16 |
| 627 | HREYVSGFGKAMRMP | 16 |
| 640 | MPMWSSYTVPQLGDT | 16 |
| 643 | WSSYTVPQLGDTSPL | 16 |
| 715 | VPMYEEFRKMWDYFH | 16 |
| 724 | MWDYFHSVLLIKHAT | 16 |
| 725 | WDYFHSVLLIKHATE | 16 |
| 756 | DGHFDAPDEITKHLA | 16 |
| 824 | EALWVEERFTAHIAR | 16 |
| 441 | TPDLPKRLHYAKNVR | 15 |
| 825 | ALWVEERFTAHIARV | 15 |
| 15 | KNTLKKYKIACIVLL | 14 |
| 30 | ALLVIMSLGLGLGLG | 14 |
| 31 | LLVIMSLGLGLGLGL | 14 |
| 32 | LVIMSLGLGLGLGLR | 14 |
| 34 | IMSLGLGLGLGLRKL | 14 |
| 36 | SLGLGLGLRKLEKQG | 14 |
| 38 | GLGLGLRKLEKQGSC | 14 |
| 63 | FRGLENCRCDVACKD | 14 |
| 105 | ETRKEASKCSCSDDC | 14 |
| 109 | EASLCSCSDDCKQKK | 14 |
| 137 | TSWLEENCDTAQQSQ | 14 |
| 158 | LPPVILFSMDGFRAE | 14 |
| 160 | PVILFSMDGFRAEYL | 14 |
| 171 | AEYLYTWDTLMPNIN | 14 |
| 184 | INKLKTCGIHSKYMR | 14 |
| 194 | SKYMRAMYPTKTFPN | 14 |
| 209 | HYTIVTGLYPESHGI | 14 |
| 210 | YTIVTGLYPESHGII | 14 |
| 220 | SHGIIDNNMYDVNLN | 14 |
| 221 | HGIIDNNMYDVNLNK | 14 |
| 257 | LTAMYQGLKAATYFW | 14 |
| 261 | YQGLKAATYFWPGSE | 14 |
| 284 | SIYMPYNGSVPFEER | 14 |
| 296 | EERISTLLKWLDLPK | 14 |
| 299 | ISTLLKWLDLPKAER | 14 |
| 336 | ARVIKALQVVDHAFG | 14 |
| 341 | ALQVVDHAFGMLMEG | 14 |
| 348 | AFGMLMEGLKQRNLH | 14 |
| 349 | FGMLMEGLKQRNLHN | 14 |
| 362 | HNCVNIILLADHGMD | 14 |
| 367 | IILLADHGMDQTYCN | 14 |
| 372 | DHGMDQTYCNKMEYM | 14 |
| 383 | MEYMTDYFPRINFFY | 14 |
| 390 | FPRINFFYMYEGPAP | 14 |
| 395 | FFYMYEGPAPRIRAH | 14 |
| 421 | EEIVRNLSCRKPDQH | 14 |
| 451 | AKNVRIDKVHLFVDQ | 14 |
| 453 | NVRIDKVHLFVDQQW | 14 |
| 456 | IDKVHLFVDQQWLAV | 14 |
| 489 | FRSMEAIFLAHGPSF | 14 |
| 492 | MEAIFLAHGPSFKEK | 14 |
| 494 | AIFLAHGPSFKEKTE | 14 |
| 522 | CDLLRIQPAPNNGTH | 14 |
| 536 | HGSLNHLLKVPFYEP | 14 |
| 539 | LNHLLKVPFYEPSHA | 14 |
| 540 | NHLLKVPFYEPSHAE | 14 |
| 542 | LLKVPFYEPSHAEEV | 14 |
| 553 | AEEVSKFSVCGFANP | 14 |
| 565 | ANPLPTESLDCFCPH | 14 |
| 590 | NQMLNLTQEEITATV | 14 |
| 597 | QEEITATVKVNLPFG | 14 |
| 605 | KVNLPFGRPRVLQKN | 14 |
| 613 | PRVLQKNVDHCLLYH | 14 |
| 621 | DHCLLYHREYVSGFG | 14 |
| 628 | REYVSGFGKAMRMPM | 14 |
| 645 | SYTVPQLGDTSPLPP | 14 |
| 654 | TSPLPPTVPDCLRAD | 14 |
| 668 | DVRVPPSESQKCSFY | 14 |
| 706 | YDALITSNLVPMYEE | 14 |

TABLE XLVIII-continued

| Pos | 123456789012345 | score |
|---|---|---|
| 712 | SNLVPMYEEFRKMWD | 14 |
| 731 | VLLIKHATERNGVNV | 14 |
| 740 | RNGVNVVSGPIFDYN | 14 |
| 743 | VNVVSGPIFDYNYDG | 14 |
| 773 | DVPIPTHYFVVLTSC | 14 |
| 778 | HYFVVLTSCKNKSHT | 14 |
| 780 | YFVVLTSCKNKSHTP | 14 |
| 781 | FVVLTSCKNKSHTPE | 14 |
| 798 | PGWLDVLPFIIPHRP | 14 |
| 800 | WLDVLPFIIPHRPTN | 14 |
| 801 | LDVLPFIIPHRPTNV | 14 |
| 804 | LPFIIPHRPTNVESC | 14 |
| 836 | IARVRDVELLTGLDF | 14 |
| 839 | VRDVELLTGLDFYQD | 14 |
| 841 | DVELLTGLDFYQDKV | 14 |
| 842 | VELLTGLDFYQDKVQ | 14 |
| 845 | LTGLDFYQDKVQPVS | 14 |

V2-HLA-DR1-0401-15mers-161P2F10B
Each peptide is a position of SEQ ID NO: 84; each start position is specified, the length of the peptide is 15 amino acids and the end position for each peptide is the start position plus 14.

| Pos | 123456789012345 | score |
|---|---|---|
| 2 | EASLCSCSDDCLQRK | 14 |
| 5 | LCSCSDDCLQRKDCC | 12 |
| 7 | SCSDDCLQRKDCCAD | 12 |
| 14 | QRKDCCADYKSVCQG | 12 |
| 1 | LEASLCSCSDDCLQR | 6 |
| 3 | ASLCSCSDDCLQRKD | 6 |
| 4 | SLCSCSDDCLQRKDC | 6 |
| 6 | CSCSDDCLQRKDCCA | 6 |
| 11 | DCLQRKDCCADYKSV | 6 |
| 12 | CLQRKDCCADYKSVC | 6 |
| 13 | LQRKDCCADYKSVCQ | 6 |
| 15 | RJDCCADYKSVCQGE | 6 |

V3-HLA-DR1-0401-15mers-161P2F10B
Each peptide is a position of SEQ ID NO: 87; each start position is specified, the length of the peptide is 15 amino acids and the end position for each peptide is the start position plus 14.

| Pos | 123456789012345 | score |
|---|---|---|
| 1 | FIIPHRPTNVESCPG | 12 |
| 4 | PHRPTNVESCPGGKP | 12 |
| 7 | PTNVESCPGGKPEAL | 8 |
| 5 | HRPTNVESCPGGKPE | 6 |
| 6 | RPTNVESCPGGKPEA | 6 |
| 9 | NVESCPGGKPEALWV | 6 |
| 10 | VESCPGGKPEALWVE | 6 |
| 12 | SCPGGKPEALWVEER | 6 |
| 13 | CPGGKPEALWVEERF | 6 |
| 14 | PGGKPEALWVEERFT | 6 |
| 15 | GGKPEALWVEERFTA | 6 |

V4-HLA-DR1-0401-15mers-161P2F10B
Each peptide is a position of SEQ ID NO: 90; each start position is specified, the length of the peptide is 15 amino acids and the end position for each peptide is the start position plus 14.

| Pos | 123456789012345 | score |
|---|---|---|
| 2 | ILQLKTYLPTFETPI | 8 |

TABLE XLIX

| Pos | 123456789012345 | score |
|---|---|---|

V1-HLA-DRB1-1101-15mers-161P2F10B
Each peptide is a portion of SEQ ID NO: 81; each start position is specified, the length of the peptide is 15 amino acids and the end position for each peptide is the start position plus 14.

| Pos | 123456789012345 | score |
|---|---|---|
| 339 | IKALQVVDHAFGMLM | 27 |
| 42 | GLGLRKLEKQGSCRK | 26 |
| 518 | YNLMCDLLRIQPAPN | 26 |
| 207 | PNHYTIVTGLYPESH | 24 |

TABLE XLIX-continued

| Pos | 123456789012345 | score |
|---|---|---|
| 302 | LLKWLDLPKAERPRF | 24 |
| 750 | IFDYNYDGHFDAPDE | 24 |
| 392 | RINFFYMYEGPAPRI | 23 |
| 417 | SFNSEEIVRNLSCRK | 23 |
| 313 | RPRFYTMYFEEPDSS | 22 |
| 662 | PDCLRAOVRVPPSES | 22 |
| 160 | PVILFSMDGFRAEYL | 21 |
| 178 | DTLMPNINKLKTCGI | 21 |
| 296 | EERISTLLKWLDLPK | 21 |
| 759 | FDAPDEITKHLANTD | 21 |
| 780 | YFVVIJSCKNKSHTP | 21 |
| 823 | PEALWVEERFTAHIA | 21 |
| 227 | NMYDVNLNKNFSLSS | 20 |
| 421 | EEIVRNLSGRKPDQH | 20 |
| 447 | RLHYAKNVRIDKVHL | 20 |
| 491 | SMEAIFLAHGPSFKE | 20 |
| 536 | HGSLNHLLKVPFYEP | 20 |
| 728 | FHSVLLIKHATERNG | 20 |
| 798 | PGWLDVLPFIIPHRP | 20 |
| 801 | LDVLPFIIPHRPTNV | 20 |
| 29 | LALLVIMSLGLGLGL | 19 |
| 31 | LLVIMSLGLGLGLGL | 19 |
| 56 | KKCFDASFRGLENCR | 19 |
| 300 | STLLKWLDLPKAERP | 19 |
| 678 | KCSFYLADKNITHGF | 19 |
| 848 | LDFYQOKVQPVSEIL | 19 |
| 858 | VSEILQLKTYLPTFE | 19 |
| 25 | CIVLLALLVIMSLGL | 18 |
| 60 | DASFRGLENCRCDVA | 18 |
| 234 | NKNFSLSSKEQNNPA | 18 |
| 266 | AATYFWPGSEVAING | 18 |
| 380 | CNKMEYMTDYFPRIN | 18 |
| 482 | NHGYNNEFRSMEAIF | 18 |
| 489 | FRSMEAIFLAHGPSF | 18 |
| 539 | LNHLLKVPFYEPSHA | 18 |
| 544 | KVPFYEPSHAEEVSK | 18 |
| 597 | QEEITATVKVNLPFG | 18 |
| 631 | VSGFGKAMRMPMWSS | 18 |
| 645 | SYTVPQLGDTSPLPP | 18 |
| 715 | VPMYEEFRKMWDYFH | 18 |
| 777 | PTHYFVVLTSCKNKS | 18 |
| 778 | THYFVVLTSCKNKSH | 18 |
| 803 | VLPFIIPHRPTNVES | 18 |
| 836 | IARVRDVELLTGLDF | 18 |
| 68 | NCRCDVACKDRGDCC | 17 |
| 93 | TRIWMCNKFRCGETR | 17 |
| 174 | LYTWDTLMPNINKLK | 17 |
| 283 | PSIYMPYNGSVPFEE | 17 |
| 317 | YTMYFEEPDSSGHAG | 17 |
| 346 | DHAFGMLMEGLKQRN | 17 |
| 463 | VDQQWLAVRSKSNTN | 17 |
| 515 | IEVYNLMCDLLRIQP | 17 |
| 441 | TPDLPKRLHYAKNVR | 14 |
| 450 | YAKNVRIDKVHLFVD | 14 |
| 550 | PSHAEEVSKFSVCGF | 14 |
| 602 | ATVKVNLPFGRPRVL | 14 |
| 628 | REYVSGFGKAMRMPM | 14 |
| 658 | PPTVPDCLPADVRVP | 14 |
| 682 | YLADKNITHGFLYPP | 14 |
| 685 | DKNITHGFLYPPASN | 14 |
| 714 | LVPMYEEFRKMWDYF | 14 |
| 724 | MWDYFHSVLLIKHAT | 14 |
| 727 | YFHSVLLIKHATERN | 14 |
| 740 | RNGVNVVSGPIFDYN | 14 |
| 771 | NTDVPIPTHYFVVLT | 14 |
| 814 | NVESCPEGKPEALVN | 14 |
| 829 | EERFTAHIARVRDVE | 14 |
| 842 | VELLTGLDFYQDKVQ | 14 |
| 23 | IACIVLLALLVIMSL | 13 |
| 27 | VLLALLVIMSLGLGL | 13 |
| 28 | LLALLVIMSLGLGLG | 13 |
| 33 | VIMSLGLGLGLRK | 13 |
| 63 | FRGLENCRCDVACKD | 13 |
| 194 | SKYMRAMYPTKTFPN | 13 |
| 225 | DNNMYDVNLNKNFSL | 13 |
| 350 | GMLMEGLKQRNLHNC | 13 |
| 434 | QHFKPYLTPDLPKRL | 13 |
| 453 | NVRIDKVHLFVDQQW | 13 |
| 514 | NIEVYNLMCDLLRIQ | 13 |
| 540 | NHLLKVPFYEPSHAE | 13 |
| 558 | KFSVGGFANPLPTES | 13 |
| 583 | STQLEQVNQMLNLTQ | 13 |
| 598 | EEITATVKVNLPFGR | 13 |
| 621 | DHCLLYHREYVSGFG | 13 |
| 643 | WSSYTVPQLGDTSPL | 13 |
| 651 | LGDTSPLPPTVPDCL | 13 |
| 726 | DYFHSVLLIKHATER | 13 |
| 731 | VLLIKHATERNGVNV | 13 |
| 766 | TKHLANTDVPIPTHY | 13 |
| 812 | PTNVESCPEGKPEAL | 13 |
| 852 | QDKVQPVSEILQLKT | 13 |
| 855 | VQPVSEILQLKTYLP | 13 |
| 556 | VSKFSVCGFANPLPT | 17 |
| 691 | GFLYPPASNRTSDSQ | 17 |
| 725 | WDYFHSVLLIKHATE | 17 |
| 797 | CPGWLDVLPFIIPHR | 17 |
| 92 | STRIWMCNKFRCGET | 16 |
| 126 | CADYKSVCQGETSWL | 16 |
| 136 | ETSWLEENCOTAQQS | 16 |
| 258 | TAMYQGLKAATYFWP | 16 |
| 279 | NGSFPSIYMPYNGSV | 16 |
| 305 | WLDLPKAERPRFYTM | 16 |
| 349 | FGMLMEGLKQRNLHN | 16 |
| 387 | TDYFPRINFFYMYEG | 16 |
| 393 | INFFYMYEGPAPRIR | 16 |
| 397 | YMYEGPAPRIRAHNI | 16 |
| 438 | PYLTPDLPKRLHYAK | 16 |
| 464 | DQQWLAVRSKSNTNC | 16 |
| 486 | NNEFRSMEAIFLAHG | 16 |
| 500 | GPSFKEKTEVEPFEN | 16 |
| 509 | VEPFENIEVYNLMCD | 16 |
| 561 | VCGFANPLPTESLDC | 16 |
| 610 | FGRPRVLQKNVDHCL | 16 |
| 703 | DSQYDALITSNLVPM | 16 |
| 718 | YEEFRKMWDYFHSVL | 16 |
| 802 | DVLPFIIPHRPTNVE | 16 |
| 830 | ERFTAHIARVRDVEL | 16 |
| 12 | PVKKNTLKKYKIACI | 15 |
| 38 | GLGLGLGLRKLEKQG | 15 |
| 213 | VTGLYPESHGIIDNN | 15 |
| 254 | PMWLTAMYQGLKAAT | 15 |
| 332 | GPVSARVIKALQVVD | 15 |
| 401 | GPAPRIRAHNIPHDF | 15 |
| 427 | LSCRKPDQHFKPYLT | 15 |
| 458 | KVHLFVDQQWLAVRS | 15 |
| 465 | QQWLAVRSKSNTNCG | 15 |
| 533 | NGTHGSLNHLLKVPF | 15 |
| 614 | RVLQKNVDHCLLYHR | 15 |
| 619 | NVDHCLLYHREYVSG | 15 |
| 721 | FRKMWDYFHSVLLIK | 15 |
| 846 | TGLDFYQOKVQPVSE | 15 |
| 7 | LATEQPVKKNTLKKY | 14 |
| 20 | KYKIACIVLLALLVI | 14 |
| 26 | IVLLALLVIMSLGLG | 14 |
| 39 | LGLGLGLRKLEKQGS | 14 |
| 70 | RCDVACKDRGDCCWD | 14 |
| 94 | RIWMCNKFRCGETRL | 14 |
| 99 | NKFRCGETRLEASLC | 14 |
| 114 | SCSDDCLQKKDCCAD | 14 |
| 180 | LMPNINKLKTCGIHS | 14 |
| 196 | YMRAMYPTKTFPNHY | 14 |
| 210 | YTIVTGLYPESHGII | 14 |
| 243 | EQNNPAWWHGQPMWL | 14 |
| 257 | LTAMYQGLKAATYFW | 14 |
| 290 | NGSVPFEERISTLLK | 14 |
| 303 | LKWLDLPKAERPRFY | 14 |
| 321 | FEEPDSSGHAGGPVS | 14 |
| 365 | VNIILLADHGMDQTY | 14 |
| 405 | RIRAHNIPHDFFSFN | 14 |
| 441 | TPDLPKRLHYAKNVR | 14 |
| 450 | YAKNVRIDKVHLFVD | 14 |
| 550 | PSHAEEVSKFSVCGF | 14 |
| 602 | ATVKVNLPFGRPRVL | 14 |
| 628 | REYVSGFGKAMRMPM | 14 |

TABLE XLIX-continued

| Pos | 123456789012345 | score |
|---|---|---|
| 658 | PPTVPDCLRADVRVP | 14 |
| 682 | YLADKNITHGFLYPP | 14 |
| 685 | DKNITHGFLYPPASN | 14 |
| 714 | LVPMYEEFRKMWDYF | 14 |
| 724 | MWDYFHSVLLIKHAT | 14 |
| 727 | YFHSVLLIKHATERN | 14 |
| 740 | RNGVNVVSGPIFDYN | 14 |
| 771 | NTDVPIPTHYFVVLT | 14 |
| 814 | NVESCPEGKPEALWV | 14 |
| 829 | EERFTAHIARVRDVE | 14 |
| 842 | VELLTGLDFYQDKVQ | 14 |
| 23 | IACIVLLALLVIMSL | 13 |
| 27 | VLLALLVIMSLGLGL | 13 |
| 28 | LLALLVIMSLGLGLG | 13 |
| 33 | VIMSLGLGLGLGLRK | 13 |
| 63 | FRGLENCRCDVACKD | 13 |
| 194 | SKYMRAMYPTKTFPN | 13 |
| 225 | DNNMYDVNLNKNFSL | 13 |
| 350 | GMLMEGLKQRNLHNC | 13 |
| 434 | QHFKPYLTPDLPKRL | 13 |
| 453 | NVRIDKVHLFVDQQW | 13 |
| 514 | NIEVYNLMCDLLRIQ | 13 |
| 540 | NHLLKVPFYEPSHAE | 13 |
| 558 | KFSVCGFANPLPTES | 13 |
| 583 | STQLEQVNQMLNLTQ | 13 |
| 598 | EEITATVKVNLPFGR | 13 |
| 621 | DHCLLYHREYVSGFG | 13 |
| 643 | WSSYTVPQLGDTSPL | 13 |
| 651 | LGDTSPLPPTVPDCL | 13 |
| 726 | DYFHSVLLIKHATER | 13 |
| 731 | VLLIKHATERNGVNV | 13 |
| 766 | TKHLANTDVPIPTHY | 13 |
| 812 | PTNVESCPEGKPEAL | 13 |
| 852 | QDKVQPVSEILQLKT | 13 |
| 855 | VQPVSEILQLKTYLP | 13 |

V2-DRB1-1101-15mers-161P2F10B
Each peptide is a portion of SEQ ID NO: 84; each start position is specified, the length of the peptide is 15 amino acids and the end position for each peptide is the start position plus 14.

| Pos | 123456789012345 | score |
|---|---|---|
| 7 | SCSDDCLQRKOCCAD | 14 |
| 15 | RKDCCADYKSVCQGE | 9 |
| 8 | CSDDCLQRKDCCADY | 8 |
| 13 | LQRKDCCADYKSVCQ | 7 |
| 2 | EASLCSCSDDCLQRK | 6 |
| 9 | SDDCLQRKDCCADYK | 6 |
| 10 | DDCLQRKDCCADYKS | 6 |

V3-HLA-DRB1-1101-15mers-161P2F10B
Each peptide is a portion of SEQ ID NO: 87; each start position is specified, the length of the peptide is 15 amino acids and the end position for each peptide is the start position plus 14.

| Pos | 123456789012345 | score |
|---|---|---|
| 4 | PHRPTNVESCPGGKP | 14 |
| 9 | NVESCPGGKPEALWV | 14 |
| 7 | PTNVESCPGGKPEAL | 13 |
| 3 | IPHRPTNVESCPGGK | 8 |
| 5 | HRPTNVESCPGGKPE | 7 |
| 1 | FIIPHRPTNVESCPG | 6 |
| 15 | GGKPEALWVEERFTA | 6 |

V4-HLA-DRB1-1101-15mers-161P2F10B
Each peptide is a portion of SEQ ID NO: 90; each start position is specified, the length of the peptide is 15 amino acids and the end position for each peptide is the start position plus 14.

| Pos | 123456789012345 | score |
|---|---|---|
| 2 | ILQLKTYLPTFETPI | 6 |

TABLE L

Properties of 161P2F10B

| Feature | Bioinformatic Program | Outcome |
|---|---|---|
| ORF (includes stop codon) | ORF finder | |
| # of amino acids | | 875 |
| Transmembrane region | TM Pred | One TM, aa 23–41 |
| | HMMTop | One TM, aa 23–45 |
| | Sosui | One TM, aa 23–45 |
| | TMHMM | One TM, aa 23–45 |
| Signal Peptide | Signal P | None |
| pI | pI/MW tool | 6.12 |
| Molecular weight | pI/MW tool | 100.09 kDa |
| Localization | PSORT | Plasma membrane 74% Golgi 30% |
| | PSORT II | Endoplasmic 30.4% Golgi 21.7% |
| Motifs | Pfam | Somatomedin B, Type I phosphodiesterase/ nucleotide pyrophosphatase |
| | Prints | Cell Attachment RGD |
| | Blocks | Somatomedin B, DNA/RNA non-specific endonuclease, |
| | Prosite | Somatomedin B |

TABLE LI

| Nucleotide sequence of transcript variant 161P2F10B v.6 | (SEQ ID NO: 91) |
|---|---|
| atacagtttc tctttgccag actagactaa agaaggagca ctactttatt ctgataaaac | 60 |
| aggtctatgc agctaccagg acaatggaat ctacgttgac tttagcaacg gaacaacctg | 120 |
| ttaagaagaa cactcttaag aaatataaaa tagcttgcat tgttcttctt gctttgctgg | 180 |
| tgatcatgtc acttggatta ggcctggggc ttggactcag gaaactggaa aagcaagyca | 240 |
| gctgcaggaa gaagtgctttt gatgcatcat ttagaggact ggagaactgc cggtgtgatg | 300 |
| tggcatgtaa agaccgaggt gattgctgct gggattttga agacacctgt gtggaatcaa | 360 |

TABLE LI-continued

| Nucleotide sequence of transcript variant 161P2F10B v.6 | (SEQ ID NO: 91) |
|---|---|

| | |
|---|---|
| ctcgaatatg gatgtgcaat aaatttcgtt gtggagagac cagattagag gccagccttt | 420 |
| gctcttgttc agatgactgt ttgcagagga aagattgctg tgctgactat aagagtgttt | 480 |
| gccaaggaga aacctcatgg ctggaagaaa actgtgacac agcccagcag tctcagtgcc | 540 |
| cagaaggytt tgacctgcca ccagttatct tgttttctat ggatggattt agagccgaat | 600 |
| atttatacac atgygatact ttaatgccaa atatcaataa actgaaaaca tgtggaattc | 660 |
| attcaaaata catyagagct atgtatccta ccaaaacctt cccaaatcat acaccattg | 720 |
| tcacgggctt gtatccggag tcacatggca tcattgacaa taatatgtat gatgtaaatc | 780 |
| tcaacaagaa tttttcactt tcttcaaagg aacaaaataa tccagcctgg tggcatgggc | 840 |
| aaccaatgtg gctgacagca atgtatcaag gtttaaaagc cgctacctac ttttggcccg | 900 |
| gatcagaagt ggctataaat ggctcctttc cttccatata catgccttac aacggaagtg | 960 |
| tcccatttga agagaggatt ctacactgt taaaatggct ggacctgccc aaagctgaga | 1020 |
| gacccaggtt ttataccaty ttttttgaag aacctgattc ctctggacat gcaggtggac | 1080 |
| cagtcagtgc cagagtaatt aaagccttac aggtagtaga tcatgctttt gggatgttga | 1140 |
| tggaaggcct gaagcagcgg aatttgcaca actgtgtcaa tatcatcctt ctggctgacc | 1200 |
| atggaatgga ccagacttat tgtaacaaga tggaatacat gactgattat tttcccagaa | 1260 |
| taaacttctt ctacatgtac gaagggcctg cccccgcgt ccgagctcat aatatacctc | 1320 |
| atgacttttt tagttttaat tctgaggaaa ttgttagaaa cctcagttgc cgaaaacctg | 1380 |
| atcagcattt caagccctat ttgactcctg atttgccaaa gcgactgcac tatgccaaga | 1440 |
| acgtcagaat cgacaaagtt catctctttg tggatcaaca gtggctggct gttaggagta | 1500 |
| aatcaaatac aaattgtgga gyaggcaacc atgyttataa caatgagttt aggagcatgg | 1560 |
| aggctatctt tctggcacat ggacccagtt ttaaagagaa gactgaagtt gaaccatttg | 1620 |
| aaaatattga agtctataac ctaatgtgtg atcttctacg cattcaacca gcaccaaaca | 1680 |
| atggaaccca tggtagttta aaccatcttc tgaaggtgcc ttttttatgag ccatcccatg | 1740 |
| cagaggaggt gtcaaagttt tctgtttgtg gctttgctaa tccattgccc acagagtctc | 1800 |
| ttgactgttt ctgccctcac ctacaaaata gtactcagct ggaacaagtg aatcagatgc | 1860 |
| taaatctcac ccaagaagaa ataacagcaa cagtgaaagt aaatttgcca tttgggaggc | 1920 |
| ctagggtact gcagaagaac gtggaccact gtctccttta ccacagggaa tatgtcagtg | 1980 |
| gatttggaaa agctatgagg atgcccatgt ggagttcata cacagtcccc cagttgggag | 2040 |
| acacatcgcc tctgcctccc actgtcccag actgtctgcg ggctgatgtc agggttcctc | 2100 |
| cttctgagag ccaaaaatgt tccttctatt tagcagacaa gaatatcacc cacggcttcc | 2160 |
| tctatcctcc tgccagcaat agaacatcag atagccaata tgatgcttta attactagca | 2220 |
| atttggtacc tatgtatgaa gaattcagaa aaatgtggga ctacttccac agtgttcttc | 2280 |
| ttataaaaca tgccacagaa agaaatggag taaatgtggt tagtgaccca atatttgatt | 2340 |
| ataattatga tggccatttt gatgctccag atgaaattac caaacattta gccaacactg | 2400 |
| atgttcccat cccaacacac tactttgtgg tgctgaccag ttgtaaaaac aagagccaca | 2460 |
| caccggaaaa ctgccctggg tggctggatg tcctacccett tatcatccct caccgaccta | 2520 |
| ccaacgtgga gagctgtcct gaaggtaaac cagaagctct ttgggttgaa gaaagattta | 2580 |
| cagctcacat tgcccgggtc cgtgatgtag aacttctcac tgggcttgac ttctatcagg | 2640 |

TABLE LI-continued

| Nucleotide sequence of transcript variant 161P2F10B v.6 | (SEQ ID NO: 91) |
|---|---|
| ataaagtgca gcctgtctct gaaattttgc aactaaagac atatttacca acatttgaaa | 2700 |
| ccactattta acttaataat gtctacttaa tatataattt actgtataaa gtaattttgg | 2760 |
| caaaatataa gtgatttttt tctggagaat tgtaaaataa agttttctat ttttccttaa | 2820 |
| gtcccctaaa agccataatt tttattattc cttttctct tttttcaatt ctatgaatat | 2880 |
| gtattatttt aaagttatat ttttcacaca gagatgatgc tatattacac cttcccttt | 2940 |
| ttgttggttt cttaaactct aatctcatga cagattatac cttccttatt acttgtttta | 3000 |
| tcttactcag aatctttgaa tatatttttc tgcccagaat tatctaaaca aaagggagaa | 3060 |
| caaaagaagt atgtctcact tgggaactga atcaactcta aatcagtttt gtcacaaaac | 3120 |
| tttttgtatt tgactggcaa tgctgattaa aattaaaaat gcaca | 3165 |

TABLE LII

| Nucleotide sequence alignment of 161P2F10B v.1 (SEQ ID NO: 92) and 161P2F10B v.6 (SEQ ID NO: 93) |
|---|

Score = 5301 bits (2757), Expect 0.0Identities = 2774/2780 (99%), Gaps = 1/2780 (0%) Strand = Plus/Plus

```
v.1:    1 ctactttattctgataaaacaggtctatgcagctaccaggacaatggaatctacgttgac   60
          |||||||||||||||    ||||||||||||||||||||||||||||||||||||||||
v.6:   41 ctactttattctgatccccaggtctatgcagctaccaggacaatggaatctacgttgac  100 v.1:   61 tttagcaacggaacaacctgttaagaagaacactcttaagaaatataaaatagcttgcat  120
          ||||||||||||||||||||||||||||||||||||||||||||||||||||||||||||
v.6:  101 tttagcaacggaacaacctgttaagaagaacactcttaagaaatataaaatagcttgcat  160 v.1:  121 tgttcttcttgctttgctggtgatcatgtcacttggattaggcctggggcttggactcag  180
          ||||||||||||||||||||||||||||||||||||||||||||||||||||||||||||
v.6:  161 tgttcttcttgctttgctggtgatcatgtcacttggattaggcctggggcttggactcag  220 v.1:  181 gaaactggaaaagcaaggcagctgcaggaagaagtgctttgatgcatcatttagaggact  240
          ||||||||||||||||||||||||||||||||||||||||||||||||||||||||||||
v.6:  161 gaaactggaaaagcaaggcagctgcaggaagaagtgctttgatgcatcatttagaggact  280 v.1:  241 ggagaactgccggtgtgatgtggcatgtaaagaccgaggtgattgctgctgggattttga  300
          ||||||||||||||||||||||||||||||||||||||||||||||||||||||||||||
v.6:  281 ggagaactgccggtgtgatgtggcatgtaaagaccgaggtgattgctgctgggattttga  340 v.1:  301 agacacctgtgtggaatcaactcgaatatggatgtgcaataaatttcgttgtggagagac  360
          ||||||||||||||||||||||||||||||||||||||||||||||||||||||||||||
v.6:  341 agacacctgtgtggaatcaactcgaatatggatgtgcaataaatttcgttgtggagagac  400 v.1:  361 cagattagaggccagcctttgctcttgttcagatgactgtttgcagaagaaagattgctg  420
          |||||||||||||||||||||||||||||||||||||||||||||||| |||||||||||
v.6:  401 cagattagaggccagcctttgctcttgttcagatgactgtttgcagaggaaagattgctg  460 v.1:  421 tgctgactataagagtgtttgccaaggagaaacctcatggctggaagaaaactgtgacac  480
          ||||||||||||||||||||||||||||||||||||||||||||||||||||||||||||
v.6:  461 tgctgactataagagtgtttgccaaggagaaacctcatggctggaagaaaactgtgacac  520 v.1:  481 agcccagcagtctcagtgcccagaagggtttgacctgccaccagttatcttgttttctat  540
          ||||||||||||||||||||||||||||||||||||||||||||||||||||||||||||
v.6:  521 agcccagcagtctcagtgcccagaagggtttgacctgccaccagttatcttgttttctat  580 v.1:  541 ggatggatttagagctgaatatttatacacatgggatactttaatgccaaatatcaataa  600
          ||||||||||||||||||||||||||||||||||||||||||||||||||||||||||||
v.6:  581 ggatggatttagagctgaatatttatacacatgggatactttaatgccaaatatcaataa  640 v.1:  601 actgaaaacatgtggaattcattcaaaatacatgagagctatgtatcctaccaaaacctt  660
          ||||||||||||||||||||||||||||||||||||||||||||||||||||||||||||
v.6:  641 actgaaaacatgtggaattcattcaaaatacatgagagctatgtatcctaccaaaacctt  700 v.1:  661 cccaaatcattacaccattgtcacgggcttgtatccagagtcacatggcatcattgacaa  720
          |||||||||||||||||||||||||||||||||  ||||| |||||||||||||||||||
v.6:  701 cccaaatcattacaccattgtcacgggcttgtatccggagtcacatggcatcattgacaa  760
```

TABLE LII-continued

Nucleotide sequence alignment of 161P2F10B v.1 (SEQ ID NO: 92) and 161P2F10B v.6 (SEQ ID NO: 93)

```
v.1:  721 taatatgtatgatgtaaatctcaacaagaattttttcactttcttcaaaggaacaaaataa  780
          ||||||||||||||||||||||||||||||||||||||||||||||||||||||||||||
v.6:  761 taatatgtatgatgtaaatctcaacaagaattttttcactttcttcaaaggaacaaaataa  820 v.1:  781 tccagcctggtggcatgggcaaccaatgtggctgacagcaatgtatcaaggtttaaaagc  840
          ||||||||||||||||||||||||||||||||||||||||||||||||||||||||||||
v.6:  821 tccagcctggtggcatgggcaaccaatgtggctgacagcaatgtatcaaggtttaaaagc  880 v.1:  841 cgctacctacttttggcccggatcagaagtggctataaatggctcctttccttccatata  900
          ||||||||||||||||||||||||||||||||||||||||||||||||||||||||||||
v.6:  881 cgctacctacttttggcccggatcagaagtggctataaatggctcctttccttccatata  940 v.1:  901 catgccttacaacggaagtgtcccatttgaagagaggatttctacactgttaaaatggct  960
          |||||||||||| |||||||||||||||||||||||||||||||||||||||||||||||
v.6:  941 catgccttacaacgaaagtgtcccatttgaagagaggatttctacactgttaaaatggct 1000 v.1:  961 ggacctgcccaaagctgaaagacccaggttttataccatgtattttgaagaacctgattc 1020
          ||||||||||||||||| ||||||||||||||||||||||| | ||||||||||||||||
v.6: 1001 ggacctgcccaaagctgagagacccaggttttataccatgttttttgaagaacctgattc 1060 v.1: 1021 ctctggacatgcaggtggaccagtcagtgccagagtaattaaagccttacaggtagtaga 1080
          ||||||||||||||||||||||||||||||||||||||||||||||||||||||||||||
v.6: 1061 ctctggacatgcaggtggaccagtcagtgccagagtaattaaagccttacaggtagtaga 1120 v.1: 1081 tcatgcttttgggatgttgatggaaggcctgaagcagcggaatttgcacaactgtgtcaa 1140
          ||||||||||||||||||||||||||||||||||||||||||||||||||||||||||||
v.6: 1121 tcatgcttttgggatgttgatggaaggcctgaagcagcggaatttgcacaactgtgtcaa 1180 v.1: 1141 tatcatccttctggctgaccatggaatggaccagacttattgtaacaagatggaatacat 1200
          ||||||||||||||||||||||||||||||||||||||||||||||||||||||||||||
v.6: 1181 tatcatccttctggctgaccatggaatggaccagacttattgtaacaagatggaatacat 1240 v.1: 1201 gactgattattttcccagaataaacttcttctacatgtacgaagggcctgcccccgcat 1260
          |||||||||||||||||||||||||||||||||||||||||||||||||||||||||| |
v.6: 1241 gactgattattttcccagaataaacttcttctacatgtacgaagggcctgcccccgcgt 1300 v.1: 1261 ccgagctcataatatacctcatgactttttagttttaattctgaggaaattgttagaaa 1320
          ||||||||||||||||||||||||||||||||||||||||||||||||||||||||||||
v.6: 1301 ccgagctcataatatacctcatgactttttagttttaattctgaggaaattgttagaaa 1360 v.1: 1321 cctcagttgccgaaaacctgatcagcatttcaagccctatttgactcctgatttgccaaa 1380
          ||||||||||||||||||||||||||||||||||||||||||||||||||||||||||||
v.6: 1361 cctcagttgccgaaaacctgatcagcatttcaagccctatttgactcctgatttgccaaa 1420 v.1: 1381 gcgactgcactatgccaagaacgtcagaatcgacaaagttcatctctttgtggatcaaca 1440
          ||||||||||||||||||||||||||||||||||||||||||||||||||||||||||||
v.6: 1421 gcgactgcactatgccaagaacgtcagaatcgacaaagttcatctctttgtggatcaaca 1480 v.1: 1441 gtggctggctgttaggagtaaatcaaatacaaattgtggaggaggcaaccatggttataa 1500
          ||||||||||||||||||||||||||||||||||||||||||||||||||||||||||||
v.6: 1481 gtggctggctgttaggagtaaatcaaatacaaattgtggaggaggcaaccatggttataa 1540 v.1: 1501 caatgagtttaggagcatggaggctatctttctggcacatggacccagttttaaagagaa 1560
          ||||||||||||||||||||||||||||||||||||||||||||||||||||||||||||
v.6: 1541 caatgagtttaggagcatggaggctatctttctggcacatggacccagttttaaagagaa 1600 v.1: 1561 gactgaagttgaaccatttgaaaatattgaagtctataacctaatgtgtgatcttctacg 1620
          ||||||||||||||||||||||||||||||||||||||||||||||||||||||||||||
v.6: 1601 gactgaagttgaaccatttgaaaatattgaagtctataacctaatgtgtgatcttctacg 1660 v.1: 1621 cattcaaccagcaccaaacaatggaacccatggtagtttaaaccatcttctgaaggtgcc 1680
          ||||||||||||||||||||||||||||||||||||||||||||||||||||||||||||
v.6: 1661 cattcaaccagcaccaaacaatggaacccatggtagtttaaaccatcttctgaaggtgcc 1720 v.1: 1681 tttttatgagccatcccatgcagaggaggtgtcaaagttttctgtttgtggctttgctaa 1740
          ||||||||||||||||||||||||||||||||||||||||||||||||||||||||||||
v.6: 1621 tttttatgagccatcccatgcagaggaggtgtcaaagttttctgtttgtggctttgctaa 1720 v.1: 1741 tccattgcccacagagtctcttgactgtttctgccctcacctacaaaatagtactcagct 1800
          ||||||||||||||||||||||||||||||||||||||||||||||||||||||||||||
v.6: 1781 tccattgcccacagagtctcttgactgtttctgccctcacctacaaaatagtactcagct 1840
```

TABLE LII-continued

Nucleotide sequence alignment of 161P2F10B v.1 (SEQ ID NO: 92) and 161P2F10B v.6 (SEQ ID NO: 93)

```
v.1: 1801  ggaacaagtgaatcagatgctaaatctcacccaagaagaaataacagcaacagtgaaagt  1860
           ||||||||||||||||||||||||||||||||||||||||||||||||||||||||||||
v.6: 1841  ggaacaagtgaatcagatgctaaatctcacccaagaagaaataacagcaacagtgaaagt  1900 v.1: 1861  aaatttgccatttgggaggcctagggtactgcagaagaacgtggaccactgtctccttta  1920
           ||||||||||||||||||||||||||||||||||||||||||||||||||||||||||||
v.6: 1901  aaatttgccatttgggaggcctagggtactgcagaagaacgtggaccactgtctccttta  1960 v.1: 1921  ccacagggaatatgtcagtggatttggaaaagctatgaggatgcccatgtggagttcata  1980
           ||||||||||||||||||||||||||||||||||||||||||||||||||||||||||||
v.6: 1961  ccacagggaatatgtcagtggatttggaaaagctatgaggatgcccatgtggagttcata  2020 v.1: 1981  cacagtccccagttgggagacacatcgcctctgcctcccactgtcccagactgtctgcg   2040
           ||||||||||||||||||||||||||||||||||||||||||||||||||||||||||||
v.6: 2021  cacagtccccagttgggagacacatcgcctctgcctcccactgtcccagactgtctgcg   2080 v.1: 2041  ggctgatgtcagggttcctccttctgagagccaaaaatgttccttctatttagcagacaa  2100
           ||||||||||||||||||||||||||||||||||||||||||||||||||||||||||||
v.6: 2081  ggctgatgtcagggttcctccttctgagagccaaaaatgttccttctatttagcagacaa  2140 v.1: 2101  gaatatcacccacggcttcctctatcctcctgccagcaatagaacatcagatagccaata  2160
           ||||||||||||||||||||||||||||||||||||||||||||||||||||||||||||
v.6: 2141  gaatatcacccacggcttcctctatcctcctgccagcaatagaacatcagatagccaata  2200 v.1: 2161  tgatgctttaattactagcaatttggtacctatgtatgaagaattcagaaaaatgtggga  2220
           ||||||||||||||||||||||||||||||||||||||||||||||||||||||||||||
v.6: 2201  tgatgctttaattactagcaatttggtacctatgtatgaagaattcagaaaaatgtggga  2260 v.1: 2221  ctacttccacagtgttcttcttataaaacatgccacagaaagaaatggagtaaatgtggt  2280
           ||||||||||||||||||||||||||||||||||||||||||||||||||||||||||||
v.6: 2261  ctacttccacagtgttcttcttataaaacatgccacagaaagaaatggagtaaatgtggt  2320 v.1: 2281  tagtggaccaatatttgattataattatgatggccattttgatgctccagatgaaattac  2340
           ||||||||||||||||||||||||||||||||||||||||||||||||||||||||||||
v.6: 2321  tagtggaccaatatttgattataattatgatggccattttgatgctccagatgaaattac  2380 v.1: 2341  caaacatttagccaacactgatgttcccatcccaacacactactttgtggtgctgaccag  2400
           ||||||||||||||||||||||||||||||||||||||||||||||||||||||||||||
v.6: 2381  caaacatttagccaacactgatgttcccatcccaacacactactttgtggtgctgaccag  2440 v.1: 2401  ttgtaaaaacaagagccacacaccggaaaactgccctgggtggctggatgtcctacccctt  2460
           ||||||||||||||||||||||||||||||||||||||||||||||||||||||||||||
v.6: 2441  ttgtaaaaacaagagccacacaccggaaaactgccctgggtggctggatgtcctacccctt  2500 v.1: 2461  tatcatccctcaccgacctaccaacgtggagagctgtcctgaaggtaaaccagaagctct  2520
           ||||||||||||||||||||||||||||||||||||||||||||||||||||||||||||
v.6: 2501  tatcatccctcaccgacctaccaacgtggagagctgtcctgaaggtaaaccagaagctct  2560 v.1: 2521  ttgggttgaagaaagatttacagctcacattgcccgggtccgtgatgtagaacttctcac  2580
           ||||||||||||||||||||||||||||||||||||||||||||||||||||||||||||
v.6: 2561  ttgggttgaagaaagatttacagctcacattgcccgggtccgtgatgtagaacttctcac  2620 v.1: 2581  tgggcttgacttctatcaggataaagtgcagcctgtctctgaaattttgcaactaaagac  2640
           ||||||||||||||||||||||||||||||||||||||||||||||||||||||||||||
v.6: 2621  tgggcttgacttctatcaggataaagtgcagcctgtctctgaaattttgcaactaaagac  2680 v.1: 2641  atatttaccaacatttgaaaccactatttaacttaataatgtctacttaatatataattt  2700
           ||||||||||||||||||||||||||||||||||||||||||||||||||||||||||||
v.6: 2681  atatttaccaacatttgaaaccactatttaacttaataatgtctacttaatatataattt  2740 v.1: 2701  actgtataaagtaattttggcaaaatataagtga-ttttttctggagaattgtaaaataa  2759
           ||||||||||||||||||||||||||||||||||  |||||||||||||||||||||||
v.6: 2741  actgtataaagtaattttggcaaaatataagtgatttttttctggagaattgtaaaataa  2800 v.1: 2760  agttttctattttccttaa                                           2779
           |||||||||||||||||||
v.6: 2801  agttttctattttccttaa                                           2820
```

TABLE LIII

| Peptide sequences of protein coded by 161p2f10b V.6 | (SEQ ID NO: 94) |
|---|---|
| MESTLTLATE QPVKKNTLKK YKIACIVLLA LLVIMSLGLG LGLGLRKLEK QGSCRKKCFD | 60 |
| ASFRGLENCR CDVACKDRGD CCWDFEDTCV ESTRIWMCNK FRCGETRLEA SLCSCSDDCL | 120 |
| QKKDCCADYK SVCQGETSWL EENCDTAQQS ACPEGFDLPP VILFSMDGFR AEYLYTWDTL | 180 |
| MPNINKLKTC GIHSKYMRAM YPTKTFPNHY TIVTGLYPES HGIIDNNMYD VNLNKNFSLS | 240 |
| SKEQNNPAWW HGQPMWLTAM YQGLKAATYF WPGSEVAING SFPSIYMPYN GSVPFEERIS | 300 |
| TLLKWLDLPK AERPRFYTMY FEEPDSSGHA GGPVSARVIK ALQVVDHAFG MLMEGLKQRN | 360 |
| LHNCVNIILL ADHGMDQTYC NKMEYMTDYF PRINFFYMYE GPAPRIRAHN IPHDFFSFNS | 420 |
| EEIVRNLSCR KPDQHFKPYL TPDLPKRLHY AKNVRIDKVH LFVDQQWLAV RSKSNTNCGG | 480 |
| GNHGYNNEFR SMEAIFLAHG PSFKEKTEVE PFENIEVYNL MCDLLRIQPA PNNGTHGSLN | 540 |
| HLLKVPFYEP SHAEEVSKFS VCGFANPLPT ESLDCFCPHL QNSTQLEQVN QMLNLTQEEI | 600 |
| TATVKVNLPF GRPRVLQKNV DHCLLYHREY VSGFGKAMRM PMWSSYTVPQ LGDTSPLPPT | 660 |
| VPDCLRADVR VPPSESQKCS FYLADKNITH GFLYPPASNR TSDSQYDALI TSNLVPMYEE | 720 |
| FRKMWDYFHS VLLIKHATER NGVNVVSGPI FDYNYDGHFD APDEITKHLA NTDVPIPTHY | 780 |
| FVVLTSCKNK SHTPENCPGW LDVLPFIIPH RPTNVESCPE GKPEALWVEE RFTAHIARVR | 840 |
| DVELLTGLDF YQDKVQPVSE ILQLKTYLPT FETTI | 875 |

TABLE LIV

| Amino acid sequence alignment of 161P2F10Bv.1 v.1 (SEQ ID NO: 95) and 161P2F10B v.6 (SEQ ID NO: 96) |
|---|

```
Score = 1855 bits (4804),   Expect = 0.0   Identities = 875/875 (100%),
                    Positives = 875/875 (100%)

161P2F10Bv.1:    1 MESTLTLATEQPVKKNTLKKYKIACIVLLALLVIMSLGLGLGLGLRKLEKQGSCRKKCFD  60
                   MESTLTLATEQPVKKNTLKKYKIACIVLLALLVIMSLGLGLGLGLRKLEKQGSCRKKCFD
161P2F10Bv.6:    1 MESTLTLATEQPVKKNTLKKYKIACIVLLALLVIMSLGLGLGLGLRKLEKQGSCRKKCFD  60

161P2F10Bv.1:   61 ASFRGLENCRCDVACKDRGDCCWDFEDTCVESTRIWMCNKFRCGETRLEASLCSCSDDCL 120
                   ASFRGLENCRCDVACKDRGDCCWDFEDTCVESTRIWMCNKFRCGETRLEASLCSCSDDCL
161P2F10Bv.6:   61 ASFRGLENCRCDVACKDRGDCCWDFEDTCVESTRIWMCNKFRCGETRLEASLCSCSDDCL 120

161P2F10Bv.1:  121 QKKDCCADYKSVCQGETSWLEENCDTAQQSQCPEGFDLPPVILFSMDGFRAEYLYTWDTL 180
                   QKKDCCADYKSVCQGETSWLEENCDTAQQSQCPEGFDLPPVILFSMDGFRAEYLYTWDTL
161P2F10Bv.6:  121 QKKDCCADYKSVCQGETSWLEENCDTAQQSQCPEGFDLPPVILFSMDGFRAEYLYTWDTL 180

161P2F10Bv.1:  181 MPNINKLKTCGIHSKYMRAMYPTKTFPNHYTIVTGLYPESHGIIDNNMYDVNLNKNFSLS 240
                   MPNINKLKTCGIHSKYMRAMYPTKTFPNHYTIVTGLYPESHGIIDNNMYDVNLNKNFSLS
161P2F10Bv.6:  181 MPNINKLKTCGIHSKYMRAMYPTKTFPNHYTIVTGLYPESHGIIDNNMYDVNLNKNFSLS 240

161P2F10Bv.1:  241 SKEQNNPAWWHGQPMWLTAMYQGLKAATYFWPGSEVAINGSFPSIYMPYNGSVPFEERIS 300
                   SKEQNNPAWWHGQPMWLTAMYQGLKAATYFWPGSEVAINGSFPSIYMPYNGSVPFEERIS
161P2F10Bv.6:  241 SKEQNNPAWWHGQPMWLTAMYQGLKAATYFWPGSEVAINGSFPSIYMPYNGSVPFEERIS 300

161P2F10Bv.1:  301 TLLKWLDLPKAERPRFYTMYFEEPDSSGHAGGPVSARVIKALQVVDHAFGMLMEGLKQRN 360
                   TLLKWLDLPKAERPRFYTMYFEEPDSSGHAGGPVSARVIKALQVVDHAFGMLMEGLKQRN
161P2F10Bv.6:  301 TLLKWLDLPKAERPRFYTMYFEEPDSSGHAGGPVSARVIKALQVVDHAFGMLMEGLKQRN 360

161P2F10Bv.1:  361 LHNCVNIILLADHGMDQTYCNKMEYMTDYFPRINFFYMYEGPAPRIRAHNIPHDFFSFNS 420
                   LHNCVNIILLADHGMDQTYCNKMEYMTDYFPRINFFYMYEGPAPRIRAHNIPHDFFSFNS
161P2F10Bv.6:  361 LHNCVNIILLADHGMDQTYCNKMEYMTDYFPRINFFYMYEGPAPRIRAHNIPHDFFSFNS 420

161P2F10Bv.1:  421 EEIVRNLSCRKPDQHFKPYLTPDLPKRLHYAKNVRIDKVHLFVDQQWLAVRSKSNTNCGG 480
                   EEIVRNLSCRKPDQHFKPYLTPDLPKRLHYAKNVRIDKVHLFVDQQWLAVRSKSNTNCGG
161P2F10Bv.6:  421 EEIVRNLSCRKPDQHFKPYLTPDLPKRLHYAKNVRIDKVHLFVDQQWLAVRSKSNTNCGG 480

161P2F10Bv.1:  481 GNHGYNNEFRSMEAIFLAHGPSFKEKTEVEPFENIEVYNLMCDLLRIQPAPNNGTHGSLN 540
                   GNHGYNNEFRSMEAIFLAHGPSFKEKTEVEPFENIEVYNLMCDLLRIQPAPNNGTHGSLN
161P2F10Bv.6:  481 GNHGYNNEFRSMEAIFLAHGPSFKEKTEVEPFENIEVYNLMCDLLRIQPAPNNGTHGSLN 540
```

TABLE LIV-continued

Amino acid sequence alignment of 161P2F10Bv.1 v.1 (SEQ ID NO: 95)
and 161P2F10B v.6 (SEQ ID NO: 96)

```
161P2F10Bv.1:  541  HLLKVPFYEPSHAEEVSKFSVCGFANPLPTESLDCFCPHLQNSTQLEQVNQMLNLTQEEI  600
                    HLLKVPFYEPSHAEEVSKFSVCGFANPLPTESLDCFCPHLQNSTQLEQVNQMLNLTQEEI
161P2F10Bv.6:  541  HLLKVPFYEPSHAEEVSKFSVCGFANPLPTESLDCFCPHLQNSTQLEQVNQMLNLTQEEI  600

161P2F10Bv.1:  601  TATVKVNLPFGRPRVLQKNVDHCLLYHREYVSGFGKAMRMPMWSSYTVPQLGDTSPLPPT  660
                    TATVKVNLPFGRPRVLQKNVDHCLLYHREYVSGFGKAMRMPMWSSYTVPQLGDTSPLPPT
161P2F10Bv.6:  601  TATVKVNLPFGRPRVLQKNVDHCLLYHREYVSGFGKAMRMPMWSSYTVPQLGDTSPLPPT  660

161P2F10Bv.1:  661  VPDCLRADVRVPPSESQKCSFYLADKNITHGFLYPPASNRTSDSQYDALITSNLVPMYEE  720
                    VPDCLRADVRVPPSESQKCSFYLADKNITHGFLYPPASNRTSDSQYDALITSNLVPMYEE
161P2F10Bv.6:  661  VPDCLRADVRVPPSESQKCSFYLADKNITHGFLYPPASNRTSDSQYDALITSNLVPMYEE  720

161P2F10Bv.1:  721  FRKMWDYFHSVLLIKHATERNGVNVVSGPIFDYNYDGHFDAPDEITKHLANTDVPIPTHY  780
                    FRKMWDYFHSVLLIKHATERNGVNVVSGPIFDYNYDGHFDAPDEITKHLANTDVPIPTHY
161P2F10Bv.6:  721  FRKMWDYFHSVLLIKHATERNGVNVVSGPIFDYNYDGHFDAPDEITKHLANTDVPIPTHY  780

161P2F10Bv.1:  781  FVVLTSCKNKSHTPENCPGWLDVLPFIIPHRPTNVESCPEGKPEALWVEERFTAHIARVR  840
                    FVVLTSCKNKSHTPENCPGWLDVLPFIIPHRPTNVESCPEGKPEALWVEERFTAHIARVR
161P2F10Bv.6:  781  FVVLTSCKNKSHTPENCPGWLDVLPFIIPHRPTNVESCPEGKPEALWVEERFTAHIARVR  840

161P2F10Bv.1:  841  DVELLTGLDFYQDKVQPVSEILQLKTYLPTFETTI                           875
                    DVELLTGLDFYQDKVQPVSEILQLKTYLPTFETTI
161P2F10Bv.6:  841  DVELLTGLDFYQDKVQPVSEILQLKTYLPTFETTI                           875
```

TABLE LV

| Nucleotide sequence of transcript variant 161P2P10B v.7 | (SEQ ID NO: 97) |
|---|---|

```
ctactttatt ctgataaaac aggtctatgc agctaccagg acaatggaat ctacgttgac     60
tttagcaacg gaacaacctg ttaagaagaa cactcttaag aaatataaaa tagcttgcat    120
tacagggtct ctctcctttg ggatctcacc tcaccacaac ctctgtttcc caggctcaag    180
tgatcctcct gcctcagcct cctgagtagc ttggaccaca ggcacatgcc acaaggctca    240
gctaagtttt tgttcttctt gctttgctgg tgatcatgtc acttggatta ggcctggggc    300
ttggactcag gaaactggaa agcaaggca gctgcaggaa gaagtgcttt gatgcatcat     360
ttagaggact ggagaactgc cggtgtgatg tggcatgtaa agaccgaggt gattgctgct    420
gggattttga agacacctgt gtggaatcaa ctcgaatatg gatgtgcaat aaatttcgtt    480
gtggagagac cagattagag gccagccttt gctcttgttc agatgactgt ttgcagaaga    540
aagattgctg tgctgactat aagagtgttt gccaaggaga aacctcatgg ctggaagaaa    600
actgtgacac agcccagcag tctcagtgcc cagaagggtt tgacctgcca ccagttatct    660
tgttttctat ggatggattt agagctgaat atttatacac atgggatact ttaatgccaa    720
atatcaataa actgaaaaca tgtggaattc attcaaaata catgagagct atgtatccta    780
ccaaaacctt cccaaatcat tacaccattg tcacgggctt gtatccagag tcacatggca    840
tcattgacaa taatatgtat gatgtaaatc tcaacaagaa ttttttcactt tcttcaaagg    900
aacaaaataa tccagcctgg tggcatgggc aaccaatgtg gctgacagca atgtatcaag    960
gtttaaaagc cgctacctac ttttggcccg gatcagaagt ggctataaat ggctcctttc   1020
cttccatata catgccttac aacggaagtg tcccatttga agagaggatt tctacactgt   1080
taaaatggct ggacctgccc aaagctgaaa gacccaggtt ttataccatg tatttttgaag  1140
aacctgattc ctctggacat gcaggtggac cagtcagtgc cagagtaatt aaagccttac   1200
aggtagtaga tcatgctttt gggatgttga tggaaggcct gaagcagcgg aatttgcaca   1260
actgtgtcaa tatcatcctt ctggctgacc atggaatgga ccagacttat tgtaacaaga   1320
```

TABLE LV-continued

| Nucleotide sequence of transcript variant 161P2P10B v.7 | (SEQ ID NO: 97) |
|---|---|
| tggaatacat gactgattat tttcccagaa taaacttctt ctacatgtac gaagggcctg | 1380 |
| cccccccgcat ccgagctcat aatatacctc atgactttt tagtttaat tctgaggaaa | 1440 |
| ttgttagaaa cctcagttgc cgaaaacctg atcagcattt caagccctat ttgactcctg | 1500 |
| atttgccaaa gcgactgcac tatgccaaga acgtcagaat cgacaaagtt catctctttg | 1560 |
| tggatcaaca gtggctggct gttaggagta aatcaaatac aaattgtgga ggaggcaacc | 1620 |
| atggttataa caatgagttt aggagcatgg aggctatctt tctggcacat ggacccagtt | 1680 |
| ttaaagagaa gactgaagtt gaaccatttg aaaatattga agtctataac ctaatgtgtg | 1740 |
| atcttctacg cattcaacca gcaccaaaca atggaaccca tggtagttta aaccatcttc | 1800 |
| tgaaggtgcc tttttatgag ccatcccatg cagaggaggt gtcaaagttt tctgtttgtg | 1860 |
| gctttgctaa tccattgccc acagagtctc ttgactgttt ctgccctcac ctacaaaata | 1920 |
| gtactcagct ggaacaagtg aatcagatgc taaatctcac ccaagaagaa ataacagcaa | 1980 |
| cagtgaaagt aaatttgcca tttgggaggc ctagggtact gcagaagaac gtggaccact | 2040 |
| gtctccttta ccacagggaa tatgtcagtg gatttggaaa agctatgagg atgcccatgt | 2100 |
| ggagttcata cacagtcccc cagttgggag acacatcgcc tctgcctccc actgtcccag | 2160 |
| actgtctgcg ggctgatgtc agggttcctc cttctgagag ccaaaaatgt tccttctatt | 2220 |
| tagcagacaa gaatatcacc cacggcttcc tctatcctcc tgccagcaat agaacatcag | 2280 |
| atagccaata tgatgctta attactagca atttggtacc tatgtatgaa gaattcagaa | 2340 |
| aaatgtggga ctacttccac agtgttcttc ttataaaaca tgccacagaa agaaatggag | 2400 |
| taaatgtggt tagtggacca atatttgatt ataattatga tggccatttt gatgctccag | 2460 |
| atgaaattac caaacattta gccaacactg atgttcccat cccaacacac tactttgtgg | 2520 |
| tgctgaccag ttgtaaaaac aagagccaca caccggaaaa ctgccctggg tggctggatg | 2580 |
| tcctacccttt tatcatccct caccgaccta ccaacgtgga gagctgtcct gaaggtaaac | 2640 |
| cagaagctct ttgggttgaa gaaagattta cagctcacat tgcccgggtc cgtgatgtag | 2700 |
| aacttctcac tgggcttgac ttctatcagg ataaagtgca gcctgtctct gaaattttgc | 2760 |
| aactaaagac atatttacca acatttgaaa ccactattta acttaataat gtctacttaa | 2820 |
| tatataattt actgtataaa gtaattttgg caaaatataa gtgatttttt ctggagaatt | 2880 |
| gtaaaataaa gtttttctatt tttccttaaa aaaaaaacgg gaattccggg cttgggaggc | 2940 |
| tgaggcagga gactcgcttg aacccgggag gcagaggttc cagtgagcca agattgcgcc | 3000 |
| attgcactcc agagcctggg tgacagagca agactacatc tcaaaaaata aataaataaa | 3060 |
| ataaaagtaa caataaaaat aaaaagaaca gcagagagaa tgagcaagga gaaatgtcac | 3120 |
| aaactattgc aaaatactgt tacactgggt tggctctcca agaagatact ggaatctctt | 3180 |
| cagccatttg cttttcagaa gtagaaacca gcaaaccacc tctaagcgga gaacatacga | 3240 |
| ttctttatta agtagctctg gggaaggaaa gaataaaagt tgatagctcc ctgattggga | 3300 |
| aaaaatgcac aattaataaa gaatgaagat gaaagaaagc atgcttatgt tgtaacacaa | 3360 |
| aaaaaattca caaacgttgg tggaaggaaa acagtataga aaacattact ttaactaaaa | 3420 |
| gctggaaaaa ttttcagttg ggatgcgact gacaaaaaga acgggatttc caggcataaa | 3480 |
| gttggcgtga gctacagagg gcaccatgtg gctcagtgga agaccttca agattcaaag | 3540 |
| ttccatttga cagagcaaag gcacttcgca aggagaaggg tttaaattat gggtccaaaa | 3600 |
| gccaagtggt aaagcgagca atttgcagca taactgcttc tcctagacag ggctgagtgg | 3660 |

TABLE LV-continued

| Nucleotide sequence of transcript variant 161P2P10B v.7 | (SEQ ID NO: 97) |
|---|---|

```
gcaaaatacg acagtacaca cagtgactat tagccactgc cagaaacagg ctgaacagcc    3720
ctgggagaca agggaaggca ggtggtggga gttgttcatg gagagaaagg agagttttag    3780
aaccagcaca tccactggag atgctgggcc accagacccc tcccagtcaa taaagtctgg    3840
tgcctcattt gatctcagcc tcatcatgac cctggagaga ccctgatacc atctgccagt    3900
ccccgacagc ttaggcactc cttgccatca acctgacccc ccgagtggtt ctccaggctc    3960
cctgccccac ccattcaggc cggaattc                                       3988
```

TABLE LVI

Nucleotide sequence alignment of 161P2F10B v.1 (SEQ ID NO: 98) and
161P2F10B v.7 (SEQ ID NO: 99)

Score = 233 bits (121), Expect = 2e-57 Identities = 121/121 (100%) Strand = Plus/Plus

```
v.1:   1 ctactttattctgataaaacaggtctatgcagctaccaggacaatggaatctacgttgac    60
         ||||||||||||||||||||||||||||||||||||||||||||||||||||||||||||
v.7:   1 ctactttattctgataaaacaggtctatgcagctaccaggacaatggaatctacgttgac    60 v.1:  61 tttagcaacggaacaacctgttaagaagaacactattaagaaatataaaatagcttgcat   120
         ||||||||||||||||||||||||||||||||||||||||||||||||||||||||||||
v.7:  61 tttagcaacggaacaacctgttaagaagaacactattaagaaatataaaatagcttgcat   120 v.1: 121 t                                                              121
         |
v.7: 121 t                                                              121
```

Score = 7189 bits (3739), Expect = 0.0 Identities = 3739/3739 (100%) Strand = Plus/Plus

```
v.1: 120 ttgttcttcttgctttgctggtgatcatgtcacttggattaggcctggggcttggactca   179
         ||||||||||||||||||||||||||||||||||||||||||||||||||||||||||||
v.7: 250 ttgttcttcttgctttgctggtgatcatgtcacttggattaggcctggggcttggactca   309 v.1: 180 ggaaactggaaaagcaaggcagctgcaggaagaagtgctttgatgcatcatttagaggac   239
         ||||||||||||||||||||||||||||||||||||||||||||||||||||||||||||
v.7: 310 ggaaactggaaaagcaaggcagctgcaggaagaagtgctttgatgcatcatttagaggac   369 v.1: 240 tggagaactgccggtgtgatgtggcatgtaaagaccgaggtgattgctgctgggattttg   299
         ||||||||||||||||||||||||||||||||||||||||||||||||||||||||||||
v.7: 370 tggagaactgccggtgtgatgtggcatgtaaagaccgaggtgattgctgctgggattttg   429 v.1: 300 aagacacctgtgtggaatcaactcgaatatggatgtgcaataaatttcgttgtggagaga   359
         ||||||||||||||||||||||||||||||||||||||||||||||||||||||||||||
v.7: 430 aagacacctgtgtggaatcaactcgaatatggatgtgcaataaatttcgttgtggagaga   489 v.1: 360 ccagattagaggccagcctttgctcttgttcagatgactgtttgcagaagaaagattgct   419
         ||||||||||||||||||||||||||||||||||||||||||||||||||||||||||||
v.7: 490 ccagattagaggccagcctttgctcttgttcagatgactgtttgcagaagaaagattgct   549 v.1: 420 gtgctgactataagagtgtttgccaaggagaaacctcatggctggaagaaaactgtgaca   479
         ||||||||||||||||||||||||||||||||||||||||||||||||||||||||||||
v.7: 550 gtgctgactataagagtgtttgccaaggagaaacctcatggctggaagaaaactgtgaca   609 v.1: 480 cagcccagcagtctcagtgcccagaagggtttgacctgccaccagttatcttgtttttcta   539
         ||||||||||||||||||||||||||||||||||||||||||||||||||||||||||||
v.7: 610 cagcccagcagtctcagtgcccagaagggtttgacctgccaccagttatcttgtttttcta   669 v.1: 540 tggatggatttagagctgaatatttatacacatgggatactttaatgccaaatatcaata   599
         ||||||||||||||||||||||||||||||||||||||||||||||||||||||||||||
v.7: 670 tggatggatttagagctgaatatttatacacatgggatactttaatgccaaatatcaata   729 v.1: 600 aactgaaaacatgtggaattcattcaaaatacatgagagctatgtatcctaccaaaacct   659
         ||||||||||||||||||||||||||||||||||||||||||||||||||||||||||||
v.7: 730 aactgaaaacatgtggaattcattcaaaatacatgagagctatgtatcctaccaaaacct   789 v.1: 660 tcccaaatcattacaccattgtcacgggcttgtatccagagtcacatggcatcattgaca   719
         ||||||||||||||||||||||||||||||||||||||||||||||||||||||||||||
v.7: 790 tcccaaatcattacaccattgtcacgggcttgtatccagagtcacatggcatcattgaca   849
```

TABLE LVI-continued

Nucleotide sequence alignment of 161P2F10B v.1 (SEQ ID NO: 98) and 161P2F10B v.7 (SEQ ID NO: 99)

```
v.1:  720 ataatatgtatgatgtaaatctcaacaagaattttttcactttcttcaaaggaacaaaata  779
          ||||||||||||||||||||||||||||||||||||||||||||||||||||||||||||
v.7:  850 ataatatgtatgatgtaaatctcaacaagaattttttcactttcttcaaaggaacaaaata  909 v.1:  780 atccagcctggtggcatgggcaaccaatgtggctgacagcaatgtatcaaggtttaaaag   839
          ||||||||||||||||||||||||||||||||||||||||||||||||||||||||||||
v.7:  910 atccagcctggtggcatgggcaaccaatgtggctgacagcaatgtatcaaggtttaaaag   969 v.1:  840 ccgctacctacttttggcccggatcagaagtggctataaatggctcctttccttccatat   899
          ||||||||||||||||||||||||||||||||||||||||||||||||||||||||||||
v.7:  970 ccgctacctacttttggcccggatcagaagtggctataaatggctcctttccttccatat  1029 v.1:  900 acatgccttacaacggaagtgtcccatttgaagagaggatttctacactgttaaaatggc   959
          ||||||||||||||||||||||||||||||||||||||||||||||||||||||||||||
v.7: 1030 acatgccttacaacggaagtgtcccatttgaagagaggatttctacactgttaaaatggc  1089 v.1:  960 tggacctgcccaaagctgaaagacccaggttttataccatgtattttgaagaacctgatt  1019
          ||||||||||||||||||||||||||||||||||||||||||||||||||||||||||||
v.7: 1090 tggacctgcccaaagctgaaagacccaggttttataccatgtattttgaagaacctgatt  1149 v.1: 1020 cctctggacatgcaggtggaccagtcagtgccagagtaattaaagccttacaggtagtag  1079
          ||||||||||||||||||||||||||||||||||||||||||||||||||||||||||||
v.7: 1150 cctctggacatgcaggtggaccagtcagtgccagagtaattaaagccttacaggtagtag  1209 v.1: 1080 atcatgcttttgggatgttgatggaaggcctgaagcagcggaatttgcacaactgtgtca  1139
          ||||||||||||||||||||||||||||||||||||||||||||||||||||||||||||
v.7: 1210 atcatgcttttgggatgttgatggaaggcctgaagcagcggaatttgcacaactgtgtca  1269 v.1: 1140 atatcatccttctggctgaccatggaatggaccagacttattgtaacaagatggaataca  1199
          ||||||||||||||||||||||||||||||||||||||||||||||||||||||||||||
v.7: 1270 atatcatccttctggctgaccatggaatggaccagacttattgtaacaagatggaataca  1329 v.1: 1200 tgactgattattttcccagaataaacttcttctacatgtacgaagggcctgccccccgca  1259
          ||||||||||||||||||||||||||||||||||||||||||||||||||||||||||||
v.7: 1330 tgactgattattttcccagaataaacttcttctacatgtacgaagggcctgccccccgca  1389 v.1: 1260 tccgagctcataatatacctcatgacttttttagttttaattctgaggaaattgttagaa  1319
          ||||||||||||||||||||||||||||||||||||||||||||||||||||||||||||
v.7: 1390 tccgagctcataatatacctcatgacttttttagttttaattctgaggaaattgttagaa  1449 v.1: 1320 acctcagttgccgaaaacctgatcagcatttcaagccctatttgactcctgatttgccaa  1379
          ||||||||||||||||||||||||||||||||||||||||||||||||||||||||||||
v.7: 1450 acctcagttgccgaaaacctgatcagcatttcaagccctatttgactcctgatttgccaa  1509 v.1: 1380 agcgactgcactatgccaagaacgtcagaatcgacaaagttcatctctttgtggatcaac  1439
          ||||||||||||||||||||||||||||||||||||||||||||||||||||||||||||
v.7: 1510 agcgactgcactatgccaagaacgtcagaatcgacaaagttcatctctttgtggatcaac  1569 v.1: 1440 agtggctggctgttaggagtaaatcaaatacaaattgtggaggaggcaaccatggttata  1499
          ||||||||||||||||||||||||||||||||||||||||||||||||||||||||||||
v.7: 1570 agtggctggctgttaggagtaaatcaaatacaaattgtggaggaggcaaccatggttata  1629 v.1: 1500 acaatgagtttaggagcatggaggctatctttctggcacatggacccagtttttaaagaga  1559
          ||||||||||||||||||||||||||||||||||||||||||||||||||||||||||||
v.7: 1630 acaatgagtttaggagcatggaggctatctttctggcacatggacccagtttttaaagaga  1689 v.1: 1560 agactgaagttgaaccatttgaaaatattgaagtctataacctaatgtgtgatcttctac  1619
          ||||||||||||||||||||||||||||||||||||||||||||||||||||||||||||
v.7: 1690 agactgaagttgaaccatttgaaaatattgaagtctataacctaatgtgtgatcttctac  1749 v.1: 1620 gcattcaaccagcaccaaacaatggaacccatggtagtttaaaccatcttctgaaggtgc  1679
          ||||||||||||||||||||||||||||||||||||||||||||||||||||||||||||
v.7: 1750 gcattcaaccagcaccaaacaatggaacccatggtagtttaaaccatcttctgaaggtgc  1809 v.1: 1680 cttttttatgagccatcccatgcagaggaggtgtcaaagttttctgtttgtggctttgcta  1739
          ||||||||||||||||||||||||||||||||||||||||||||||||||||||||||||
v.7: 1810 cttttttatgagccatcccatgcagaggaggtgtcaaagttttctgtttgtggctttgcta  1869 v.1: 1740 atccattgcccacagagtctcttgactgtttctgccctcacctacaaaatagtactcagc  1799
          ||||||||||||||||||||||||||||||||||||||||||||||||||||||||||||
v.7: 1870 atccattgcccacagagtctcttgactgtttctgccctcacctacaaaatagtactcagc  1929
```

TABLE LVI-continued

Nucleotide sequence alignment of 161P2F10B v.1 (SEQ ID NO: 98) and 161P2F10B v.7 (SEQ ID NO: 99)

```
v.1: 1800  tggaacaagtgaatcagatgctaaatctcacccaagaagaaataacagcaacagtgaaag  1859
           ||||||||||||||||||||||||||||||||||||||||||||||||||||||||||||
v.7: 1930  tggaacaagtgaatcagatgctaaatctcacccaagaagaaataacagcaacagtgaaag  1989 v.1: 1860  taaatttgccatttgggaggcctagggtactgcagaagaacgtggaccactgtctccttt  1919
           ||||||||||||||||||||||||||||||||||||||||||||||||||||||||||||
v.7: 1990  taaatttgccatttgggaggcctagggtactgcagaagaacgtggaccactgtctccttt  2049 v.1: 1920  accacagggaatatgtcagtggatttggaaaagctatgaggatgcccatgtggagttcat  1979
           ||||||||||||||||||||||||||||||||||||||||||||||||||||||||||||
v.7: 2050  accacagggaatatgtcagtggatttggaaaagctatgaggatgcccatgtggagttcat  2109 v.1: 1980  acacagtcccccagttgggagacacatcgcctctgcctcccactgtcccagactgtctgc  2039
           ||||||||||||||||||||||||||||||||||||||||||||||||||||||||||||
v.7: 2110  acacagtcccccagttgggagacacatcgcctctgcctcccactgtcccagactgtctgc  2169 v.1: 2040  gggctgatgtcagggttcctccttctgagagccaaaaatgttccttctatttagcagaca  2099
           ||||||||||||||||||||||||||||||||||||||||||||||||||||||||||||
v.7: 2170  gggctgatgtcagggttcctccttctgagagccaaaaatgttccttctatttagcagaca  2229 v.1: 2100  agaatatcacccacggcttcctctatcctcctgccagcaatagaacatcagatagccaat  2159
           ||||||||||||||||||||||||||||||||||||||||||||||||||||||||||||
v.7: 2230  agaatatcacccacggcttcctctatcctcctgccagcaatagaacatcagatagccaat  2289 v.1: 2160  atgatgctttaattactagcaatttggtacctatgtatgaagaattcagaaaaatgtggg  2219
           ||||||||||||||||||||||||||||||||||||||||||||||||||||||||||||
v.7: 2290  atgatgctttaattactagcaatttggtacctatgtatgaagaattcagaaaaatgtggg  2349 v.1: 2220  actacttccacagtgttcttcttataaaacatgccacagaaagaaatggagtaaatgtgg  2279
           ||||||||||||||||||||||||||||||||||||||||||||||||||||||||||||
v.7: 2350  actacttccacagtgttcttcttataaaacatgccacagaaagaaatggagtaaatgtgg  2409 v.1: 2280  ttagtggaccaatatttgattataattatgatggccattttgatgctccagatgaaatta  2339
           ||||||||||||||||||||||||||||||||||||||||||||||||||||||||||||
v.7: 2410  ttagtggaccaatatttgattataattatgatggccattttgatgctccagatgaaatta  2469 v.1: 2340  ccaaacatttagccaacactgatgttcccatcccaacacactactttgtggtgctgacca  2399
           ||||||||||||||||||||||||||||||||||||||||||||||||||||||||||||
v.7: 2470  ccaaacatttagccaacactgatgttcccatcccaacacactactttgtggtgctgacca  2529 v.1: 2400  gttgtaaaaacaagagccacacaccggaaaactgccctgggtggctggatgtcctaccct  2459
           ||||||||||||||||||||||||||||||||||||||||||||||||||||||||||||
v.7: 2530  gttgtaaaaacaagagccacacaccggaaaactgccctgggtggctggatgtcctaccct  2589 v.1: 2460  ttatcatccctcaccgacctaccaacgtggagagctgtcctgaaggtaaaccagaagctc  2519
           ||||||||||||||||||||||||||||||||||||||||||||||||||||||||||||
v.7: 2590  ttatcatccctcaccgacctaccaacgtggagagctgtcctgaaggtaaaccagaagctc  2649 v.1: 2520  tttgggttgaagaaagatttacagctcacattgcccgggtccgtgatgtagaacttctca  2579
           ||||||||||||||||||||||||||||||||||||||||||||||||||||||||||||
v.7: 2650  tttgggttgaagaaagatttacagctcacattgcccgggtccgtgatgtagaacttctca  2709 v.1: 2580  ctgggcttgacttctatcaggataaagtgcagcctgtctctgaaattttgcaactaaaga  2639
           ||||||||||||||||||||||||||||||||||||||||||||||||||||||||||||
v.7: 2710  ctgggcttgacttctatcaggataaagtgcagcctgtctctgaaattttgcaactaaaga  2769 v.1: 2640  catatttaccaacatttgaaaccactatttaacttaataatgtctacttaatatataatt  2699
           ||||||||||||||||||||||||||||||||||||||||||||||||||||||||||||
v.7: 2770  catatttaccaacatttgaaaccactatttaacttaataatgtctacttaatatataatt  2829 v.1: 2700  tactgtataaagtaattttggcaaaatataagtgatttttctggagaattgtaaaataa   2759
           ||||||||||||||||||||||||||||||||||||||||||||||||||||||||||||
v.7: 2830  tactgtataaagtaattttggcaaaatataagtgatttttctggagaattgtaaaataa   2889 v.1: 2760  agttttctattttttccttaaaaaaaaaaccggaattccgggcttgggaggctgaggcagg  2819
           ||||||||||||||||||||||||||||||||||||||||||||||||||||||||||||
v.7: 2890  agttttctattttttccttaaaaaaaaaaccggaattccgggcttgggaggctgaggcagg  2949 v.1: 2820  agactcgcttgaacccgggaggcagaggttgcagtgagccaagattgcgccattgcactc  2879
           ||||||||||||||||||||||||||||||||||||||||||||||||||||||||||||
v.7: 2950  agactcgcttgaacccgggaggcagaggttgcagtgagccaagattgcgccattgcactc  3009
```

TABLE LVI-continued

Nucleotide sequence alignment of 161P2F10B v.1 (SEQ ID NO: 98) and 161P2F10B v.7 (SEQ ID NO: 99)

```
v.1: 2880 cagagcctgggtgacagagcaagactacatctcaaaaaataaataaataaaataaaagta 2939
          ||||||||||||||||||||||||||||||||||||||||||||||||||||||||||||
v.7: 3010 cagagcctgggtgacagagcaagactacatctcaaaaaataaataaataaaataaaagta 3069 v.1: 2940 acaataaaaataaaaagaacagcagagagaatgagcaaggagaaatgtcacaaactattg 2999
          ||||||||||||||||||||||||||||||||||||||||||||||||||||||||||||
v.7: 3070 acaataaaaataaaaagaacagcagagagaatgagcaaggagaaatgtcacaaactattg 3129 v.1: 3000 caaaatactgttacactggg ttggctctccaagaagatactggaatctcttcagccattt 3059
          ||||||||||||||||||||||||||||||||||||||||||||||||||||||||||||
v.7: 3130 caaaatactgttacactgggttggctctccaagaagatactggaatctcttcagccattt 3189 v.1: 3060 gcttttcagaagtagaaaccagcaaaccacctctaagcggagaacatacgattctttatt 3119
          ||||||||||||||||||||||||||||||||||||||||||||||||||||||||||||
v.7: 3190 gcttttcagaagtagaaaccagcaaaccacctctaagcggagaacatacgattctttatt 3249 v.1: 3120 aagtagctctggggaaggaaagaataaaagttgatagctccctgattgggaaaaaatgca 3179
          ||||||||||||||||||||||||||||||||||||||||||||||||||||||||||||
v.7: 3250 aagtagctctggggaaggaaagaataaaagttgatagctccctgattgggaaaaaatgca 3309 v.1: 3180 caattaataaagaatgaagatgaaagaaagcatgcttatgttgtaacacaaaaaaaattc 3239
          ||||||||||||||||||||||||||||||||||||||||||||||||||||||||||||
v.7: 3310 caattaataaagaatgaagatgaaagaaagcatgcttatgttgtaacacaaaaaaaattc 3369 v.1: 3240 acaaacgttggtggaaggaaaacagtatagaaaacattactttaactaaaagctggaaaa 3299
          ||||||||||||||||||||||||||||||||||||||||||||||||||||||||||||
v.7: 3370 acaaacgttggtggaaggaaaacagtatagaaaacattactttaactaaaagctggaaaa 3429 v.1: 3300 attttcagttgggatgcgactgacaaaaagaacgggatttccaggcataaagttggcgtg 3359
          ||||||||||||||||||||||||||||||||||||||||||||||||||||||||||||
v.7: 3430 attttcagttgggatgcgactgacaaaaagaacgggatttccaggcataaagttggcgtg 3489 v.1: 3360 agctacagagggcaccatgtggctcagtggaagacccttcaagattcaaagttccatttg 3419
          ||||||||||||||||||||||||||||||||||||||||||||||||||||||||||||
v.7: 3490 agctacagagggcaccatgtggctcagtggaagacccttcaagattcaaagttccatttg 3549 v.1: 3420 acagagcaaaggcacttcgcaaggagaagggtttaaattatgggtccaaaagccaagtgg 3479
          ||||||||||||||||||||||||||||||||||||||||||||||||||||||||||||
v.7: 3550 acagagcaaaggcacttcgcaaggagaagggtttaaattatgggtccaaaagccaagtgg 3609 v.1: 3480 taaagcgagcaatttgcagcataactgcttctcctagacagggctgagtgggcaaaatac 3539
          ||||||||||||||||||||||||||||||||||||||||||||||||||||||||||||
v.7: 3610 taaagcgagcaatttgcagcataactgcttctcctagacagggctgagtgggcaaaatac 3669 v.1: 3540 gacagtacacacagtgactattagccactgccagaaacaggctgaacagccctgggagac 3599
          ||||||||||||||||||||||||||||||||||||||||||||||||||||||||||||
v.7: 3670 gacagtacacacagtgactattagccactgccagaaacaggctgaacagccctgggagac 3729 v.1: 3600 aagggaaggcaggtggtgggagttgttcatggagagaaaggagagttttagaaccagcac 3659
          ||||||||||||||||||||||||||||||||||||||||||||||||||||||||||||
v.7: 3730 aagggaaggcaggtggtgggagttgttcatggagagaaaggagagttttagaaccagcac 3789 v.1: 3660 atccactggagatgctgggccaccagacccctcccagtcaataaagtctggtgcctcatt 3719
          ||||||||||||||||||||||||||||||||||||||||||||||||||||||||||||
v.7: 3790 atccactggagatgctgggccaccagacccctcccagtcaataaagtctggtgcctcatt 3849 v.1: 3720 tgatctcagcctcatcatgaccctggagagaccctgataccatctgccagtccccgacag 3779
          ||||||||||||||||||||||||||||||||||||||||||||||||||||||||||||
v.7: 3850 tgatctcagcctcatcatgaccctggagagaccctgataccatctgccagtccccgacag 3909 v.1: 3780 cttaggcactccttgccatcaacctgaccccccgagtggttctccaggctccctgccca 3839
          ||||||||||||||||||||||||||||||||||||||||||||||||||||||||||||
v.7: 3910 cttaggcactccttgccatcaacctgaccccccgagtggttctccaggctccctgccca 3969 v.1: 3840 cccattcaggccggaattc                                          3858
          |||||||||||||||||||
v.7: 3970 cccattcaggccggaattc                                          3988
```

TABLE LVII

Peptide sequences of protein coded by 161P2F10B v.7      (SEQ ID NO: 100)

| | | | | | |
|---|---|---|---|---|---|
| MSLGLGLGLG | LRKLEKQGSC | RKKCFDASFR | GLENCRCDVA | CKDRGDCCWD | FEDTCVESTR | 60 |
| IWMCNKFRCG | ETRLEASLCS | CSDDCLQRKD | CCADYKSVCQ | GETSWLEENC | DTAQQSQCPE | 120 |
| GFDLPPVILF | SMDGFRAEYL | YTWDTLMPNI | NKLKTCGIHS | KYMRAMYPTK | TFPNHYTIVT | 180 |
| GLYPESHGII | DNNMYDVNLN | KNFSLSSKEQ | NNPAWWHGQP | MWLTAMYQGL | KAATYFWPGS | 240 |
| EVAINGSFPS | IYMPYNGSVP | FEERISTLLK | WLDLPKAERP | RFYTMFFEEP | DSSGHAGGPV | 300 |
| SARVIKALQV | VDHAFGMLME | GLKQRNLHNC | VNIILLADHG | MDQTYCNKME | YMTDYFPRIN | 360 |
| FFYMYEGPAP | RVRAHNIPHD | FFSFNSEEIV | RNLSCRKPDQ | HFKPYLTPDL | PKRLHYAKNV | 420 |
| RIDKVHLFVD | QQWLAVRSKS | NTNCGGGNHG | YNNEFRSMEA | IFLAHGPSFK | EKTEVEPFEN | 480 |
| IEVYNLMCDL | LRIQPAPNNG | THGSLNHLLK | VPFYEPSHAE | EVSKFSVCGF | ANPLPTESLD | 540 |
| CFCPHLQNST | QLEQVNQMLN | LTQEEITATV | KVNLPFGRPR | VLQKNVDHCL | LYHREYVSGF | 600 |
| GKAMRMPMWS | SYTVPQLGDT | SPLPPTVPDC | LRADVRVPPS | ESQKCSFYLA | DKNITHGFLY | 660 |
| PPASNRTSDS | QYDALITSNL | VPMYEEFRKM | WDYFHSVLLI | KHATERNGVN | VVSGPIFDYN | 720 |
| YDGHFDAPDE | ITKHLANTDV | PIPTHYFVVL | TSCKNKSHTP | ENCPGWLDVL | PFIIPHRPTN | 780 |
| VESCPEGKPE | ALWVEERFTA | HIARVRDVEL | LTGLDFYQDK | VQPVSEILQL | KTYLPTFETT | 840 |
| I | | | | | | 841 |

TABLE LVIII

Amino acid sequence alignment of 161P2F10Bv.1. v.1 (SEQ ID NO: 101)
and 161P2F10B v.7 (SEQ ID NO: 102)

Score = 1789 bits (4634), Expect = 0.0 Identities = 838/841 (99%),
Positives = 841/841 (99%)

```
161P2F10Bv.1:  35 MSLGLGLGLGLRKLEKQGSCRKKCFDASFRGLENCRCDVACKDRGDCCWDFEDTCVESTR  94
                  MSLGLGLGLGLRKLEKQGSCRKKCFDASFRGLENCRCDVACKDRGDCCWDFEDTCVESTR
161P2F10Bv.7:   1 MSLGLGLGLGLRKLEKQGSCRKKCFDASFRGLENCRCDVACKDRGDCCWDFEDTCVESTR  60

161P2F10Bv.1:  95 IWMCNKFRCGETRLEASLCSCSDDCLQKKDCCADYKSVCQGETSWLEENCDTAQQSQCPE 154
                  IWMCNKFRCGETRLEASLCSCSDDCLQKKDCCADYKSVCQGETSWLEENCDTAQQSQCPE
161P2F10Bv.7:  61 IWMCNKFRCGETRLEASLCSCSDDCLQKKDCCADYKSVCQGETSWLEENCDTAQQSQCPE 120

161P2F10Bv.1: 155 GFDLPPVILFSMDGFRAEYLYTWDTLMPNINKLKTCGIHSKYMRAMYPTKTFPNHYTIVT 214
                  GFDLPPVILFSMDGFRAEYLYTWDTLMPNINKLKTCGIHSKYMRAMYPTKTFPNHYTIVT
161P2F10Bv.7: 121 GFDLPPVILFSMDGFRAEYLYTWDTLMPNINKLKTCGIHSKYMRAMYPTKTFPNHYTIVT 180

161P2F10Bv.1: 215 GLYPESHGIIDNNMYDVNLNKNFSLSSKEQNNPAWWHGQPMWLTAMYQGLKAATYFWPGS 274
                  GLYPESHGIIDNNMYDVNLNKNFSLSSKEQNNPAWWHGQPMWLTAMYQGLKAATYFWPGS
161P2F10Bv.7: 181 GLYPESHGIIDNNMYDVNLNKNFSLSSKEQNNPAWWHGQPMWLTAMYQGLKAATYFWPGS 240

161P2F10Bv.1: 275 EVAINGSFPSIYMPYNGSVPFEERISTLLKWLDLPKAERPRFYTMYFEEPDSSGHAGGPV 334
                  EVAINGSFPSIYMPYNGSVPFEERISTLLKWLDLPKAERPRFYTMYFEEPDSSGHAGGPV
161P2F10Bv.7: 241 EVAINGSFPSIYMPYNGSVPFEERISTLLKWLDLPKAERPRFYTMYFEEPDSSGHAGGPV 300

161P2F10Bv.1: 335 SARVIKALQVVDHAFGMLMEGLKQRNLHNCVNIILLADHGMDQTYCNKMEYMTDYFPRIN 394
                  SARVIKALQVVDHAFGMLMEGLKQRNLHNCVNIILLADHGMDQTYCNKMEYMTDYFPRIN
161P2F10Bv.7: 301 SARVIKALQVVDHAFGMLMEGLKQRNLHNCVNIILLADHGMDQTYCNKMEYMTDYFPRIN 360

161P2F10Bv.1: 395 FFYMYEGPAPRIRAHNIPHDFFSFNSEEIVRNLSCRKPDQHFKPYLTPDLPKRLHYAKNV 454
                  FFYMYEGPAPRIRAHNIPHDFFSFNSEEIVRNLSCRKPDQHFKPYLTPDLPKRLHYAKNV
161P2F10Bv.7: 361 FFYMYEGPAPRIRAHNIPHDFFSFNSEEIVRNLSCRKPDQHFKPYLTPDLPKRLHYAKNV 420

161P2F10Bv.1: 455 RIDKVHLFVDQQWLAVRSKSNTNCGGGNHGYNNEFRSMEAIFLAHGPSFKEKTEVEPFEN 514
                  RIDKVHLFVDQQWLAVRSKSNTNCGGGNHGYNNEFRSMEAIFLAHGPSFKEKTEVEPFEN
161P2F10Bv.7: 421 RIDKVHLFVDQQWLAVRSKSNTNCGGGNHGYNNEFRSMEAIFLAHGPSFKEKTEVEPFEN 480

161P2F10Bv.1: 515 IEVYNLMCDLLRIQPAPNNGTHGSLNHLLFVPFYEPSHAEEVSKFSVCGFANPLPTESLD 574
                  IEVYNLMCDLLRIQPAPNNGTHGSLNHLLFVPFYEPSHAEEVSKFSVCGFANPLPTESLD
161P2F10Bv.7: 481 IEVYNLMCDLLRIQPAPNNGTHGSLNHLLFVPFYEPSHAEEVSKFSVCGFANPLPTESLD 540
```

TABLE LVIII-continued

Amino acid sequence alignment of 161P2F10Bv.1. v.1 (SEQ ID NO: 101)
and 161P2F10B v.7 (SEQ ID NO: 102)

```
161P2F10Bv.1:  575  CFCPHLQNSTQLEQVNQMLNLTQEEITATVKVNLPFGRPRVLQKNVDHCLLYHREYVSGF  634
                    CFCPHLQNSTQLEQVNQMLNLTQEEITATVKVNLPFGRPRVLQKNVDHCLLYHREYVSGF
161P2F10Bv.7:  541  CFCPHLQNSTQLEQVNQMLNLTQEEITATVKVNLPFGRPRVLQKNVDHCLLYHREYVSGF  600

161P2F10Bv.1:  635  GKAMRMPMWSSYTVPQLGDTSPLPPTVPDCLRADVRVPPSESQKCSFYLADKNITHGFLY  694
                    GKAMRMPMWSSYTVPQLGDTSPLPPTVPDCLRADVRVPPSESQKCSFYLADKNITHGFLY
161P2F10Bv.7:  601  GKAMRMPMWSSYTVPQLGDTSPLPPTVPDCLRADVRVPPSESQKCSFYLADKNITHGFLY  660

161P2F10Bv.1:  695  PPASNRTSDSQYDALITSNLVPMYEEFRKMWDYFHSVLLIKHATERNGVNVVSGPIFDYN  754
                    PPASNRTSDSQYDALITSNLVPMYEEFRKMWDYFHSVLLIKHATERNGVNVVSGPIFDYN
161P2F10Bv.7:  661  PPASNRTSDSQYDALITSNLVPMYEEFRKMWDYFHSVLLIKHATERNGVNVVSGPIFDYN  720

161P2F10Bv.1:  755  YDGHFDAPDEITKHLANTDVPIPTHYFVVLTSCKNKSHTPENCPGWLDVLPFIIPHRPTN  814
                    YDGHFDAPDEITKHLANTDVPIPTHYFVVLTSCKNKSHTPENCPGWLDVLPFIIPHRPTN
161P2F10Bv.7:  721  YDGHFDAPDEITKHLANTDVPIPTHYFVVLTSCKNKSHTPENCPGWLDVLPFIIPHRPTN  780

161P2F10Bv.1:  815  VESCPEGKPEALWVEERFTAHIARVRDVELLTGLDFYQDKVQPVSEILQLKTYLPTFETT  874
                    VESCPEGKPEALWVEERFTAHIARVRDVELLTGLDFYQDKVQPVSEILQLKTYLPTFETT
161P2F10Bv.7:  781  VESCPEGKPEALWVEERFTAHIARVRDVELLTGLDFYQDKVQPVSEILQLKTYLPTFETT  840

161P2F10Bv.1:  875  I                                                             875
                    I
161P2F10Bv.7:  841  I                                                             841
```

TABLE LIX

161P2F10B Expression in Kidney Cancer

| | Clear cell | Papillary | Chromophobe | Transitional | Oncocytoma |
|---|---|---|---|---|---|
| RNA analysis: | 33/34 (97%) | 16/19 (84%) | 2/3 (67%) | 3/7 (42%) | 0/3 (0%) |
| Protein analysis: | 12/12 (100%) | 5/5 (100%) | 1/3 (33%) | 0/3 (0%) | 0/2 (0%) |

TABLE LX

161P2F10B protein expression in normal tissues

| TISSUE | FREQUENCY |
|---|---|
| Kidney | 5/5 |
| Prostate | 4/8 |
| Bladder | 1/4* |
| Colon | 2/5* |
| Lung | 1/4* |
| Brain | 0/1 |
| Breast | 0/2 |
| Heart | 0/1 |
| Liver | 0/3 |
| Ovary | 0/1 |
| Pancreas | 0/2 |
| Placenta | 0/1 |
| Skin | 0/1 |
| Spleen | 0/1 |
| Testis | 0/4 |
| Thymus | 0/1 |
| Uterus | 0/1 |

The invention claimed is:

1. A method of inhibiting the growth of a cancer cell that expresses the protein of SEQ ID NO: 3, the method comprising:
   administering to the cancer cell a composition whereby the growth of the cancer cell is inhibited, wherein the composition comprises an antibody or antigen binding fragment thereof that specifically binds to the protein, and wherein the antibody or the antigen binding fragment thereof is conjugated to an agent selected from the group consisting of a radioactive isotope, a chemotherapeutic agent and a toxin.

2. The method of claim 1, wherein the cancer cell is a cell from a tissue selected from the group consisting of kidney, pancreatic, prostate, colon, lung, breast, and ovarian.

3. The method of claim 1, wherein the antibody is a monoclonal antibody or an antigen binding fragment thereof.

4. The method of claim 3, wherein the antigen binding fragment is an Fab, F(ab')2, Fv or sFv fragment.

5. The method of claim 1, wherein the radioactive isotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

6. The method of claim 1, wherein the chemotherapeutic agent is selected from the group consisting of taxol, actinomycin, mitomycin, etoposide, tenoposide, vincristine, vinbiastine, colchicine, gelonin, and calicheamicin.

7. The method of claim 1, wherein the toxin is selected from the group consisting of diphtheria toxin, enomycin, phenomycin, *Pseudomonas exotoxin* (PE) A, PE40, abrin, abrin A chain, mitogellin, modeccin A chain, and alpha-sarcin.

8. The method of claim 3, wherein the monoclonal antibody is secreted by the hybridoma entitled X41(3)15 (Patent Deposit Designation No. PTA-4791).

9. The method of claim 3, wherein the monoclonal antibody is secreted by the hybridoma entitled X41(3)37 (Patent Deposit Designation No. PTA-4791).

10. The method of claim 3, wherein the monoclonal antibody is secreted by the hybridoma entitled X41(4)6 (Patent Deposit Designation No. PTA-4794).

11. The method of claim 3, wherein the monoclonal antibody is secreted by the hybridoma entitled X41(3)17 (Patent Deposit Designation No. PTA-4792).

12. The method of claim 3, wherein the monoclonal antibody is secreted by the hybridoma entitled X41(3)50 (Patent Deposit Designation No. PTA-4793).

13. The method of claim 3, wherein the monoclonal antibody is secreted by the hybridoma entitled X41(3)29 (Patent Deposit Designation No. PTA-4791).

* * * * *

SEQUENCE LISTING

```
<160> NUMBER OF SEQ ID NOS: 103

<210> SEQ ID NO 1
<211> LENGTH: 182
<212> TYPE: DNA
<213> ORGANISM: Homo Sapiens
<220> FEATURE:
<221> NAME/KEY: misc_feature
<222> LOCATION: 19
<223> OTHER INFORMATION: n = A,T,C or G

<400> SEQUENCE: 1
gatcacacat taggttatng acttcaatat tttcaaatgg ttcaacttca gtcttctctt     60
```

```
taaaactggg tccatgtgcc aagaaagata gcctccatgc tcctaaactc attgttataa      120
ccatggttgc ctcctccaca atttgtattt gatttactcc taacagccag ccactgttga      180
tc                                                                     182

<210> SEQ ID NO 2
<211> LENGTH: 3858
<212> TYPE: DNA
<213> ORGANISM: Homo Sapiens
<220> FEATURE:
<221> NAME/KEY: CDS
<222> LOCATION: (44)...(2671)

<400> SEQUENCE: 2
ctactttatt ctgataaaac aggtctatgc agctaccagg aca atg gaa tct acg         55
                                             Met Glu Ser Thr
                                              1 ttg act tta gca acg gaa caa cct gtt aag aag aac act ctt aag aaa        103
Leu Thr Leu Ala Thr Glu Gln Pro Val Lys Lys Asn Thr Leu Lys Lys
  5              10                  15                  20 tat aaa ata gct tgc att gtt ctt ctt gct ttg ctg gtg atc atg tca        151
Tyr Lys Ile Ala Cys Ile Val Leu Leu Ala Leu Leu Val Ile Met Ser
             25                  30                  35 ctt gga tta ggc ctg ggg ctt gga ctc agg aaa ctg gaa aag caa ggc        199
Leu Gly Leu Gly Leu Gly Leu Gly Leu Arg Lys Leu Glu Lys Gln Gly
         40                  45                  50 agc tgc agg aag aag tgc ttt gat gca tca ttt aga gga ctg gag aac        247
Ser Cys Arg Lys Lys Cys Phe Asp Ala Ser Phe Arg Gly Leu Glu Asn
     55                  60                  65 tgc cgg tgt gat gtg gca tgt aaa gac cga ggt gat tgc tgc tgg gat        295
Cys Arg Cys Asp Val Ala Cys Lys Asp Arg Gly Asp Cys Cys Trp Asp
 70                  75                  80 ttt gaa gac acc tgt gtg gaa tca act cga ata tgg atg tgc aat aaa        343
Phe Glu Asp Thr Cys Val Glu Ser Thr Arg Ile Trp Met Cys Asn Lys
 85                  90                  95                 100 ttt cgt tgt gga gag acc aga tta gag gcc agc ctt tgc tct tgt tca        391
Phe Arg Cys Gly Glu Thr Arg Leu Glu Ala Ser Leu Cys Ser Cys Ser
             105                 110                 115 gat gac tgt ttg cag aag aaa gat tgc tgt gct gac tat aag agt gtt        439
Asp Asp Cys Leu Gln Lys Lys Asp Cys Cys Ala Asp Tyr Lys Ser Val
         120                 125                 130 tgc caa gga gaa acc tca tgg ctg gaa gaa aac tgt gac aca gcc cag        487
Cys Gln Gly Glu Thr Ser Trp Leu Glu Glu Asn Cys Asp Thr Ala Gln
     135                 140                 145 cag tct cag tgc cca gaa ggg ttt gac ctg cca cca gtt atc ttg ttt        535
Gln Ser Gln Cys Pro Glu Gly Phe Asp Leu Pro Pro Val Ile Leu Phe
150                 155                 160 tct atg gat gga ttt aga gct gaa tat tta tac aca tgg gat act tta        583
Ser Met Asp Gly Phe Arg Ala Glu Tyr Leu Tyr Thr Trp Asp Thr Leu
165                 170                 175                 180 atg cca aat atc aat aaa ctg aaa aca tgt gga att cat tca aaa tac        631
Met Pro Asn Ile Asn Lys Leu Lys Thr Cys Gly Ile His Ser Lys Tyr
             185                 190                 195 atg aga gct atg tat cct acc aaa acc ttc cca aat cat tac acc att        679
Met Arg Ala Met Tyr Pro Thr Lys Thr Phe Pro Asn His Tyr Thr Ile
         200                 205                 210 gtc acg ggc ttg tat cca gag tca cat ggc atc att gac aat aat atg        727
Val Thr Gly Leu Tyr Pro Glu Ser His Gly Ile Ile Asp Asn Asn Met
     215                 220                 225 tat gat gta aat ctc aac aag aat ttt tca ctt tct tca aag gaa caa        775
```

```
                Tyr Asp Val Asn Leu Asn Lys Asn Phe Ser Leu Ser Ser Lys Glu Gln
                    230                 235                 240 aat aat cca gcc tgg tgg cat ggg caa cca atg tgg ctg aca gca atg        823
Asn Asn Pro Ala Trp Trp His Gly Gln Pro Met Trp Leu Thr Ala Met
245                 250                 255                 260 tat caa ggt tta aaa gcc gct acc tac ttt tgg ccc gga tca gaa gtg        871
Tyr Gln Gly Leu Lys Ala Ala Thr Tyr Phe Trp Pro Gly Ser Glu Val
                    265                 270                 275 gct ata aat ggc tcc ttt cct tcc ata tac atg cct tac aac gga agt        919
Ala Ile Asn Gly Ser Phe Pro Ser Ile Tyr Met Pro Tyr Asn Gly Ser
                280                 285                 290 gtc cca ttt gaa gag agg att tct aca ctg tta aaa tgg ctg gac ctg        967
Val Pro Phe Glu Glu Arg Ile Ser Thr Leu Leu Lys Trp Leu Asp Leu
            295                 300                 305 ccc aaa gct gaa aga ccc agg ttt tat acc atg tat ttt gaa gaa cct       1015
Pro Lys Ala Glu Arg Pro Arg Phe Tyr Thr Met Tyr Phe Glu Glu Pro
310                 315                 320 gat tcc tct gga cat gca ggt gga cca gtc agt gcc aga gta att aaa       1063
Asp Ser Ser Gly His Ala Gly Gly Pro Val Ser Ala Arg Val Ile Lys
325                 330                 335                 340 gcc tta cag gta gta gat cat gct ttt ggg atg ttg atg gaa ggc ctg       1111
Ala Leu Gln Val Val Asp His Ala Phe Gly Met Leu Met Glu Gly Leu
                    345                 350                 355 aag cag cgg aat ttg cac aac tgt gtc aat atc atc ctt ctg gct gac       1159
Lys Gln Arg Asn Leu His Asn Cys Val Asn Ile Ile Leu Leu Ala Asp
                360                 365                 370 cat gga atg gac cag act tat tgt aac aag atg gaa tac atg act gat       1207
His Gly Met Asp Gln Thr Tyr Cys Asn Lys Met Glu Tyr Met Thr Asp
            375                 380                 385 tat ttt ccc aga ata aac ttc ttc tac atg tac gaa ggg cct gcc ccc       1255
Tyr Phe Pro Arg Ile Asn Phe Phe Tyr Met Tyr Glu Gly Pro Ala Pro
390                 395                 400 cgc atc cga gct cat aat ata cct cat gac ttt ttt agt ttt aat tct       1303
Arg Ile Arg Ala His Asn Ile Pro His Asp Phe Phe Ser Phe Asn Ser
405                 410                 415                 420 gag gaa att gtt aga aac ctc agt tgc cga aaa cct gat cag cat ttc       1351
Glu Glu Ile Val Arg Asn Leu Ser Cys Arg Lys Pro Asp Gln His Phe
                    425                 430                 435 aag ccc tat ttg act cct gat ttg cca aag cga ctg cac tat gcc aag       1399
Lys Pro Tyr Leu Thr Pro Asp Leu Pro Lys Arg Leu His Tyr Ala Lys
                440                 445                 450 aac gtc aga atc gac aaa gtt cat ctc ttt gtg gat caa cag tgg ctg       1447
Asn Val Arg Ile Asp Lys Val His Leu Phe Val Asp Gln Gln Trp Leu
            455                 460                 465 gct gtt agg agt aaa tca aat aca aat tgt gga gga ggc aac cat ggt       1495
Ala Val Arg Ser Lys Ser Asn Thr Asn Cys Gly Gly Gly Asn His Gly
470                 475                 480 tat aac aat gag ttt agg agc atg gag gct atc ttt ctg gca cat gga       1543
Tyr Asn Asn Glu Phe Arg Ser Met Glu Ala Ile Phe Leu Ala His Gly
485                 490                 495                 500 ccc agt ttt aaa gag aag act gaa gtt gaa cca ttt gaa aat att gaa       1591
Pro Ser Phe Lys Glu Lys Thr Glu Val Glu Pro Phe Glu Asn Ile Glu
                    505                 510                 515 gtc tat aac cta atg tgt gat ctt cta cgc att caa cca gca cca aac       1639
Val Tyr Asn Leu Met Cys Asp Leu Leu Arg Ile Gln Pro Ala Pro Asn
                520                 525                 530 aat gga acc cat ggt agt tta aac cat ctt ctg aag gtg cct ttt tat       1687
Asn Gly Thr His Gly Ser Leu Asn His Leu Leu Lys Val Pro Phe Tyr
            535                 540                 545
```

```
gag cca tcc cat gca gag gag gtg tca aag ttt tct gtt tgt ggc ttt         1735
Glu Pro Ser His Ala Glu Glu Val Ser Lys Phe Ser Val Cys Gly Phe
    550                 555                 560 gct aat cca ttg ccc aca gag tct ctt gac tgt ttc tgc cct cac cta         1783
Ala Asn Pro Leu Pro Thr Glu Ser Leu Asp Cys Phe Cys Pro His Leu
565                 570                 575                 580 caa aat agt act cag ctg gaa caa gtg aat cag atg cta aat ctc acc         1831
Gln Asn Ser Thr Gln Leu Glu Gln Val Asn Gln Met Leu Asn Leu Thr
                    585                 590                 595 caa gaa gaa ata aca gca aca gtg aaa gta aat ttg cca ttt ggg agg         1879
Gln Glu Glu Ile Thr Ala Thr Val Lys Val Asn Leu Pro Phe Gly Arg
                600                 605                 610 cct agg gta ctg cag aag aac gtg gac cac tgt ctc ctt tac cac agg         1927
Pro Arg Val Leu Gln Lys Asn Val Asp His Cys Leu Leu Tyr His Arg
            615                 620                 625 gaa tat gtc agt gga ttt gga aaa gct atg agg atg ccc atg tgg agt         1975
Glu Tyr Val Ser Gly Phe Gly Lys Ala Met Arg Met Pro Met Trp Ser
630                 635                 640 tca tac aca gtc ccc cag ttg gga gac aca tcg cct ctg cct ccc act         2023
Ser Tyr Thr Val Pro Gln Leu Gly Asp Thr Ser Pro Leu Pro Pro Thr
645                 650                 655                 660 gtc cca gac tgt ctg cgg gct gat gtc agg gtt cct cct tct gag agc         2071
Val Pro Asp Cys Leu Arg Ala Asp Val Arg Val Pro Pro Ser Glu Ser
                    665                 670                 675 caa aaa tgt tcc ttc tat tta gca gac aag aat atc acc cac ggc ttc         2119
Gln Lys Cys Ser Phe Tyr Leu Ala Asp Lys Asn Ile Thr His Gly Phe
                680                 685                 690 ctc tat cct cct gcc agc aat aga aca tca gat agc caa tat gat gct         2167
Leu Tyr Pro Pro Ala Ser Asn Arg Thr Ser Asp Ser Gln Tyr Asp Ala
            695                 700                 705 tta att act agc aat ttg gta cct atg tat gaa gaa ttc aga aaa atg         2215
Leu Ile Thr Ser Asn Leu Val Pro Met Tyr Glu Glu Phe Arg Lys Met
710                 715                 720 tgg gac tac ttc cac agt gtt ctt ctt ata aaa cat gcc aca gaa aga         2263
Trp Asp Tyr Phe His Ser Val Leu Leu Ile Lys His Ala Thr Glu Arg
725                 730                 735                 740 aat gga gta aat gtg gtt agt gga cca ata ttt gat tat aat tat gat         2311
Asn Gly Val Asn Val Val Ser Gly Pro Ile Phe Asp Tyr Asn Tyr Asp
                    745                 750                 755 ggc cat ttt gat gct cca gat gaa att acc aaa cat tta gcc aac act         2359
Gly His Phe Asp Ala Pro Asp Glu Ile Thr Lys His Leu Ala Asn Thr
                760                 765                 770 gat gtt ccc atc cca aca cac tac ttt gtg gtg ctg acc agt tgt aaa         2407
Asp Val Pro Ile Pro Thr His Tyr Phe Val Val Leu Thr Ser Cys Lys
            775                 780                 785 aac aag agc cac aca ccg gaa aac tgc cct ggg tgg ctg gat gtc cta         2455
Asn Lys Ser His Thr Pro Glu Asn Cys Pro Gly Trp Leu Asp Val Leu
790                 795                 800 ccc ttt atc atc cct cac cga cct acc aac gtg gag agc tgt cct gaa         2503
Pro Phe Ile Ile Pro His Arg Pro Thr Asn Val Glu Ser Cys Pro Glu
805                 810                 815                 820 ggt aaa cca gaa gct ctt tgg gtt gaa gaa aga ttt aca gct cac att         2551
Gly Lys Pro Glu Ala Leu Trp Val Glu Glu Arg Phe Thr Ala His Ile
                    825                 830                 835 gcc cgg gtc cgt gat gta gaa ctt ctc act ggg ctt gac ttc tat cag         2599
Ala Arg Val Arg Asp Val Glu Leu Leu Thr Gly Leu Asp Phe Tyr Gln
                840                 845                 850 gat aaa gtg cag cct gtc tct gaa att ttg caa cta aag aca tat tta         2647
Asp Lys Val Gln Pro Val Ser Glu Ile Leu Gln Leu Lys Thr Tyr Leu
            855                 860                 865
```

```
cca aca ttt gaa acc act att taa cttaataatg tctacttaat atataattta    2701
Pro Thr Phe Glu Thr Thr Ile  *
    870                 875 ctgtataaag taattttggc aaaatataag tgatttttc tggagaattg taaaataaag     2761
ttttctattt ttccttaaaa aaaaaaccgg aattccgggc ttgggaggct gaggcaggag    2821
actcgcttga acccgggagg cagaggttgc agtgagccaa gattgcgcca ttgcactcca    2881
gagcctgggt gacagagcaa gactacatct caaaaaataa ataaataaaa taaaagtaac    2941
aataaaaata aaaagaacag cagagagaat gagcaaggag aaatgtcaca aactattgca    3001
aaatactgtt acactgggtt ggctctccaa gaagatactg gaatctcttc agccatttgc    3061
ttttcagaag tagaaaccag caaaccacct ctaagcggag aacatacgat tctttattaa    3121
gtagctctgg ggaaggaaag aataaaagtt gatagctccc tgattgggaa aaaatgcaca    3181
attaataaag aatgaagatg aaagaaagca tgcttatgtt gtaacacaaa aaaaattcac    3241
aaacgttggt ggaaggaaaa cagtatagaa acattactt taactaaaag ctggaaaaat    3301
tttcagttgg gatgcgactg acaaaaagaa cgggatttcc aggcataaag ttggcgtgag    3361
ctacagaggg caccatgtgg ctcagtggaa gacccttcaa gattcaaagt tccatttgac    3421
agagcaaagg cacttcgcaa ggagaagggt ttaaattatg ggtccaaaag ccaagtggta    3481
aagcgagcaa tttgcagcat aactgcttct cctagacagg gctgagtggg caaaatacga    3541
cagtacacac agtgactatt agccactgcc agaaacaggc tgaacagccc tgggagacaa    3601
gggaaggcag gtggtgggag ttgttcatgg agagaaagga gagttttaga accagcacat    3661
ccactggaga tgctgggcca ccagacccct cccagtcaat aaagtctggt gcctcatttg    3721
atctcagcct catcatgacc ctggagagac cctgatacca tctgccagtc cccgacagct    3781
taggcactcc ttgccatcaa cctgaccccc cgagtggttc tccaggctcc ctgccccacc    3841
cattcaggcc ggaattc                                                   3858

<210> SEQ ID NO 3
<211> LENGTH: 875
<212> TYPE: PRT
<213> ORGANISM: Homo Sapiens

<400> SEQUENCE: 3

Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
             20                  25                  30

Val Ile Met Ser Leu Gly Leu Gly Leu Gly Leu Gly Leu Arg Lys Leu
         35                  40                  45

Glu Lys Gln Gly Ser Cys Arg Lys Lys Cys Phe Asp Ala Ser Phe Arg
     50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
    130                 135                 140
```

```
Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
            165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
        210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
            245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Arg Ile Ser Thr Leu Leu Lys
        290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
            325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
        370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
            405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
        450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
            485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560
```

-continued

Val Cys Gly Phe Ala Asn Pro Leu Pro Thr Glu Ser Leu Asp Cys Phe
            565                 570                 575

Cys Pro His Leu Gln Asn Ser Thr Gln Leu Glu Gln Val Asn Gln Met
        580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
    675                 680                 685

Thr His Gly Phe Leu Tyr Pro Pro Ala Ser Asn Arg Thr Ser Asp Ser
690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
    755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
    835                 840                 845

Asp Phe Tyr Gln Asp Lys Val Gln Pro Val Ser Glu Ile Leu Gln Leu
850                 855                 860

Lys Thr Tyr Leu Pro Thr Phe Glu Thr Thr Ile
865                 870                 875

<210> SEQ ID NO 4
<211> LENGTH: 3858
<212> TYPE: DNA
<213> ORGANISM: Homo Sapiens
<220> FEATURE:
<221> NAME/KEY: CDS
<222> LOCATION: (44)...(2671)

<400> SEQUENCE: 4
ctactttatt ctgataaaac aggtctatgc agctaccagg aca atg gaa tct acg      55
                                              Met Glu Ser Thr
                                                1 ttg act tta gca acg gaa caa cct gtt aag aag aac act ctt aag aaa     103
Leu Thr Leu Ala Thr Glu Gln Pro Val Lys Lys Asn Thr Leu Lys Lys
  5                  10                  15                  20

-continued

| | |
|---|---|
| tat aaa ata gct tgc att gtt ctt ctt gct ttg ctg gtg atc atg tca<br>Tyr Lys Ile Ala Cys Ile Val Leu Leu Ala Leu Leu Val Ile Met Ser<br>                  25                              30                        35 | 151 |
| ctt gga tta ggc ctg ggg ctt gga ctc agg aaa ctg gaa aag caa ggc<br>Leu Gly Leu Gly Leu Gly Leu Gly Leu Arg Lys Leu Glu Lys Gln Gly<br>                40                              45                        50 | 199 |
| agc tgc agg aag aag tgc ttt gat gca tca ttt aga gga ctg gag aac<br>Ser Cys Arg Lys Lys Cys Phe Asp Ala Ser Phe Arg Gly Leu Glu Asn<br>        55                            60                            65 | 247 |
| tgc cgg tgt gat gtg gca tgt aaa gac cga ggt gat tgc tgc tgg gat<br>Cys Arg Cys Asp Val Ala Cys Lys Asp Arg Gly Asp Cys Cys Trp Asp<br>  70                            75                            80 | 295 |
| ttt gaa gac acc tgt gtg gaa tca act cga ata tgg atg tgc aat aaa<br>Phe Glu Asp Thr Cys Val Glu Ser Thr Arg Ile Trp Met Cys Asn Lys<br>85                            90                            95                        100 | 343 |
| ttt cgt tgt gga gag acc aga tta gag gcc agc ctt tgc tct tgt tca<br>Phe Arg Cys Gly Glu Thr Arg Leu Glu Ala Ser Leu Cys Ser Cys Ser<br>                  105                            110                        115 | 391 |
| gat gac tgt ttg cag agg aaa gat tgc tgt gct gac tat aag agt gtt<br>Asp Asp Cys Leu Gln Arg Lys Asp Cys Cys Ala Asp Tyr Lys Ser Val<br>                120                            125                        130 | 439 |
| tgc caa gga gaa acc tca tgg ctg gaa gaa aac tgt gac aca gcc cag<br>Cys Gln Gly Glu Thr Ser Trp Leu Glu Glu Asn Cys Asp Thr Ala Gln<br>            135                            140                            145 | 487 |
| cag tct cag tgc cca gaa ggg ttt gac ctg cca cca gtt atc ttg ttt<br>Gln Ser Gln Cys Pro Glu Gly Phe Asp Leu Pro Pro Val Ile Leu Phe<br>      150                            155                            160 | 535 |
| tct atg gat gga ttt aga gct gaa tat tta tac aca tgg gat act tta<br>Ser Met Asp Gly Phe Arg Ala Glu Tyr Leu Tyr Thr Trp Asp Thr Leu<br>165                          170                            175                        180 | 583 |
| atg cca aat atc aat aaa ctg aaa aca tgt gga att cat tca aaa tac<br>Met Pro Asn Ile Asn Lys Leu Lys Thr Cys Gly Ile His Ser Lys Tyr<br>                  185                            190                        195 | 631 |
| atg aga gct atg tat cct acc aaa acc ttc cca aat cat tac acc att<br>Met Arg Ala Met Tyr Pro Thr Lys Thr Phe Pro Asn His Tyr Thr Ile<br>            200                            205                            210 | 679 |
| gtc acg ggc ttg tat cca gag tca cat ggc atc att gac aat aat atg<br>Val Thr Gly Leu Tyr Pro Glu Ser His Gly Ile Ile Asp Asn Asn Met<br>      215                            220                            225 | 727 |
| tat gat gta aat ctc aac aag aat ttt tca ctt tct tca aag gaa caa<br>Tyr Asp Val Asn Leu Asn Lys Asn Phe Ser Leu Ser Ser Lys Glu Gln<br>230                          235                            240 | 775 |
| aat aat cca gcc tgg tgg cat ggg caa cca atg tgg ctg aca gca atg<br>Asn Asn Pro Ala Trp Trp His Gly Gln Pro Met Trp Leu Thr Ala Met<br>245                          250                            255                        260 | 823 |
| tat caa ggt tta aaa gcc gct acc tac ttt tgg ccc gga tca gaa gtg<br>Tyr Gln Gly Leu Lys Ala Ala Thr Tyr Phe Trp Pro Gly Ser Glu Val<br>                  265                            270                        275 | 871 |
| gct ata aat ggc tcc ttt cct tcc ata tac atg cct tac aac gga agt<br>Ala Ile Asn Gly Ser Phe Pro Ser Ile Tyr Met Pro Tyr Asn Gly Ser<br>            280                            285                            290 | 919 |
| gtc cca ttt gaa gag agg att tct aca ctg tta aaa tgg ctg gac ctg<br>Val Pro Phe Glu Glu Arg Ile Ser Thr Leu Leu Lys Trp Leu Asp Leu<br>      295                            300                            305 | 967 |
| ccc aaa gct gaa aga ccc agg ttt tat acc atg tat ttt gaa gaa cct<br>Pro Lys Ala Glu Arg Pro Arg Phe Tyr Thr Met Tyr Phe Glu Glu Pro<br>          310                            315                            320 | 1015 |
| gat tcc tct gga cat gca ggt gga cca gtc agt gcc aga gta att aaa<br>Asp Ser Ser Gly His Ala Gly Gly Pro Val Ser Ala Arg Val Ile Lys<br>325                          330                            335                        340 | 1063 |

```
gcc tta cag gta gta gat cat gct ttt ggg atg ttg atg gaa ggc ctg      1111
Ala Leu Gln Val Val Asp His Ala Phe Gly Met Leu Met Glu Gly Leu
            345                 350                 355 aag cag cgg aat ttg cac aac tgt gtc aat atc atc ctt ctg gct gac      1159
Lys Gln Arg Asn Leu His Asn Cys Val Asn Ile Ile Leu Leu Ala Asp
    360                 365                 370 cat gga atg gac cag act tat tgt aac aag atg gaa tac atg act gat      1207
His Gly Met Asp Gln Thr Tyr Cys Asn Lys Met Glu Tyr Met Thr Asp
        375                 380                 385 tat ttt ccc aga ata aac ttc ttc tac atg tac gaa ggg cct gcc ccc      1255
Tyr Phe Pro Arg Ile Asn Phe Phe Tyr Met Tyr Glu Gly Pro Ala Pro
390                 395                 400 cgc atc cga gct cat aat ata cct cat gac ttt ttt agt ttt aat tct      1303
Arg Ile Arg Ala His Asn Ile Pro His Asp Phe Phe Ser Phe Asn Ser
405                 410                 415                 420 gag gaa att gtt aga aac ctc agt tgc cga aaa cct gat cag cat ttc      1351
Glu Glu Ile Val Arg Asn Leu Ser Cys Arg Lys Pro Asp Gln His Phe
                425                 430                 435 aag ccc tat ttg act cct gat ttg cca aag cga ctg cac tat gcc aag      1399
Lys Pro Tyr Leu Thr Pro Asp Leu Pro Lys Arg Leu His Tyr Ala Lys
            440                 445                 450 aac gtc aga atc gac aaa gtt cat ctc ttt gtg gat caa cag tgg ctg      1447
Asn Val Arg Ile Asp Lys Val His Leu Phe Val Asp Gln Gln Trp Leu
        455                 460                 465 gct gtt agg agt aaa tca aat aca aat tgt gga gga ggc aac cat ggt      1495
Ala Val Arg Ser Lys Ser Asn Thr Asn Cys Gly Gly Gly Asn His Gly
470                 475                 480 tat aac aat gag ttt agg agc atg gag gct atc ttt ctg gca cat gga      1543
Tyr Asn Asn Glu Phe Arg Ser Met Glu Ala Ile Phe Leu Ala His Gly
485                 490                 495                 500 ccc agt ttt aaa gag aag act gaa gtt gaa cca ttt gaa aat att gaa      1591
Pro Ser Phe Lys Glu Lys Thr Glu Val Glu Pro Phe Glu Asn Ile Glu
                505                 510                 515 gtc tat aac cta atg tgt gat ctt cta cgc att caa cca gca cca aac      1639
Val Tyr Asn Leu Met Cys Asp Leu Leu Arg Ile Gln Pro Ala Pro Asn
            520                 525                 530 aat gga acc cat ggt agt tta aac cat ctt ctg aag gtg cct ttt tat      1687
Asn Gly Thr His Gly Ser Leu Asn His Leu Leu Lys Val Pro Phe Tyr
        535                 540                 545 gag cca tcc cat gca gag gag gtg tca aag ttt tct gtt tgt ggc ttt      1735
Glu Pro Ser His Ala Glu Glu Val Ser Lys Phe Ser Val Cys Gly Phe
550                 555                 560 gct aat cca ttg ccc aca gag tct ctt gac tgt ttc tgc cct cac cta      1783
Ala Asn Pro Leu Pro Thr Glu Ser Leu Asp Cys Phe Cys Pro His Leu
565                 570                 575                 580 caa aat agt act cag ctg gaa caa gtg aat cag atg cta aat ctc acc      1831
Gln Asn Ser Thr Gln Leu Glu Gln Val Asn Gln Met Leu Asn Leu Thr
                585                 590                 595 caa gaa gaa ata aca gca aca gtg aaa gta aat ttg cca ttt ggg agg      1879
Gln Glu Glu Ile Thr Ala Thr Val Lys Val Asn Leu Pro Phe Gly Arg
            600                 605                 610 cct agg gta ctg cag aag aac gtg gac cac tgt ctc ctt tac cac agg      1927
Pro Arg Val Leu Gln Lys Asn Val Asp His Cys Leu Leu Tyr His Arg
        615                 620                 625 gaa tat gtc agt gga ttt gga aaa gct atg agg atg ccc atg tgg agt      1975
Glu Tyr Val Ser Gly Phe Gly Lys Ala Met Arg Met Pro Met Trp Ser
630                 635                 640 tca tac aca gtc ccc cag ttg gga gac aca tcg cct ctg cct ccc act      2023
Ser Tyr Thr Val Pro Gln Leu Gly Asp Thr Ser Pro Leu Pro Pro Thr
```

```
                                              -continued
645                 650                 655                 660 gtc cca gac tgt ctg cgg gct gat gtc agg gtt cct cct tct gag agc         2071
Val Pro Asp Cys Leu Arg Ala Asp Val Arg Val Pro Pro Ser Glu Ser
            665                 670                 675 caa aaa tgt tcc ttc tat tta gca gac aag aat atc acc cac ggc ttc         2119
Gln Lys Cys Ser Phe Tyr Leu Ala Asp Lys Asn Ile Thr His Gly Phe
            680                 685                 690 ctc tat cct cct gcc agc aat aga aca tca gat agc caa tat gat gct         2167
Leu Tyr Pro Pro Ala Ser Asn Arg Thr Ser Asp Ser Gln Tyr Asp Ala
            695                 700                 705 tta att act agc aat ttg gta cct atg tat gaa gaa ttc aga aaa atg         2215
Leu Ile Thr Ser Asn Leu Val Pro Met Tyr Glu Glu Phe Arg Lys Met
710                 715                 720 tgg gac tac ttc cac agt gtt ctt ctt ata aaa cat gcc aca gaa aga         2263
Trp Asp Tyr Phe His Ser Val Leu Leu Ile Lys His Ala Thr Glu Arg
725                 730                 735                 740 aat gga gta aat gtg gtt agt gga cca ata ttt gat tat aat tat gat         2311
Asn Gly Val Asn Val Val Ser Gly Pro Ile Phe Asp Tyr Asn Tyr Asp
                745                 750                 755 ggc cat ttt gat gct cca gat gaa att acc aaa cat tta gcc aac act         2359
Gly His Phe Asp Ala Pro Asp Glu Ile Thr Lys His Leu Ala Asn Thr
            760                 765                 770 gat gtt ccc atc cca aca cac tac ttt gtg gtg ctg acc agt tgt aaa         2407
Asp Val Pro Ile Pro Thr His Tyr Phe Val Val Leu Thr Ser Cys Lys
            775                 780                 785 aac aag agc cac aca ccg gaa aac tgc cct ggg tgg ctg gat gtc cta         2455
Asn Lys Ser His Thr Pro Glu Asn Cys Pro Gly Trp Leu Asp Val Leu
790                 795                 800 ccc ttt atc atc cct cac cga cct acc aac gtg gag agc tgt cct gaa         2503
Pro Phe Ile Ile Pro His Arg Pro Thr Asn Val Glu Ser Cys Pro Glu
805                 810                 815                 820 ggt aaa cca gaa gct ctt tgg gtt gaa gaa aga ttt aca gct cac att         2551
Gly Lys Pro Glu Ala Leu Trp Val Glu Glu Arg Phe Thr Ala His Ile
                825                 830                 835 gcc cgg gtc cgt gat gta gaa ctt ctc act ggg ctt gac ttc tat cag         2599
Ala Arg Val Arg Asp Val Glu Leu Leu Thr Gly Leu Asp Phe Tyr Gln
            840                 845                 850 gat aaa gtg cag cct gtc tct gaa att ttg caa cta aag aca tat tta         2647
Asp Lys Val Gln Pro Val Ser Glu Ile Leu Gln Leu Lys Thr Tyr Leu
            855                 860                 865 cca aca ttt gaa acc act att taa cttaataatg tctacttaat atataattta       2701
Pro Thr Phe Glu Thr Thr Ile *
    870                 875 ctgtataaag taattttggc aaaatataag tgattttttc tggagaattg taaaataaag      2761
ttttctattt ttccttaaaa aaaaaaccgg aattccgggc ttgggaggct gaggcaggag      2821
actcgcttga acccgggagg cagaggttgc agtgagccaa gattgcgcca ttgcactcca      2881
gagcctgggt gacagagcaa gactacatct caaaaaataa ataaataaaa taaaagtaac      2941
aataaaaata aaaagaacag cagagagaat gagcaaggag aaatgtcaca aactattgca      3001
aaatactgtt acactgggtt ggctctccaa gaagatactg gaatctcttc agccatttgc      3061
ttttcagaag tagaaaccag caaaccacct ctaagcggag aacatacgat tctttattaa      3121
gtagctctgg ggaaggaaag aataaaagtt gatagctccc tgattgggaa aaaatgcaca      3181
attaataaag aatgaagatg aaagaaagca tgcttatgtt gtaacacaaa aaaaattcac      3241
aaacgttggt ggaaggaaaa cagtatagaa aacattactt taactaaaag ctggaaaaat      3301
tttcagttgg gatgcgactg acaaaaagaa cgggatttcc aggcataaag ttggcgtgag      3361
```

-continued

```
ctacagaggg caccatgtgg ctcagtggaa gacccttcaa gattcaaagt tccatttgac      3421
agagcaaagg cacttcgcaa ggagaagggt ttaaattatg ggtccaaaag ccaagtggta      3481
aagcgagcaa tttgcagcat aactgcttct cctagacagg gctgagtggg caaaatacga      3541
cagtacacac agtgactatt agccactgcc agaaacaggc tgaacagccc tgggagacaa      3601
gggaaggcag gtggtgggag ttgttcatgg agagaaagga gagttttaga accagcacat      3661
ccactggaga tgctgggcca ccagacccct cccagtcaat aaagtctggt gcctcatttg      3721
atctcagcct catcatgacc ctggagagac cctgatacca tctgccagtc ccgacagct       3781 taggcactcc ttgccatcaa cctgaccccc cgagtggttc tccaggctcc ctgccccacc      3841
cattcaggcc ggaattc                                                    3858
```

<210> SEQ ID NO 5
<211> LENGTH: 875
<212> TYPE: PRT
<213> ORGANISM: Homo Sapiens

<400> SEQUENCE: 5

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Arg Lys Leu
        35                  40                  45

Glu Lys Gln Gly Ser Cys Arg Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
```

-continued

```
              275                 280                 285
Tyr Asn Gly Ser Val Pro Phe Glu Glu Arg Ile Ser Thr Leu Leu Lys
        290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Pro Val Ser Ala
                325                 330                 335
Arg Val Ile Lys Ala Leu Gln Val Val Asp His Ala Phe Gly Met Leu
                340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
        370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
                420                 425                 430
Asp Gln His Phe Lys Pro Tyr Leu Thr Pro Asp Leu Pro Lys Arg Leu
            435                 440                 445
His Tyr Ala Lys Asn Val Arg Ile Asp Lys Val His Leu Phe Val Asp
        450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
                500                 505                 510
Glu Asn Ile Glu Val Tyr Asn Leu Met Cys Asp Leu Leu Arg Ile Gln
            515                 520                 525
Pro Ala Pro Asn Asn Gly Thr His Gly Ser Leu Asn His Leu Leu Lys
530                 535                 540
Val Pro Phe Tyr Glu Pro Ser His Ala Glu Glu Val Ser Lys Phe Ser
545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
                580                 585                 590
Leu Asn Leu Thr Gln Glu Glu Ile Thr Ala Thr Val Lys Val Asn Leu
            595                 600                 605
Pro Phe Gly Arg Pro Arg Val Leu Gln Lys Asn Val Asp His Cys Leu
        610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
            675                 680                 685
Thr His Gly Phe Leu Tyr Pro Pro Ala Ser Asn Arg Thr Ser Asp Ser
        690                 695                 700
```

```
Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
850                 855                 860

Lys Thr Tyr Leu Pro Thr Phe Glu Thr Thr Ile
865                 870                 875

<210> SEQ ID NO 6
<211> LENGTH: 3858
<212> TYPE: DNA
<213> ORGANISM: Homo Sapiens
<220> FEATURE:
<221> NAME/KEY: CDS
<222> LOCATION: (44)...(2671)

<400> SEQUENCE: 6
ctactttatt ctgataaaac aggtctatgc agctaccagg aca atg gaa tct acg         55
                                            Met Glu Ser Thr
                                             1 ttg act tta gca acg gaa caa cct gtt aag aag aac act ctt aag aaa        103
Leu Thr Leu Ala Thr Glu Gln Pro Val Lys Lys Asn Thr Leu Lys Lys
 5                  10                  15                  20 tat aaa ata gct tgc att gtt ctt ctt gct ttg ctg gtg atc atg tca       151
Tyr Lys Ile Ala Cys Ile Val Leu Leu Ala Leu Leu Val Ile Met Ser
                25                  30                  35 ctt gga tta ggc ctg ggg ctt gga ctc agg aaa ctg gaa aag caa ggc       199
Leu Gly Leu Gly Leu Gly Leu Gly Leu Arg Lys Leu Glu Lys Gln Gly
            40                  45                  50 agc tgc agg aag aag tgc ttt gat gca tca ttt aga gga ctg gag aac       247
Ser Cys Arg Lys Lys Cys Phe Asp Ala Ser Phe Arg Gly Leu Glu Asn
        55                  60                  65 tgc cgg tgt gat gtg gca tgt aaa gac cga ggt gat tgc tgc tgg gat       295
Cys Arg Cys Asp Val Ala Cys Lys Asp Arg Gly Asp Cys Cys Trp Asp
    70                  75                  80 ttt gaa gac acc tgt gtg gaa tca act cga ata tgg atg tgc aat aaa       343
Phe Glu Asp Thr Cys Val Glu Ser Thr Arg Ile Trp Met Cys Asn Lys
85                  90                  95                 100 ttt cgt tgt gga gag acc aga tta gag gcc agc ctt tgc tct tgt tca       391
Phe Arg Cys Gly Glu Thr Arg Leu Glu Ala Ser Leu Cys Ser Cys Ser
                105                 110                 115 gat gac tgt ttg cag aag aaa gat tgc tgt gct gac tat aag agt gtt       439
Asp Asp Cys Leu Gln Lys Lys Asp Cys Cys Ala Asp Tyr Lys Ser Val
```

-continued

```
                120                      125                      130
tgc caa gga gaa acc tca tgg ctg gaa gaa aac tgt gac aca gcc cag       487
Cys Gln Gly Glu Thr Ser Trp Leu Glu Glu Asn Cys Asp Thr Ala Gln
            135                      140                  145 cag tct cag tgc cca gaa ggg ttt gac ctg cca cca gtt atc ttg ttt       535
Gln Ser Gln Cys Pro Glu Gly Phe Asp Leu Pro Pro Val Ile Leu Phe
        150                      155                      160 tct atg gat gga ttt aga gct gaa tat tta tac aca tgg gat act tta       583
Ser Met Asp Gly Phe Arg Ala Glu Tyr Leu Tyr Thr Trp Asp Thr Leu
165                      170                      175              180 atg cca aat atc aat aaa ctg aaa aca tgt gga att cat tca aaa tac       631
Met Pro Asn Ile Asn Lys Leu Lys Thr Cys Gly Ile His Ser Lys Tyr
                    185                      190                  195 atg aga gct atg tat cct acc aaa acc ttc cca aat cat tac acc att       679
Met Arg Ala Met Tyr Pro Thr Lys Thr Phe Pro Asn His Tyr Thr Ile
                200                      205                  210 gtc acg ggc ttg tat cca gag tca cat ggc atc att gac aat aat atg       727
Val Thr Gly Leu Tyr Pro Glu Ser His Gly Ile Ile Asp Asn Asn Met
            215                      220                  225 tat gat gta aat ctc aac aag aat ttt tca ctt tct tca aag gaa caa       775
Tyr Asp Val Asn Leu Asn Lys Asn Phe Ser Leu Ser Ser Lys Glu Gln
230                      235                      240 aat aat cca gcc tgg tgg cat ggg caa cca atg tgg ctg aca gca atg       823
Asn Asn Pro Ala Trp Trp His Gly Gln Pro Met Trp Leu Thr Ala Met
245                      250                      255              260 tat caa ggt tta aaa gcc gct acc tac ttt tgg ccc gga tca gaa gtg       871
Tyr Gln Gly Leu Lys Ala Ala Thr Tyr Phe Trp Pro Gly Ser Glu Val
                    265                      270                  275 gct ata aat ggc tcc ttt cct tcc ata tac atg cct tac aac gga agt       919
Ala Ile Asn Gly Ser Phe Pro Ser Ile Tyr Met Pro Tyr Asn Gly Ser
                280                      285                  290 gtc cca ttt gaa gag agg att tct aca ctg tta aaa tgg ctg gac ctg       967
Val Pro Phe Glu Glu Arg Ile Ser Thr Leu Leu Lys Trp Leu Asp Leu
            295                      300                  305 ccc aaa gct gaa aga ccc agg ttt tat acc atg tat ttt gaa gaa cct      1015
Pro Lys Ala Glu Arg Pro Arg Phe Tyr Thr Met Tyr Phe Glu Glu Pro
            310                      315                  320 gat tcc tct gga cat gca ggt gga cca gtc agt gcc aga gta att aaa      1063
Asp Ser Ser Gly His Ala Gly Gly Pro Val Ser Ala Arg Val Ile Lys
325                      330                      335              340 gcc tta cag gta gta gat cat gct ttt ggg atg ttg atg gaa ggc ctg      1111
Ala Leu Gln Val Val Asp His Ala Phe Gly Met Leu Met Glu Gly Leu
                    345                      350                  355 aag cag cgg aat ttg cac aac tgt gtc aat atc atc ctt ctg gct gac      1159
Lys Gln Arg Asn Leu His Asn Cys Val Asn Ile Ile Leu Leu Ala Asp
                360                      365                  370 cat gga atg gac cag act tat tgt aac aag atg gaa tac atg act gat      1207
His Gly Met Asp Gln Thr Tyr Cys Asn Lys Met Glu Tyr Met Thr Asp
            375                      380                  385 tat ttt ccc aga ata aac ttc ttc tac atg tac gaa ggg cct gcc ccc      1255
Tyr Phe Pro Arg Ile Asn Phe Phe Tyr Met Tyr Glu Gly Pro Ala Pro
390                      395                      400 cgc atc cga gct cat aat ata cct cat gac ttt ttt agt ttt aat tct      1303
Arg Ile Arg Ala His Asn Ile Pro His Asp Phe Phe Ser Phe Asn Ser
405                      410                      415              420 gag gaa att gtt aga aac ctc agt tgc cga aaa cct gat cag cat ttc      1351
Glu Glu Ile Val Arg Asn Leu Ser Cys Arg Lys Pro Asp Gln His Phe
                    425                      430                  435 aag ccc tat ttg act cct gat ttg cca aag cga ctg cac tat gcc aag      1399
```

```
                                                        -continued
Lys Pro Tyr Leu Thr Pro Asp Leu Pro Lys Arg Leu His Tyr Ala Lys
            440                 445                 450 aac gtc aga atc gac aaa gtt cat ctc ttt gtg gat caa cag tgg ctg        1447
Asn Val Arg Ile Asp Lys Val His Leu Phe Val Asp Gln Gln Trp Leu
            455                 460                 465 gct gtt agg agt aaa tca aat aca aat tgt gga gga ggc aac cat ggt        1495
Ala Val Arg Ser Lys Ser Asn Thr Asn Cys Gly Gly Gly Asn His Gly
            470                 475                 480 tat aac aat gag ttt agg agc atg gag gct atc ttt ctg gca cat gga        1543
Tyr Asn Asn Glu Phe Arg Ser Met Glu Ala Ile Phe Leu Ala His Gly
485                 490                 495                 500 ccc agt ttt aaa gag aag act gaa gtt gaa cca ttt gaa aat att gaa        1591
Pro Ser Phe Lys Glu Lys Thr Glu Val Glu Pro Phe Glu Asn Ile Glu
                505                 510                 515 gtc tat aac cta atg tgt gat ctt cta cgc att caa cca gca cca aac        1639
Val Tyr Asn Leu Met Cys Asp Leu Leu Arg Ile Gln Pro Ala Pro Asn
            520                 525                 530 aat gga acc cat ggt agt tta aac cat ctt ctg aag gtg cct ttt tat        1687
Asn Gly Thr His Gly Ser Leu Asn His Leu Leu Lys Val Pro Phe Tyr
            535                 540                 545 gag cca tcc cat gca gag gag gtg tca aag ttt tct gtt tgt ggc ttt        1735
Glu Pro Ser His Ala Glu Glu Val Ser Lys Phe Ser Val Cys Gly Phe
            550                 555                 560 gct aat cca ttg ccc aca gag tct ctt gac tgt ttc tgc cct cac cta        1783
Ala Asn Pro Leu Pro Thr Glu Ser Leu Asp Cys Phe Cys Pro His Leu
565                 570                 575                 580 caa aat agt act cag ctg gaa caa gtg aat cag atg cta aat ctc acc        1831
Gln Asn Ser Thr Gln Leu Glu Gln Val Asn Gln Met Leu Asn Leu Thr
                585                 590                 595 caa gaa gaa ata aca gca aca gtg aaa gta aat ttg cca ttt ggg agg        1879
Gln Glu Glu Ile Thr Ala Thr Val Lys Val Asn Leu Pro Phe Gly Arg
            600                 605                 610 cct agg gta ctg cag aag aac gtg gac cac tgt ctc ctt tac cac agg        1927
Pro Arg Val Leu Gln Lys Asn Val Asp His Cys Leu Leu Tyr His Arg
            615                 620                 625 gaa tat gtc agt gga ttt gga aaa gct atg agg atg ccc atg tgg agt        1975
Glu Tyr Val Ser Gly Phe Gly Lys Ala Met Arg Met Pro Met Trp Ser
            630                 635                 640 tca tac aca gtc ccc cag ttg gga gac aca tcg cct ctg cct ccc act        2023
Ser Tyr Thr Val Pro Gln Leu Gly Asp Thr Ser Pro Leu Pro Pro Thr
645                 650                 655                 660 gtc cca gac tgt ctg cgg gct gat gtc agg gtt cct cct tct gag agc        2071
Val Pro Asp Cys Leu Arg Ala Asp Val Arg Val Pro Pro Ser Glu Ser
                665                 670                 675 caa aaa tgt tcc ttc tat tta gca gac aag aat atc acc cac ggc ttc        2119
Gln Lys Cys Ser Phe Tyr Leu Ala Asp Lys Asn Ile Thr His Gly Phe
            680                 685                 690 ctc tat cct cct gcc agc aat aga aca tca gat agc caa tat gat gct        2167
Leu Tyr Pro Pro Ala Ser Asn Arg Thr Ser Asp Ser Gln Tyr Asp Ala
            695                 700                 705 tta att act agc aat ttg gta cct atg tat gaa gaa ttc aga aaa atg        2215
Leu Ile Thr Ser Asn Leu Val Pro Met Tyr Glu Glu Phe Arg Lys Met
            710                 715                 720 tgg gac tac ttc cac agt gtt ctt ctt ata aaa cat gcc aca gaa aga        2263
Trp Asp Tyr Phe His Ser Val Leu Leu Ile Lys His Ala Thr Glu Arg
725                 730                 735                 740 aat gga gta aat gtg gtt agt gga cca ata ttt gat tat aat tat gat        2311
Asn Gly Val Asn Val Val Ser Gly Pro Ile Phe Asp Tyr Asn Tyr Asp
                745                 750                 755
```

```
ggc cat ttt gat gct cca gat gaa att acc aaa cat tta gcc aac act      2359
Gly His Phe Asp Ala Pro Asp Glu Ile Thr Lys His Leu Ala Asn Thr
            760                 765                 770 gat gtt ccc atc cca aca cac tac ttt gtg gtg ctg acc agt tgt aaa      2407
Asp Val Pro Ile Pro Thr His Tyr Phe Val Val Leu Thr Ser Cys Lys
        775                 780                 785 aac aag agc cac aca ccg gaa aac tgc cct ggg tgg ctg gat gtc cta      2455
Asn Lys Ser His Thr Pro Glu Asn Cys Pro Gly Trp Leu Asp Val Leu
    790                 795                 800 ccc ttt atc atc cct cac cga cct acc aac gtg gag agc tgt cct gga      2503
Pro Phe Ile Ile Pro His Arg Pro Thr Asn Val Glu Ser Cys Pro Gly
805                 810                 815                 820 ggt aaa cca gaa gct ctt tgg gtt gaa gaa aga ttt aca gct cac att      2551
Gly Lys Pro Glu Ala Leu Trp Val Glu Glu Arg Phe Thr Ala His Ile
                825                 830                 835 gcc cgg gtc cgt gat gta gaa ctt ctc act ggg ctt gac ttc tat cag      2599
Ala Arg Val Arg Asp Val Glu Leu Leu Thr Gly Leu Asp Phe Tyr Gln
            840                 845                 850 gat aaa gtg cag cct gtc tct gaa att ttg caa cta aag aca tat tta      2647
Asp Lys Val Gln Pro Val Ser Glu Ile Leu Gln Leu Lys Thr Tyr Leu
        855                 860                 865 cca aca ttt gaa acc act att taa cttaataatg tctacttaat atataattta    2701
Pro Thr Phe Glu Thr Thr Ile *
    870                 875 ctgtataaag taattttggc aaaatataag tgattttttc tggagaattg taaaataaag    2761
ttttctattt ttccttaaaa aaaaaaccgg aattccgggc ttgggaggct gaggcaggag    2821
actcgcttga acccggggag cagaggttgc agtgagccaa gattgcgcca ttgcactcca    2881
gagcctgggt gacagagcaa gactacatct caaaaaataa ataaataaaa taaaagtaac    2941
aataaaaata aaaagaacag cagagagaat gagcaaggag aaatgtcaca aactattgca    3001
aaatactgtt acactgggtt ggctctccaa gaagatactg gaatctcttc agccatttgc    3061
ttttcagaag tagaaaccag caaaccacct ctaagcggag aacatacgat tctttattaa    3121
gtagctctgg ggaaggaaag aataaaagtt gatagctccc tgattgggaa aaaatgcaca    3181
attaataaag aatgaagatg aaagaaagca tgcttatgtt gtaacacaaa aaaaattcac    3241
aaacgttggt ggaaggaaaa cagtatagaa acattactt taactaaaag ctggaaaaat    3301
tttcagttgg gatgcgactg acaaaaagaa cgggatttcc aggcataaag ttggcgtgag    3361
ctacagaggg caccatgtgg ctcagtggaa gacccttcaa gattcaaagt tccatttgac    3421
agagcaaagg cacttcgcaa ggagaagggt ttaaattatg ggtccaaaag ccaagtggta    3481
aagcgagcaa tttgcagcat aactgcttct cctagacagg gctgagtggg caaaatacga    3541
cagtacacac agtgactatt agccactgcc agaaacaggc tgaacagccc tgggagacaa    3601
gggaaggcag gtggtgggag ttgttcatgg agagaaagga gagttttaga accagcacat    3661
ccactggaga tgctgggcca ccagacccct cccagtcaat aaagtctggt gcctcatttg    3721
atctcagcct catcatgacc ctggagagac cctgatacca tctgccagtc cccgacagct    3781
taggcactcc ttgccatcaa cctgaccccc cgagtggttc tccaggctcc ctgccccacc    3841
cattcaggcc ggaattc                                                   3858
```

<210> SEQ ID NO 7
<211> LENGTH: 875
<212> TYPE: PRT
<213> ORGANISM: Homo Sapiens

<400> SEQUENCE: 7

-continued

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Leu Ala Leu Leu
             20                  25                  30

Val Ile Met Ser Leu Gly Leu Gly Leu Gly Leu Arg Lys Leu
         35                  40                  45

Glu Lys Gln Gly Ser Cys Arg Lys Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
             85                  90                  95

Met Cys Asn Lys Phe Arg Cys Gly Glu Thr Arg Leu Glu Ala Ser Leu
             100                 105                 110

Cys Ser Cys Ser Asp Asp Cys Leu Gln Lys Lys Asp Cys Cys Ala Asp
             115                 120                 125

Tyr Lys Ser Val Cys Gln Gly Glu Thr Ser Trp Leu Glu Glu Asn Cys
 130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
             165                 170                 175

Trp Asp Thr Leu Met Pro Asn Ile Asn Lys Leu Lys Thr Cys Gly Ile
             180                 185                 190

His Ser Lys Tyr Met Arg Ala Met Tyr Pro Thr Lys Thr Phe Pro Asn
             195                 200                 205

His Tyr Thr Ile Val Thr Gly Leu Tyr Pro Glu Ser His Gly Ile Ile
 210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
             245                 250                 255

Leu Thr Ala Met Tyr Gln Gly Leu Lys Ala Ala Thr Tyr Phe Trp Pro
             260                 265                 270

Gly Ser Glu Val Ala Ile Asn Gly Ser Phe Pro Ser Ile Tyr Met Pro
             275                 280                 285

Tyr Asn Gly Ser Val Pro Phe Glu Glu Arg Ile Ser Thr Leu Leu Lys
             290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His His Gly Gly Pro Val Ser Ala
             325                 330                 335

Arg Val Ile Lys Ala Leu Gln Val Val Asp His Ala Phe Gly Met Leu
             340                 345                 350

Met Glu Gly Leu Lys Gln Arg Asn Leu His Asn Cys Val Asn Ile Ile
             355                 360                 365

Leu Leu Ala Asp His Gly Met Asp Gln Thr Tyr Cys Asn Lys Met Glu
             370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
             405                 410                 415
```

-continued

```
Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His Ala
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Gly Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
```

```
                835                 840                  845
Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 8
<211> LENGTH: 3858
<212> TYPE: DNA
<213> ORGANISM: Homo Sapiens
<220> FEATURE:
<221> NAME/KEY: CDS
<222> LOCATION: (44)...(2671)

<400> SEQUENCE: 8
ctactttatt ctgataaaac aggtctatgc agctaccagg aca atg gaa tct acg       55
                                            Met Glu Ser Thr
                                              1 ttg act tta gca acg gaa caa cct gtt aag aag aac act ctt aag aaa      103
Leu Thr Leu Ala Thr Glu Gln Pro Val Lys Lys Asn Thr Leu Lys Lys
  5                  10                  15                  20 tat aaa ata gct tgc att gtt ctt ctt gct ttg ctg gtg atc atg tca      151
Tyr Lys Ile Ala Cys Ile Val Leu Leu Ala Leu Leu Val Ile Met Ser
             25                  30                  35 ctt gga tta ggc ctg ggg ctt gga ctc agg aaa ctg gaa aag caa ggc      199
Leu Gly Leu Gly Leu Gly Leu Gly Leu Arg Lys Leu Glu Lys Gln Gly
         40                  45                  50 agc tgc agg aag aag tgc ttt gat gca tca ttt aga gga ctg gag aac      247
Ser Cys Arg Lys Lys Cys Phe Asp Ala Ser Phe Arg Gly Leu Glu Asn
     55                  60                  65 tgc cgg tgt gat gtg gca tgt aaa gac cga ggt gat tgc tgc tgg gat      295
Cys Arg Cys Asp Val Ala Cys Lys Asp Arg Gly Asp Cys Cys Trp Asp
 70                  75                  80 ttt gaa gac acc tgt gtg gaa tca act cga ata tgg atg tgc aat aaa      343
Phe Glu Asp Thr Cys Val Glu Ser Thr Arg Ile Trp Met Cys Asn Lys
 85                  90                  95                 100 ttt cgt tgt gga gag acc aga tta gag gcc agc ctt tgc tct tgt tca      391
Phe Arg Cys Gly Glu Thr Arg Leu Glu Ala Ser Leu Cys Ser Cys Ser
                105                 110                 115 gat gac tgt ttg cag aag aaa gat tgc tgt gct gac tat aag agt gtt      439
Asp Asp Cys Leu Gln Lys Lys Asp Cys Cys Ala Asp Tyr Lys Ser Val
            120                 125                 130 tgc caa gga gaa acc tca tgg ctg gaa gaa aac tgt gac aca gcc cag      487
Cys Gln Gly Glu Thr Ser Trp Leu Glu Glu Asn Cys Asp Thr Ala Gln
        135                 140                 145 cag tct cag tgc cca gaa ggg ttt gac ctg cca cca gtt atc ttg ttt      535
Gln Ser Gln Cys Pro Glu Gly Phe Asp Leu Pro Pro Val Ile Leu Phe
    150                 155                 160 tct atg gat gga ttt aga gct gaa tat tta tac aca tgg gat act tta      583
Ser Met Asp Gly Phe Arg Ala Glu Tyr Leu Tyr Thr Trp Asp Thr Leu
165                 170                 175                 180 atg cca aat atc aat aaa ctg aaa aca tgt gga att cat tca aaa tac      631
Met Pro Asn Ile Asn Lys Leu Lys Thr Cys Gly Ile His Ser Lys Tyr
                185                 190                 195 atg aga gct atg tat cct acc aaa acc ttc cca aat cat tac acc att      679
Met Arg Ala Met Tyr Pro Thr Lys Thr Phe Pro Asn His Tyr Thr Ile
            200                 205                 210 gtc acg ggc ttg tat cca gag tca cat ggc atc att gac aat aat atg      727
Val Thr Gly Leu Tyr Pro Glu Ser His Gly Ile Ile Asp Asn Asn Met
        215                 220                 225
```

```
tat gat gta aat ctc aac aag aat ttt tca ctt tct tca aag gaa caa       775
Tyr Asp Val Asn Leu Asn Lys Asn Phe Ser Leu Ser Ser Lys Glu Gln
    230                 235                 240 aat aat cca gcc tgg tgg cat ggg caa cca atg tgg ctg aca gca atg       823
Asn Asn Pro Ala Trp Trp His Gly Gln Pro Met Trp Leu Thr Ala Met
245                 250                 255                 260 tat caa ggt tta aaa gcc gct acc tac ttt tgg ccc gga tca gaa gtg       871
Tyr Gln Gly Leu Lys Ala Ala Thr Tyr Phe Trp Pro Gly Ser Glu Val
                265                 270                 275 gct ata aat ggc tcc ttt cct tcc ata tac atg cct tac aac gga agt       919
Ala Ile Asn Gly Ser Phe Pro Ser Ile Tyr Met Pro Tyr Asn Gly Ser
            280                 285                 290 gtc cca ttt gaa gag agg att tct aca ctg tta aaa tgg ctg gac ctg       967
Val Pro Phe Glu Glu Arg Ile Ser Thr Leu Leu Lys Trp Leu Asp Leu
        295                 300                 305 ccc aaa gct gaa aga ccc agg ttt tat acc atg tat ttt gaa gaa cct      1015
Pro Lys Ala Glu Arg Pro Arg Phe Tyr Thr Met Tyr Phe Glu Glu Pro
    310                 315                 320 gat tcc tct gga cat gca ggt gga cca gtc agt gcc aga gta att aaa      1063
Asp Ser Ser Gly His Ala Gly Gly Pro Val Ser Ala Arg Val Ile Lys
325                 330                 335                 340 gcc tta cag gta gta gat cat gct ttt ggg atg ttg atg gaa ggc ctg      1111
Ala Leu Gln Val Val Asp His Ala Phe Gly Met Leu Met Glu Gly Leu
                345                 350                 355 aag cag cgg aat ttg cac aac tgt gtc aat atc atc ctt ctg gct gac      1159
Lys Gln Arg Asn Leu His Asn Cys Val Asn Ile Ile Leu Leu Ala Asp
            360                 365                 370 cat gga atg gac cag act tat tgt aac aag atg gaa tac atg act gat      1207
His Gly Met Asp Gln Thr Tyr Cys Asn Lys Met Glu Tyr Met Thr Asp
        375                 380                 385 tat ttt ccc aga ata aac ttc ttc tac atg tac gaa ggg cct gcc ccc      1255
Tyr Phe Pro Arg Ile Asn Phe Phe Tyr Met Tyr Glu Gly Pro Ala Pro
    390                 395                 400 cgc atc cga gct cat aat ata cct cat gac ttt ttt agt ttt aat tct      1303
Arg Ile Arg Ala His Asn Ile Pro His Asp Phe Phe Ser Phe Asn Ser
405                 410                 415                 420 gag gaa att gtt aga aac ctc agt tgc cga aaa cct gat cag cat ttc      1351
Glu Glu Ile Val Arg Asn Leu Ser Cys Arg Lys Pro Asp Gln His Phe
                425                 430                 435 aag ccc tat ttg act cct gat ttg cca aag cga ctg cac tat gcc aag      1399
Lys Pro Tyr Leu Thr Pro Asp Leu Pro Lys Arg Leu His Tyr Ala Lys
            440                 445                 450 aac gtc aga atc gac aaa gtt cat ctc ttt gtg gat caa cag tgg ctg      1447
Asn Val Arg Ile Asp Lys Val His Leu Phe Val Asp Gln Gln Trp Leu
        455                 460                 465 gct gtt agg agt aaa tca aat aca aat tgt gga gga ggc aac cat ggt      1495
Ala Val Arg Ser Lys Ser Asn Thr Asn Cys Gly Gly Gly Asn His Gly
470                 475                 480 tat aac aat gag ttt agg agc atg gag gct atc ttt ctg gca cat gga      1543
Tyr Asn Asn Glu Phe Arg Ser Met Glu Ala Ile Phe Leu Ala His Gly
                485                 490                 495                 500 ccc agt ttt aaa gag aag act gaa gtt gaa cca ttt gaa aat att gaa      1591
Pro Ser Phe Lys Glu Lys Thr Glu Val Glu Pro Phe Glu Asn Ile Glu
            505                 510                 515 gtc tat aac cta atg tgt gat ctt cta cgc att caa cca gca cca aac      1639
Val Tyr Asn Leu Met Cys Asp Leu Leu Arg Ile Gln Pro Ala Pro Asn
        520                 525                 530 aat gga acc cat ggt agt tta aac cat ctt ctg aag gtg cct ttt tat      1687
Asn Gly Thr His Gly Ser Leu Asn His Leu Leu Lys Val Pro Phe Tyr
535                 540                 545
```

-continued

| | |
|---|---|
| gag cca tcc cat gca gag gag gtg tca aag ttt tct gtt tgt ggc ttt<br>Glu Pro Ser His Ala Glu Glu Val Ser Lys Phe Ser Val Cys Gly Phe<br>550                                  555                           560 | 1735 |
| gct aat cca ttg ccc aca gag tct ctt gac tgt ttc tgc cct cac cta<br>Ala Asn Pro Leu Pro Thr Glu Ser Leu Asp Cys Phe Cys Pro His Leu<br>565                                  570                          575                  580 | 1783 |
| caa aat agt act cag ctg gaa caa gtg aat cag atg cta aat ctc acc<br>Gln Asn Ser Thr Gln Leu Glu Gln Val Asn Gln Met Leu Asn Leu Thr<br>                        585                          590                          595 | 1831 |
| caa gaa gaa ata aca gca aca gtg aaa gta aat ttg cca ttt ggg agg<br>Gln Glu Glu Ile Thr Ala Thr Val Lys Val Asn Leu Pro Phe Gly Arg<br>                   600                          605                          610 | 1879 |
| cct agg gta ctg cag aag aac gtg gac cac tgt ctc ctt tac cac agg<br>Pro Arg Val Leu Gln Lys Asn Val Asp His Cys Leu Leu Tyr His Arg<br>            615                          620                          625 | 1927 |
| gaa tat gtc agt gga ttt gga aaa gct atg agg atg ccc atg tgg agt<br>Glu Tyr Val Ser Gly Phe Gly Lys Ala Met Arg Met Pro Met Trp Ser<br>630                                  635                          640 | 1975 |
| tca tac aca gtc ccc cag ttg gga gac aca tcg cct ctg cct ccc act<br>Ser Tyr Thr Val Pro Gln Leu Gly Asp Thr Ser Pro Leu Pro Pro Thr<br>645                                  650                          655                  660 | 2023 |
| gtc cca gac tgt ctg cgg gct gat gtc agg gtt cct cct tct gag agc<br>Val Pro Asp Cys Leu Arg Ala Asp Val Arg Val Pro Pro Ser Glu Ser<br>                   665                          670                          675 | 2071 |
| caa aaa tgt tcc ttc tat tta gca gac aag aat atc acc cac ggc ttc<br>Gln Lys Cys Ser Phe Tyr Leu Ala Asp Lys Asn Ile Thr His Gly Phe<br>            680                          685                          690 | 2119 |
| ctc tat cct cct gcc agc aat aga aca tca gat agc caa tat gat gct<br>Leu Tyr Pro Pro Ala Ser Asn Arg Thr Ser Asp Ser Gln Tyr Asp Ala<br>695                                  700                          705 | 2167 |
| tta att act agc aat ttg gta cct atg tat gaa gaa ttc aga aaa atg<br>Leu Ile Thr Ser Asn Leu Val Pro Met Tyr Glu Glu Phe Arg Lys Met<br>710                                  715                          720 | 2215 |
| tgg gac tac ttc cac agt gtt ctt ctt ata aaa cat gcc aca gaa aga<br>Trp Asp Tyr Phe His Ser Val Leu Leu Ile Lys His Ala Thr Glu Arg<br>725                                  730                          735                  740 | 2263 |
| aat gga gta aat gtg gtt agt gga cca ata ttt gat tat aat tat gat<br>Asn Gly Val Asn Val Val Ser Gly Pro Ile Phe Asp Tyr Asn Tyr Asp<br>                   745                          750                          755 | 2311 |
| ggc cat ttt gat gct cca gat gaa att acc aaa cat tta gcc aac act<br>Gly His Phe Asp Ala Pro Asp Glu Ile Thr Lys His Leu Ala Asn Thr<br>            760                          765                          770 | 2359 |
| gat gtt ccc atc cca aca cac tac ttt gtg gtg ctg acc agt tgt aaa<br>Asp Val Pro Ile Pro Thr His Tyr Phe Val Val Leu Thr Ser Cys Lys<br>775                                  780                          785 | 2407 |
| aac aag agc cac aca ccg gaa aac tgc cct ggg tgg ctg gat gtc cta<br>Asn Lys Ser His Thr Pro Glu Asn Cys Pro Gly Trp Leu Asp Val Leu<br>790                                  795                          800 | 2455 |
| ccc ttt atc atc cct cac cga cct acc aac gtg gag agc tgt cct gaa<br>Pro Phe Ile Ile Pro His Arg Pro Thr Asn Val Glu Ser Cys Pro Glu<br>805                                  810                          815                  820 | 2503 |
| ggt aaa cca gaa gct ctt tgg gtt gaa gaa aga ttt aca gct cac att<br>Gly Lys Pro Glu Ala Leu Trp Val Glu Glu Arg Phe Thr Ala His Ile<br>                        825                          830                          835 | 2551 |
| gcc cgg gtc cgt gat gta gaa ctt ctc act ggg ctt gac ttc tat cag<br>Ala Arg Val Arg Asp Val Glu Leu Leu Thr Gly Leu Asp Phe Tyr Gln<br>                   840                          845                          850 | 2599 |
| gat aaa gtg cag cct gtc tct gaa att ttg caa cta aag aca tat tta<br>Asp Lys Val Gln Pro Val Ser Glu Ile Leu Gln Leu Lys Thr Tyr Leu | 2647 |

-continued

```
                855               860               865
cca aca ttt gaa acc cct att taa cttaataatg tctacttaat atataattta    2701
Pro Thr Phe Glu Thr Pro Ile  *
        870               875 ctgtataaag taattttggc aaaatataag tgattttttc tggagaattg taaaataaag   2761
ttttctattt ttccttaaaa aaaaaaccgg aattccgggc ttgggaggct gaggcaggag   2821
actcgcttga acccgggagg cagaggttgc agtgagccaa gattgcgcca ttgcactcca   2881
gagcctgggt gacagagcaa gactacatct caaaaaataa ataaataaaa taaaagtaac   2941
aataaaaata aaaagaacag cagagagaat gagcaaggag aaatgtcaca aactattgca   3001
aaatactgtt acactgggtt ggctctccaa gaagatactg gaatctcttc agccatttgc   3061
ttttcagaag tagaaaccag caaaccacct ctaagcggag aacatacgat tctttattaa   3121
gtagctctgg ggaaggaaag aataaaagtt gatagctccc tgattgggaa aaaatgcaca   3181
attaataaag aatgaagatg aaagaaagca tgcttatgtt gtaacacaaa aaaaattcac   3241
aaacgttggt ggaaggaaaa cagtatagaa acattactt taactaaaag ctggaaaaat    3301
tttcagttgg gatgcgactg acaaaaagaa cgggatttcc aggcataaag ttggcgtgag   3361
ctacagaggg caccatgtgg ctcagtggaa gacccttcaa gattcaaagt tccatttgac   3421
agagcaaagg cacttcgcaa ggagaagggt ttaaattatg ggtccaaaag ccaagtggta   3481
aagcgagcaa tttgcagcat aactgcttct cctagacagg gctgagtggg caaaatacga   3541
cagtacacac agtgactatt agccactgcc agaaacaggc tgaacagccc tgggagacaa   3601
gggaaggcag gtggtgggag ttgttcatgg agagaaagga gagttttaga accagcacat   3661
ccactggaga tgctgggcca ccagacccct cccagtcaat aaagtctggt gcctcatttg   3721
atctcagcct catcatgacc ctggagagac cctgatacca tctgccagtc cccgacagct   3781
taggcactcc ttgccatcaa cctgacccc cgagtggttc tccaggctcc ctgccccacc   3841
cattcaggcc ggaattc                                                   3858
```

<210> SEQ ID NO 9
<211> LENGTH: 875
<212> TYPE: PRT
<213> ORGANISM: Homo Sapiens

<400> SEQUENCE: 9

```
Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Arg Lys Leu
                35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
```

-continued

```
                130                 135                 140
Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
                180                 185                 190

His Ser Lys Tyr Met Arg Ala Met Tyr Pro Thr Lys Thr Phe Pro Asn
                195                 200                 205

His Tyr Thr Ile Val Thr Gly Leu Tyr Pro Glu Ser His Gly Ile Ile
                210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
                260                 265                 270

Gly Ser Glu Val Ala Ile Asn Gly Ser Phe Pro Ser Ile Tyr Met Pro
                275                 280                 285

Tyr Asn Gly Ser Val Pro Phe Glu Glu Arg Ile Ser Thr Leu Leu Lys
                290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
                340                 345                 350

Met Glu Gly Leu Lys Gln Arg Asn Leu His Asn Cys Val Asn Ile Ile
                355                 360                 365

Leu Leu Ala Asp His Gly Met Asp Gln Thr Tyr Cys Asn Lys Met Glu
                370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
                435                 440                 445

His Tyr Ala Lys Asn Val Arg Ile Asp Lys Val His Leu Phe Val Asp
                450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
                500                 505                 510

Glu Asn Ile Glu Val Tyr Asn Leu Met Cys Asp Leu Leu Arg Ile Gln
                515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560
```

-continued

```
Val Cys Gly Phe Ala Asn Pro Leu Pro Thr Glu Ser Leu Asp Cys Phe
            565                 570                 575
Cys Pro His Leu Gln Asn Ser Thr Gln Leu Glu Gln Val Asn Gln Met
        580                 585                 590
Leu Asn Leu Thr Gln Glu Glu Ile Thr Ala Thr Val Lys Val Asn Leu
    595                 600                 605
Pro Phe Gly Arg Pro Arg Val Leu Gln Lys Asn Val Asp His Cys Leu
610                 615                 620
Leu Tyr His Arg Glu Tyr Val Ser Gly Phe Lys Ala Met Arg Met
625                 630                 635                 640
Pro Met Trp Ser Ser Tyr Thr Val Pro Gln Leu Gly Asp Thr Ser Pro
            645                 650                 655
Leu Pro Pro Thr Val Pro Asp Cys Leu Arg Ala Asp Val Arg Val Pro
        660                 665                 670
Pro Ser Glu Ser Gln Lys Cys Ser Phe Tyr Leu Ala Asp Lys Asn Ile
    675                 680                 685
Thr His Gly Phe Leu Tyr Pro Pro Ala Ser Asn Arg Thr Ser Asp Ser
690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Ile Lys His
            725                 730                 735
Ala Thr Glu Arg Asn Gly Val Asn Val Val Ser Gly Pro Ile Phe Asp
        740                 745                 750
Tyr Asn Tyr Asp Gly His Phe Asp Ala Pro Asp Glu Ile Thr Lys His
    755                 760                 765
Leu Ala Asn Thr Asp Val Pro Ile Pro Thr His Tyr Phe Val Val Leu
770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
            805                 810                 815
Ser Cys Pro Glu Gly Lys Pro Glu Ala Leu Trp Val Glu Arg Phe
        820                 825                 830
Thr Ala His Ile Ala Arg Val Arg Asp Val Glu Leu Leu Thr Gly Leu
    835                 840                 845
Asp Phe Tyr Gln Asp Lys Val Gln Pro Val Ser Glu Ile Leu Gln Leu
850                 855                 860
Lys Thr Tyr Leu Pro Thr Phe Glu Thr Pro Ile
865                 870                 875

<210> SEQ ID NO 10
<211> LENGTH: 3858
<212> TYPE: DNA
<213> ORGANISM: Homo Sapiens
<220> FEATURE:
<221> NAME/KEY: CDS
<222> LOCATION: (44)...(2671)

<400> SEQUENCE: 10
ctactttatt ctgataaaac aggtctatgc agctaccagg aca atg gaa tct acg      55
                                            Met Glu Ser Thr
                                              1 ttg act tta gca acg gaa caa cct gtt aag aag aac act ctt aag aaa    103
Leu Thr Leu Ala Thr Glu Gln Pro Val Lys Lys Asn Thr Leu Lys Lys
  5                  10                  15                  20
```

```
tat aaa ata gct tgc att gtt ctt ctt gct ttg ctg gtg atc atg tca    151
Tyr Lys Ile Ala Cys Ile Val Leu Leu Ala Leu Leu Val Ile Met Ser
            25                  30                  35 ctt gga tta ggc ctg ggg ctt gga ctc agg aaa ctg gaa aag caa ggc    199
Leu Gly Leu Gly Leu Gly Leu Gly Leu Arg Lys Leu Glu Lys Gln Gly
        40                  45                  50 agc tgc agg aag aag tgc ttt gat gca tca ttt aga gga ctg gag aac    247
Ser Cys Arg Lys Lys Cys Phe Asp Ala Ser Phe Arg Gly Leu Glu Asn
        55                  60                  65 tgc cgg tgt gat gtg gca tgt aaa gac cga ggt gat tgc tgc tgg gat    295
Cys Arg Cys Asp Val Ala Cys Lys Asp Arg Gly Asp Cys Cys Trp Asp
    70                  75                  80 ttt gaa gac acc tgt gtg gaa tca act cga ata tgg atg tgc aat aaa    343
Phe Glu Asp Thr Cys Val Glu Ser Thr Arg Ile Trp Met Cys Asn Lys
85                  90                  95                  100 ttt cgt tgt gga gag acc aga tta gag gcc agc ctt tgc tct tgt tca    391
Phe Arg Cys Gly Glu Thr Arg Leu Glu Ala Ser Leu Cys Ser Cys Ser
                105                 110                 115 gat gac tgt ttg cag aag aaa gat tgc tgt gct gac tat aag agt gtt    439
Asp Asp Cys Leu Gln Lys Lys Asp Cys Cys Ala Asp Tyr Lys Ser Val
            120                 125                 130 tgc caa gga gaa acc tca tgg ctg gaa gaa aac tgt gac aca gcc cag    487
Cys Gln Gly Glu Thr Ser Trp Leu Glu Glu Asn Cys Asp Thr Ala Gln
        135                 140                 145 cag tct cag tgc cca gaa ggg ttt gac ctg cca cca gtt atc ttg ttt    535
Gln Ser Gln Cys Pro Glu Gly Phe Asp Leu Pro Pro Val Ile Leu Phe
        150                 155                 160 tct atg gat gga ttt aga gct gaa tat tta tac aca tgg gat act tta    583
Ser Met Asp Gly Phe Arg Ala Glu Tyr Leu Tyr Thr Trp Asp Thr Leu
165                 170                 175                 180 atg cca aat atc aat aaa ctg aaa aca tgt gga att cat tca aaa tac    631
Met Pro Asn Ile Asn Lys Leu Lys Thr Cys Gly Ile His Ser Lys Tyr
                185                 190                 195 atg aga gct atg tat cct acc aaa acc ttc cca aat cat tac acc att    679
Met Arg Ala Met Tyr Pro Thr Lys Thr Phe Pro Asn His Tyr Thr Ile
            200                 205                 210 gtc acg ggc ttg tat cca gag tca cat ggc atc att gac aat aat atg    727
Val Thr Gly Leu Tyr Pro Glu Ser His Gly Ile Ile Asp Asn Asn Met
        215                 220                 225 tat gat gta aat ctc aac aag aat ttt tca ctt tct tca aag gaa caa    775
Tyr Asp Val Asn Leu Asn Lys Asn Phe Ser Leu Ser Ser Lys Glu Gln
        230                 235                 240 aat aat cca gcc tgg tgg cat ggg caa cca atg tgg ctg aca gca atg    823
Asn Asn Pro Ala Trp Trp His Gly Gln Pro Met Trp Leu Thr Ala Met
245                 250                 255                 260 tat caa ggt tta aaa gcc gct acc tac ttt tgg ccc gga tca gaa gtg    871
Tyr Gln Gly Leu Lys Ala Ala Thr Tyr Phe Trp Pro Gly Ser Glu Val
                265                 270                 275 gct ata aat ggc tcc ttt cct tcc ata tac atg cct tac aac gga agt    919
Ala Ile Asn Gly Ser Phe Pro Ser Ile Tyr Met Pro Tyr Asn Gly Ser
            280                 285                 290 gtc cca ttt gaa gag agg att tct aca ctg tta aaa tgg ctg gac ctg    967
Val Pro Phe Glu Glu Arg Ile Ser Thr Leu Leu Lys Trp Leu Asp Leu
        295                 300                 305 ccc aaa gct gaa aga ccc agg ttt tat acc atg tat ttt gaa gaa cct    1015
Pro Lys Ala Glu Arg Pro Arg Phe Tyr Thr Met Tyr Phe Glu Glu Pro
310                 315                 320 gat tcc tct gga cat gca ggt gga cca gtc agt gcc aga gta att aaa    1063
Asp Ser Ser Gly His Ala Gly Gly Pro Val Ser Ala Arg Val Ile Lys
```

```
                                                          -continued
325             330              335              340 gcc tta cag gta gta gat cat gct ttt ggg atg ttg atg gaa ggc ctg         1111
Ala Leu Gln Val Val Asp His Ala Phe Gly Met Leu Met Glu Gly Leu
                345              350              355 aag cag cgg aat ttg cac aac tgt gtc aat atc atc ctt ctg gct gac         1159
Lys Gln Arg Asn Leu His Asn Cys Val Asn Ile Ile Leu Leu Ala Asp
            360              365              370 cat gga atg gac cag act tat tgt aac aag atg gaa tac atg act gat         1207
His Gly Met Asp Gln Thr Tyr Cys Asn Lys Met Glu Tyr Met Thr Asp
        375              380              385 tat ttt ccc aga ata aac ttc ttc tac atg tac gaa ggg cct gcc ccc         1255
Tyr Phe Pro Arg Ile Asn Phe Phe Tyr Met Tyr Glu Gly Pro Ala Pro
    390              395              400 cgc atc cga gct cat aat ata cct cat gac ttt ttt agt ttt aat tct         1303
Arg Ile Arg Ala His Asn Ile Pro His Asp Phe Phe Ser Phe Asn Ser
405              410              415              420 gag gaa att gtt aga aac ctc agt tgc cga aaa cct gat cag cat ttc         1351
Glu Glu Ile Val Arg Asn Leu Ser Cys Arg Lys Pro Asp Gln His Phe
                425              430              435 aag ccc tat ttg act cct gat ttg cca aag cga ctg cac tat gcc aag         1399
Lys Pro Tyr Leu Thr Pro Asp Leu Pro Lys Arg Leu His Tyr Ala Lys
            440              445              450 aac gtc aga atc gac aaa gtt cat ctc ttt gtg gat caa cag tgg ctg         1447
Asn Val Arg Ile Asp Lys Val His Leu Phe Val Asp Gln Gln Trp Leu
        455              460              465 gct gtt agg agt aaa tca aat aca aat tgt gga gga ggc aac cat ggt         1495
Ala Val Arg Ser Lys Ser Asn Thr Asn Cys Gly Gly Gly Asn His Gly
    470              475              480 tat aac aat gag ttt agg agc atg gag gct atc ttt ctg gca cat gga         1543
Tyr Asn Asn Glu Phe Arg Ser Met Glu Ala Ile Phe Leu Ala His Gly
485              490              495              500 ccc agt ttt aaa gag aag act gaa gtt gaa cca ttt gaa aat att gaa         1591
Pro Ser Phe Lys Glu Lys Thr Glu Val Glu Pro Phe Glu Asn Ile Glu
                505              510              515 gtc tat aac cta atg tgt gat ctt cta cgc att caa cca gca cca aac         1639
Val Tyr Asn Leu Met Cys Asp Leu Leu Arg Ile Gln Pro Ala Pro Asn
            520              525              530 aat gga acc cat ggt agt tta aac cat ctt ctg aag gtg cct ttt tat         1687
Asn Gly Thr His Gly Ser Leu Asn His Leu Leu Lys Val Pro Phe Tyr
        535              540              545 gag cca tcc cat gca gag gag gtg tca aag ttt tct gtt tgt ggc ttt         1735
Glu Pro Ser His Ala Glu Glu Val Ser Lys Phe Ser Val Cys Gly Phe
    550              555              560 gct aat cca ttg ccc aca gag tct ctt gac tgt ttc tgc cct cac cta         1783
Ala Asn Pro Leu Pro Thr Glu Ser Leu Asp Cys Phe Cys Pro His Leu
565              570              575              580 caa aat agt act cag ctg gaa caa gtg aat cag atg cta aat ctc acc         1831
Gln Asn Ser Thr Gln Leu Glu Gln Val Asn Gln Met Leu Asn Leu Thr
                585              590              595 caa gaa gaa ata aca gca aca gtg aaa gta aat ttg cca ttt ggg agg         1879
Gln Glu Glu Ile Thr Ala Thr Val Lys Val Asn Leu Pro Phe Gly Arg
            600              605              610 cct agg gta ctg cag aag aac gtg gac cac tgt ctc ctt tac cac agg         1927
Pro Arg Val Leu Gln Lys Asn Val Asp His Cys Leu Leu Tyr His Arg
        615              620              625 gaa tat gtc agt gga ttt gga aaa gct atg agg atg ccc atg tgg agt         1975
Glu Tyr Val Ser Gly Phe Gly Lys Ala Met Arg Met Pro Met Trp Ser
    630              635              640 tca tac aca gtc ccc cag ttg gga gac aca tcg cct ctg cct ccc act         2023
```

-continued

| | | |
|---|---|---|
| Ser Tyr Thr Val Pro Gln Leu Gly Asp Thr Ser Pro Leu Pro Pro Thr<br>645                      650                      655                      660 | | |
| gtc cca gac tgt ctg cgg gct gat gtc agg gtt cct cct tct gag agc<br>Val Pro Asp Cys Leu Arg Ala Asp Val Arg Val Pro Pro Ser Glu Ser<br>                      665                      670                      675 | 2071 |
| caa aaa tgt tcc ttc tat tta gca gac aag aat atc acc cac ggc ttc<br>Gln Lys Cys Ser Phe Tyr Leu Ala Asp Lys Asn Ile Thr His Gly Phe<br>                680                      685                      690 | 2119 |
| ctc tat cct cct gcc agc aat aga aca tca gat agc caa tat gat gct<br>Leu Tyr Pro Pro Ala Ser Asn Arg Thr Ser Asp Ser Gln Tyr Asp Ala<br>        695                      700                      705 | 2167 |
| tta att act agc aat ttg gta cct atg tat gaa gaa ttc aga aaa atg<br>Leu Ile Thr Ser Asn Leu Val Pro Met Tyr Glu Glu Phe Arg Lys Met<br>710                      715                      720 | 2215 |
| tgg gac tac ttc cac agt gtt ctt ctt ata aaa cat gcc aca gaa aga<br>Trp Asp Tyr Phe His Ser Val Leu Leu Ile Lys His Ala Thr Glu Arg<br>725                      730                      735                      740 | 2263 |
| aat gga gta aat gtg gtt agt gga cca ata ttt gat tat aat tat gat<br>Asn Gly Val Asn Val Val Ser Gly Pro Ile Phe Asp Tyr Asn Tyr Asp<br>                      745                      750                      755 | 2311 |
| ggc cat ttt gat gct cca gat gaa att acc aaa cat tta gcc aac act<br>Gly His Phe Asp Ala Pro Asp Glu Ile Thr Lys His Leu Ala Asn Thr<br>            760                      765                      770 | 2359 |
| gat gtt ccc atc cca aca cac tac ttt gtg gtg ctg acc agt tgt aaa<br>Asp Val Pro Ile Pro Thr His Tyr Phe Val Val Leu Thr Ser Cys Lys<br>775                      780                      785 | 2407 |
| aac aag agc cac aca ccg gaa aac tgc cct ggg tgg ctg gat gtc cta<br>Asn Lys Ser His Thr Pro Glu Asn Cys Pro Gly Trp Leu Asp Val Leu<br>        790                      795                      800 | 2455 |
| ccc ttt atc atc cct cac cga cct acc aac gtg gag agc tgt cct gaa<br>Pro Phe Ile Ile Pro His Arg Pro Thr Asn Val Glu Ser Cys Pro Glu<br>805                      810                      815                      820 | 2503 |
| ggt aaa cca gaa gct ctt tgg gtt gaa gaa aga ttt aca gct cac att<br>Gly Lys Pro Glu Ala Leu Trp Val Glu Glu Arg Phe Thr Ala His Ile<br>                      825                      830                      835 | 2551 |
| gcc cgg gtc cgt gat gta gaa ctt ctc act ggg ctt gac ttc tat cag<br>Ala Arg Val Arg Asp Val Glu Leu Leu Thr Gly Leu Asp Phe Tyr Gln<br>            840                      845                      850 | 2599 |
| gat aaa gtg cag cct gtc tct gaa att ttg caa cta aag aca tat tta<br>Asp Lys Val Gln Pro Val Ser Glu Ile Leu Gln Leu Lys Thr Tyr Leu<br>855                      860                      865 | 2647 |
| cca aca ttt gaa acc act att taa cttaataatg tctacttaat atataattta<br>Pro Thr Phe Glu Thr Thr Ile *<br>        870                      875 | 2701 |
| ctgtataaag taattttggc aaaatataag tgatttttc tggagaattg taaaataaag | 2761 |
| ttttctattt ttccttaaaa aaaaaaccgg aattccgggc ttgggaggct gaggcaggag | 2821 |
| actcgcttga acccgggagg cagaggttgc agtgagccaa gattgcgcca ttgcactcca | 2881 |
| gagcctgggt gacagagcaa gactacatct caaaaaataa ataaataaaa taaaagtaac | 2941 |
| aataaaaata aaaagaacag cagagagaat gagcaaggag aaatgtcaca aactattgca | 3001 |
| aaatactgtt acactgggtt ggctctccaa gaagatactg gaatctcttc agccatttgc | 3061 |
| ttttcagaag tagaaaccag caaaccacct ctaagcggag aacatacgat tctttattaa | 3121 |
| gtagctctgg ggaaggaaag aataaaagtt gatagctccc tgattgggaa aaaatgcaca | 3181 |
| attaataaag aatgaagatg aaagaaagca tgcttatgtt gtaacacaaa acaaattcac | 3241 |
| aaacgttggt ggaaggaaaa cagtatagaa aacattactt taactaaaag ctggaaaaat | 3301 |

-continued

```
tttcagttgg gatgcgactg acaaaaagaa cgggatttcc aggcataaag ttggcgtgag   3361
ctacagaggg caccatgtgg ctcagtggaa gaccctcaa gattcaaagt tccatttgac   3421
agagcaaagg cacttcgcaa ggagaaggt ttaaattatg ggtccaaaag ccaagtggta   3481
aagcgagcaa tttgcagcat aactgcttct cctagacagg gctgagtggg caaaatacga   3541
cagtacacac agtgactatt agccactgcc agaaacaggc tgaacagccc tgggagacaa   3601
gggaaggcag gtggtgggag ttgttcatgg agagaaagga gagttttaga accagcacat   3661
ccactggaga tgctgggcca ccagacccct cccagtcaat aaagtctggt gcctcatttg   3721
atctcagcct catcatgacc ctggagagac cctgatacca tctgccagtc ccgacagct   3781 taggcactcc ttgccatcaa cctgaccccc cgagtggttc tccaggctcc ctgccccacc   3841
cattcaggcc ggaattc                                                  3858
```

<210> SEQ ID NO 11
<211> LENGTH: 875
<212> TYPE: PRT
<213> ORGANISM: Homo Sapiens

<400> SEQUENCE: 11

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270
```

-continued

```
Gly Ser Glu Val Ala Ile Asn Gly Ser Phe Pro Ser Ile Tyr Met Pro
        275                 280                 285

Tyr Asn Gly Ser Val Pro Phe Glu Arg Ile Ser Thr Leu Leu Lys
        290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
                340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
        370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
        530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
```

-continued

```
                690               695               700
Gln Tyr Asp Ala Leu Ile Thr Ser Asn Leu Val Pro Met Tyr Glu Glu
705               710               715               720

Phe Arg Lys Met Trp Asp Tyr Phe His Ser Val Leu Leu Ile Lys His
              725               730               735

Ala Thr Glu Arg Asn Gly Val Asn Val Val Ser Gly Pro Ile Phe Asp
              740               745               750

Tyr Asn Tyr Asp Gly His Phe Asp Ala Pro Asp Glu Ile Thr Lys His
          755               760               765

Leu Ala Asn Thr Asp Val Pro Ile Pro Thr His Tyr Phe Val Val Leu
770               775               780

Thr Ser Cys Lys Asn Lys Ser His Thr Pro Glu Asn Cys Pro Gly Trp
785               790               795               800

Leu Asp Val Leu Pro Phe Ile Ile Pro His Arg Pro Thr Asn Val Glu
              805               810               815

Ser Cys Pro Glu Gly Lys Pro Glu Ala Leu Trp Val Glu Glu Arg Phe
              820               825               830

Thr Ala His Ile Ala Arg Val Arg Asp Val Glu Leu Leu Thr Gly Leu
              835               840               845

Asp Phe Tyr Gln Asp Lys Val Gln Pro Val Ser Glu Ile Leu Gln Leu
850               855               860

Lys Thr Tyr Leu Pro Thr Phe Glu Thr Thr Ile
865               870               875

<210> SEQ ID NO 12
<211> LENGTH: 3165
<212> TYPE: DNA
<213> ORGANISM: Homo Sapiens
<220> FEATURE:
<221> NAME/KEY: CDS
<222> LOCATION: (84)...(2711)

<400> SEQUENCE: 12 tacagtttc tctttgccag actagactaa agaaggagca ctactttatt ctgataaaac        60
aggtctatgc agctaccagg aca atg gaa tct acg ttg act tta gca acg gaa       113
                         Met Glu Ser Thr Leu Thr Leu Ala Thr Glu
                           1               5                  10 caa cct gtt aag aag aac act ctt aag aaa tat aaa ata gct tgc att         161
Gln Pro Val Lys Lys Asn Thr Leu Lys Lys Tyr Lys Ile Ala Cys Ile
                15                  20                  25 gtt ctt ctt gct ttg ctg gtg atc atg tca ctt gga tta ggc ctg ggg         209
Val Leu Leu Ala Leu Leu Val Ile Met Ser Leu Gly Leu Gly Leu Gly
            30                  35                  40 ctt gga ctc agg aaa ctg gaa aag caa ggc agc tgc agg aag aag tgc         257
Leu Gly Leu Arg Lys Leu Glu Lys Gln Gly Ser Cys Arg Lys Lys Cys
        45                  50                  55 ttt gat gca tca ttt aga gga ctg gag aac tgc cgg tgt gat gtg gca         305
Phe Asp Ala Ser Phe Arg Gly Leu Glu Asn Cys Arg Cys Asp Val Ala
    60                  65                  70 tgt aaa gac cga ggt gat tgc tgc tgg gat ttt gaa gac acc tgt gtg         353
Cys Lys Asp Arg Gly Asp Cys Cys Trp Asp Phe Glu Asp Thr Cys Val
75                  80                  85                  90 gaa tca act cga ata tgg atg tgc aat aaa ttt cgt tgt gga gag acc         401
Glu Ser Thr Arg Ile Trp Met Cys Asn Lys Phe Arg Cys Gly Glu Thr
                95                 100                 105 aga tta gag gcc agc ctt tgc tct tgt tca gat gac tgt ttg cag agg         449
Arg Leu Glu Ala Ser Leu Cys Ser Cys Ser Asp Asp Cys Leu Gln Arg
            110                 115                 120
```

```
aaa gat tgc tgt gct gac tat aag agt gtt tgc caa gga gaa acc tca      497
Lys Asp Cys Cys Ala Asp Tyr Lys Ser Val Cys Gln Gly Glu Thr Ser
        125                 130                 135 tgg ctg gaa gaa aac tgt gac aca gcc cag cag tct cag tgc cca gaa      545
Trp Leu Glu Glu Asn Cys Asp Thr Ala Gln Gln Ser Gln Cys Pro Glu
140                 145                 150 ggg ttt gac ctg cca cca gtt atc ttg ttt tct atg gat gga ttt aga      593
Gly Phe Asp Leu Pro Pro Val Ile Leu Phe Ser Met Asp Gly Phe Arg
155                 160                 165                 170 gct gaa tat tta tac aca tgg gat act tta atg cca aat atc aat aaa      641
Ala Glu Tyr Leu Tyr Thr Trp Asp Thr Leu Met Pro Asn Ile Asn Lys
                175                 180                 185 ctg aaa aca tgt gga att cat tca aaa tac atg aga gct atg tat cct      689
Leu Lys Thr Cys Gly Ile His Ser Lys Tyr Met Arg Ala Met Tyr Pro
                190                 195                 200 acc aaa acc ttc cca aat cat tac acc att gtc acg ggc ttg tat ccg      737
Thr Lys Thr Phe Pro Asn His Tyr Thr Ile Val Thr Gly Leu Tyr Pro
            205                 210                 215 gag tca cat ggc atc att gac aat aat atg tat gat gta aat ctc aac      785
Glu Ser His Gly Ile Ile Asp Asn Asn Met Tyr Asp Val Asn Leu Asn
220                 225                 230 aag aat ttt tca ctt tct tca aag gaa caa aat aat cca gcc tgg tgg      833
Lys Asn Phe Ser Leu Ser Ser Lys Glu Gln Asn Asn Pro Ala Trp Trp
235                 240                 245                 250 cat ggg caa cca atg tgg ctg aca gca atg tat caa ggt tta aaa gcc      881
His Gly Gln Pro Met Trp Leu Thr Ala Met Tyr Gln Gly Leu Lys Ala
                255                 260                 265 gct acc tac ttt tgg ccc gga tca gaa gtg gct ata aat ggc tcc ttt      929
Ala Thr Tyr Phe Trp Pro Gly Ser Glu Val Ala Ile Asn Gly Ser Phe
                270                 275                 280 cct tcc ata tac atg cct tac aac gga agt gtc cca ttt gaa gag agg      977
Pro Ser Ile Tyr Met Pro Tyr Asn Gly Ser Val Pro Phe Glu Glu Arg
            285                 290                 295 att tct aca ctg tta aaa tgg ctg gac ctg ccc aaa gct gag aga ccc     1025
Ile Ser Thr Leu Leu Lys Trp Leu Asp Leu Pro Lys Ala Glu Arg Pro
300                 305                 310 agg ttt tat acc atg ttt ttt gaa gaa cct gat tcc tct gga cat gca     1073
Arg Phe Tyr Thr Met Phe Phe Glu Glu Pro Asp Ser Ser Gly His Ala
315                 320                 325                 330 ggt gga cca gtc agt gcc aga gta att aaa gcc tta cag gta gta gat     1121
Gly Gly Pro Val Ser Ala Arg Val Ile Lys Ala Leu Gln Val Val Asp
                335                 340                 345 cat gct ttt ggg atg ttg atg gaa ggc ctg aag cag cgg aat ttg cac     1169
His Ala Phe Gly Met Leu Met Glu Gly Leu Lys Gln Arg Asn Leu His
                350                 355                 360 aac tgt gtc aat atc atc ctt ctg gct gac cat gga atg gac cag act     1217
Asn Cys Val Asn Ile Ile Leu Leu Ala Asp His Gly Met Asp Gln Thr
            365                 370                 375 tat tgt aac aag atg gaa tac atg act gat tat ttt ccc aga ata aac     1265
Tyr Cys Asn Lys Met Glu Tyr Met Thr Asp Tyr Phe Pro Arg Ile Asn
380                 385                 390 ttc ttc tac atg tac gaa ggg cct gcc ccc cgc gtc cga gct cat aat     1313
Phe Phe Tyr Met Tyr Glu Gly Pro Ala Pro Arg Val Arg Ala His Asn
395                 400                 405                 410 ata cct cat gac ttt ttt agt ttt aat tct gag gaa att gtt aga aac     1361
Ile Pro His Asp Phe Phe Ser Phe Asn Ser Glu Glu Ile Val Arg Asn
                415                 420                 425 ctc agt tgc cga aaa cct gat cag cat ttc aag ccc tat ttg act cct     1409
Leu Ser Cys Arg Lys Pro Asp Gln His Phe Lys Pro Tyr Leu Thr Pro
```

-continued

```
                430                    435                    440
gat ttg cca aag cga ctg cac tat gcc aag aac gtc aga atc gac aaa         1457
Asp Leu Pro Lys Arg Leu His Tyr Ala Lys Asn Val Arg Ile Asp Lys
        445                    450                    455 gtt cat ctc ttt gtg gat caa cag tgg ctg gct gtt agg agt aaa tca         1505
Val His Leu Phe Val Asp Gln Gln Trp Leu Ala Val Arg Ser Lys Ser
    460                    465                    470 aat aca aat tgt gga gga ggc aac cat ggt tat aac aat gag ttt agg         1553
Asn Thr Asn Cys Gly Gly Gly Asn His Gly Tyr Asn Asn Glu Phe Arg
475                    480                    485                    490 agc atg gag gct atc ttt ctg gca cat gga ccc agt ttt aaa gag aag         1601
Ser Met Glu Ala Ile Phe Leu Ala His Gly Pro Ser Phe Lys Glu Lys
                495                    500                    505 act gaa gtt gaa cca ttt gaa aat att gaa gtc tat aac cta atg tgt         1649
Thr Glu Val Glu Pro Phe Glu Asn Ile Glu Val Tyr Asn Leu Met Cys
            510                    515                    520 gat ctt cta cgc att caa cca gca cca aac aat gga acc cat ggt agt         1697
Asp Leu Leu Arg Ile Gln Pro Ala Pro Asn Asn Gly Thr His Gly Ser
        525                    530                    535 tta aac cat ctt ctg aag gtg cct ttt tat gag cca tcc cat gca gag         1745
Leu Asn His Leu Leu Lys Val Pro Phe Tyr Glu Pro Ser His Ala Glu
    540                    545                    550 gag gtg tca aag ttt tct gtt tgt ggc ttt gct aat cca ttg ccc aca         1793
Glu Val Ser Lys Phe Ser Val Cys Gly Phe Ala Asn Pro Leu Pro Thr
555                    560                    565                    570 gag tct ctt gac tgt ttc tgc cct cac cta caa aat agt act cag ctg         1841
Glu Ser Leu Asp Cys Phe Cys Pro His Leu Gln Asn Ser Thr Gln Leu
                575                    580                    585 gaa caa gtg aat cag atg cta aat ctc acc caa gaa gaa ata aca gca         1889
Glu Gln Val Asn Gln Met Leu Asn Leu Thr Gln Glu Glu Ile Thr Ala
            590                    595                    600 aca gtg aaa gta aat ttg cca ttt ggg agg cct agg gta ctg cag aag         1937
Thr Val Lys Val Asn Leu Pro Phe Gly Arg Pro Arg Val Leu Gln Lys
        605                    610                    615 aac gtg gac cac tgt ctc ctt tac cac agg gaa tat gtc agt gga ttt         1985
Asn Val Asp His Cys Leu Leu Tyr His Arg Glu Tyr Val Ser Gly Phe
    620                    625                    630 gga aaa gct atg agg atg ccc atg tgg agt tca tac aca gtc ccc cag         2033
Gly Lys Ala Met Arg Met Pro Met Trp Ser Ser Tyr Thr Val Pro Gln
635                    640                    645                    650 ttg gga gac aca tcg cct ctg cct ccc act gtc cca gac tgt ctg cgg         2081
Leu Gly Asp Thr Ser Pro Leu Pro Pro Thr Val Pro Asp Cys Leu Arg
                655                    660                    665 gct gat gtc agg gtt cct cct tct gag agc caa aaa tgt tcc ttc tat         2129
Ala Asp Val Arg Val Pro Pro Ser Glu Ser Gln Lys Cys Ser Phe Tyr
            670                    675                    680 tta gca gac aag aat atc acc cac ggc ttc ctc tat cct cct gcc agc         2177
Leu Ala Asp Lys Asn Ile Thr His Gly Phe Leu Tyr Pro Pro Ala Ser
        685                    690                    695 aat aga aca tca gat agc caa tat gat gct tta att act agc aat ttg         2225
Asn Arg Thr Ser Asp Ser Gln Tyr Asp Ala Leu Ile Thr Ser Asn Leu
    700                    705                    710 gta cct atg tat gaa gaa ttc aga aaa atg tgg gac tac ttc cac agt         2273
Val Pro Met Tyr Glu Glu Phe Arg Lys Met Trp Asp Tyr Phe His Ser
715                    720                    725                    730 gtt ctt ctt ata aaa cat gcc aca gaa aga aat gga gta aat gtg gtt         2321
Val Leu Leu Ile Lys His Ala Thr Glu Arg Asn Gly Val Asn Val Val
                735                    740                    745 agt gga cca ata ttt gat tat aat tat gat ggc cat ttt gat gct cca         2369
Ser Gly Pro Ile Phe Asp Tyr Asn Tyr Asp Gly His Phe Asp Ala Pro
```

```
                                                               -continued

Ser Gly Pro Ile Phe Asp Tyr Asn Tyr Asp Gly His Phe Asp Ala Pro
            750                 755                 760 gat gaa att acc aaa cat tta gcc aac act gat gtt ccc atc cca aca      2417
Asp Glu Ile Thr Lys His Leu Ala Asn Thr Asp Val Pro Ile Pro Thr
            765                 770                 775 cac tac ttt gtg gtg ctg acc agt tgt aaa aac aag agc cac aca ccg      2465
His Tyr Phe Val Val Leu Thr Ser Cys Lys Asn Lys Ser His Thr Pro
            780                 785                 790 gaa aac tgc cct ggg tgg ctg gat gtc cta ccc ttt atc atc cct cac      2513
Glu Asn Cys Pro Gly Trp Leu Asp Val Leu Pro Phe Ile Ile Pro His
795                 800                 805                 810 cga cct acc aac gtg gag agc tgt cct gaa ggt aaa cca gaa gct ctt      2561
Arg Pro Thr Asn Val Glu Ser Cys Pro Glu Gly Lys Pro Glu Ala Leu
                815                 820                 825 tgg gtt gaa gaa aga ttt aca gct cac att gcc cgg gtc cgt gat gta      2609
Trp Val Glu Glu Arg Phe Thr Ala His Ile Ala Arg Val Arg Asp Val
            830                 835                 840 gaa ctt ctc act ggg ctt gac ttc tat cag gat aaa gtg cag cct gtc      2657
Glu Leu Leu Thr Gly Leu Asp Phe Tyr Gln Asp Lys Val Gln Pro Val
            845                 850                 855 tct gaa att ttg caa cta aag aca tat tta cca aca ttt gaa acc act      2705
Ser Glu Ile Leu Gln Leu Lys Thr Tyr Leu Pro Thr Phe Glu Thr Thr
            860                 865                 870 att taa cttaataatg tctacttaat atataattta ctgtataaag taattttggc       2761
Ile *
875 aaaatataag tgatttttt ctggagaatt gtaaaataaa gttttctatt tttccttaag     2821 tcccctaaaa gccataattt ttattattcc tttttctctt ttttcaattc tatgaatatg    2881 tattatttta aagttatatt tttcacacag agatgatgct atattacacc ttcccttttt    2941 tgttggtttc ttaaactcta atctcatgac agattatacc ttccttatta cttgttttat   3001 cttactcaga atctttgaat atattttct gcccagaatt atctaaacaa aagggagaac     3061 aaaagaagta tgtctcactt gggaactgaa tcaactctaa atcagttttg tcacaaaact    3121 ttttgtattt gactggcaat gctgattaaa attaaaaatg caca                     3165

<210> SEQ ID NO 13
<211> LENGTH: 875
<212> TYPE: PRT
<213> ORGANISM: Homo Sapiens

<400> SEQUENCE: 13

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Arg Lys Asp Cys Cys Ala Asp
```

-continued

```
            115                 120                 125
Tyr Lys Ser Val Cys Gln Gly Glu Thr Ser Trp Leu Glu Glu Asn Cys
130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
                180                 185                 190

His Ser Lys Tyr Met Arg Ala Met Tyr Pro Thr Lys Thr Phe Pro Asn
                195                 200                 205

His Tyr Thr Ile Val Thr Gly Leu Tyr Pro Glu Ser His Gly Ile Ile
210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
                260                 265                 270

Gly Ser Glu Val Ala Ile Asn Gly Ser Phe Pro Ser Ile Tyr Met Pro
                275                 280                 285

Tyr Asn Gly Ser Val Pro Phe Glu Glu Arg Ile Ser Thr Leu Leu Lys
290                 295                 300

Trp Leu Asp Leu Pro Lys Ala Glu Arg Pro Arg Phe Tyr Thr Met Phe
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
                340                 345                 350

Met Glu Gly Leu Lys Gln Arg Asn Leu His Asn Cys Val Asn Ile Ile
                355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Tyr Met Tyr Glu
385                 390                 395                 400

Gly Pro Ala Pro Arg Val Arg Ala His Asn Ile Pro His Asp Phe Phe
                405                 410                 415

Ser Phe Asn Ser Glu Glu Ile Val Arg Asn Leu Ser Cys Arg Lys Pro
                420                 425                 430

Asp Gln His Phe Lys Pro Tyr Leu Thr Pro Asp Leu Pro Lys Arg Leu
                435                 440                 445

His Tyr Ala Lys Asn Val Arg Ile Asp Lys Val His Leu Phe Val Asp
450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
                500                 505                 510

Glu Asn Ile Glu Val Tyr Asn Leu Met Cys Asp Leu Leu Arg Ile Gln
                515                 520                 525

Pro Ala Pro Asn Asn Gly Thr His Gly Ser Leu Asn His Leu Leu Lys
530                 535                 540
```

```
Val Pro Phe Tyr Glu Pro Ser His Ala Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875
```

<210> SEQ ID NO 14
<211> LENGTH: 3988
<212> TYPE: DNA
<213> ORGANISM: Homo Sapiens
<220> FEATURE:
<221> NAME/KEY: CDS
<222> LOCATION: (276)...(2801)

<400> SEQUENCE: 14

```
ctactttatt ctgataaaac aggtctatgc agctaccagg acaatggaat ctacgttgac      60
tttagcaacg gaacaacctg ttaagaagaa cactcttaag aaatataaaa tagcttgcat     120
```

-continued

```
tacagggtct ctctcctttg ggatctcacc tcaccacaac ctctgtttcc caggctcaag      180
tgatcctcct gcctcagcct cctgagtagc ttggaccaca gcacatgcc acaaggctca      240 gctaagtttt tgttcttctt gctttgctgg tgatc atg tca ctt gga tta ggc       293
                                        Met Ser Leu Gly Leu Gly
                                         1               5 ctg ggg ctt gga ctc agg aaa ctg gaa aag caa ggc agc tgc agg aag      341
Leu Gly Leu Gly Leu Arg Lys Leu Glu Lys Gln Gly Ser Cys Arg Lys
             10                  15                  20 aag tgc ttt gat gca tca ttt aga gga ctg gag aac tgc cgg tgt gat      389
Lys Cys Phe Asp Ala Ser Phe Arg Gly Leu Glu Asn Cys Arg Cys Asp
         25                  30                  35 gtg gca tgt aaa gac cga ggt gat tgc tgc tgg gat ttt gaa gac acc      437
Val Ala Cys Lys Asp Arg Gly Asp Cys Cys Trp Asp Phe Glu Asp Thr
     40                  45                  50 tgt gtg gaa tca act cga ata tgg atg tgc aat aaa ttt cgt tgt gga      485
Cys Val Glu Ser Thr Arg Ile Trp Met Cys Asn Lys Phe Arg Cys Gly
 55                  60                  65                  70 gag acc aga tta gag gcc agc ctt tgc tct tgt tca gat gac tgt ttg      533
Glu Thr Arg Leu Glu Ala Ser Leu Cys Ser Cys Ser Asp Asp Cys Leu
                 75                  80                  85 cag aag aaa gat tgc tgt gct gac tat aag agt gtt tgc caa gga gaa      581
Gln Lys Lys Asp Cys Cys Ala Asp Tyr Lys Ser Val Cys Gln Gly Glu
             90                  95                 100 acc tca tgg ctg gaa gaa aac tgt gac aca gcc cag cag tct cag tgc      629
Thr Ser Trp Leu Glu Glu Asn Cys Asp Thr Ala Gln Gln Ser Gln Cys
         105                 110                 115 cca gaa ggg ttt gac ctg cca cca gtt atc ttg ttt tct atg gat gga      677
Pro Glu Gly Phe Asp Leu Pro Pro Val Ile Leu Phe Ser Met Asp Gly
     120                 125                 130 ttt aga gct gaa tat tta tac aca tgg gat act tta atg cca aat atc      725
Phe Arg Ala Glu Tyr Leu Tyr Thr Trp Asp Thr Leu Met Pro Asn Ile
135                 140                 145                 150 aat aaa ctg aaa aca tgt gga att cat tca aaa tac atg aga gct atg      773
Asn Lys Leu Lys Thr Cys Gly Ile His Ser Lys Tyr Met Arg Ala Met
                 155                 160                 165 tat cct acc aaa acc ttc cca aat cat tac acc att gtc acg ggc ttg      821
Tyr Pro Thr Lys Thr Phe Pro Asn His Tyr Thr Ile Val Thr Gly Leu
             170                 175                 180 tat cca gag tca cat ggc atc att gac aat aat atg tat gat gta aat      869
Tyr Pro Glu Ser His Gly Ile Ile Asp Asn Asn Met Tyr Asp Val Asn
         185                 190                 195 ctc aac aag aat ttt tca ctt tct tca aag gaa caa aat aat cca gcc      917
Leu Asn Lys Asn Phe Ser Leu Ser Ser Lys Glu Gln Asn Asn Pro Ala
     200                 205                 210 tgg tgg cat ggg caa cca atg tgg ctg aca gca atg tat caa ggt tta      965
Trp Trp His Gly Gln Pro Met Trp Leu Thr Ala Met Tyr Gln Gly Leu
215                 220                 225                 230 aaa gcc gct acc tac ttt tgg ccc gga tca gaa gtg gct ata aat ggc     1013
Lys Ala Ala Thr Tyr Phe Trp Pro Gly Ser Glu Val Ala Ile Asn Gly
                 235                 240                 245 tcc ttt cct tcc ata tac atg cct tac aac gga agt gtc cca ttt gaa     1061
Ser Phe Pro Ser Ile Tyr Met Pro Tyr Asn Gly Ser Val Pro Phe Glu
             250                 255                 260 gag agg att tct aca ctg tta aaa tgg ctg gac ctg ccc aaa gct gaa     1109
Glu Arg Ile Ser Thr Leu Leu Lys Trp Leu Asp Leu Pro Lys Ala Glu
         265                 270                 275 aga ccc agg ttt tat acc atg tat ttt gaa gaa cct gat tcc tct gga     1157
Arg Pro Arg Phe Tyr Thr Met Tyr Phe Glu Glu Pro Asp Ser Ser Gly
     280                 285                 290
```

-continued

| | | |
|---|---|---|
| cat gca ggt gga cca gtc agt gcc aga gta att aaa gcc tta cag gta<br>His Ala Gly Gly Pro Val Ser Ala Arg Val Ile Lys Ala Leu Gln Val<br>295                           300                    305                 310 | 1205 |
| gta gat cat gct ttt ggg atg ttg atg gaa ggc ctg aag cag cgg aat<br>Val Asp His Ala Phe Gly Met Leu Met Glu Gly Leu Lys Gln Arg Asn<br>               315                   320                  325 | 1253 |
| ttg cac aac tgt gtc aat atc atc ctt ctg gct gac cat gga atg gac<br>Leu His Asn Cys Val Asn Ile Ile Leu Leu Ala Asp His Gly Met Asp<br>         330                   335                   340 | 1301 |
| cag act tat tgt aac aag atg gaa tac atg act gat tat ttt ccc aga<br>Gln Thr Tyr Cys Asn Lys Met Glu Tyr Met Thr Asp Tyr Phe Pro Arg<br>       345                   350                   355 | 1349 |
| ata aac ttc ttc tac atg tac gaa ggg cct gcc ccc cgc atc cga gct<br>Ile Asn Phe Phe Tyr Met Tyr Glu Gly Pro Ala Pro Arg Ile Arg Ala<br>360                           365                    370 | 1397 |
| cat aat ata cct cat gac ttt ttt agt ttt aat tct gag gaa att gtt<br>His Asn Ile Pro His Asp Phe Phe Ser Phe Asn Ser Glu Glu Ile Val<br>375                         380                   385               390 | 1445 |
| aga aac ctc agt tgc cga aaa cct gat cag cat ttc aag ccc tat ttg<br>Arg Asn Leu Ser Cys Arg Lys Pro Asp Gln His Phe Lys Pro Tyr Leu<br>               395                   400                  405 | 1493 |
| act cct gat ttg cca aag cga ctg cac tat gcc aag aac gtc aga atc<br>Thr Pro Asp Leu Pro Lys Arg Leu His Tyr Ala Lys Asn Val Arg Ile<br>           410                   415                   420 | 1541 |
| gac aaa gtt cat ctc ttt gtg gat caa cag tgg ctg gct gtt agg agt<br>Asp Lys Val His Leu Phe Val Asp Gln Gln Trp Leu Ala Val Arg Ser<br>               425                   430                  435 | 1589 |
| aaa tca aat aca aat tgt gga gga ggc aac cat ggt tat aac aat gag<br>Lys Ser Asn Thr Asn Cys Gly Gly Gly Asn His Gly Tyr Asn Asn Glu<br>440                           445                    450 | 1637 |
| ttt agg agc atg gag gct atc ttt ctg gca cat gga ccc agt ttt aaa<br>Phe Arg Ser Met Glu Ala Ile Phe Leu Ala His Gly Pro Ser Phe Lys<br>455                         460                   465               470 | 1685 |
| gag aag act gaa gtt gaa cca ttt gaa aat att gaa gtc tat aac cta<br>Glu Lys Thr Glu Val Glu Pro Phe Glu Asn Ile Glu Val Tyr Asn Leu<br>               475                   480                  485 | 1733 |
| atg tgt gat ctt cta cgc att caa cca gca cca aac aat gga acc cat<br>Met Cys Asp Leu Leu Arg Ile Gln Pro Ala Pro Asn Asn Gly Thr His<br>           490                   495                   500 | 1781 |
| ggt agt tta aac cat ctt ctg aag gtg cct ttt tat gag cca tcc cat<br>Gly Ser Leu Asn His Leu Leu Lys Val Pro Phe Tyr Glu Pro Ser His<br>               505                   510                  515 | 1829 |
| gca gag gag gtg tca aag ttt tct gtt tgt ggc ttt gct aat cca ttg<br>Ala Glu Glu Val Ser Lys Phe Ser Val Cys Gly Phe Ala Asn Pro Leu<br>520                           525                    530 | 1877 |
| ccc aca gag tct ctt gac tgt ttc tgc cct cac cta caa aat agt act<br>Pro Thr Glu Ser Leu Asp Cys Phe Cys Pro His Leu Gln Asn Ser Thr<br>535                         540                   545               550 | 1925 |
| cag ctg gaa caa gtg aat cag atg cta aat ctc acc caa gaa gaa ata<br>Gln Leu Glu Gln Val Asn Gln Met Leu Asn Leu Thr Gln Glu Glu Ile<br>               555                   560                  565 | 1973 |
| aca gca aca gtg aaa gta aat ttg cca ttt ggg agg cct agg gta ctg<br>Thr Ala Thr Val Lys Val Asn Leu Pro Phe Gly Arg Pro Arg Val Leu<br>           570                   575                   580 | 2021 |
| cag aag aac gtg gac cac tgt ctc ctt tac cac agg gaa tat gtc agt<br>Gln Lys Asn Val Asp His Cys Leu Leu Tyr His Arg Glu Tyr Val Ser<br>               585                   590                  595 | 2069 |
| gga ttt gga aaa gct atg agg atg ccc atg tgg agt tca tac aca gtc<br>Gly Phe Gly Lys Ala Met Arg Met Pro Met Trp Ser Ser Tyr Thr Val | 2117 |

```
                600             605             610
ccc cag ttg gga gac aca tcg cct ctg cct ccc act gtc cca gac tgt        2165
Pro Gln Leu Gly Asp Thr Ser Pro Leu Pro Pro Thr Val Pro Asp Cys
615                 620                 625                 630 ctg cgg gct gat gtc agg gtt cct cct tct gag agc caa aaa tgt tcc        2213
Leu Arg Ala Asp Val Arg Val Pro Pro Ser Glu Ser Gln Lys Cys Ser
            635                 640                 645 ttc tat tta gca gac aag aat atc acc cac ggc ttc ctc tat cct cct        2261
Phe Tyr Leu Ala Asp Lys Asn Ile Thr His Gly Phe Leu Tyr Pro Pro
        650                 655                 660 gcc agc aat aga aca tca gat agc caa tat gat gct tta att act agc        2309
Ala Ser Asn Arg Thr Ser Asp Ser Gln Tyr Asp Ala Leu Ile Thr Ser
    665                 670                 675 aat ttg gta cct atg tat gaa gaa ttc aga aaa atg tgg gac tac ttc        2357
Asn Leu Val Pro Met Tyr Glu Glu Phe Arg Lys Met Trp Asp Tyr Phe
680                 685                 690 cac agt gtt ctt ctt ata aaa cat gcc aca gaa aga aat gga gta aat        2405
His Ser Val Leu Leu Ile Lys His Ala Thr Glu Arg Asn Gly Val Asn
695                 700                 705                 710 gtg gtt agt gga cca ata ttt gat tat aat tat gat ggc cat ttt gat        2453
Val Val Ser Gly Pro Ile Phe Asp Tyr Asn Tyr Asp Gly His Phe Asp
            715                 720                 725 gct cca gat gaa att acc aaa cat tta gcc aac act gat gtt ccc atc        2501
Ala Pro Asp Glu Ile Thr Lys His Leu Ala Asn Thr Asp Val Pro Ile
        730                 735                 740 cca aca cac tac ttt gtg gtg ctg acc agt tgt aaa aac aag agc cac        2549
Pro Thr His Tyr Phe Val Val Leu Thr Ser Cys Lys Asn Lys Ser His
    745                 750                 755 aca ccg gaa aac tgc cct ggg tgg ctg gat gtc cta ccc ttt atc atc        2597
Thr Pro Glu Asn Cys Pro Gly Trp Leu Asp Val Leu Pro Phe Ile Ile
760                 765                 770 cct cac cga cct acc aac gtg gag agc tgt cct gaa ggt aaa cca gaa        2645
Pro His Arg Pro Thr Asn Val Glu Ser Cys Pro Glu Gly Lys Pro Glu
775                 780                 785                 790 gct ctt tgg gtt gaa gaa aga ttt aca gct cac att gcc cgg gtc cgt        2693
Ala Leu Trp Val Glu Glu Arg Phe Thr Ala His Ile Ala Arg Val Arg
            795                 800                 805 gat gta gaa ctt ctc act ggg ctt gac ttc tat cag gat aaa gtg cag        2741
Asp Val Glu Leu Leu Thr Gly Leu Asp Phe Tyr Gln Asp Lys Val Gln
        810                 815                 820 cct gtc tct gaa att ttg caa cta aag aca tat tta cca aca ttt gaa        2789
Pro Val Ser Glu Ile Leu Gln Leu Lys Thr Tyr Leu Pro Thr Phe Glu
    825                 830                 835 acc act att taa cttaataatg tctacttaat atataattta ctgtataaag            2841
Thr Thr Ile *
    840 taatttggc aaaatataag tgatttttc tggagaattg taaaataaag ttttctattt         2901
ttccttaaaa aaaaaccgg aattccgggc ttgggaggct gaggcaggag actcgcttga        2961
acccgggagg cagaggttgc agtgagccaa gattgcgcca ttgcactcca gagcctgggt      3021
gacagagcaa gactacatct caaaaaataa ataaataaaa taaagtaac aataaaaata       3081 aaaagaacag cagagagaat gagcaaggag aaatgtcaca aactattgca aaatactgtt      3141
acactgggtt ggctctccaa gaagatactg gaatctcttc agccatttgc ttttcagaag     3201
tagaaaccag caaaccacct ctaagcggag aacatacgat tctttattaa gtagctctgg    3261
ggaaggaaaa aataaaagtt gatagctccc tgattgggaa aaaatgcaca attaataaag     3321
aatgaagatg aaagaaagca tgcttatgtt gtaacacaaa aaaaattcac aaacgttggt     3381
```

-continued

```
ggaaggaaaa cagtatagaa aacattactt taactaaaag ctggaaaaat tttcagttgg    3441
gatgcgactg acaaaaagaa cgggatttcc aggcataaag ttggcgtgag ctacagaggg    3501
caccatgtgg ctcagtggaa gacccttcaa gattcaaagt tccatttgac agagcaaagg    3561
cacttcgcaa ggagaagggt ttaaattatg ggtccaaaag ccaagtggta aagcgagcaa    3621
tttgcagcat aactgcttct cctagacagg gctgagtggg caaaatacga cagtacacac    3681
agtgactatt agccactgcc agaaacaggc tgaacagccc tgggagacaa gggaaggcag    3741
gtggtgggag ttgttcatgg agagaaagga gagtttttaga accagcacat ccactggaga    3801
tgctgggcca ccagacccct cccagtcaat aaagtctggt gcctcatttg atctcagcct    3861
catcatgacc ctggagagac cctgatacca tctgccagtc cccgacagct taggcactcc    3921
ttgccatcaa cctgaccccc cgagtggttc tccaggctcc ctgccccacc cattcaggcc    3981
ggaattc                                                              3988
```

<210> SEQ ID NO 15
<211> LENGTH: 841
<212> TYPE: PRT
<213> ORGANISM: Homo Sapiens

<400> SEQUENCE: 15

```
Met Ser Leu Gly Leu Gly Leu Gly Leu Gly Leu Arg Lys Leu Glu Lys
  1               5                  10                  15

Gln Gly Ser Cys Arg Lys Lys Cys Phe Asp Ala Ser Phe Arg Gly Leu
             20                  25                  30

Glu Asn Cys Arg Cys Asp Val Ala Cys Lys Asp Arg Gly Asp Cys Cys
         35                  40                  45

Trp Asp Phe Glu Asp Thr Cys Val Glu Ser Thr Arg Ile Trp Met Cys
     50                  55                  60

Asn Lys Phe Arg Cys Gly Glu Thr Arg Leu Glu Ala Ser Leu Cys Ser
 65                  70                  75                  80

Cys Ser Asp Asp Cys Leu Gln Lys Lys Asp Cys Cys Ala Asp Tyr Lys
                 85                  90                  95

Ser Val Cys Gln Gly Glu Thr Ser Trp Leu Glu Glu Asn Cys Asp Thr
            100                 105                 110

Ala Gln Gln Ser Gln Cys Pro Glu Gly Phe Asp Leu Pro Pro Val Ile
        115                 120                 125

Leu Phe Ser Met Asp Gly Phe Arg Ala Glu Tyr Leu Tyr Thr Trp Asp
    130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr
                165                 170                 175

Thr Ile Val Thr Gly Leu Tyr Pro Glu Ser His Gly Ile Ile Asp Asn
            180                 185                 190

Asn Met Tyr Asp Val Asn Leu Asn Lys Asn Phe Ser Leu Ser Ser Lys
        195                 200                 205

Glu Gln Asn Asn Pro Ala Trp Trp His Gly Gln Pro Met Trp Leu Thr
    210                 215                 220

Ala Met Tyr Gln Gly Leu Lys Ala Ala Thr Tyr Phe Trp Pro Gly Ser
225                 230                 235                 240

Glu Val Ala Ile Asn Gly Ser Phe Pro Ser Ile Tyr Met Pro Tyr Asn
                245                 250                 255
```

```
Gly Ser Val Pro Phe Glu Glu Arg Ile Ser Thr Leu Leu Lys Trp Leu
            260                 265                 270

Asp Leu Pro Lys Ala Glu Arg Pro Arg Phe Tyr Thr Met Tyr Phe Glu
            275                 280             285

Glu Pro Asp Ser Ser Gly His Ala Gly Gly Pro Val Ser Ala Arg Val
        290                 295             300

Ile Lys Ala Leu Gln Val Val Asp His Ala Phe Gly Met Leu Met Glu
305                 310             315                     320

Gly Leu Lys Gln Arg Asn Leu His Asn Cys Val Asn Ile Ile Leu Leu
                325             330                     335

Ala Asp His Gly Met Asp Gln Thr Tyr Cys Asn Lys Met Glu Tyr Met
            340                 345             350

Thr Asp Tyr Phe Pro Arg Ile Asn Phe Phe Tyr Met Tyr Glu Gly Pro
            355                 360             365

Ala Pro Arg Ile Arg Ala His Asn Ile Pro His Asp Phe Phe Ser Phe
370                 375             380

Asn Ser Glu Glu Ile Val Arg Asn Leu Ser Cys Arg Lys Pro Asp Gln
385                 390             395                     400

His Phe Lys Pro Tyr Leu Thr Pro Asp Leu Pro Lys Arg Leu His Tyr
                405                 410                 415

Ala Lys Asn Val Arg Ile Asp Lys Val His Leu Phe Val Asp Gln Gln
            420                 425             430

Trp Leu Ala Val Arg Ser Lys Ser Asn Thr Asn Cys Gly Gly Gly Asn
            435                 440             445

His Gly Tyr Asn Asn Glu Phe Arg Ser Met Glu Ala Ile Phe Leu Ala
            450                 455             460

His Gly Pro Ser Phe Lys Glu Lys Thr Glu Val Glu Pro Phe Glu Asn
465                 470             475                     480

Ile Glu Val Tyr Asn Leu Met Cys Asp Leu Leu Arg Ile Gln Pro Ala
                485                 490                 495

Pro Asn Asn Gly Thr His Gly Ser Leu Asn His Leu Leu Lys Val Pro
            500                 505             510

Phe Tyr Glu Pro Ser His Ala Glu Glu Val Ser Lys Phe Ser Val Cys
            515                 520             525

Gly Phe Ala Asn Pro Leu Pro Thr Glu Ser Leu Asp Cys Phe Cys Pro
            530                 535             540

His Leu Gln Asn Ser Thr Gln Leu Glu Gln Val Asn Gln Met Leu Asn
545                 550             555                     560

Leu Thr Gln Glu Glu Ile Thr Ala Thr Val Lys Val Asn Leu Pro Phe
                565             570                     575

Gly Arg Pro Arg Val Leu Gln Lys Asn Val Asp His Cys Leu Leu Tyr
            580                 585             590

His Arg Glu Tyr Val Ser Gly Phe Gly Lys Ala Met Arg Met Pro Met
            595                 600             605

Trp Ser Ser Tyr Thr Val Pro Gln Leu Gly Asp Thr Ser Pro Leu Pro
610                 615             620

Pro Thr Val Pro Asp Cys Leu Arg Ala Asp Val Arg Val Pro Pro Ser
625                 630             635                     640

Glu Ser Gln Lys Cys Ser Phe Tyr Leu Ala Asp Lys Asn Ile Thr His
                645             650                     655

Gly Phe Leu Tyr Pro Pro Ala Ser Asn Arg Thr Ser Asp Ser Gln Tyr
            660                 665             670

Asp Ala Leu Ile Thr Ser Asn Leu Val Pro Met Tyr Glu Glu Phe Arg
```

-continued

```
                675                 680                 685
Lys Met Trp Asp Tyr Phe His Ser Val Leu Leu Ile Lys His Ala Thr
        690                 695                 700
Glu Arg Asn Gly Val Asn Val Val Ser Gly Pro Ile Phe Asp Tyr Asn
705                 710                 715                 720
Tyr Asp Gly His Phe Asp Ala Pro Asp Glu Ile Thr Lys His Leu Ala
                725                 730                 735
Asn Thr Asp Val Pro Ile Pro Thr His Tyr Phe Val Val Leu Thr Ser
                740                 745                 750
Cys Lys Asn Lys Ser His Thr Pro Glu Asn Cys Pro Gly Trp Leu Asp
                755                 760                 765
Val Leu Pro Phe Ile Ile Pro His Arg Pro Thr Asn Val Glu Ser Cys
770                 775                 780
Pro Glu Gly Lys Pro Glu Ala Leu Trp Val Glu Arg Phe Thr Ala
785                 790                 795                 800
His Ile Ala Arg Val Arg Asp Val Glu Leu Leu Thr Gly Leu Asp Phe
                805                 810                 815
Tyr Gln Asp Lys Val Gln Pro Val Ser Glu Ile Leu Gln Leu Lys Thr
                820                 825                 830
Tyr Leu Pro Thr Phe Glu Thr Thr Ile
        835                 840

<210> SEQ ID NO 16
<211> LENGTH: 875
<212> TYPE: PRT
<213> ORGANISM: Homo Sapiens

<400> SEQUENCE: 16

Met Glu Ser Thr Leu Thr Leu Ala Thr Glu Gln Pro Val Lys Lys Asn
1               5                   10                  15
Thr Leu Lys Lys Tyr Lys Ile Ala Cys Ile Val Leu Leu Ala Leu Leu
                20                  25                  30
Val Ile Met Ser Leu Gly Leu Gly Leu Gly Leu Gly Leu Arg Lys Leu
            35                  40                  45
Glu Lys Gln Gly Ser Cys Arg Lys Cys Phe Asp Ala Ser Phe Arg
        50                  55                  60
Gly Leu Glu Asn Cys Arg Cys Asp Val Ala Cys Lys Asp Arg Gly Asp
65                  70                  75                  80
Cys Cys Trp Asp Phe Glu Asp Thr Cys Val Glu Ser Thr Arg Ile Trp
                85                  90                  95
Met Cys Asn Lys Phe Arg Cys Gly Glu Thr Arg Leu Glu Ala Ser Leu
                100                 105                 110
Cys Ser Cys Ser Asp Asp Cys Leu Gln Lys Lys Asp Cys Cys Ala Asp
            115                 120                 125
Tyr Lys Ser Val Cys Gln Gly Glu Thr Ser Trp Leu Glu Glu Asn Cys
        130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
Trp Asp Thr Leu Met Pro Asn Ile Asn Lys Leu Lys Thr Cys Gly Ile
                180                 185                 190
His Ser Lys Tyr Met Arg Ala Met Tyr Pro Thr Lys Thr Phe Pro Asn
            195                 200                 205
```

-continued

His Tyr Thr Ile Val Thr Gly Leu Tyr Pro Glu Ser His Gly Ile Ile
210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
            245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met

```
                    625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
                675                 680                 685
Thr His Gly Phe Leu Tyr Pro Pro Ala Ser Asn Arg Thr Ser Asp Ser
                690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Leu Ile Lys His
                725                 730                 735
Ala Thr Glu Arg Asn Gly Val Asn Val Val Ser Gly Pro Ile Phe Asp
                740                 745                 750
Tyr Asn Tyr Asp Gly His Phe Asp Ala Pro Asp Glu Ile Thr Lys His
                755                 760                 765
Leu Ala Asn Thr Asp Val Pro Ile Pro Thr His Tyr Phe Val Val Leu
770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
                805                 810                 815
Ser Cys Pro Glu Gly Lys Pro Glu Ala Leu Trp Val Glu Glu Arg Phe
                820                 825                 830
Thr Ala His Ile Ala Arg Val Arg Asp Val Glu Leu Leu Thr Gly Leu
                835                 840                 845
Asp Phe Tyr Gln Asp Lys Val Gln Pro Val Ser Glu Ile Leu Gln Leu
                850                 855                 860
Lys Thr Tyr Leu Pro Thr Phe Glu Thr Thr Ile
865                 870                 875

<210> SEQ ID NO 17
<211> LENGTH: 875
<212> TYPE: PRT
<213> ORGANISM: Homo Sapiens

<400> SEQUENCE: 17

Met Glu Ser Thr Leu Thr Leu Ala Thr Glu Gln Pro Val Lys Lys Asn
1               5                   10                  15
Thr Leu Lys Lys Tyr Lys Ile Ala Cys Ile Val Leu Ala Leu Leu
                20                  25                  30
Val Ile Met Ser Leu Gly Leu Gly Leu Gly Leu Gly Leu Arg Lys Leu
                35                  40                  45
Glu Lys Gln Gly Ser Cys Arg Lys Lys Cys Phe Asp Ala Ser Phe Arg
            50                  55                  60
Gly Leu Glu Asn Cys Arg Cys Asp Val Ala Cys Lys Asp Arg Gly Asp
65                  70                  75                  80
Cys Cys Trp Asp Phe Glu Asp Thr Cys Val Glu Ser Thr Arg Ile Trp
                85                  90                  95
Met Cys Asn Lys Phe Arg Cys Gly Glu Thr Arg Leu Glu Ala Ser Leu
                100                 105                 110
Cys Ser Cys Ser Asp Asp Cys Leu Gln Arg Lys Asp Cys Cys Ala Asp
                115                 120                 125
```

```
Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                405                 410                 415

Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
    450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
    530                 535                 540

Val Pro Phe Tyr Glu Pro Ser His Ala Glu Glu Val Ser Lys Phe Ser
```

-continued

```
                545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
                580                 585                 590
Leu Asn Leu Thr Gln Glu Glu Ile Thr Ala Thr Val Lys Val Asn Leu
                595                 600                 605
Pro Phe Gly Arg Pro Arg Val Leu Gln Lys Asn Val Asp His Cys Leu
                610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
                675                 680                 685
Thr His Gly Phe Leu Tyr Pro Pro Ala Ser Asn Arg Thr Ser Asp Ser
                690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Leu Ile Lys His
                725                 730                 735
Ala Thr Glu Arg Asn Gly Val Asn Val Val Ser Gly Pro Ile Phe Asp
                740                 745                 750
Tyr Asn Tyr Asp Gly His Phe Asp Ala Pro Asp Glu Ile Thr Lys His
                755                 760                 765
Leu Ala Asn Thr Asp Val Pro Ile Pro Thr His Tyr Phe Val Val Leu
                770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
                805                 810                 815
Ser Cys Pro Glu Gly Lys Pro Glu Ala Leu Trp Val Glu Arg Phe
                820                 825                 830
Thr Ala His Ile Ala Arg Val Arg Asp Val Glu Leu Leu Thr Gly Leu
                835                 840                 845
Asp Phe Tyr Gln Asp Lys Val Gln Pro Val Ser Glu Ile Leu Gln Leu
                850                 855                 860
Lys Thr Tyr Leu Pro Thr Phe Glu Thr Thr Ile
865                 870                 875

<210> SEQ ID NO 18
<211> LENGTH: 875
<212> TYPE: PRT
<213> ORGANISM: Homo Sapiens

<400> SEQUENCE: 18

Met Glu Ser Thr Leu Thr Leu Ala Thr Glu Gln Pro Val Lys Lys Asn
1               5                   10                  15
Thr Leu Lys Lys Tyr Lys Ile Ala Cys Ile Val Leu Leu Ala Leu Leu
                20                  25                  30
Val Ile Met Ser Leu Gly Leu Gly Leu Gly Leu Arg Lys Leu
                35                  40                  45
```

```
Glu Lys Gln Gly Ser Cys Arg Lys Lys Cys Phe Asp Ala Ser Phe Arg
     50                  55                  60
Gly Leu Glu Asn Cys Arg Cys Asp Val Ala Cys Lys Asp Arg Gly Asp
 65                  70                  75                  80
Cys Cys Trp Asp Phe Glu Asp Thr Cys Val Glu Ser Thr Arg Ile Trp
                 85                  90                  95
Met Cys Asn Lys Phe Arg Cys Gly Glu Thr Arg Leu Glu Ala Ser Leu
            100                 105                 110
Cys Ser Cys Ser Asp Asp Cys Leu Gln Lys Lys Asp Cys Cys Ala Asp
            115                 120                 125
Tyr Lys Ser Val Cys Gln Gly Glu Thr Ser Trp Leu Glu Glu Asn Cys
    130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
Trp Asp Thr Leu Met Pro Asn Ile Asn Lys Leu Lys Thr Cys Gly Ile
            180                 185                 190
His Ser Lys Tyr Met Arg Ala Met Tyr Pro Thr Lys Thr Phe Pro Asn
    195                 200                 205
His Tyr Thr Ile Val Thr Gly Leu Tyr Pro Glu Ser His Gly Ile Ile
210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
            260                 265                 270
Gly Ser Glu Val Ala Ile Asn Gly Ser Phe Pro Ser Ile Tyr Met Pro
            275                 280                 285
Tyr Asn Gly Ser Val Pro Phe Glu Glu Arg Ile Ser Thr Leu Leu Lys
    290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
            340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
    370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
            435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
```

-continued

```
            465                 470                 475                 480
        Gly Asn His Gly Tyr Asn Asn Glu Phe Arg Ser Met Glu Ala Ile Phe
                        485                 490                 495
        Leu Ala His Gly Pro Ser Phe Lys Glu Lys Thr Glu Val Glu Pro Phe
                        500                 505                 510
        Glu Asn Ile Glu Val Tyr Asn Leu Met Cys Asp Leu Leu Arg Ile Gln
                        515                 520                 525
        Pro Ala Pro Asn Asn Gly Thr His Gly Ser Leu Asn His Leu Leu Lys
                        530                 535                 540
        Val Pro Phe Tyr Glu Pro Ser His Ala Glu Val Ser Lys Phe Ser
        545                 550                 555                 560
        Val Cys Gly Phe Ala Asn Pro Leu Pro Thr Glu Ser Leu Asp Cys Phe
                        565                 570                 575
        Cys Pro His Leu Gln Asn Ser Thr Gln Leu Glu Gln Val Asn Gln Met
                        580                 585                 590
        Leu Asn Leu Thr Gln Glu Glu Ile Thr Ala Thr Val Lys Val Asn Leu
                        595                 600                 605
        Pro Phe Gly Arg Pro Arg Val Leu Gln Lys Asn Val Asp His Cys Leu
                        610                 615                 620
        Leu Tyr His Arg Glu Tyr Val Ser Gly Phe Gly Lys Ala Met Arg Met
        625                 630                 635                 640
        Pro Met Trp Ser Ser Tyr Thr Val Pro Gln Leu Gly Asp Thr Ser Pro
                        645                 650                 655
        Leu Pro Pro Thr Val Pro Asp Cys Leu Arg Ala Asp Val Arg Val Pro
                        660                 665                 670
        Pro Ser Glu Ser Gln Lys Cys Ser Phe Tyr Leu Ala Asp Lys Asn Ile
                        675                 680                 685
        Thr His Gly Phe Leu Tyr Pro Pro Ala Ser Asn Arg Thr Ser Asp Ser
                        690                 695                 700
        Gln Tyr Asp Ala Leu Ile Thr Ser Asn Leu Val Pro Met Tyr Glu Glu
        705                 710                 715                 720
        Phe Arg Lys Met Trp Asp Tyr Phe His Ser Val Leu Leu Ile Lys His
                        725                 730                 735
        Ala Thr Glu Arg Asn Gly Val Asn Val Val Ser Gly Pro Ile Phe Asp
                        740                 745                 750
        Tyr Asn Tyr Asp Gly His Phe Asp Ala Pro Asp Glu Ile Thr Lys His
                        755                 760                 765
        Leu Ala Asn Thr Asp Val Pro Ile Pro Thr His Tyr Phe Val Val Leu
                        770                 775                 780
        Thr Ser Cys Lys Asn Lys Ser His Thr Pro Glu Asn Cys Pro Gly Trp
        785                 790                 795                 800
        Leu Asp Val Leu Pro Phe Ile Ile Pro His Arg Pro Thr Asn Val Glu
                        805                 810                 815
        Ser Cys Pro Gly Gly Lys Pro Glu Ala Leu Trp Val Glu Glu Arg Phe
                        820                 825                 830
        Thr Ala His Ile Ala Arg Val Arg Asp Val Glu Leu Leu Thr Gly Leu
                        835                 840                 845
        Asp Phe Tyr Gln Asp Lys Val Gln Pro Val Ser Glu Ile Leu Gln Leu
                        850                 855                 860
        Lys Thr Tyr Leu Pro Thr Phe Glu Thr Thr Ile
        865                 870                 875

<210> SEQ ID NO 19
```

<211> LENGTH: 875
<212> TYPE: PRT
<213> ORGANISM: Homo Sapiens

<400> SEQUENCE: 19

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
             20                  25                  30

Val Ile Met Ser Leu Gly Leu Gly Leu Gly Leu Arg Lys Leu
             35                  40                  45

Glu Lys Gln Gly Ser Cys Arg Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Lys Lys Asp Cys Cys Ala Asp
            115                 120                 125

Tyr Lys Ser Val Cys Gln Gly Glu Thr Ser Trp Leu Glu Glu Asn Cys
130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro
            260                 265                 270

Gly Ser Glu Val Ala Ile Asn Gly Ser Phe Pro Ser Ile Tyr Met Pro
        275                 280                 285

Tyr Asn Gly Ser Val Pro Phe Glu Glu Arg Ile Ser Thr Leu Leu Lys
    290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
                325                 330                 335

Arg Val Ile Lys Ala Leu Gln Val Val Asp His Ala Phe Gly Met Leu
            340                 345                 350

Met Glu Gly Leu Lys Gln Arg Asn Leu His Asn Cys Val Asn Ile Ile
        355                 360                 365

Leu Leu Ala Asp His Gly Met Asp Gln Thr Tyr Cys Asn Lys Met Glu
    370                 375                 380

Tyr Met Thr Asp Tyr Phe Pro Arg Ile Asn Phe Phe Tyr Met Tyr Glu
```

-continued

```
           385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
                420                 425                 430
Asp Gln His Phe Lys Pro Tyr Leu Thr Pro Asp Leu Pro Lys Arg Leu
                435                 440                 445
His Tyr Ala Lys Asn Val Arg Ile Asp Lys Val His Leu Phe Val Asp
            450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
                500                 505                 510
Glu Asn Ile Glu Val Tyr Asn Leu Met Cys Asp Leu Leu Arg Ile Gln
            515                 520                 525
Pro Ala Pro Asn Asn Gly Thr His Gly Ser Leu Asn His Leu Leu Lys
530                 535                 540
Val Pro Phe Tyr Glu Pro Ser His Ala Glu Glu Val Ser Lys Phe Ser
545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
                580                 585                 590
Leu Asn Leu Thr Gln Glu Glu Ile Thr Ala Thr Val Lys Val Asn Leu
            595                 600                 605
Pro Phe Gly Arg Pro Arg Val Leu Gln Lys Asn Val Asp His Cys Leu
            610                 615                 620
Leu Tyr His Arg Glu Tyr Val Ser Gly Phe Lys Ala Met Arg Met
625                 630                 635                 640
Pro Met Trp Ser Ser Tyr Thr Val Pro Gln Leu Gly Asp Thr Ser Pro
                645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
            675                 680                 685
Thr His Gly Phe Leu Tyr Pro Pro Ala Ser Asn Arg Thr Ser Asp Ser
            690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Leu Ile Lys His
                725                 730                 735
Ala Thr Glu Arg Asn Gly Val Asn Val Val Ser Gly Pro Ile Phe Asp
                740                 745                 750
Tyr Asn Tyr Asp Gly His Phe Asp Ala Pro Asp Glu Ile Thr Lys His
            755                 760                 765
Leu Ala Asn Thr Asp Val Pro Ile Pro Thr His Tyr Phe Val Val Leu
            770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
                805                 810                 815
```

```
Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Pro Ile
865                 870                 875

<210> SEQ ID NO 20
<211> LENGTH: 841
<212> TYPE: PRT
<213> ORGANISM: Homo Sapiens

<400> SEQUENCE: 20

Met Ser Leu Gly Leu Gly Leu Gly Leu Arg Lys Leu Glu Lys
 1               5                  10                  15

Gln Gly Ser Cys Arg Lys Lys Cys Phe Asp Ala Ser Phe Arg Gly Leu
            20                  25                  30

Glu Asn Cys Arg Cys Asp Val Ala Cys Lys Asp Arg Gly Asp Cys Cys
        35                  40                  45

Trp Asp Phe Glu Asp Thr Cys Val Glu Ser Thr Arg Ile Trp Met Cys
    50                  55                  60

Asn Lys Phe Arg Cys Gly Glu Thr Arg Leu Glu Ala Ser Leu Cys Ser
65                  70                  75                  80

Cys Ser Asp Asp Cys Leu Gln Arg Lys Asp Cys Cys Ala Asp Tyr Lys
                85                  90                  95

Ser Val Cys Gln Gly Glu Thr Ser Trp Leu Glu Glu Asn Cys Asp Thr
            100                 105                 110

Ala Gln Gln Ser Gln Cys Pro Glu Gly Phe Asp Leu Pro Pro Val Ile
        115                 120                 125

Leu Phe Ser Met Asp Gly Phe Arg Ala Glu Tyr Leu Tyr Thr Trp Asp
    130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr
                165                 170                 175

Thr Ile Val Thr Gly Leu Tyr Pro Glu Ser His Gly Ile Ile Asp Asn
            180                 185                 190

Asn Met Tyr Asp Val Asn Leu Asn Lys Asn Phe Ser Leu Ser Ser Lys
        195                 200                 205

Glu Gln Asn Asn Pro Ala Trp Trp His Gly Gln Pro Met Trp Leu Thr
    210                 215                 220

Ala Met Tyr Gln Gly Leu Lys Ala Ala Thr Tyr Phe Trp Pro Gly Ser
225                 230                 235                 240

Glu Val Ala Ile Asn Gly Ser Phe Pro Ser Ile Tyr Met Pro Tyr Asn
                245                 250                 255

Gly Ser Val Pro Phe Glu Glu Arg Ile Ser Thr Leu Leu Lys Trp Leu
            260                 265                 270

Asp Leu Pro Lys Ala Glu Arg Pro Arg Phe Tyr Thr Met Phe Phe Glu
        275                 280                 285

Glu Pro Asp Ser Ser Gly His His Ala Gly Gly Pro Val Ser Ala Arg Val
    290                 295                 300

Ile Lys Ala Leu Gln Val Val Asp His Ala Phe Gly Met Leu Met Glu
```

-continued

```
            305                 310                 315                 320
Gly Leu Lys Gln Arg Asn Leu His Asn Cys Val Asn Ile Ile Leu Leu
                325                 330                 335
Ala Asp His Gly Met Asp Gln Thr Tyr Cys Asn Lys Met Glu Tyr Met
                340                 345                 350
Thr Asp Tyr Phe Pro Arg Ile Asn Phe Phe Tyr Met Tyr Glu Gly Pro
                355                 360                 365
Ala Pro Arg Val Arg Ala His Asn Ile Pro His Asp Phe Phe Ser Phe
        370                 375                 380
Asn Ser Glu Glu Ile Val Arg Asn Leu Ser Cys Arg Lys Pro Asp Gln
385                 390                 395                 400
His Phe Lys Pro Tyr Leu Thr Pro Asp Leu Pro Lys Arg Leu His Tyr
                405                 410                 415
Ala Lys Asn Val Arg Ile Asp Lys Val His Leu Phe Val Asp Gln Gln
                420                 425                 430
Trp Leu Ala Val Arg Ser Lys Ser Asn Thr Asn Cys Gly Gly Gly Asn
        435                 440                 445
His Gly Tyr Asn Asn Glu Phe Arg Ser Met Glu Ala Ile Phe Leu Ala
        450                 455                 460
His Gly Pro Ser Phe Lys Glu Lys Thr Glu Val Glu Pro Phe Glu Asn
465                 470                 475                 480
Ile Glu Val Tyr Asn Leu Met Cys Asp Leu Leu Arg Ile Gln Pro Ala
                485                 490                 495
Pro Asn Asn Gly Thr His Gly Ser Leu Asn His Leu Leu Lys Val Pro
                500                 505                 510
Phe Tyr Glu Pro Ser His Ala Glu Glu Val Ser Lys Phe Ser Val Cys
                515                 520                 525
Gly Phe Ala Asn Pro Leu Pro Thr Glu Ser Leu Asp Cys Phe Cys Pro
        530                 535                 540
His Leu Gln Asn Ser Thr Gln Leu Glu Gln Val Asn Gln Met Leu Asn
545                 550                 555                 560
Leu Thr Gln Glu Glu Ile Thr Ala Thr Val Lys Val Asn Leu Pro Phe
                565                 570                 575
Gly Arg Pro Arg Val Leu Gln Lys Asn Val Asp His Cys Leu Leu Tyr
                580                 585                 590
His Arg Glu Tyr Val Ser Gly Phe Gly Lys Ala Met Arg Met Pro Met
                595                 600                 605
Trp Ser Ser Tyr Thr Val Pro Gln Leu Gly Asp Thr Ser Pro Leu Pro
        610                 615                 620
Pro Thr Val Pro Asp Cys Leu Arg Ala Asp Val Arg Val Pro Pro Ser
625                 630                 635                 640
Glu Ser Gln Lys Cys Ser Phe Tyr Leu Ala Asp Lys Asn Ile Thr His
                645                 650                 655
Gly Phe Leu Tyr Pro Pro Ala Ser Asn Arg Thr Ser Asp Ser Gln Tyr
                660                 665                 670
Asp Ala Leu Ile Thr Ser Asn Leu Val Pro Met Tyr Glu Glu Phe Arg
        675                 680                 685
Lys Met Trp Asp Tyr Phe His Ser Val Leu Leu Ile Lys His Ala Thr
        690                 695                 700
Glu Arg Asn Gly Val Asn Val Val Ser Gly Pro Ile Phe Asp Tyr Asn
705                 710                 715                 720
Tyr Asp Gly His Phe Asp Ala Pro Asp Glu Ile Thr Lys His Leu Ala
                725                 730                 735
```

-continued

Asn Thr Asp Val Pro Ile Pro Thr His Tyr Phe Val Val Leu Thr Ser
            740                 745                 750

Cys Lys Asn Lys Ser His Thr Pro Glu Asn Cys Pro Gly Trp Leu Asp
        755                 760                 765

Val Leu Pro Phe Ile Ile Pro His Arg Pro Thr Asn Val Glu Ser Cys
    770                 775                 780

Pro Glu Gly Lys Pro Glu Ala Leu Trp Val Glu Glu Arg Phe Thr Ala
785                 790                 795                 800

His Ile Ala Arg Val Arg Asp Val Glu Leu Leu Thr Gly Leu Asp Phe
                805                 810                 815

Tyr Gln Asp Lys Val Gln Pro Val Ser Glu Ile Leu Gln Leu Lys Thr
            820                 825                 830

Tyr Leu Pro Thr Phe Glu Thr Thr Ile
        835                 840

<210> SEQ ID NO 21
<211> LENGTH: 875
<212> TYPE: PRT
<213> ORGANISM: Homo Sapiens

<400> SEQUENCE: 21

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80

Cys Cys Trp Asp Phe Glu Asp Thr Cys Val Glu Ser Thr Arg Ile Trp
                85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
            180                 185                 190

His Ser Lys Tyr Met Arg Ala Met Tyr Pro Thr Lys Thr Phe Pro Asn
        195                 200                 205

His Tyr Thr Ile Val Thr Gly Leu Tyr Pro Glu Ser His Gly Ile Ile
    210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                245                 250                 255

Leu Thr Ala Met Tyr Gln Gly Leu Lys Ala Ala Thr Tyr Phe Trp Pro

-continued

```
                260                 265                 270
Gly Ser Glu Val Ala Ile Asn Gly Ser Phe Pro Ser Ile Tyr Met Pro
            275                 280                 285
Tyr Asn Gly Ser Val Pro Phe Glu Glu Arg Ile Ser Thr Leu Leu Lys
            290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                        325                 330                 335
Arg Val Ile Lys Ala Leu Gln Val Val Asp His Ala Phe Gly Met Leu
                340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
            370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                        405                 410                 415
Ser Phe Asn Ser Glu Glu Ile Val Arg Asn Leu Ser Cys Arg Lys Pro
                420                 425                 430
Asp Gln His Phe Lys Pro Tyr Leu Thr Pro Asp Leu Pro Lys Arg Leu
            435                 440                 445
His Tyr Ala Lys Asn Val Arg Ile Asp Lys Val His Leu Phe Val Asp
            450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                        485                 490                 495
Leu Ala His Gly Pro Ser Phe Lys Glu Lys Thr Glu Val Glu Pro Phe
                500                 505                 510
Glu Asn Ile Glu Val Tyr Asn Leu Met Cys Asp Leu Leu Arg Ile Gln
            515                 520                 525
Pro Ala Pro Asn Asn Gly Thr His Gly Ser Leu Asn His Leu Leu Lys
            530                 535                 540
Val Pro Phe Tyr Glu Pro Ser His Ala Glu Glu Val Ser Lys Phe Ser
545                 550                 555                 560
Val Cys Gly Phe Ala Asn Pro Leu Pro Thr Glu Ser Leu Asp Cys Phe
                        565                 570                 575
Cys Pro His Leu Gln Asn Ser Thr Gln Leu Glu Gln Val Asn Gln Met
                580                 585                 590
Leu Asn Leu Thr Gln Glu Glu Ile Thr Ala Thr Val Lys Val Asn Leu
            595                 600                 605
Pro Phe Gly Arg Pro Arg Val Leu Gln Lys Asn Val Asp His Cys Leu
            610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
                        645                 650                 655
Leu Pro Pro Thr Val Pro Asp Cys Leu Arg Ala Asp Val Arg Val Pro
                660                 665                 670
Pro Ser Glu Ser Gln Lys Cys Ser Phe Tyr Leu Ala Asp Lys Asn Ile
            675                 680                 685
```

```
Thr His Gly Phe Leu Tyr Pro Pro Ala Ser Asn Arg Thr Ser Asp Ser
    690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
    770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 22
<211> LENGTH: 875
<212> TYPE: PRT
<213> ORGANISM: Homo Sapiens

<400> SEQUENCE: 22

Met Glu Ser Thr Leu Thr Leu Ala Thr Glu Gln Pro Val Lys Lys Asn
  1               5                  10                  15

Thr Leu Lys Lys Tyr Lys Ile Ala Cys Ile Val Leu Leu Ala Leu Leu
             20                  25                  30

Val Ile Met Ser Leu Gly Leu Gly Leu Gly Leu Arg Lys Leu
             35                  40                  45

Glu Lys Gln Gly Ser Cys Arg Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
            100                 105                 110

Cys Ser Cys Ser Asp Asp Cys Leu Gln Lys Lys Asp Cys Cys Ala Asp
        115                 120                 125

Tyr Lys Ser Val Cys Gln Gly Glu Thr Ser Trp Leu Glu Glu Asn Cys
    130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                165                 170                 175

Trp Asp Thr Leu Met Pro Asn Ile Asn Lys Leu Lys Thr Cys Gly Ile
```

-continued

```
                180                 185                 190
His Ser Lys Tyr Met Arg Ala Met Tyr Pro Thr Lys Thr Phe Pro Asn
            195                 200                 205
His Tyr Thr Ile Val Thr Gly Leu Tyr Pro Glu Ser His Gly Ile Ile
        210                 215                 220
Asp Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
            260                 265                 270
Gly Ser Glu Val Ala Ile Asn Gly Ser Phe Pro Ser Ile Tyr Met Pro
        275                 280                 285
Tyr Asn Gly Ser Val Pro Phe Glu Glu Arg Ile Ser Thr Leu Leu Lys
        290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
                340                 345                 350
Met Glu Gly Leu Lys Gln Arg Asn Leu His Asn Cys Val Asn Ile Ile
            355                 360                 365
Leu Leu Ala Asp His Gly Met Asp Gln Thr Tyr Cys Asn Lys Met Glu
        370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
                420                 425                 430
Asp Gln His Phe Lys Pro Tyr Leu Thr Pro Asp Leu Pro Lys Arg Leu
        435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
            500                 505                 510
Glu Asn Ile Glu Val Tyr Asn Leu Met Cys Asp Leu Leu Arg Ile Gln
        515                 520                 525
Pro Ala Pro Asn Asn Gly Thr His Gly Ser Leu Asn His Leu Leu Lys
        530                 535                 540
Val Pro Phe Tyr Glu Pro Ser His Ala Glu Glu Val Ser Lys Phe Ser
545                 550                 555                 560
Val Cys Gly Phe Ala Asn Pro Leu Pro Thr Glu Ser Leu Asp Cys Phe
                565                 570                 575
Cys Pro His Leu Gln Asn Ser Thr Gln Leu Glu Gln Val Asn Gln Met
                580                 585                 590
Leu Asn Leu Thr Gln Glu Glu Ile Thr Ala Thr Val Lys Val Asn Leu
            595                 600                 605
```

```
Pro Phe Gly Arg Pro Arg Val Leu Gln Lys Asn Val Asp His Cys Leu
    610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
            645                 650                 655

Leu Pro Pro Thr Val Pro Asp Cys Leu Arg Ala Asp Val Arg Val Pro
        660                 665                 670

Pro Ser Glu Ser Gln Lys Cys Ser Phe Tyr Leu Ala Asp Lys Asn Ile
    675                 680                 685

Thr His Gly Phe Leu Tyr Pro Pro Ala Ser Asn Arg Thr Ser Asp Ser
690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His
            725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
            805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
            835                 840                 845

Asp Phe Tyr Gln Asp Lys Val Gln Pro Val Ser Glu Ile Leu Gln Leu
850                 855                 860

Lys Thr Tyr Leu Pro Thr Phe Glu Thr Thr Ile
865                 870                 875

<210> SEQ ID NO 23
<211> LENGTH: 385
<212> TYPE: PRT
<213> ORGANISM: Homo Sapiens

<400> SEQUENCE: 23

Pro Met Glu Ala Ile Phe Leu Ala His Gly Pro Ser Phe Lys Glu Lys
1               5                   10                  15

Thr Glu Val Glu Pro Phe Glu Asn Ile Glu Val Tyr Asn Leu Met Cys
            20                  25                  30

Asp Leu Leu Arg Ile Gln Pro Ala Pro Asn Asn Gly Thr His Gly Ser
        35                  40                  45

Leu Asn His Leu Leu Lys Val Pro Phe Tyr Glu Pro Ser His Ala Glu
50                  55                  60

Glu Val Ser Lys Phe Ser Val Cys Gly Phe Ala Asn Pro Leu Pro Thr
65                  70                  75                  80

Glu Ser Leu Asp Cys Phe Cys Pro His Leu Gln Asn Ser Thr Gln Leu
            85                  90                  95

Glu Gln Val Asn Gln Met Leu Asn Leu Thr Gln Glu Glu Ile Thr Ala
```

-continued

```
                100                 105                 110
Thr Val Lys Val Asn Leu Pro Phe Gly Arg Pro Arg Val Leu Gln Lys
            115                 120                 125

Asn Val Asp His Cys Leu Leu Tyr His Arg Glu Tyr Val Ser Gly Phe
        130                 135                 140

Gly Lys Ala Met Arg Met Pro Met Trp Ser Ser Tyr Thr Val Pro Gln
145                 150                 155                 160

Leu Gly Asp Thr Ser Pro Leu Pro Pro Thr Val Pro Asp Cys Leu Arg
                165                 170                 175

Ala Asp Val Arg Val Pro Pro Ser Glu Ser Gln Lys Cys Ser Phe Tyr
            180                 185                 190

Leu Ala Asp Lys Asn Ile Thr His Gly Phe Leu Tyr Pro Pro Ala Ser
        195                 200                 205

Asn Arg Thr Ser Asp Ser Gln Tyr Asp Ala Leu Ile Thr Ser Asn Leu
    210                 215                 220

Val Pro Met Tyr Glu Glu Phe Arg Lys Met Trp Asp Tyr Phe His Ser
225                 230                 235                 240

Val Leu Leu Ile Lys His Ala Thr Glu Arg Asn Gly Val Asn Val Val
                245                 250                 255

Ser Gly Pro Ile Phe Asp Tyr Asn Tyr Asp Gly His Phe Asp Ala Pro
            260                 265                 270

Asp Glu Ile Thr Lys His Leu Ala Asn Thr Asp Val Pro Ile Pro Thr
        275                 280                 285

His Tyr Phe Val Val Leu Thr Ser Cys Lys Asn Lys Ser His Thr Pro
    290                 295                 300

Glu Asn Cys Pro Gly Trp Leu Asp Val Leu Pro Phe Ile Ile Pro His
305                 310                 315                 320

Arg Pro Thr Asn Val Glu Ser Cys Pro Glu Gly Lys Pro Glu Ala Leu
                325                 330                 335

Trp Val Glu Glu Arg Phe Thr Ala His Ile Ala Arg Val Arg Asp Val
            340                 345                 350

Glu Leu Leu Thr Gly Leu Asp Phe Tyr Gln Asp Lys Val Gln Pro Val
        355                 360                 365

Ser Glu Ile Leu Gln Leu Lys Thr Tyr Leu Pro Thr Phe Glu Thr Thr
    370                 375                 380

Ile
385

<210> SEQ ID NO 24
<211> LENGTH: 384
<212> TYPE: PRT
<213> ORGANISM: Homo Sapiens

<400> SEQUENCE: 24

Met Glu Ala Ile Phe Leu Ala His Gly Pro Ser Phe Lys Glu Lys Thr
1               5                   10                  15

Glu Val Glu Pro Phe Glu Asn Ile Glu Val Tyr Asn Leu Met Cys Asp
            20                  25                  30

Leu Leu Arg Ile Gln Pro Ala Pro Asn Asn Gly Thr His Gly Ser Leu
        35                  40                  45

Asn His Leu Leu Lys Val Pro Phe Tyr Glu Pro Ser His Ala Glu Glu
    50                  55                  60

Val Ser Lys Phe Ser Val Cys Gly Phe Ala Asn Pro Leu Pro Thr Glu
65                  70                  75                  80
```

-continued

```
Ser Leu Asp Cys Phe Cys Pro His Leu Gln Asn Ser Thr Gln Leu Glu
            85                  90                  95

Gln Val Asn Gln Met Leu Asn Leu Thr Gln Glu Ile Thr Ala Thr
        100                 105                 110

Val Lys Val Asn Leu Pro Phe Gly Arg Pro Arg Val Leu Gln Lys Asn
        115                 120                 125

Val Asp His Cys Leu Leu Tyr His Arg Glu Tyr Val Ser Gly Phe Gly
    130                 135                 140

Lys Ala Met Arg Met Pro Met Trp Ser Ser Tyr Thr Val Pro Gln Leu
145                 150                 155                 160

Gly Asp Thr Ser Pro Leu Pro Pro Thr Val Pro Asp Cys Leu Arg Ala
                165                 170                 175

Asp Val Arg Val Pro Pro Ser Glu Ser Gln Lys Cys Ser Phe Tyr Leu
            180                 185                 190

Ala Asp Lys Asn Ile Thr His Gly Phe Leu Tyr Pro Pro Ala Ser Asn
        195                 200                 205

Arg Thr Ser Asp Ser Gln Tyr Asp Ala Leu Ile Thr Ser Asn Leu Val
    210                 215                 220

Pro Met Tyr Glu Glu Phe Arg Lys Met Trp Asp Tyr Phe His Ser Val
225                 230                 235                 240

Leu Leu Ile Lys His Ala Thr Glu Arg Asn Gly Val Asn Val Val Ser
                245                 250                 255

Gly Pro Ile Phe Asp Tyr Asn Tyr Asp Gly His Phe Asp Ala Pro Asp
            260                 265                 270

Glu Ile Thr Lys His Leu Ala Asn Thr Asp Val Pro Ile Pro Thr His
        275                 280                 285

Tyr Phe Val Leu Thr Ser Cys Lys Asn Lys Ser His Thr Pro Glu
    290                 295                 300

Asn Cys Pro Gly Trp Leu Asp Val Leu Pro Phe Ile Ile Pro His Arg
305                 310                 315                 320

Pro Thr Asn Val Glu Ser Cys Pro Glu Gly Lys Pro Glu Ala Leu Trp
                325                 330                 335

Val Glu Glu Arg Phe Thr Ala His Ile Ala Arg Val Arg Asp Val Glu
            340                 345                 350

Leu Leu Thr Gly Leu Asp Phe Tyr Gln Asp Lys Val Gln Pro Val Ser
        355                 360                 365

Glu Ile Leu Gln Leu Lys Thr Tyr Leu Pro Thr Phe Glu Thr Pro Ile
    370                 375                 380

<210> SEQ ID NO 25
<211> LENGTH: 14
<212> TYPE: PRT
<213> ORGANISM: Tetanus toxoid

<400> SEQUENCE: 25

Gln Tyr Ile Lys Ala Asn Ser Lys Phe Ile Gly Ile Thr Glu
1               5                   10

<210> SEQ ID NO 26
<211> LENGTH: 21
<212> TYPE: PRT
<213> ORGANISM: Plasmodium falciparum

<400> SEQUENCE: 26

Asp Ile Glu Lys Lys Ile Ala Lys Met Glu Lys Ala Ser Ser Val Phe
1               5                   10                  15
```

-continued

Asn Val Val Asn Ser
            20

<210> SEQ ID NO 27
<211> LENGTH: 16
<212> TYPE: PRT
<213> ORGANISM: Streptococcus aureus

<400> SEQUENCE: 27

Gly Ala Val Asp Ser Ile Leu Gly Gly Val Ala Thr Tyr Gly Ala Ala
 1               5                  10                  15

<210> SEQ ID NO 28
<211> LENGTH: 13
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = either cyclohexylalanine, phenylalanine,
      or tyrosine
<221> NAME/KEY: VARIANT
<222> LOCATION: 1, 13
<223> OTHER INFORMATION: Xaa =  D-alanine or L-alanine
<220> FEATURE:
<223> OTHER INFORMATION: Pan-DR-binding Epitope

<400> SEQUENCE: 28

Xaa Lys Xaa Val Ala Ala Trp Thr Leu Lys Ala Ala Xaa
 1               5                  10

<210> SEQ ID NO 29
<211> LENGTH: 14
<212> TYPE: DNA
<213> ORGANISM: Artificial Sequence
<220> FEATURE:
<223> OTHER INFORMATION: Primer

<400> SEQUENCE: 29
ttttgatcaa gctt                                                         14

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
ctaatacgac tcactatagg gctcgagcgg ccgcccgggc ag                           42

<210> SEQ ID NO 31
<211> LENGTH: 12
<212> TYPE: DNA
<213> ORGANISM: Artificial Sequence
<220> FEATURE:
<223> OTHER INFORMATION: Primer

<400> SEQUENCE: 31
gatcctgccc gg                                                           12

<210> SEQ ID NO 32
<211> LENGTH: 40
<212> TYPE: DNA
<213> ORGANISM: Artificial Sequence
<220> FEATURE:
<223> OTHER INFORMATION: Primer

<400> SEQUENCE: 32
gtaatacgac tcactatagg gcagcgtggt cgcggccgag                    40

<210> SEQ ID NO 33
<211> LENGTH: 10
<212> TYPE: DNA
<213> ORGANISM: Artificial Sequence
<220> FEATURE:
<223> OTHER INFORMATION: Primer

<400> SEQUENCE: 33
gatcctcggc                                                    10

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
ctaatacgac tcactatagg gc                                      22

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
tcgagcggcc gcccgggcag ga                                      22

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
agcgtggtcg cggccgagga                                         20

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
atatcgccgc gctcgtcgtc gacaa                                   25

<210> SEQ ID NO 38
<211> LENGTH: 26
<212> TYPE: DNA
<213> ORGANISM: Artificial Sequence
<220> FEATURE:
<223> OTHER INFORMATION: Primer

<400> SEQUENCE: 38
agccacacgc agctcattgt agaagg                                  26

<210> SEQ ID NO 39
<211> LENGTH: 19

```
<212> TYPE: DNA
<213> ORGANISM: Homo Sapiens

<400> SEQUENCE: 39
gaaucuacgu ugacuuuag                                                    19

<210> SEQ ID NO 40
<211> LENGTH: 22
<212> TYPE: PRT
<213> ORGANISM: Homo Sapiens

<400> SEQUENCE: 40

Cys Gly Ile His Ser Lys Tyr Met Arg Ala Met Tyr Pro Thr Lys Thr
1               5                   10                  15

Phe Pro Asn His Tyr Thr
            20

<210> SEQ ID NO 41
<211> LENGTH: 4
<212> TYPE: PRT
<213> ORGANISM: Homo Sapiens

<400> SEQUENCE: 41

Asn Phe Ser Leu
1

<210> SEQ ID NO 42
<211> LENGTH: 4
<212> TYPE: PRT
<213> ORGANISM: Homo Sapiens

<400> SEQUENCE: 42

Asn Gly Ser Phe
1

<210> SEQ ID NO 43
<211> LENGTH: 4
<212> TYPE: PRT
<213> ORGANISM: Homo Sapiens

<400> SEQUENCE: 43

Asn Gly Ser Val
1

<210> SEQ ID NO 44
<211> LENGTH: 4
<212> TYPE: PRT
<213> ORGANISM: Homo Sapiens

<400> SEQUENCE: 44

Asn Leu Ser Cys
1

<210> SEQ ID NO 45
<211> LENGTH: 4
<212> TYPE: PRT
<213> ORGANISM: Homo Sapiens

<400> SEQUENCE: 45

Asn Gly Thr His
1

<210> SEQ ID NO 46
<211> LENGTH: 4
```

-continued

```
<212> TYPE: PRT
<213> ORGANISM: Homo Sapiens

<400> SEQUENCE: 46

Asn Ser Thr Gln
 1

<210> SEQ ID NO 47
<211> LENGTH: 4
<212> TYPE: PRT
<213> ORGANISM: Homo Sapiens

<400> SEQUENCE: 47

Asn Leu Thr Gln
 1

<210> SEQ ID NO 48
<211> LENGTH: 4
<212> TYPE: PRT
<213> ORGANISM: Homo Sapiens

<400> SEQUENCE: 48

Asn Ile Thr His
 1

<210> SEQ ID NO 49
<211> LENGTH: 4
<212> TYPE: PRT
<213> ORGANISM: Homo Sapiens

<400> SEQUENCE: 49

Asn Arg Thr Ser
 1

<210> SEQ ID NO 50
<211> LENGTH: 4
<212> TYPE: PRT
<213> ORGANISM: Homo Sapiens

<400> SEQUENCE: 50

Asn Lys Ser His
 1

<210> SEQ ID NO 51
<211> LENGTH: 4
<212> TYPE: PRT
<213> ORGANISM: Homo Sapiens

<400> SEQUENCE: 51

Lys Lys Asn Thr
 1

<210> SEQ ID NO 52
<211> LENGTH: 4
<212> TYPE: PRT
<213> ORGANISM: Homo Sapiens

<400> SEQUENCE: 52

Thr Cys Val Glu
 1

<210> SEQ ID NO 53
<211> LENGTH: 4
<212> TYPE: PRT
<213> ORGANISM: Homo Sapiens
```

```
<400> SEQUENCE: 53

Thr Arg Leu Glu
1

<210> SEQ ID NO 54
<211> LENGTH: 4
<212> TYPE: PRT
<213> ORGANISM: Homo Sapiens

<400> SEQUENCE: 54

Ser Cys Ser Asp
1

<210> SEQ ID NO 55
<211> LENGTH: 4
<212> TYPE: PRT
<213> ORGANISM: Homo Sapiens

<400> SEQUENCE: 55

Ser Trp Leu Glu
1

<210> SEQ ID NO 56
<211> LENGTH: 4
<212> TYPE: PRT
<213> ORGANISM: Homo Sapiens

<400> SEQUENCE: 56

Ser Ser Lys Glu
1

<210> SEQ ID NO 57
<211> LENGTH: 4
<212> TYPE: PRT
<213> ORGANISM: Homo Sapiens

<400> SEQUENCE: 57

Ser Phe Lys Glu
1

<210> SEQ ID NO 58
<211> LENGTH: 4
<212> TYPE: PRT
<213> ORGANISM: Homo Sapiens

<400> SEQUENCE: 58

Thr Glu Val Glu
1

<210> SEQ ID NO 59
<211> LENGTH: 4
<212> TYPE: PRT
<213> ORGANISM: Homo Sapiens

<400> SEQUENCE: 59

Ser His Ala Glu
1

<210> SEQ ID NO 60
<211> LENGTH: 4
<212> TYPE: PRT
<213> ORGANISM: Homo Sapiens

<400> SEQUENCE: 60
```

Thr Gln Leu Glu
1

<210> SEQ ID NO 61
<211> LENGTH: 4
<212> TYPE: PRT
<213> ORGANISM: Homo Sapiens

<400> SEQUENCE: 61

Thr Gln Glu Glu
1

<210> SEQ ID NO 62
<211> LENGTH: 4
<212> TYPE: PRT
<213> ORGANISM: Homo Sapiens

<400> SEQUENCE: 62

Thr Val Pro Asp
1

<210> SEQ ID NO 63
<211> LENGTH: 4
<212> TYPE: PRT
<213> ORGANISM: Homo Sapiens

<400> SEQUENCE: 63

Ser Gln Tyr Asp
1

<210> SEQ ID NO 64
<211> LENGTH: 4
<212> TYPE: PRT
<213> ORGANISM: Homo Sapiens

<400> SEQUENCE: 64

Thr Asn Val Glu
1

<210> SEQ ID NO 65
<211> LENGTH: 4
<212> TYPE: PRT
<213> ORGANISM: Homo Sapiens

<400> SEQUENCE: 65

Ser Cys Pro Glu
1

<210> SEQ ID NO 66
<211> LENGTH: 4
<212> TYPE: PRT
<213> ORGANISM: Homo Sapiens

<400> SEQUENCE: 66

Thr Gly Leu Asp
1

<210> SEQ ID NO 67
<211> LENGTH: 7
<212> TYPE: PRT
<213> ORGANISM: Homo Sapiens

<400> SEQUENCE: 67

Arg Thr Ser Asp Ser Gln Tyr

```
<210> SEQ ID NO 68
<211> LENGTH: 6
<212> TYPE: PRT
<213> ORGANISM: Homo Sapiens

<400> SEQUENCE: 68

Gly Leu Gly Leu Gly Leu
1               5

<210> SEQ ID NO 69
<211> LENGTH: 6
<212> TYPE: PRT
<213> ORGANISM: Homo Sapiens

<400> SEQUENCE: 69

Gly Leu Gly Leu Gly Leu
1               5

<210> SEQ ID NO 70
<211> LENGTH: 6
<212> TYPE: PRT
<213> ORGANISM: Homo Sapiens

<400> SEQUENCE: 70

Gly Leu Gly Leu Gly Leu
1               5

<210> SEQ ID NO 71
<211> LENGTH: 6
<212> TYPE: PRT
<213> ORGANISM: Homo Sapiens

<400> SEQUENCE: 71

Gly Leu Gly Leu Gly Leu
1               5

<210> SEQ ID NO 72
<211> LENGTH: 6
<212> TYPE: PRT
<213> ORGANISM: Homo Sapiens

<400> SEQUENCE: 72

Gly Leu Glu Asn Cys Arg
1               5

<210> SEQ ID NO 73
<211> LENGTH: 6
<212> TYPE: PRT
<213> ORGANISM: Homo Sapiens

<400> SEQUENCE: 73

Gly Ile Ile Asp Asn Asn
1               5

<210> SEQ ID NO 74
<211> LENGTH: 6
<212> TYPE: PRT
<213> ORGANISM: Homo Sapiens

<400> SEQUENCE: 74

Gly Leu Lys Ala Ala Thr
1               5
```

```
<210> SEQ ID NO 75
<211> LENGTH: 6
<212> TYPE: PRT
<213> ORGANISM: Homo Sapiens

<400> SEQUENCE: 75

Gly Ser Glu Val Ala Ile
1               5

<210> SEQ ID NO 76
<211> LENGTH: 6
<212> TYPE: PRT
<213> ORGANISM: Homo Sapiens

<400> SEQUENCE: 76

Gly Ser Phe Pro Ser Ile
1               5

<210> SEQ ID NO 77
<211> LENGTH: 6
<212> TYPE: PRT
<213> ORGANISM: Homo Sapiens

<400> SEQUENCE: 77

Gly Gly Pro Val Ser Ala
1               5

<210> SEQ ID NO 78
<211> LENGTH: 6
<212> TYPE: PRT
<213> ORGANISM: Homo Sapiens

<400> SEQUENCE: 78

Gly Met Asp Gln Thr Tyr
1               5

<210> SEQ ID NO 79
<211> LENGTH: 21
<212> TYPE: PRT
<213> ORGANISM: Homo Sapiens

<400> SEQUENCE: 79

Cys Arg Cys Asp Val Ala Cys Lys Asp Arg Gly Asp Cys Cys Trp Asp
1               5                   10                  15

Phe Glu Asp Thr Cys
            20

<210> SEQ ID NO 80
<211> LENGTH: 21
<212> TYPE: PRT
<213> ORGANISM: Homo Sapiens

<400> SEQUENCE: 80

Cys Ser Cys Ser Asp Asp Cys Leu Gln Lys Lys Asp Cys Cys Ala Asp
1               5                   10                  15

Tyr Lys Ser Val Cys
            20

<210> SEQ ID NO 81
<211> LENGTH: 875
<212> TYPE: PRT
<213> ORGANISM: Homo Sapiens

<400> SEQUENCE: 81
```

-continued

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
             20                  25                  30

Val Ile Met Ser Leu Gly Leu Gly Leu Gly Leu Arg Lys Leu
         35                  40                  45

Glu Lys Gln Gly Ser Cys Arg Lys Lys Cys Phe Asp Ala Ser Phe Arg
     50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                 85                  90                  95

Met Cys Asn Lys Phe Arg Cys Gly Glu Thr Arg Leu Glu Ala Ser Leu
             100                 105                 110

Cys Ser Cys Ser Asp Asp Cys Leu Gln Lys Lys Asp Cys Cys Ala Asp
         115                 120                 125

Tyr Lys Ser Val Cys Gln Gly Glu Thr Ser Trp Leu Glu Glu Asn Cys
     130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
                 165                 170                 175

Trp Asp Thr Leu Met Pro Asn Ile Asn Lys Leu Lys Thr Cys Gly Ile
             180                 185                 190

His Ser Lys Tyr Met Arg Ala Met Tyr Pro Thr Lys Thr Phe Pro Asn
         195                 200                 205

His Tyr Thr Ile Val Thr Gly Leu Tyr Pro Glu Ser His Gly Ile Ile
     210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
                 245                 250                 255

Leu Thr Ala Met Tyr Gln Gly Leu Lys Ala Ala Thr Tyr Phe Trp Pro
             260                 265                 270

Gly Ser Glu Val Ala Ile Asn Gly Ser Phe Pro Ser Ile Tyr Met Pro
         275                 280                 285

Tyr Asn Gly Ser Val Pro Phe Glu Glu Arg Ile Ser Thr Leu Leu Lys
     290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His His Ala Gly Pro Val Ser Ala
                 325                 330                 335

Arg Val Ile Lys Ala Leu Gln Val Val Asp His Ala Phe Gly Met Leu
             340                 345                 350

Met Glu Gly Leu Lys Gln Arg Asn Leu His Asn Cys Val Asn Ile Ile
         355                 360                 365

Leu Leu Ala Asp His Gly Met Asp Gln Thr Tyr Cys Asn Lys Met Glu
     370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
                 405                 410                 415
```

```
Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
        595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His
                725                 730                 735

Ala Thr Glu Arg Asn Gly Val Asn Val Ser Gly Pro Ile Phe Asp
            740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
```

```
                835                 840                 845
Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 82
<211> LENGTH: 17
<212> TYPE: PRT
<213> ORGANISM: Homo Sapiens

<400> SEQUENCE: 82

Ser Cys Ser Asp Asp Cys Leu Gln Arg Lys Asp Cys Cys Ala Asp Tyr
1               5                   10                  15

Lys

<210> SEQ ID NO 83
<211> LENGTH: 19
<212> TYPE: PRT
<213> ORGANISM: Homo Sapiens

<400> SEQUENCE: 83

Cys Ser Cys Ser Asp Asp Cys Leu Gln Arg Lys Asp Cys Cys Ala Asp
1               5                   10                  15

Tyr Lys Ser

<210> SEQ ID NO 84
<211> LENGTH: 29
<212> TYPE: PRT
<213> ORGANISM: Homo Sapiens

<400> SEQUENCE: 84

Leu Glu Ala Ser Leu Cys Ser Cys Ser Asp Asp Cys Leu Gln Arg Lys
1               5                   10                  15

Asp Cys Cys Ala Asp Tyr Lys Ser Val Cys Gln Gly Glu
            20                  25

<210> SEQ ID NO 85
<211> LENGTH: 17
<212> TYPE: PRT
<213> ORGANISM: Homo Sapiens

<400> SEQUENCE: 85

Pro Thr Asn Val Glu Ser Cys Pro Gly Gly Lys Pro Glu Ala Leu Trp
1               5                   10                  15

Val

<210> SEQ ID NO 86
<211> LENGTH: 19
<212> TYPE: PRT
<213> ORGANISM: Homo Sapiens

<400> SEQUENCE: 86

Arg Pro Thr Asn Val Glu Ser Cys Pro Gly Gly Lys Pro Glu Ala Leu
1               5                   10                  15

Trp Val Glu

<210> SEQ ID NO 87
<211> LENGTH: 29
<212> TYPE: PRT
<213> ORGANISM: Homo Sapiens
```

-continued

```
<400> SEQUENCE: 87

Phe Ile Ile Pro His Arg Pro Thr Asn Val Glu Ser Cys Pro Gly Gly
1               5                   10                  15

Lys Pro Glu Ala Leu Trp Val Glu Glu Arg Phe Thr Ala
            20                  25

<210> SEQ ID NO 88
<211> LENGTH: 10
<212> TYPE: PRT
<213> ORGANISM: Homo Sapiens

<400> SEQUENCE: 88

Thr Tyr Leu Pro Thr Phe Glu Thr Pro Ile
1               5                   10

<210> SEQ ID NO 89
<211> LENGTH: 11
<212> TYPE: PRT
<213> ORGANISM: Homo Sapiens

<400> SEQUENCE: 89

Lys Thr Tyr Leu Pro Thr Phe Glu Thr Pro Ile
1               5                   10

<210> SEQ ID NO 90
<211> LENGTH: 16
<212> TYPE: PRT
<213> ORGANISM: Homo Sapiens

<400> SEQUENCE: 90

Glu Ile Leu Gln Leu Lys Thr Tyr Leu Pro Thr Phe Glu Thr Pro Ile
1               5                   10                  15

<210> SEQ ID NO 91
<211> LENGTH: 3165
<212> TYPE: DNA
<213> ORGANISM: Homo Sapiens

<400> SEQUENCE: 91
atacagtttc tctttgccag actagactaa agaaggagca ctactttatt ctgataaaac      60
aggtctatgc agctaccagg acaatggaat ctacgttgac tttagcaacg gaacaacctg     120
ttaagaagaa cactcttaag aaatataaaa tagcttgcat tgttcttctt gctttgctgg     180
tgatcatgtc acttggatta ggcctgggc ttggactcag gaaactggaa aagcaaggca     240
gctgcaggaa gaagtgcttt gatgcatcat ttagaggact ggagaactgc cggtgtgatg     300
tggcatgtaa agaccgaggt gattgctgct gggattttga agacacctgt gtggaatcaa     360
ctcgaatatg gatgtgcaat aaatttcgtt gtggagagac cagattagag gccagccttt     420
gctcttgttc agatgactgt ttgcagagga aagattgctg tgctgactat aagagtgttt     480
gccaaggaga aacctcatgg ctggaagaaa actgtgacac agcccagcag tctcagtgcc     540
cagaagggtt tgacctgcca ccagttatct tgttttctat ggatggattt agagctgaat     600
atttatacac atgggatact ttaatgccaa atatcaataa actgaaaaca tgtggaattc     660
attcaaaata catgagagct atgtatccta ccaaaacctt cccaaatcat acaccattg     720 tcacgggctt gtatccggag tcacatggca tcattgacaa taatatgtat gatgtaaatc     780
tcaacaagaa ttttttcactt tcttcaaagg aacaaaataa tccagcctgg tggcatgggc     840
aaccaatgtg gctgacagca atgtatcaag gtttaaaagc cgctacctac ttttggcccg     900
```

```
gatcagaagt ggctataaat ggctcctttc cttccatata catgccttac aacggaagtg    960
tcccatttga agagaggatt tctacactgt taaaatggct ggacctgccc aaagctgaga   1020
gacccaggtt ttataccatg ttttttgaag aacctgattc ctctggacat gcaggtggac   1080
cagtcagtgc cagagtaatt aaagccttac aggtagtaga tcatgctttt gggatgttga   1140
tggaaggcct gaagcagcgg aatttgcaca actgtgtcaa tatcatcctt ctggctgacc   1200
atggaatgga ccagacttat tgtaacaaga tggaatacat gactgattat tttcccagaa   1260
taaacttctt ctacatgtac gaagggcctg cccccccgcgt ccgagctcat aatatacctc   1320
atgacttttt tagttttaat tctgaggaaa ttgttagaaa cctcagttgc cgaaaacctg   1380
atcagcattt caagccctat ttgactcctg atttgccaaa cgactgcac tatgccaaga   1440
acgtcagaat cgacaaagtt catctctttg tggatcaaca gtggctggct gttaggagta   1500
aatcaaatac aaattgtgga ggaggcaacc atggttataa caatgagttt aggagcatgg   1560
aggctatctt tctggcacat ggacccagtt ttaaagagaa gactgaagtt gaaccatttg   1620
aaaatattga agtctataac ctaatgtgtg atcttctacg cattcaacca gcaccaaaca   1680
atggaaccca tggtagttta aaccatcttc tgaaggtgcc tttttatgag ccatcccatg   1740
cagaggaggt gtcaaagttt tctgtttgtg gctttgctaa tccattgccc acagagtctc   1800
ttgactgttt ctgccctcac ctacaaaata gtactcagct ggaacaagtg aatcagatgc   1860
taaatctcac caagaagaa ataacagcaa cagtgaaagt aaatttgcca tttgggaggc   1920
ctagggtact gcagaagaac gtggaccact gtctcctta ccacagggaa tatgtcagtg   1980
gatttggaaa agctatgagg atgcccatgt ggagttcata cacagtcccc cagttgggag   2040
acacatcgcc tctgcctccc actgtcccag actgtctgcg ggctgatgtc agggttcctc   2100
cttctgagag ccaaaaatgt tccttctatt tagcagacaa gaatatcacc cacggcttcc   2160
tctatcctcc tgccagcaat agaacatcag atagccaata tgatgcttta attactagca   2220
atttggtacc tatgtatgaa gaattcagaa aaatgtggga ctacttccac agtgttcttc   2280
ttataaaaca tgccacagaa agaaatggag taaatgtggt tagtgaccca atatttgatt   2340
ataattatga tggccatttt gatgctccag atgaaattac caaacattta gccaacactg   2400
atgttcccat cccaacacac tactttgtgg tgctgaccag ttgtaaaaac aagagccaca   2460
caccggaaaa ctgccctggg tggctggatg tcctacccctt tatcatccct caccgaccta   2520
ccaacgtgga gagctgtcct gaaggtaaac cagaagctct ttgggttgaa gaaagattta   2580
cagctcacat tgcccgggtc cgtgatgtag aacttctcac tgggcttgac ttctatcagg   2640
ataaagtgca gcctgtctct gaaatttgc aactaaagac atatttacca acatttgaaa   2700
ccactatttta acttaataat gtctacttaa tatataattt actgtataaa gtaattttgg   2760
caaaatataa gtgatttttt tctggagaat tgtaaaataa agttttctat ttttccttaa   2820
gtcccctaaa agccataatt tttattattc cttttttctct tttttcaatt ctatgaatat   2880
gtattatttt aaagttatat ttttcacaca gagatgatgc tatattacac cttcccttt    2940
ttgttggttt cttaaactct aatctcatga cagattatac cttccttatt acttgttta    3000
tcttactcag aatcttttgaa tatttttttc tgcccagaat tatctaaaca aagggagaa   3060
caaaagaagt atgtctcact tgggaactga atcaactcta aatcagtttt gtcacaaaac   3120
ttttgtatt tgactggcaa tgctgattaa aattaaaaat gcaca                    3165
```

<210> SEQ ID NO 92

-continued

<211> LENGTH: 2719
<212> TYPE: DNA
<213> ORGANISM: Homo Sapiens

<400> SEQUENCE: 92

```
ctactttatt ctgataaaac aggtctatgc agctaccagg acaatggaat ctacgttgac     60
tgttcttctt gctttgctgg tgatcatgtc acttggatta ggcctggggc ttggactcag    120
gaaactggaa aagcaaggca gctgcaggaa gaagtgcttt gatgcatcat ttagaggact    180
ggagaactgc cggtgtgatg tggcatgtaa agaccgaggt gattgctgct gggattttga    240
agacacctgt gtggaatcaa ctcgaatatg gatgtgcaat aaatttcgtt gtggagagac    300
cagattagag gccagccttt gctcttgttc agatgactgt tgcagaagaa agattgctg    360
tgctgactat aagagtgttt gccaaggaga aacctcatgg ctggaagaaa actgtgacac    420
agcccagcag tctcagtgcc cagaagggtt tgacctgcca ccagttatct tgttttctat    480
ggatggattt agagctgaat atttatacac atgggatact ttaatgccaa atatcaataa    540
actgaaaaca tgtggaattc attcaaaata catgagagct atgtatccta ccaaaacctt    600
cccaaatcat tacaccattg tcacgggctt gtatccagag tcacatgcca tcattgacaa    660
taatatgtat gatgtaaatc tcaacaagaa ttttcacttt tcttcaaagg aacaaaataa    720
tccagcctgg tggcatgggc aaccaatgtg gctgacagca atgtatcaag gtttaaaagc    780
cgctacctac ttttggcccg gatcagaagt ggctataaat ggctccttc cttccatata    840
catgccttac aacggaagtg tcccatttga agagaggatt tctacactgt taaaatggct    900
ggacctgccc aaagctgaaa gacccaggtt ttataccatg tattttgaag aacctgattc    960
ctctggacat gcaggtggac cagtcagtgc cagagtaatt aaagccttac aggtagtaga   1020
tcatgctttt gggatgttga tggaaggcct gaagcagcgg aatttgcaca actgtgtcaa   1080
tatcatcctt ctggctgacc atggaatgga ccagacttat tgtaacaaga tggaatacat   1140
gactgattat tttcccagaa taaacttctt ctacatgtac gaagggcctg cccccgcat   1200
ccgagctcat aatatacctc atgactttt tagttttaat tctgaggaaa ttgttagaaa   1260
cctcagttgc cgaaaacctg atcagcattt caagccctat ttgactcctg atttgccaaa   1320
gcgactgcac tatgccaaga acgtcagaat cgacaaagtt catctctttg tggatcaaca   1380
gtggctggct gttaggagta aatcaaatac aaattgtgga ggaggcaacc atggttataa   1440
caatgagttt aggagcatgg aggctatctt tctggcacat ggacccagtt ttaaagagaa   1500
gactgaagtt gaaccatttg aaaatattga agtctataac ctaatgtgtg atcttctacg   1560
cattcaacca gcaccaaaca atggaaccca tggtagttta aaccatcttc tgaaggtgcc   1620
tttttatgag ccatcccatg cagaggaggt gtcaaagttt tctgtttgtg gctttgctaa   1680
tccattgccc acagagtctc ttgactgttt ctgccctcac ctacaaaata gtactcagct   1740
ggaacaagtg aatcagatgc taaatctcac ccaagaagaa ataacagcaa cagtgaaagt   1800
aaatttgcca tttgggaggc ctagggtact gcagaagaac gtggaccact gtctccttta   1860
ccacagggaa tatgtcagtg gatttggaaa agctatgagg atgcccatgt ggagttcata   1920
cacagtcccc cagttgggag acacatcgcc tctgcctccc actgtcccag actgtctgcg   1980
ggctgatgtc agggttcctc cttctgagag ccaaaaatgt tccttctatt tagcagacaa   2040
gaatatcacc cacggcttcc tctatcctcc tgccagcaat agaacatcag atagccaata   2100
tgatgcttta attactagca atttggtacc tatgtatgaa gaattcagaa aaatgtggga   2160
ctacttccac agtgttcttc ttataaaaaca tgccacagaa agaaatggag taaatgtggt   2220
```

-continued

```
tagtggacca atatttgatt ataattatga tggccatttt gatgctccag atgaaattac    2280
caaacattta gccaacactg atgttcccat cccaacacac tactttgtgg tgctgaccag    2340
ttgtaaaaac aagagccaca caccggaaaa ctgccctggg tggctggatg tcctacccct    2400
tatcatccct caccgaccta ccaacgtgga gagctgtcct gaaggtaaac cagaagctct    2460
ttgggttgaa gaaagattta cagctcacat gcccgggtc cgtgatgtag aacttctcac     2520
tgggcttgac ttctatcagg ataaagtgca gcctgtctct gaaattttgc aactaaagac    2580
atatttacca acatttgaaa ccactatttta acttaataat gtctacttaa tatataattt   2640
actgtataaa gtaattttgg caaaatataa gtgattttttt ctggagaatt gtaaaataaa   2700
gttttctatt tttccttaa                                                 2719
```

<210> SEQ ID NO 93
<211> LENGTH: 2780
<212> TYPE: DNA
<213> ORGANISM: Homo Sapiens

<400> SEQUENCE: 93

```
ctactttatt ctgataaaac aggtctatgc agctaccagg acaatggaat ctacgttgac      60
tttagcaacg gaacaacctg ttaagaagaa cactcttaag aaatataaaa tagcttgcat     120
tgttcttctt gctttgctgg tgatcatgtc acttggatta ggcctggggc ttggactcag     180
gaaactggaa aagcaaggca gctgcaggaa gaagtgcttt gatgcatcat ttagaggact    240
ggagaactgc cggtgtgatg tggcatgtaa agaccgaggt gattgctgct gggatttttga   300 agacacctgt gtggaatcaa ctcgaatatg gatgtgcaat aaatttcgtt gtggagagac    360
cagattagag gccagccttt gctcttgttc agatgactgt ttgcagagga agattgctg     420 tgctgactat aagagtgttt gccaaggaga aacctcatgg ctggaagaaa actgtgacac   480
agcccagcag tctcagtgcc cagaagggtt tgacctgcca ccagttatct tgttttctat   540
ggatggattt agagctgaat atttatacac atgggatact ttaatgccaa atatcaataa   600
actgaaaaca tgtggaattc attcaaaata catgagagct atgtatccta ccaaaacctt   660
cccaaatcat tacaccattg tcacgggctt gtatccggag tcacatggca tcattgacaa   720
taatatgtat gatgtaaatc tcaacaagaa ttttttcactt tcttcaaagg aacaaaataa  780
tccagcctgg tggcatgggc aaccaatgtg gctgacagca atgtatcaag gtttaaaagc   840
cgctacctac ttttggcccg gatcagaagt ggctataaat ggctccttc cttccatata    900 catgccttac aacggaagtg tcccatttga agagaggatt tctacactgt taaaatggct   960
ggacctgccc aaagctgaga gacccaggtt ttataccatg ttttttgaag aacctgattc  1020
ctctggacat gcaggtggac cagtcagtgc cagagtaatt aaagccttac aggtagtaga  1080
tcatgctttt gggatgttga tggaaggcct gaagcagcgg aatttgcaca actgtgtcaa  1140
tatcatcctt ctggctgacc atggaatgga ccagactttat tgtaacaaga tggaatacat  1200
gactgattat tttcccagaa taaacttctt ctacatgtac gaagggcctg ccccccgcgt   1260
ccgagctcat aatataccctc atgactttttt tagtttaat tctgaggaaa ttgttagaaa  1320
cctcagttgc cgaaacctg atcagcattt caagccctat ttgactcctg atttgccaaa   1380
gcgactgcac tatgccaaga acgtcagaat cgacaaagtt catctctttg tggatcaaca  1440
gtggctggct gttaggagta aatcaaatac aaattgtgga ggaggcaacc atggttataa  1500
caatgagttt aggagcatgg aggctatctt tctggcacat ggacccagtt ttaaagagaa  1560
```

-continued

```
gactgaagtt gaaccatttg aaaatattga agtctataac ctaatgtgtg atcttctacg    1620
cattcaacca gcaccaaaca atggaaccca tggtagttta aaccatcttc tgaaggtgcc    1680
tttttatgag ccatcccatg cagaggaggt gtcaaagttt tctgtttgtg gctttgctaa    1740
tccattgccc acagagtctc ttgactgttt ctgccctcac ctacaaaata gtactcagct    1800
ggaacaagtg aatcagatgc taaatctcac ccaagaagaa ataacagcaa cagtgaaagt    1860
aaatttgcca tttgggaggc ctagggtact gcagaagaac gtggaccact gtctccttta    1920
ccacagggaa tatgtcagtg gatttggaaa agctatgagg atgcccatgt ggagttcata    1980
cacagtcccc cagttgggag acacatcgcc tctgcctccc actgtcccag actgtctgcg    2040
ggctgatgtc agggttcctc cttctgagag ccaaaaatgt tccttctatt tagcagacaa    2100
gaatatcacc cacggcttcc tctatcctcc tgccagcaat agaacatcag atagccaata    2160
tgatgcttta attactagca atttggtacc tatgtatgaa gaattcagaa aaatgtggga    2220
ctacttccac agtgttcttc ttataaaaca tgccacagaa agaaatggag taaatgtggt    2280
tagtggacca atatttgatt ataattatga tggccatttt gatgctccag atgaaattac    2340
caaacattta gccaacactg atgttcccat cccaacacac tactttgtgg tgctgaccag    2400
ttgtaaaaac aagagccaca caccggaaaa ctgccctggg tggctggatg tcctacccct    2460
tatcatccct caccgaccta ccaacgtgga gagctgtcct gaaggtaaac cagaagctct    2520
ttgggttgaa gaaagattta cagctcacat tgcccgggtc cgtgatgtag aacttctcac    2580
tgggcttgac ttctatcagg ataaagtgca gcctgtctct gaaattttgc aactaaagac    2640
atatttacca acatttgaaa ccactatttta acttaataat gtctacttaa tatataattt    2700
actgtataaa gtaattttgg caaaatataa gtgatttttt tctggagaat tgtaaaataa    2760
agttttctat ttttccttaa                                                 2780
```

<210> SEQ ID NO 94
<211> LENGTH: 875
<212> TYPE: PRT
<213> ORGANISM: Homo Sapiens

<400> SEQUENCE: 94

```
Met Glu Ser Thr Leu Thr Leu Ala Thr Glu Gln Pro Val Lys Lys Asn
 1               5                  10                  15

Thr Leu Lys Lys Tyr Lys Ile Ala Cys Ile Val Leu Ala Leu Leu
            20                  25                  30

Val Ile Met Ser Leu Gly Leu Gly Leu Gly Leu Arg Lys Leu
            35                  40                  45

Glu Lys Gln Gly Ser Cys Arg Lys Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
                    85                  90                  95

Met Cys Asn Lys Phe Arg Cys Gly Glu Thr Arg Leu Glu Ala Ser Leu
                100                 105                 110

Cys Ser Cys Ser Asp Asp Cys Leu Gln Lys Lys Asp Cys Cys Ala Asp
            115                 120                 125

Tyr Lys Ser Val Cys Gln Gly Glu Thr Ser Trp Leu Glu Glu Asn Cys
        130                 135                 140

Asp Thr Ala Gln Gln Ser Gln Cys Pro Glu Gly Phe Asp Leu Pro Pro
145                 150                 155                 160
```

-continued

```
Val Ile Leu Phe Ser Met Asp Gly Phe Arg Ala Glu Tyr Leu Tyr Thr
                165                 170                 175
Trp Asp Thr Leu Met Pro Asn Ile Asn Lys Leu Lys Thr Cys Gly Ile
            180                 185                 190
His Ser Lys Tyr Met Arg Ala Met Tyr Pro Thr Lys Thr Phe Pro Asn
        195                 200                 205
His Tyr Thr Ile Val Thr Gly Leu Tyr Pro Glu Ser His Gly Ile Ile
    210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
            260                 265                 270
Gly Ser Glu Val Ala Ile Asn Gly Ser Phe Pro Ser Ile Tyr Met Pro
        275                 280                 285
Tyr Asn Gly Ser Val Pro Phe Glu Glu Arg Ile Ser Thr Leu Leu Lys
    290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
            340                 345                 350
Met Glu Gly Leu Lys Gln Arg Asn Leu His Asn Cys Val Asn Ile Ile
        355                 360                 365
Leu Leu Ala Asp His Gly Met Asp Gln Thr Tyr Cys Asn Lys Met Glu
    370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
        435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
Leu Ala His Gly Pro Ser Phe Lys Glu Lys Thr Glu Val Glu Pro Phe
            500                 505                 510
Glu Asn Ile Glu Val Tyr Asn Leu Met Cys Asp Leu Leu Arg Ile Gln
        515                 520                 525
Pro Ala Pro Asn Asn Gly Thr His Gly Ser Leu Asn His Leu Leu Lys
    530                 535                 540
Val Pro Phe Tyr Glu Pro Ser His Ala Glu Val Ser Lys Phe Ser
545                 550                 555                 560
Val Cys Gly Phe Ala Asn Pro Leu Pro Thr Glu Ser Leu Asp Cys Phe
                565                 570                 575
```

```
Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
            610                 615                 620

Leu Tyr His Arg Glu Tyr Val Ser Gly Phe Lys Ala Met Arg Met
625                 630                 635                 640

Pro Met Trp Ser Ser Tyr Thr Val Pro Gln Leu Gly Asp Thr Ser Pro
            645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
            690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
            725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
            770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
            805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
            835                 840                 845

Asp Phe Tyr Gln Asp Lys Val Gln Pro Val Ser Glu Ile Leu Gln Leu
            850                 855                 860

Lys Thr Tyr Leu Pro Thr Phe Glu Thr Thr Ile
865                 870                 875

<210> SEQ ID NO 95
<211> LENGTH: 875
<212> TYPE: PRT
<213> ORGANISM: Homo Sapiens

<400> SEQUENCE: 95

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Arg Lys Leu
            35                  40                  45

Glu Lys Gln Gly Ser Cys Arg Lys Cys Phe Asp Ala Ser Phe Arg
    50                  55                  60

Gly Leu Glu Asn Cys Arg Cys Asp Val Ala Cys Lys Asp Arg Gly Asp
65                  70                  75                  80
```

-continued

```
Cys Cys Trp Asp Phe Glu Asp Thr Cys Val Glu Ser Thr Arg Ile Trp
             85                  90                  95
Met Cys Asn Lys Phe Arg Cys Gly Glu Thr Arg Leu Glu Ala Ser Leu
            100                 105                 110
Cys Ser Cys Ser Asp Asp Cys Leu Gln Lys Asp Cys Cys Ala Asp
            115                 120                 125
Tyr Lys Ser Val Cys Gln Gly Glu Thr Ser Trp Leu Glu Glu Asn Cys
            130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
Trp Asp Thr Leu Met Pro Asn Ile Lys Leu Lys Thr Cys Gly Ile
                180                 185                 190
His Ser Lys Tyr Met Arg Ala Met Tyr Pro Thr Lys Thr Phe Pro Asn
                195                 200                 205
His Tyr Thr Ile Val Thr Gly Leu Tyr Pro Glu Ser His Gly Ile Ile
210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
                260                 265                 270
Gly Ser Glu Val Ala Ile Asn Gly Ser Phe Pro Ser Ile Tyr Met Pro
                275                 280                 285
Tyr Asn Gly Ser Val Pro Phe Glu Glu Arg Ile Ser Thr Leu Leu Lys
                290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
                340                 345                 350
Met Glu Gly Leu Lys Gln Arg Asn Leu His Asn Cys Val Asn Ile Ile
                355                 360                 365
Leu Leu Ala Asp His Gly Met Asp Gln Thr Tyr Cys Asn Lys Met Glu
                370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
                420                 425                 430
Asp Gln His Phe Lys Pro Tyr Leu Thr Pro Asp Leu Pro Lys Arg Leu
                435                 440                 445
His Tyr Ala Lys Asn Val Arg Ile Asp Lys Val His Leu Phe Val Asp
                450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
```

-continued

Leu Ala His Gly Pro Ser Phe Lys Glu Lys Thr Glu Val Glu Pro Phe
        500                 505                 510

Glu Asn Ile Glu Val Tyr Asn Leu Met Cys Asp Leu Leu Arg Ile Gln
        515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
                580                 585                 590

Leu Asn Leu Thr Gln Glu Glu Ile Thr Ala Thr Val Lys Val Asn Leu
                595                 600                 605

Pro Phe Gly Arg Pro Arg Val Leu Gln Lys Asn Val Asp His Cys Leu
        610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
        660                 665                 670

Pro Ser Glu Ser Gln Lys Cys Ser Phe Tyr Leu Ala Asp Lys Asn Ile
        675                 680                 685

Thr His Gly Phe Leu Tyr Pro Pro Ala Ser Asn Arg Thr Ser Asp Ser
        690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Leu Ile Lys His
                725                 730                 735

Ala Thr Glu Arg Asn Gly Val Asn Val Val Ser Gly Pro Ile Phe Asp
        740                 745                 750

Tyr Asn Tyr Asp Gly His Phe Asp Ala Pro Asp Glu Ile Thr Lys His
        755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
        820                 825                 830

Thr Ala His Ile Ala Arg Val Arg Asp Val Glu Leu Leu Thr Gly Leu
        835                 840                 845

Asp Phe Tyr Gln Asp Lys Val Gln Pro Val Ser Glu Ile Leu Gln Leu
        850                 855                 860

Lys Thr Tyr Leu Pro Thr Phe Glu Thr Thr Ile
865                 870                 875

<210> SEQ ID NO 96
<211> LENGTH: 875
<212> TYPE: PRT
<213> ORGANISM: Homo Sapiens

<400> SEQUENCE: 96

-continued

```
Met Glu Ser Thr Leu Thr Leu Ala Thr Glu Gln Pro Val Lys Lys Asn
  1               5                  10                  15

Thr Leu Lys Lys Tyr Lys Ile Ala Cys Ile Val Leu Ala Leu Leu
             20                  25                  30

Val Ile Met Ser Leu Gly Leu Gly Leu Gly Leu Arg Lys Leu
         35                  40                  45

Glu Lys Gln Gly Ser Cys Arg Lys Lys Cys Phe Asp Ala Ser Phe Arg
 50                  55                  60

Gly Leu Glu Asn Cys Arg Cys Asp Val Ala Cys Lys Asp Arg Gly Asp
 65                  70                  75                  80

Cys Cys Trp Asp Phe Glu Asp Thr Cys Val Glu Ser Thr Arg Ile Trp
             85                  90                  95

Met Cys Asn Lys Phe Arg Cys Gly Glu Thr Arg Leu Glu Ala Ser Leu
             100                 105                 110

Cys Ser Cys Ser Asp Asp Cys Leu Gln Lys Lys Asp Cys Cys Ala Asp
         115                 120                 125

Tyr Lys Ser Val Cys Gln Gly Glu Thr Ser Trp Leu Glu Glu Asn Cys
 130                 135                 140

Asp Thr Ala Gln Gln Ser Gln Cys Pro Glu Gly Phe Asp Leu Pro Pro
145                 150                 155                 160

Val Ile Leu Phe Ser Met Asp Gly Phe Arg Ala Glu Tyr Leu Tyr Thr
             165                 170                 175

Trp Asp Thr Leu Met Pro Asn Ile Asn Lys Leu Lys Thr Cys Gly Ile
             180                 185                 190

His Ser Lys Tyr Met Arg Ala Met Tyr Pro Thr Lys Thr Phe Pro Asn
         195                 200                 205

His Tyr Thr Ile Val Thr Gly Leu Tyr Pro Glu Ser His Gly Ile Ile
 210                 215                 220

Asp Asn Asn Met Tyr Asp Val Asn Leu Asn Lys Asn Phe Ser Leu Ser
225                 230                 235                 240

Ser Lys Glu Gln Asn Asn Pro Ala Trp Trp His Gly Gln Pro Met Trp
             245                 250                 255

Leu Thr Ala Met Tyr Gln Gly Leu Lys Ala Ala Thr Tyr Phe Trp Pro
             260                 265                 270

Gly Ser Glu Val Ala Ile Asn Gly Ser Phe Pro Ser Ile Tyr Met Pro
         275                 280                 285

Tyr Asn Gly Ser Val Pro Phe Glu Glu Arg Ile Ser Thr Leu Leu Lys
 290                 295                 300

Trp Leu Asp Leu Pro Lys Ala Glu Arg Pro Arg Phe Tyr Thr Met Tyr
305                 310                 315                 320

Phe Glu Glu Pro Asp Ser Ser Gly His Ala Gly Gly Pro Val Ser Ala
             325                 330                 335

Arg Val Ile Lys Ala Leu Gln Val Val Asp His Ala Phe Gly Met Leu
             340                 345                 350

Met Glu Gly Leu Lys Gln Arg Asn Leu His Asn Cys Val Asn Ile Ile
         355                 360                 365

Leu Leu Ala Asp His Gly Met Asp Gln Thr Tyr Cys Asn Lys Met Glu
 370                 375                 380

Tyr Met Thr Asp Tyr Phe Pro Arg Ile Asn Phe Phe Tyr Met Tyr Glu
385                 390                 395                 400

Gly Pro Ala Pro Arg Ile Arg Ala His Asn Ile Pro His Asp Phe Phe
             405                 410                 415
```

-continued

```
Ser Phe Asn Ser Glu Glu Ile Val Arg Asn Leu Ser Cys Arg Lys Pro
            420                 425                 430

Asp Gln His Phe Lys Pro Tyr Leu Thr Pro Asp Leu Pro Lys Arg Leu
        435                 440                 445

His Tyr Ala Lys Asn Val Arg Ile Asp Lys Val His Leu Phe Val Asp
450                 455                 460

Gln Gln Trp Leu Ala Val Arg Ser Lys Ser Asn Thr Asn Cys Gly Gly
465                 470                 475                 480

Gly Asn His Gly Tyr Asn Asn Glu Phe Arg Ser Met Glu Ala Ile Phe
                485                 490                 495

Leu Ala His Gly Pro Ser Phe Lys Glu Lys Thr Glu Val Glu Pro Phe
            500                 505                 510

Glu Asn Ile Glu Val Tyr Asn Leu Met Cys Asp Leu Leu Arg Ile Gln
            515                 520                 525

Pro Ala Pro Asn Asn Gly Thr His Gly Ser Leu Asn His Leu Leu Lys
530                 535                 540

Val Pro Phe Tyr Glu Pro Ser His Ala Glu Glu Val Ser Lys Phe Ser
545                 550                 555                 560

Val Cys Gly Phe Ala Asn Pro Leu Pro Thr Glu Ser Leu Asp Cys Phe
                565                 570                 575

Cys Pro His Leu Gln Asn Ser Thr Gln Leu Glu Gln Val Asn Gln Met
            580                 585                 590

Leu Asn Leu Thr Gln Glu Glu Ile Thr Ala Thr Val Lys Val Asn Leu
            595                 600                 605

Pro Phe Gly Arg Pro Arg Val Leu Gln Lys Asn Val Asp His Cys Leu
610                 615                 620

Leu Tyr His Arg Glu Tyr Val Ser Gly Phe Gly Lys Ala Met Arg Met
625                 630                 635                 640

Pro Met Trp Ser Ser Tyr Thr Val Pro Gln Leu Gly Asp Thr Ser Pro
                645                 650                 655

Leu Pro Pro Thr Val Pro Asp Cys Leu Arg Ala Asp Val Arg Val Pro
            660                 665                 670

Pro Ser Glu Ser Gln Lys Cys Ser Phe Tyr Leu Ala Asp Lys Asn Ile
            675                 680                 685

Thr His Gly Phe Leu Tyr Pro Pro Ala Ser Asn Arg Thr Ser Asp Ser
            690                 695                 700

Gln Tyr Asp Ala Leu Ile Thr Ser Asn Leu Val Pro Met Tyr Glu Glu
705                 710                 715                 720

Phe Arg Lys Met Trp Asp Tyr Phe His Ser Val Leu Ile Lys His Ala
                725                 730                 735

Ala Thr Glu Arg Asn Gly Val Asn Val Val Ser Gly Pro Ile Phe Asp
            740                 745                 750

Tyr Asn Tyr Asp Gly His Phe Asp Ala Pro Asp Glu Ile Thr Lys His
            755                 760                 765

Leu Ala Asn Thr Asp Val Pro Ile Pro Thr His Tyr Phe Val Val Leu
770                 775                 780

Thr Ser Cys Lys Asn Lys Ser His Thr Pro Glu Asn Cys Pro Gly Trp
785                 790                 795                 800

Leu Asp Val Leu Pro Phe Ile Ile Pro His Arg Pro Thr Asn Val Glu
                805                 810                 815

Ser Cys Pro Glu Gly Lys Pro Glu Ala Leu Trp Val Glu Glu Arg Phe
            820                 825                 830

Thr Ala His Ile Ala Arg Val Arg Asp Val Glu Leu Leu Thr Gly Leu
```

```
             835                 840                 845
Asp Phe Tyr Gln Asp Lys Val Gln Pro Val Ser Glu Ile Leu Gln Leu
    850                 855                 860

Lys Thr Tyr Leu Pro Thr Phe Glu Thr Thr Ile
865                 870                 875

<210> SEQ ID NO 97
<211> LENGTH: 3988
<212> TYPE: DNA
<213> ORGANISM: Homo Sapiens

<400> SEQUENCE: 97
ctactttatt ctgataaaac aggtctatgc agctaccagg acaatggaat ctacgttgac      60
tttagcaacg gaacaacctg ttaagaagaa cactcttaag aaatataaaa tagcttgcat     120
tacagggtct ctctcctttg ggatctcacc tcaccacaac ctctgtttcc caggctcaag     180
tgatcctcct gcctcagcct cctgagtagc ttggaccaca gcacatgcc acaaggctca      240 gctaagtttt tgttcttctt gctttgctgg tgatcatgtc acttggatta ggcctggggc     300
ttggactcag gaaactggaa aagcaaggca gctgcaggaa gaagtgcttt gatgcatcat     360
ttagaggact ggagaactgc cggtgtgatg tggcatgtaa agaccgaggt gattgctgct     420
gggattttga agacacctgt gtggaatcaa ctcgaatatg gatgtgcaat aaatttcgtt     480
gtggagagac cagattagag gccagccttt gctcttgttc agatgactgt tgcagaaga     540 aagattgctg tgctgactat aagagtgttt gccaaggaga aacctcatgg ctggaagaaa     600
actgtgacac agcccagcag tctcagtgcc cagaagggtt tgacctgcca ccagttatct     660
tgttttctat ggatggattt agagctgaat atttatacac atgggatact ttaatgccaa     720
atatcaataa actgaaaaca tgtggaattc attcaaaata catgagagct atgtatccta     780
ccaaaacctt cccaaatcat acaccattg tcacgggctt gtatccagag tcacatggca     840
tcattgacaa taatatgtat gatgtaaatc tcaacaagaa ttttttcactt tcttcaaagg     900 aacaaaataa tccagcctgg tggcatgggc aaccaatgtg gctgacagca atgtatcaag     960
gtttaaaagc cgctacctac ttttggcccg atcagaagt ggctataaat ggctcctttc     1020
cttccatata catgccttac aacggaagtg tcccatttga agagaggatt tctacactgt     1080
taaaatggct ggacctgccc aaagctgaaa gacccaggtt ttataccatg tattttgaag     1140
aacctgattc ctctggacat gcaggtggac cagtcagtgc cagagtaatt aaagccttac     1200
aggtagtaga tcatgctttt gggatgttga tggaaggcct gaagcagcgg aatttgcaca     1260
actgtgtcaa tatcatcctt ctggctgacc atggaatgga ccagacttat tgtaacaaga     1320
tggaatacat gactgattat tttcccagaa taaacttctt ctacatgtac gaagggcctg     1380 cccccgcat ccgagctcat aatatacctc atgactttt tagtttaat tctgaggaaa      1440 ttgttagaaa cctcagttgc cgaaaacctg atcagcattt caagcccta ttgactcctg      1500 atttgccaaa gcgactgcac tatgccaaga acgtcagaat cgacaaagtt catctctttg     1560
tggatcaaca gtggctggct gttaggagta aatcaaatac aaattgtgga ggaggcaacc     1620
atggttataa caatgagttt aggagcatgg aggctatctt tctggcacat ggacccagtt     1680
ttaaagagaa gactgaagtt gaaccatttg aaaatattga agtctataac ctaatgtgtg     1740
atcttctacg cattcaacca gcaccaaaca atggaaccca tggtagttta accatcttc      1800 tgaaggtgcc ttttatgag ccatcccatg cagaggaggt gtcaaagttt tctgtttgtg     1860
gctttgctaa tccattgccc acagagtctc ttgactgttt ctgccctcac ctacaaaata     1920
```

```
gtactcagct ggaacaagtg aatcagatgc taaatctcac ccaagaagaa ataacagcaa    1980
cagtgaaagt aaatttgcca tttgggaggc ctagggtact gcagaagaac gtggaccact    2040 gtctcctttta ccacagggaa tatgtcagtg gatttggaaa agctatgagg atgcccatgt    2100
ggagttcata cacagtcccc cagttgggag acacatcgcc tctgcctccc actgtcccag    2160
actgtctgcg ggctgatgtc agggttcctc cttctgagag ccaaaaatgt tccttctatt    2220
tagcagacaa gaatatcacc cacggcttcc tctatcctcc tgccagcaat agaacatcag    2280
atagccaata tgatgcttta attactagca atttggtacc tatgtatgaa gaattcagaa    2340
aaatgtggga ctacttccac agtgttcttc ttataaaaca tgccacagaa agaaatggag    2400
taaatgtggt tagtggacca atatttgatt ataattatga tggccatttt gatgctccag    2460
atgaaattac caaacattta gccaacactg atgttcccat cccaacacac tactttgtgg    2520
tgctgaccag ttgtaaaaac aagagccaca caccggaaaa ctgccctggg tggctggatg    2580
tcctacccct tatcatccct caccgaccta ccaacgtgga gagctgtcct gaaggtaaac    2640
cagaagctct ttgggttgaa gaaagattta cagctcacat tgcccgggtc cgtgatgtag    2700
aacttctcac tgggcttgac ttctatcagg ataaagtgca gcctgtctct gaaattttgc    2760
aactaaagac atatttacca acatttgaaa ccactatttta acttaataat gtctacttaa    2820
tatataattt actgtataaa gtaattttgg caaaatataa gtgatttttt ctggagaatt    2880
gtaaaataaa gttttctatt tttccttaaa aaaaaaccg gaattccggg cttgggaggc    2940
tgaggcagga gactcgcttg aacccgggag gcagaggttg cagtgagcca agattgcgcc    3000
attgcactcc agagcctggg tgacagagca agactacatc tcaaaaaata aataaataaa    3060
ataaaagtaa caataaaaat aaaaagaaca gcagagagaa tgagcaagga gaaatgtcac    3120
aaactattgc aaaatactgt tacactgggt tggctctcca agaagatact ggaatctctt    3180
cagccatttg cttttcagaa gtagaaacca gcaaaccacc tctaagcgga gaacatacga    3240
ttctttatta agtagctctg gggaaggaaa gaataaaagt tgatagctcc ctgattggga    3300
aaaaatgcac aattaataaa gaatgaagat gaaagaaagc atgcttatgt tgtaacacaa    3360
aaaaaattca caaacgttgg tggaaggaaa acagtataga aaacattact ttaactaaaa    3420 gctgaaaaa tttttcagttg ggatgcgact gacaaaaga acgggatttc caggcataaa    3480
gttggcgtga gctacagagg gcaccatgtg gctcagtgga agacccttca agattcaaag    3540
ttccatttga cagagcaaag gcacttcgca aggagaaggg tttaaattat gggtccaaaa    3600
gccaagtggt aaagcgagca atttgcagca taactgcttc tcctagacag ggctgagtgg    3660
gcaaaatacg acagtacaca cagtgactat tagccactgc cagaaacagg ctgaacagcc    3720
ctgggagaca agggaaggca ggtggtggga gttgttcatg gagagaaagg agagttttag    3780
aaccagcaca tccactggag atgctgggcc accagacccc tcccagtcaa taaagtctgg    3840
tgcctcattt gatctcagcc tcatcatgac cctggagaga ccctgatacc atctgccagt    3900
ccccgacagc ttaggcactc cttgccatca acctgacccc ccgagtggtt ctccaggctc    3960
cctgccccac ccattcaggc cggaattc                                      3988
```

<210> SEQ ID NO 98
<211> LENGTH: 3860
<212> TYPE: DNA
<213> ORGANISM: Homo Sapiens

<400> SEQUENCE: 98

```
ctactttatt ctgataaaac aggtctatgc agctaccagg acaatggaat ctacgttgac      60
tttagcaacg gaacaacctg ttaagaagaa cactcttaag aaatataaaa tagcttgcat     120
tttgttcttc ttgctttgct ggtgatcatg tcacttggat taggcctggg gcttggactc     180
aggaaactgg aaaagcaagg cagctgcagg aagaagtgct tgatgcatc atttagagga      240 ctggagaact gccggtgtga tgtggcatgt aaagaccgag gtgattgctg ctgggatttt     300
gaagacacct gtgtggaatc aactcgaata tggatgtgca ataaatttcg ttgtggagag     360
accagattag aggccagcct tgctcttgt tcagatgact gtttgcagaa gaaagattgc      420
tgtgctgact ataagagtgt ttgccaagga gaaacctcat ggctggaaga aaactgtgac     480
acagcccagc agtctcagtg cccagaaggg tttgacctgc caccagttat cttgttttct     540
atggatggat ttagagctga atatttatac acatgggata ctttaatgcc aaatatcaat     600
aaactgaaaa catgtggaat tcattcaaaa tacatgagag ctatgtatcc taccaaaacc     660
ttcccaaatc attacaccat tgtcacgggc ttgtatccag agtcacatgg catcattgac     720
aataatatgt atgatgtaaa tctcaacaag aattttttcac tttcttcaaa ggaacaaaat     780
aatccagcct ggtggcatgg gcaaccaatg tggctgacag caatgtatca aggttttaaaa     840 gccgctacct acttttggcc cggatcagaa gtggctataa atggctcctt ccttccata      900 tacatgcctt acaacggaag tgtcccattt gaagagagga tttctacact gttaaaatgg     960
ctggacctgc ccaaagctga agacccaggt ttttatacca tgtattttga agaacctgat    1020
tcctctggac atgcaggtgg accagtcagt gccagagtaa ttaaagcctt acaggtagta    1080
gatcatgctt ttgggatgtt gatggaaggc ctgaagcagc ggaatttgca caactgtgtc    1140
aatatcatcc ttctggctga ccatggaatg gaccagactt attgtaacaa gatggaatac    1200
atgactgatt attttcccag aataaacttc ttctacatgt acgaagggcc tgccccccgc    1260
atccgagctc ataatatacc tcatgacttt ttttagttta attctgagga aattgttaga    1320
aacctcagtt gccgaaaacc tgatcagcat ttcaagccct atttgactcc tgatttgcca    1380
aagcgactgc actatgccaa gaacgtcaga atcgacaaag ttcatctctt tgtggatcaa    1440
cagtggctgg ctgttaggag taaatcaaat acaaattgtg gaggaggcaa ccatggttat    1500
aacaatgagt ttaggagcat ggaggctatc tttctggcac atggacccag ttttaaagag    1560
aagactgaag ttgaaccatt tgaaaatatt gaagtctata acctaatgtg tgatcttcta    1620
cgcattcaac cagcaccaaa caatggaacc catggtagtt taaaccatct tctgaaggtg    1680 ccttttttatg agccatccca tgcagaggag gtgtcaaagt tttctgtttg tggctttgct    1740
aatccattgc ccacagagtc tcttgactgt ttctgccctc acctacaaaa tagtactcag    1800
ctggaacaag tgaatcagat gctaaatctc acccaagaag aaataacagc aacagtgaaa    1860
gtaaatttgc catttgggag gcctagggta ctgcagaaga acgtggacca ctgtctcctt    1920
taccacaggg aaatatgtca gtggatttgga aaagctatga ggatgcccat gtggagttca    1980
tacacagtcc cccagttggg agacacatcg cctctgcctc ccactgtccc agactgtctg    2040
cgggctgatt tcagggttcc tccttctgag agccaaaaat gttccttcta tttagcagac    2100
aagaatatca cccacggctt cctctatcct cctgccagca atagaacatc agatagccaa    2160
tatgatgctt taattactag caatttggta ccctatgtatg aagaattcag aaaaatgtgg    2220
gactacttcc acagtgttct tcttataaaa catgccacag aaagaaatgg agtaaatgtg    2280
gttagtggac caatatttga ttataattat gatggccatt ttgatgctcc agatgaaatt    2340
accaaacatt tagccaacac tgatgttccc atcccaacac actactttgt ggtgctgacc    2400
```

-continued

| | |
|---|---|
| agttgtaaaa acaagagcca cacaccggaa aactgccctg ggtggctgga tgtcctaccc | 2460 |
| tttatcatcc ctcaccgacc taccaacgtg gagagctgtc ctgaaggtaa accagaagct | 2520 |
| ctttggggttg aagaaagatt tacagctcac attgcccggg tccgtgatgt agaacttctc | 2580 |
| actgggcttg acttctatca ggataaagtg cagcctgtct ctgaaatttt gcaactaaag | 2640 |
| acatatttac caacatttga aaccactatt taacttaata atgtctactt aatatataat | 2700 |
| ttactgtata aagtaatttt ggcaaaatat aagtgatttt ttctggagaa ttgtaaaata | 2760 |
| aagttttcta tttttcctta aaaaaaaaac cggaattccg ggcttgggag gctgaggcag | 2820 |
| gagactcgct tgaacccggg aggcagaggt tgcagtgagc caagattgcg ccattgcact | 2880 |
| ccagagcctg ggtgacagag caagactaca tctcaaaaaa taaataaata aaataaaagt | 2940 |
| aacaataaaa ataaaaagaa cagcagagag aatgagcaag gagaaatgtc acaaactatt | 3000 |
| gcaaaatact gttacactgg gttggctctc aagaagata ctggaatctc ttcagccatt | 3060 |
| tgcttttcag aagtagaaac cagcaaacca cctctaagcg gagaacatac gattctttat | 3120 |
| taagtagctc tggggaagga aagaataaaa gttgatagct ccctgattgg gaaaaaatgc | 3180 |
| acaattaata aagaatgaag atgaaagaaa gcatgcttat gttgtaacac aaaaaaaatt | 3240 |
| cacaaacgtt ggtggaagga aaacagtata gaaaacatta ctttaactaa aagctggaaa | 3300 |
| aattttcagt tgggatgcga ctgacaaaaa gaacgggatt tccaggcata aagttggcgt | 3360 |
| gagctacaga gggcaccatg tggctcagtg gaagacccctt caagattcaa agttccattt | 3420 |
| gacagagcaa aggcacttcg caaggagaag ggtttaaatt atgggtccaa aagccaagtg | 3480 |
| gtaaagcgag caatttgcag cataactgct tctcctagac agggctgagt gggcaaaata | 3540 |
| cgacagtaca cacagtgact attagccact gccagaaaca ggctgaacag ccctgggaga | 3600 |
| caagggaagg caggtggtgg gagttgttca tggagagaaa ggagagtttt agaaccagca | 3660 |
| catccactgg agatgctggg ccaccagacc cctcccagtc aataaagtct ggtgcctcat | 3720 |
| ttgatctcag cctcatcatg accctggaga gaccctgata ccatctgcca gtccccgaca | 3780 |
| gcttaggcac tccttgccat caacctgacc ccccgagtgg ttctccaggc tccctgcccc | 3840 |
| acccattcag gccggaattc | 3860 |

<210> SEQ ID NO 99
<211> LENGTH: 3860
<212> TYPE: DNA
<213> ORGANISM: Homo Sapiens

<400> SEQUENCE: 99

| | |
|---|---|
| ctactttatt ctgataaaac aggtctatgc agctaccagg acaatggaat ctacgttgac | 60 |
| tttagcaacg gaacaacctg ttaagaagaa cactcttaag aaatataaaa tagcttgcat | 120 |
| tttgttcttc ttgctttgct ggtgatcatg tcacttggat taggcctggg gcttggactc | 180 |
| aggaaactgg aaaagcaagg cagctgcagg aagaagtgct ttgatgcatc atttagagga | 240 |
| ctggagaact gccggtgtga tgtggcatgt aaagaccgag gtgattgctg ctgggatttt | 300 |
| gaagacacct gtgtggaatc aactcgaata tggatgtgca ataaatttcg ttgtggagag | 360 |
| accagattag aggccagcct ttgctcttgt tcagatgact gtttgcagaa gaaagattgc | 420 |
| tgtgctgact ataagagtgt tgccaagga gaaacctcat ggctggaaga aactgtgac | 480 |
| acagcccagc agtctcagtg cccagaaggg tttgacctgc caccagttat cttgttttct | 540 |
| atggatggat ttagagctga atattttatac acatgggata ctttaatgcc aaatatcaat | 600 |

```
                                  -continued aaactgaaaa catgtggaat tcattcaaaa tacatgagag ctatgtatcc taccaaaacc     660
ttcccaaatc attacaccat tgtcacgggc ttgtatccag agtcacatgg catcattgac    720
aataatatgt atgatgtaaa tctcaacaag aattttttcac tttcttcaaa ggaacaaaat   780
aatccagcct ggtggcatgg gcaaccaatg tggctgacag caatgtatca aggtttaaaa    840
gccgctacct acttttggcc cggatcagaa gtggctataa atggctcctt tccttccata    900
tacatgcctt acaacggaag tgtcccattt gaagagagga tttctacact gttaaaatgg    960
ctggacctgc ccaaagctga agacccagg ttttatacca tgtatttga agaacctgat     1020 tcctctggac atgcaggtgg accagtcagt gccagagtaa ttaaagcctt acaggtagta    1080
gatcatgctt tgggatgtt gatggaaggc ctgaagcagc ggaatttgca caactgtgtc    1140
aatatcatcc ttctggctga ccatggaatg gaccagactt attgtaacaa gatgaatac     1200 atgactgatt attttcccag aataaacttc ttctacatgt acgaagggcc tgcccccgc    1260 atccgagctc ataatatacc tcatgacttt tttagttta attctgagga aattgttaga    1320
aacctcagtt gccgaaaaacc tgatcagcat ttcaagccct atttgactcc tgatttgcca   1380
aagcgactgc actatgccaa gaacgtcaga atcgacaaag ttcatctctt tgtggatcaa    1440
cagtggctgg ctgttaggag taaatcaaat acaaattgtg gaggaggcaa ccatggttat    1500
aacaatgagt ttaggagcat ggaggctatc tttctggcac atggacccag ttttaaagag    1560
aagactgaag ttgaaccatt tgaaaatatt gaagtctata acctaatgtg tgatcttcta    1620
cgcattcaac cagcaccaaa caatggaacc catggtagtt taaccatct tctgaaggtg     1680 ccttttatg agccatccca tgcagaggag gtgtcaaagt tttctgtttg tggctttgct    1740
aatccattgc ccacagagtc tcttgactgt ttctgccctc acctacaaaa tagtactcag    1800
ctggaacaag tgaatcagat gctaaatctc acccaagaag aaataacagc aacagtgaaa    1860
gtaaatttgc catttgggag gcctagggta ctgcagaaga acgtggacca ctgtctcctt    1920
taccacaggg aatatgtcag tggatttgga aaagctatga ggatgcccat gtggagttca    1980
tacacagtcc cccagttggg agacacatcg cctctgcctc ccactgtccc agactgtctg    2040
cgggctgatg tcagggttcc tccttctgag agccaaaaat gttccttcta tttagcagac    2100
aagaatatca cccacggctt cctctatcct cctgccagca atagaacatc agatagccaa    2160
tatgatgctt taattactag caatttggta cctatgtatg aagaattcag aaaaatgtgg    2220
gactacttcc acagtgttct tcttataaaa catgccacag aaagaaatgg agtaaatgtg    2280
gttagtggac caatatttga ttataattat gatggccatt tgatgctcc agatgaaatt     2340 accaaacatt tagccaacac tgatgttccc atcccaacac actactttgt ggtgctgacc    2400
agttgtaaaa acaagagcca cacccggaaa actgccctg ggtggctgga tgtcctaccc    2460
tttatcatcc ctcaccgacc taccaacgtg gagagctgtc ctgaaggtaa accagaagct    2520
ctttgggttg aagaaagatt tacagctcac attgcccggg tccgtgatgt agaacttctc    2580
actgggcttg acttctatca ggataaagtg cagcctgtct ctgaaatttt gcaactaaag    2640
acatatttac caacatttga aaccactatt taacttaata atgtctactt aatatataat    2700
ttactgtata aagtaatttt ggcaaaatat aagtgatttt ttctggagaa ttgtaaaata    2760
aagttttcta tttttcctta aaaaaaaaac cggaattccg ggcttgggag gctgaggcag    2820
gagactcgct tgaacccggg aggcagaggt tgcagtgagc caagattgcg ccattgcact    2880
ccagagcctg ggtgacagag caagactaca tctcaaaaaa taaataaata aaataaaagt    2940
aacaataaaa ataaaaagaa cagcagagag aatgagcaag gagaaatgtc acaaactatt   3000
```

-continued

```
gcaaaatact gttacactgg gttggctctc caagaagata ctggaatctc ttcagccatt    3060
tgcttttcag aagtagaaac cagcaaacca cctctaagcg agaacatac gattctttat     3120 taagtagctc tggggaagga aagaataaaa gttgatagct ccctgattgg gaaaaaatgc    3180
acaattaata agaatgaag atgaaagaaa gcatgcttat gttgtaacac aaaaaaaatt    3240
cacaaacgtt ggtggaagga aaacagtata gaaaacatta ctttaactaa agctggaaa    3300 aattttcagt tgggatgcga ctgacaaaaa gaacgggatt ccaggcata agttggcgt     3360 gagctacaga gggcaccatg tggctcagtg aagacccctt caagattcaa agttccattt   3420
gacagagcaa aggcacttcg caaggagaag ggtttaaatt atgggtccaa agccaagtg    3480 gtaaagcgag caatttgcag cataactgct tctcctagac agggctgagt gggcaaaata   3540
cgacagtaca cacagtgact attagccact gccagaaaca ggctgaacag ccctgggaga   3600
caagggaagg caggtggtgg gagttgttca tggagagaaa ggagagtttt agaaccagca   3660
catccactgg agatgctggg ccaccagacc cctcccagtc aataaagtct ggtgcctcat   3720
ttgatctcag cctcatcatg accctggaga gaccctgata ccatctgcca gtccccgaca   3780
gcttaggcac tccttgccat caacctgacc ccccgagtgg ttctccaggc tccctgcccc   3840
acccattcag gccggaattc                                                3860
```

<210> SEQ ID NO 100
<211> LENGTH: 841
<212> TYPE: PRT
<213> ORGANISM: Homo Sapiens

<400> SEQUENCE: 100

```
Met Ser Leu Gly Leu Gly Leu Gly Leu Arg Lys Leu Glu Lys
 1               5                  10                  15

Gln Gly Ser Cys Arg Lys Lys Cys Phe Asp Ala Ser Phe Arg Gly Leu
            20                  25                  30

Glu Asn Cys Arg Cys Asp Val Ala Cys Lys Asp Arg Gly Asp Cys Cys
        35                  40                  45

Trp Asp Phe Glu Asp Thr Cys Val Glu Ser Thr Arg Ile Trp Met Cys
    50                  55                  60

Asn Lys Phe Arg Cys Gly Glu Thr Arg Leu Glu Ala Ser Leu Cys Ser
65                  70                  75                  80

Cys Ser Asp Asp Cys Leu Gln Arg Lys Asp Cys Cys Ala Asp Tyr Lys
                85                  90                  95

Ser Val Cys Gln Gly Glu Thr Ser Trp Leu Glu Glu Asn Cys Asp Thr
            100                 105                 110

Ala Gln Gln Ser Gln Cys Pro Glu Gly Phe Asp Leu Pro Pro Val Ile
        115                 120                 125

Leu Phe Ser Met Asp Gly Phe Arg Ala Glu Tyr Leu Tyr Thr Trp Asp
    130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr
                165                 170                 175

Thr Ile Val Thr Gly Leu Tyr Pro Glu Ser His Gly Ile Ile Asp Asn
            180                 185                 190

Asn Met Tyr Asp Val Asn Leu Asn Lys Asn Phe Ser Leu Ser Ser Lys
        195                 200                 205

Glu Gln Asn Asn Pro Ala Trp Trp His Gly Gln Pro Met Trp Leu Thr
```

-continued

```
            210                 215                 220
Ala Met Tyr Gln Gly Leu Lys Ala Ala Thr Tyr Phe Trp Pro Gly Ser
225                 230                 235                 240

Glu Val Ala Ile Asn Gly Ser Phe Pro Ser Ile Tyr Met Pro Tyr Asn
                245                 250                 255

Gly Ser Val Pro Phe Glu Arg Ile Ser Thr Leu Leu Lys Trp Leu
            260                 265                 270

Asp Leu Pro Lys Ala Glu Arg Pro Arg Phe Tyr Thr Met Phe Phe Glu
            275                 280                 285

Glu Pro Asp Ser Ser Gly His Ala Gly Gly Pro Val Ser Ala Arg Val
        290                 295                 300

Ile Lys Ala Leu Gln Val Val Asp His Ala Phe Gly Met Leu Met Glu
305                 310                 315                 320

Gly Leu Lys Gln Arg Asn Leu His Asn Cys Val Asn Ile Ile Leu Leu
                325                 330                 335

Ala Asp His Gly Met Asp Gln Thr Tyr Cys Asn Lys Met Glu Tyr Met
            340                 345                 350

Thr Asp Tyr Phe Pro Arg Ile Asn Phe Phe Tyr Met Tyr Glu Gly Pro
            355                 360                 365

Ala Pro Arg Val Arg Ala His Asn Ile Pro His Asp Phe Phe Ser Phe
        370                 375                 380

Asn Ser Glu Glu Ile Val Arg Asn Leu Ser Cys Arg Lys Pro Asp Gln
385                 390                 395                 400

His Phe Lys Pro Tyr Leu Thr Pro Asp Leu Pro Lys Arg Leu His Tyr
                405                 410                 415

Ala Lys Asn Val Arg Ile Asp Lys Val His Leu Phe Val Asp Gln Gln
            420                 425                 430

Trp Leu Ala Val Arg Ser Lys Ser Asn Thr Asn Cys Gly Gly Gly Asn
        435                 440                 445

His Gly Tyr Asn Asn Glu Phe Arg Ser Met Glu Ala Ile Phe Leu Ala
        450                 455                 460

His Gly Pro Ser Phe Lys Glu Lys Thr Glu Val Glu Pro Phe Glu Asn
465                 470                 475                 480

Ile Glu Val Tyr Asn Leu Met Cys Asp Leu Leu Arg Ile Gln Pro Ala
                485                 490                 495

Pro Asn Asn Gly Thr His Gly Ser Leu Asn His Leu Leu Lys Val Pro
            500                 505                 510

Phe Tyr Glu Pro Ser His Ala Glu Glu Val Ser Lys Phe Ser Val Cys
            515                 520                 525

Gly Phe Ala Asn Pro Leu Pro Thr Glu Ser Leu Asp Cys Phe Cys Pro
        530                 535                 540

His Leu Gln Asn Ser Thr Gln Leu Glu Gln Val Asn Gln Met Leu Asn
545                 550                 555                 560

Leu Thr Gln Glu Glu Ile Thr Ala Thr Val Lys Val Asn Leu Pro Phe
                565                 570                 575

Gly Arg Pro Arg Val Leu Gln Lys Asn Val Asp His Cys Leu Leu Tyr
            580                 585                 590

His Arg Glu Tyr Val Ser Gly Phe Gly Lys Ala Met Arg Met Pro Met
        595                 600                 605

Trp Ser Ser Tyr Thr Val Pro Gln Leu Gly Asp Thr Ser Pro Leu Pro
        610                 615                 620

Pro Thr Val Pro Asp Cys Leu Arg Ala Asp Val Arg Val Pro Pro Ser
625                 630                 635                 640
```

-continued

Glu Ser Gln Lys Cys Ser Phe Tyr Leu Ala Asp Lys Asn Ile Thr His
              645                 650                 655

Gly Phe Leu Tyr Pro Pro Ala Ser Asn Arg Thr Ser Asp Ser Gln Tyr
            660                 665                 670

Asp Ala Leu Ile Thr Ser Asn Leu Val Pro Met Tyr Glu Glu Phe Arg
        675                 680                 685

Lys Met Trp Asp Tyr Phe His Ser Val Leu Leu Ile Lys His Ala Thr
    690                 695                 700

Glu Arg Asn Gly Val Asn Val Val Ser Gly Pro Ile Phe Asp Tyr Asn
705                 710                 715                 720

Tyr Asp Gly His Phe Asp Ala Pro Asp Glu Ile Thr Lys His Leu Ala
                725                 730                 735

Asn Thr Asp Val Pro Ile Pro Thr His Tyr Phe Val Val Leu Thr Ser
            740                 745                 750

Cys Lys Asn Lys Ser His Thr Pro Glu Asn Cys Pro Gly Trp Leu Asp
        755                 760                 765

Val Leu Pro Phe Ile Ile Pro His Arg Pro Thr Asn Val Glu Ser Cys
    770                 775                 780

Pro Glu Gly Lys Pro Glu Ala Leu Trp Val Glu Arg Phe Thr Ala
785                 790                 795                 800

His Ile Ala Arg Val Arg Asp Val Glu Leu Leu Thr Gly Leu Asp Phe
                805                 810                 815

Tyr Gln Asp Lys Val Gln Pro Val Ser Glu Ile Leu Gln Leu Lys Thr
            820                 825                 830

Tyr Leu Pro Thr Phe Glu Thr Thr Ile
        835                 840

<210> SEQ ID NO 101
<211> LENGTH: 841
<212> TYPE: PRT
<213> ORGANISM: Homo Sapiens

<400> SEQUENCE: 101

Met Ser Leu Gly Leu Gly Leu Gly Leu Gly Arg Lys Leu Glu Lys
  1               5                  10                  15

Gln Gly Ser Cys Arg Lys Lys Cys Phe Asp Ala Ser Phe Arg Gly Leu
            20                  25                  30

Glu Asn Cys Arg Cys Asp Val Ala Cys Lys Asp Arg Gly Asp Cys Cys
        35                  40                  45

Trp Asp Phe Glu Asp Thr Cys Val Glu Ser Thr Arg Ile Trp Met Cys
    50                  55                  60

Asn Lys Phe Arg Cys Gly Glu Thr Arg Leu Glu Ala Ser Leu Cys Ser
65                  70                  75                  80

Cys Ser Asp Asp Cys Leu Gln Lys Lys Asp Cys Cys Ala Asp Tyr Lys
                85                  90                  95

Ser Val Cys Gln Gly Glu Thr Ser Trp Leu Glu Glu Asn Cys Asp Thr
            100                 105                 110

Ala Gln Gln Ser Gln Cys Pro Glu Gly Phe Asp Leu Pro Pro Val Ile
        115                 120                 125

Leu Phe Ser Met Asp Gly Phe Arg Ala Glu Tyr Leu Tyr Thr Trp Asp
    130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr

-continued

```
                165                 170                 175
Thr Ile Val Thr Gly Leu Tyr Pro Glu Ser His Gly Ile Ile Asp Asn
            180                 185                 190
Asn Met Tyr Asp Val Asn Leu Asn Lys Asn Phe Ser Leu Ser Ser Lys
        195                 200                 205
Glu Gln Asn Asn Pro Ala Trp Trp His Gly Gln Pro Met Trp Leu Thr
    210                 215                 220
Ala Met Tyr Gln Gly Leu Lys Ala Ala Thr Tyr Phe Trp Pro Gly Ser
225                 230                 235                 240
Glu Val Ala Ile Asn Gly Ser Phe Pro Ser Ile Tyr Met Pro Tyr Asn
                245                 250                 255
Gly Ser Val Pro Phe Glu Glu Arg Ile Ser Thr Leu Leu Lys Trp Leu
            260                 265                 270
Asp Leu Pro Lys Ala Glu Arg Pro Arg Phe Tyr Thr Met Tyr Phe Glu
        275                 280                 285
Glu Pro Asp Ser Ser Gly His Ala Gly Gly Pro Val Ser Ala Arg Val
    290                 295                 300
Ile Lys Ala Leu Gln Val Val Asp His Ala Phe Gly Met Leu Met Glu
305                 310                 315                 320
Gly Leu Lys Gln Arg Asn Leu His Asn Cys Val Asn Ile Ile Leu Leu
                325                 330                 335
Ala Asp His Gly Met Asp Gln Thr Tyr Cys Asn Lys Met Glu Tyr Met
            340                 345                 350
Thr Asp Tyr Phe Pro Arg Ile Asn Phe Phe Tyr Met Tyr Glu Gly Pro
        355                 360                 365
Ala Pro Arg Ile Arg Ala His Asn Ile Pro His Asp Phe Phe Ser Phe
    370                 375                 380
Asn Ser Glu Glu Ile Val Arg Asn Leu Ser Cys Arg Lys Pro Asp Gln
385                 390                 395                 400
His Phe Lys Pro Tyr Leu Thr Pro Asp Leu Pro Lys Arg Leu His Tyr
                405                 410                 415
Ala Lys Asn Val Arg Ile Asp Lys Val His Leu Phe Val Asp Gln Gln
            420                 425                 430
Trp Leu Ala Val Arg Ser Lys Ser Asn Thr Asn Cys Gly Gly Gly Asn
        435                 440                 445
His Gly Tyr Asn Asn Glu Phe Arg Ser Met Glu Ala Ile Phe Leu Ala
    450                 455                 460
His Gly Pro Ser Phe Lys Glu Lys Thr Glu Val Glu Pro Phe Glu Asn
465                 470                 475                 480
Ile Glu Val Tyr Asn Leu Met Cys Asp Leu Leu Arg Ile Gln Pro Ala
                485                 490                 495
Pro Asn Asn Gly Thr His Gly Ser Leu Asn His Leu Leu Lys Val Pro
            500                 505                 510
Phe Tyr Glu Pro Ser His Ala Glu Glu Val Ser Lys Phe Ser Val Cys
        515                 520                 525
Gly Phe Ala Asn Pro Leu Pro Thr Glu Ser Leu Asp Cys Phe Cys Pro
    530                 535                 540
His Leu Gln Asn Ser Thr Gln Leu Glu Gln Val Asn Gln Met Leu Asn
545                 550                 555                 560
Leu Thr Gln Glu Glu Ile Thr Ala Thr Val Lys Val Asn Leu Pro Phe
                565                 570                 575
Gly Arg Pro Arg Val Leu Gln Lys Asn Val Asp His Cys Leu Leu Tyr
            580                 585                 590
```

```
His Arg Glu Tyr Val Ser Gly Phe Gly Lys Ala Met Arg Met Pro Met
            595                 600                 605
Trp Ser Ser Tyr Thr Val Pro Gln Leu Gly Asp Thr Ser Pro Leu Pro
        610                 615                 620
Pro Thr Val Pro Asp Cys Leu Arg Ala Asp Val Arg Val Pro Pro Ser
625                 630                 635                 640
Glu Ser Gln Lys Cys Ser Phe Tyr Leu Ala Asp Lys Asn Ile Thr His
                645                 650                 655
Gly Phe Leu Tyr Pro Pro Ala Ser Asn Arg Thr Ser Asp Ser Gln Tyr
            660                 665                 670
Asp Ala Leu Ile Thr Ser Asn Leu Val Pro Met Tyr Glu Glu Phe Arg
        675                 680                 685
Lys Met Trp Asp Tyr Phe His Ser Val Leu Leu Ile Lys His Ala Thr
    690                 695                 700
Glu Arg Asn Gly Val Asn Val Val Ser Gly Pro Ile Phe Asp Tyr Asn
705                 710                 715                 720
Tyr Asp Gly His Phe Asp Ala Pro Asp Glu Ile Thr Lys His Leu Ala
                725                 730                 735
Asn Thr Asp Val Pro Ile Pro Thr His Tyr Phe Val Leu Thr Ser
            740                 745                 750
Cys Lys Asn Lys Ser His Thr Pro Glu Asn Cys Pro Gly Trp Leu Asp
        755                 760                 765
Val Leu Pro Phe Ile Ile Pro His Arg Pro Thr Asn Val Glu Ser Cys
    770                 775                 780
Pro Glu Gly Lys Pro Glu Ala Leu Trp Val Glu Arg Phe Thr Ala
785                 790                 795                 800
His Ile Ala Arg Val Arg Asp Val Glu Leu Leu Thr Gly Leu Asp Phe
                805                 810                 815
Tyr Gln Asp Lys Val Gln Pro Val Ser Glu Ile Leu Gln Leu Lys Thr
            820                 825                 830
Tyr Leu Pro Thr Phe Glu Thr Thr Ile
        835                 840

<210> SEQ ID NO 102
<211> LENGTH: 841
<212> TYPE: PRT
<213> ORGANISM: Homo Sapiens

<400> SEQUENCE: 102

Met Ser Leu Gly Leu Gly Leu Gly Leu Arg Lys Leu Glu Lys
1               5                   10                  15
Gln Gly Ser Cys Arg Lys Lys Cys Phe Asp Ala Ser Phe Arg Gly Leu
            20                  25                  30
Glu Asn Cys Arg Cys Asp Val Ala Cys Lys Asp Arg Gly Asp Cys Cys
        35                  40                  45
Trp Asp Phe Glu Asp Thr Cys Val Glu Ser Thr Arg Ile Trp Met Cys
    50                  55                  60
Asn Lys Phe Arg Cys Gly Glu Thr Arg Leu Glu Ala Ser Leu Cys Ser
65                  70                  75                  80
Cys Ser Asp Asp Cys Leu Gln Arg Lys Asp Cys Cys Ala Asp Tyr Lys
                85                  90                  95
Ser Val Cys Gln Gly Glu Thr Ser Trp Leu Glu Glu Asn Cys Asp Thr
            100                 105                 110
Ala Gln Gln Ser Gln Cys Pro Glu Gly Phe Asp Leu Pro Pro Val Ile
```

-continued

```
            115                 120                 125
Leu Phe Ser Met Asp Gly Phe Arg Ala Glu Tyr Leu Tyr Thr Trp Asp
        130                 135                 140

Thr Leu Met Pro Asn Ile Asn Lys Leu Lys Thr Cys Gly Ile His Ser
145                 150                 155                 160

Lys Tyr Met Arg Ala Met Tyr Pro Thr Lys Thr Phe Pro Asn His Tyr
                165                 170                 175

Thr Ile Val Thr Gly Leu Tyr Pro Glu Ser His Gly Ile Ile Asp Asn
                180                 185                 190

Asn Met Tyr Asp Val Asn Leu Asn Lys Asn Phe Ser Leu Ser Ser Lys
            195                 200                 205

Glu Gln Asn Asn Pro Ala Trp Trp His Gly Gln Pro Met Trp Leu Thr
        210                 215                 220

Ala Met Tyr Gln Gly Leu Lys Ala Ala Thr Tyr Phe Trp Pro Gly Ser
225                 230                 235                 240

Glu Val Ala Ile Asn Gly Ser Phe Pro Ser Ile Tyr Met Pro Tyr Asn
                245                 250                 255

Gly Ser Val Pro Phe Glu Glu Arg Ile Ser Thr Leu Leu Lys Trp Leu
                260                 265                 270

Asp Leu Pro Lys Ala Glu Arg Pro Arg Phe Tyr Thr Met Phe Phe Glu
            275                 280                 285

Glu Pro Asp Ser Ser Gly His Ala Gly Gly Pro Val Ser Ala Arg Val
        290                 295                 300

Ile Lys Ala Leu Gln Val Val Asp His Ala Phe Gly Met Leu Met Glu
305                 310                 315                 320

Gly Leu Lys Gln Arg Asn Leu His Asn Cys Val Asn Ile Ile Leu Leu
                325                 330                 335

Ala Asp His Gly Met Asp Gln Thr Tyr Cys Asn Lys Met Glu Tyr Met
                340                 345                 350

Thr Asp Tyr Phe Pro Arg Ile Asn Phe Phe Tyr Met Tyr Glu Gly Pro
            355                 360                 365

Ala Pro Arg Val Arg Ala His Asn Ile Pro His Asp Phe Phe Ser Phe
        370                 375                 380

Asn Ser Glu Glu Ile Val Arg Asn Leu Ser Cys Arg Lys Pro Asp Gln
385                 390                 395                 400

His Phe Lys Pro Tyr Leu Thr Pro Asp Leu Pro Lys Arg Leu His Tyr
                405                 410                 415

Ala Lys Asn Val Arg Ile Asp Lys Val His Leu Phe Val Asp Gln Gln
                420                 425                 430

Trp Leu Ala Val Arg Ser Lys Ser Asn Thr Asn Cys Gly Gly Gly Asn
            435                 440                 445

His Gly Tyr Asn Asn Glu Phe Arg Ser Met Glu Ala Ile Phe Leu Ala
        450                 455                 460

His Gly Pro Ser Phe Lys Glu Lys Thr Glu Val Glu Pro Phe Glu Asn
465                 470                 475                 480

Ile Glu Val Tyr Asn Leu Met Cys Asp Leu Leu Arg Ile Gln Pro Ala
                485                 490                 495

Pro Asn Asn Gly Thr His Gly Ser Leu Asn His Leu Leu Lys Val Pro
                500                 505                 510

Phe Tyr Glu Pro Ser His Ala Glu Glu Val Ser Lys Phe Ser Val Cys
            515                 520                 525

Gly Phe Ala Asn Pro Leu Pro Thr Glu Ser Leu Asp Cys Phe Cys Pro
        530                 535                 540
```

His Leu Gln Asn Ser Thr Gln Leu Glu Gln Val Asn Gln Met Leu Asn
545                 550                 555                 560

Leu Thr Gln Glu Glu Ile Thr Ala Thr Val Lys Val Asn Leu Pro Phe
                565                 570                 575

Gly Arg Pro Arg Val Leu Gln Lys Asn Val Asp His Cys Leu Leu Tyr
            580                 585                 590

His Arg Glu Tyr Val Ser Gly Phe Gly Lys Ala Met Arg Met Pro Met
        595                 600                 605

Trp Ser Ser Tyr Thr Val Pro Gln Leu Gly Asp Thr Ser Pro Leu Pro
    610                 615                 620

Pro Thr Val Pro Asp Cys Leu Arg Ala Asp Val Arg Val Pro Pro Ser
625                 630                 635                 640

Glu Ser Gln Lys Cys Ser Phe Tyr Leu Ala Asp Lys Asn Ile Thr His
                645                 650                 655

Gly Phe Leu Tyr Pro Pro Ala Ser Asn Arg Thr Ser Asp Ser Gln Tyr
            660                 665                 670

Asp Ala Leu Ile Thr Ser Asn Leu Val Pro Met Tyr Glu Glu Phe Arg
        675                 680                 685

Lys Met Trp Asp Tyr Phe His Ser Val Leu Leu Ile Lys His Ala Thr
    690                 695                 700

Glu Arg Asn Gly Val Asn Val Val Ser Gly Pro Ile Phe Asp Tyr Asn
705                 710                 715                 720

Tyr Asp Gly His Phe Asp Ala Pro Asp Glu Ile Thr Lys His Leu Ala
                725                 730                 735

Asn Thr Asp Val Pro Ile Pro Thr His Tyr Phe Val Val Leu Thr Ser
            740                 745                 750

Cys Lys Asn Lys Ser His Thr Pro Glu Asn Cys Pro Gly Trp Leu Asp
        755                 760                 765

Val Leu Pro Phe Ile Ile Pro His Arg Pro Thr Asn Val Glu Ser Cys
    770                 775                 780

Pro Glu Gly Lys Pro Glu Ala Leu Trp Val Glu Glu Arg Phe Thr Ala
785                 790                 795                 800

His Ile Ala Arg Val Arg Asp Val Glu Leu Leu Thr Gly Leu Asp Phe
                805                 810                 815

Tyr Gln Asp Lys Val Gln Pro Val Ser Glu Ile Leu Gln Leu Lys Thr
            820                 825                 830

Tyr Leu Pro Thr Phe Glu Thr Thr Ile
        835                 840

<210> SEQ ID NO 103
<211> LENGTH: 875
<212> TYPE: PRT
<213> ORGANISM: Homo Sapiens

<400> SEQUENCE: 103

Met Glu Ser Thr Leu Thr Leu Ala Thr Glu Gln Pro Val Lys Lys Asn
1               5                   10                  15

Thr Leu Lys Lys Tyr Lys Ile Ala Cys Ile Val Leu Leu Ala Leu Leu
            20                  25                  30

Val Ile Met Ser Leu Gly Leu Gly Leu Gly Leu Gly Leu Arg Lys Leu
        35                  40                  45

Glu Lys Gln Gly Ser Cys Arg Lys Lys Cys Phe Asp Ala Ser Phe Arg
    50                  55                  60

Gly Leu Glu Asn Cys Arg Cys Asp Val Ala Cys Lys Asp Arg Gly Asp

-continued

```
            65                  70                  75                  80
Cys Cys Trp Asp Phe Glu Asp Thr Cys Val Glu Ser Thr Arg Ile Trp
                    85                  90                  95
Met Cys Asn Lys Phe Arg Cys Gly Glu Thr Arg Leu Glu Ala Ser Leu
            100                 105                 110
Cys Ser Cys Ser Asp Asp Cys Leu Gln Lys Lys Asp Cys Cys Ala Asp
            115                 120                 125
Tyr Lys Ser Val Cys Gln Gly Glu Thr Ser Trp Leu Glu Glu Asn Cys
        130                 135                 140
Asp Thr Ala Gln Gln Ser Gln Cys Pro Glu Gly Phe Asp Leu Pro Pro
145                 150                 155                 160
Val Ile Leu Phe Ser Met Asp Gly Phe Arg Ala Glu Tyr Leu Tyr Thr
                165                 170                 175
Trp Asp Thr Leu Met Pro Asn Ile Asn Lys Leu Lys Thr Cys Gly Ile
                180                 185                 190
His Ser Lys Tyr Met Arg Ala Met Tyr Pro Thr Lys Thr Phe Pro Asn
            195                 200                 205
His Tyr Thr Ile Val Thr Gly Leu Tyr Pro Glu Ser His Gly Ile Ile
        210                 215                 220
Asp Asn Asn Met Tyr Asp Val Asn Leu Asn Lys Asn Phe Ser Leu Ser
225                 230                 235                 240
Ser Lys Glu Gln Asn Asn Pro Ala Trp Trp His Gly Gln Pro Met Trp
                245                 250                 255
Leu Thr Ala Met Tyr Gln Gly Leu Lys Ala Ala Thr Tyr Phe Trp Pro
                260                 265                 270
Gly Ser Glu Val Ala Ile Asn Gly Ser Phe Pro Ser Ile Tyr Met Pro
            275                 280                 285
Tyr Asn Gly Ser Val Pro Phe Glu Glu Arg Ile Ser Thr Leu Leu Lys
        290                 295                 300
Trp Leu Asp Leu Pro Lys Ala Glu Arg Pro Arg Phe Tyr Thr Met Tyr
305                 310                 315                 320
Phe Glu Glu Pro Asp Ser Ser Gly His Ala Gly Gly Pro Val Ser Ala
                325                 330                 335
Arg Val Ile Lys Ala Leu Gln Val Val Asp His Ala Phe Gly Met Leu
            340                 345                 350
Met Glu Gly Leu Lys Gln Arg Asn Leu His Asn Cys Val Asn Ile Ile
        355                 360                 365
Leu Leu Ala Asp His Gly Met Asp Gln Thr Tyr Cys Asn Lys Met Glu
    370                 375                 380
Tyr Met Thr Asp Tyr Phe Pro Arg Ile Asn Phe Phe Tyr Met Tyr Glu
385                 390                 395                 400
Gly Pro Ala Pro Arg Ile Arg Ala His Asn Ile Pro His Asp Phe Phe
                405                 410                 415
Ser Phe Asn Ser Glu Glu Ile Val Arg Asn Leu Ser Cys Arg Lys Pro
            420                 425                 430
Asp Gln His Phe Lys Pro Tyr Leu Thr Pro Asp Leu Pro Lys Arg Leu
        435                 440                 445
His Tyr Ala Lys Asn Val Arg Ile Asp Lys Val His Leu Phe Val Asp
    450                 455                 460
Gln Gln Trp Leu Ala Val Arg Ser Lys Ser Asn Thr Asn Cys Gly Gly
465                 470                 475                 480
Gly Asn His Gly Tyr Asn Asn Glu Phe Arg Ser Met Glu Ala Ile Phe
                485                 490                 495
```

-continued

```
Leu Ala His Gly Pro Ser Phe Lys Glu Lys Thr Glu Val Glu Pro Phe
            500                 505                 510
Glu Asn Ile Glu Val Tyr Asn Leu Met Cys Asp Leu Leu Arg Ile Gln
            515                 520                 525
Pro Ala Pro Asn Asn Gly Thr His Gly Ser Leu Asn His Leu Leu Lys
            530                 535                 540
Val Pro Phe Tyr Glu Pro Ser His Ala Glu Val Ser Lys Phe Ser
545                 550                 555                 560
Val Cys Gly Phe Ala Asn Pro Leu Pro Thr Glu Ser Leu Asp Cys Phe
            565                 570                 575
Cys Pro His Leu Gln Asn Ser Thr Gln Leu Glu Gln Val Asn Gln Met
            580                 585                 590
Leu Asn Leu Thr Gln Glu Glu Ile Thr Ala Thr Val Lys Val Asn Leu
            595                 600                 605
Pro Phe Gly Arg Pro Arg Val Leu Gln Lys Asn Val Asp His Cys Leu
            610                 615                 620
Leu Tyr His Arg Glu Tyr Val Ser Gly Phe Gly Lys Ala Met Arg Met
625                 630                 635                 640
Pro Met Trp Ser Ser Tyr Thr Val Pro Gln Leu Gly Asp Thr Ser Pro
            645                 650                 655
Leu Pro Pro Thr Val Pro Asp Cys Leu Arg Ala Asp Val Arg Val Pro
            660                 665                 670
Pro Ser Glu Ser Gln Lys Cys Ser Phe Tyr Leu Ala Asp Lys Asn Ile
            675                 680                 685
Thr His Gly Phe Leu Tyr Pro Pro Ala Ser Asn Arg Thr Ser Asp Ser
            690                 695                 700
Gln Tyr Asp Ala Leu Ile Thr Ser Asn Leu Val Pro Met Tyr Glu Glu
705                 710                 715                 720
Phe Arg Lys Met Trp Asp Tyr Phe His Ser Val Leu Leu Ile Lys His
            725                 730                 735
Ala Thr Glu Arg Asn Gly Val Asn Val Val Ser Gly Pro Ile Phe Asp
            740                 745                 750
Tyr Asn Tyr Asp Gly His Phe Asp Ala Pro Asp Glu Ile Thr Lys His
            755                 760                 765
Leu Ala Asn Thr Asp Val Pro Ile Pro Thr His Tyr Phe Val Val Leu
            770                 775                 780
Thr Ser Cys Lys Asn Lys Ser His Thr Pro Glu Asn Cys Pro Gly Trp
785                 790                 795                 800
Leu Asp Val Leu Pro Phe Ile Ile Pro His Arg Pro Thr Asn Val Glu
            805                 810                 815
Ser Cys Pro Glu Gly Lys Pro Glu Ala Leu Trp Val Glu Arg Phe
            820                 825                 830
Thr Ala His Ile Ala Arg Val Arg Asp Val Glu Leu Leu Thr Gly Leu
            835                 840                 845
Asp Phe Tyr Gln Asp Lys Val Gln Pro Val Ser Glu Ile Leu Gln Leu
            850                 855                 860
Lys Thr Tyr Leu Pro Thr Phe Glu Thr Thr Ile
865                 870                 875
```